(12) United States Patent
Fesik et al.

(10) Patent No.: US 10,501,421 B1
(45) Date of Patent: Dec. 10, 2019

(54) SUBSTITUTED BENZIMIDAZOLES AS MODULATORS OF RAS SIGNALING

(71) Applicant: VANDERBILT UNIVERSITY, Nashville, TN (US)

(72) Inventors: Steve Fesik, Nashville, TN (US); Alex Waterson, Murfreesboro, TN (US); Michael Burns, Chicago, IL (US); Qi Sun, Vernon Hills, IL (US); Jason Phan, Nashville, TN (US); James M. Salovich, Nashville, TN (US); Jason R. Abbott, Nashville, TN (US); Andrew Little, Boston, MA (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 15/418,274

(22) Filed: Jan. 27, 2017

(51) Int. Cl.
| | |
|---|---|
| *C07D 235/30* | (2006.01) |
| *C07D 401/04* | (2006.01) |
| *C07D 401/12* | (2006.01) |
| *C07D 403/04* | (2006.01) |
| *C07D 403/12* | (2006.01) |
| *C07D 405/12* | (2006.01) |
| *C07D 409/04* | (2006.01) |
| *C07D 471/04* | (2006.01) |
| *C07D 487/04* | (2006.01) |
| *C07D 495/04* | (2006.01) |

(52) U.S. Cl.
CPC ......... *C07D 235/30* (2013.01); *C07D 401/04* (2013.01); *C07D 401/12* (2013.01); *C07D 403/04* (2013.01); *C07D 403/12* (2013.01); *C07D 405/12* (2013.01); *C07D 409/04* (2013.01); *C07D 471/04* (2013.01); *C07D 487/04* (2013.01); *C07D 495/04* (2013.01)

(58) Field of Classification Search
None
See application file for complete search history.

(56) References Cited

U.S. PATENT DOCUMENTS

| | | | | | |
|---|---|---|---|---|---|
| 3,265,691 | A | * | 8/1966 | Helmer | C07D 235/06 544/139 |
| 5,256,665 | A | * | 10/1993 | Orjales-Venero | C07D 235/30 514/254.06 |
| 5,314,903 | A | * | 5/1994 | Axelsson | C07D 235/30 514/388 |

FOREIGN PATENT DOCUMENTS

| | | |
|---|---|---|
| DE | 102005012874 A1 | 9/2006 |
| EP | 0628549 A1 | 12/1994 |
| WO | WO2011023812 A1 | 3/2011 |

OTHER PUBLICATIONS

Orjales, Aurelio. New 2-Piperazinylbenzimidazole Derivatives as 5-HT3 Antagonists. Synthesis and Pharmacological Evaluation. J. Med. Chem. (1997), 40, 586-593.*
Database Registry Chemical Abstracts Service, Columbus, Ohio, Accession No. RN 1503124-92-2, RN 1503060-13-6, RN 1502927-42-5 Entered STN: Dec. 25, 2013.*
Goker, Hakan. Synthesis and Antihistaminic H1 Activity of 1,2,5(6)-Trisubstituted Benzimidazoles. Heterocycles. 51(11), 1999, 2561-2573.*
Spinks, Daniel. Design, Synthesis and Biological Evaluation of Novel Inhibitors of Trypanosoma brucei Pteridine Reducta se 1. ChemMedChem. 2011, 6, 302-308.*
Database Registry Chemical Abstracts Service, Columbus, Ohio, Accession No. RN 1071543-97-9, Entered STN: Nov. 7, 2008.*
Database Registry Chemical Abstracts Service, Columbus, Ohio, Accession No. RN 1550517-12-8, Entered STN: Feb. 20, 2014.*
Burns, et al., High-throughput screening identifies small molecules that bind to the RAS:SOS:RAS complex and perturb RAS signaling, Analytical Biochemistry 548 (2018) 44-52.
Abbott, et al., Discovery of Aminopiperidine Indoles That Activate the Guanine Nucleotide Exchange Factor SOS1 and Modulate RAS Signaling, J. Med. Chem. 2018, 61, 6002-6017.
Morreale, et al., Arylpiperazines with Serotonin-3 Antagonist Activity: A Comparative Molecular Field Analysis, J. Med. Chem. 1998, 41, 2029-2039.
Orjales, et al., New 2-Piperazinylbenzimidazole Derivatives as 5-HT3 Antagonists. Synthesis and Pharmacological Evaluation, J. Med. Chem. 1997, 40, 586-593.
Goker, et al., Synthesis of 1,2,5(6)-Trisubstituted Benzimidazoles and Evaluation of Their Antimicrobial Activities, Arch Pharm (Weinheim)3 28,425-430, 1995.

* cited by examiner

*Primary Examiner* — Samantha L Shterengarts
(74) *Attorney, Agent, or Firm* — Stites & Harbison PLLC; Richard S. Myers, Jr.

(57) ABSTRACT

Benzimidazole compounds that increase the rate of SOS-mediated nucleotide exchange on Ras by binding to a functionally relevant, chemically tractable pocket on the SOS protein, as part of the Ras:SOS:Ras complex.

16 Claims, 1 Drawing Sheet

Effects on Ras signaling for example compounds.
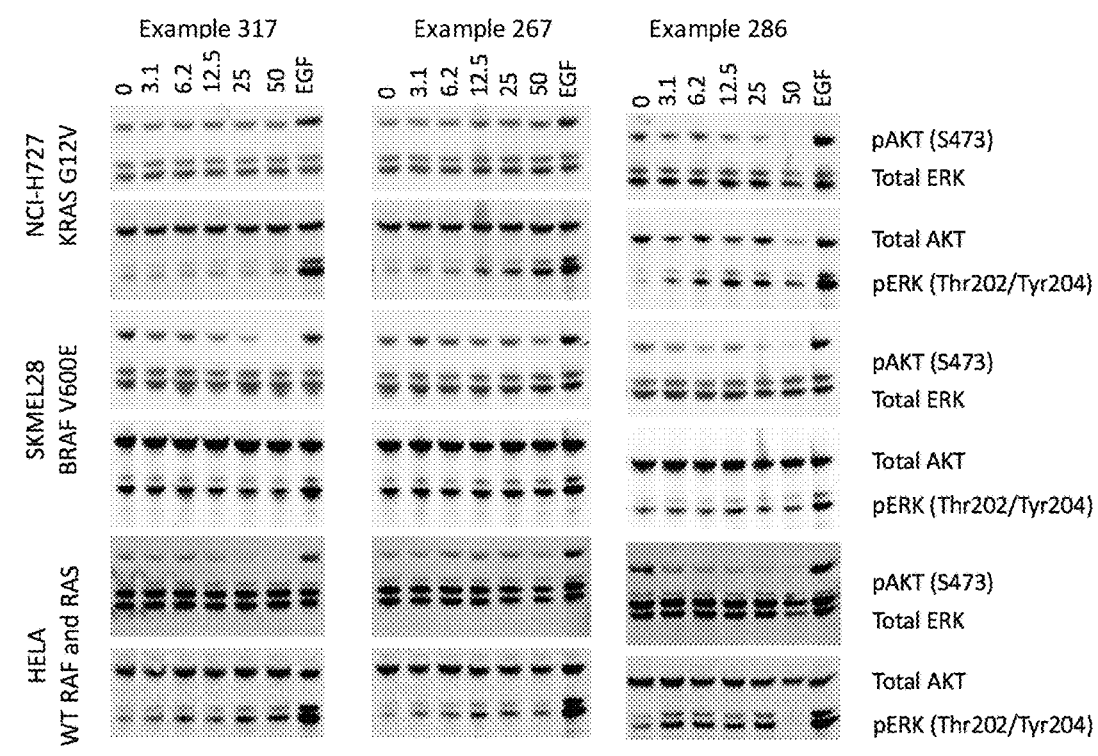

SUBSTITUTED BENZIMIDAZOLES AS MODULATORS OF RAS SIGNALING

BACKGROUND

Ras is one of the most highly validated targets for cancer drug discovery; however, the discovery of potent inhibitors of Ras has been difficult due to a lack of suitable binding pockets on the surface of Ras. The present inventors have discovered a binding pocket on the SOS protein, as part of the Ras:SOS:Ras complex, and small molecules that bind to this pocket and alter Ras activity in biochemical and cell-based experiments. These compounds are useful for treating cancer.

Without being bound by theory or mechanism, the Ras family of small GTPases function as molecular switches, cycling between inactive (GDP-bound) and active (GTP-bound) states to relay cellular signals in response to extracellular stimuli. The activation of Ras is tightly regulated by guanine nucleotide exchange factors (GEFs), such as Son of Sevenless (SOS), which catalyze nucleotide exchange, and GTPase-activating proteins (GAPs), which aid in GTP hydrolysis. Upon activation, GTP-bound Ras exerts its functions through protein-protein interactions with effectors such as Raf kinase and phosphoinositide 3-kinase to promote cell growth and survival.

Aberrant activation of Ras by increased upstream signaling, loss of GAP function, or oncogenic mutation results in the deregulation of cellular signals in cancer. Indeed, aberrant Ras signaling plays a role in up to 30% of all human cancers, with the highest incidence of Ras mutations occurring in carcinomas of the pancreas (63-90%), colon (36-50%), and lung (19-30%). Active Ras endows cells with capabilities that represent many of the hallmarks of cancer, including the ability to proliferate, evade programmed cell death, alter metabolism, induce angiogenesis, increase invasion and metastasis, and evade immune destruction. Importantly, inactivation of oncogenic Ras has been shown to be a promising therapeutic strategy in in vitro and in vivo models of cancer.

Embodiments of the present invention include compounds that increase the rate of SOS-mediated nucleotide exchange on Ras by binding to a functionally relevant, chemically tractable pocket on the SOS protein, as part of the Ras:SOS:Ras complex. High resolution X-ray co-crystal structures reveal the location of the binding pocket in the CDC25 domain near the catalytic site of SOS, adjacent to the Switch II region of Ras, and provide a detailed understanding of protein-ligand interactions. Mutational analyses confirmed the functional relevance of this binding site and showed it to be essential for compound activity. Perturbation of Ras signaling in HeLa and other cancer cells with these molecules demonstrates their ability to alter Ras activity in the setting of full-length proteins. The present invention is a new approach for targeting Ras signaling and provides compounds can be used to treat tumors.

Early attempts to inhibit Ras-driven tumors have focused on disrupting the posttranslational modification and localization of Ras or inhibiting Ras effectors. In contrast, embodiments of the present invention include that activate nucleotide exchange by binding to a hydrophobic pocket on the SOS protein, as part of the Ras:SOS:Ras complex. Further, these compounds perturb Ras signaling in cancer cells and kill cancer cells. This discovery represents a new approach to alter Ras activity.

Compound-mediated activation of SOS-catalyzed nucleotide exchange of the present invention is novel compared to previously reported mechanisms that increase nucleotide exchange. Mechanisms involving chelation of the divalent magnesium ion, destabilization of bound nucleotide, or activation via the allosteric Ras binding site on SOS were inconsistent with the results obtained in in vitro nucleotide exchange assays. In contrast, the present inventors discovered compounds of the present invention that increase nucleotide exchange by binding to a hydrophobic pocket on the SOS protein, as part of the Ras:SOS:Ras ternary complex.

Based on in vitro biochemical studies, the present inventors discovered that treatment of cells with compounds of the present invention resulted in diverse set of cellular responses. Indeed, Ras-GTP levels increased following the treatment of HeLa and other cancer cells with the compounds of the present invention, consistent with the observed increase in nucleotide exchange activity. Treatment of HeLa and other cancer cells would result in an increase of in downstream MAPK pathway signaling at low doses, but a decrease in MAPK signaling at higher doses. Further, downstream PI3K pathway signaling decreases in a dose-responsive manner. The present inventors thus discovered that rapid SOS-mediated activation of Ras, in the absence of other cooperative signal inputs, perturbs both MAPK and PI3K signaling.

SUMMARY

In accordance with the purpose(s) of the invention, as embodied and broadly described herein, the invention, in one aspect, relates to compounds useful as modulators of Ras activity, methods of making same, pharmaceutical compositions comprising same, and methods of treating cancer associated with alterations in Ras activity. Further disclosed are methods and pharmaceutical compositions useful for treating a disease related to Ras activity. In one aspect, the disclosed compounds can affect the efficiency at which SOS can activate Ras. The disclosed compounds can also affect the activity of the Ras:SOS:Ras ternary complex. The modulator of Ras activity can offer advantages over a molecule that blocks the GTP/GDP or SOS binding pockets, since basal signaling would not be inhibited.

Embodiments of the present invention are compounds of the following formula (I):

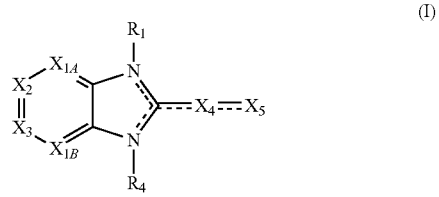

$X_{1A}$ is N, C—R; $X_{1B}$ is N, C—$R_6$; $X_2$ is N, C—$R_6$; $X_3$ is N, C—$R_6$; $X_4$ is optionally present and is substituted or unsubstituted and selected from $C_{1-6}$alkyl, $C_{1-6}$alkenyl, $C_{1-6}$alkynyl, cycloalkyl, $C_{0-6}$alkyl-cycloalkyl-$C_{0-6}$ alkyl, aryl, $C_{0-6}$ alkyl-aryl-$C_{0-6}$ alkyl, —O—, alkoxy, —O—($C_1$-$C_6$); $X_5$ is substituted or unsubstituted and selected from N, NH, —$NR_2R_3$, cyclic amine, —$NR_2$-alkyl-$NR_2R_3$; R is unsubstituted or substituted with one or more independent $R_5$, and is independently chosen from H, alkyl, cycloalkyl, phenyl, hydroxyl, heterocycloalkyl, cyclic amine, halogen, $CF_3$, Cl, $CONR_3R_4$, aryl, heteroaryl, O—$R_4$, O-alkyl-$R_4$, O-aryl, O-heteroaryl, N—$R_4$, N-aryl, N-heteroaryl, $NHR_4$, NR$_2$R$_3$, heteroalkyl, benzyl, heteroaryl benzyl (CH$_2$heteroaryl), alkenyl, alkynyl, alkyl-cycloalkyl, CH$_2$-cycloalkyl, CH$_2$—CF$_3$, hydroxyalkyl, alkyl-alkoxy, alkyl-cycloheteroalkyl, alkyl-heteroaryl, alkyl-carboxylic acid, CO—CF$_3$, alkyl-CO—O-alkyl, alkyl-CO—NR$_3$R$_4$, CO-alkyl-sulfonyl-alkyl, CO-cycloheteroalkyl, CO—NH-cycloalkyl, CN, alkoxy-cycloalkyl, alkoxy-cycloheteroalkyl, O-alkoxy, O-dioxothian, alkoxy, O-heteroalkyl, alkoxy-heteroalkyl, methylsulfonyl, O-cycloheteroalkyl, O-alkoxy-cycloheteroalkyl, O-alkoxy-aryl, O-heteroaryl, NR$_3$COR$_2$, amino-cycloalkyl, amino-cycloheteroalkyl, NR$_3$-alkoxy, NR$_3$-dioxothian, NR$_3$-heteroalkyl, amino-heteroalkyl, NR$_3$-cycloheteroalkyl, NR$_3$-cycloheteroalkyl, NR$_3$-aryl, NR$_3$-heteroaryl, NR$_3$—CO—CF$_3$, alkyl-CO—NR$_3$R$_4$, NR$_3$—CO-alkyl-sulfonyl-alkyl, NR$_3$—CO—cycloheteroalkyl, CO—NR$_3$-cycloalkyl, alkyl-carboxylic acid, alkoxy-heteroaryl, alkyl-phenyl, cycloheteroalkyl, amino, amino-heteroaryl, amino-phenyl, CO-alkyl, CONR$_3$-alkyl, CH$_3$, NH$_2$, alkyl-amino, pyridine, pyrazole, furan, thiophene, pyrimidine, thiazole, isothiazole, oxazole, isoxazole, piperazine, pyrrole, pyrazine, dioxane, morpholine, thiomorpholine, triazole, imidazole, alkoxy; R$_1$, when present, is substituted by one or more R$_5$, or H, alkyl, alkene, alkyne, or optionally forms a 3-8 membered ring with X$_5$; R$_2$ is substituted by one or more R$_5$, or unsubstituted and is selected from H, alkyl, alkene, alkyne, alkyl-heteroaryl, alkyl-heterocycloalkyl, alkyl-amino, or together with R$_3$ forms a 3-6 membered ring; R$_3$ is substituted by one or more R$_5$ or unsubstituted and is selected from H, alkyl, alkenyl, alkynyl, alkyl-heteroaryl, alkyl-heterocycloalkyl, alkyl-amino, or together with R$_2$ forms a ring; R$_4$ is substituted by one or more R$_5$, or unsubstituted and is selected from benzyl, methylcycloalkyl, cycloalkyl, alkyl-cycloalkyl; each R$_5$ is independent, substituted or unsubstituted, and selected from H, halogen, alkyl, cycloalkyl, cycloheteroalkyl, amino, cyclic amino, aminoalkyl, alkenyl, alkynyl, CF$_3$, alkoxy, heterocycle, phenyl, aryl, heteroaryl, amidyl; R$_6$ is independent and optionally substituted H, alkyl, cycloalkyl, alkenyl, alkynyl, alkoxy, halogen, CH$_3$, alkyl-amino, amino-alkyl, CF$_3$, hydroxyl, NH$_2$, O-alkyl, NMe$_2$, CH$_2$OH, CH$_2$OMe, CH$_2$NHMe, CH$_2$NMe$_2$; or a pharmaceutically acceptable salt thereof or a pharmaceutically acceptable derivative thereof.

Also disclosed are methods for enhancing SOS mediated nucleotide exchange on Ras in a subject comprising the step of administering to the subject at least one compound having a structure represented by a compound of the following formula:

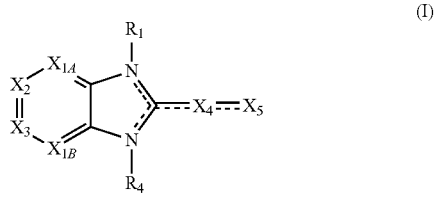

(I)

X$_{1A}$ is N, C—R; X$_{1B}$ is N, C—R$_6$; X$_2$ is N, C—R$_6$; X$_3$ is N, C—R$_6$; X$_4$ is optionally present and is substituted or unsubstituted and selected from C$_{1-6}$alkyl, C$_{1-6}$alkenyl, C$_{1-6}$alkynyl, cycloalkyl, C$_{0-6}$alkyl-cycloalkyl-C$_{0-6}$ alkyl, aryl, C$_{0-6}$ alkyl-aryl-C$_{0-6}$ alkyl, —O—, alkoxy, —O—(C$_1$-C$_6$); X$_5$ is substituted or unsubstituted and selected from N, NH, —NR$_2$R$_3$, cyclic amine, —NR$_2$-alkyl-NR$_2$R$_3$; R is unsubstituted or substituted with one or more independent R$_5$, and is independently chosen from H, alkyl, cycloalkyl, phenyl, hydroxyl, heterocycloalkyl, cyclic amine, halogen, CF$_3$, Cl, CONR$_3$R$_4$, aryl, heteroaryl, O—R$_4$, O-alkyl-R$_4$, O-aryl, O-heteroaryl, N—R$_4$, N-aryl, N-heteroaryl, NHR$_4$, NR$_2$R$_3$, heteroalkyl, benzyl, heteroaryl benzyl (CH$_2$heteroaryl), alkenyl, alkynyl, alkyl-cycloalkyl, CH$_2$-cycloalkyl, CH$_2$—CF$_3$, hydroxyalkyl, alkyl-alkoxy, alkyl-cycloheteroalkyl, alkyl-heteroaryl, alkyl-carboxylic acid, CO—CF$_3$, alkyl-CO—O-alkyl, alkyl-CO—NR$_3$R$_4$, CO-alkyl-sulfonyl-alkyl, CO-cycloheteroalkyl, CO—NH-cycloalkyl, CN, alkoxy-cycloalkyl, alkoxy-cycloheteroalkyl, O-alkoxy, O-dioxothian, alkoxy, O-heteroalkyl, alkoxy-heteroalkyl, methylsulfonyl, O-cycloheteroalkyl, O-alkoxy-cycloheteroalkyl, O-alkoxy-aryl, O-heteroaryl, NR$_3$COR$_2$, amino-cycloalkyl, amino-cycloheteroalkyl, NR$_3$-alkoxy, NR$_3$-dioxothian, NR$_3$-heteroalkyl, amino-heteroalkyl, NR$_3$-cycloheteroalkyl, NR$_3$-cycloheteroalkyl, NR$_3$-aryl, NR$_3$-heteroaryl, NR$_3$—CO—CF$_3$, alkyl-CO—NR$_3$R$_4$, NR$_3$—CO-alkyl-sulfonyl-alkyl, NR$_3$—CO—cycloheteroalkyl, CO—NR$_3$-cycloalkyl, alkyl-carboxylic acid, alkoxy-heteroaryl, alkyl-phenyl, cycloheteroalkyl, amino, amino-heteroaryl, amino-phenyl, CO-alkyl, CONR$_3$-alkyl, CH$_3$, NH$_2$, alkyl-amino, pyridine, pyrazole, furan, thiophene, pyrimidine, thiazole, isothiazole, oxazole, isoxazole, piperazine, pyrrole, pyrazine, dioxane, morpholine, thiomorpholine, triazole, imidazole, alkoxy; R$_A$ is unsubstituted or substituted with one or more independent R$_5$, and is independently chosen from H, alkyl, cycloalkyl, phenyl, hydroxyl, heterocycloalkyl, cyclic amine, halogen, CF$_3$, Cl, CONR$_3$R$_4$, aryl, heteroaryl, O—R$_3$, O-alkyl-R$_3$, O-aryl, O-heteroaryl, N—R$_3$, N-aryl, N-heteroaryl, NR$_2$R$_3$, heteroalkyl, benzyl, heteroaryl benzyl (CH$_2$heteroaryl), alkenyl, alkynyl, alkyl-cycloalkyl, CH$_2$-cycloalkyl, CH$_2$—CF$_3$, hydroxyalkyl, alkyl-alkoxy, alkyl-cycloheteroalkyl, alkyl-heteroaryl, alkyl-carboxylic acid, CO—CF$_3$, alkyl-CO—O-alkyl, alkyl-CO—NR$_3$R$_4$, CO-alkyl-sulfonyl-alkyl, CO-cycloheteroalkyl, CO—NH-cycloalkyl, CN, alkoxy-cycloalkyl, alkoxy-cycloheteroalkyl, O-alkoxy, O-dioxothian, alkoxy, O-heteroalkyl, alkoxy-heteroalkyl, methylsulfonyl, O-cycloheteroalkyl, O-alkoxy-cycloheteroalkyl, O-alkoxy-aryl, O-heteroaryl, $NR_3COR_2$, amino-cycloalkyl, amino-cycloheteroalkyl, $NR_3$-alkoxy, $NR_3$-dioxothian, $NR_3$-heteroalkyl, amino-heteroalkyl, $NR_3$-cycloheteroalkyl, $NR_3$-cycloheteroalkyl, $NR_3$-aryl, $NR_3$-heteroaryl, $NR_3$—CO—$CF_3$, alkyl-CO—$NR_3R_4$, $NR_3$—CO-alkyl-sulfonyl-alkyl, $NR_3$—CO— cycloheteroalkyl, CO—$NR_3$-cycloalkyl, alkyl-carboxylic acid, alkoxy-heteroaryl, alkyl-phenyl, cycloheteroalkyl, amino, amino-heteroaryl, amino-phenyl, CO-alkyl, $CONR_3$-alkyl, $CH_3$, $NH_2$, alkyl-amino, pyridine, pyrazole, furan, thiophene, pyrimidine, thiazole, isothiazole, oxazole, isoxazole, piperazine, pyrrole, pyrazine, dioxane, morpholine, thiomorpholine, triazole, imidazole, alkoxy; $R_1$, when present, is substituted by one or more $R_5$, or H, alkyl, alkene, alkyne, or optionally forms a 3-8 membered ring with $X_5$; $R_2$ is substituted by one or more $R_5$, or unsubstituted and is selected from H, alkyl, alkene, alkyne, alkyl-heteroaryl, alkyl-heterocycloalkyl, alkyl-amino, or together with $R_3$ forms a 3-6 membered ring; $R_3$ is substituted by one or more $R_5$ or unsubstituted and is selected from H, alkyl, alkenyl, alkynyl, alkyl-heteroaryl, alkyl-heterocycloalkyl, alkyl-amino, or together with $R_2$ forms a ring; $R_4$ is substituted by one or more $R_5$, or unsubstituted and is selected from benzyl, methylcycloalkyl, cycloalkyl, alkyl-cycloalkyl; each $R_5$ is independent, substituted or unsubstituted, and selected from H, halogen, alkyl, cycloalkyl, cycloheteroalkyl, amino, cyclic amino, aminoalkyl, alkenyl, alkynyl, $CF_3$, alkoxy, heterocycle, phenyl, aryl, heteroaryl, amidyl; $R_6$ is independent and optionally substituted H, alkyl, cycloalkyl, alkenyl, alkynyl, alkoxy, halogen, $CH_3$, alkyl-amino, amino-alkyl, $CF_3$, hydroxyl, $NH_2$, O-alkyl, $NMe_2$, $CH_2OH$, $CH_2OMe$, $CH_2NHMe$, $CH_2NMe_2$; or a pharmaceutically acceptable salt thereof or a pharmaceutically acceptable derivative thereof, in a dosage and amount effective to modulate Ras signaling in the subject.

Also disclosed are methods for modulating Ras signaling in at least one cell comprising the step of contacting at least one cell with at least one compound having a structure represented by a compound of the following formula:

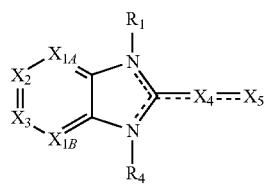

(I)

$X_{1A}$ is N, C—R; $X_{1B}$ is N, C—$R_6$; $X_2$ is N, C—$R_6$; $X_3$ is N, C—$R_6$; $X_4$ is optionally present and is substituted or unsubstituted and selected from $C_{1-6}$alkyl, $C_{1-6}$alkenyl, $C_{1-6}$alkynyl, cycloalkyl, $C_{0-6}$alkyl-cycloalkyl-$C_{0-6}$ alkyl, aryl, $C_{0-6}$ alkyl-aryl-$C_{0-6}$ alkyl, —O—, alkoxy, —O—($C_1$-$C_6$); $X_5$ is substituted or unsubstituted and selected from N, NH, —$NR_2R_3$, cyclic amine, —$NR_2$-alkyl-$NR_2R_3$; R is unsubstituted or substituted with one or more independent $R_5$, and is independently chosen from H, alkyl, cycloalkyl, phenyl, hydroxyl, heterocycloalkyl, cyclic amine, halogen, $CF_3$, Cl, $CONR_3R_4$, aryl, heteroaryl, O—$R_4$, O-alkyl-$R_4$, O-aryl, O-heteroaryl, N—$R_4$, N-aryl, N-heteroaryl, $NHR_4$, $NR_2R_3$, heteroalkyl, benzyl, heteroaryl benzyl ($CH_2$heteroaryl), alkenyl, alkynyl, alkyl-cycloalkyl, $CH_2$-cycloalkyl, $CH_2$—$CF_3$, hydroxyalkyl, alkyl-alkoxy, alkyl-cycloheteroalkyl, alkyl-heteroaryl, alkyl-carboxylic acid, CO—$CF_3$, alkyl-CO—O-alkyl, alkyl-CO—$NR_3R_4$, CO-alkyl-sulfonyl-alkyl, CO-cycloheteroalkyl, CO—NH-cycloalkyl, CN, alkoxy-cycloalkyl, alkoxy-cycloheteroalkyl, O-alkoxy, O-dioxothian, alkoxy, O-heteroalkyl, alkoxy-heteroalkyl, methylsulfonyl, O-cycloheteroalkyl, O-alkoxy-cycloheteroalkyl, O-alkoxy-aryl, O-heteroaryl, $NR_3COR_2$, amino-cycloalkyl, amino-cycloheteroalkyl, $NR_3$-alkoxy, $NR_3$-dioxothian, $NR_3$-heteroalkyl, amino-heteroalkyl, $NR_3$-cycloheteroalkyl, $NR_3$-cycloheteroalkyl, $NR_3$-aryl, $NR_3$-heteroaryl, $NR_3$—CO—$CF_3$, alkyl-CO—$NR_3R_4$, $NR_3$—CO-alkyl-sulfonyl-alkyl, $NR_3$—CO— cycloheteroalkyl, CO—$NR_3$-cycloalkyl, alkyl-carboxylic acid, alkoxy-heteroaryl, alkyl-phenyl, cycloheteroalkyl, amino, amino-heteroaryl, amino-phenyl, CO-alkyl, $CONR_3$-alkyl, $CH_3$, $NH_2$, alkyl-amino, pyridine, pyrazole, furan, thiophene, pyrimidine, thiazole, isothiazole, oxazole, isoxazole, piperazine, pyrrole, pyrazine, dioxane, morpholine, thiomorpholine, triazole, imidazole, alkoxy; $R_A$ is unsubstituted or substituted with one or more independent $R_5$, and is independently chosen from H, alkyl, cycloalkyl, phenyl, hydroxyl, heterocycloalkyl, cyclic amine, halogen, $CF_3$, Cl, $CONR_3R_4$, aryl, heteroaryl, O—$R_3$, O-alkyl-$R_3$, O-aryl, O-heteroaryl, N—$R_3$, N-aryl, N-heteroaryl, $NR_2R_3$, heteroalkyl, benzyl, heteroaryl benzyl ($CH_2$heteroaryl), alkenyl, alkynyl, alkyl-cycloalkyl, $CH_2$-cycloalkyl, $CH_2$—$CF_3$, hydroxyalkyl, alkyl-alkoxy, alkyl-cycloheteroalkyl, alkyl-heteroaryl, alkyl-carboxylic acid, CO—$CF_3$, alkyl-CO—O-alkyl, alkyl-CO—$NR_3R_4$, CO-alkyl-sulfonyl-alkyl, CO-cycloheteroalkyl, CO—NH-cycloalkyl, CN, alkoxy-cycloalkyl, alkoxy-cycloheteroalkyl, O-alkoxy, O-dioxothian, alkoxy, O-heteroalkyl, alkoxy-heteroalkyl, methylsulfonyl, O-cycloheteroalkyl, O-alkoxy-cycloheteroalkyl, O-alkoxy-aryl, O-heteroaryl, $NR_3COR_2$, amino-cycloalkyl, amino-cycloheteroalkyl, $NR_3$-alkoxy, $NR_3$-dioxothian, $NR_3$-heteroalkyl, amino-heteroalkyl, $NR_3$-cycloheteroalkyl, $NR_3$-cycloheteroalkyl, $NR_3$-aryl, $NR_3$-heteroaryl, $NR_3$—CO—$CF_3$, alkyl-CO—$NR_3R_4$, $NR_3$—CO-alkyl-sulfonyl-alkyl, $NR_3$—CO— cycloheteroalkyl, CO—$NR_3$-cycloalkyl, alkyl-carboxylic acid, alkoxy-heteroaryl, alkyl-phenyl, cycloheteroalkyl, amino, amino-heteroaryl, amino-phenyl, CO-alkyl, $CONR_3$-alkyl, $CH_3$, $NH_2$, alkyl-amino, pyridine, pyrazole, furan, thiophene, pyrimidine, thiazole, isothiazole, oxazole, isoxazole, piperazine, pyrrole, pyrazine, dioxane, morpholine, thiomorpholine, triazole, imidazole, alkoxy; $R_1$, when present, is substituted by one or more $R_5$, or H, alkyl, alkene, alkyne, or optionally forms a 3-8 membered ring with $X_5$; $R_2$ is substituted by one or more $R_5$, or unsubstituted and is selected from H, alkyl, alkene, alkyne, alkyl-heteroaryl, alkyl-heterocycloalkyl, alkyl-amino, or together with $R_3$ forms a 3-6 membered ring; $R_3$ is substituted by one or more $R_5$ or unsubstituted and is selected from H, alkyl, alkenyl, alkynyl, alkyl-heteroaryl, alkyl-heterocycloalkyl, alkyl-amino, or together with $R_2$ forms a ring; $R_4$ is substituted by one or more $R_5$, or unsubstituted and is selected from benzyl, methylcycloalkyl, cycloalkyl, alkyl-cycloalkyl; each $R_5$ is independent, substituted or unsubstituted, and selected from H, halogen, alkyl, cycloalkyl, cycloheteroalkyl, amino, cyclic amino, aminoalkyl, alkenyl, alkynyl, $CF_3$, alkoxy, heterocycle, phenyl, aryl, heteroaryl, amidyl; $R_6$ is independent and optionally substituted H, alkyl, cycloalkyl, alkenyl, alkynyl, alkoxy, halogen, $CH_3$, alkyl-amino, amino-alkyl, $CF_3$, hydroxyl, $NH_2$, O-alkyl, $NMe_2$, $CH_2OH$, $CH_2OMe$, $CH_2NHMe$, $CH_2NMe_2$; or a pharmaceutically acceptable salt thereof or a pharmaceutically acceptable derivative thereof, in at an amount effective to modulate Ras signaling in at least one cell.

Also disclosed are compounds having a structure represented by a compound of the following formula:

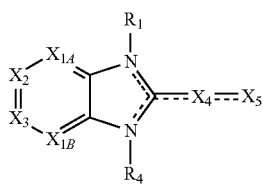

(I)

$X_{1A}$ is N, C—R; $X_{1B}$ is N, C—$R_6$; $X_2$ is N, C—$R_6$; $X_3$ is N, C—$R_6$; $X_4$ is optionally present and is substituted or unsubstituted and selected from $C_{1-6}$alkyl, $C_{1-6}$alkenyl, $C_{1-6}$alkynyl, cycloalkyl, $C_{0-6}$alkyl-cycloalkyl-$C_{0-6}$ alkyl, aryl, $C_{0-6}$ alkyl-aryl-$C_{0-6}$ alkyl, —O—, alkoxy, —O—($C_1$-$C_6$); $X_5$ is substituted or unsubstituted and selected from N, NH, —$NR_2R_3$, cyclic amine, —$NR_2$-alkyl-$NR_2R_3$; R is unsubstituted or substituted with one or more independent $R_5$, and is independently chosen from H, alkyl, cycloalkyl, phenyl, hydroxyl, heterocycloalkyl, cyclic amine, halogen, $CF_3$, Cl, $CONR_3R_4$, aryl, heteroaryl, O—$R_4$, O-alkyl-$R_4$, O-aryl, O-heteroaryl, N—$R_4$, N-aryl, N-heteroaryl, $NHR_4$, $NR_2R_3$, heteroalkyl, benzyl, heteroaryl benzyl ($CH_2$-heteroaryl), alkenyl, alkynyl, alkyl-cycloalkyl, $CH_2$-cycloalkyl, $CH_2$—$CF_3$, hydroxyalkyl, alkyl-alkoxy, alkyl-cycloheteroalkyl, alkyl-heteroaryl, alkyl-carboxylic acid, CO—$CF_3$, alkyl-CO—O-alkyl, alkyl-CO—$NR_3R_4$, CO-alkyl-sulfonyl-alkyl, CO-cycloheteroalkyl, CO—NH-cycloalkyl, CN, alkoxy-cycloalkyl, alkoxy-cycloheteroalkyl, O-alkoxy, O-dioxothian, alkoxy, O-heteroalkyl, alkoxy-heteroalkyl, methylsulfonyl, O-cycloheteroalkyl, O-alkoxy-cycloheteroalkyl, O-alkoxy-aryl, O-heteroaryl, $NR_3COR_2$, amino-cycloalkyl, amino-cycloheteroalkyl, $NR_3$-alkoxy, $NR_3$-dioxothian, $NR_3$-heteroalkyl, amino-heteroalkyl, $NR_3$-cycloheteroalkyl, $NR_3$-cycloheteroalkyl, $NR_3$-aryl, $NR_3$-heteroaryl, $NR_3$—CO—$CF_3$, alkyl-CO—$NR_3R_4$, $NR_3$—CO-alkyl-sulfonyl-alkyl, $NR_3$—CO— cycloheteroalkyl, CO—$NR_3$-cycloalkyl, alkyl-carboxylic acid, alkoxy-heteroaryl, alkyl-phenyl, cycloheteroalkyl, amino, amino-heteroaryl, amino-phenyl, CO-alkyl, $CONR_3$-alkyl, $CH_3$, $NH_2$, alkyl-amino, pyridine, pyrazole, furan, thiophene, pyrimidine, thiazole, isothiazole, oxazole, isoxazole, piperazine, pyrrole, pyrazine, dioxane, morpholine, thiomorpholine, triazole, imidazole, alkoxy; $R_A$ is unsubstituted or substituted with one or more independent $R_5$, and is independently chosen from H, alkyl, cycloalkyl, phenyl, hydroxyl, heterocycloalkyl, cyclic amine, halogen, $CF_3$, Cl, $CONR_3R_4$, aryl, heteroaryl, O—$R_3$, O-alkyl-$R_3$, O-aryl, O-heteroaryl, N—$R_3$, N-aryl, N-heteroaryl, $NR_2R_3$, heteroalkyl, benzyl, heteroaryl benzyl ($CH_2$heteroaryl), alkenyl, alkynyl, alkyl-cycloalkyl, $CH_2$-cycloalkyl, $CH_2$—$CF_3$, hydroxyalkyl, alkyl-alkoxy, alkyl-cycloheteroalkyl, alkyl-heteroaryl, alkyl-carboxylic acid, CO—$CF_3$, alkyl-CO—O-alkyl, alkyl-CO—$NR_3R_4$, CO-alkyl-sulfonyl-alkyl, CO-cycloheteroalkyl, CO—NH-cycloalkyl, CN, alkoxy-cycloalkyl, alkoxy-cycloheteroalkyl, O-alkoxy, O-dioxothian, alkoxy, O-heteroalkyl, alkoxy-heteroalkyl, methylsulfonyl, O-cycloheteroalkyl, O-alkoxy-cycloheteroalkyl, O-alkoxy-aryl, O-heteroaryl, $NR_3COR_2$, amino-cycloalkyl, amino-cycloheteroalkyl, $NR_3$-alkoxy, $NR_3$-dioxothian, $NR_3$-heteroalkyl, amino-heteroalkyl, $NR_3$-cycloheteroalkyl, $NR_3$-cycloheteroalkyl, $NR_3$-aryl, $NR_3$-heteroaryl, $NR_3$—CO—$CF_3$, alkyl-CO—$NR_3R_4$, $NR_3$—CO-alkyl-sulfonyl-alkyl, $NR_3$—CO— cycloheteroalkyl, CO—$NR_3$-cycloalkyl, alkyl-carboxylic acid, alkoxy-heteroaryl, alkyl-phenyl, cycloheteroalkyl, amino, amino-heteroaryl, amino-phenyl, CO-alkyl, $CONR_3$-alkyl, $CH_3$, $NH_2$, alkyl-amino, pyridine, pyrazole, furan, thiophene, pyrimidine, thiazole, isothiazole, oxazole, isoxazole, piperazine, pyrrole, pyrazine, dioxane, morpholine, thiomorpholine, triazole, imidazole, alkoxy; $R_1$, when present, is substituted by one or more $R_5$, or H, alkyl, alkene, alkyne, or optionally forms a 3-8 membered ring with $X_5$; $R_2$ is substituted by one or more $R_5$, or unsubstituted and is selected from H, alkyl, alkene, alkyne, alkyl-heteroaryl, alkyl-heterocycloalkyl, alkyl-amino, or together with $R_3$ forms a 3-6 membered ring; $R_3$ is substituted by one or more $R_5$ or unsubstituted and is selected from H, alkyl, alkenyl, alkynyl, alkyl-heteroaryl, alkyl-heterocycloalkyl, alkyl-amino, or together with $R_2$ forms a ring; $R_4$ is substituted by one or more $R_5$, or unsubstituted and is selected from benzyl, methylcycloalkyl, cycloalkyl, alkyl-cycloalkyl; each $R_5$ is independent, substituted or unsubstituted, and selected from H, halogen, alkyl, cycloalkyl, cycloheteroalkyl, amino, cyclic amino, aminoalkyl, alkenyl, alkynyl, $CF_3$, alkoxy, heterocycle, phenyl, aryl, heteroaryl, amidyl; $R_6$ is independent and optionally substituted H, alkyl, cycloalkyl, alkenyl, alkynyl, alkoxy, halogen, $CH_3$, alkyl-amino, amino-alkyl, $CF_3$, hydroxyl, $NH_2$, O-alkyl, $NMe_2$, $CH_2OH$, $CH_2OMe$, $CH_2NHMe$, $CH_2NMe_2$; or a pharmaceutically acceptable salt thereof or a pharmaceutically acceptable derivative thereof.

Also disclosed are pharmaceutical compositions comprising compounds disclosed herein, including those having a structure represented by a compound of the following formula:

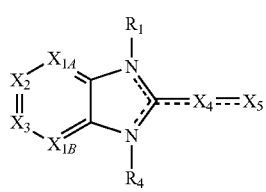

(I)

$X_{1A}$ is N, C—R; $X_{1B}$ is N, C—$R_6$; $X_2$ is N, C—$R_6$; $X_3$ is N, C—$R_6$; $X_4$ is optionally present and is substituted or unsubstituted and selected from $C_{1-6}$alkyl, $C_{1-6}$alkenyl, $C_{1-6}$alkynyl, cycloalkyl, $C_{0-6}$alkyl-cycloalkyl-$C_{0-6}$ alkyl, aryl, $C_{0-6}$ alkyl-aryl-$C_{0-6}$ alkyl, —O—, alkoxy, —O—($C_1$-$C_6$); $X_5$ is substituted or unsubstituted and selected from N, NH, —$NR_2R_3$, cyclic amine, —$NR_2$-alkyl-$NR_2R_3$; R is unsubstituted or substituted with one or more independent $R_5$, and is independently chosen from H, alkyl, cycloalkyl, phenyl, hydroxyl, heterocycloalkyl, cyclic amine, halogen, $CF_3$, Cl, $CONR_3R_4$, aryl, heteroaryl, O—$R_4$, O-alkyl-$R_4$, O-aryl, O-heteroaryl, N—$R_4$, N-aryl, N-heteroaryl, $NHR_4$, $NR_2R_3$, heteroalkyl, benzyl, heteroaryl benzyl ($CH_2$-heteroaryl), alkenyl, alkynyl, alkyl-cycloalkyl, $CH_2$-cycloalkyl, $CH_2$—$CF_3$, hydroxyalkyl, alkyl-alkoxy, alkyl-cycloheteroalkyl, alkyl-heteroaryl, alkyl-carboxylic acid, CO—$CF_3$, alkyl-CO—O-alkyl, alkyl-CO—$NR_3R_4$, CO-alkyl-sulfonyl-alkyl, CO-cycloheteroalkyl, CO—NH-cycloalkyl, CN, alkoxy-cycloalkyl, alkoxy-cycloheteroalkyl, O-alkoxy, O-dioxothian, alkoxy, O-heteroalkyl, alkoxy-heteroalkyl, methylsulfonyl, O-cycloheteroalkyl, O-alkoxy-cycloheteroalkyl, O-alkoxy-aryl, O-heteroaryl, $NR_3COR_2$, amino-cycloalkyl, amino-cycloheteroalkyl, $NR_3$-alkoxy, $NR_3$-dioxothian, $NR_3$-heteroalkyl, amino-heteroalkyl, $NR_3$-cycloheteroalkyl, $NR_3$-cycloheteroalkyl, $NR_3$-aryl, $NR_3$- heteroaryl, $NR_3$—CO—$CF_3$, alkyl-CO—$NR_3R_4$, $NR_3$—CO-alkyl-sulfonyl-alkyl, $NR_3$—CO— cycloheteroalkyl, CO—$NR_3$-cycloalkyl, alkyl-carboxylic acid, alkoxy-heteroaryl, alkyl-phenyl, cycloheteroalkyl, amino, amino-heteroaryl, amino-phenyl, CO-alkyl, $CONR_3$-alkyl, $CH_3$, $NH_2$, alkyl-amino, pyridine, pyrazole, furan, thiophene, pyrimidine, thiazole, isothiazole, oxazole, isoxazole, piperazine, pyrrole, pyrazine, dioxane, morpholine, thiomorpholine, triazole, imidazole, alkoxy; $R_4$ is unsubstituted or substituted with one or more independent $R_5$, and is independently chosen from H, alkyl, cycloalkyl, phenyl, hydroxyl, heterocycloalkyl, cyclic amine, halogen, $CF_3$, Cl, $CONR_3R_4$, aryl, heteroaryl, O—$R_3$, O-alkyl-$R_3$, O-aryl, O-heteroaryl, N—$R_3$, N-aryl, N-heteroaryl, $NR_2R_3$, heteroalkyl, benzyl, heteroaryl benzyl ($CH_2$heteroaryl), alkenyl, alkynyl, alkyl-cycloalkyl, $CH_2$-cycloalkyl, $CH_2$—$CF_3$, hydroxyalkyl, alkyl-alkoxy, alkyl-cycloheteroalkyl, alkyl-heteroaryl, alkyl-carboxylic acid, CO—$CF_3$, alkyl-CO—O-alkyl, alkyl-CO—$NR_3R_4$, CO-alkyl-sulfonyl-alkyl, CO-cycloheteroalkyl, CO—NH-cycloalkyl, CN, alkoxy-cycloalkyl, alkoxy-cycloheteroalkyl, O-alkoxy, O-dioxothian, alkoxy, O-heteroalkyl, alkoxy-heteroalkyl, methylsulfonyl, O-cycloheteroalkyl, O-alkoxy-cycloheteroalkyl, O-alkoxy-aryl, O-heteroaryl, $NR_3COR_2$, amino-cycloalkyl, amino-cycloheteroalkyl, $NR_3$-alkoxy, $NR_3$-dioxothian, $NR_3$-heteroalkyl, amino-heteroalkyl, $NR_3$-cycloheteroalkyl, $NR_3$-cycloheteroalkyl, $NR_3$-aryl, $NR_3$-heteroaryl, $NR_3$—CO—$CF_3$, alkyl-CO—$NR_3R_4$, $NR_3$—CO-alkyl-sulfonyl-alkyl, $NR_3$—CO— cycloheteroalkyl, CO—$NR_3$-cycloalkyl, alkyl-carboxylic acid, alkoxy-heteroaryl, alkyl-phenyl, cycloheteroalkyl, amino, amino-heteroaryl, amino-phenyl, CO-alkyl, $CONR_3$-alkyl, $CH_3$, $NH_2$, alkyl-amino, pyridine, pyrazole, furan, thiophene, pyrimidine, thiazole, isothiazole, oxazole, isoxazole, piperazine, pyrrole, pyrazine, dioxane, morpholine, thiomorpholine, triazole, imidazole, alkoxy; $R_1$, when present, is substituted by one or more $R_5$, or H, alkyl, alkene, alkyne, or optionally forms a 3-8 membered ring with $X_5$; $R_2$ is substituted by one or more $R_5$, or unsubstituted and is selected from H, alkyl, alkene, alkyne, alkyl-heteroaryl, alkyl-heterocycloalkyl, alkyl-amino, or together with $R_3$ forms a 3-6 membered ring; $R_3$ is substituted by one or more $R_5$ or unsubstituted and is selected from H, alkyl, alkenyl, alkynyl, alkyl-heteroaryl, alkyl-heterocycloalkyl, alkyl-amino, or together with $R_2$ forms a ring; $R_4$ is substituted by one or more $R_5$, or unsubstituted and is selected from benzyl, methylcycloalkyl, cycloalkyl, alkyl-cycloalkyl; each $R_5$ is independent, substituted or unsubstituted, and selected from H, halogen, alkyl, cycloalkyl, cycloheteroalkyl, amino, cyclic amino, aminoalkyl, alkenyl, alkynyl, $CF_3$, alkoxy, heterocycle, phenyl, aryl, heteroaryl, amidyl; $R_6$ is independent and optionally substituted H, alkyl, cycloalkyl, alkenyl, alkynyl, alkoxy, halogen, $CH_3$, alkyl-amino, amino-alkyl, $CF_3$, hydroxyl, $NH_2$, O-alkyl, $NMe_2$, $CH_2OH$, $CH_2OMe$, $CH_2NHMe$, $CH_2NMe_2$; or a pharmaceutically acceptable salt thereof or a pharmaceutically acceptable derivative thereof; and a pharmaceutically acceptable carrier.

Also disclosed are methods for modulating Ras signaling in at least one cell comprising the step of contacting at least one cell with at least one disclosed compound in an amount effective to modulate Ras signaling in at least one cell.

Also disclosed herein are methods for modulating Ras signaling in a subject comprising the step of administering to the subject a therapeutically effective amount of at least one disclosed compound in a dosage and amount effective to modulate Ras signaling in the subject.

Also disclosed are methods for the treatment of diseases associated with dysfunctional Ras signaling or cancer associated with dysfunctional Ras signaling comprising the step of administering to the mammal at least one disclosed compound in a dosage and amount effective to treat the disorder in the mammal.

Also disclosed are methods for making a compound comprising the steps of providing a benzimidazole compound having a structure represented by a compound of the following formula:

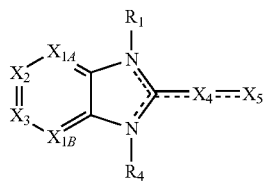

As shown in the Examples below, wherein the variables are defined herein.

Also disclosed are the products of the disclosed methods of making compounds of the present invention.

Also disclosed are methods for the manufacture of a medicament for modulating Ras signaling in a mammal comprising combining a compound of the following formula:

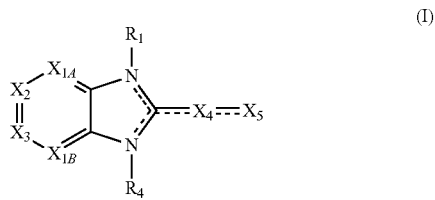

(I)

$X_{1A}$ is N, C—R; $X_{1B}$ is N, C—$R_6$; $X_2$ is N, C—$R_6$; $X_3$ is N, C—$R_6$; $X_4$ is optionally present and is substituted or unsubstituted and selected from $C_{1-6}$alkyl, $C_{1-6}$alkenyl, $C_{1-6}$alkynyl, cycloalkyl, $C_{0-6}$alkyl-cycloalkyl-$C_{0-6}$ alkyl, aryl, $C_{0-6}$ alkyl-aryl-$C_{0-6}$ alkyl, —O—, alkoxy, —O—($C_1$-$C_6$); $X_5$ is substituted or unsubstituted and selected from N, NH, —$NR_2R_3$, cyclic amine, —$NR_2$-alkyl-$NR_2R_3$; R is unsubstituted or substituted with one or more independent $R_5$, and is independently chosen from H, alkyl, cycloalkyl, phenyl, hydroxyl, heterocycloalkyl, cyclic amine, halogen, $CF_3$, Cl, $CONR_3R_4$, aryl, heteroaryl, O—$R_4$, O-alkyl-$R_4$, O-aryl, O-heteroaryl, N—$R_4$, N-aryl, N-heteroaryl, $NHR_4$, $NR_2R_3$, heteroalkyl, benzyl, heteroaryl benzyl ($CH_2$-heteroaryl), alkenyl, alkynyl, alkyl-cycloalkyl, $CH_2$-cycloalkyl, $CH_2$—$CF_3$, hydroxyalkyl, alkyl-alkoxy, alkyl-cycloheteroalkyl, alkyl-heteroaryl, alkyl-carboxylic acid, CO—$CF_3$, alkyl-CO—O-alkyl, alkyl-CO—$NR_3R_4$, CO-alkyl-sulfonyl-alkyl, CO-cycloheteroalkyl, CO—NH-cycloalkyl, CN, alkoxy-cycloalkyl, alkoxy-cycloheteroalkyl, O-alkoxy, O-dioxothian, alkoxy, O-heteroalkyl, alkoxy-heteroalkyl, methylsulfonyl, O-cycloheteroalkyl, O-alkoxy-cycloheteroalkyl, O-alkoxy-aryl, O-heteroaryl, $NR_3COR_2$, amino-cycloalkyl, amino-cycloheteroalkyl, $NR_3$-alkoxy, $NR_3$-dioxothian, $NR_3$-heteroalkyl, amino-heteroalkyl, $NR_3$-cycloheteroalkyl, $NR_3$-cycloheteroalkyl, $NR_3$-aryl, $NR_3$-heteroaryl, $NR_3$—CO—$CF_3$, alkyl-CO—$NR_3R_4$, $NR_3$—CO-alkyl-sulfonyl-alkyl, $NR_3$—CO— cycloheteroalkyl, CO—$NR_3$-cycloalkyl, alkyl-carboxylic acid, alkoxy-heteroaryl, alkyl-phenyl, amino, amino-heteroaryl, amino-phenyl, CO-alkyl, $CONR_3$-alkyl, $CH_3$, $NH_2$, alkyl-amino, pyridine, pyrazole, furan, thiophene, pyrimidine, thiazole, isothiazole, oxazole, isoxazole, piperazine, pyrrole, pyrazine, dioxane, morpholine, thiomorpholine, triazole, imidazole, alkoxy; $R_4$ is unsubstituted or substituted with one or more independent $R_5$, and is independently chosen from H, alkyl, cycloalkyl, phenyl, hydroxyl, heterocycloalkyl, cyclic amine, halogen, $CF_3$, Cl, $CONR_3R_4$, aryl, heteroaryl, O—$R_3$, O-alkyl-$R_3$, O-aryl, O-heteroaryl, N—$R_3$, N-aryl, N-heteroaryl, $NR_2R_3$, heteroalkyl, benzyl, heteroaryl benzyl ($CH_2$-heteroaryl), alkenyl, alkynyl, alkyl-cycloalkyl, $CH_2$-cycloalkyl, $CH_2$—$CF_3$, hydroxyalkyl, alkyl-alkoxy, alkyl-cycloheteroalkyl, alkyl-heteroaryl, alkyl-carboxylic acid, CO—$CF_3$, alkyl-CO—O-alkyl, alkyl-CO—$NR_3R_4$, CO-alkyl-sulfonyl-alkyl, CO-cycloheteroalkyl, CO—NH-cycloalkyl, CN, alkoxy-cycloalkyl, alkoxy-cycloheteroalkyl, O-alkoxy, O-dioxothian, alkoxy, O-heteroalkyl, alkoxy-heteroalkyl, methylsulfonyl, O-cycloheteroalkyl, O-alkoxy-cycloheteroalkyl, O-alkoxy-aryl, O-heteroaryl, $NR_3COR_2$, amino-cycloalkyl, amino-cycloheteroalkyl, $NR_3$-alkoxy, $NR_3$-dioxothian, $NR_3$-heteroalkyl, amino-heteroalkyl, $NR_3$-cycloheteroalkyl, $NR_3$-cycloheteroalkyl, $NR_3$-aryl, $NR_3$-heteroaryl, $NR_3$—CO—$CF_3$, alkyl-CO—$NR_3R_4$, $NR_3$—CO-alkyl-sulfonyl-alkyl, $NR_3$—CO— cycloheteroalkyl, CO—$NR_3$-cycloalkyl, alkyl-carboxylic acid, alkoxy-heteroaryl, alkyl-phenyl, cycloheteroalkyl, amino, amino-heteroaryl, amino-phenyl, CO-alkyl, $CONR_3$-alkyl, $CH_3$, $NH_2$, alkyl-amino, pyridine, pyrazole, furan, thiophene, pyrimidine, thiazole, isothiazole, oxazole, isoxazole, piperazine, pyrrole, pyrazine, dioxane, morpholine, thiomorpholine, triazole, imidazole, alkoxy; $R_1$, when present, is substituted by one or more $R_5$, or H, alkyl, alkene, alkyne, or optionally forms a 3-8 membered ring with $X_5$; $R_2$ is substituted by one or more $R_5$, or unsubstituted and is selected from H, alkyl, alkene, alkyne, alkyl-heteroaryl, alkyl-heterocycloalkyl, alkyl-amino, or together with $R_3$ forms a 3-6 membered ring; $R_3$ is substituted by one or more $R_5$ or unsubstituted and is selected from H, alkyl, alkenyl, alkynyl, alkyl-heteroaryl, alkyl-heterocycloalkyl, alkyl-amino, or together with $R_2$ forms a ring; $R_4$ is substituted by one or more $R_5$, or unsubstituted and is selected from benzyl, methylcycloalkyl, cycloalkyl, alkyl-cycloalkyl; each $R_5$ is independent, substituted or unsubstituted, and selected from H, halogen, alkyl, cycloalkyl, cycloheteroalkyl, amino, cyclic amino, aminoalkyl, alkenyl, alkynyl, $CF_3$, alkoxy, heterocycle, phenyl, aryl, heteroaryl, amidyl; $R_6$ is independent and optionally substituted H, alkyl, cycloalkyl, alkenyl, alkynyl, alkoxy, halogen, $CH_3$, alkyl-amino, amino-alkyl, $CF_3$, hydroxyl, $NH_2$, O-alkyl, $NMe_2$, $CH_2OH$, $CH_2OMe$, $CH_2NHMe$, $CH_2NMe_2$; or a pharmaceutically acceptable salt thereof or a pharmaceutically acceptable derivative thereof; with a pharmaceutically acceptable carrier.

Also disclosed are the products of the disclosed methods for the manufacture of medicament.

Also disclosed are uses of a compound for modulating Ras signaling in a mammal, wherein the compound has a structure represented by the following formula:

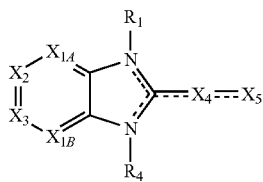

(I)

$X_{1A}$ is N, C—R; $X_{1B}$ is N, C—$R_6$; $X_2$ is N, C—$R_6$; $X_3$ is N, C—$R_6$; $X_4$ is optionally present and is substituted or unsubstituted and selected from $C_{1-6}$alkyl, $C_{1-6}$alkenyl, $C_{1-6}$alkynyl, cycloalkyl, $C_{0-6}$alkyl-cycloalkyl-$C_{0-6}$ alkyl, aryl, $C_{0-6}$ alkyl-aryl-$C_{0-6}$ alkyl, —O—, alkoxy, —O—($C_1$-$C_6$); $X_5$ is substituted or unsubstituted and selected from N, NH, —$NR_2R_3$, cyclic amine, —$NR_2$-alkyl-$NR_2R_3$; R is unsubstituted or substituted with one or more independent $R_5$, and is independently chosen from H, alkyl, cycloalkyl, phenyl, hydroxyl, heterocycloalkyl, cyclic amine, halogen, $CF_3$, Cl, $CONR_3R_4$, aryl, heteroaryl, O—$R_4$, O-alkyl-$R_4$, O-aryl, O-heteroaryl, N—$R_4$, N-aryl, N-heteroaryl, $NHR_4$, $NR_2R_3$, heteroalkyl, benzyl, heteroaryl benzyl ($CH_2$heteroaryl), alkenyl, alkynyl, alkyl-cycloalkyl, $CH_2$-cycloalkyl, $CH_2$—$CF_3$, hydroxyalkyl, alkyl-alkoxy, alkyl-cycloheteroalkyl, alkyl-heteroaryl, alkyl-carboxylic acid, CO—$CF_3$, alkyl-CO—O-alkyl, alkyl-CO—$NR_3R_4$, CO-alkyl-sulfonyl-alkyl, CO-cycloheteroalkyl, CO—NH-cycloalkyl, CN, alkoxy-cycloalkyl, alkoxy-cycloheteroalkyl, O-alkoxy, O-dioxothian, alkoxy, O-heteroalkyl, alkoxy-heteroalkyl, methylsulfonyl, O-cycloheteroalkyl, O-alkoxy-cycloheteroalkyl, O-alkoxy-aryl, O-heteroaryl, $NR_3COR_2$, amino-cycloalkyl, amino-cycloheteroalkyl, $NR_3$-alkoxy, $NR_3$-dioxothian, $NR_3$-heteroalkyl, amino-heteroalkyl, $NR_3$-cycloheteroalkyl, $NR_3$-cycloheteroalkyl, $NR_3$-aryl, $NR_3$-heteroaryl, $NR_3$—CO—$CF_3$, alkyl-CO—$NR_3R_4$, $NR_3$—CO-alkyl-sulfonyl-alkyl, $NR_3$—CO— cycloheteroalkyl, CO—$NR_3$-cycloalkyl, alkyl-carboxylic acid, alkoxy-heteroaryl, alkyl-phenyl, cycloheteroalkyl, amino, amino-heteroaryl, amino-phenyl, CO-alkyl, $CONR_3$-alkyl, $CH_3$, $NH_2$, alkyl-amino, pyridine, pyrazole, furan, thiophene, pyrimidine, thiazole, isothiazole, oxazole, isoxazole, piperazine, pyrrole, pyrazine, dioxane, morpholine, thiomorpholine, triazole, imidazole, alkoxy; $R_4$ is unsubstituted or substituted with one or more independent $R_5$, and is independently chosen from H, alkyl, cycloalkyl, phenyl, hydroxyl, heterocycloalkyl, cyclic amine, halogen, $CF_3$, Cl, $CONR_3R_4$, aryl, heteroaryl, O—$R_3$, O-alkyl-$R_3$, O-aryl, O-heteroaryl, N—$R_3$, N-aryl, N-heteroaryl, $NR_2R_3$, heteroalkyl, benzyl, heteroaryl benzyl ($CH_2$heteroaryl), alkenyl, alkynyl, alkyl-cycloalkyl, $CH_2$-cycloalkyl, $CH_2$—$CF_3$, hydroxyalkyl, alkyl-alkoxy, alkyl-cycloheteroalkyl, alkyl-heteroaryl, alkyl-carboxylic acid, CO—$CF_3$, alkyl-CO—O-alkyl, alkyl-CO—$NR_3R_4$, CO-alkyl-sulfonyl-alkyl, CO-cycloheteroalkyl, CO—NH-cycloalkyl, CN, alkoxy-cycloalkyl, alkoxy-cycloheteroalkyl, O-alkoxy, O-dioxothian, alkoxy, O-heteroalkyl, alkoxy-heteroalkyl, methylsulfonyl, O-cycloheteroalkyl, O-alkoxy-cycloheteroalkyl, O-alkoxy-aryl, O-heteroaryl, $NR_3COR_2$, amino-cycloalkyl, amino-cycloheteroalkyl, $NR_3$-alkoxy, $NR_3$-dioxothian, $NR_3$-heteroalkyl, amino-heteroalkyl, $NR_3$-cycloheteroalkyl, $NR_3$-cycloheteroalkyl, $NR_3$-aryl, $NR_3$-heteroaryl, $NR_3$—CO—$CF_3$, alkyl-CO—$NR_3R_4$, $NR_3$—CO-alkyl-sulfonyl-alkyl, $NR_3$—CO— cycloheteroalkyl, CO—$NR_3$-cycloalkyl, alkyl-carboxylic acid, alkoxy-heteroaryl, alkyl-phenyl, cycloheteroalkyl, amino, amino-heteroaryl, amino-phenyl, CO-alkyl, $CONR_3$-alkyl, $CH_3$, $NH_2$, alkyl-amino, pyridine, pyrazole, furan, thiophene, pyrimidine, thiazole, isothiazole, oxazole, isoxazole, piperazine, pyrrole, pyrazine, dioxane, morpholine, thiomorpholine, triazole, imidazole, alkoxy; $R_1$, when present, is substituted by one or more $R_5$, or H, alkyl, alkene, alkyne, or optionally forms a 3-8 membered ring with $X_5$; $R_2$ is substituted by one or more $R_5$, or unsubstituted and is selected from H, alkyl, alkene, alkyne, alkyl-heteroaryl, alkyl-heterocycloalkyl, alkyl-amino, or together with $R_3$ forms a 3-6 membered ring; $R_3$ is substituted by one or more $R_5$ or unsubstituted and is selected from H, alkyl, alkenyl, alkynyl, alkyl-heteroaryl, alkyl-heterocycloalkyl, alkyl-amino, or together with $R_2$ forms a ring; $R_4$ is substituted by one or more $R_5$, or unsubstituted and is selected from benzyl, methylcycloalkyl, cycloalkyl, alkyl-cycloalkyl; each $R_5$ is independent, substituted or unsubstituted, and selected from H, halogen, alkyl, cycloalkyl, cycloheteroalkyl, amino, cyclic amino, aminoalkyl, alkenyl, alkynyl, $CF_3$, alkoxy, heterocycle, phenyl, aryl, heteroaryl, amidyl; $R_6$ is independent and optionally substituted H, alkyl, cycloalkyl, alkenyl, alkynyl, alkoxy, halogen, $CH_3$, alkyl-amino, amino-alkyl, $CF_3$, hydroxyl, $NH_2$, O-alkyl, $NMe_2$, $CH_2OH$, $CH_2OMe$, $CH_2NHMe$, $CH_2NMe_2$; or a pharmaceutically acceptable salt thereof or a pharmaceutically acceptable derivative thereof.

Also disclosed are methods for the treatment of diseases associated with dysfunctional Ras signaling in a mammal comprising the step of co-administering to the mammal at least one compound in a dosage and amount effective to treat the dysfunction in the mammal, the composition having a structure represented by the following formula:

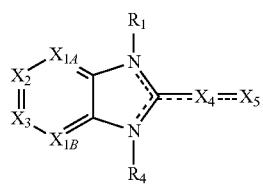

(I)

$X_{1A}$ is N, C—R; $X_{1B}$ is N, C—$R_6$; $X_2$ is N, C—$R_6$; $X_3$ is N, C—$R_6$; $X_4$ is optionally present and is substituted or unsubstituted and selected from $C_{1-6}$alkyl, $C_{1-6}$alkenyl, $C_{1-6}$alkynyl, cycloalkyl, $C_{0-6}$alkyl-cycloalkyl-$C_{0-6}$ alkyl, aryl, $C_{0-6}$ alkyl-aryl-$C_{0-6}$ alkyl, —O—, alkoxy, —O—($C_1$-$C_6$); $X_5$ is substituted or unsubstituted and selected from N, NH, —$NR_2R_3$, cyclic amine, —$NR_2$-alkyl-$NR_2R_3$; R is unsubstituted or substituted with one or more independent $R_5$, and is independently chosen from H, alkyl, cycloalkyl, phenyl, hydroxyl, heterocycloalkyl, cyclic amine, halogen, $CF_3$, Cl, $CONR_3R_4$, aryl, heteroaryl, O—$R_4$, O-alkyl-$R_4$, O-aryl, O-heteroaryl, N—$R_4$, N-aryl, N-heteroaryl, $NHR_4$, $NR_2R_3$, heteroalkyl, benzyl, heteroaryl benzyl ($CH_2$-heteroaryl), alkenyl, alkynyl, alkyl-cycloalkyl, $CH_2$-cycloalkyl, $CH_2$—$CF_3$, hydroxyalkyl, alkyl-alkoxy, alkyl-cycloheteroalkyl, alkyl-heteroaryl, alkyl-carboxylic acid, CO—$CF_3$, alkyl-CO—O-alkyl, alkyl-CO—$NR_3R_4$, CO-alkyl-sulfonyl-alkyl, CO-cycloheteroalkyl, CO—NH-cycloalkyl, CN, alkoxy-cycloalkyl, alkoxy-cycloheteroalkyl, O-alkoxy, O-dioxothian, alkoxy, O-heteroalkyl, alkoxy-heteroalkyl, methylsulfonyl, O-cycloheteroalkyl, O-alkoxy-cycloheteroalkyl, O-alkoxy-aryl, O-heteroaryl, $NR_3COR_2$, amino-cycloalkyl, amino-cycloheteroalkyl, $NR_3$-alkoxy, $NR_3$-dioxothian, $NR_3$-heteroalkyl, amino-heteroalkyl, $NR_3$-cycloheteroalkyl, $NR_3$-cycloheteroalkyl, $NR_3$-aryl, $NR_3$-heteroaryl, $NR_3$—CO—$CF_3$, alkyl-CO—$NR_3R_4$, $NR_3$—CO-alkyl-sulfonyl-alkyl, $NR_3$—CO— cycloheteroalkyl, CO—$NR_3$-cycloalkyl, alkyl-carboxylic acid, alkoxy-heteroaryl, alkyl-phenyl, cycloheteroalkyl, amino, amino-heteroaryl, amino-phenyl, CO-alkyl, $CONR_3$-alkyl, $CH_3$, $NH_2$, alkyl-amino, pyridine, pyrazole, furan, thiophene, pyrimidine, thiazole, isothiazole, oxazole, isoxazole, piperazine, pyrrole, pyrazine, dioxane, morpholine, thiomorpholine, triazole, imidazole, alkoxy; $R_4$ is unsubstituted or substituted with one or more independent $R_5$, and is independently chosen from H, alkyl, cycloalkyl, phenyl, hydroxyl, heterocycloalkyl, cyclic amine, halogen, $CF_3$, Cl, $CONR_3R_4$, aryl, heteroaryl, O—$R_3$, O-alkyl-$R_3$, O-aryl, O-heteroaryl, N—$R_3$, N-aryl, N-heteroaryl, $NR_2R_3$, heteroalkyl, benzyl, heteroaryl benzyl ($CH_2$heteroaryl), alkenyl, alkynyl, alkyl-cycloalkyl, $CH_2$-cycloalkyl, $CH_2$—$CF_3$, hydroxyalkyl, alkyl-alkoxy, alkyl-cycloheteroalkyl, alkyl-heteroaryl, alkyl-carboxylic acid, CO—$CF_3$, alkyl-CO—O-alkyl, alkyl-CO—$NR_3R_4$, CO-alkyl-sulfonyl-alkyl, CO-cycloheteroalkyl, CO—NH-cycloalkyl, CN, alkoxy-cycloalkyl, alkoxy-cycloheteroalkyl, O-alkoxy, O-dioxothian, alkoxy, O-heteroalkyl, alkoxy-heteroalkyl, methylsulfonyl, O-cycloheteroalkyl, O-alkoxy-cycloheteroalkyl, O-alkoxy-aryl, O-heteroaryl, $NR_3COR_2$, amino-cycloalkyl, amino-cycloheteroalkyl, $NR_3$-alkoxy, $NR_3$-dioxothian, $NR_3$-heteroalkyl, amino-heteroalkyl, $NR_3$-cycloheteroalkyl, $NR_3$-cycloheteroalkyl, $NR_3$-aryl, $NR_3$-heteroaryl, $NR_3$—CO—$CF_3$, alkyl-CO—$NR_3R_4$, $NR_3$—CO-alkyl-sulfonyl-alkyl, $NR_3$—CO— cycloheteroalkyl, CO—$NR_3$-cycloalkyl, alkyl-carboxylic acid, alkoxy-heteroaryl, alkyl-phenyl, cycloheteroalkyl, amino, amino-heteroaryl, amino-phenyl, CO-alkyl, $CONR_3$-alkyl, $CH_3$, $NH_2$, alkyl-amino, pyridine, pyrazole, furan, thiophene, pyrimidine, thiazole, isothiazole, oxazole, isoxazole, piperazine, pyrrole, pyrazine, dioxane, morpholine, thiomorpholine, triazole, imidazole, alkoxy; $R_1$, when present, is substituted by one or more $R_5$, or H, alkyl, alkene, alkyne, or optionally forms a 3-8 membered ring with $X_5$; $R_2$ is substituted by one or more $R_5$, or unsubstituted and is selected from H, alkyl, alkene, alkyne, alkyl-heteroaryl, alkyl-heterocycloalkyl, alkyl-amino, or together with $R_3$ forms a 3-6 membered ring; $R_3$ is substituted by one or more $R_5$ or unsubstituted and is selected from H, alkyl, alkenyl, alkynyl, alkyl-heteroaryl, alkyl-heterocycloalkyl, alkyl-amino, or together with $R_2$ forms a ring; $R_4$ is substituted by one or more $R_5$, or unsubstituted and is selected from benzyl, methylcycloalkyl, cycloalkyl, alkyl-cycloalkyl; each $R_5$ is independent, substituted or unsubstituted, and selected from H, halogen, alkyl, cycloalkyl, cycloheteroalkyl, amino, cyclic amino, aminoalkyl, alkenyl, alkynyl, $CF_3$, alkoxy, heterocycle, phenyl, aryl, heteroaryl, amidyl; $R_6$ is independent and optionally substituted H, alkyl, cycloalkyl, alkenyl, alkynyl, alkoxy, halogen, $CH_3$, alkyl-amino, amino-alkyl, $CF_3$, hydroxyl, $NH_2$, O-alkyl, $NMe_2$, $CH_2OH$, $CH_2OMe$, $CH_2NHMe$, $CH_2NMe_2$; or a pharmaceutically acceptable salt thereof or a pharmaceutically acceptable derivative thereof, with a drug having a known side-effect of increasing SOS activity.

Also disclosed are methods for the treatment of diseases associated with dysfunctional Ras signaling in a mammal comprising the step of co-administering to the mammal at least one compound in a dosage and amount effective to treat the dysfunction in the mammal, the composition having a structure represented by the following formula:

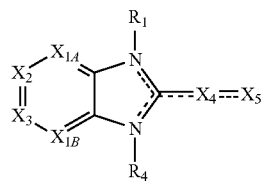

(I)

$X_{1A}$ is N, C—R; $X_{1B}$ is N, C—$R_6$; $X_2$ is N, C—$R_6$; $X_3$ is N, C—$R_6$; $X_4$ is optionally present and is substituted or unsubstituted and selected from $C_{1-6}$alkyl, $C_{1-6}$alkenyl, $C_{1-6}$alkynyl, cycloalkyl, $C_{0-6}$alkyl-cycloalkyl-$C_{0-6}$ alkyl, aryl, $C_{0-6}$ alkyl-aryl-$C_{0-6}$ alkyl, —O—, alkoxy, —O—($C_1$-$C_6$); $X_5$ is substituted or unsubstituted and selected from N, NH, —$NR_2R_3$, cyclic amine, —$NR_2$-alkyl-$NR_2R_3$; R is unsubstituted or substituted with one or more independent $R_5$, and is independently chosen from H, alkyl, cycloalkyl, phenyl, hydroxyl, heterocycloalkyl, cyclic amine, halogen, $CF_3$, Cl, $CONR_3R_4$, aryl, heteroaryl, O—$R_4$, O-alkyl-$R_4$, O-aryl, O-heteroaryl, N—$R_4$, N-aryl, N-heteroaryl, $NHR_4$, $NR_2R_3$, heteroalkyl, benzyl, heteroaryl benzyl ($CH_2$-heteroaryl), alkenyl, alkynyl, alkyl-cycloalkyl, $CH_2$-cycloalkyl, $CH_2$—$CF_3$, hydroxyalkyl, alkyl-alkoxy, alkyl-cycloheteroalkyl, alkyl-heteroaryl, alkyl-carboxylic acid, CO—$CF_3$, alkyl-CO—O-alkyl, alkyl-CO—$NR_3R_4$, CO-alkyl-sulfonyl-alkyl, CO-cycloheteroalkyl, CO—NH-cycloalkyl, CN, alkoxy-cycloalkyl, alkoxy-cycloheteroalkyl, O-alkoxy, O-dioxothian, alkoxy, O-heteroalkyl, alkoxy-heteroalkyl, methylsulfonyl, O-cycloheteroalkyl, O-alkoxy-cycloheteroalkyl, O-alkoxy-aryl, O-heteroaryl, $NR_3COR_2$, amino-cycloalkyl, amino-cycloheteroalkyl, $NR_3$-alkoxy, $NR_3$-dioxothian, $NR_3$-heteroalkyl, amino-heteroalkyl, $NR_3$-cycloheteroalkyl, $NR_3$-cycloheteroalkyl, $NR_3$-aryl, $NR_3$-heteroaryl, $NR_3$—CO—$CF_3$, alkyl-CO—$NR_3R_4$, $NR_3$—CO-alkyl-sulfonyl-alkyl, $NR_3$—CO— cycloheteroalkyl, CO—$NR_3$-cycloalkyl, alkyl-carboxylic acid, alkoxy-heteroaryl, alkyl-phenyl, cycloheteroalkyl, amino, amino-heteroaryl, amino-phenyl, CO-alkyl, $CONR_3$-alkyl, $CH_3$, $NH_2$, alkyl-amino, pyridine, pyrazole, furan, thiophene, pyrimidine, thiazole, isothiazole, oxazole, isoxazole, piperazine, pyrrole, pyrazine, dioxane, morpholine, thiomorpholine, triazole, imidazole, alkoxy; $R_4$ is unsubstituted or substituted with one or more independent $R_5$, and is independently chosen from H, alkyl, cycloalkyl, phenyl, hydroxyl, heterocycloalkyl, cyclic amine, halogen, $CF_3$, Cl, $CONR_3R_4$, aryl, heteroaryl, O—$R_3$, O-alkyl-$R_3$, O-aryl, O-heteroaryl, N—$R_3$, N-aryl, N-heteroaryl, $NR_2R_3$, heteroalkyl, benzyl, heteroaryl benzyl ($CH_2$heteroaryl), alkenyl, alkynyl, alkyl-cycloalkyl, $CH_2$-cycloalkyl, $CH_2$—$CF_3$, hydroxyalkyl, alkyl-alkoxy, alkyl-cycloheteroalkyl, alkyl-heteroaryl, alkyl-carboxylic acid, CO—$CF_3$, alkyl-CO—O-alkyl, alkyl-CO—$NR_3R_4$, CO-alkyl-sulfonyl-alkyl, CO-cycloheteroalkyl, CO—NH-cycloalkyl, CN, alkoxy-cycloalkyl, alkoxy-cycloheteroalkyl, O-alkoxy, O-dioxothian, alkoxy, O-heteroalkyl, alkoxy-heteroalkyl, methylsulfonyl, O-cycloheteroalkyl, O-alkoxy-cycloheteroalkyl, O-alkoxy-aryl, O-heteroaryl, $NR_3COR_2$, amino-cycloalkyl, amino-cycloheteroalkyl, $NR_3$-alkoxy, $NR_3$-dioxothian, $NR_3$-heteroalkyl, amino-heteroalkyl, $NR_3$-cycloheteroalkyl, $NR_3$-cycloheteroalkyl, $NR_3$-aryl, $NR_3$-heteroaryl, $NR_3$—CO—$CF_3$, alkyl-CO—$NR_3R_4$, $NR_3$—CO-alkyl-sulfonyl-alkyl, $NR_3$—CO— cycloheteroalkyl, CO—$NR_3$-cycloalkyl, alkyl-carboxylic acid, alkoxy-heteroaryl, alkyl-phenyl, cycloheteroalkyl, amino, amino-heteroaryl, amino-phenyl, CO-alkyl, $CONR_3$-alkyl, $CH_3$, $NH_2$, alkyl-amino, pyridine, pyrazole, furan, thiophene, pyrimidine, thiazole, isothiazole, oxazole, isoxazole, piperazine, pyrrole, pyrazine, dioxane, morpholine, thiomorpholine, triazole, imidazole, alkoxy; $R_1$, when present, is substituted by one or more $R_5$, or H, alkyl, alkene, alkyne, or optionally forms a 3-8 membered ring with $X_5$; $R_2$ is substituted by one or more $R_5$, or unsubstituted and is selected from H, alkyl, alkene, alkyne, alkyl-heteroaryl, alkyl-heterocycloalkyl, alkyl-amino, or together with $R_3$ forms a 3-6 membered ring; $R_3$ is substituted by one or more $R_5$ or unsubstituted and is selected from H, alkyl, alkenyl, alkynyl, alkyl-heteroaryl, alkyl-heterocycloalkyl, alkyl-amino, or together with $R_2$ forms a ring; $R_4$ is substituted by one or more $R_5$, or unsubstituted and is selected from benzyl, methylcycloalkyl, cycloalkyl, alkyl-cycloalkyl; each $R_5$ is independent, substituted or unsubstituted, and selected from H, halogen, alkyl, cycloalkyl, cycloheteroalkyl, amino, cyclic amino, aminoalkyl, alkenyl, alkynyl, $CF_3$, alkoxy, heterocycle, phenyl, aryl, heteroaryl, amidyl; $R_6$ is independent and optionally substituted H, alkyl, cycloalkyl, alkenyl, alkynyl, alkoxy, halogen, $CH_3$, alkyl-amino, amino-alkyl, $CF_3$, hydroxyl, $NH_2$, O-alkyl, $NMe_2$, $CH_2OH$, $CH_2OMe$, $CH_2NHMe$, $CH_2NMe_2$; or a pharmaceutically acceptable salt thereof or a pharmaceutically acceptable derivative thereof; with a drug having a known side-effect of modulating Ras signaling.

Also disclosed are methods for the treatment of diseases associated with dysfunctional Ras signaling in a mammal comprising the step of co-administering to the mammal at least one compound in a dosage and amount effective to treat the dysfunction in the mammal, the composition having a structure represented by the following formula:

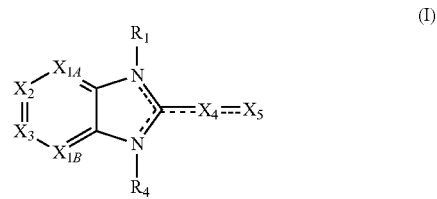

(I)

$X_{1A}$ is N, C—R; $X_{1B}$ is N, C—$R_6$; $X_2$ is N, C—$R_6$; $X_3$ is N, C—$R_6$; $X_4$ is optionally present and is substituted or unsubstituted and selected from $C_{1-6}$alkyl, $C_{1-6}$alkenyl, $C_{1-6}$alkynyl, cycloalkyl, $C_{0-6}$alkyl-cycloalkyl-$C_{0-6}$ alkyl, aryl, $C_{0-6}$ alkyl-aryl-$C_{0-6}$ alkyl, —O—, alkoxy, —O—($C_1$-$C_6$); $X_5$ is substituted or unsubstituted and selected from N, NH, —$NR_2R_3$, cyclic amine, —$NR_2$-alkyl-$NR_2R_3$; R is unsubstituted or substituted with one or more independent $R_5$, and is independently chosen from H, alkyl, cycloalkyl, phenyl, hydroxyl, heterocycloalkyl, cyclic amine, halogen, $CF_3$, Cl, $CONR_3R_4$, aryl, heteroaryl, O—$R_4$, O-alkyl-$R_4$, O-aryl, O-heteroaryl, N—$R_4$, N-aryl, N-heteroaryl, $NHR_4$, $NR_2R_3$, heteroalkyl, benzyl, heteroaryl benzyl ($CH_2$heteroaryl), alkenyl, alkynyl, alkyl-cycloalkyl, $CH_2$-cycloalkyl, $CH_2$—$CF_3$, hydroxyalkyl, alkyl-alkoxy, alkyl-cycloheteroalkyl, alkyl-heteroaryl, alkyl-carboxylic acid, CO—$CF_3$, alkyl-CO—O-alkyl, alkyl-CO—$NR_3R_4$, CO-alkyl-sulfonyl-alkyl, CO-cycloheteroalkyl, CO—NH-cycloalkyl, CN, alkoxy-cycloalkyl, alkoxy-cycloheteroalkyl, O-alkoxy, O-dioxothian, alkoxy, O-heteroalkyl, alkoxy-heteroalkyl, methylsulfonyl, O-cycloheteroalkyl, O-alkoxy-cycloheteroalkyl, O-alkoxy-aryl, O-heteroaryl, $NR_3COR_2$, amino-cycloalkyl, amino-cycloheteroalkyl, $NR_3$-alkoxy, $NR_3$-dioxothian, $NR_3$-heteroalkyl, amino-heteroalkyl, $NR_3$-cycloheteroalkyl, $NR_3$-cycloheteroalkyl, $NR_3$-aryl, $NR_3$-heteroaryl, $NR_3$—CO—$CF_3$, alkyl-CO—$NR_3R_4$, $NR_3$—CO-alkyl-sulfonyl-alkyl, $NR_3$—CO— cycloheteroalkyl, CO—$NR_3$-cycloalkyl, alkyl-carboxylic acid, alkoxy-heteroaryl, alkyl-phenyl, cycloheteroalkyl, amino, amino-heteroaryl, amino-phenyl, CO-alkyl, $CONR_3$-alkyl, $CH_3$, $NH_2$, alkyl-amino, pyridine, pyrazole, furan, thiophene, pyrimidine, thiazole, isothiazole, oxazole, isoxazole, piperazine, pyrrole, pyrazine, dioxane, morpholine, thiomorpholine, triazole, imidazole, alkoxy; $R_4$ is unsubstituted or substituted with one or more independent $R_5$, and is independently chosen from H, alkyl, cycloalkyl, phenyl, hydroxyl, heterocycloalkyl, cyclic amine, halogen, $CF_3$, Cl, $CONR_3R_4$, aryl, heteroaryl, O—$R_3$, O-alkyl-$R_3$, O-aryl, O-heteroaryl, N—$R_3$, N-aryl, N-heteroaryl, $NR_2R_3$, heteroalkyl, benzyl, heteroaryl benzyl ($CH_2$heteroaryl), alkenyl, alkynyl, alkyl-cycloalkyl, $CH_2$-cycloalkyl, $CH_2$—$CF_3$, hydroxyalkyl, alkyl-alkoxy, alkyl-cycloheteroalkyl, alkyl-heteroaryl, alkyl-carboxylic acid, CO—$CF_3$, alkyl-CO—O-alkyl, alkyl-CO—$NR_3R_4$, CO-alkyl-sulfonyl-alkyl, CO-cycloheteroalkyl, CO—NH-cycloalkyl, CN, alkoxy-cycloalkyl, alkoxy-cycloheteroalkyl, O-alkoxy, O-dioxothian, alkoxy, O-heteroalkyl, alkoxy-heteroalkyl, methylsulfonyl, O-cycloheteroalkyl, O-alkoxy-cycloheteroalkyl, O-alkoxy-aryl, O-heteroaryl, $NR_3COR_2$, amino-cycloalkyl, amino-cycloheteroalkyl, $NR_3$-alkoxy, $NR_3$-dioxothian, $NR_3$-heteroalkyl, amino-heteroalkyl, $NR_3$-cycloheteroalkyl, $NR_3$-cycloheteroalkyl, $NR_3$-aryl, $NR_3$-heteroaryl, $NR_3$—CO—$CF_3$, alkyl-CO—$NR_3R_4$, $NR_3$—CO-alkyl-sulfonyl-alkyl, $NR_3$—CO— cycloheteroalkyl, CO—$NR_3$-cycloalkyl, alkyl-carboxylic acid, alkoxy-heteroaryl, alkyl-phenyl, cycloheteroalkyl, amino, amino-heteroaryl, amino-phenyl, CO-alkyl, $CONR_3$-alkyl, $CH_3$, $NH_2$, alkyl-amino, pyridine, pyrazole, furan, thiophene, pyrimidine, thiazole, isothiazole, oxazole, isoxazole, piperazine, pyrrole, pyrazine, dioxane, morpholine, thiomorpholine, triazole, imidazole, alkoxy; $R_1$, when present, is substituted by one or more $R_5$, or H, alkyl, alkene, alkyne, or optionally forms a 3-8 membered ring with $X_5$; $R_2$ is substituted by one or more $R_5$, or unsubstituted and is selected from H, alkyl, alkene, alkyne, alkyl-heteroaryl, alkyl-heterocycloalkyl, alkyl-amino, or together with $R_3$ forms a 3-6 membered ring; $R_3$ is substituted by one or more $R_5$ or unsubstituted and is selected from H, alkyl, alkenyl, alkynyl, alkyl-heteroaryl, alkyl-heterocycloalkyl, alkyl-amino, or together with $R_2$ forms a ring; $R_4$ is substituted by one or more $R_5$, or unsubstituted and is selected from benzyl, methylcycloalkyl, cycloalkyl, alkyl-cycloalkyl; each $R_5$ is independent, substituted or unsubstituted, and selected from H, halogen, alkalkyl, cycloalkyl, cycloheteroalkyl, amino, cyclic amino, aminoalkyl, alkenyl, alkynyl, $CF_3$, alkoxy, heterocycle, phenyl, aryl, heteroaryl, amidyl; $R_6$ is independent and optionally substituted H, alkyl, cycloalkyl, alkenyl, alkynyl, alkoxy, halogen, $CH_3$, alkyl-amino, amino-alkyl, $CF_3$, hydroxyl, $NH_2$, O-alkyl, $NMe_2$, $CH_2OH$, $CH_2OMe$, $CH_2NHMe$, $CH_2NMe_2$; or a pharmaceutically acceptable salt thereof or a pharmaceutically acceptable derivative thereof, with a drug having a known side-effect of having anti-cancer activity.

Also disclosed are methods for the treatment of diseases associated with dysfunctional Ras signaling in a mammal comprising the step of co-administering to the mammal at least one compound in a dosage and amount effective to treat the dysfunction in the mammal, the composition having a structure represented by the following formula:

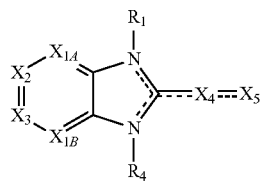

(I)

$X_{1A}$ is N, C—R; $X_{1B}$ is N, C—$R_6$; $X_2$ is N, C—$R_6$; $X_3$ is N, C—$R_6$; $X_4$ is optionally present and is substituted or unsubstituted and selected from $C_{1-6}$alkyl, $C_{1-6}$alkenyl, $C_{1-6}$alkynyl, cycloalkyl, $C_{0-6}$alkyl-cycloalkyl-$C_{0-6}$ alkyl, aryl, $C_{0-6}$ alkyl-aryl-$C_{0-6}$ alkyl, —O—, alkoxy, —O—($C_1$-$C_6$); $X_5$ is substituted or unsubstituted and selected from N, NH, —$NR_2R_3$, cyclic amine, —$NR_2$-alkyl-$NR_2R_3$; R is unsubstituted or substituted with one or more independent $R_5$, and is independently chosen from H, alkyl, cycloalkyl, phenyl, hydroxyl, heterocycloalkyl, cyclic amine, halogen, $CF_3$, Cl, $CONR_3R_4$, aryl, heteroaryl, O—$R_4$, O-alkyl-$R_4$, O-aryl, O-heteroaryl, N—$R_4$, N-aryl, N-heteroaryl, $NHR_4$, $NR_2R_3$, heteroalkyl, benzyl, heteroaryl benzyl ($CH_2$heteroaryl), alkenyl, alkynyl, alkyl-cycloalkyl, $CH_2$-cycloalkyl, $CH_2$—$CF_3$, hydroxyalkyl, alkyl-alkoxy, alkyl-cycloheteroalkyl, alkyl-heteroaryl, alkyl-carboxylic acid, CO—$CF_3$, alkyl-CO—O-alkyl, alkyl-CO—$NR_3R_4$, CO-alkyl-sulfonyl-alkyl, CO-cycloheteroalkyl, CO—NH-cycloalkyl, CN, alkoxy-cycloalkyl, alkoxy-cycloheteroalkyl, O-alkoxy, O-dioxothian, alkoxy, O-heteroalkyl, alkoxy-heteroalkyl, methylsulfonyl, O-cycloheteroalkyl, O-alkoxy-cycloheteroalkyl, O-alkoxy-aryl, O-heteroaryl, $NR_3COR_2$, amino-cycloalkyl, amino-cycloheteroalkyl, $NR_3$-alkoxy, $NR_3$-dioxothian, $NR_3$-heteroalkyl, amino-heteroalkyl, $NR_3$-cycloheteroalkyl, $NR_3$-cycloheteroalkyl, $NR_3$-aryl, $NR_3$-heteroaryl, $NR_3$—CO—$CF_3$, alkyl-CO—$NR_3R_4$, $NR_3$—CO-alkyl-sulfonyl-alkyl, $NR_3$—CO— cycloheteroalkyl, CO—$NR_3$-cycloalkyl, alkyl-carboxylic acid, alkoxy-heteroaryl, alkyl-phenyl, cycloheteroalkyl, amino, amino-heteroaryl, amino-phenyl, CO-alkyl, $CONR_3$-alkyl, $CH_3$, $NH_2$, alkyl-amino, pyridine, pyrazole, furan, thiophene, pyrimidine, thiazole, isothiazole, oxazole, isoxazole, piperazine, pyrrole, pyrazine, dioxane, morpholine, thiomorpholine, triazole, imidazole, alkoxy; $R_A$ is unsubstituted or substituted with one or more independent $R_5$, and is independently chosen from H, alkyl, cycloalkyl, phenyl, hydroxyl, heterocycloalkyl, cyclic amine, halogen, $CF_3$, Cl, $CONR_3R_4$, aryl, heteroaryl, O—$R_3$, O-alkyl-$R_3$, O-aryl, O-heteroaryl, N—$R_3$, N-aryl, N-heteroaryl, $NR_2R_3$, heteroalkyl, benzyl, heteroaryl benzyl ($CH_2$heteroaryl), alkenyl, alkynyl, alkyl-cycloalkyl, $CH_2$-cycloalkyl, $CH_2$—$CF_3$, hydroxyalkyl, alkyl-alkoxy, alkyl-cycloheteroalkyl, alkyl-heteroaryl, alkyl-carboxylic acid, CO—$CF_3$, alkyl-CO—O-alkyl, alkyl-CO—$NR_3R_4$, CO-alkyl-sulfonyl-alkyl, CO-cycloheteroalkyl, CO—NH-cycloalkyl, CN, alkoxy-cycloalkyl, alkoxy-cycloheteroalkyl, O-alkoxy, O-dioxothian, alkoxy, O-heteroalkyl, alkoxy-heteroalkyl, methylsulfonyl, O-cycloheteroalkyl, O-alkoxy-cycloheteroalkyl, O-alkoxy-aryl, O-heteroaryl, $NR_3COR_2$, amino-cycloalkyl, amino-cycloheteroalkyl, $NR_3$-alkoxy, $NR_3$-dioxothian, $NR_3$-heteroalkyl, amino-heteroalkyl, $NR_3$-cycloheteroalkyl, $NR_3$-cycloheteroalkyl, $NR_3$-aryl, $NR_3$-heteroaryl, $NR_3$—CO—$CF_3$, alkyl-CO—$NR_3R_4$, $NR_3$—CO-alkyl-sulfonyl-alkyl, $NR_3$—CO— cycloheteroalkyl, CO—$NR_3$-cycloalkyl, alkyl-carboxylic acid, alkoxy-heteroaryl, alkyl-phenyl, cycloheteroalkyl, amino, amino-heteroaryl, amino-phenyl, CO-alkyl, $CONR_3$-alkyl, $CH_3$, $NH_2$, alkyl-amino, pyridine, pyrazole, furan, thiophene, pyrimidine, thiazole, isothiazole, oxazole, isoxazole, piperazine, pyrrole, pyrazine, dioxane, morpholine, thiomorpholine, triazole, imidazole, alkoxy; $R_1$, when present, is substituted by one or more $R_5$, or H, alkyl, alkene, alkyne, or optionally forms a 3-8 membered ring with $X_5$; $R_2$ is substituted by one or more $R_5$, or unsubstituted and is selected from H, alkyl, alkene, alkyne, alkyl-heteroaryl, alkyl-heterocycloalkyl, alkyl-amino, or together with $R_3$ forms a 3-6 membered ring; $R_3$ is substituted by one or more $R_5$ or unsubstituted and is selected from H, alkyl, alkenyl, alkynyl, alkyl-heteroaryl, alkyl-heterocycloalkyl, alkyl-amino, or together with $R_2$ forms a ring; $R_4$ is substituted by one or more $R_5$, or unsubstituted and is selected from benzyl, methylcycloalkyl, cycloalkyl, alkyl-cycloalkyl; each $R_5$ is independent, substituted or unsubstituted, and selected from H, halogen, alkyl, cycloalkyl, cycloheteroalkyl, amino, cyclic amino, aminoalkyl, alkenyl, alkynyl, $CF_3$, alkoxy, heterocycle, phenyl, aryl, heteroaryl, amidyl; $R_6$ is independent and optionally substituted H, alkyl, cycloalkyl, alkenyl, alkynyl, alkoxy, halogen, $CH_3$, alkyl-amino, amino-alkyl, $CF_3$, hydroxyl, $NH_2$, O-alkyl, $NMe_2$, $CH_2OH$, $CH_2OMe$, $CH_2NHMe$, $CH_2NMe_2$; or a pharmaceutically acceptable salt thereof or a pharmaceutically acceptable derivative thereof, with a drug known to treat cancer.

BRIEF DESCRIPTION OF THE FIGURE

FIG. 1 shows effects on Ras signaling for example compounds.

DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which need to be independently confirmed.

Definitions

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance can or cannot occur, and that the description includes instances where said event or circumstance occurs and instances where it does not.

As used herein the term "modulate" can refer to enhancement of activity or inhibition of activity.

As used herein, the term "subject" refers to a target of administration. The subject of the herein disclosed methods can be a mammal. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with a disorder treatable by a modulation of Ras signaling" means having been subjected to a physical examination by a person of skill, for example, a physician, and found to have a condition that can be diagnosed or treated by a compound or composition that can modulate Ras signaling. Such a diagnosis can be in reference to a disorder, such as cancer, and the like, as discussed herein.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

The term "cancer" refers to disorders characterized by cellular proliferation, evasion of programmed cell death, altered cellular metabolism, induction of angiogenesis, enhancement of cellular invasion and metastasis, alterations to tumor suppressor genes causing a reduction in activity, alterations to oncogenes casing enhancement of activity, or evasion of immunological destruction. Cancer can refer to a tissue or organ type and can also spread from one tissue or organ to another tissue type or organ. Cancer can occur in any cell of any type including but not limited to breast, prostate, skin, lung, pancreatic, stomach, brain, kidney, uterine, ovarian, testicular, endothelial, colon, bladder, bone as well as cells of the blood to produce various forms of leukemia.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O-units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents. Unless otherwise specified, the substituents are all independent from one another.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, optionally substituted alkyl, cycloalkyl, alkoxy, amino, ether, halide, hydroxy, nitro, silyl, thioether, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbomyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, optionally substituted alkyl, cycloalkyl, alkoxy, amino, ether, halide, hydroxy, nitro, silyl, sulfo-oxo, or thiol as described herein.

The terms "alkoxy" and "alkoxyl" as used herein to refer to an alkyl or cycloalkyl group bonded through an ether linkage; that is, an "alkoxy" group can be defined as $-OA^1$ where $A^1$ is alkyl or cycloalkyl as defined above. "Alkoxy" also includes polymers of alkoxy groups as just described; that is, an alkoxy can be a polyether such as $-OA^1-OA^2$ or $-OA^1-(OA^2)_a-OA^3$, where "a" is an integer of from 1 to 200 and $A^1$, $A^2$, and $A^3$ are alkyl and/or cycloalkyl groups.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by a formula —C(O)H. Throughout this specification "C(O)" is a short hand notation for a carbonyl group, i.e., C=O.

The terms "amine" or "amino" as used herein are represented by a formula $NA^1A^2A^3$, where $A^1$, $A^2$, and $A^3$ can be, independently, hydrogen or optionally substituted alkyl, cycloalkyl, alkenyl, cycloalkenyl, alkynyl, cycloalkynyl, aryl, or heteroaryl group as described herein.

The term "heterocycle," as used herein refers to single and multi-cyclic aromatic or non-aromatic ring systems in which at least one of the ring members is other than carbon. Heterocycle includes pyrimidine, furan, thiophene, pyrrole, isoxazole, isothiazole, pyrazole, oxazole, thiazole, imidazole, oxazole, oxadiazole including, for example, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridine, pyridazine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, imidazothiadiazole, imidazooxadiazole, imidazothiazole, thiazolotriazole, and the like.

The term "hydroxyl" as used herein is represented by a formula —OH.

The term "thiol" as used herein is represented by a formula —SH.

The term "thioester" as used herein is represented by a formula —S—CH$_3$.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compounds disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

In some aspects, a structure of a compound can be represented by a formula:

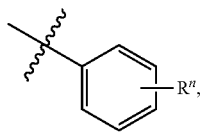

which is understood to be equivalent to a formula:

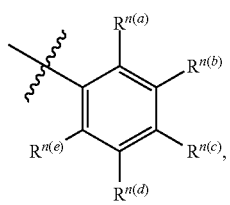

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance. Likewise, when a group R is defined as four substituents, R is understood to represent four independent substituents, $R^a$, $R^b$, $R^c$, and $R^d$. Unless indicated to the contrary, the substituents are not limited to any particular order or arrangement.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

Compounds

In one aspect, the invention relates to compounds, or pharmaceutically acceptable derivatives thereof, useful as modulators of Ras signaling. In general, it is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

In one aspect the invention relates to compounds having a structure represented by formula:

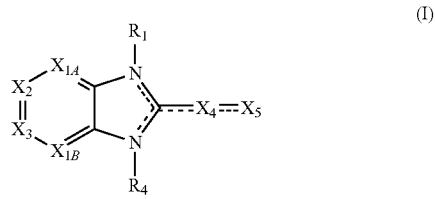

$X_{1A}$ is N, C—R;
$X_{1B}$ is N, C—$R_6$;
$X_2$ is N, C—$R_6$;
$X_3$ is N, C—$R_6$;
$X_4$ is optionally present and is substituted or unsubstituted and selected from $C_{1-6}$alkyl, $C_{1-6}$alkenyl, $C_{1-6}$alkynyl, cycloalkyl, $C_{0-6}$alkyl-cycloalkyl-$C_{0-6}$ alkyl, aryl, $C_{0-6}$ alkyl-aryl-$C_{0-6}$ alkyl, —O—, alkoxy, —O—($C_1$-$C_6$);
$X_5$ is substituted or unsubstituted and selected from N, NH, —$NR_2R_3$, cyclic amine, —$NR_2$-alkyl-$NR_2R_3$;
R is unsubstituted or substituted with one or more independent $R_5$, and is independently chosen from H, alkyl, cycloalkyl, phenyl, hydroxyl, heterocycloalkyl, cyclic amine, halogen, $CF_3$, Cl, $CONR_3R_4$, aryl, heteroaryl, O—$R_4$, O-alkyl-$R_4$, O-aryl, O-heteroaryl, N—$R_4$, N-aryl, N-heteroaryl, $NHR_4$, $NR_2R_3$, heteroalkyl, benzyl, heteroaryl benzyl ($CH_2$_heteroaryl), alkenyl, alkynyl, alkyl-cycloalkyl, $CH_2$-cycloalkyl, $CH_2$—$CF_3$, hydroxyalkyl, alkyl-alkoxy, alkyl-cycloheteroalkyl, alkyl-heteroaryl, alkyl-carboxylic acid, CO—$CF_3$, alkyl-CO—O-alkyl, alkyl-CO—$NR_3R_4$, CO-alkyl-sulfonyl-alkyl, CO-cycloheteroalkyl, CO—NH-cycloalkyl, CN, alkoxy-cycloalkyl, alkoxy-cycloheteroalkyl, O-alkoxy, O-dioxothian, alkoxy, O-heteroalkyl, alkoxy-heteroalkyl, methylsulfonyl, O-cycloheteroalkyl, O-alkoxy-cycloheteroalkyl, O-alkoxy-aryl, O-heteroaryl, $NR_3COR_2$, amino-cycloalkyl, amino-cycloheteroalkyl, $NR_3$-alkoxy, $NR_3$-dioxothian, $NR_3$-heteroalkyl, amino-heteroalkyl, $NR_3$-cycloheteroalkyl, $NR_3$-cycloheteroalkyl, $NR_3$-aryl, $NR_3$-heteroaryl, $NR_3$—CO—$CF_3$, alkyl-CO—$NR_3R_4$, $NR_3$—CO-alkyl-sulfonyl-alkyl, $NR_3$—CO-cycloheteroalkyl, CO—$NR_3$-cycloalkyl, alkyl-carboxylic acid, alkoxy-heteroaryl, alkyl-phenyl, cycloheteroalkyl, amino, amino-heteroaryl, amino-phenyl, CO-alkyl, $CONR_3$-alkyl, $CH_3$, $NH_2$, alkyl-amino, pyridine, pyrazole, furan, thiophene, pyrimidine, thiazole, isothiazole, oxazole, isoxazole, piperazine, pyrrole, pyrazine, dioxane, morpholine, thiomorpholine, triazole, imidazole, alkoxy;
$R_4$ is unsubstituted or substituted with one or more independent $R_5$, and is independently chosen from H, alkyl, cycloalkyl, phenyl, hydroxyl, heterocycloalkyl, cyclic amine, halogen, $CF_3$, Cl, $CONR_3R_4$, aryl, heteroaryl, O—$R_3$, O-alkyl-$R_3$, O-aryl, O-heteroaryl, N—$R_3$, N-aryl, N-heteroaryl, $NR_2R_3$, heteroalkyl, benzyl, heteroaryl benzyl ($CH_2$_heteroaryl), alkenyl, alkynyl, alkyl-cycloalkyl, $CH_2$-cycloalkyl, $CH_2$—$CF_3$, hydroxyalkyl, alkyl-alkoxy, alkyl-cycloheteroalkyl, alkyl-heteroaryl, alkyl-carboxylic acid, CO—CF$_3$, alkyl-CO—O-alkyl, alkyl-CO—NR$_3$R$_4$, CO-alkyl-sulfonyl-alkyl, CO-cycloheteroalkyl, CO—NH-cycloalkyl, CN, alkoxy-cycloalkyl, alkoxy-cycloheteroalkyl, O-alkoxy, O-dioxothian, alkoxy, O-heteroalkyl, alkoxy-heteroalkyl, methylsulfonyl, O-cycloheteroalkyl, O-alkoxy-cycloheteroalkyl, O-alkoxy-aryl, O-heteroaryl, NR$_3$COR$_2$, amino-cycloalkyl, amino-cycloheteroalkyl, NR$_3$-alkoxy, NR$_3$-dioxothian, NR$_3$-heteroalkyl, amino-heteroalkyl, NR$_3$-cycloheteroalkyl, NR$_3$-cycloheteroalkyl, NR$_3$-aryl, NR$_3$-heteroaryl, NR$_3$—CO—CF$_3$, alkyl-CO—NR$_3$R$_4$, NR$_3$—CO-alkyl-sulfonyl-alkyl, NR$_3$—CO-cycloheteroalkyl, CO—NR$_3$-cycloalkyl, alkyl-carboxylic acid, alkoxy-heteroaryl, alkyl-phenyl, cycloheteroalkyl, amino, amino-heteroaryl, amino-phenyl, CO-alkyl, CONR$_3$-alkyl, CH$_3$, NH$_2$, alkyl-amino, pyridine, pyrazole, furan, thiophene, pyrimidine, thiazole, isothiazole, oxazole, isoxazole, piperazine, pyrrole, pyrazine, dioxane, morpholine, thiomorpholine, triazole, imidazole, alkoxy;

R$_1$, when present, is substituted by one or more R$_5$, or H, alkyl, alkene, alkyne, or optionally forms a 3-8 membered ring with X$_5$;

R$_2$ is substituted by one or more R$_5$, or unsubstituted and is selected from H, alkyl, alkene, alkyne, alkyl-heteroaryl, alkyl-heterocycloalkyl, alkyl-amino, or together with R$_3$ forms a 3-6 membered ring;

R$_3$ is substituted by one or more R$_5$ or unsubstituted and is selected from H, alkyl, alkenyl, alkynyl, alkyl-heteroaryl, alkyl-heterocycloalkyl, alkyl-amino, or together with R$_2$ forms a ring;

R$_4$ is substituted by one or more R$_5$, or unsubstituted and is selected from benzyl, methylcycloalkyl, cycloalkyl, alkyl-cycloalkyl;

each R$_5$ is independent, substituted or unsubstituted, and selected from H, halogen, alkyl, cycloalkyl, cycloheteroalkyl, amino, cyclic amino, aminoalkyl, alkenyl, alkynyl, CF$_3$, alkoxy, heterocycle, phenyl, aryl, heteroaryl, amidyl;

R$_6$ is independent and optionally substituted H, alkyl, cycloalkyl, alkenyl, alkynyl, alkoxy, halogen, CH$_3$, alkyl-amino, amino-alkyl, CF$_3$, hydroxyl, NH$_2$, O-alkyl, NMe$_2$, CH$_2$OH, CH$_2$OMe, CH—$_2$NHMe, CH$_2$NMe$_2$;

or a pharmaceutically acceptable salt thereof or a pharmaceutically acceptable derivative thereof.

Also disclosed are compounds of the following formula:

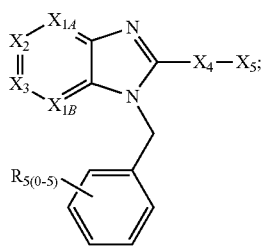

wherein each R$_5$ is independent, substituted or unsubstituted, and selected from H, halogen, alkyl, cycloalkyl, cycloheteroalkyl, amino, cyclic amino, aminoalkyl, alkenyl, alkynyl, CF$_3$, alkoxy, heterocycle, phenyl, aryl, heteroaryl, amidyl;

or a pharmaceutically acceptable salt thereof or a pharmaceutically acceptable derivative thereof.

Also disclosed are compounds wherein R$_5$ is halogen, alkyl, alkenyl, alkynyl, cycloalkyl, O-alkyl, or CH$_3$.

Also disclosed are compounds of the following formula:

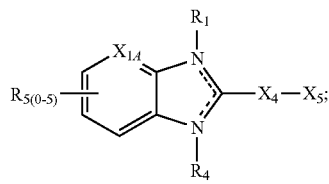

wherein each R$_5$ is independent, substituted or unsubstituted, and selected from H, halogen, alkyl, cycloalkyl, cycloheteroalkyl, amino, cyclic amino, aminoalkyl, alkenyl, alkynyl, CF$_3$, alkoxy, heterocycle, phenyl, aryl, heteroaryl, amidyl;

or a pharmaceutically acceptable salt thereof or a pharmaceutically acceptable derivative thereof.

Also disclosed are compounds wherein R$_5$ is halogen or CH$_3$.

Also disclosed are compounds wherein X$_{1A}$ is C—R; wherein R is of the following formula:

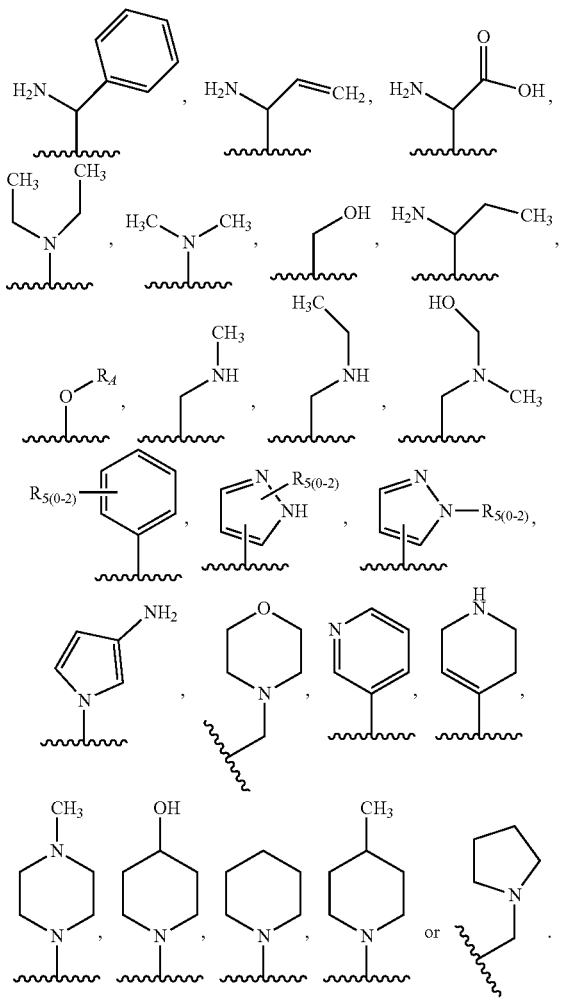

wherein each R$_5$ is independent, substituted or unsubstituted, and selected from H, halogen, alkyl, cycloalkyl, cycloheteroalkyl, amino, cyclic amino, aminoalkyl, alkenyl, alkynyl, CF$_3$, alkoxy, heterocycle, phenyl, aryl, heteroaryl, amidyl;

or a pharmaceutically acceptable salt thereof or a pharmaceutically acceptable derivative thereof.

Also disclosed are compounds wherein $R_6$ is H, halogen, or $C_{1-6}$ alkyl.

Also disclosed are compounds wherein $X_{1B}$ is C—R6; and $R_6$ is halogen, $C_1$-$C_3$ alkyl, hydroxyl, or $CF_3$.

Also disclosed are compounds wherein

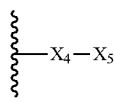

is:

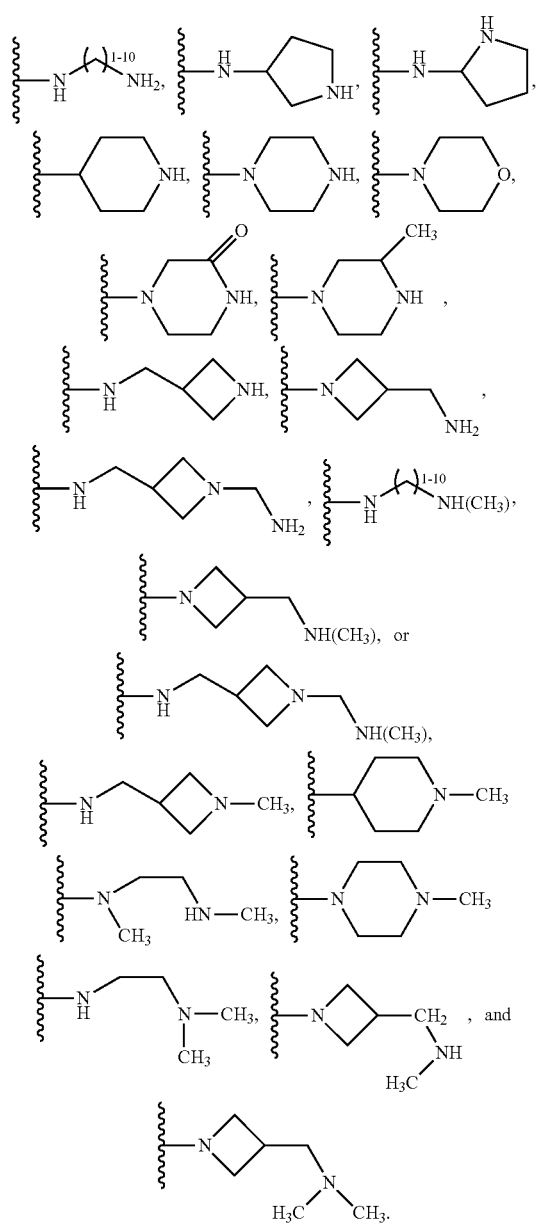

Also disclosed are compounds wherein $X_4$ and $X_5$ together form piperazine, piperadine, amino-piperadine, amino-pyrrolidine, alkyl-$NR_2R_3$, cyclobenzene-$NR_2R_3$, aminoalkyl, azetidine, azetidine-alkylamino, pyrrolidine, morpholino.

Also disclosed are compounds wherein $R_2$ is selected from H, alkyl, alkyl-heterocycloalkyl, alkyl-azetidine, alkyl-amino.

Also disclosed are compounds wherein $R_3$ is selected from H, alkyl, alkyl-heterocycloalkyl, alkyl-azetidine, alkyl-amino.

Also disclosed are compounds wherein $R_5$ is independently selected from H, halogen, alkyl, $CH_3$, alkene, heteroaryl, amino-alkyl, alkoxy. Also disclosed are compounds wherein $R_5$ is piperazine, or piperidine.

Also disclosed are compounds wherein $R_1$ and $X_5$ further cyclize form a 6-membered ring containing one or two nitrogen ring members.

Also disclosed are compounds wherein $R_4$ is halo-substituted benzyl, methyl-substituted benzyl, or halogen and methyl-substituted benzyl.

Also disclosed are compounds wherein $X_{1A}$ is C—R, and R is chosen from:

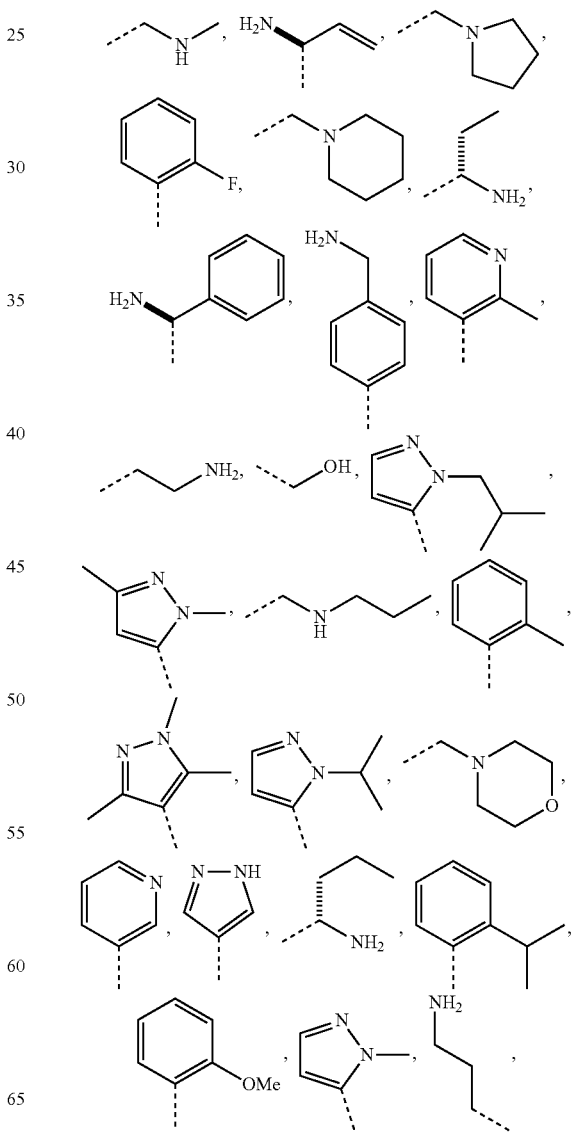

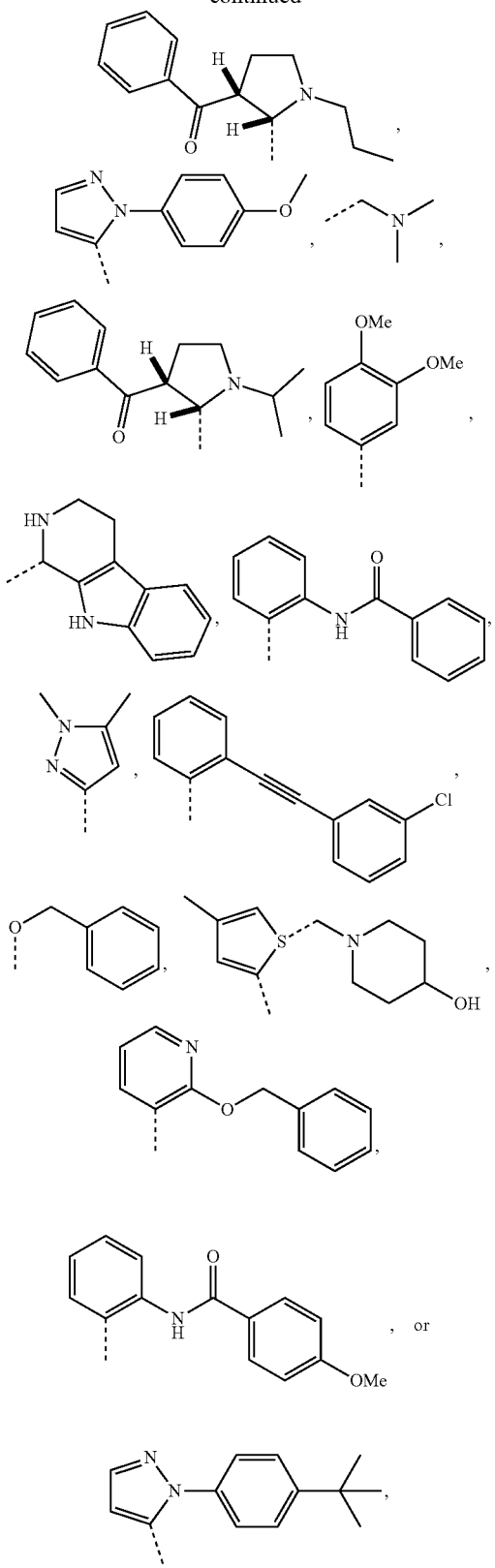

and stereoisomers thereof.

Another embodiment of the present invention is compounds of the following formula (I):

wherein
X$_{1A}$ is N, C—R;
X$_{1B}$ is N, C—R$_6$;
X$_2$ is N, C—R$_6$;
X$_3$ is N, C—R$_6$;
X$_4$ is optionally present and is substituted or unsubstituted and selected from C$_{1-6}$alkyl, C$_{1-6}$alkenyl, C$_{1-6}$alkynyl, cycloalkyl, C$_{0-6}$alkyl-cycloalkyl-C$_{0-6}$ alkyl, aryl, C$_{0-6}$ alkyl-aryl-C$_{0-6}$ alkyl, —O—, alkoxy, —O—(C$_1$-C$_6$);
X$_5$ is substituted or unsubstituted and selected from N, NH, —NR$_2$R$_3$, cyclic amine, —NR$_2$-alkyl-NR$_2$R$_3$;
R is unsubstituted or substituted with one or more independent R$_5$, and is independently chosen from H, alkyl, cycloalkyl, phenyl, hydroxyl, heterocycloalkyl, cyclic amine, halogen, CF$_3$, Cl, CONR$_3$R$_4$, aryl, heteroaryl, O—R$_4$, O-alkyl-R$_4$, O-aryl, O-heteroaryl, N—R$_4$, N-aryl, N-heteroaryl, NHR$_4$, NR$_2$R$_3$, heteroalkyl, benzyl, heteroaryl benzyl (CH$_2$-heteroaryl), alkenyl, alkynyl, alkyl-cycloalkyl, CH$_2$-cycloalkyl, CH$_2$—CF$_3$, hydroxyalkyl, alkyl-alkoxy, alkyl-cycloheteroalkyl, alkyl-heteroaryl, alkyl-carboxylic acid, CO—CF$_3$, alkyl-CO—O-alkyl, alkyl-CO—NR$_3$R$_4$, CO-alkyl-sulfonyl-alkyl, CO-cycloheteroalkyl, CO—NH-cycloalkyl, CN, alkoxy-cycloalkyl, alkoxy-cycloheteroalkyl, O-alkoxy, O-dioxothian, alkoxy, O-heteroalkyl, alkoxy-heteroalkyl, methylsulfonyl, O-cycloheteroalkyl, O-alkoxy-cycloheteroalkyl, O-alkoxy-aryl, O-heteroaryl, NR$_3$COR$_2$, amino-cycloalkyl, amino-cycloheteroalkyl, NR$_3$-alkoxy, NR$_3$-dioxothian, NR$_3$-heteroalkyl, amino-heteroalkyl, NR$_3$-cycloheteroalkyl, NR$_3$-cycloheteroalkyl, NR$_3$-aryl, NR$_3$-heteroaryl, NR$_3$—CO—CF$_3$, alkyl-CO—NR$_3$R$_4$, NR$_3$—CO-alkyl-sulfonyl-alkyl, NR$_3$—CO-cycloheteroalkyl, CO—NR$_3$-cycloalkyl, alkyl-carboxylic acid, alkoxy-heteroaryl, alkyl-phenyl, cycloheteroalkyl, amino, amino-heteroaryl, amino-phenyl, CO-alkyl, CONR$_3$-alkyl, CH$_3$, NH$_2$, alkyl-amino, pyridine, pyrazole, furan, thiophene, pyrimidine, thiazole, isothiazole, oxazole, isoxazole, piperazine, pyrrole, pyrazine, dioxane, morpholine, thiomorpholine, triazole, imidazole, alkoxy;
R$_A$ is unsubstituted or substituted with one or more independent R$_5$, and is independently chosen from H, alkyl, cycloalkyl, phenyl, hydroxyl, heterocycloalkyl, cyclic amine, halogen, CF$_3$, Cl, CONR$_3$R$_4$, aryl, heteroaryl, O—R$_3$, O-alkyl-R$_3$, O-aryl, O-heteroaryl, N—R$_3$, N-aryl, N-heteroaryl, NR$_2$R$_3$, heteroalkyl, benzyl, heteroaryl benzyl (CH$_2$_heteroaryl), alkenyl, alkynyl, alkyl-cycloalkyl, CH$_2$-cycloalkyl, CH$_2$—CF$_3$, hydroxyalkyl, alkyl-alkoxy, alkyl-cycloheteroalkyl, alkyl-heteroaryl, alkyl-carboxylic acid, CO—CF$_3$, alkyl-CO—O-alkyl, alkyl-CO—NR$_3$R$_4$, CO-alkyl-sulfonyl-alkyl, CO-cycloheteroalkyl, CO—NH-cycloalkyl, CN, alkoxy-cycloalkyl, alkoxy-cycloheteroalkyl, O-alkoxy, O-dioxothian, alkoxy, O-heteroalkyl, alkoxy-heteroalkyl, methylsulfonyl, O-cycloheteroalkyl, O-alkoxy-cycloheteroalkyl, O-alkoxy-aryl, O-heteroaryl, NR$_3$COR$_2$, amino-cycloalkyl, amino-cycloheteroalkyl, NR$_3$-alkoxy, NR$_3$-dioxothian, NR$_3$-heteroalkyl, amino-heteroalkyl, NR$_3$-cycloheteroalkyl, NR$_3$-cycloheteroalkyl, NR$_3$-aryl, NR$_3$-heteroaryl, NR$_3$—CO—CF$_3$, alkyl-CO—NR$_3$R$_4$, NR$_3$—CO-alkyl-sulfonyl-alkyl, NR$_3$—CO-cycloheteroalkyl, CO—NR$_3$-cycloalkyl, alkyl-carboxylic acid, alkoxy-heteroaryl, alkyl-phenyl, cycloheteroalkyl, amino, amino-heteroaryl, amino-phenyl, CO-alkyl, CONR$_3$-alkyl, CH$_3$, NH$_2$, alkyl-amino, pyridine, pyrazole, furan, thiophene, pyrimidine, thiazole, isothiazole, oxazole, isoxazole, piperazine, pyrrole, pyrazine, dioxane, morpholine, thiomorpholine, triazole, imidazole, alkoxy;

R$_1$, when present, is substituted by one or more R$_5$, or H, alkyl, alkene, alkyne, or optionally forms a 3-8 membered ring with X$_5$;

R$_2$ is substituted by one or more R$_5$, or unsubstituted and is selected from H, alkyl, alkene, alkyne, alkyl-heteroaryl, alkyl-heterocycloalkyl, alkyl-amino, or together with R$_3$ forms a 3-6 membered ring;

R$_3$ is substituted by one or more R$_5$ or unsubstituted and is selected from H, alkyl, alkenyl, alkynyl, alkyl-heteroaryl, alkyl-heterocycloalkyl, alkyl-amino, or together with R$_2$ forms a ring;

R$_4$ is substituted by one or more R$_5$, or unsubstituted and is selected from benzyl, methylcycloalkyl, cycloalkyl, alkyl-cycloalkyl;

each R$_5$ is independent, substituted or unsubstituted, and selected from H, halogen, alkyl, cycloalkyl, cycloheteroalkyl, amino, cyclic amino, aminoalkyl, alkenyl, alkynyl, CF$_3$, alkoxy, heterocycle, phenyl, aryl, heteroaryl, amidyl;

R$_6$ is independent and optionally substituted H, alkyl, cycloalkyl, alkenyl, alkynyl, alkoxy, halogen, CH$_3$, alkyl-amino, amino-alkyl, CF$_3$, hydroxyl, NH$_2$, O-alkyl, NMe$_2$, CH$_2$OH, CH$_2$OMe, CH—$_2$NHMe, CH$_2$NMe$_2$;

X$_6$ is chosen from:

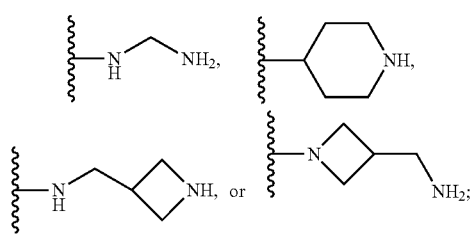

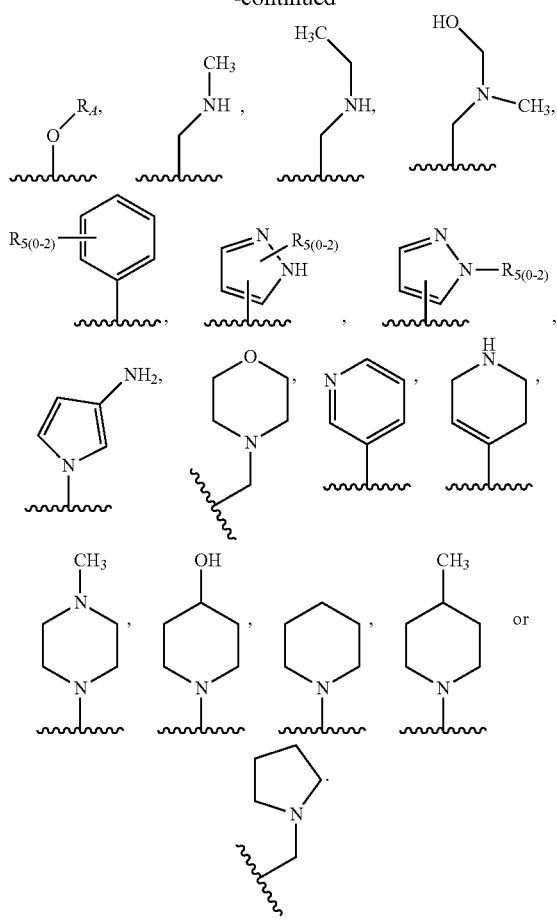

or a pharmaceutically acceptable salt thereof or a pharmaceutically acceptable derivative thereof.

Also disclosed are compounds wherein X$_{1,4}$ is C—R; wherein R is of the following formula:

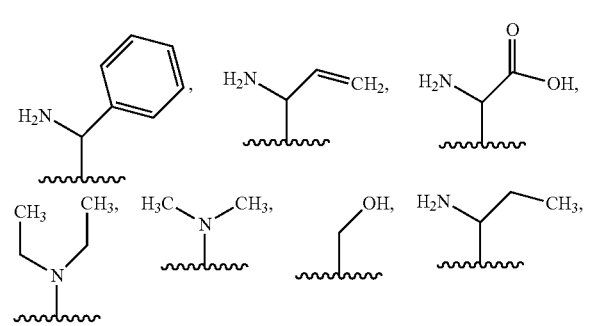

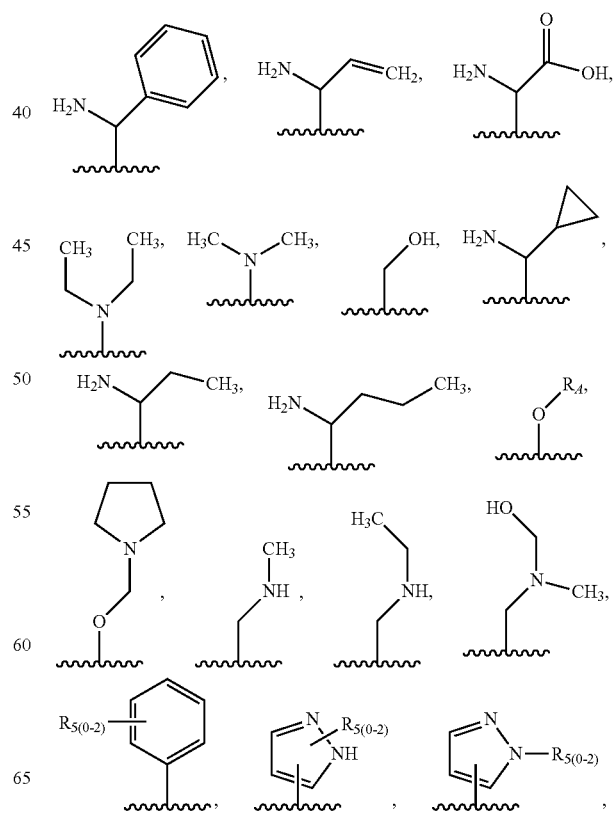

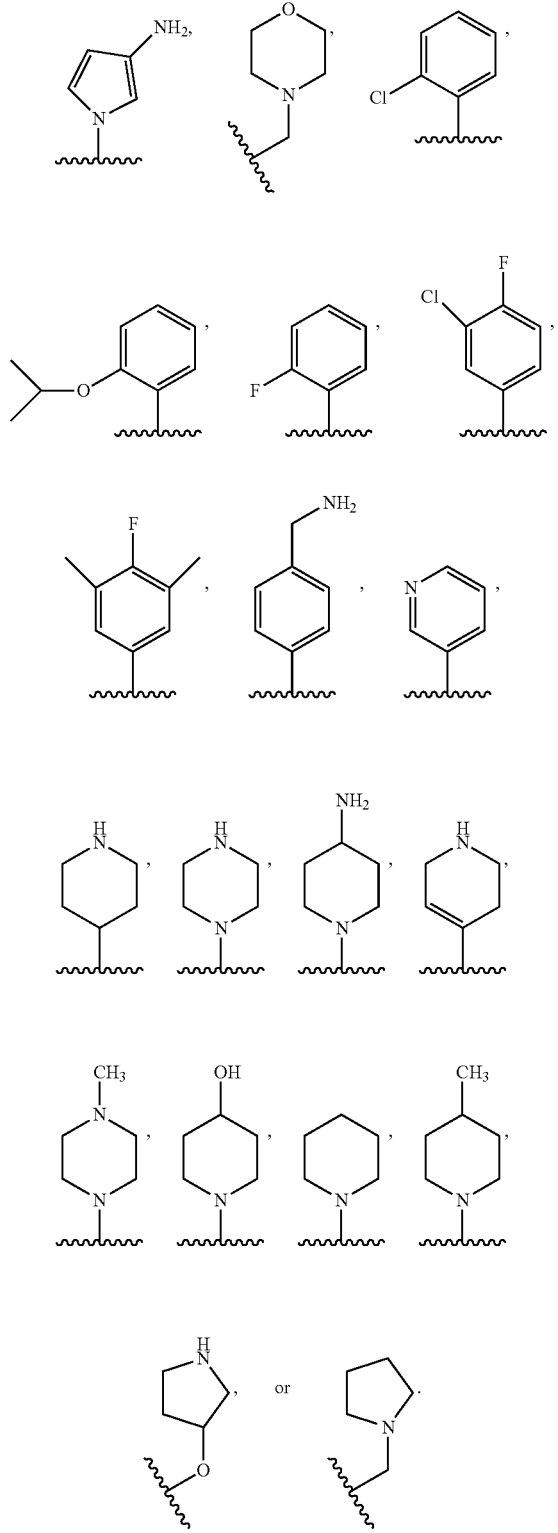
wherein R₅ is independently H, halogen, alkyl, aminoalkyl, o-alkyl;
or a pharmaceutically acceptable salt thereof or a pharmaceutically acceptable derivative thereof.
Embodiments of the present invention include the following compounds:
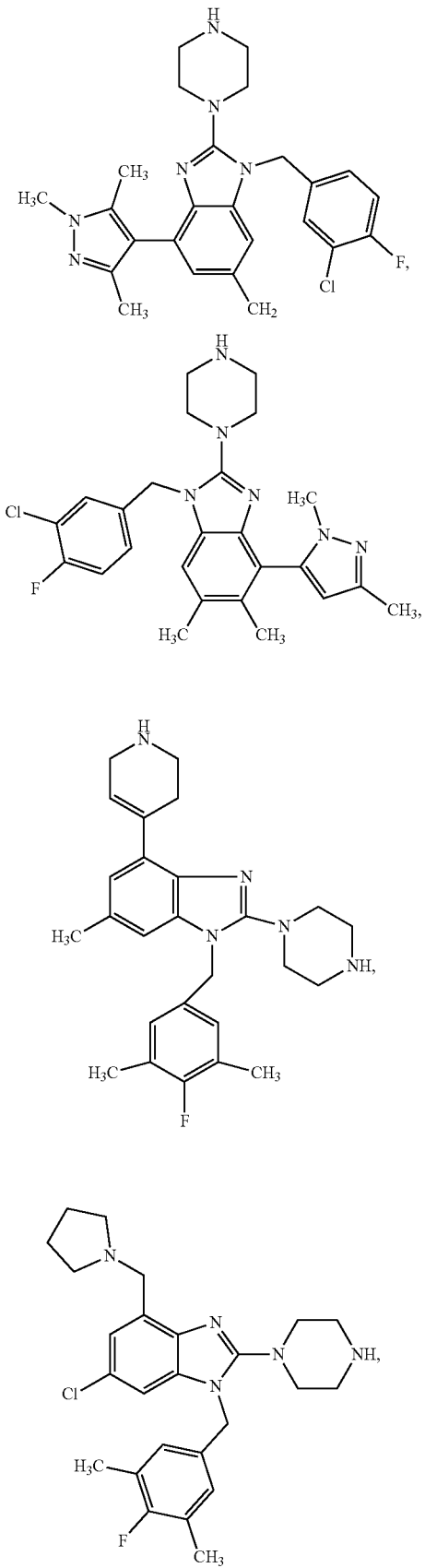

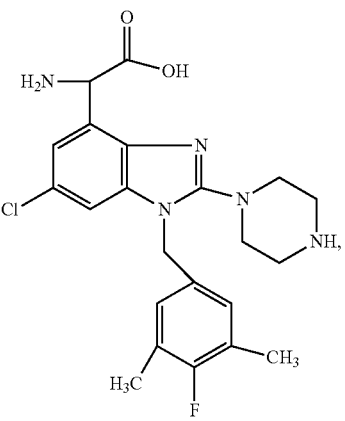
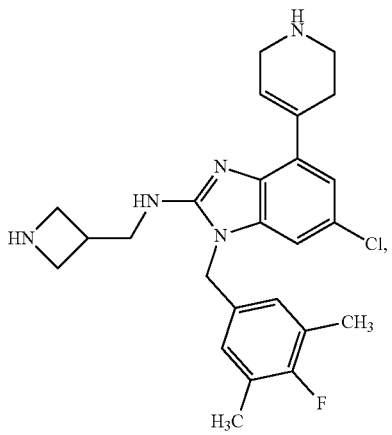 [SMILES: Cc1cc(Cn2c(NCC3CNC3)nc3c(C4=CCNCC4)cc(Cl)cc32)cc(C)c1F]
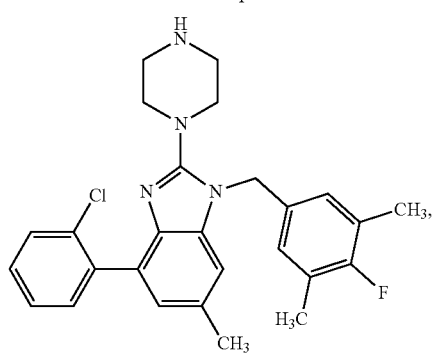
Embodiments of the present invention also include the following compounds:
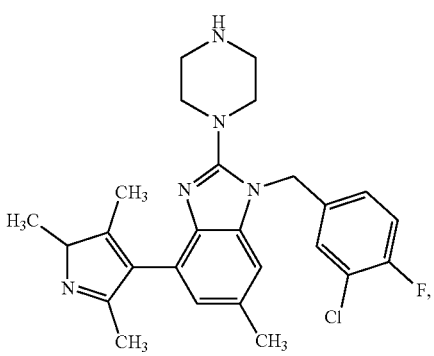
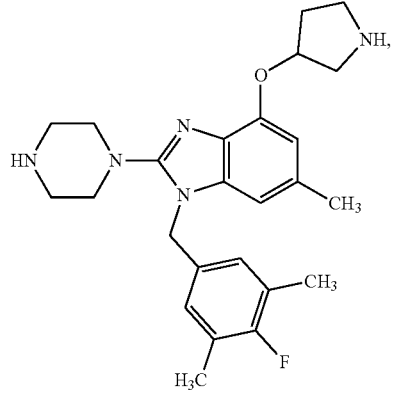
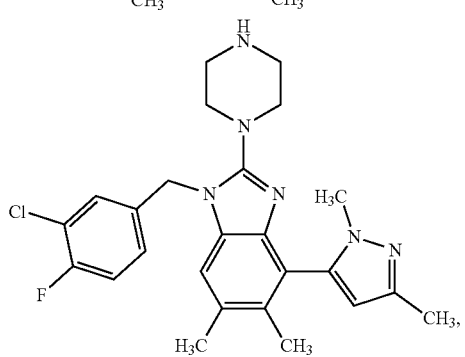
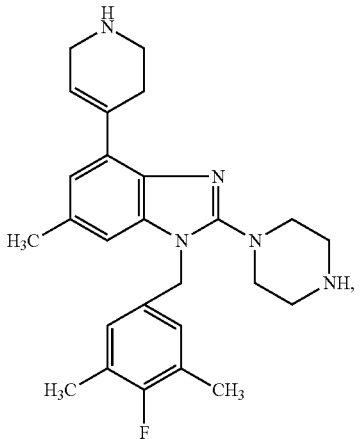

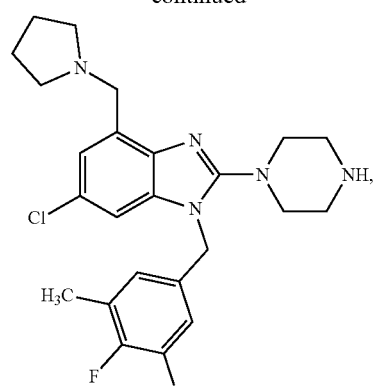
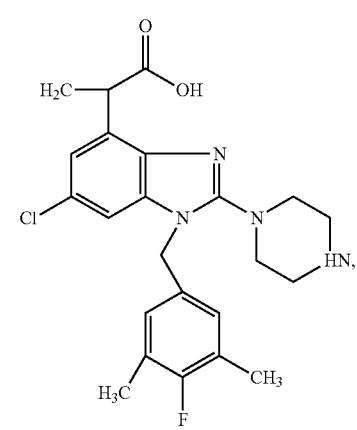
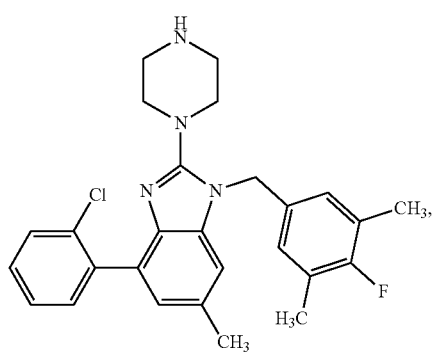
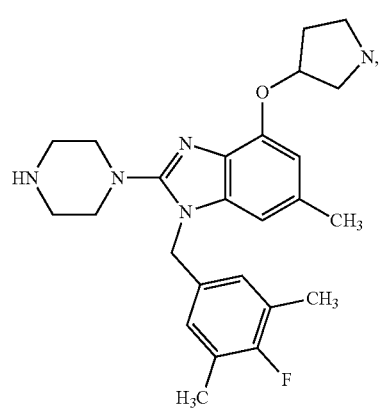
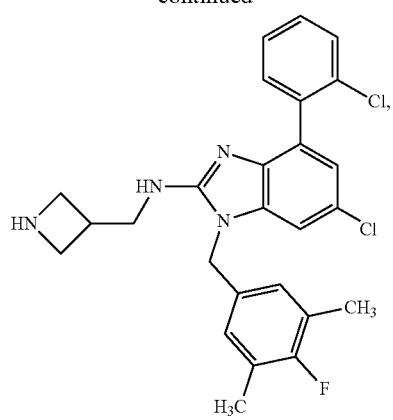
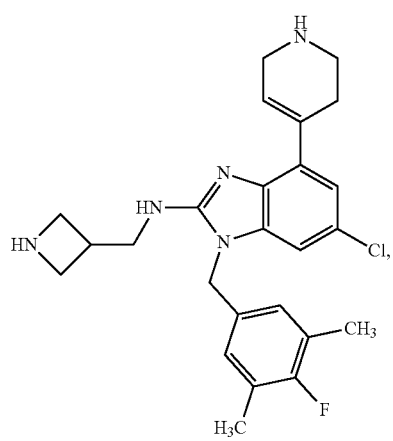 [SMILES: Cc1cc(Cn2c(NCC3CNC3)nc3c(C4=CCNCC4)cc(Cl)cc32)cc(C)c1F]
Embodiments of the present invention also include the following compounds:
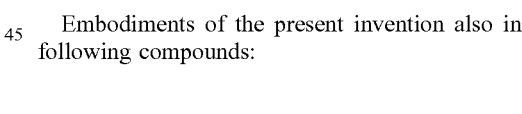

41
-continued
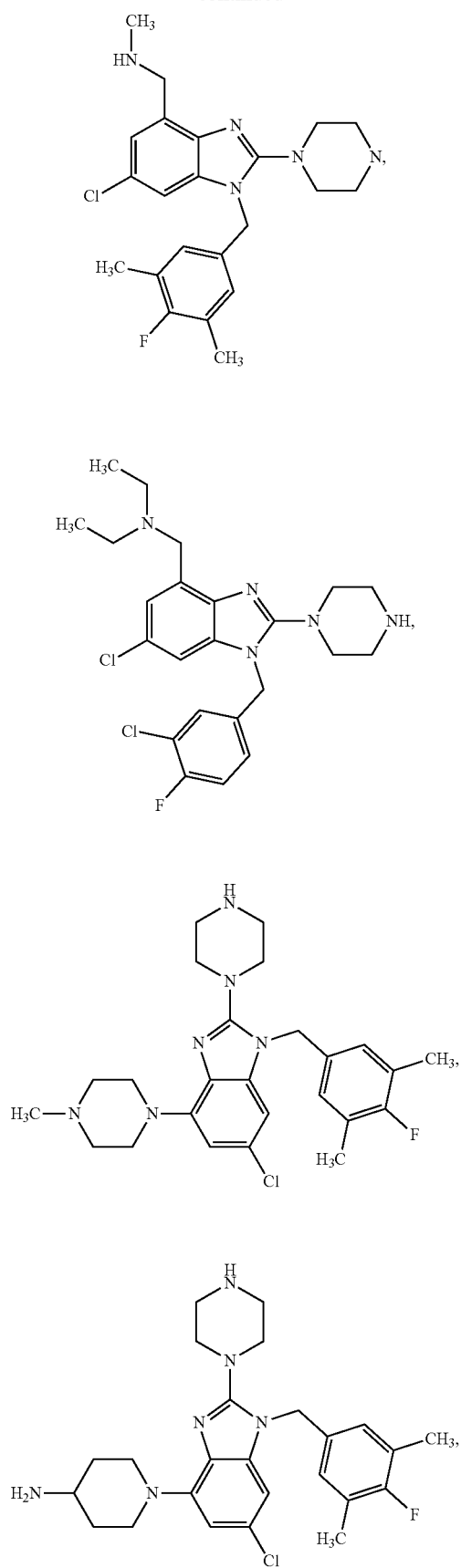
42
-continued
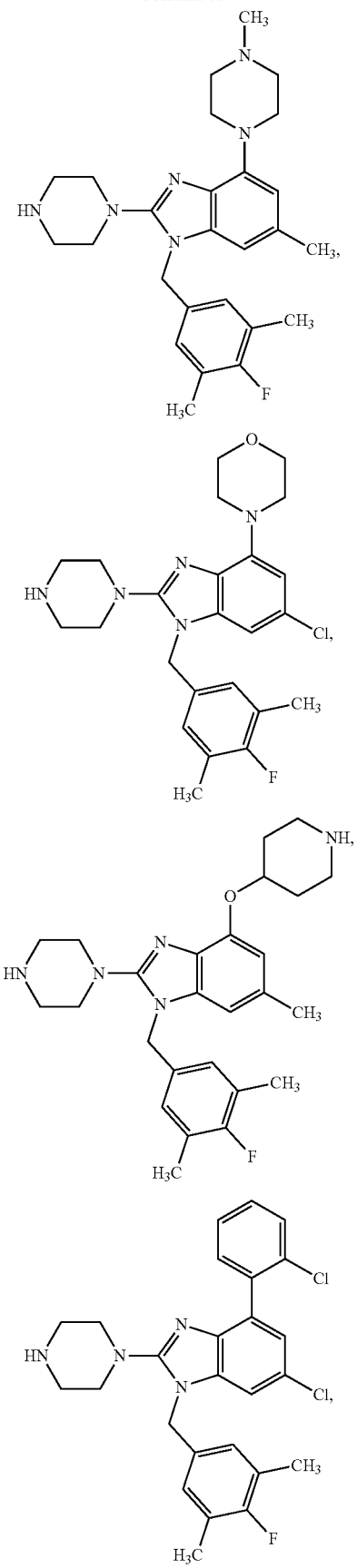

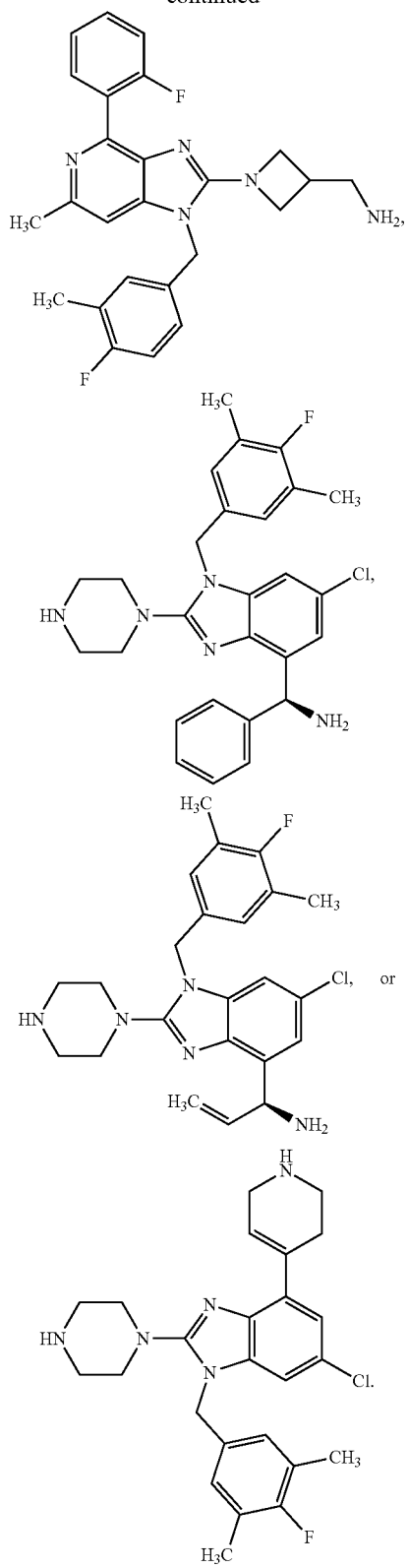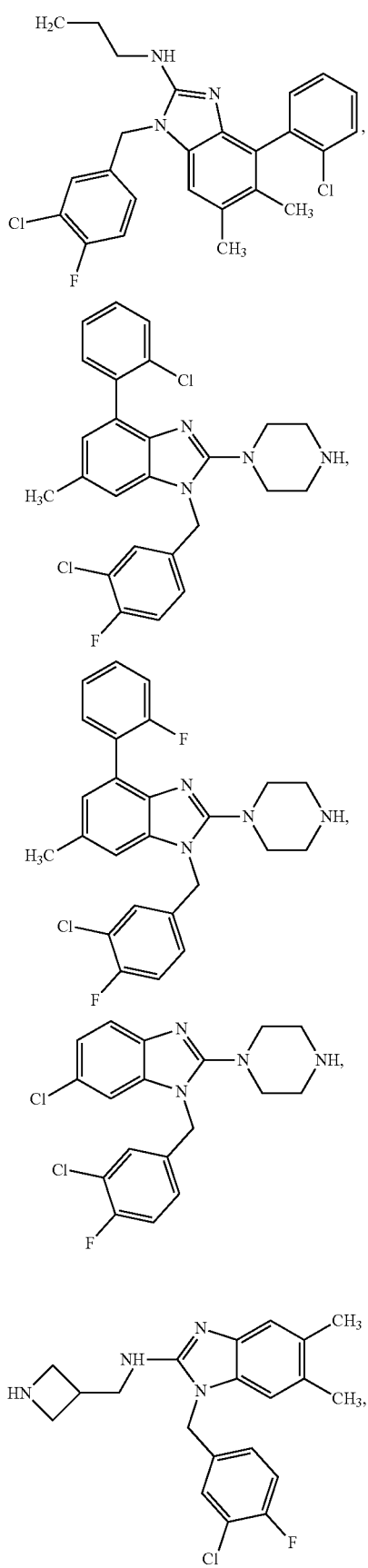
Embodiments of the present invention also include the following compounds:

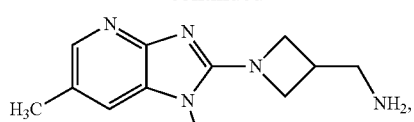
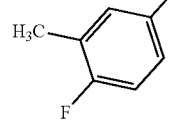
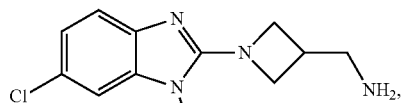
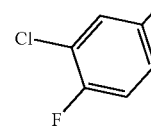
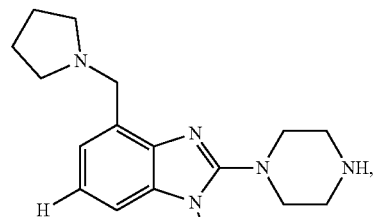
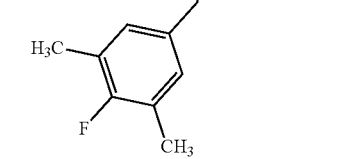
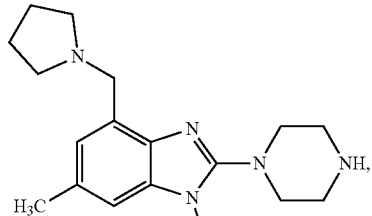
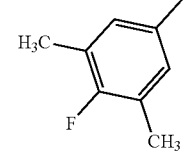
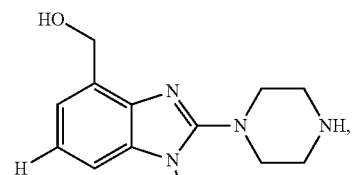
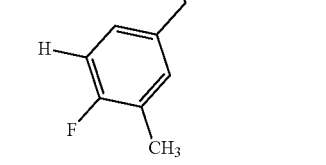
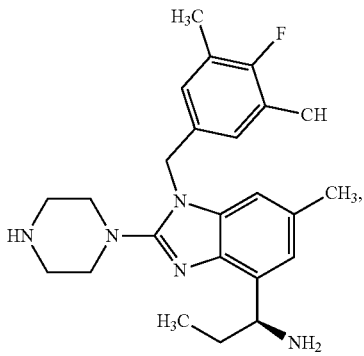
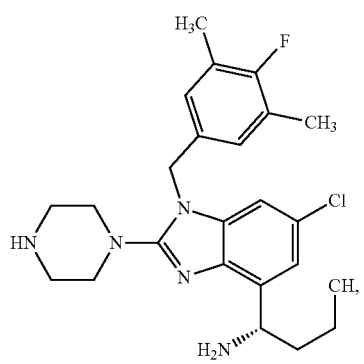
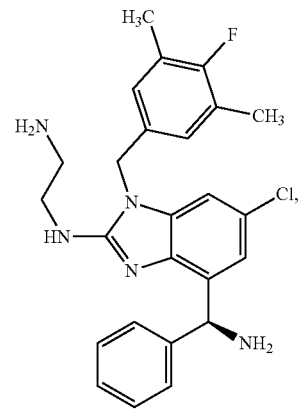
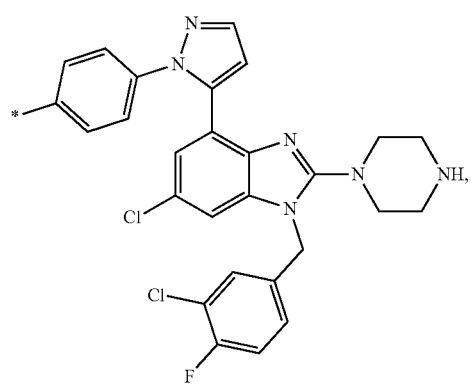

47
-continued
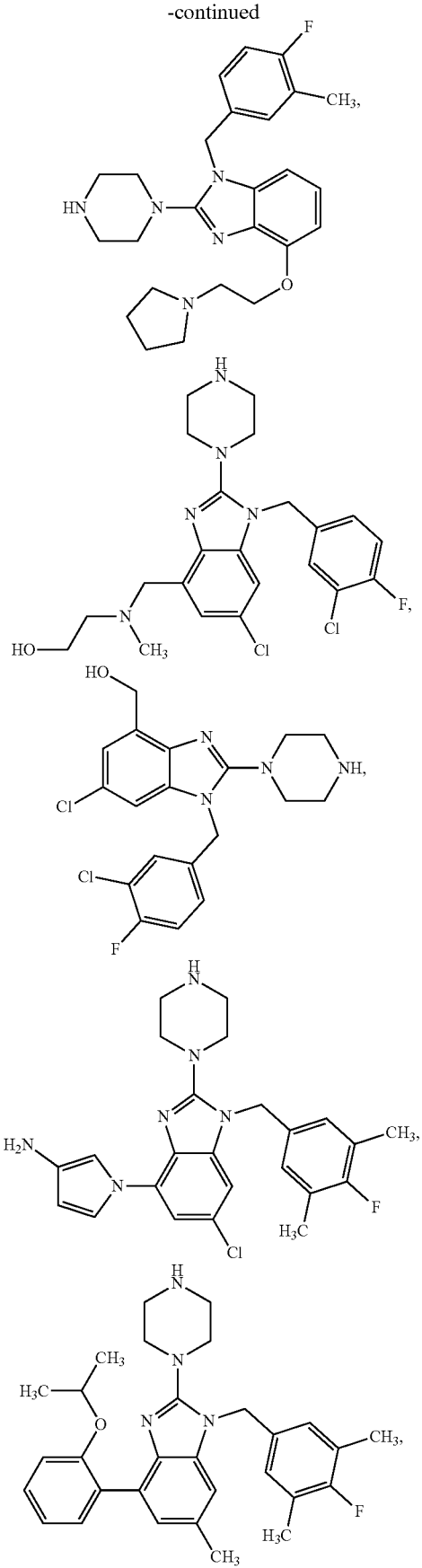
48
-continued
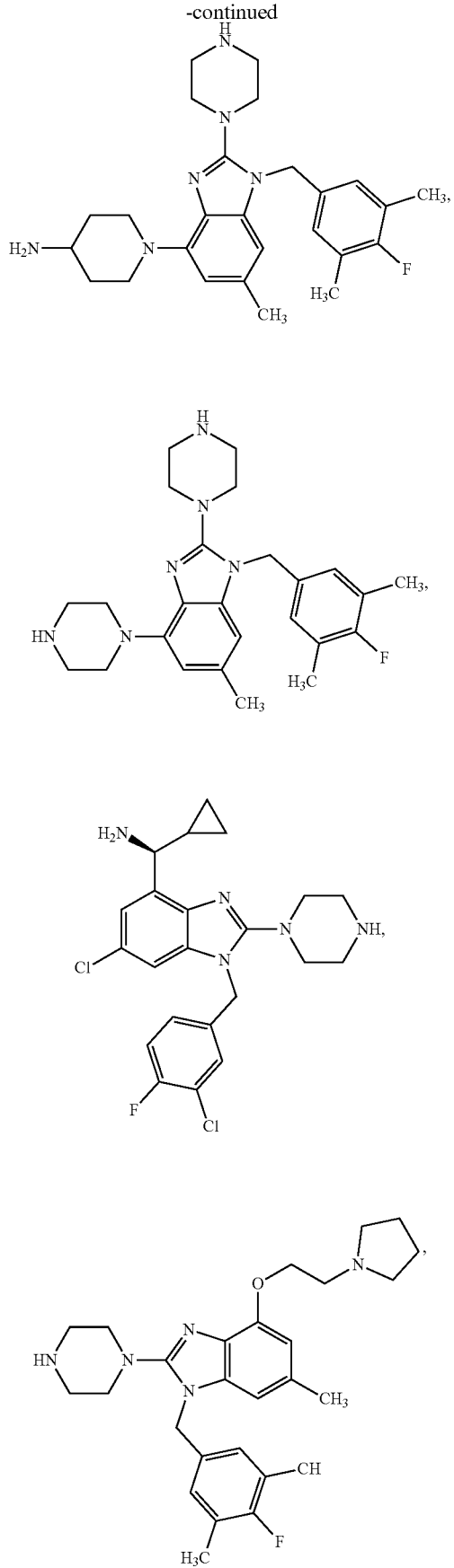

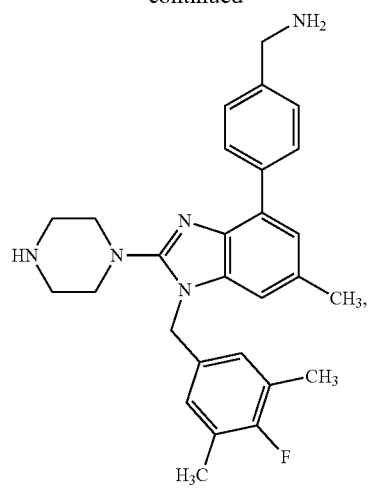
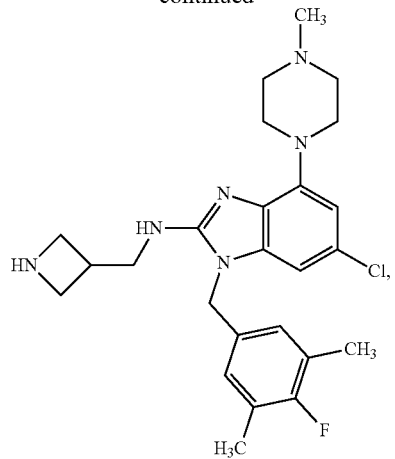
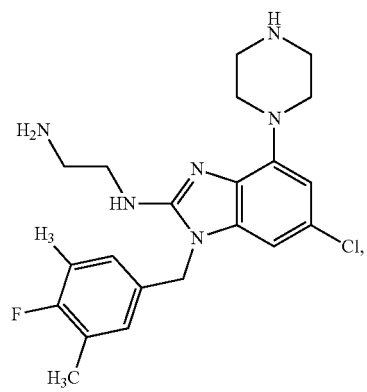
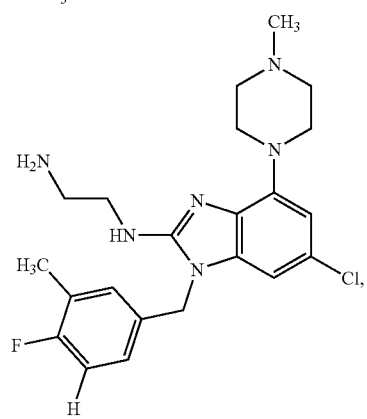
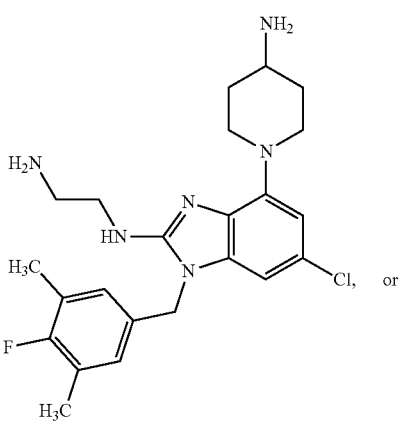

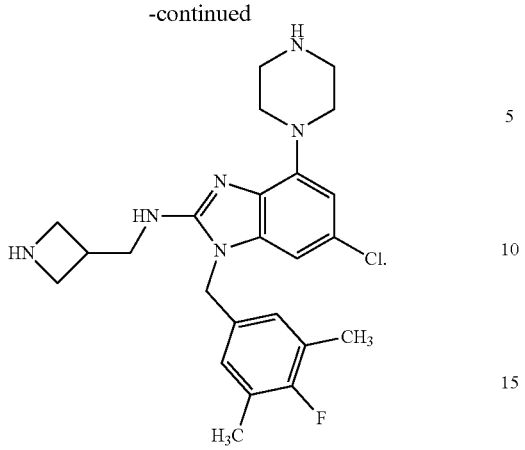
Embodiments of the present invention also include the following compounds:
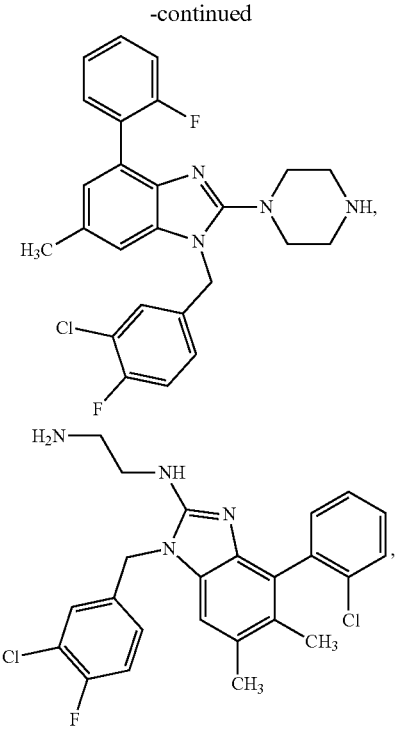
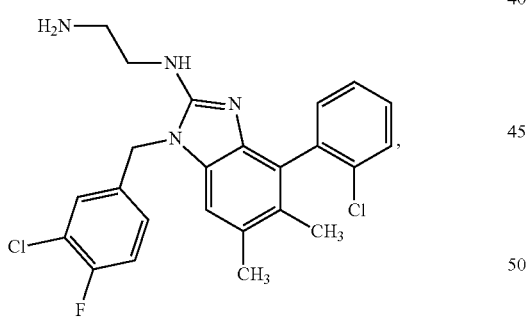
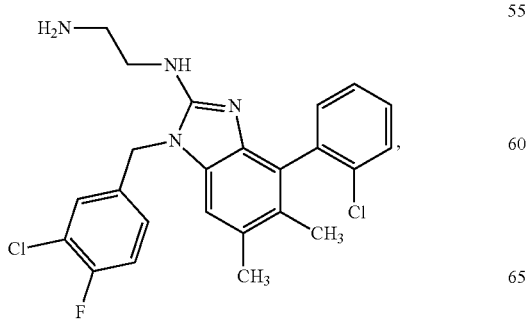
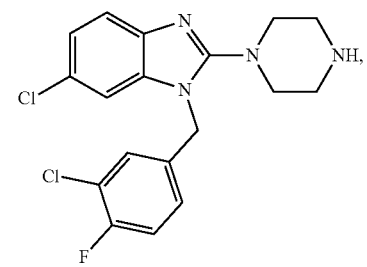
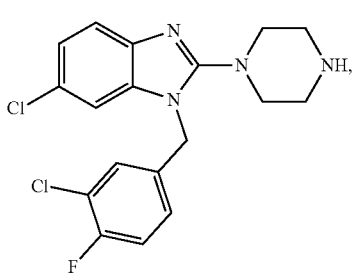

-continued
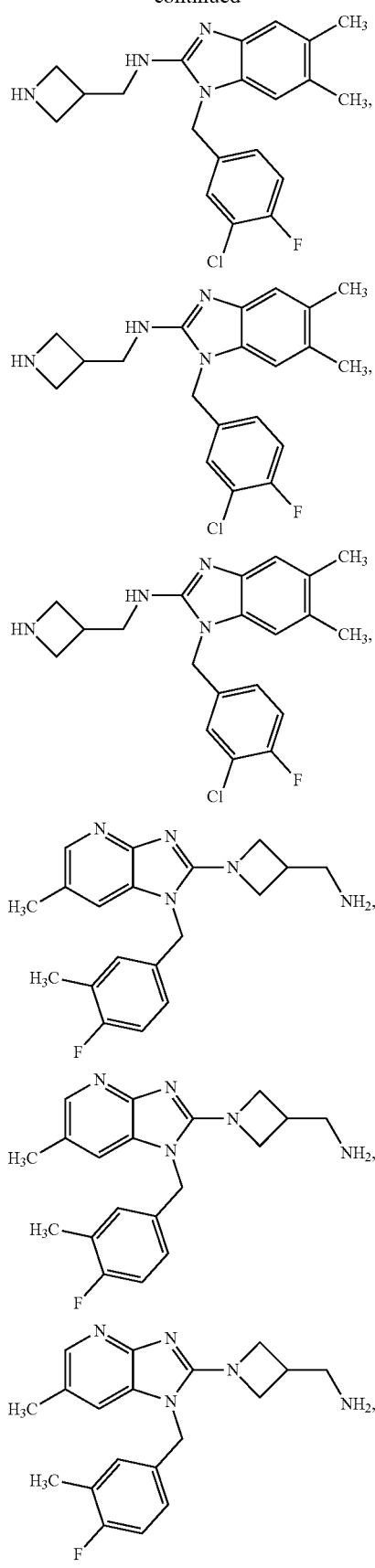
-continued
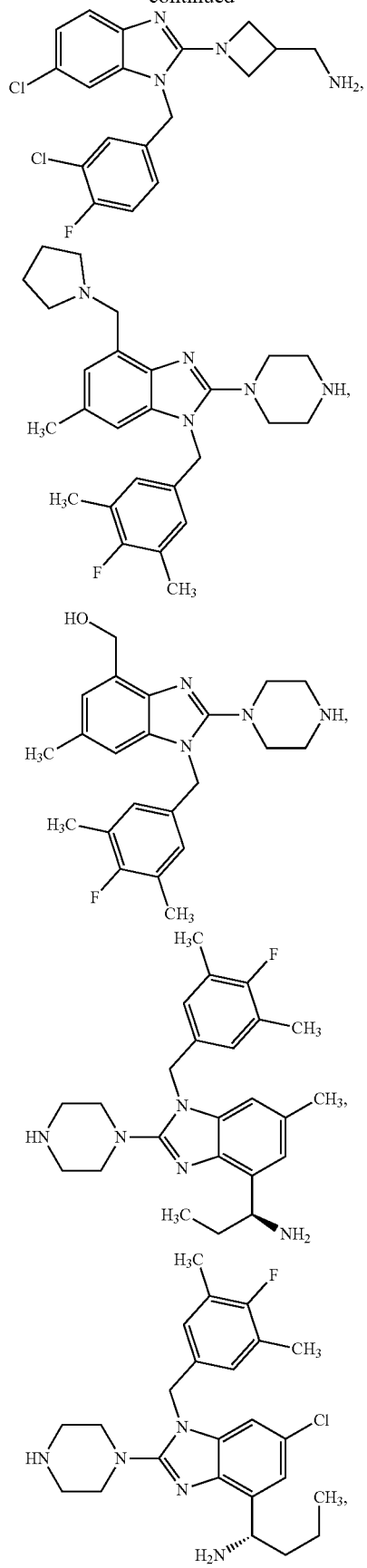

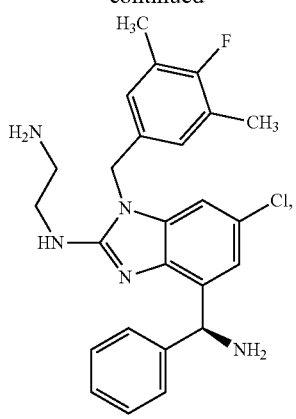
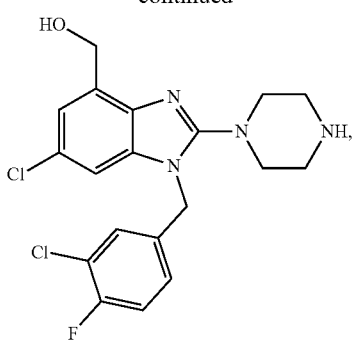
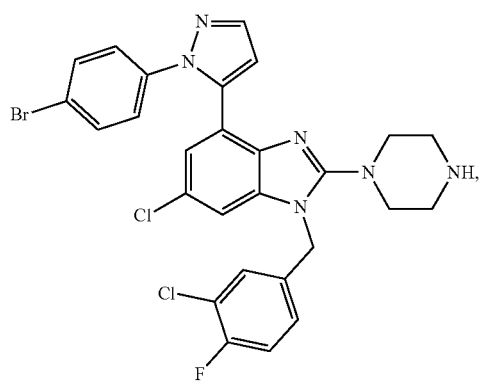
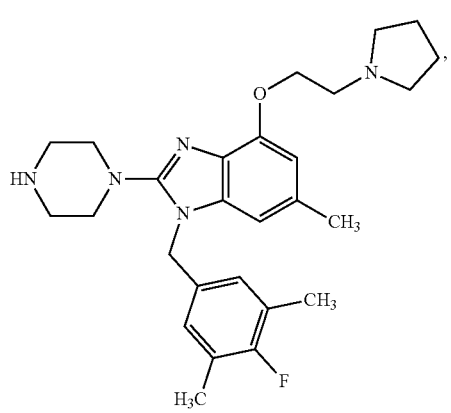
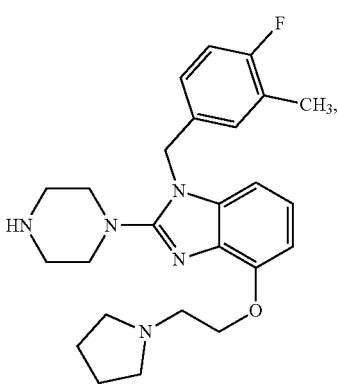
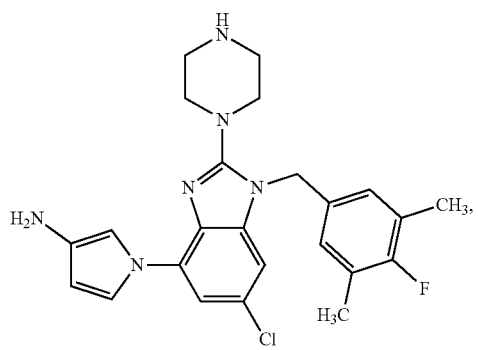
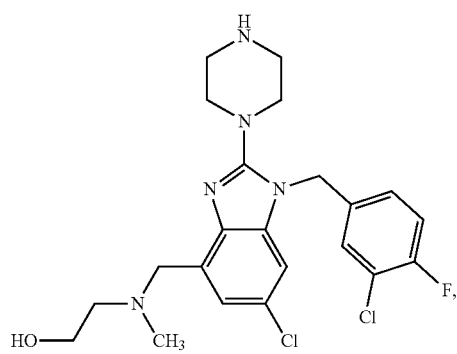
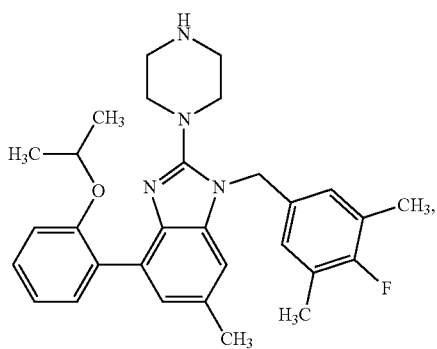

57
-continued
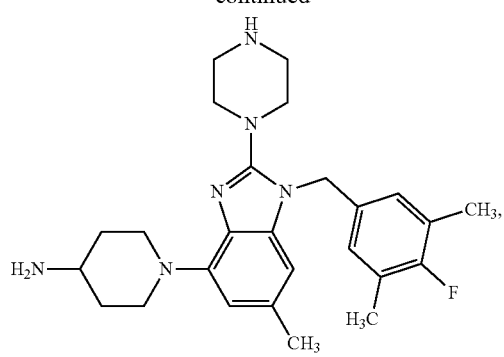
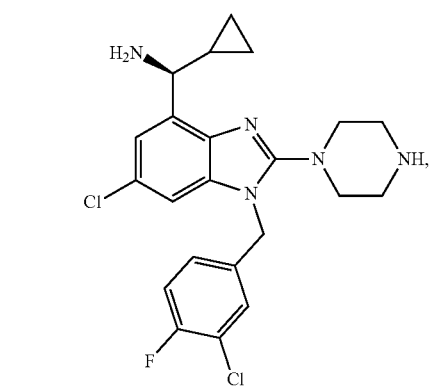
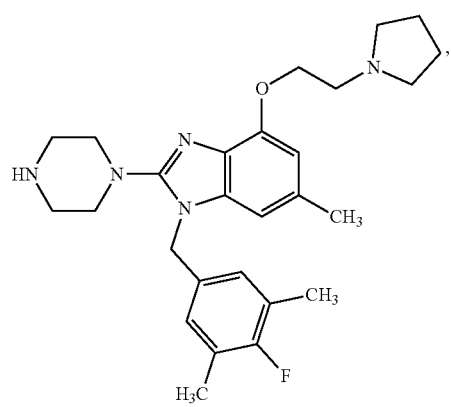
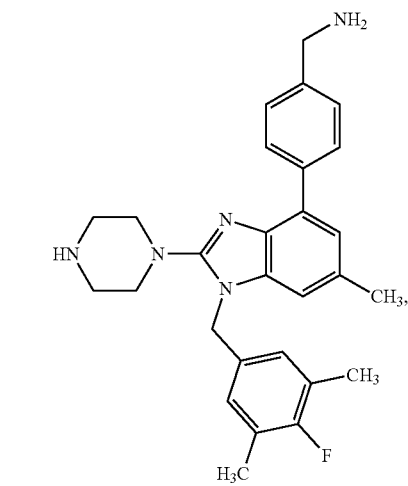
58
-continued
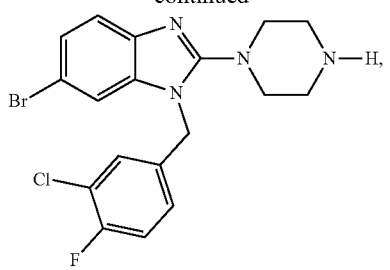
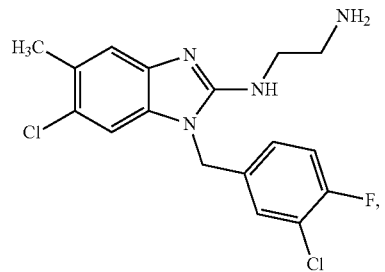
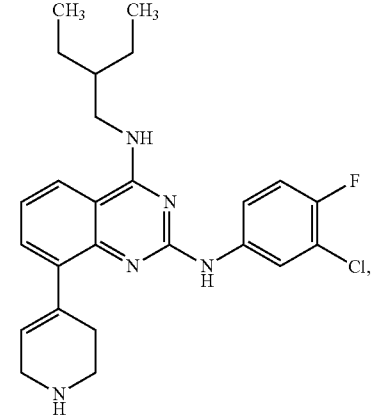
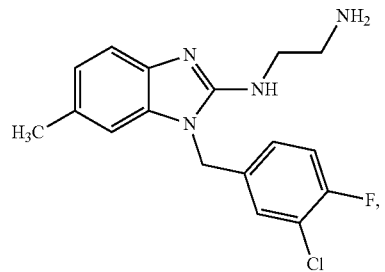
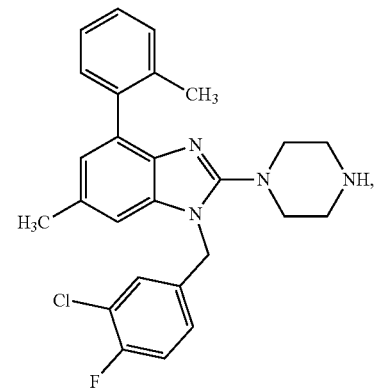

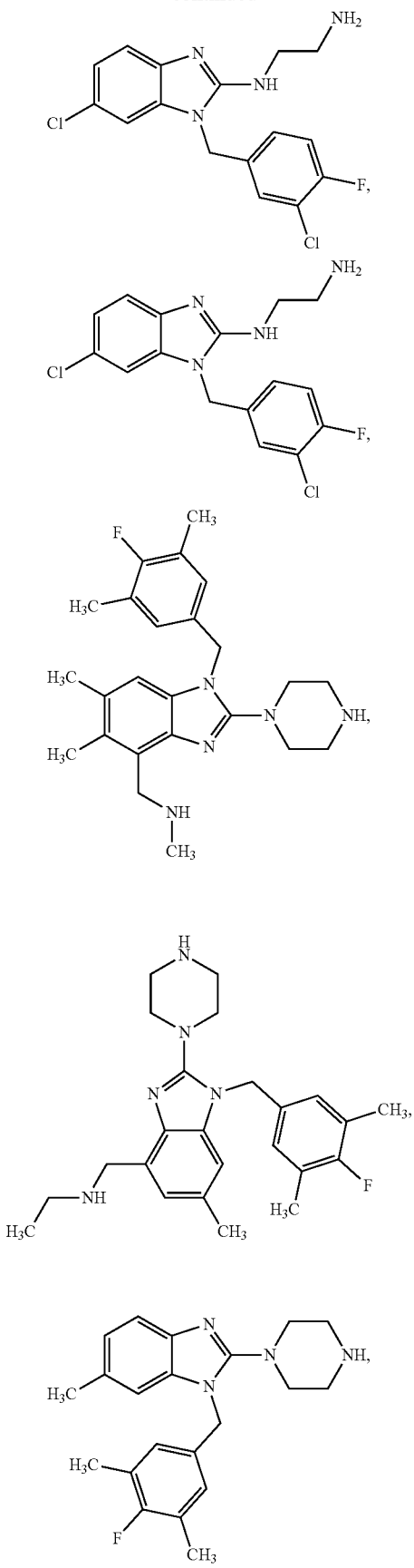

-continued
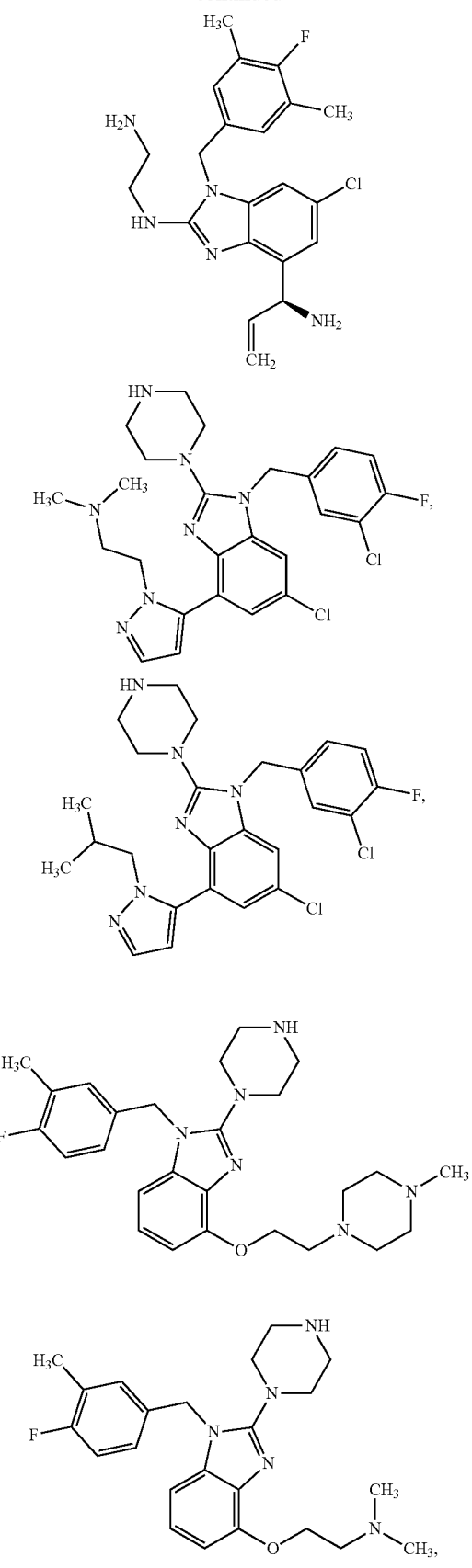
-continued
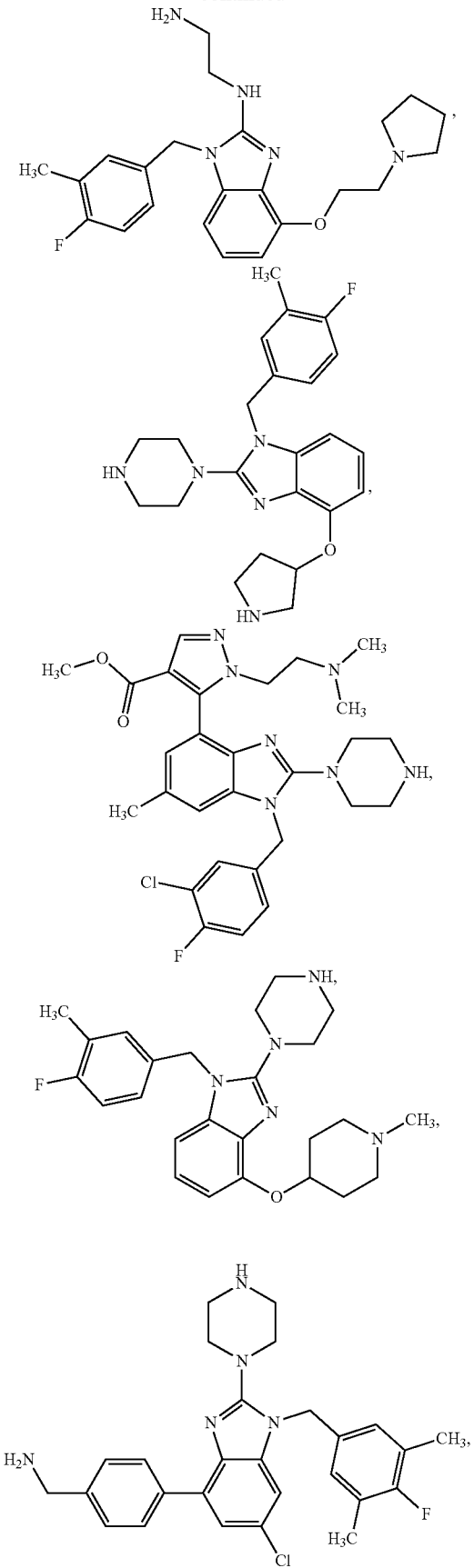

63
-continued
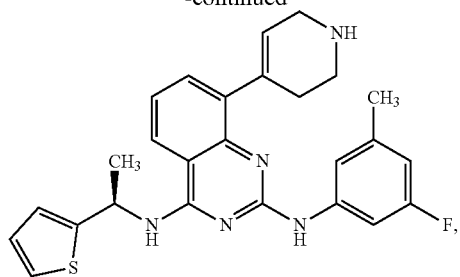
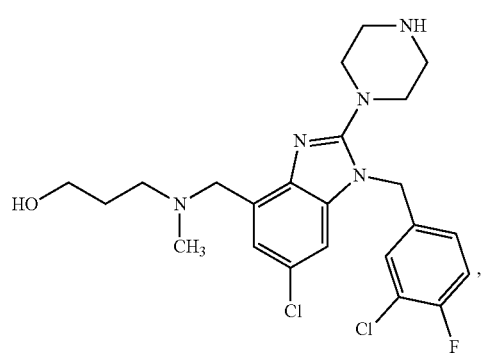
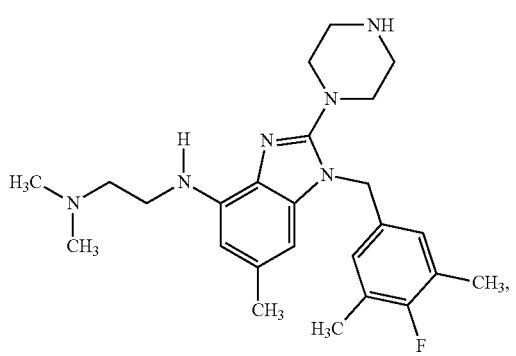
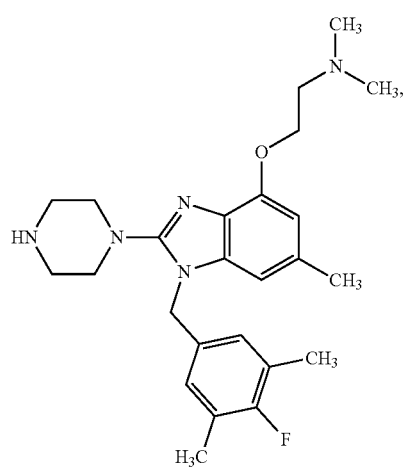
64
-continued
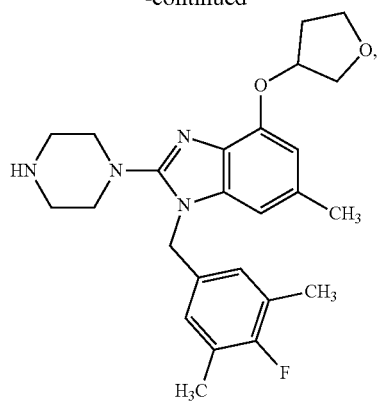
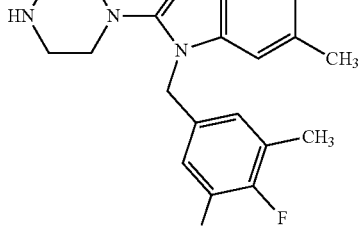
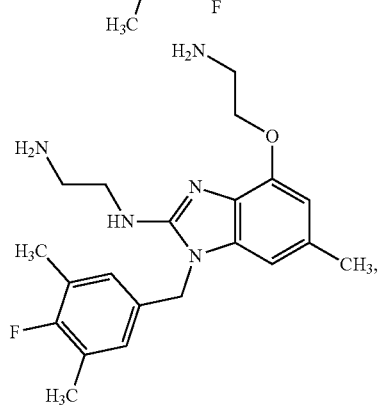
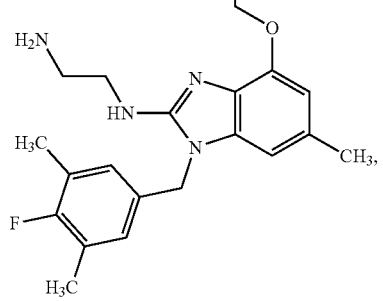

-continued

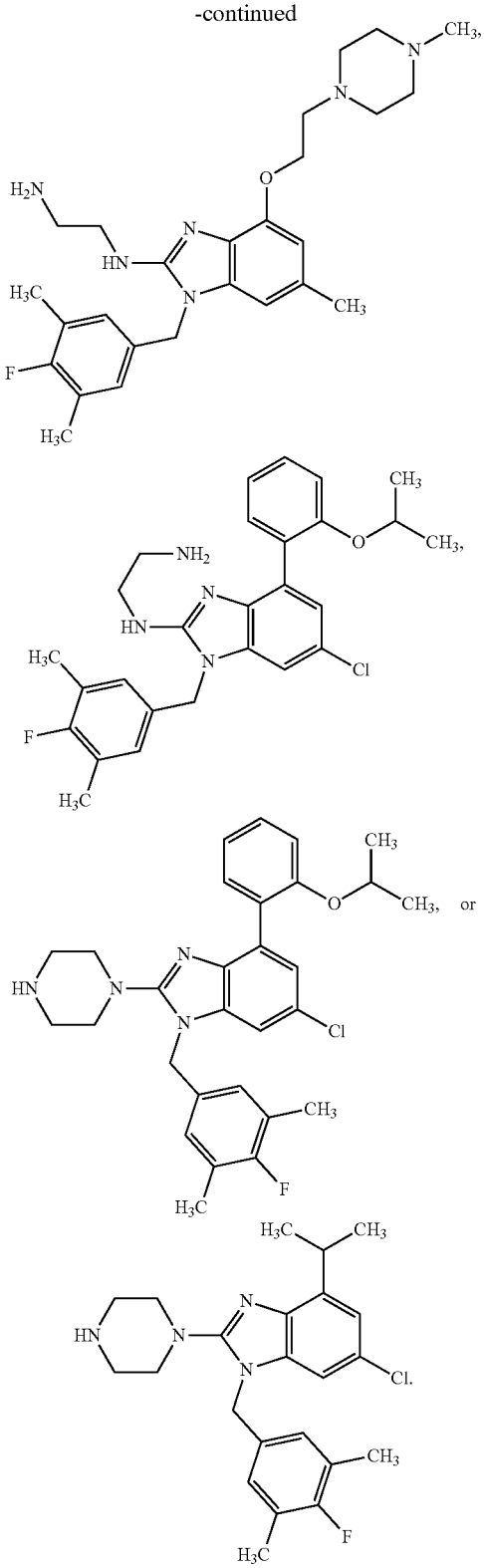

Pharmaceutical Compositions

In one aspect, the invention relates to pharmaceutical compositions comprising the disclosed compounds. That is, a pharmaceutical composition can be provided comprising a therapeutically effective amount of at least one disclosed compound or at least one product of a disclosed method and a pharmaceutically acceptable carrier.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds. The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques.

A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention can comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in moulds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

It is understood that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

The disclosed pharmaceutical compositions can further comprise other therapeutically active compounds, which are usually applied in the treatment of the above mentioned pathological conditions.

It is understood that the disclosed compositions can be prepared from the disclosed compounds. It is also understood that the disclosed compositions can be employed in the disclosed methods of using.

Further disclosed herein are pharmaceutical compositions comprising one or more of the disclosed modulators of Ras signaling and a pharmaceutically acceptable carrier.

Accordingly, the pharmaceutical compositions of the present invention include those that contain one or more other active ingredients, in addition to a compound of the present invention.

The above combinations include combinations of a disclosed compound not only with one other active compound, but also with two or more other active compounds. Likewise, disclosed compounds may be used in combination with other drugs that are used in the prevention, treatment, control, amelioration, or reduction of risk of the diseases or conditions for which disclosed compounds are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the second active ingredient can be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element can be prior to, concurrent to, or subsequent to the administration of other agent(s).

Accordingly, the subject compounds can be used alone or in combination with other agents which are known to be beneficial in the subject indications or other drugs that affect receptors or enzymes that either increase the efficacy, safety, convenience, or reduce unwanted side effects or toxicity of the disclosed compounds. The subject compound and the other agent may be co-administered, either in concomitant therapy or in a fixed combination.

In one aspect, the compound can be employed in combination with at least one additional therapeutic agent. In one aspect of the invention the at least one additional therapeutic agent may be a cancer chemotherapeutic agent. In one aspect, the chemotherapeutic agent(s) may be platinum compounds, topoisomerase inhibitors, peptide antibiotics, alkylators, anthrcyclines, taxenes, histone deacetylase inhibitors, epothilones, kinase inhibitors, nucleotide analogues, retinoids, vinca alkaloids and derivatives, or any combination of chemotherapeutics. The platinum compound(s) may be carboplatin, cisplatin, or oxaliplatin. The topoisomerase inhibitor(s) may be irinotecan, topotecan, etoposide, teniposide, or tafluposide. The peptide antibiotic(s) may be bleomycin or actinomycin. The alkylator(s) may be cyclophosphamide, mechlorethamine, chlorambucil, or melphalan. The anthracycline(s) may be daunorubicin, doxorubicin, epirubicin, mitoxntrone, or valirubicin. The taxene(s) may be paclitaxel or docetaxel. The histone deacetylase inhibitor(s) may be vorinostat or romidepsin. The epothilone(s) may be ixabepilone, patupilone, or sagopilone. The kinase inhibitor(s) may be bortezomib, dabrafenib, erlotinib, gefitinib, imatinib, tremetinib, vemurafenib, or vismodegib. The nucleotide analogue(s) may be azacitidine, azathioprine, capecitabine, cytarabine, flurouracil, gemcitabine, hydroxyurea, mercaptopurine, methotrexate, or tioguanine.

In one aspect, the invention relates to pharmaceutical compositions comprising a compound having a structure represented by a formula:

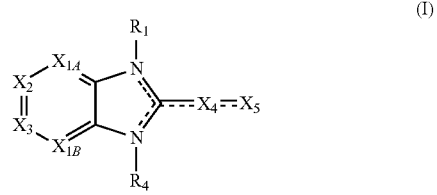

(I)

$X_{1A}$ is N, C—R; $X_{1B}$ is N, C—$R_6$; $X_2$ is N, C—$R_6$; $X_3$ is N, C—$R_6$; $X_4$ is optionally present and is substituted or unsubstituted and selected from $C_{1-6}$alkyl, $C_{1-6}$alkenyl, $C_{1-6}$alkynyl, cycloalkyl, $C_{0-6}$alkyl-cycloalkyl-$C_{0-6}$ alkyl, aryl, $C_{0-6}$ alkyl-aryl-$C_{0-6}$ alkyl, —O—, alkoxy, —O—($C_1$-$C_6$); $X_5$ is substituted or unsubstituted and selected from N, NH, —$NR_2R_3$, cyclic amine, —$NR_2$-alkyl-$NR_2R_3$; R is unsubstituted or substituted with one or more independent $R_5$, and is independently chosen from H, alkyl, cycloalkyl, phenyl, hydroxyl, heterocycloalkyl, cyclic amine, halogen, $CF_3$, Cl, $CONR_3R_4$, aryl, heteroaryl, O—$R_4$, O-alkyl-$R_4$, O-aryl, O-heteroaryl, N—$R_4$, N-aryl, N-heteroaryl, $NHR_4$, $NR_2R_3$, heteroalkyl, benzyl, heteroaryl benzyl ($CH_2$heteroaryl), alkenyl, alkynyl, alkyl-cycloalkyl, $CH_2$-cycloalkyl, $CH_2$—$CF_3$, hydroxyalkyl, alkyl-alkoxy, alkyl-cycloheteroalkyl, alkyl-heteroaryl, alkyl-carboxylic acid, CO—$CF_3$, alkyl-CO—O-alkyl, alkyl-CO—$NR_3R_4$, CO-alkyl-sulfonyl-alkyl, CO-cycloheteroalkyl, CO—NH-cycloalkyl, CN, alkoxy-cycloalkyl, alkoxy-cycloheteroalkyl, O-alkoxy, O-dioxothian, alkoxy, O-heteroalkyl, alkoxy-heteroalkyl, methylsulfonyl, O-cycloheteroalkyl, O-alkoxy-cycloheteroalkyl, O-alkoxy-aryl, O-heteroaryl, $NR_3COR_2$, amino-cycloalkyl, amino-cycloheteroalkyl, $NR_3$-alkoxy, $NR_3$-dioxothian, $NR_3$-heteroalkyl, amino-heteroalkyl, $NR_3$-cycloheteroalkyl, $NR_3$-cycloheteroalkyl, $NR_3$-aryl, $NR_3$-heteroaryl, $NR_3$—CO—$CF_3$, alkyl-CO—$NR_3R_4$, $NR_3$—CO-alkyl-sulfonyl-alkyl, $NR_3$—CO—cycloheteroalkyl, CO—$NR_3$-cycloalkyl, alkyl-carboxylic acid, alkoxy-heteroaryl, alkyl-phenyl, cycloheteroalkyl, amino, amino-heteroaryl, amino-phenyl, CO-alkyl, $CONR_3$-alkyl, $CH_3$, $NH_2$, alkyl-amino, pyridine, pyrazole, furan, thiophene, pyrimidine, thiazole, isothiazole, oxazole, isoxazole, piperazine, pyrrole, pyrazine, dioxane, morpholine, thiomorpholine, triazole, imidazole, alkoxy; $R_4$ is unsubstituted or substituted with one or more independent $R_5$, and is independently chosen from H, alkyl, cycloalkyl, phenyl, hydroxyl, heterocycloalkyl, cyclic amine, halogen, $CF_3$, Cl, $CONR_3R_4$, aryl, heteroaryl, O—$R_3$, O-alkyl-$R_3$, O-aryl, O-heteroaryl, N—$R_3$, N-aryl, N-heteroaryl, $NR_2R_3$, heteroalkyl, benzyl, heteroaryl benzyl ($CH_2$heteroaryl), alkenyl, alkynyl, alkyl-cycloalkyl, $CH_2$-cycloalkyl, $CH_2$—$CF_3$, hydroxyalkyl, alkyl-alkoxy, alkyl-cycloheteroalkyl, alkyl-heteroaryl, alkyl-carboxylic acid, CO—$CF_3$, alkyl-CO—O-alkyl, alkyl-CO—$NR_3R_4$, CO-alkyl-sulfonyl-alkyl, CO-cycloheteroalkyl, CO—NH-cycloalkyl, CN, alkoxy-cycloalkyl, alkoxy-cycloheteroalkyl, O-alkoxy, O-dioxothian, alkoxy, O-heteroalkyl, alkoxy-heteroalkyl, methylsulfonyl, O-cycloheteroalkyl, O-alkoxy-cycloheteroalkyl, O-alkoxy-aryl, O-heteroaryl, $NR_3COR_2$, amino-cycloalkyl, amino-cycloheteroalkyl, $NR_3$-alkoxy, $NR_3$-dioxothian, $NR_3$-heteroalkyl, amino-heteroalkyl, $NR_3$-cycloheteroalkyl, $NR_3$-cycloheteroalkyl, $NR_3$-aryl, $NR_3$-heteroaryl, $NR_3$—CO—$CF_3$, alkyl-CO—$NR_3R_4$, $NR_3$—CO-alkyl-sulfonyl-alkyl, $NR_3$—CO— cycloheteroalkyl, CO—$NR_3$-cycloalkyl, alkyl-carboxylic acid, alkoxy-heteroaryl, alkyl-phenyl, cycloheteroalkyl, amino, amino-heteroaryl, amino-phenyl, CO-alkyl, $CONR_3$-alkyl, $CH_3$, $NH_2$, alkyl-amino, pyridine, pyrazole, furan, thiophene, pyrimidine, thiazole, isothiazole, oxazole, isoxazole, piperazine, pyrrole, pyrazine, dioxane, morpholine, thiomorpholine, triazole, imidazole, alkoxy; $R_1$, when present, is substituted by one or more $R_5$, or H, alkyl, alkene, alkyne, or optionally forms a 3-8 membered ring with $X_5$; $R_2$ is substituted by one or more $R_5$, or unsubstituted and is selected from H, alkyl, alkene, alkyne, alkyl-heteroaryl, alkyl-heterocycloalkyl, alkyl-amino, or together with $R_3$ forms a 3-6 membered ring; $R_3$ is substituted by one or more $R_5$ or unsubstituted and is selected from H, alkyl, alkenyl, alkynyl, alkyl-heteroaryl, alkyl-heterocycloalkyl, alkyl-amino, or together with $R_2$ forms a ring; $R_4$ is substituted by one or more $R_5$, or unsubstituted and is selected from benzyl, methylcycloalkyl, cycloalkyl, alkyl-cycloalkyl; each $R_5$ is independent, substituted or unsubstituted, and selected from H, halogen, alkyl, cycloalkyl, cycloheteroalkyl, amino, cyclic amino, aminoalkyl, alkenyl, alkynyl, $CF_3$, alkoxy, heterocycle, phenyl, aryl, heteroaryl, amidyl; $R_6$ is independent and optionally substituted H, alkyl, cycloalkyl, alkenyl, alkynyl, alkoxy, halogen, $CH_3$, alkyl-amino, amino-alkyl, $CF_3$, hydroxyl, $NH_2$, O-alkyl, $NMe_2$, $CH_2OH$, $CH_2OMe$, $CH_2NHMe$, $CH_2NMe_2$; or a pharmaceutically acceptable salt thereof or a pharmaceutically acceptable derivative thereof.

Uses of Compounds

In some embodiments, the present invention provides methods for the treatment of a cancer or the primary or secondary prophylaxis of cancer, which includes the steps of administering to a patient (for example, a human) in need thereof a therapeutically effective amount of a compound of Formula I or stereoisomers, tautomers, pharmaceutically acceptable salts, prodrug esters, or solvates thereof.

Cancer may be selected from the group consisting of pancreatic ductal carcinoma, colorectal adenocarcinoma, multiple myeloma, lung adenocarcinoma, skin cutaneous melanoma, uterinecorpus endometrial carcinoma, uterine carcinosarcoma, thyroid carcinoma, acute myeloid leukemia, bladder urothelial carcinoma, gastric adrenocarcinoma, cervical adrenocarcinoma, head and neck squamous cell carcinoma, diffuse large B cell lymphoma, oesophageal adenocarcinoma, adenoid cystic carcinoma, chromophobe renal cell carcinoma, hepatocellular carcinoma, breast invasive carcinoma, cervical squamous cell carcinoma, ovarian seros adenocarcinoma, adrenocortical carcinoma, prostate adenocarcinoma, neuroblastoma, brain lower grade glioma, glioblastoma, medulloblastoma and kidney renal clear cell carcinoma as well as others as referenced in the literature. (Pylaveva-Gupta et al. RAS oncogenes: weaving a tumorigenic web. *Nature Rev. Cancer.* 11 761-773 (2011); Cox et al. Drugging the undruggable RAS: Mission Impossible? *Nature Rev. Drug Discovery.* 13 828-851(2014)).

In some embodiments, the present invention includes a method of inhibiting or preventing cellular proliferation and transformation which includes the step of administering to a subject (such as a human) in need thereof a therapeutically effective amount of a modulator of Ras signaling, which is a compound of Formula I.

In some embodiments, the invention provides a method of treatment or prophylaxis of cancer involving administering to a subject in need thereof (e.g., a human) a therapeutically effective amount of a compound that binds to SOS (such as a compound of Formula I of the invention) and increases the rate of nucleotide exchange of Ras or modulates Ras signaling.

In some embodiments, the present invention provides a compound of the present invention or stereoisomers, tautomers, pharmaceutically acceptable salts, solvates, or prodrug esters thereof, for use in therapy for the treatment or prophylaxis of cancer.

In some embodiments, the present invention also provides the use of a compound of the present invention or stereoisomers, tautomers, pharmaceutically acceptable salts, solvates, or prodrug esters thereof, for the manufacture of a medicament for the treatment or prophylaxis of cancer.

In some embodiments, compounds of the present invention may be co-administered with at least one additional drug or therapeutic agent. In certain embodiments of the present invention, at least one additional therapeutic agent(s) are cancer chemotherapeutics or a combination thereof. Examples of chemotherapeutic agents include platinum compounds, topoisomerase inhibitors, peptide antibiotics, alkylators, anthrcyclines, taxenes, histone deacetylase inhibitors, epothilones, kinase inhibitors, nucleotide analogues, retinoids, or vinca alkaloids and derivatives.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

In one aspect, the invention relates to uses of a compound for modulating Ras signaling in a mammal, wherein the compound has a structure represented by the following formula:

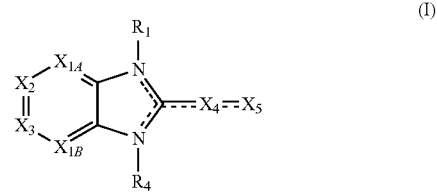

(I)

$X_{1A}$ is N, C—R; $X_{1B}$ is N, C—$R_6$; $X_2$ is N, C—$R_6$; $X_3$ is N, C—$R_6$; $X_4$ is optionally present and is substituted or unsubstituted and selected from $C_{1-6}$alkyl, $C_{1-6}$alkenyl, $C_{1-6}$alkynyl, cycloalkyl, $C_{0-6}$alkyl-cycloalkyl-$C_{0-6}$ alkyl, aryl, $C_{0-6}$ alkyl-aryl-$C_{0-6}$ alkyl, —O—, alkoxy, —O—($C_1$-$C_6$); $X_5$ is substituted or unsubstituted and selected from N, NH, —$NR_2R_3$, cyclic amine, —$NR_2$-alkyl-$NR_2R_3$; R is unsubstituted or substituted with one or more independent $R_5$, and is independently chosen from H, alkyl, cycloalkyl, phenyl, hydroxyl, heterocycloalkyl, cyclic amine, halogen, $CF_3$, Cl, $CONR_3R_4$, aryl, heteroaryl, O—$R_4$, O-alkyl-$R_4$, O-aryl, O-heteroaryl, N—$R_4$, N-aryl, N-heteroaryl, $NHR_4$, $NR_2R_3$, heteroalkyl, benzyl, heteroaryl benzyl ($CH_2$heteroaryl), alkenyl, alkynyl, alkyl-cycloalkyl, $CH_2$-cycloalkyl, $CH_2$—$CF_3$, hydroxyalkyl, alkyl-alkoxy, alkyl-cycloheteroalkyl, alkyl-heteroaryl, alkyl-carboxylic acid, CO—$CF_3$, alkyl-CO—O-alkyl, alkyl-CO—$NR_3R_4$, CO-alkyl-sulfonyl-alkyl, CO-cycloheteroalkyl, CO—NH-cycloalkyl, CN, alkoxy-cycloalkyl, alkoxy-cycloheteroalkyl, O-alkoxy, O-dioxothian, alkoxy, O-heteroalkyl, alkoxy-heteroalkyl, methylsulfonyl, O-cycloheteroalkyl, O-alkoxy-cycloheteroalkyl, O-alkoxy-aryl, O-heteroaryl, $NR_3COR_2$, amino-cycloalkyl, amino-cycloheteroalkyl, $NR_3$-alkoxy, $NR_3$-dioxothian, $NR_3$-heteroalkyl, amino-heteroalkyl, $NR_3$-cycloheteroalkyl, $NR_3$-cycloheteroalkyl, $NR_3$-aryl, $NR_3$-heteroaryl, $NR_3$—CO—$CF_3$, alkyl-CO—$NR_3R_4$, $NR_3$—CO-alkyl-sulfonyl-alkyl, $NR_3$—CO—cycloheteroalkyl, CO—$NR_3$-cycloalkyl, alkyl-carboxylic acid, alkoxy-heteroaryl, alkyl-phenyl, cycloheteroalkyl, amino, amino-heteroaryl, amino-phenyl, CO-alkyl, $CONR_3$-alkyl, $CH_3$, $NH_2$, alkyl-amino, pyridine, pyrazole, furan, thiophene, pyrimidine, thiazole, isothiazole, oxazole, isoxazole, piperazine, pyrrole, pyrazine, dioxane, morpholine, thiomorpholine, triazole, imidazole, alkoxy; $R_4$ is unsubstituted or substituted with one or more independent $R_5$, and is independently chosen from H, alkyl, cycloalkyl, phenyl, hydroxyl, heterocycloalkyl, cyclic amine, halogen, $CF_3$, Cl, $CONR_3R_4$, aryl, heteroaryl, O—$R_3$, O-alkyl-$R_3$, O-aryl, O-heteroaryl, N—$R_3$, N-aryl, N-heteroaryl, $NR_2R_3$, heteroalkyl, benzyl, heteroaryl benzyl ($CH_2$-heteroaryl), alkenyl, alkynyl, alkyl-cycloalkyl, $CH_2$-cycloalkyl, $CH_2$—$CF_3$, hydroxyalkyl, alkyl-alkoxy, alkyl-cycloheteroalkyl, alkyl-heteroaryl, alkyl-carboxylic acid, CO—$CF_3$, alkyl-CO—O-alkyl, alkyl-CO—$NR_3R_4$, CO-alkyl-sulfonyl-alkyl, CO-cycloheteroalkyl, CO—NH-cycloalkyl, CN, alkoxy-cycloalkyl, alkoxy-cycloheteroalkyl, O-alkoxy, O-dioxothian, alkoxy, O-heteroalkyl, alkoxy-heteroalkyl, methylsulfonyl, O-cycloheteroalkyl, O-alkoxy-cycloheteroalkyl, O-alkoxy-aryl, O-heteroaryl, $NR_3COR_2$, amino-cycloalkyl, amino-cycloheteroalkyl, $NR_3$-alkoxy, $NR_3$-dioxothian, $NR_3$-heteroalkyl, amino-heteroalkyl, $NR_3$-cycloheteroalkyl, $NR_3$-cycloheteroalkyl, $NR_3$-aryl, $NR_3$-heteroaryl, $NR_3$—CO—$CF_3$, alkyl-CO—$NR_3R_4$, $NR_3$—CO-alkyl-sulfonyl-alkyl, $NR_3$—CO— cycloheteroalkyl, CO—$NR_3$-cycloalkyl, alkyl-carboxylic acid, alkoxy-heteroaryl, alkyl-phenyl, cycloheteroalkyl, amino, amino-heteroaryl, amino-phenyl, CO-alkyl, $CONR_3$-alkyl, $CH_3$, $NH_2$, alkyl-amino, pyridine, pyrazole, furan, thiophene, pyrimidine, thiazole, isothiazole, oxazole, isoxazole, piperazine, pyrrole, pyrazine, dioxane, morpholine, thiomorpholine, triazole, imidazole, alkoxy; $R_1$, when present, is substituted by one or more $R_5$, or H, alkyl, alkene, alkyne, or optionally forms a 3-8 membered ring with $X_5$; $R_2$ is substituted by one or more $R_5$, or unsubstituted and is selected from H, alkyl, alkene, alkyne, alkyl-heteroaryl, alkyl-heterocycloalkyl, alkyl-amino, or together with $R_3$ forms a 3-6 membered ring; $R_3$ is substituted by one or more $R_5$ or unsubstituted and is selected from H, alkyl, alkenyl, alkynyl, alkyl-heteroaryl, alkyl-heterocycloalkyl, alkyl-amino, or together with $R_2$ forms a ring; $R_4$ is substituted by one or more $R_5$, or unsubstituted and is selected from benzyl, methylcycloalkyl, cycloalkyl, alkyl-cycloalkyl; each $R_5$ is independent, substituted or unsubstituted, and selected from H, halogen, alkyl, cycloalkyl, cycloheteroalkyl, amino, cyclic amino, aminoalkyl, alkenyl, alkynyl, $CF_3$, alkoxy, heterocycle, phenyl, aryl, heteroaryl, amidyl; $R_6$ is independent and optionally substituted H, alkyl, cycloalkyl, alkenyl, alkynyl, alkoxy, halogen, $CH_3$, alkyl-amino, amino-alkyl, $CF_3$, hydroxyl, $NH_2$, O-alkyl, $NMe_2$, $CH_2OH$, $CH_2OMe$, $CH_2NHMe$, $CH_2NMe_2$; or a pharmaceutically acceptable salt thereof or a pharmaceutically acceptable derivative thereof.

The disclosed uses for modulating Ras signaling in a mammal can further be directed for use in treating one or more disorders, for example cancer, and other disease states associated with Ras dysfunction (e.g., Ras-associated autoimmune leukoproliferative disorder, or certain types of mitochondrial dysfuction) in a subject, for example a mammal or a human.

Experimental/Examples

The following examples are present to provide those of ordinary skill in the art with a more complete disclosure and description of how compounds of the present invention are made and used and are intended to be purely exemplary of the present invention and are not intended to limit the scope of what the inventors regard as their invention.

General:

All non-aqueous reactions were performed in flame-dried or oven dried round-bottomed flasks under an atmosphere of argon. Stainless steel syringes or cannulae were used to transfer air- and moisture-sensitive liquids. Reaction temperatures were controlled using a thermocouple thermometer and analog hotplate stirrer. Reactions were conducted at room temperature (rt, approximately 23° C.) unless otherwise noted. Analytical thin-layer chromatography (TLC) was performed on E. Merck silica gel 60 F254 plates and visualized using UV, ceric ammonium molybdate, iodine absorbed onto silica gel, potassium permanganate, and anisaldehyde stains. Yields were reported as isolated, spectroscopically pure compounds, unless otherwise noted.

Instrumentation:

HPLC purification was conducted on a Gilson HPLC system using a Gemini-NX Su C18 column. $^1$H NMR spectra were recorded on Bruker 402 MHz spectrometers and are reported relative to residual non-deuterated solvent signals. Data for $^1$H NMR spectra are reported as follows: chemical shift (δ ppm), multiplicity (s=singlet, d=doublet, t=triplet, quin=quintuplet, sep=septet, dd=double of doublets, dt=doublet of triplets, q=quartet, m=multiplet, b=broad, app=apparent), coupling constants (Hz), and integration. LCMS was conducted and recorded on an Agilent Technologies 6140 Quadrupole instrument. Microwave reactions were conducted on a Biotage Initiator 2.0 microwave reactor.

General Procedure A for Benzimidazole Preparation

Some benzimidazole analogs of the current invention may be prepared by the procedure outlined in Scheme 1. This procedure is exemplified by Example 1.

Scheme 1: Synthesis of 2-aminobenzimidazoles.

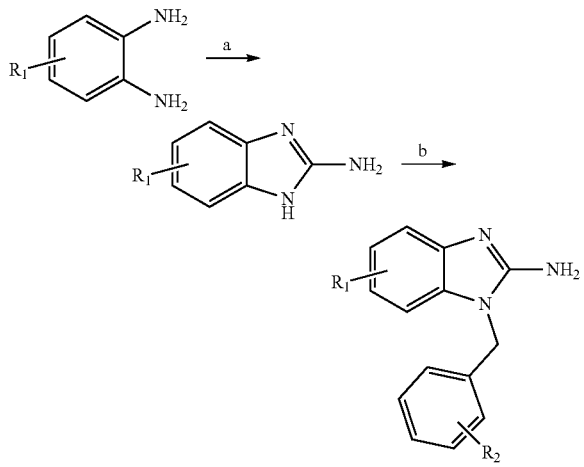

Reagents and Conditions: a) cyanogen bromide, MeCN, rt. b) benzyl bromide, $K_2CO_3$, DMF General Procedure B for Benzimidazole Preparation Some benzimidazole analogs of the current invention may be prepared by the procedure outlined in Scheme 2. This procedure is exemplified by Example 7.

Scheme 2: Synthesis of 2-substituted benzimidazoles.

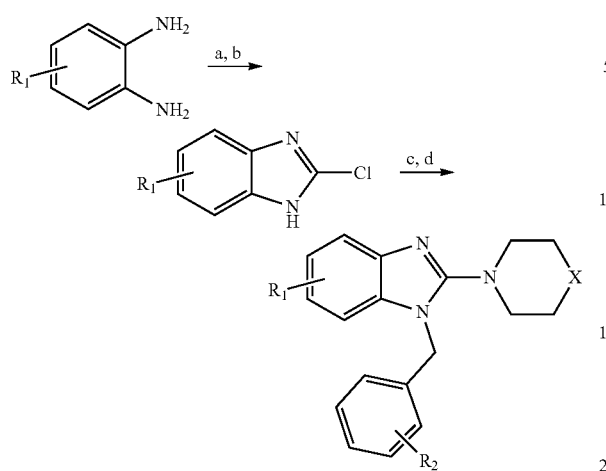

Reagents and Conditions: a) Urea, xylenes, reflux, 18 h; b) POCl₃, reflux; c) benzyl bromide, K₂CO₃, DMF. d) amine, DMA, 165 C., uW.

General Procedure C for Benzimidazole Preparation

Some benzimidazole analogs of the current invention may be prepared by the procedure outlined in Scheme 3. This procedure is exemplified by Example 53.

Scheme 3: Synthesis of 2-pyridinylbenzimidazoles.

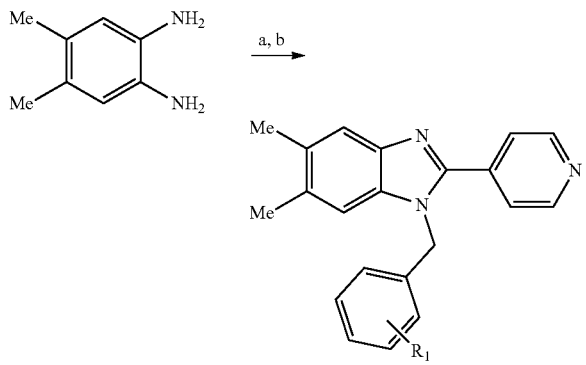

Reagents and Conditions: a) isonicotinic acid, HOBt, EDCi, DIEA, DCM, then AcOH reflux; b) benzyl bromide, K₂CO₃, DMF General Procedure D for Benzimidazole Preparation Some benzimidazole analogs of the current invention may be prepared by the procedure outlined in Scheme 4. This procedure is exemplified by Example 55.

Scheme 4: Synthesis of 2-piperdinylbenzimidazoles.

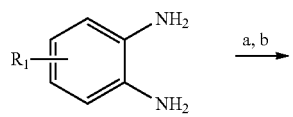

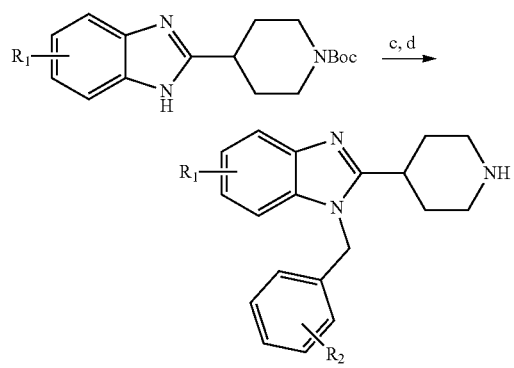

Reagents and Conditions: a) pipericine-4-carboxylic acid, 4M HCl, reflux; b) Boc₂O, THF; c) benzyl bromide, K₂CO₃, DMF; d) TFA/DCM General Procedure E for Benzimidazole Preparation Some benzimidazole analogs of the current invention may be prepared by the procedure outlined in Scheme 5. This procedure is exemplified by Example 60.

Scheme 5: Synthesis of benzimidazoles.

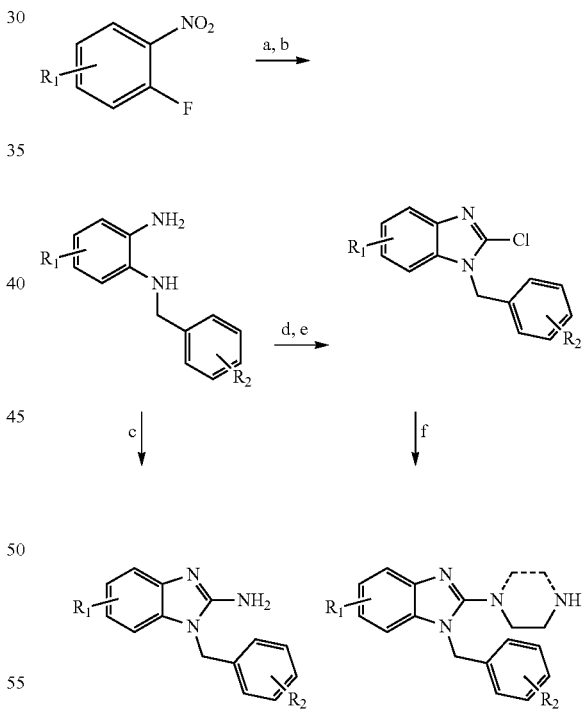

Reagents and Conditions: a) benzylamine, K₂CO₃, DMF, RT; b) Zn/NH₄Cl, MeOH, 0 - RT; c) cyanogen bromide, MeCN, rt; d) CDI, DMAP, DCM, RT; e) POCl₃, reflux; f) amine, DMA, 165 C., microwave, 45 min General Procedure F for Benzimidazole Preparation Some benzimidazole analogs of the current invention may be prepared by the procedure outlined in Scheme 6. This procedure is exemplified by Example 79.

Scheme 6: Synthesis of 4-Arylbenzimidazoles.

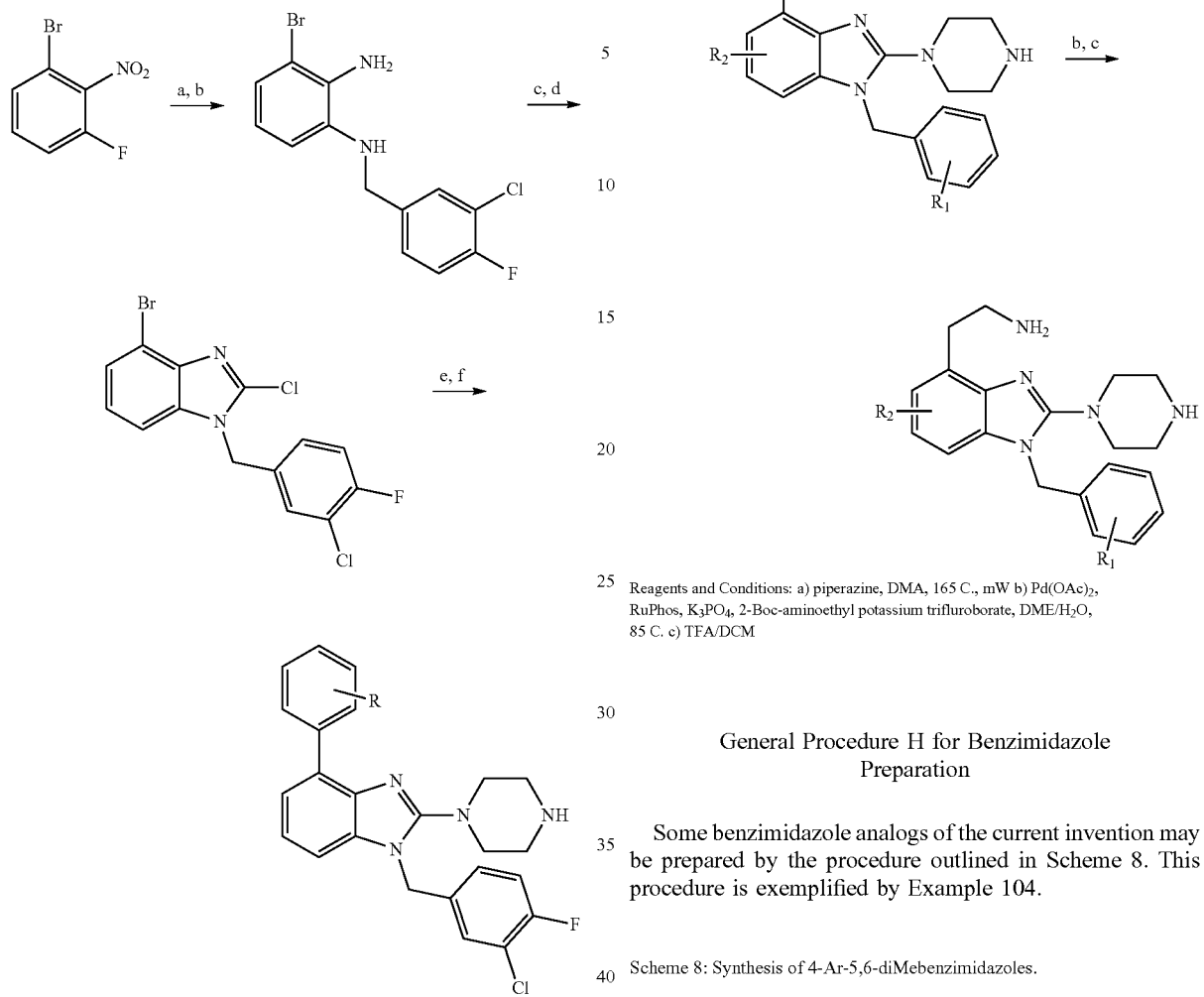

Reagents and Conditions: a) benzylamine, K₂CO₃, DMF, RT; b) Zn/NH₄Cl, MeOH, 0 - RT; c) CDI, DMAP, DCM, RT; d) POCl₃, reflux; e) piperazine, DMA, 165 C., microwave, 45 min; f) Pd(OAc)₂, PCy₃HBF₄, K₃PO₄, boronic acid, DME/H₂O, 85 C.

General Procedure G for Benzimidazole Preparation

Some benzimidazole analogs of the current invention may be prepared by the procedure outlined in Scheme 7. This procedure is exemplified by Example 98.

Scheme 7: Synthesis of 4-ethylaminobenzimidazoles.

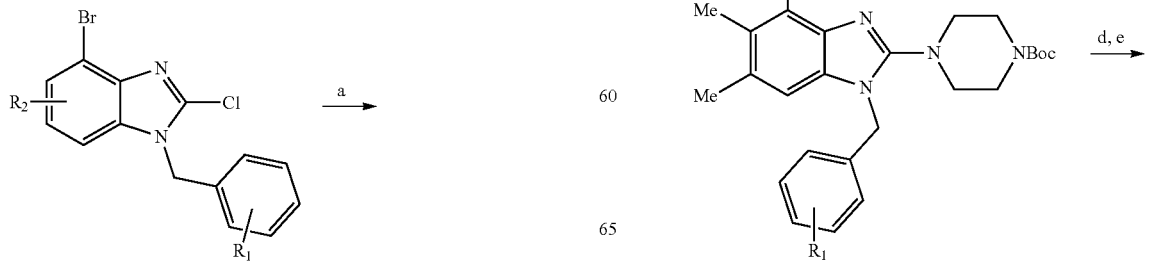

Reagents and Conditions: a) piperazine, DMA, 165 C., mW b) Pd(OAc)₂, RuPhos, K₃PO₄, 2-Boc-aminoethyl potassium trifluroborate, DME/H₂O, 85 C. c) TFA/DCM

General Procedure H for Benzimidazole Preparation

Some benzimidazole analogs of the current invention may be prepared by the procedure outlined in Scheme 8. This procedure is exemplified by Example 104.

Scheme 8: Synthesis of 4-Ar-5,6-diMebenzimidazoles.

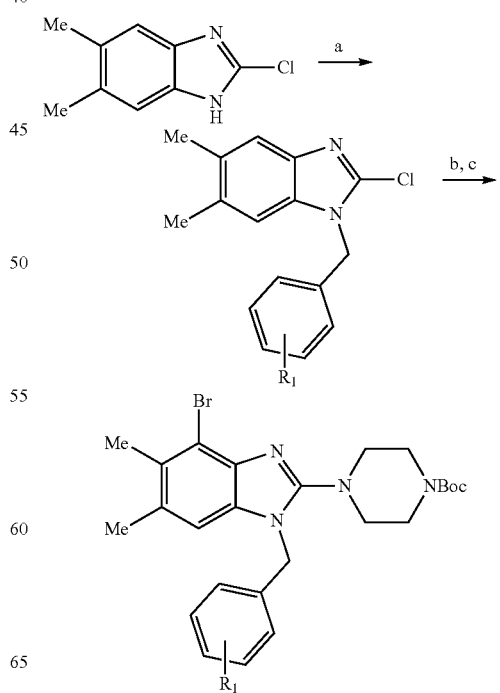

79
-continued

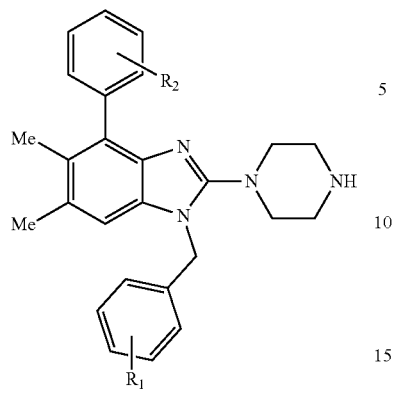

Reagents and Conditions: a) benzylbromide, K₂CO₃, DMF, 40 C.; b) NBS, DMF; c) 1-BOC-piperazine, K₂CO₃, DMSO, 90 C.; d) Pd(OAc)₂, PCy₃HBF₄, K₃PO₄, boronic acid, DME/H₂O, 85 C.; e) TFA/DCM General Procedure I for Benzimidazole Preparation Some benzimidazole analogs of the current invention may be prepared by the procedure outlined in the Scheme 9. This procedure is exemplified by Example 118.

Scheme 9: Synthesis of 4-Ar-benzimidazoles.

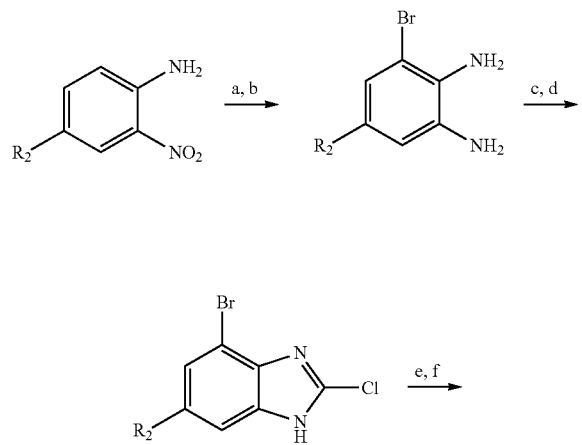

80
-continued

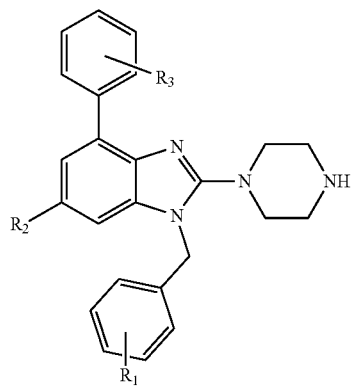

Reagents and Conditions: a) Br₂, AcOH, RT; b) Zn/NH₂Cl, MeOH, RT; c) CDI, DMAP, DCM, RT; d) POCl₃, reflux; e) benzylbromide, K₂CO₃ DMF; f) 1-BOC-piperazine, K₂CO₃, DMSO, 90 C.; g) Pd(OAc)₂, PCy₃HBF₄, K₃PO₄, boronic acid, DME/H₂O, 85 C.; h) TFA/DCM General Procedure J for Benzimidazole Preparation Some benzimidazole analogs of the current invention may be prepared by the procedure outlined in Scheme 10. This procedure is exemplified by Example 124.

Scheme 10: Synthesis of 4-alkylaminobenzimidazoles.

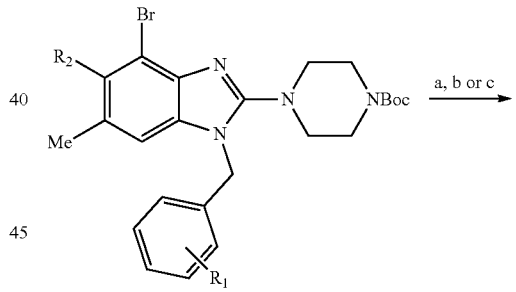

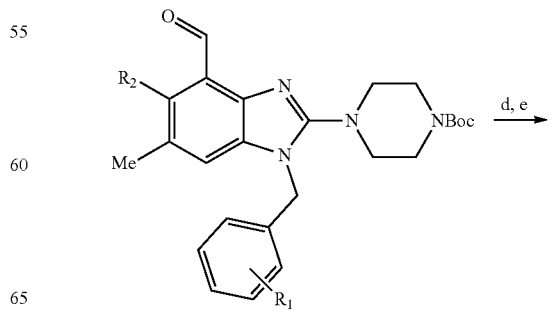

-continued

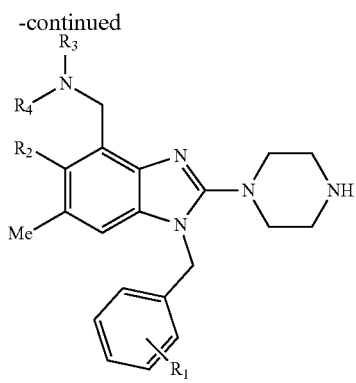

Reagents and Conditions: a) Pd(OAc)$_2$, PCy$_3$HBF$_4$, K$_3$PO$_4$, vinylboronic acid pinnacol ester; DME/H$_2$O, 85 C.; b) OsO$_4$, NaIO$_4$, Acetone/H$_2$O, RT; c) n-BuLi, THF, -78 C., then DMF; d) HNR$_3$R$_4$, NABH(OAc)$_3$, DCM, 0 C., e) TFA/DCM

General Procedure K for Benzimidazole Preparation

Some benzimidazole analogs of the current invention may be prepared by the procedure outlined in Scheme 11. This procedure is exemplified by Example 142.

Scheme 11: Synthesis of 2-H-benzimidazoles

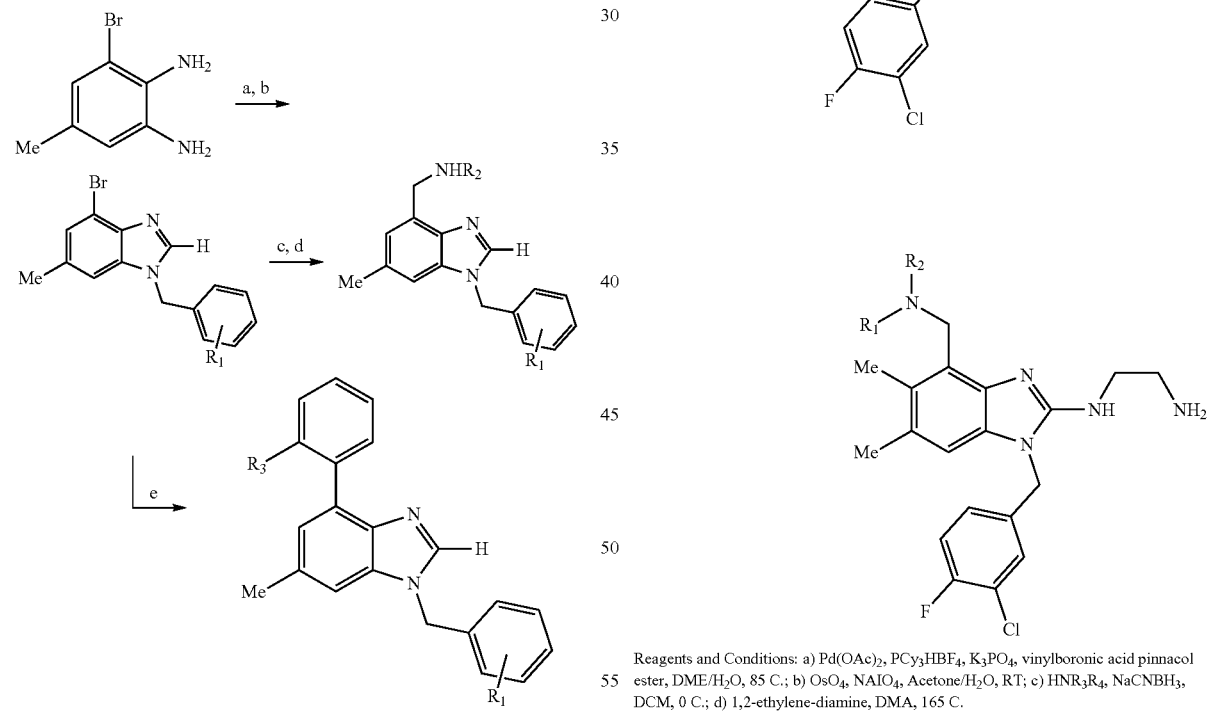

Reagents and Conditions: a) trimethylorthoformate, DMF b) benzyl bromide, K$_2$CO$_3$, DMF c) Pd(OAC)$_2$, PCy$_3$HBF$_4$, K$_3$PO$_4$, vinylboronic acid pinnacol ester, DME/H$_2$O, 85 C.; d) OsO$_4$ NAIO$_4$, Acetone/H$_2$O, RT; e) HNR$_3$R$_4$, NaCNBH$_3$, DCM, 0 C.; e) Pd(OAc)$_2$, PCy$_3$HBF$_4$, K$_3$PO$_4$, boronic acid, DME/H$_2$O, 85 C.

General Procedure L for Benzimidazole Preparation

Some benzimidazole analogs of the current invention may be prepared by the procedure outlined in Scheme 12. This procedure is exemplified by Example 146.

Scheme 12: Synthesis of 4-alkylaminobenzimidazoles.

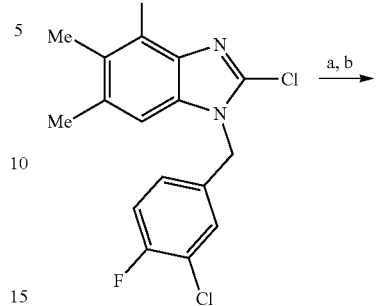

Reagents and Conditions: a) Pd(OAc)$_2$, PCy$_3$HBF$_4$, K$_3$PO$_4$, vinylboronic acid pinnacol ester, DME/H$_2$O, 85 C.; b) OsO$_4$, NAIO$_4$, Acetone/H$_2$O, RT; c) HNR$_3$R$_4$, NaCNBH$_3$, DCM, 0 C.; d) 1,2-ethylene-diamine, DMA, 165 C.

General Procedure M for Benzimidazole Preparation

Some benzimidazole analogs of the current invention may be prepared by the procedure outlined in Scheme 13. This procedure is exemplified by Example 148.

83

Scheme 13: Synthesis of 4-pyrrolidino-benzimidazoles.

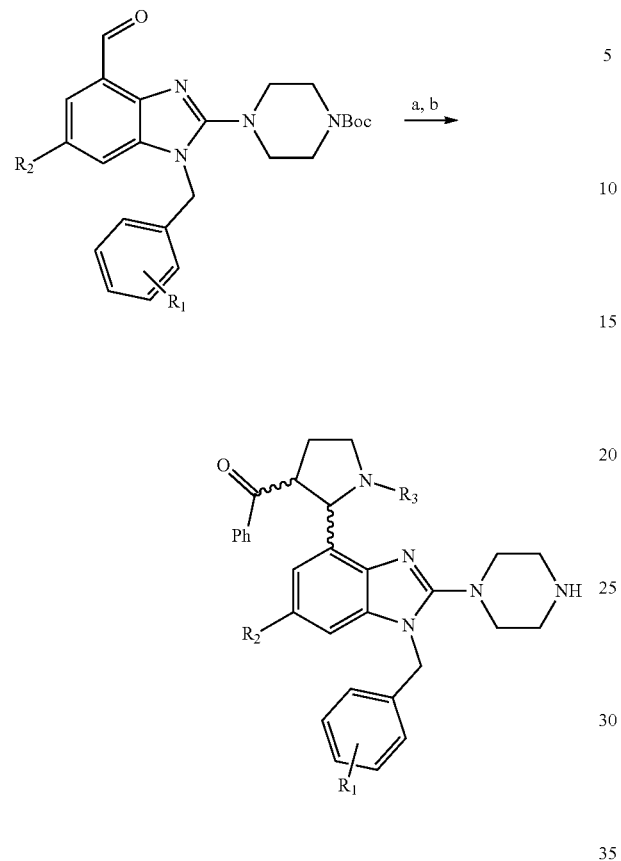

Reagents and Conditions a) MgI$_2$, cyclopropyl phenylketone, amine, THF, 80 C.; b) TFA/DCM

General Procedure N for Benzimidazole Preparation

Some benzimidazole analogs of the current invention may be prepared by the procedure outlined in Scheme 14. This procedure is exemplified by Example 155.

Scheme 14: Synthesis of branched 4-alkylaminobenzimidazoles.

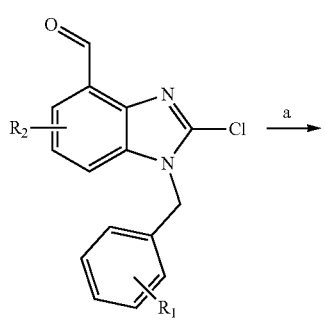

84

-continued

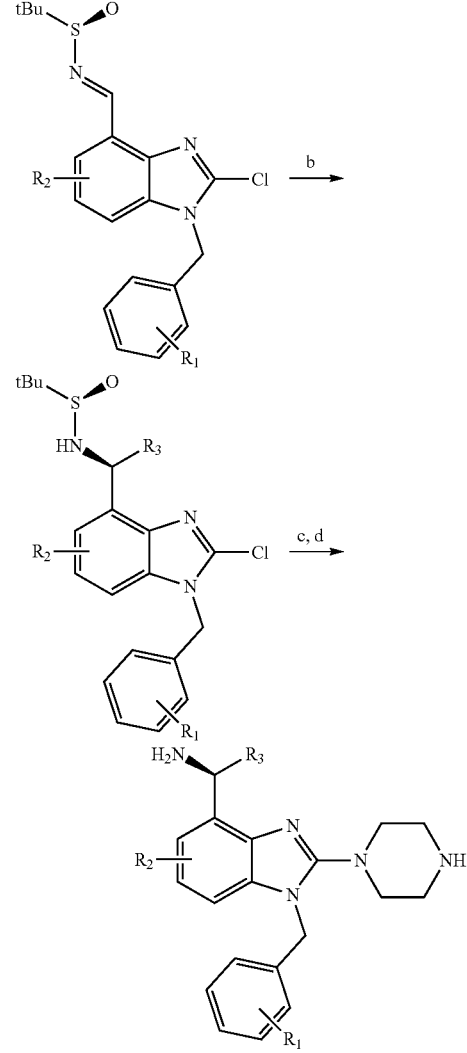

Reagents and Conditions: a) (R)-(+)-t-BuSONH$_2$, Ti(OEt)$_4$, THF, RT; b) R$_3$MgBr, DCM, -78 C., 4 hr; c) 1-BOC-piperazine, K$_2$CO$_3$, DMSO, 90 C.; 4M HCL, dioxane

General Procedure O for Benzimidazole Preparation

Some benzimidazole analogs of the current invention may be prepared by the procedure outlined in Scheme 15. This procedure is exemplified by Example 168.

Scheme 15: Synthesis of 4-pyrazolebenzimidazoles.

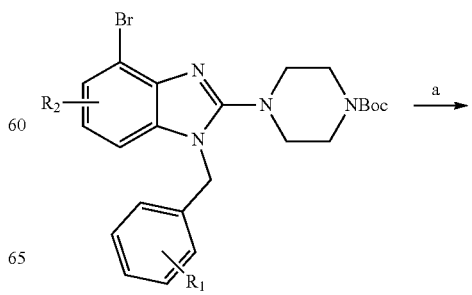

85

-continued

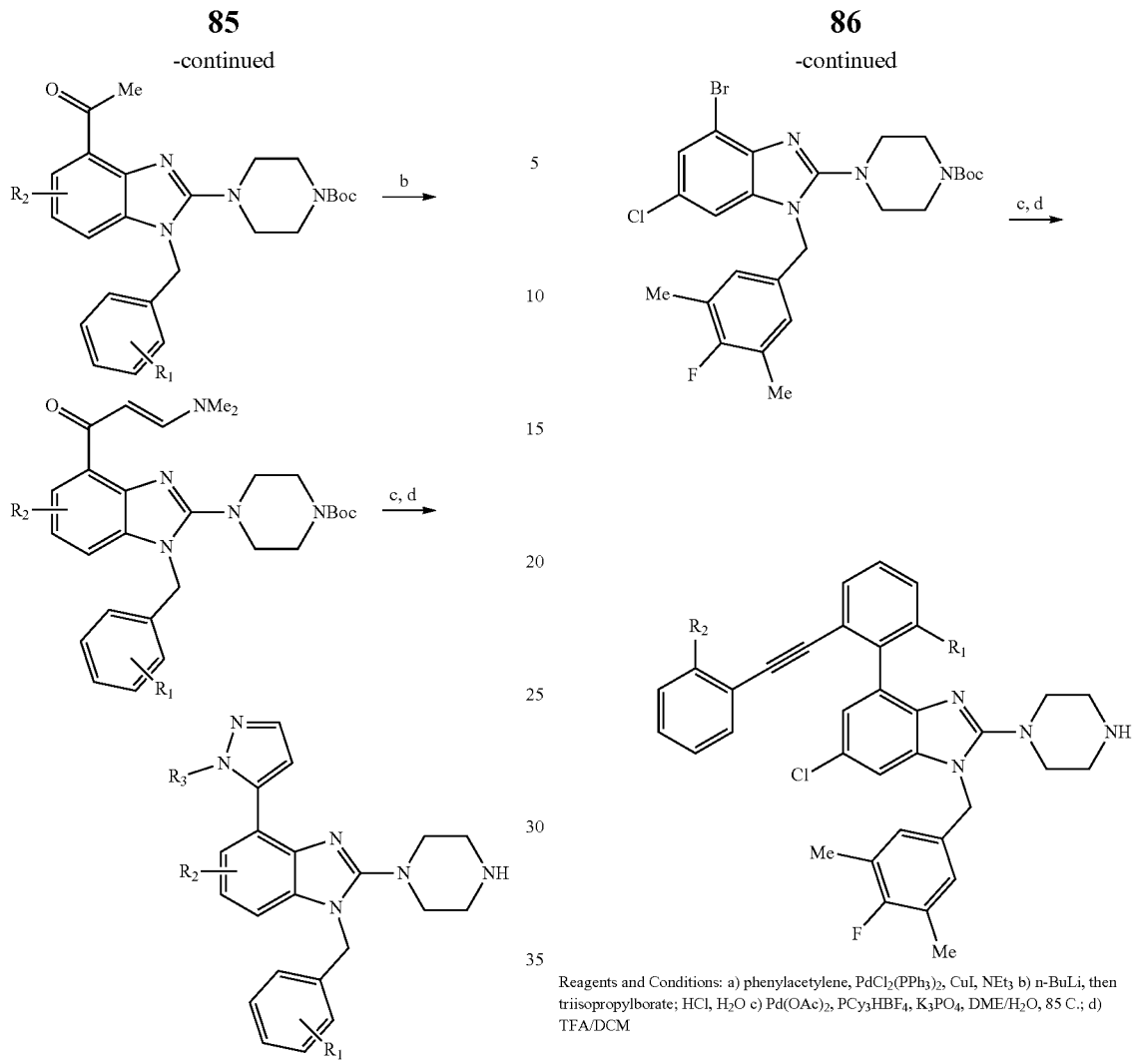

Reagents and Conditions: a) Pd(dppf)Cl₂, tributyl(1-ethoxyvinyl)stannane, DMA, 130° C., 45 m, then HCl/H₂O; b) DMFDMA, 100° C.; c) R₃NHNH₃Cl, EtOH, 75° C., microwave, 3 h; d) TFA/DCM

86

-continued

Reagents and Conditions: a) phenylacetylene, PdCl₂(PPh₃)₂, CuI, NEt₃ b) n-BuLi, then triisopropylborate; HCl, H₂O c) Pd(OAc)₂, PCy₃HBF₄, K₃PO₄, DME/H₂O, 85 C.; d) TFA/DCM General Procedure Q for Benzimidazole Preparation Some benzimidazole analogs of the current invention may be prepared by the procedure outlined in Scheme 17. This procedure is exemplified by Example 188.

Scheme 17: Synthesis of 4-aminobenzimidazoles.

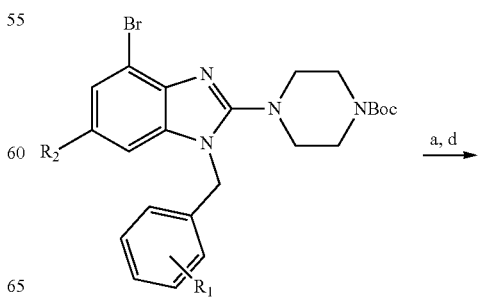

General Procedure P for Benzimidazole Preparation

Some benzimidazole analogs of the current invention may be prepared by the procedure outlined in the Scheme 16. This procedure is exemplified by Example 182.

Scheme 16: Synthesis of phenylacetylenes.

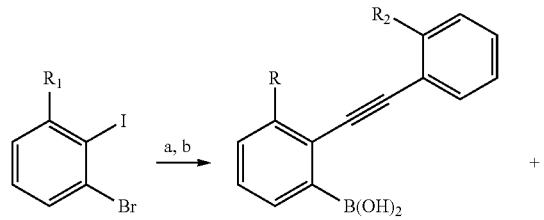

87

-continued

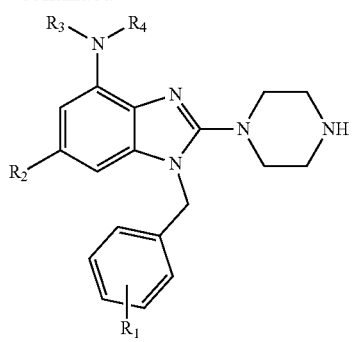

Reagents and Conditions a) Pd(OAc)₂, RuPhos, K₃PO₄, amine, DME, 100 C.; b) TFA/DCM General Procedure R for Benzimidazole Preparation Some benzimidazole analogs of the current invention may be prepared by the procedure outlined in Scheme 18. This procedure is exemplified by Example 199.

Scheme 18: Synthesis of 4-alkoxybenzimidazoles.

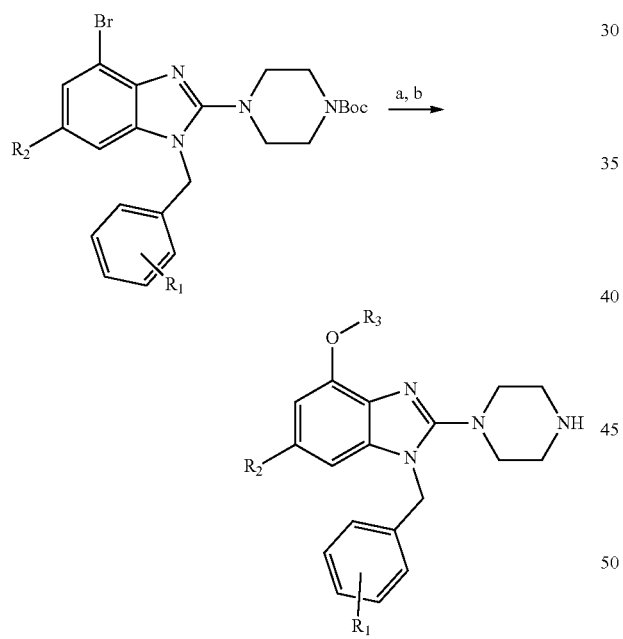

Reagents and Conditions: a) Pd(OAc)₂, RuPhos, K₃PO₄, amine, DME, 100 C; b) R₃OH, K₃PO₄, CuI General Procedure S for Benzimidazole Preparation Some benzimidazole analogs of the current invention may be prepared by the procedure outlined in Scheme 19. This procedure is exemplified by Example 205.

88

Scheme 19: Synthesis of 4-alkoxybenzimidazole analogs.

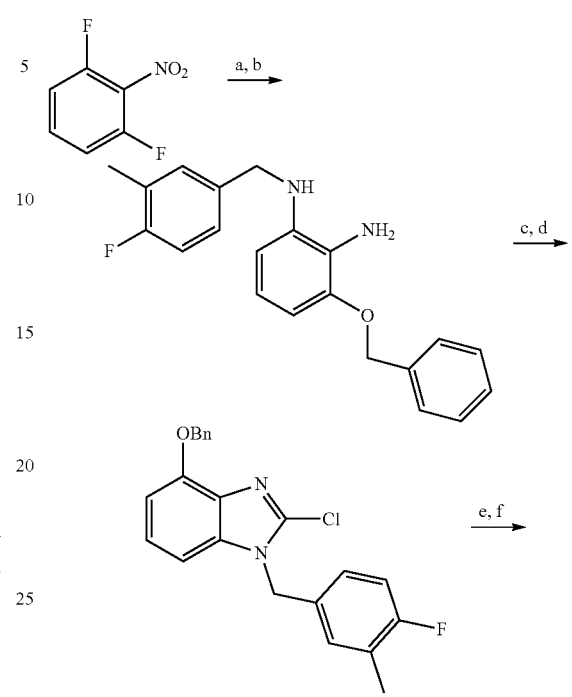

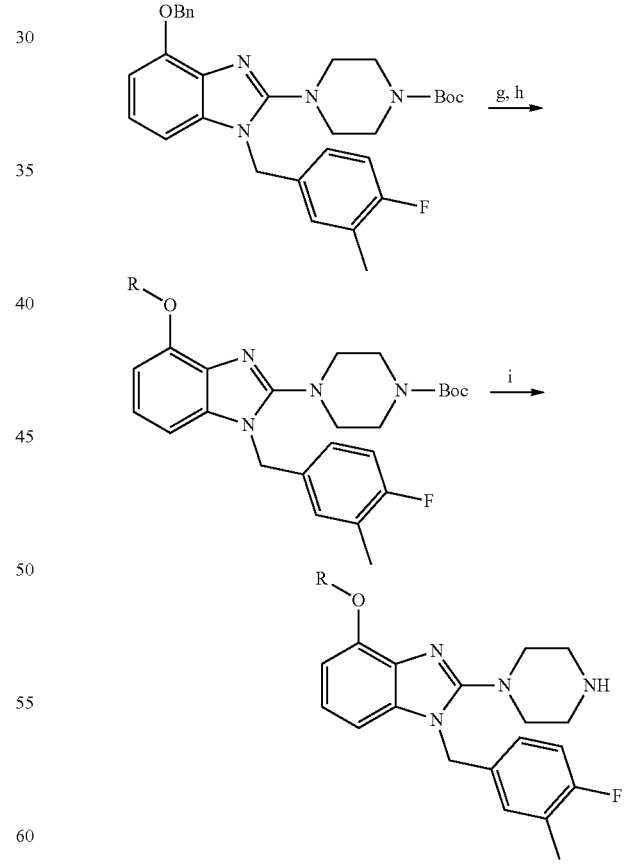

Reagent and Conditions: a) benzyl alcohol, NaH, DMF, 0-RT; b) benzylamine, K₂CO₃, DMF, 90° C.; c) H₂ (1 atm), rainey nickel, MeOH/THF, RT; d) CDI, DMAP, DMF, 85° C.; e) POCl₃, reflux; f) N-boc-piperazine, DIEA, NMP, 110° C.; g) H₂(1 atm), 10% Pd/C, EtOH/THF, RT; h) R-OH, DIAD, Ph₃P, THF, 0-RT; i) TFA, DCM, RT.

General Procedure T for Benzimidazole Preparation

Some benzimidazole analogs of the current invention may be prepared by the procedure outlined in Scheme 20. This procedure is exemplified by Example 212.

Scheme 20: Synthesis or tricyclic benzimidazole analogs.

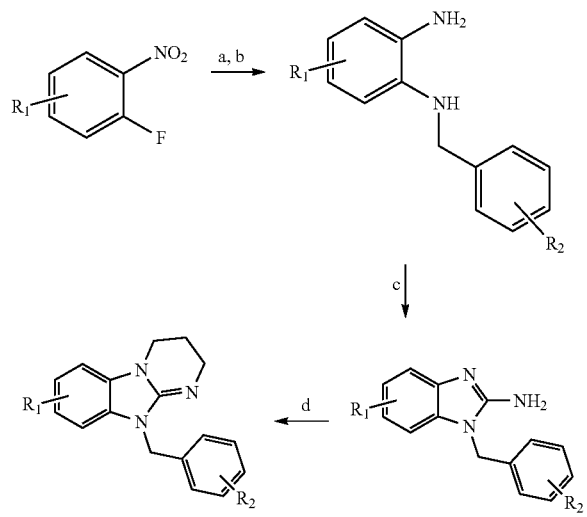

Reagents and Conditions: a) benzylamine, K$_2$CO$_3$, DMF, RT; b) Zn/NH$_4$Cl, MeOH, 0 - RT; c) cyanogen bromide, MeCN, rt; d) 1,3-dibromopropane, NaH, DMF.

General Procedure U for Imidazopyridine Preparation

Some imidazopyridine analogs of the current invention may be prepared by the procedure outlined in Scheme 21. This procedure is exemplified by Example 216.

Scheme 21: Synthesis of imidazo[4,5-c]pyridines.

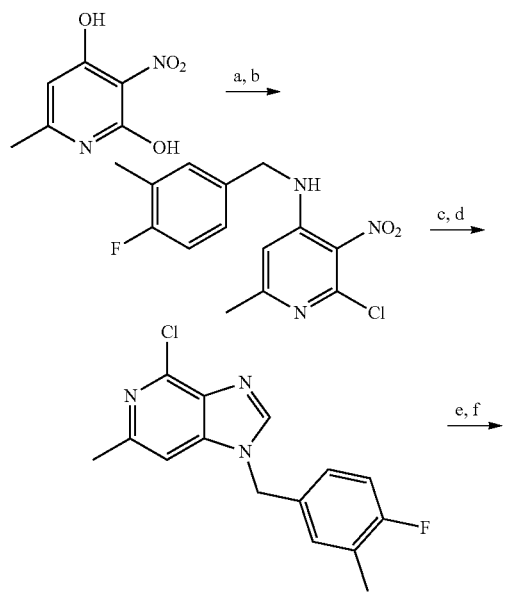

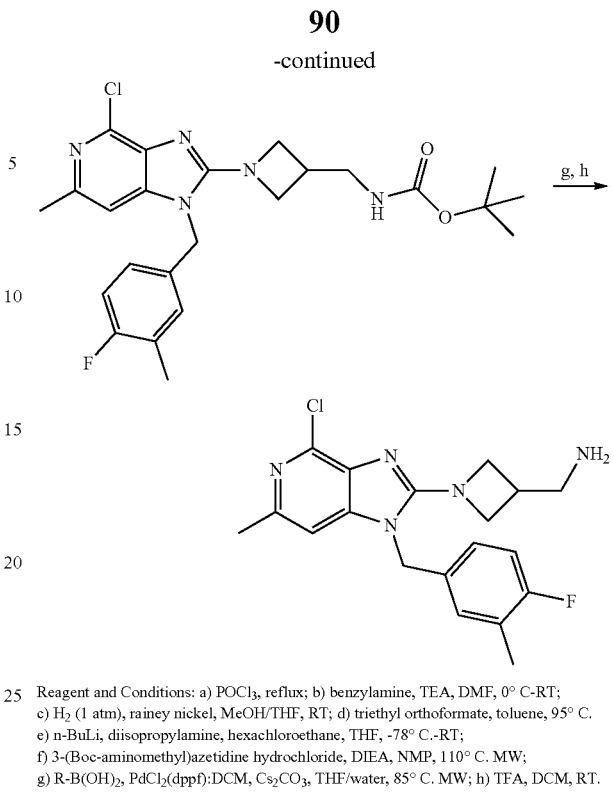

Reagent and Conditions: a) POCl$_3$, reflux; b) benzylamine, TEA, DMF, 0° C-RT; c) H$_2$ (1 atm), rainey nickel, MeOH/THF, RT; d) triethyl orthoformate, toluene, 95° C. e) n-BuLi, diisopropylamine, hexachloroethane, THF, -78° C.-RT; f) 3-(Boc-aminomethyl)azetidine hydrochloride, DIEA, NMP, 110° C. MW; g) R-B(OH)$_2$, PdCl$_2$(dppf):DCM, Cs$_2$CO$_3$, THF/water, 85° C. MW; h) TFA, DCM, RT.

General Procedure V for Imidazopyridine Preparation

Some imidazopyridine analogs of the current invention may be prepared by the procedure outlined in Scheme 22. This procedure is exemplified by Example 217.

Scheme 22: Synthesis of imidazo[4,5-c]pyridines.

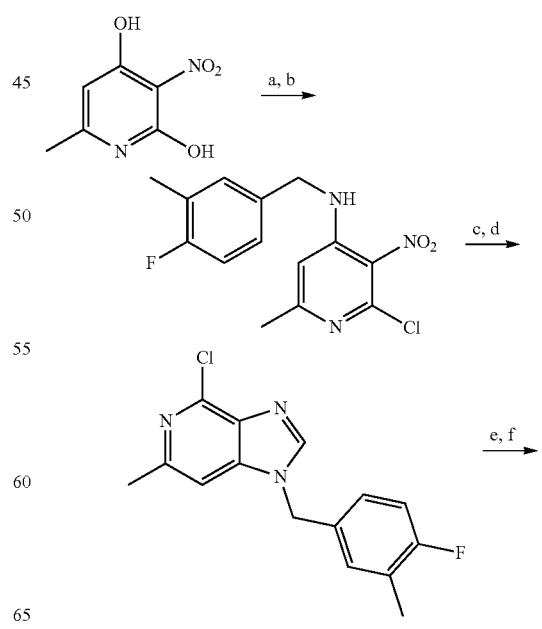

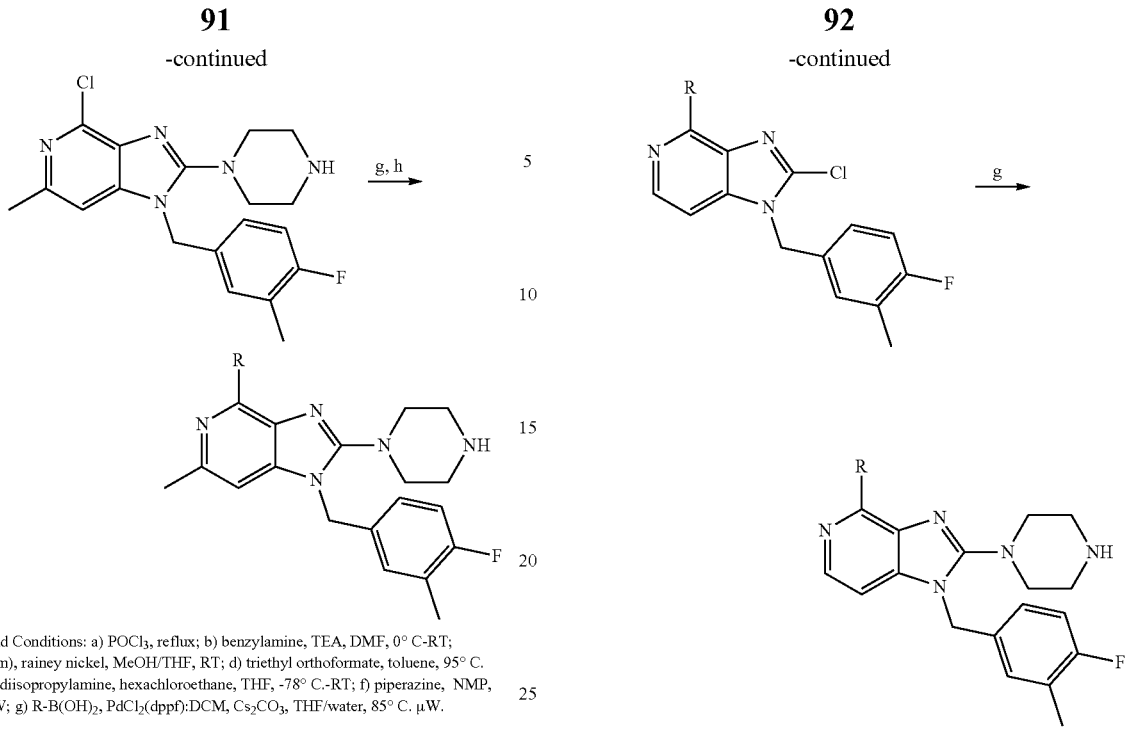

Reagent and Conditions: a) POCl₃, reflux; b) benzylamine, TEA, DMF, 0° C-RT; c) H₂ (1 atm), rainey nickel, MeOH/THF, RT; d) triethyl orthoformate, toluene, 95° C. e) n-BuLi, diisopropylamine, hexachloroethane, THF, -78° C.-RT; f) piperazine, NMP, 150° C. μW; g) R-B(OH)₂, PdCl₂(dppf):DCM, Cs₂CO₃, THF/water, 85° C. μW.

General Procedure W for Imidazopyridine Preparation

Some imidazopyridine analogs of the current invention may be prepared by the procedure outlined in Scheme 23. This procedure is exemplified by Example 221.

Scheme 23: Synthesis of imidazo[4,5-c]pyridines.

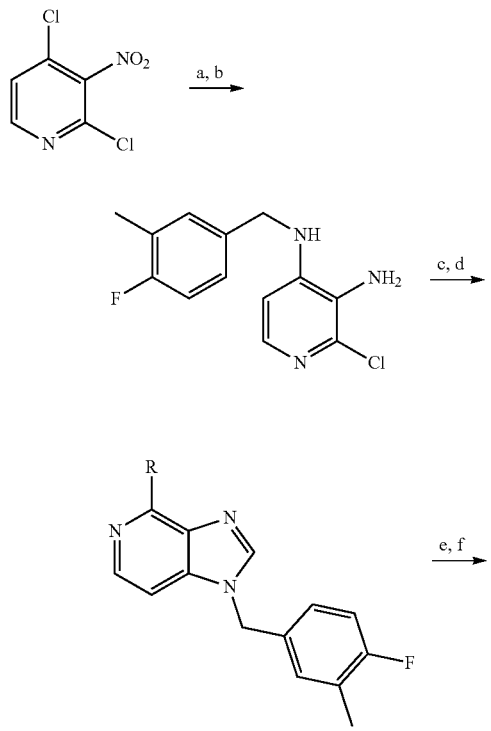

Reagent and Conditions: a) POCl₃, reflux; b) benzylamine, TEA, DMF, 0° C-RT; c) H₂ (1 atm), rainey nickel, MeOH/THF, RT; d) triethyl orthoformate, toluene, 95° C.; e) R-B(OH)₂, PdCl₂(dppf): DCM, Cs₂CO₃, THF/water, 85° C. μW; f) n-BuLi, diisopropylamine, hexachloroethane, THF, -78° C. RT; g) piperazine, NMP 120° C. μW.

General Procedure X for Imidazopyridine Preparation

Some imidazopyridine analogs of the current invention may be prepared by the procedure outlined in Scheme 24. This procedure is exemplified by Example 224.

Scheme 24: Synthesis of imidazo[4,5-c]pyridines.

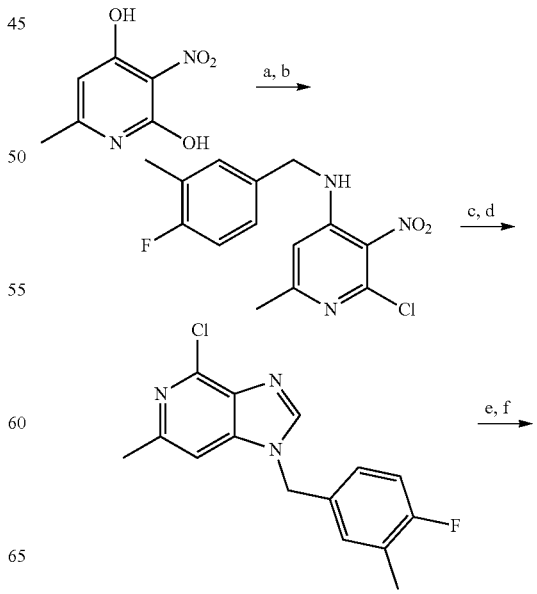

93
-continued

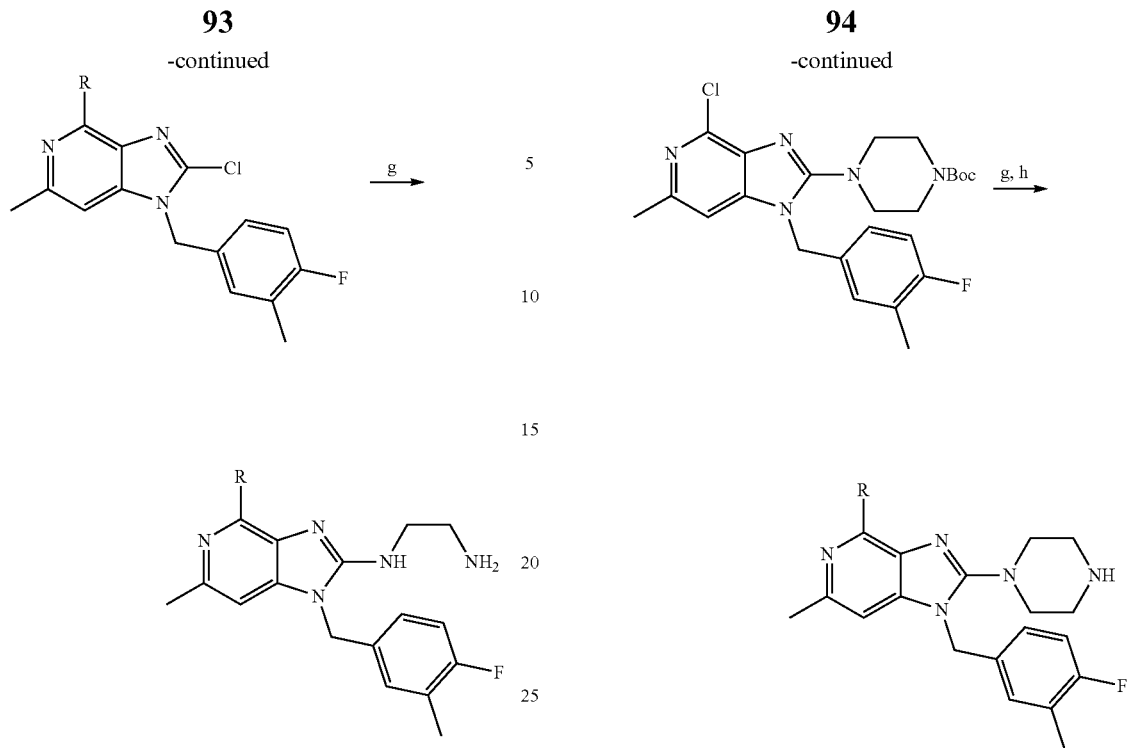

Reagent and Conditions: a) POCl₃, reflux; b) benzylamine, TEA, DMF, 0° C-RT; c) H₂ (1 atm), rainey nickel, MeOH/THF, RT; d) triethyl orthoformate, toluene, 95° C.; e) R-B(OH)₂, PdCl₂(dppf): DCM, Cs₂CO₃, THF/water, 85° C. μW; f) n-BuLi,; diisopropylamine, hexachloroethane, THF, -78° C.-RT; g) ethylenediamine, NMP 150° C. μW.

94
-continued

Reagent and Conditions: a) POCl₃, reflux; b) benzylamine, TEA, DMF, 0° C-RT; c) H₂ (1 atm), rainey nickel, MeOH/THF, RT; d) 1,1′-carbonyldiimidazole, DMAP, DMF, 75° C.; e) POCl₃, reflux; f) N-boc-piperazine, DIEA, NMP, 80° C.; g) R-B(OH)₂, Pd(OAc)₂, P(Cy)₃HBF₄K₃PO₄, DME/water, 105° C.; h) TFA, DCM.

General Procedure Y for Imidazopyridine Preparation

Some imidazopyridine analogs of the current invention may be prepared by the procedure outlined in Scheme 25. This procedure is exemplified by Example 226.

General Procedure Z for Imidazopyridine Preparation

Some imidazopyridine analogs of the current invention may be prepared by the procedure outlined in Scheme 26. This procedure is exemplified by Example 231.

Scheme 25: Synthesis of imidazo[4,5-c]pyridines.

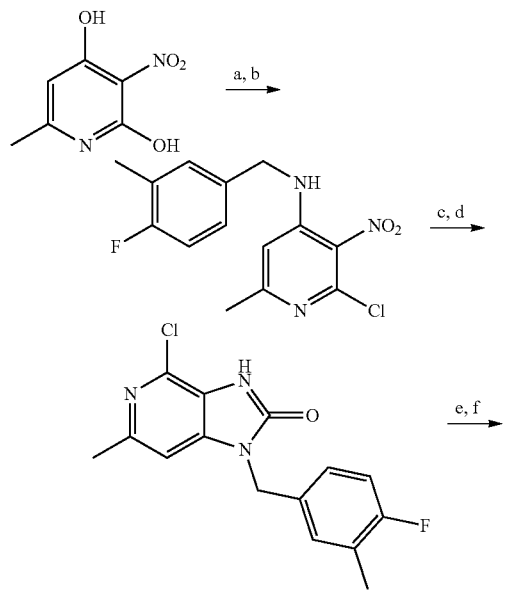

Scheme 26: Synthesis of imidazo[4,5-c]pyridines.

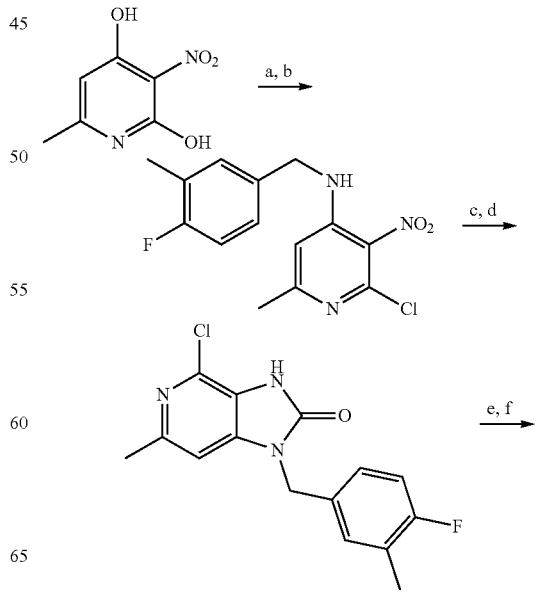

-continued

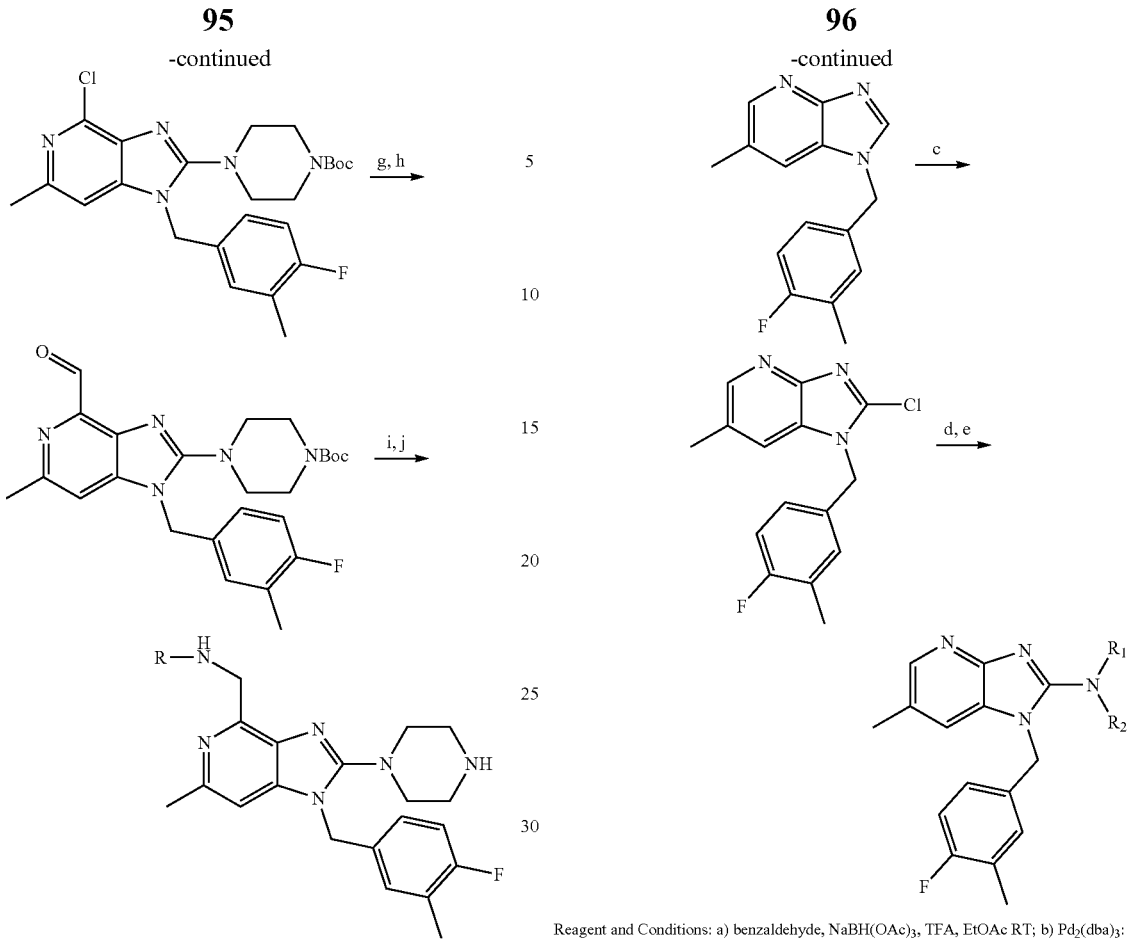

Reagent and Conditions: a) POCl₃, reflux; b) benzylamine, TEA, DMF, 0° C-RT; c) H₂ (1 atm), rainey nickel, MeOH/THF, RT; d) 1,1'-carbonyldiimidazole, DMAP, DMF, 75° C.; e) POCl₃, reflux; f) N-boc-piperazine, DIEA, NMP, 80° C.; g) vinyl-boronic acid pinacol ester, Pd(OAc)₂, P(Cy)₃HBF₄K₃PO₄, DME/water, 105° C.; h) OsO₄, NaIO₄, dioxane/water; i) R-NH₂, NaBH(OAc)₃, acetic acid, DCE; j) TFA, DCM.

General Procedure AA for Imidazopyridine Preparation

Some imidazopyridine analogs of the current invention may be prepared by the procedure outlined in Scheme 27. This procedure is exemplified by Example 240.

Scheme 27: Synthesis of imidazo[4,5-c]pyridines.

Reagent and Conditions: a) benzaldehyde, NaBH(OAc)₃, TFA, EtOAc RT; b) Pd₂(dba)₃: CHCl₃, Me-tert-butylXPhos, K₃PO₄, tert-butanol, 110° C.; c) n-BuLi, diisopropylamine, hexachloroethane, THF, -78° C. -RT; d) HNR₁R₂, DIEA, NMP, 120° C. μW; e) TFA, DCM General Procedure AB for Imidazopyridine Preparation Some imidazopyridine analogs of the current invention may be prepared by the procedure outlined in Scheme 28. This procedure is exemplified by Example 249.

Scheme 28: Synthesis of imidazo[4,5-b]pyridines.

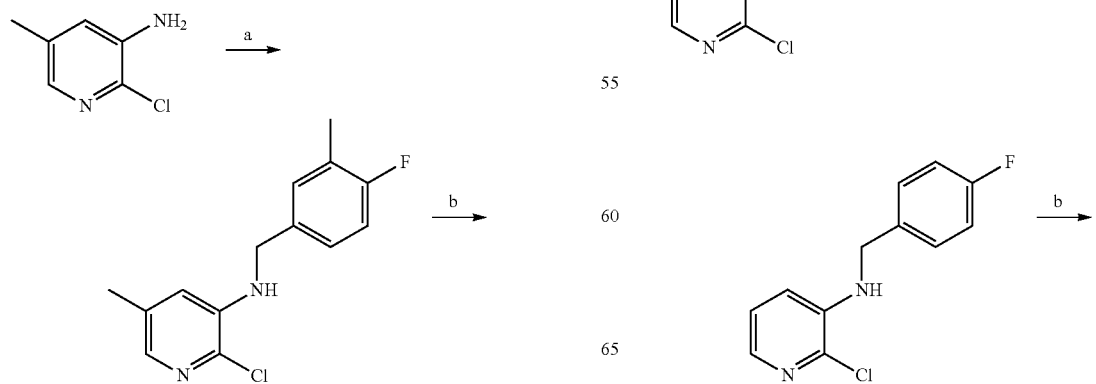

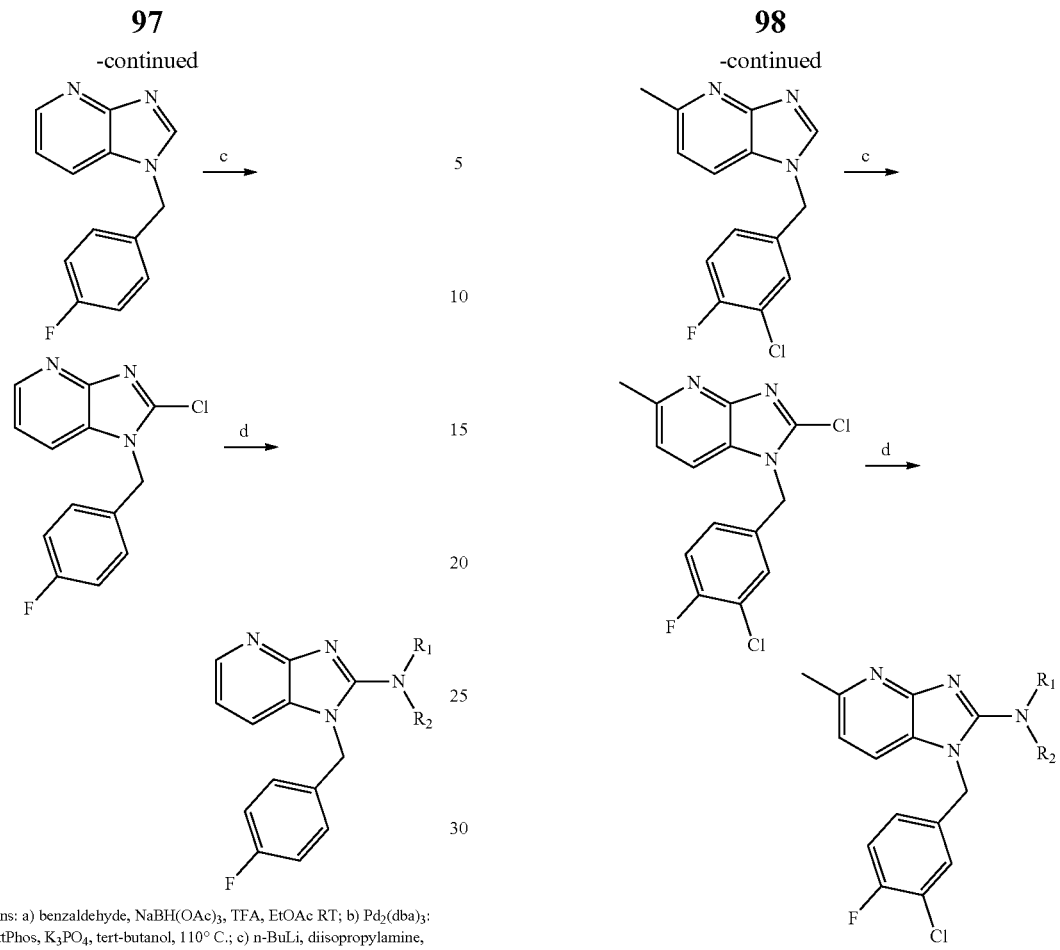

Reagent and Conditions: a) benzaldehyde, NaBH(OAc)$_3$, TFA, EtOAc RT; b) Pd$_2$(dba)$_3$:CHCl$_3$, tert-ButylBrettPhos, K$_3$PO$_4$, tert-butanol, 110° C.; c) n-BuLi, diisopropylamine, hexachloroethane, THF, -78° C.-RT; d) HNR$_1$R$_2$, NMP, 110° C.;

Reagent and Conditions: a) benzaldehyde, NaBH(OAc)$_3$, TFA, EtOAc RT; b) Pd$_2$(dba)$_3$:CHCl$_3$, Me-t-butylBrettPhos, K$_3$PO$_4$, tert-butanol, 110° C.; c) n-BuLi, diisopropylamine, hexachloroethane, THF, -78° C.-RT; d) HNR$_1$R$_2$, DMSO, 55° C.;

General Procedure AC for Imidazopyridine Preparation

Some imidazopyridine analogs of the current invention may be prepared by the procedure outlined in Scheme 29. This procedure is exemplified by Example 256.

Scheme 29: Synthesis of imidazo[4,5-b]pyridines.

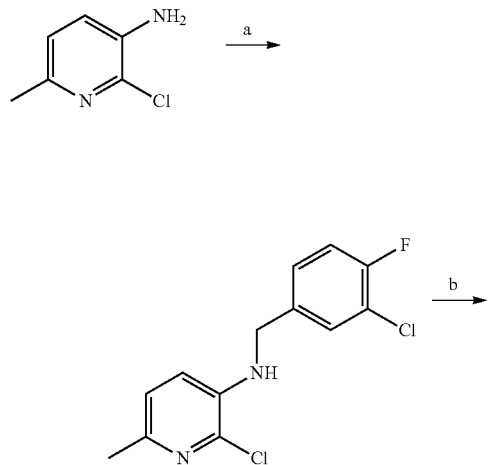

General Procedure AD for Imidazopyridine Preparation

Some imidazopyridine analogs of the current invention may be prepared by the procedure outlined in Scheme 30. This procedure is exemplified by Example 258.

Scheme 30: Synthesis of imidazo[4,5-b]pyridines.

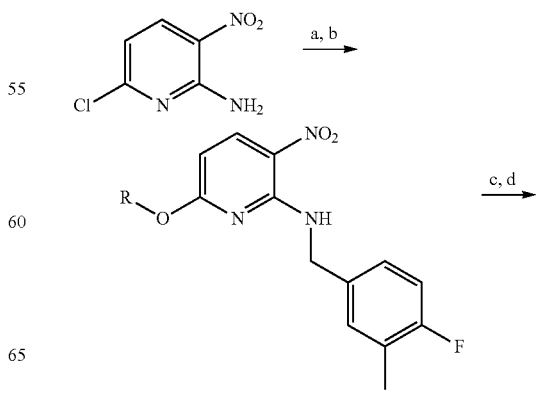

-continued

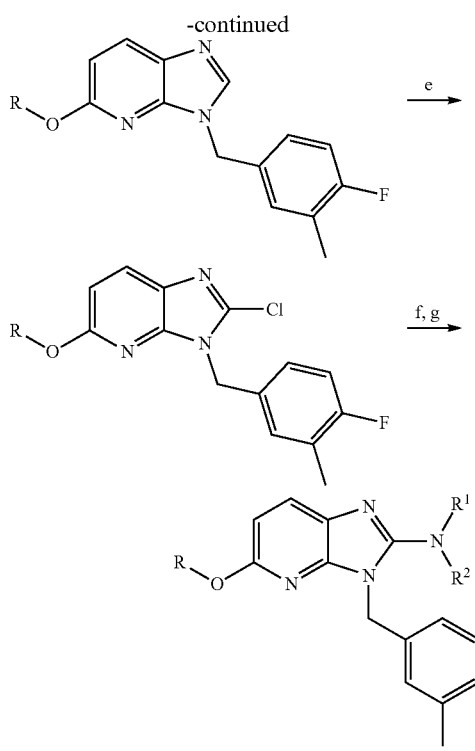

Reagent and Conditions: a) benzaldehyde, NaH, DMF, 0° C.-RT; b) R-OH, NaH, DMF, 0° C.-RT; c) H₂ (1atm), 10% Pd/C, MeOH/THF, RT; d) formic acid, 90° C.; e) n-BuLi, diisopropylamine, hexachloroethane, THF, -78° C.-RT; f) NHR¹R², NMP, 125° C.; g) TFA, DCM.

General Procedure AE for Benzimidazole Preparation

Some benzimidazole analogs of the current invention may be prepared by the procedure outlined in Scheme 31. This procedure is exemplified by Example 199.

Scheme 31: Synthesis of 4-alkoxybenzimdiazoles.

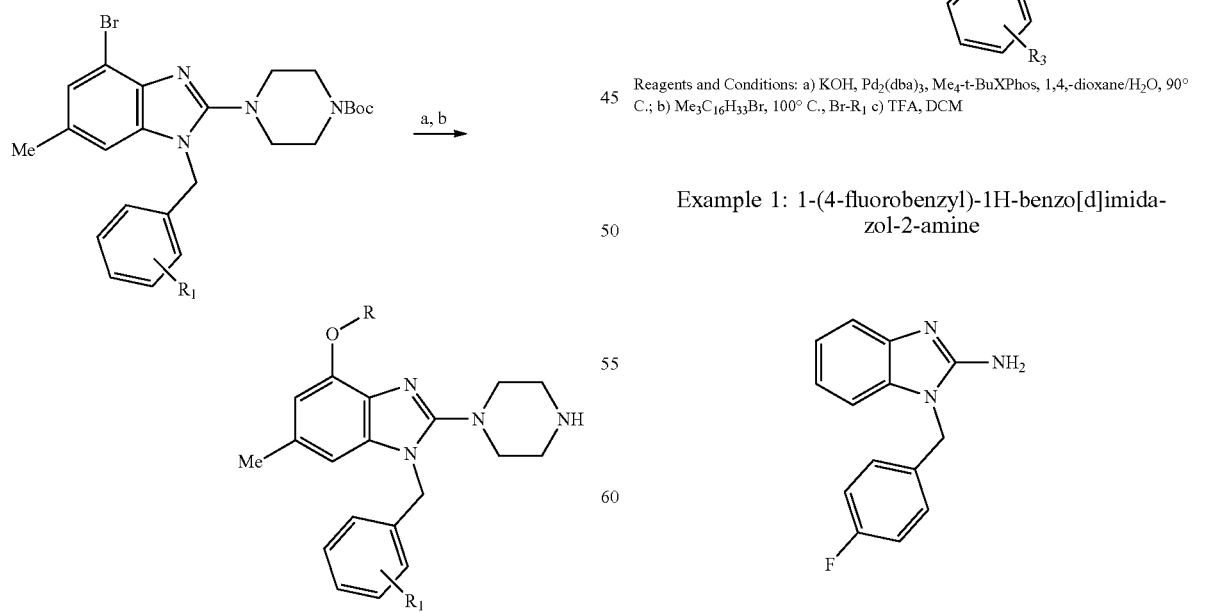

Reagents and Conditions: a) HOR, CuI, 8-Hydroxyquinoline, K₃PO₄, 110° C.; b) TFA, DCM General Procedure AF for Benzimidazole Preparation Some benzimidazole analogs of the current invention may be prepared by the procedure outlined in Scheme 32. This procedure is exemplified by Example 211.

Scheme 32: Synthesis of 4-alkoxybenzimdiazoles.

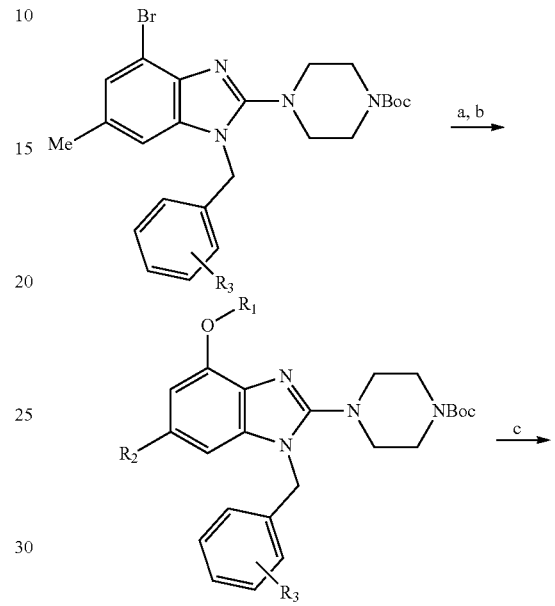

Reagents and Conditions: a) KOH, Pd₂(dba)₃, Me₄-t-BuXPhos, 1,4,-dioxane/H₂O, 90° C.; b) Me₃C₁₆H₃₃Br, 100° C., Br-R₁ c) TFA, DCM Example 1: 1-(4-fluorobenzyl)-1H-benzo[d]imidazol-2-amine Step A: To a stirred solution of 1,2-diaminobenzene (2.0 g, 18.5 mmol, 1 eq.) in acetonitrile (25 mL) and water (5 mL) was added a 5 M solution of cyanogen bromide in acetonitrile (4.0 mL, 20.4 mmol, 1.1 eq). The reaction was stirred at room temperature and the conversion of starting material was monitored by LCMS. Upon conversion by LCMS, the solvent was removed in vacuo and dried under high vacuum. The crude 1H-benzo[d]imidazol-2-amine was used without any further purification (2.4 g, quantitative yield).

Step B: The crude 1H-benzo[d]imidazol-2-amine (75 mg, 0.564 mmol, 1 eq) was dissolved in DMF (5 mL) in a reaction vessel. Potassium carbonate (93 mg, 0.67 mmol, 1.2 eq) was added to the reaction, followed by 4-fluorobenzyl-bromide (0.093 mL, 0.606 mmol, 1.3 eq). The reaction was stirred at room temperature and monitored by LCMS. Upon conversion of the starting material, the reaction was diluted with water and extracted with ethyl acetate. The organic layer was washed with water (2×) and a brine solution, dried over magnesium sulfate, and concentrated to afford a crude solid. The crude solid was purified by reverse-phase HPLC to provide the 1-(4-fluorobenzyl)-1H-benzo[d]imidazol-2-amine as a white solid (75 mg, 55%). $^1$H NMR (400 MHz, CD$_3$OD) δ 7.44 (d, J=8.0 Hz, 1H), 7.34 (ovlp m, 5H), 7.14 (t, J=8.8 Hz, 2H), 5.41 (s, 2H). MS (ESI) (M+H$^+$) m/z=242.20. LCMS Ret time (UV 214/254): 1.093 min.

Example 2: 1-(3-chloro-4-fluorobenzyl)-1H-benzo[d]imidazol-2-amine

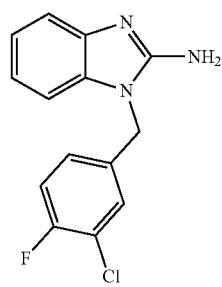 [SMILES: Nc1nc2ccccc2n1Cc1ccc(F)c(Cl)c1]

The title compound was obtained according to a procedure analogous to general procedure A. 50% yield. $^1$H NMR (400 MHz, CD$_3$OD) δ 7.46 (ovlp m, 2H), 7.35 (ovlp m, 3H), 7.27 (ovlp m, 2H), 5.42 (s, 2H). MS (ESI) (M+H$^+$) m/z=276.10. LCMS Ret time (UV 214/254): 1.165 min.

Example 3: 1-(4-fluorobenzyl)-5,6-dimethyl-1H-benzo[d]imidazol-2-amine

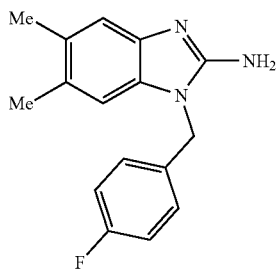 [SMILES: Cc1cc2nc(N)n(Cc3ccc(F)cc3)c2cc1C]

The title compound was obtained according to a procedure analogous to general procedure A, replacing with 4,5-dimethyl-1,2-diaminobenzene. 40% yield. $^1$H NMR (400 MHz, CD$_3$OD) δ 7.32 (d, J=5.2, 1H), 7.30 (d, J=5.2 Hz, 1H), 7.21 (s, 1H), 7.15 (s, 1H), 7.13 (t, J=5.2 Hz, 2H), 5.36 (s, 2H), 2.35 (s, 3H), 2.32 (s, 3H). MS (ESI) (M+H$^+$) m/z=270.10. LCMS Ret time (UV 214/254): 1.257 min.

Example 4: 1-(3-chloro-4-fluorobenzyl)-5,6-dimethyl-1H-benzo[d]imidazol-2-amine

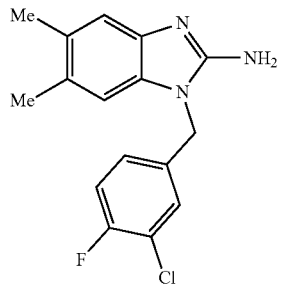 [SMILES: Cc1cc2nc(N)n(Cc3ccc(F)c(Cl)c3)c2cc1C]

The title compound was obtained according to a procedure analogous to general procedure A, replacing with 4,5-dimethyl-1,2-diaminobenzene. 53% yield. $^1$H NMR (400 MHz, CD$_3$OD) δ 7.43 (dd, J=6.8, 2.1 Hz, 1H), 7.27 (t, J=8.7 Hz, 1H), 7.23 (s, 1H), 7.21 (m, 1H), 7.16 (s, 1H), 5.36 (s, 2H), 2.36 (s, 3H), 2.33 (s, 3H). MS (ESI) (M+H$^+$) m/z=304.10. LCMS Ret time (UV 214/254): 1.345 min.

Example 5: 1-(4-chlorobenzyl)-5,6-dimethyl-1H-benzo[d]imidazol-2-amine

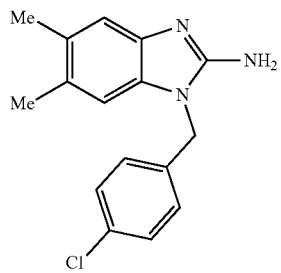 [SMILES: Cc1cc2nc(N)n(Cc3ccc(Cl)cc3)c2cc1C]

The title compound was obtained according to a procedure analogous to general procedure A, replacing with 4,5-dimethyl-1,2-diaminobenzene. 40% yield. MS (ESI) (M+H$^+$) m/z=286.10. LCMS Ret time (UV 214/254): 1.339 min.

Example 6: 1-(3,5-difluorobenzyl)-5,6-dimethyl-1H-benzo[d]imidazol-2-amine

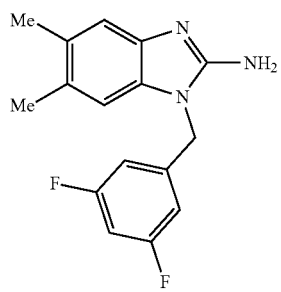 [SMILES: Cc1cc2nc(N)n(Cc3cc(F)cc(F)c3)c2cc1C]

The title compound was obtained according to a procedure analogous to general procedure A, replacing with 4,5-dimethyl-1,2-diaminobenzene. 60% yield. MS (ESI) (M+H⁺) m/z=288.10. LCMS Ret time (UV 214/254): 1.295 min.

Example 7: 1-(3-chloro-4-fluorobenzyl)-2-(piperazin-1-yl)-1H-benzo[d]imidazole trifluoroacetate

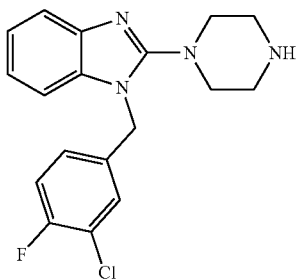 [SMILES: Fc1ccc(Cn2c(N3CCNCC3)nc3ccccc32)cc1Cl]

Step A: 1,2-diaminobenzene (5.0 g, 46.3 mmol, 1 eq) was placed in a 250 mL round bottom flask equipped with a stir bar. Xylenes (100 mL) was added to the flask, followed by urea (3.11 g, 51.8 mmol, 1.1 eq). The reaction mixture was heated at 130° C. under a reflux condenser. The solids dissolved when elevated temperatures were reached. Upon conversion by LCMS (18 hr), the reaction was cooled to room temperature and the solid product was filtered and dried over air. The crude 1,3-dihydro-2H-benzo[d]imidazol-2-one was used without any further purification.

Step B: The crude 1,3-dihydro-2H-benzo[d]imidazol-2-one was placed in 250 mL RBF flask with stir bar and POCl3 (100 mL) was added. The reaction mixture was heated at 100° C. under a reflux condenser. Upon conversion by LCMS of a reaction aliquot, the flask was cooled to room temperature, then 0° C. The solution was carefully and slowly (batch-wise) added to a large Erlenmeyer flask containing ice water. After all of the excess POCl₃ was quenched at 0° C., solid NaOH pellets were added to the flask at 0° C. to neutral pH. The resulting solid was filtered and dried to obtain the 2-chlorobenzimidazole as a white solid (5.5 g, 78% yield).

Step C: The crude 2-chlorobenzimidazole (100 mg, 0.575 mmol, 1 eq) was dissolved in DMF (5 mL) in a reaction vial. Potassium carbonate (95 mg, 0.69 mmol, 1.2 eq) was added to the reaction, followed by 4-fluoro-3-chlorobenzylbromide (0.093 mL, 0.69 mmol, 1.3 eq). The reaction was stirred at room temperature and monitored by LCMS. Upon conversion of the starting material, the reaction was diluted with water and extracted with ethyl acetate. The organic layer was washed with water (2×) and a brine solution, dried over magnesium sulfate, and concentrated to afford a crude solid. The crude solid was purified by column chromatography to afford the 2-chloro-1-(3-chloro-4-fluorobenzyl)-1H-benzo[d]imidazole as a white solid (120 mg, 71%).

Step D: The 2-chloro-1-(3-chloro-4-fluorobenzyl)-1H-benzo[d]imidazole (55 mg, 0.192, 1 eq) was dissolved in DMA (1.5 mL) in a microwave tube. Piperazine (82 mg, 0.96 mmol, 5 eq) was added to the tube, which was then sealed and heated in a microwave reactor at 165° C. for 45 min. Upon conversion of the starting material by LCMS, the reaction was diluted with water and extracted with dichloromethane and then passed through a phase separator. The organic layer was concentrated to a crude oil, which was purified by reverse-phase HPLC to afford 1-(3-chloro-4-fluorobenzyl)-2-(piperazin-1-yl)-1H-benzo[d]imidazole trifluoroacetate as a white TFA salt (30 mg, 45% yield). ¹H NMR (400 MHz, CD₃OD) δ ☐7.62 (d, J=7.8 Hz, 1H), 7.43 (dd, J=6.9, 2.2 Hz, 1H), 7.37 (m, 1H), 7.32 (ovlp m, 2H), 7.27 (t, J=8.8 Hz, 1H), 7.18 (m, 1H), 5.47 (s, 2H), 3.64 (t, J=5.2 Hz, 4H), 3.46 (t, J=5.2 Hz, 4H). MS (ESI) (M+H⁺) m/z=345.10. LCMS Ret time (UV 214/254): 1.073 min.

Example 8: 4-(1-(3-chloro-4-fluorobenzyl)-1H-benzo[d]imidazol-2-yl)morpholine

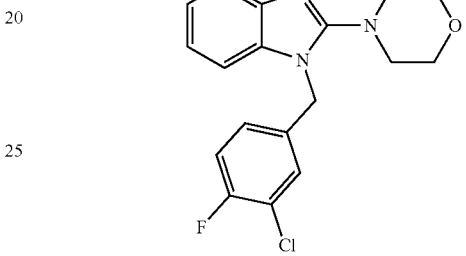

The title compound was obtained according to a procedure analogous to general procedure B: 41% yield. ¹H NMR (400 MHz, CD₃OD) δ ☐7.59 (d, J=8.0 Hz, 1H), 7.48 (d, J=4.8 Hz, 1H), 7.43 (t, J=6.5 Hz, 1H), 7.37 (ovlp m, 2H), 7.28 (d, J=8.0 Hz, 1H), 7.24 (m, 1H), 5.49 (s, 1H), 3.85 (t, J=4.7 Hz, 4H), 3.50 (t, J=4.7 Hz, 4H). MS (ESI) (M+H⁺) m/z=346.00. LCMS Ret time (UV 214/254): 1.230 min.

Example 9: 4-(1-(4-fluorobenzyl)-1H-benzo[d]imidazol-2-yl)morpholine

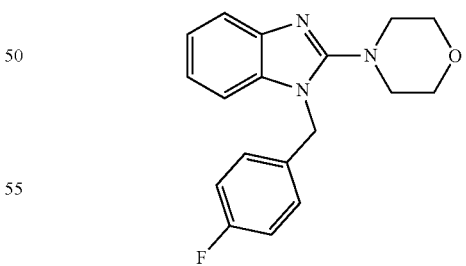

The title compound was obtained according to a procedure analogous to general procedure B: 66% yield. MS (ESI) (M+H⁺) m/z=312.10. LCMS Ret time (UV 214/254): 1.130 min.

Example 10: 1-(4-fluorobenzyl)-2-(piperazin-1-yl)-1H-benzo[d]imidazole trifluoroacetate

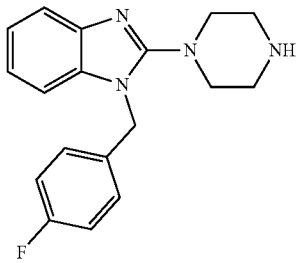 [SMILES: Fc1ccc(Cn2c(N3CCNCC3)nc3ccccc32)cc1]

The title compound was obtained according to a procedure analogous to general procedure B: 60% yield. MS (ESI) (M+H$^+$) m/z=311.10. LCMS Ret time (UV 214/254): 0.981 min.

Example 11: 1-(4-chlorobenzyl)-2-(piperazin-1-yl)-1H-benzo[d]imidazole trifluoroacetate

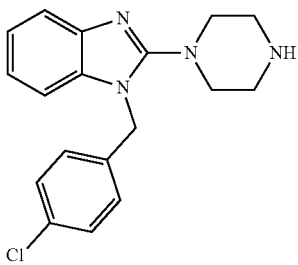 [SMILES: Clc1ccc(Cn2c(N3CCNCC3)nc3ccccc32)cc1]

The title compound was obtained according to a procedure analogous to general procedure B: 55% yield. $^1$H NMR (400 MHz, CD$_3$OD) δ □7.65 (d, J=8.0 Hz, 2H), 7.42 (ovlp m, 5H), 7.29 (d, J=8.0 Hz, 2H), 5.55 (s, 2H), 3.77 (t, J=5.2 Hz, 4H), 3.47 (t, J=5.2 Hz, 4H). MS (ESI) (M+H$^+$) m/z=327.10. LCMS Ret time (UV 214/254): 1.053 min.

Example 12: N$^1$-(1-(4-chlorobenzyl)-1H-benzo[d]imidazol-2-yl)ethane-1,2-diamine trifluoroacetate

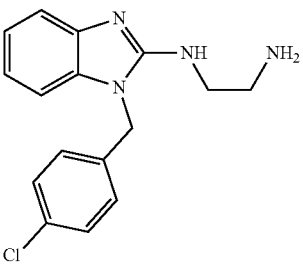 [SMILES: NCCNc1nc2ccccc2n1Cc1ccc(Cl)cc1]

The title compound was obtained according to a procedure analogous to general procedure B: 23% yield. MS (ESI) (M+H$^+$) m/z=301.20. LCMS Ret time (UV 214/254): 1.077 min.

Example 13: 4-(1-(3,5-difluorobenzyl)-1H-benzo[d]imidazol-2-yl)morpholine

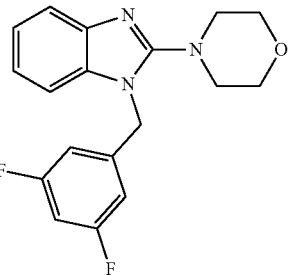

The title compound was obtained according to a procedure analogous to general procedure B: 38% yield. MS (ESI) (M+H$^+$) m/z=330.10. LCMS Ret time (UV 214/254): 1.168 min.

Example 14: 1-(3,5-difluorobenzyl)-2-(piperazin-1-yl)-1H-benzo[d]imidazole trifluoroacetate

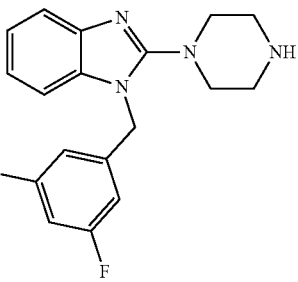

The title compound was obtained according to a procedure analogous to general procedure B: 3836% yield. MS (ESI) (M+H$^+$) m/z=329.10. LCMS Ret time (UV 214/254): 0.942 min.

Example 15: N$^1$-(1-(3,5-difluorobenzyl)-1H-benzo[d]imidazol-2-yl)ethane-1,2-diamine trifluoroacetate

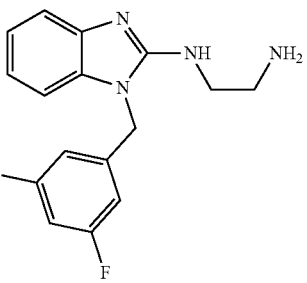

The title compound was obtained according to a procedure analogous to general procedure B: 17% yield. MS (ESI) (M+H$^+$) m/z=303.10. LCMS Ret time (UV 214/254): 1.030 min.

Example 16: 1-(3-chloro-4-fluorobenzyl)-5,6-dimethyl-2-(piperazin-1-yl)-1H-benzo[d]imidazole trifluoroacetate

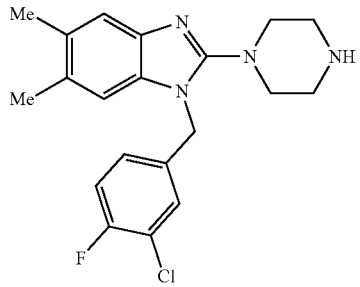 [SMILES: Cc1cc2nc(N3CCNCC3)n(Cc3ccc(F)c(Cl)c3)c2cc1C]

The title compound was obtained according to a procedure analogous to general procedure B: 28% yield. MS (ESI) (M+H$^+$) m/z=373.10. LCMS Ret time (UV 214/254): 1.239 min.

Example 17: N1-(1-(3-chloro-4-fluorobenzyl)-5,6-dimethyl-1H-benzo[d]imidazol-2-yl)ethane-1,2-diamine trifluoroacetate

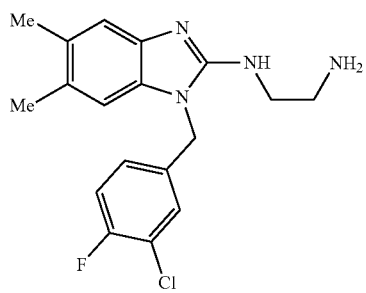 [SMILES: Cc1cc2nc(NCCN)n(Cc3ccc(F)c(Cl)c3)c2cc1C]

The title compound was obtained according to a procedure analogous to general procedure B wherein the reaction parameters were modified to the following: i-Pr$_2$NEt, NMP, 150° C. μW.: 15% yield. $^1$H NMR (400 MHz, CD$_3$OD) δ 7.43 (dd, J=7.0, 1.9 Hz, 1H), 7.29 (s, 1H), 7.22 (2m ovlp, 2H), 7.13 (s, 1H), 5.39 (s, 2H), 3.85 (t, J=6.0 Hz, 2H), 3.33 (m, 2H), 2.36 (s, 3H), 2.32 (s, 3H). MS (ESI) (M+H$^+$) m/z=347.20. LCMS Ret time (UV 214/254): 1.154 min.

Example 18: 1-(3,5-difluorobenzyl)-5,6-dimethyl-2-(piperazin-1-yl)-1H-benzo[d]imidazole trifluoroacetate

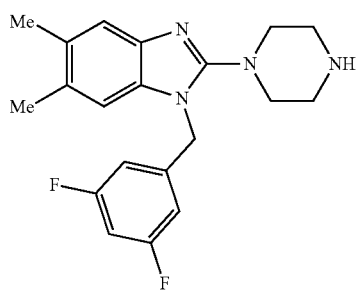 [SMILES: Cc1cc2nc(N3CCNCC3)n(Cc3cc(F)cc(F)c3)c2cc1C]

The title compound was obtained according to a procedure analogous to general procedure B: 39% yield. MS (ESI) (M+H$^+$) m/z=357.10. LCMS Ret time (UV 214/254): 1.201 min.

Example 19: 1-(4-chlorobenzyl)-5,6-dimethyl-2-(piperazin-1-yl)-1H-benzo[d]imidazole trifluoroacetate

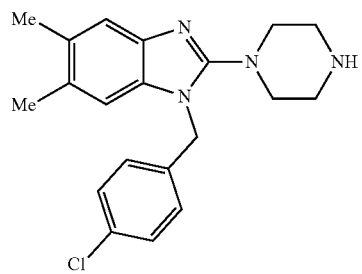 [SMILES: Cc1cc2nc(N3CCNCC3)n(Cc3ccc(Cl)cc3)c2cc1C]

The title compound was obtained according to a procedure analogous to general procedure B: 35% yield. MS (ESI) (M+H$^+$) m/z=355.10. LCMS Ret time (UV 214/254): 1.190 min.

Example 20: N$^1$-(1-(4-chlorobenzyl)-5,6-dimethyl-1H-benzo[d]imidazol-2-yl)ethane-1,2-diamine trifluoroacetate

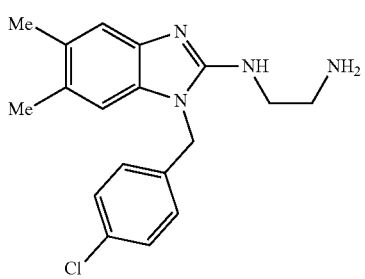 [SMILES: Cc1cc2nc(NCCN)n(Cc3ccc(Cl)cc3)c2cc1C]

The title compound was obtained according to a procedure analogous to general procedure B: 21% yield. MS (ESI) (M+H$^+$) m/z=329.10. LCMS Ret time (UV 214/254): 1.326 min.

Example 21: 1-(4-fluorobenzyl)-5,6-dimethyl-2-(piperazin-1-yl)-1H-benzo[d]imidazole trifluoroacetate

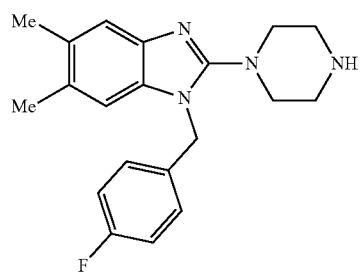 [SMILES: Cc1cc2nc(N3CCNCC3)n(Cc3ccc(F)cc3)c2cc1C]

The title compound was obtained according to a procedure analogous to general procedure B: 34% yield. MS (ESI) (M+H$^+$) m/z=339.10. LCMS Ret time (UV 214/254): 1.147 min.

Example 22: N$^1$-(1-(4-fluorobenzyl)-5,6-dimethyl-1H-benzo[d]imidazol-2-yl)ethane-1,2-diamine trifluoroacetate

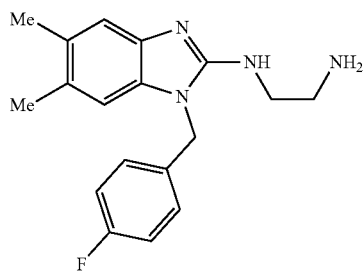 [SMILES: Cc1cc2nc(NCCN)n(Cc3ccc(F)cc3)c2cc1C]

The title compound was obtained according to a procedure analogous to general procedure B: 15% yield. MS (ESI) (M+H$^+$) m/z=313.20. LCMS Ret time (UV 214/254): 1.196 min.

Example 23: 2-((1-(4-fluorobenzyl)-5,6-dimethyl-1H-benzo[d]imidazol-2-yl)amino)ethan-1-ol

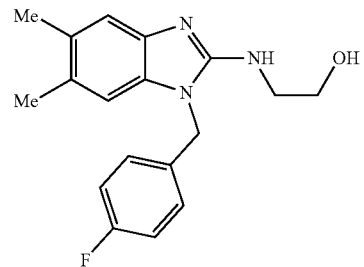 [SMILES: Cc1cc2nc(NCCO)n(Cc3ccc(F)cc3)c2cc1C]

The title compound was obtained according to a procedure analogous to general procedure B: 19% yield. MS (ESI) (M+H$^+$) m/z=314.20. LCMS Ret time (UV 214/254): 1.209 min.

Example 24: 1-(4-fluorobenzyl)-5,6-dimethyl-2-(4-methylpiperazin-1-yl)-1H-benzo[d]imidazole trifluoroacetate

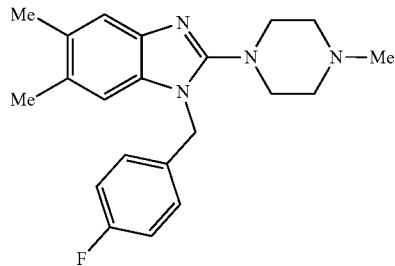 [SMILES: Cc1cc2nc(N3CCN(C)CC3)n(Cc3ccc(F)cc3)c2cc1C]

The title compound was obtained according to a procedure analogous to general procedure B: 45% yield. MS (ESI) (M+H$^+$) m/z=353.20. LCMS Ret time (UV 214/254): 1.078 min.

Example 25: N$^1$-(1-(4-fluorobenzyl)-5,6-dimethyl-1H-benzo[d]imidazol-2-yl)-N,N2-dimethylethane-1,2-diamine trifluoroacetate

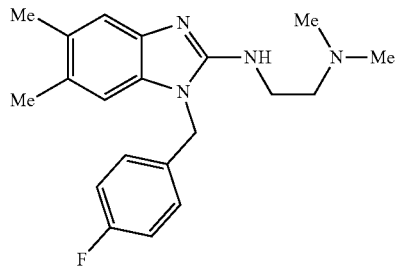 [SMILES: Cc1cc2nc(NCCN(C)C)n(Cc3ccc(F)cc3)c2cc1C]

The title compound was obtained according to a procedure analogous to general procedure B: 18% yield. $^1$H NMR (400 MHz, CDCl$_3$) δ 9.90 (br s, 1H), 7.32 (s, 1H) 7.19 (dd, J=8.5, 5.2 Hz, 2H), 7.03 (t, J=8.5 Hz, 2H), 6.98 (s, 1H), 5.30 (s, 2H), 4.08 (br s, 4H), 3.53 (br s, 4H), 2.90 (s, 6H), 2.36 (s, 3H), 2.34 (s, 3H). MS (ESI) (M+H$^+$) m/z=341.20. LCMS Ret time (UV 214/254): 1.105 min.

Example 26: 2-((1-(3-chloro-4-fluorobenzyl)-5,6-dimethyl-1H-benzo[d]imidazol-2-yl)amino)ethan-1-ol

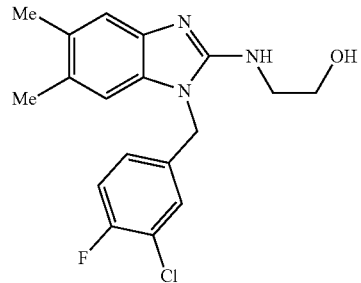 [SMILES: Cc1cc2nc(NCCO)n(Cc3ccc(F)c(Cl)c3)c2cc1C]

The title compound was obtained according to a procedure analogous to general procedure B: 17% yield. MS (ESI) (M+H$^+$) m/z=348.10. LCMS Ret time (UV 214/254): 1.283 min.

Example 27: 1-(3-chloro-4-fluorobenzyl)-5,6-dimethyl-2-(4-methylpiperazin-1-yl)-1H-benzo[d]imidazole trifluoroacetate

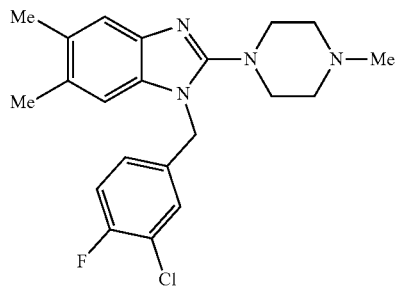 [SMILES: Cc1cc2nc(N3CCN(C)CC3)n(Cc3ccc(F)c(Cl)c3)c2cc1C]

The title compound was obtained according to a procedure analogous to general procedure B: 39% yield. ¹H NMR (400 MHz, CD₃OD) δ 7.38 (s, 1H), 7.25 (m, 2H), 7.14 (m, 1H), 7.09 (s, 1H), 5.40 (s, 2H), 3.54 (ovlp br s, 4H), 3.51 (ovlp br s, 4H), 2.99 (s, 3H), 2.38 (s, 3H), 2.34 (s, 3H). MS (ESI) (M+H⁺) m/z=387.10. LCMS Ret time (UV 214/254): 1.157 min.

Example 28: N¹-(1-(3-chloro-4-fluorobenzyl)-5,6-dimethyl-1H-benzo[d]imidazol-2-yl)-N²,N²-dimethylethane-1,2-diamine trifluoroacetate

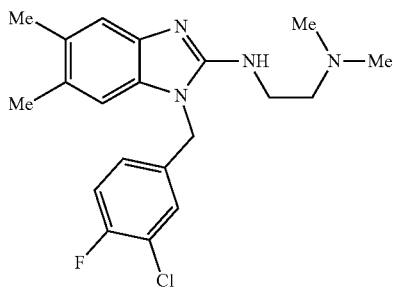 [SMILES: Cc1cc2nc(NCCN(C)C)n(Cc3ccc(F)c(Cl)c3)c2cc1C]

The title compound was obtained according to a procedure analogous to general procedure B: 20% yield. MS (ESI) (M+H⁺) m/z=375.10. LCMS Ret time (UV 214/254): 1.182 min.

Example 29: 1-(4-fluorobenzyl)-5,6-dimethyl-N-(2-morpholinoethyl)-1H-benzo[d]imidazol-2-amine trifluoroacetate

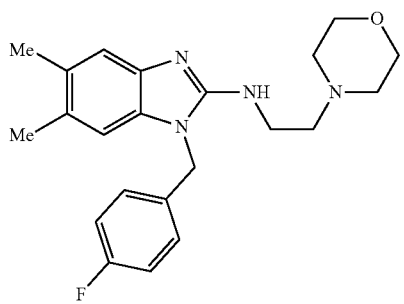 [SMILES: Cc1cc2nc(NCCN3CCOCC3)n(Cc3ccc(F)cc3)c2cc1C]

The title compound was obtained according to a procedure analogous to general procedure B: 45% yield. ¹H NMR (400 MHz, CDCl₃) δ 9.95 (br s, 1H), 7.29 (s, 1H), 7.16 (dd, J=8.5, 2.0 Hz, 2H), 7.01 (t, J=8.7 Hz, 2H), 6.98 (s, 1H), 5.28 (s, 2H), 4.10 (d, J=4.5 Hz, 2H), 3.93 (ovlp, 4H), 3.49 (t, J=6.0 Hz, 2H), 3.28 (d, J=12.1 Hz, 2H), 3.10 (t, J=6.0 Hz, 2H), 2.35 (s, 3H), 2.33 (s, 3H). MS (ESI) (M+H⁺) m/z=383.20. LCMS Ret time (UV 214/254): 1.116 min.

Example 30: 1-(3-chloro-4-fluorobenzyl)-5,6-dimethyl-N-(2-morpholinoethyl)-1H-benzo[d]imidazol-2-amine trifluoroacetate

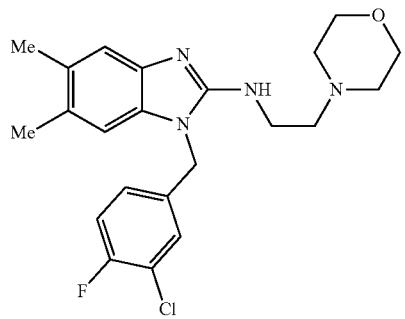 [SMILES: Cc1cc2nc(NCCN3CCOCC3)n(Cc3ccc(F)c(Cl)c3)c2cc1C]

The title compound was obtained according to a procedure analogous to general procedure B: 40% yield. MS (ESI) (M+H⁺) m/z=417.10. LCMS Ret time (UV 214/254): 1.189 min.

Example 31: 1-(3,5-difluorobenzyl)-5,6-dimethyl-N-(2-morpholinoethyl)-1H-benzo[d]imidazol-2-amine trifluoroacetate

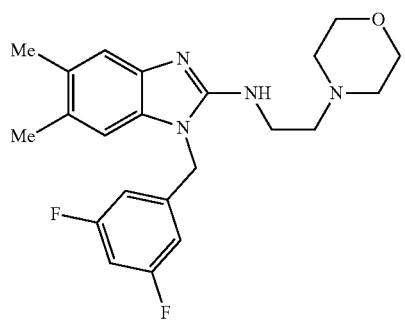 [SMILES: Cc1cc2nc(NCCN3CCOCC3)n(Cc3cc(F)cc(F)c3)c2cc1C]

The title compound was obtained according to a procedure analogous to general procedure B: 37% yield. MS (ESI) (M+H⁺) m/z=401.10. LCMS Ret time (UV 214/254): 1.159 min.

Example 32: 5,6-dimethyl-2-(piperazin-1-yl)-1-(3-(trifluoromethyl)benzyl)-1H-benzo[d]imidazole trifluoroacetate

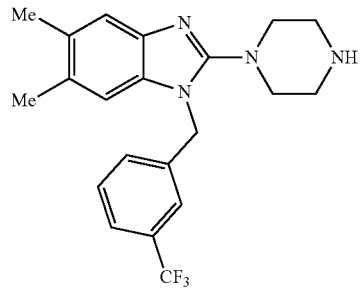 [SMILES: Cc1cc2nc(N3CCNCC3)n(Cc3cccc(C(F)(F)F)c3)c2cc1C]

The title compound was obtained according to a procedure analogous to general procedure B: 17% yield. MS (ESI) (M+H⁺) m/z=389.10. LCMS Ret time (UV 214/254): 1.173 min.

Example 33: N¹-(5,6-dimethyl-1-(3-(trifluoromethyl)benzyl)-1H-benzo[d]imidazol-2-yl)ethane-1,2-diamine trifluoroacetate

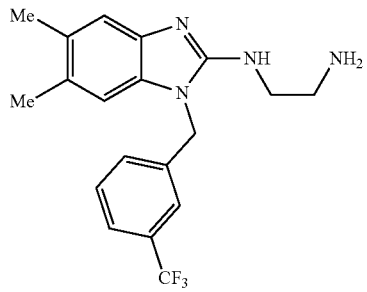 [SMILES: Cc1cc2nc(NCCN)n(Cc3cccc(C(F)(F)F)c3)c2cc1C]

The title compound was obtained according to a procedure analogous to general procedure B: 11% yield. MS (ESI) (M+H⁺) m/z=363.10. LCMS Ret time (UV 214/254): 1.183 min.

Example 34: 1-(3-bromobenzyl)-5,6-dimethyl-2-(piperazin-1-yl)-1H-benzo[d]imidazole trifluoroacetate

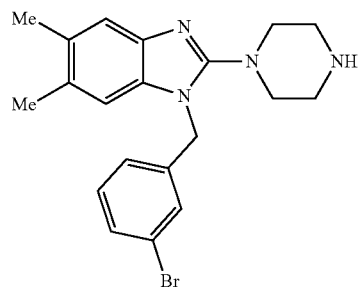 [SMILES: Cc1cc2nc(N3CCNCC3)n(Cc3cccc(Br)c3)c2cc1C]

The title compound was obtained according to a procedure analogous to general procedure B: 6% yield. ¹H NMR (400 MHz, CDCl₃) δ 7.50 (d, J=7.7 Hz, 2H), 7.37 (br m, 1H), 7.25 (s, 1H), 7.08 (d, J=6.9 Hz, 1H), 6.92 (s, 1H), 5.31 (s, 2H), 3.80 (br s, 4H), 3.42 (br s, 4H), 2.34 (s, 3H), 2.32 (s, 3H). MS (ESI) (M+H⁺) m/z=399.00. LCMS Ret time (UV 214/254): 1.136 min.

Example 35: N¹-(1-(3-bromobenzyl)-5,6-dimethyl-1H-benzo[d]imidazol-2-yl)ethane-1,2-diamine trifluoroacetate

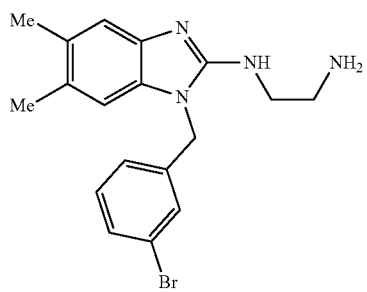 [SMILES: Cc1cc2nc(NCCN)n(Cc3cccc(Br)c3)c2cc1C]

The title compound was obtained according to a procedure analogous to general procedure B: 5% yield. MS (ESI) (M+H⁺) m/z=373.00. LCMS Ret time (UV 214/254): 1.157 min.

Example 36: 1-(3-chloro-4-fluorobenzyl)-2-(1,4-diazepan-1-yl)-5,6-dimethyl-1H-benzo[d]imidazole trifluoroacetate

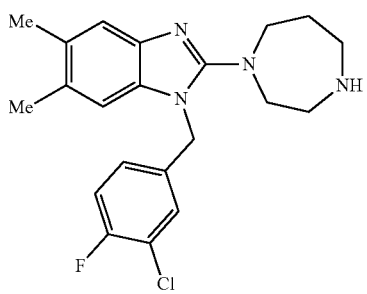 [SMILES: Cc1cc2nc(N3CCCNCC3)n(Cc3ccc(F)c(Cl)c3)c2cc1C]

The title compound was obtained according to a procedure analogous to general procedure B: 48% yield. ¹H NMR (400 MHz, CD₃OD) δ 7.48 (d, J=6.6 Hz, 1H), 7.36 (s, 1H), 7.32 (t, J=8.7 Hz, 1H), 7.24 (m, 1H), 7.19 (s, 1H), 5.51 (s, 2H), 3.99 (t, J=2.3 Hz, 2H), 3.83 (t, J=2.3 Hz, 2H), 3.55 (t, J=4.8 Hz, 2H), 3.43 (t, J=5.4 Hz, 2H), 2.41 (s, 3H), 2.36 (s, 3H), 2.26 (t, i=4.9 Hz, 2H). MS (ESI) (M+H⁺) m/z=387.10. LCMS Ret time (UV 214/254): 1.152 min.

Example 37: 1-(cyclohexylmethyl)-5,6-dimethyl-2-(piperazin-1-yl)-1H-benzo[d]imidazole trifluoroacetate

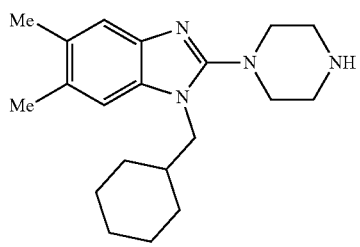 [SMILES: Cc1cc2nc(N3CCNCC3)n(CC3CCCCC3)c2cc1C]

The title compound was obtained according to a procedure analogous to general procedure B: 25% yield. 1H NMR (400 MHz, CD3OD) δ 7.50 (s, 1H), 7.40 (s, 1H), 4.14 (d, J=7.5 Hz, 2H), 3.78 (t, J=3.5 Hz, 4H), 3.52 (t, J=3.5 Hz, 4H), 2.45 (s, 3H), 2.42 (s, 3H), 2.01 (h, J=3.6 Hz, 1H), 1.73 (m, 4H), 1.55 (d, J=12.4 Hz, 2H), 1.12 (m, 4H). MS (ESI) (M+H⁺) m/z=327.30. LCMS Ret time (UV 214/254): 1.133 min.

Example 38: N[1]-(1-(cyclohexylmethyl)-5,6-dimethyl-1H-benzo[d]imidazol-2-yl)ethane-1,2-diamine trifluoroacetate

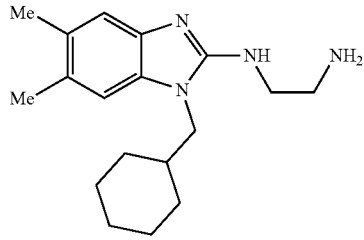 [SMILES: Cc1cc2nc(NCCN)n(CC3CCCCC3)c2cc1C]

The title compound was obtained according to a procedure analogous to general procedure B: 5% yield. MS (ESI) (M+H+) m/z=301.20. LCMS Ret time (UV 214/254): 1.176 min.

Example 39: 1-(4-bromo-3-chlorobenzyl)-5,6-dimethyl-2-(piperazin-1-yl)-1H-benzo[d]imidazole trifluoroacetate

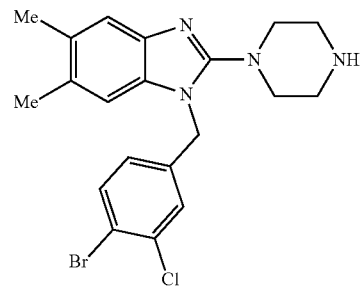 [SMILES: Cc1cc2nc(N3CCNCC3)n(Cc3ccc(Br)c(Cl)c3)c2cc1C]

The title compound was obtained according to a procedure analogous to general procedure B: 35% yield. $^1$H NMR (400 MHz, CD$_3$OD) δ 7.74 (d, J=8.3 Hz, 1H) 7.53 (d, J=2.0 Hz, 1H), 7.43 (s, 1H), 7.19 (s, 1H), 7.12 (dd, J=8.4, 2.1 Hz, 1H), 5.5 (s, 2H), 3.75 (t, J=5.2 Hz, 4H), 3.47 (t, J=5.2 Hz, 4H), 2.42 (s, 3H), 2.36 (s, 3H). MS (ESI) (M+H+) m/z=433.0. LCMS Ret time (UV 214/254): 1.203 min.

Example 40: 1-(4-fluoro-3-(trifluoromethyl)benzyl)-5,6-dimethyl-2-(piperazin-1-yl)-1H-benzo[d]imidazole trifluoroacetate

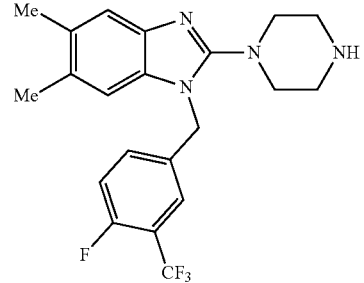

The title compound was obtained according to a procedure analogous to general procedure B: 29% yield. $^1$H NMR (400 MHz, CD$_3$OD) δ 7.74 (s, 1H) 7.53 (s, 1H), 7.43 (s, 1H), 7.39 (t, J=9.5 Hz, 1H), 7.18 (s, 1H), 5.58 (s, 2H), 3.49 (d, J=5.1 Hz, 4H), 3.49 (d, J=5.1 Hz, 4H), 2.41 (s, 3H), 2.35 (s, 3H). MS (ESI) (M+H+) m/z=407.10. LCMS Ret time (UV 214/254): 1.189 min.

Example 41: 1-(4-fluoro-3,5-dimethylbenzyl)-5,6-dimethyl-2-(piperazin-1-yl)-1H-benzo[d]imidazole trifluoroacetate

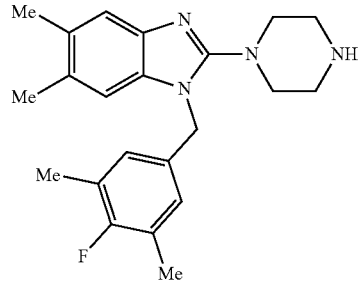 [SMILES: Cc1cc2nc(N3CCNCC3)n(Cc3cc(C)c(F)c(C)c3)c2cc1C]

The title compound was obtained according to a procedure analogous to general procedure B: 20% yield. MS (ESI) (M+H+) m/z=367.20. LCMS Ret time (UV 214/254): 1.192 min.

Example 42: N[1]-(1-(4-fluoro-3,5-dimethylbenzyl)-5,6-dimethyl-1H-benzo[d]imidazol-2-yl)ethane-1,2-diamine trifluoroacetate

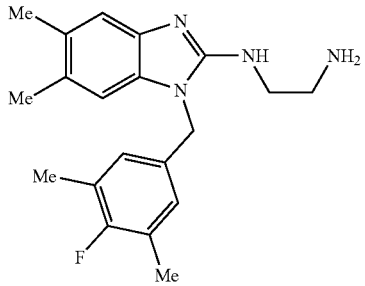 [SMILES: Cc1cc2nc(NCCN)n(Cc3cc(C)c(F)c(C)c3)c2cc1C]

The title compound was obtained according to a procedure analogous to general procedure B: 10% yield. $^1$H NMR (400 MHz, CD$_3$OD) δ □7.30 (s, 1H) 7.20 (d, J=6.7 Hz, 1H), 7.13 (s, 1H), 6.95 (d, J=6.6 Hz, 1H), 5.31 (s, 2H), 3.86 (t, J=6.1 Hz, 2H), 3.36 (t, J=6.1 Hz, 2H), 2.38 (s, 3H), 2.33 (s, 3H), 2.22 (s, 6H). MS (ESI) (M+H+) m/z=341.20. LCMS Ret time (UV 214/254): 1.218 min.

Example 43: N[1]-(1-(4-fluoro-3,5-dimethylbenzyl)-5,6-dimethyl-1H-benzo[d]imidazol-2-yl)propane-1,3-diamine trifluoroacetate

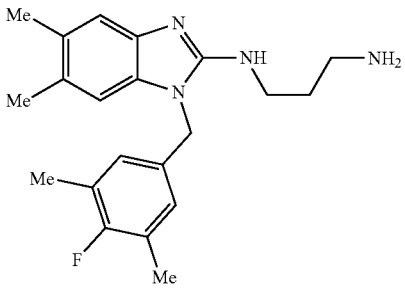 [SMILES: Cc1cc2nc(NCCCN)n(Cc3cc(C)c(F)c(C)c3)c2cc1C]

The title compound was obtained according to a procedure analogous to general procedure B: 36% yield. $^1$H NMR (400 MHz, CD$_3$OD) δ 7.28 (s, 1H), 7.15 (s, 1H), 6.93 (s, 1H), 6.91 (s, 1H), 5.30 (s, 2H), 3.63 (t, J=7.0 Hz, 2H), 3.07 (t, J=7.0 Hz, 2H), 2.37 (s, 3H), 2.33 (s, 3H), 2.22 (s, 6H), 2.11 (quint, J=7.6 Hz, 2H). MS (ESI) (M+H$^+$) m/z=355.20. LCMS Ret time (UV 214/254): 1.195 min.

Example 44: N$^1$-(1-(4-fluoro-3,5-dimethylbenzyl)-5,6-dimethyl-1H-benzo[d]imidazol-2-yl)-N$^2$,N$^2$-dimethylethane-1,2-diamine trifluoroacetate

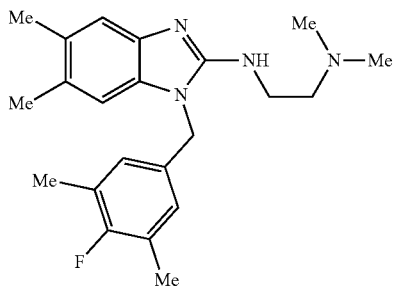 [SMILES: Cc1cc2nc(NCCN(C)C)n(Cc3cc(C)c(F)c(C)c3)c2cc1C]

The title compound was obtained according to a procedure analogous to general procedure B: 28% yield. $^1$H NMR (400 MHz, DMSO) δ 7.37 (s, 1H), 7.12 (s, 1H), 6.96 (s, 1H), 6.94 (s, 1H), 5.40 (s, 2H), 3.84 (t, J=6.6 Hz, 2H), 3.50 (t, J=6.6 Hz, 2H), 2.90 (s, 6H), 2.40 (s, 3H), 2.35 (s, 3H), 2.24 (s, 6H). MS (ESI) (M+H$^+$) m/z=383.20. LCMS Ret time (UV 214/254): 1.203 min.

Example 45: N$^1$-(1-(4-fluoro-3,5-dimethylbenzyl)-5,6-dimethyl-1H-benzo[d]imidazol-2-yl)-N$^1$,N$^2$-dimethylethane-1,2-diamine trifluoroacetate

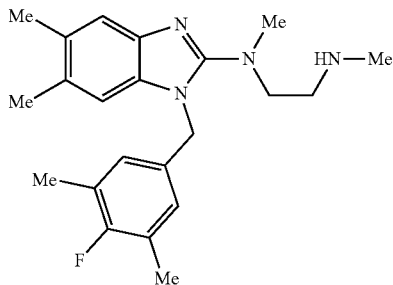 [SMILES: CNCCN(C)c1nc2cc(C)c(C)cc2n1Cc1cc(C)c(F)c(C)c1]

The title compound was obtained according to a procedure analogous to general procedure B: 12% yield. MS (ESI) (M+H$^+$) m/z=369.20. LCMS Ret time (UV 214/254): 1.209 min.

Example 46: 1-(4-fluoro-3,5-divinylbenzyl)-5,6-dimethyl-2-(piperazin-1-yl)-1H-benzo[d]imidazole trifluoroacetate

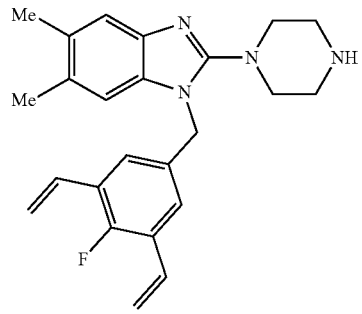 [SMILES: C=Cc1cc(Cn2c(N3CCNCC3)nc3cc(C)c(C)cc32)cc(C=C)c1F]

The title compound was obtained according to a procedure analogous to general procedure B: 25% yield. $^1$H NMR (400 MHz, CD$_3$OD) δ 7.43 (s, 1H), 7.39 (d, J=6.4, 1H), 7.22 (s, 1H), 6.88 (dd, J=17.8, 11.3, 2H), 5.83 (d, J=17.8 Hz, 2H), 5.50 (s, 2H), 5.43 (d, J=11.3 Hz, 2H), 3.74 (t, J=5.2 Hz, 4H), 3.46 (t, J=5.2 Hz, 4H), 2.42 (s, 3H), 2.35 (s, 3H). MS (ESI) (M+H$^+$) m/z=391.20. LCMS Ret time (UV 214/254): 1.266 min.

Example 47: 1-(3-chloro-4-fluoro-5-vinylbenzyl)-5,6-dimethyl-2-(piperazin-1-yl)-1H-benzo[d]imidazole trifluoroacetate

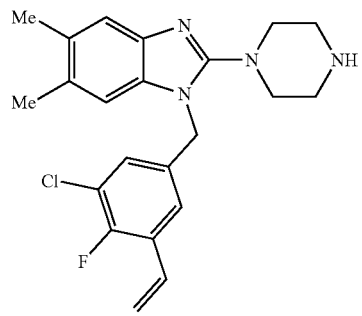 [SMILES: C=Cc1cc(Cn2c(N3CCNCC3)nc3cc(C)c(C)cc32)cc(Cl)c1F]

The title compound was obtained according to a procedure analogous to general procedure B: 20% yield. MS (ESI) (M+H$^+$) m/z=399.10. LCMS Ret time (UV 214/254): 1.238 min.

Example 48: 1-(3-chloro-5-ethyl-4-fluorobenzyl)-5,6-dimethyl-2-(piperazin-1-yl)-1H-benzo[d]imidazole trifluoroacetate

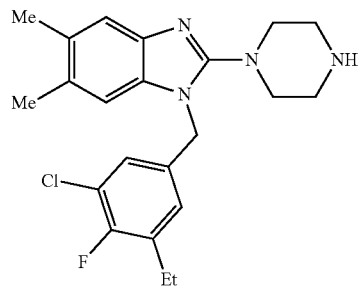

The title compound was obtained according to a procedure analogous to general procedure B: 20% yield. $^1$H NMR (400 MHz, CD$_3$OD) δ 7.43 (s, 1H), 7.26 (dd, J=6.4, 2.2, 1H), 7.20 (dd, J=6.4, 2.2, 1H), 7.18 (s, 1H), 5.48 (s, 2H), 3.78 (t, J=5.2 Hz, 4H), 3.48 (t, J=5.2 Hz, 4H), 2.71 (q, J=7.5 Hz, 2H), 2.42 (s, 3H), 2.35 (s, 3H), 1.22 (t, J=7.5 Hz, 3H). MS (ESI) (M+H$^+$) m/z=401.10. LCMS Ret time (UV 214/254): 1.251 min.

Example 49: 1-(3,5-diethyl-4-fluorobenzyl)-5,6-dimethyl-2-(piperazin-1-yl)-1H-benzo[d]imidazole trifluoroacetate

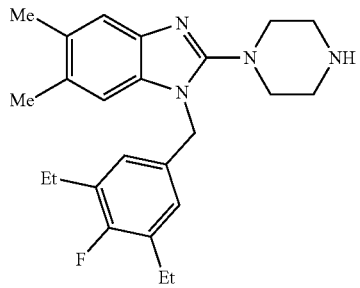 [SMILES: CCc1cc(Cn2c(N3CCNCC3)nc3cc(C)c(C)cc32)cc(Cl)c1F]

The title compound was obtained according to a procedure analogous to general procedure B: 18% yield. MS (ESI) (M+H$^+$) m/z=395.20. LCMS Ret time (UV 214/254): 1.302 min.

Example 50: 1-(3-ethyl-4-fluorobenzyl)-5,6-dimethyl-2-(piperazin-1-yl)-1H-benzo[d]imidazole trifluoroacetate

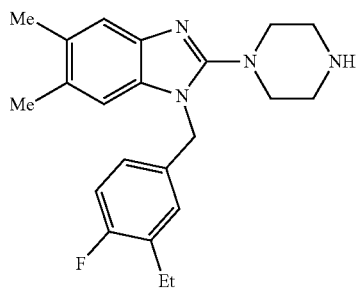

The title compound was obtained according to a procedure analogous to general procedure B: 30% yield. MS (ESI) (M+H$^+$) m/z=367.20. LCMS Ret time (UV 214/254): 1.159 min.

Example 51: 1-(3-cyclopropyl-4-fluorobenzyl)-5,6-dimethyl-2-(piperazin-1-yl)-1H-benzo[d]imidazole trifluoroacetate

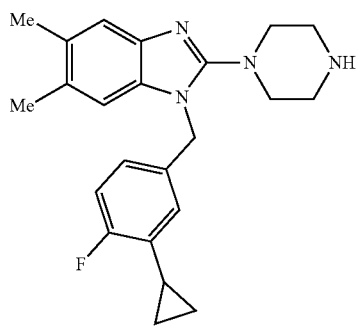 [SMILES: Cc1cc2nc(N3CCNCC3)n(Cc3ccc(F)c(C4CC4)c3)c2cc1C]

The title compound was obtained according to a procedure analogous to general procedure B: 35% yield. $^1$H NMR (400 MHz, CD$_3$OD) δ 7.42 (s, 1H), 7.19 (s, 1H), 7.07 (t, J=9.2, 1H), 6.99 (m, 2H), 5.45 (s, 2H), 3.75 (t, J=5.2 Hz, 4H), 3.45 (t, J=5.2 Hz, 4H), 2.42 (s, 3H), 2.36 (s, 3H), 2.10 (m, 1H), 1.02 (ddd, J=6.4, 4.5, 2.0 Hz, 1H). 0.71 (ddd, J=5.0, 4.5, 1.6 Hz, 1H). MS (ESI) (M+H$^+$) m/z=379.20. LCMS Ret time (UV 214/254): 1.168 min.

Example 52: 1-(4-fluoro-3-vinylbenzyl)-5,6-dimethyl-2-(piperazin-1-yl)-1H-benzo[d]imidazole trifluoroacetate

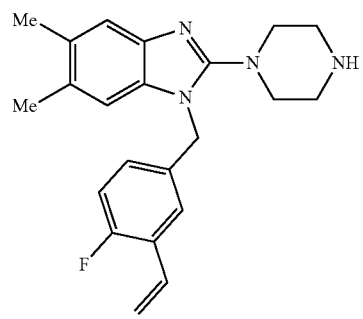 [SMILES: C=Cc1cc(Cn2c(N3CCNCC3)nc3cc(C)c(C)cc32)ccc1F]

The title compound was obtained according to a procedure analogous to general procedure B: 24% yield. MS (ESI) (M+H$^+$) m/z=365.20. LCMS Ret time (UV 214/254): 1.140 min.

Example 53: 1-(3,5-difluorobenzyl)-5,6-dimethyl-2-(pyridin-4-yl)-1H-benzo[d]imidazole

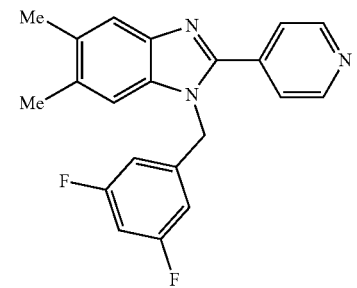 [SMILES: Cc1cc2nc(-c3ccncc3)n(Cc3cc(F)cc(F)c3)c2cc1C]

Step A: To a 100 mL RBF was added 4,5-dimethyl-1,2-diaminoebenzene (500 mg, 3.68 mmol, 1 eq), isonicotinic acid (543 mg, 4.41 mmol, 1.2 eq), HOBT (497 mg, 3.6 mmol, 1.0 eq) and EDCI-HCl salt (918.5 mg, 4.78 mmol, 1.3 eq). Dichloromethane (20 mL) and diisopropylethylamine (1.29 mL, 7.36 mmol, 2 eq) were added to the reaction, which was stirred at room temperature for 18 hours. Upon conversion of the starting material by LCMS, the reaction was diluted with water and dichloromethane and passed through a phase separator. The organic layer was concentrated to afford a crude solid, which was dissolved in acetic acid (30 mL) and heated at 95° C. for several hours. After conversion of the starting material by LCMS, the reaction was cooled to room temperature and concentrated in vacuo. The crude residue was diluted with ethyl acetate and water, washed with aqueous sodium bicarbonate, dried over magnesium sulfate, and concentrated to a crude solid (200 mg, 25% yield). The crude 5,6-dimethyl-2-(pyridin-4-yl)-1H-benzo[d]imidazole was used without any further purification.

Step B: The crude 5,6-dimethyl-2-(pyridin-4-yl)-1H-benzo[d]imidazole (50 mg, 0.223 mmol, 1 eq) was dissolved in DMF (1.5 mL) in a reaction vial. Potassium carbonate (62 mg, 0.45 mmol, 2 eq) was added to the reaction, followed by 3,5-difluorobenzylbromide (0.035 mL, 0.268 mmol, 1.2 eq). The reaction was stirred at room temperature and monitored by LCMS. Upon conversion of the starting material, the reaction was diluted with water and extracted with dichloromethane. The reaction mixture was passed through a phase separator and concentrated to afford a crude solid. The crude solid was purified by reverse-phase HPLC to afford 1-(3,5-difluorobenzyl)-5,6-dimethyl-2-(pyridin-4-yl)-1H-benzo[d]imidazole as a white solid (34 mg, 42%). $^1$H NMR (400 MHz, CD$_3$OD) δ 8.76 (dd, J=8.0, 2.1, 2H), 7.75 (dd, J=8.0, 2.1 Hz, 2H), 7.60 (s, 1H), 7.38 (s, 1H), 7.17 (m, 1H), 6.71 (d, J=6.4 Hz, 2H), 5.68 (s, 2H), 2.36 (s, 3H), 2.34 (s, 3H). MS (ESI) (M+H$^+$) m/z=350.10. LCMS Ret time (UV 214/254): 1.263 min.

Example 54: 1-(3-chloro-4-fluorobenzyl)-5,6-dimethyl-2-(pyridin-4-yl)-1H-benzo[d]imidazole

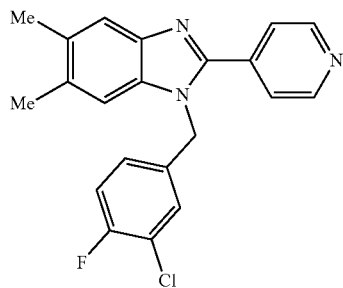 [SMILES: Cc1cc2nc(-c3ccncc3)n(Cc3ccc(F)c(Cl)c3)c2cc1C]

The title compound was obtained according to a procedure analogous to general procedure C: 36% yield. MS (ESI) (M+H$^+$) m/z=366.10. LCMS Ret time (UV 214/254): 1.315 min.

Example 55: 1-(3-chloro-4-fluorobenzyl)-2-(piperidin-4-yl)-1H-benzo[d]imidazole trifluoroacetate

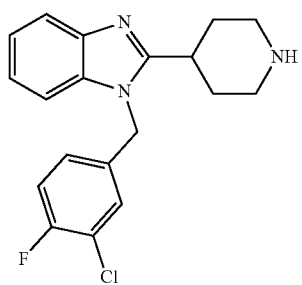 [SMILES: Fc1ccc(Cn2c(C3CCNCC3)nc3ccccc32)cc1Cl]

Step A: 1,2-diaminobenzene (1.0 g, 9.25 mmol, 1 eq) was added to a 100 mL round bottom flask equipped with a stir bar. Piperdine-4-carboxylic acid (3.5 g, 27.8 mmol, 3 eq) was added to the flask, followed by aqueous 4 M HCl (30 mL). The reaction was heated for 36 hours under reflux and monitored by LCMS. Upon conversion of the starting material, the reaction was cooled to 0° C. and basified with sodium hydroxide pellets. The resulting sodium salt crashed out of solution, which was collected by filtration to afford a crude yellow solid. The solid, 2-(piperidin-4-yl)-1H-benzo[d]imidazole, was used without any further purification.

Step B: The crude 2-(piperidin-4-yl)-1H-benzo[d]imidazole from the previous step was dissolved in THF (25 mL) followed by addition of Boc anhydride (2.03 g, 9.25 mmol, 1 eq). The reaction was stirred at room temperature for 2 hours until full conversion by LCMS. The solution was diluted with ethyl acetate, washed with water, dried over magnesium sulfate, and concentrated to afford a clear oil product. The tert-butyl 4-(1H-benzo[d]imidazol-2-yl)piperidine-1-carboxylate was used without any further purification.

Step C: The tert-butyl 4-(1H-benzo[d]imidazol-2-yl)piperidine-1-carboxylate from step B (75 mg, 0.25 mmol, 1 eq) was dissolved in DMF (3 mL) in a reaction vial. Potassium carbonate (41 mg, 0.30 mmol, 1.2 eq) was added to the reaction, followed by 4-fluoro-3-chlorobenzylbromide (0.037 mL, 0.275 mmol, 1.1 eq). The reaction was stirred at room temperature and monitored by LCMS. Upon conversion of the starting material, the reaction was diluted with water and extracted with ethyl acetate. The organic layer was washed with water (2×) and a brine solution, dried over magnesium sulfate, and concentrated to afford a crude solid. The crude solid was dissolved in a 2/1 mixture of dichloromethane/TFA and stirred at room temperature for 30 min. Upon completion of the reaction by LCMS, the volatiles were removed in vacuo to afford a crude solid. The solid was purified by reverse-phase HPLC to provide title compound as a white solid (30 mg, 35% yield). $^1$H NMR (400 MHz, CD$_3$OD) δ 7.85 (d, J=7.4 Hz, 1H), 7.66 (d, J=7.4 Hz, 1H), 7.56 (m, 1H), 7.47 (dd, J=6.8, 2.2 Hz, 1H), 7.27 (t, J=8.8 Hz, 1H), 7.16 (m, 1H), 5.80 (s, 2H), 3.78 (m, 1H), 3.60 (d, J=13.0 Hz, 2H), 3.22 (td, J=13.0, 3.8 Hz, 2H), 2.24 (m, 4H). MS (ESI) (M+H$^+$) m/z=344.10. LCMS Ret time (UV 214/254): 1.039 min.

Example 56: 1-(4-fluorobenzyl)-2-(piperidin-4-yl)-1H-benzo[d]imidazole trifluoroacetate

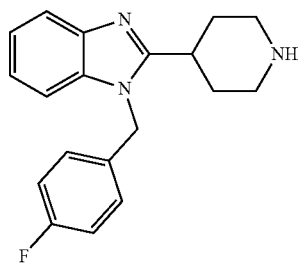 [SMILES: Fc1ccc(Cn2c(C3CCNCC3)nc3ccccc32)cc1]

The title compound was obtained according to a procedure analogous to general procedure D: 30% yield. $^1$H NMR (400 MHz, CD$_3$OD) δ 7.76 (dd, J=8.5, 1.0 Hz, 1H), 7.57 (dd, J=8.5, 1.0 Hz, 1H), 7.43 (m, 2H), 7.23 (d, J=5.2 Hz, 1H), 7.21 (d, J=5.2 Hz, 1H), 7.12 (t, J=8.8 Hz, 2H), 5.69 (s, 2H), 3.54 (m, 3H), 3.17 (td, J=12.9, 3.6, 2H), 2.14 (m, 4H). MS (ESI) (M+H$^+$) m/z=310.20. LCMS Ret time (UV 214/254): 0.947 min.

Example 57: 1-(3,5-difluorobenzyl)-2-(piperidin-4-yl)-1H-benzo[d]imidazole trifluoroacetate

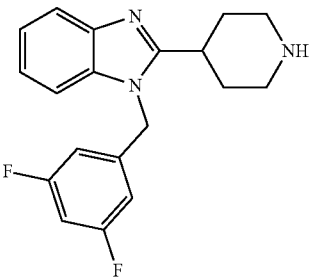 [SMILES: Fc1cc(F)cc(Cn2c(C3CCNCC3)nc3ccccc32)c1]

The title compound was obtained according to a procedure analogous to general procedure D: 36% yield. MS (ESI) (M+H$^+$) m/z=328.20. LCMS Ret time (UV 214/254): 0.977 min.

Example 58: 1-(4-chlorobenzyl)-2-(piperidin-4-yl)-1H-benzo[d]imidazole trifluoroacetate

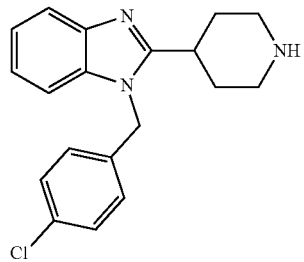 [SMILES: Clc1ccc(Cn2c(C3CCNCC3)nc3ccccc32)cc1]

The title compound was obtained according to a procedure analogous to general procedure D: 29% yield. MS (ESI) (M+H$^+$) m/z=326.20. LCMS Ret time (UV 214/254): 1.016 min.

Example 59: 1-(3-chloro-4-fluorobenzyl)-5,6-dimethyl-2-(piperidin-4-yl)-1H-benzo[d]imidazole trifluoroacetate

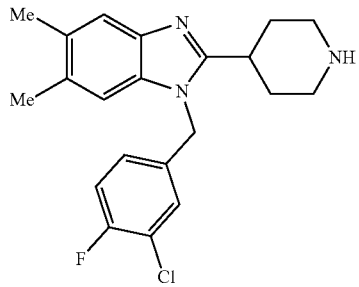 [SMILES: Cc1cc2nc(C3CCNCC3)n(Cc3ccc(F)c(Cl)c3)c2cc1C]

The title compound was obtained according to a procedure analogous to general procedure D: 41% yield. $^1$H NMR (400 MHz, CDCl$_3$) δ 7.60 (s, 1H), 7.46 (s, 1H), 7.44 (ovlp d, J=1.9 Hz, 1H), 7.28 (t, J=8.8 Hz, 1H), 7.15 (m, 1H), 5.76 (s, 2H), 3.73 (m, 1H), 3.59 (d, J=13.2, 2H), 3.20 (m, 2H), 2.46 (s, 3H), 2.43 (s, 3H), 2.20 (m, 4H). MS (ESI) (M+H$^+$) m/z=372.10. LCMS Ret time (UV 214/254): 1.141 min.

Example 60: N$^1$-(1-(3-chloro-4-fluorobenzyl)-6-methyl-1H-benzo[d]imidazol-2-yl)ethane-1,2-diamine trifluoroacetate

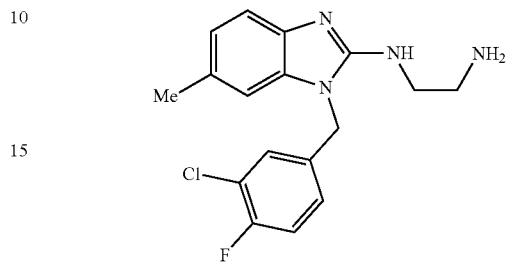

Step A: To a stirred solution of 3-chloro-4-fluorobenzylamine (487 µL, 3.87 mmol, 1.2 eq) in DMF (11 mL) was added potassium carbonate (778 mg, 5.63 mmol, 1.5 eq) at room temperature. After five min, solid 2-fluoro-4-methylnitrobenzene (500 mg, 3.22 mmol, 1 eq) was added at room temperature. The reaction was stirred at room temperature for 18 hours and monitored by LCMS. Upon conversion to the aniline product, the reaction was quenched with 10% aqueous HCl and diluted with water, then extracted with ethyl acetate (×2). The organic phase was washed with water and a brine solution, dried over magnesium sulfate, and concentrated to afford a dark crude solid. The crude N-(3-chloro-4-fluorobenzyl)-5-methyl-2-nitroaniline was used without further purification on the subsequent step.

Step B: The crude N-(3-chloro-4-fluorobenzyl)-5-methyl-2-nitroaniline from Step A was dissolved in methanol (20 mL) and stirred at 0° C. in an ice bath. Zinc powder (1.05 g, 16 mmol, 5 eq) and solid ammonium chloride (870 mg, 16 mmol, 5 eq) was added to the reaction. The reaction was slowly warmed to room temperature and monitored by LCMS. Upon conversion to the reduced product, the solution was filtered to remove excess zinc powder and then concentrated in vacuo. The crude residue was diluted with water and extracted with ethyl acetate. The organic phase was dried over magnesium sulfate and concentrated to provide N-(3-chloro-4-fluorobenzyl)-5-methylbenzene-1,2-diamine as a crude solid (770 mg, 90% yield). The solid was used without further purification.

Step C: The N$^1$-(3-chloro-4-fluorobenzyl)-5-methylbenzene-1,2-diamine obtained from Step B (770 mg, 2.92 mmol, 1 eq) was dissolved in DCM (30 mL). DMAP (35 mg, 0.3 mmol, 0.1 eq) and CDI (707 mg, 4.4 mmol, 1.5 eq) were added and the reaction was stirred overnight at room temperature. Upon conversion of the starting material, the solid precipitate was filtered off of the reaction mixture and dried for the next step. The solid was dissolved in POCl3 (10 mL) and heated at 90° C. The reaction was complete by LCMS after 4 hours and was cooled to 0° C. The reaction was carefully and slowly added to ice water to quench the excess POCl$_3$ and then solid NaOH pellets were added until the solution was neutral. The solid precipitate was filtered off and dried to afford the 2-chloro-1-(3-chloro-4-fluorobenzyl)-6-methyl-1H-benzo[d]imidazole (650 mg, 72% yield over two steps), which was used without any further purification.

Step D: The 2-chloro-1-(3-chloro-4-fluorobenzyl)-6-methyl-1H-benzo[d]imidazole (30 mg, 0.09 mmol, 1 eq) was dissolved in N,N-DMA (1.0 mL) in a microwave tube equipped with a stir bar. 1,2-diaminoethane (30 μL, 5 eq) was added to the tube and then the tube was sealed. The reaction was heated in a microwave reactor at 165° C. for 45 min. Upon conversion by LCMS, the reaction was diluted with water and then extracted with DCM. The resulting crude solution was passed through a phase separator and the organic layer was concentrated. The crude residue was purified by reverse-phase preparative HPLC to afford title compound as a TFA salt (5.0 mg, 16% yield). $^1$H NMR (400 MHz, CD$_3$OD) δ 7.46 (dd, J=6.9, 2.2 Hz, 1H), 7.42 (d, J=8.2 Hz, 1H), 7.27 (t, J=8.3 Hz, 1H), 7.24 (m, 2H), 7.20 (s, 1H), 5.43 (s, 2H), 3.87 (t, J=6.1 Hz, 2H), 3.36 (t, J=6.1 Hz, 2H), 2.44 (s, 3H). MS (ESI) (M+H$^+$) m/z=333.10. LCMS Ret time (UV 214/254): 1.106 min.

Example 61: 1-(3-chloro-4-fluorobenzyl)-6-methyl-2-(piperazin-1-yl)-1H-benzo[d]imidazole trifluoroacetate

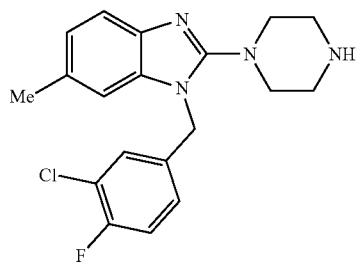 [SMILES: Cc1ccc2nc(N3CCNCC3)n(Cc3ccc(F)c(Cl)c3)c2c1]

The title compound was obtained according to a procedure analogous to general procedure E: 22% yield. MS (ESI) (M+H$^+$) m/z=359.20. LCMS Ret time (UV 214/254): 1.081

Example 62: 1-(3-chloro-4-fluorobenzyl)-6-cyclopropyl-2-(piperazin-1-yl)-1H-benzo[d]imidazole trifluoroacetate

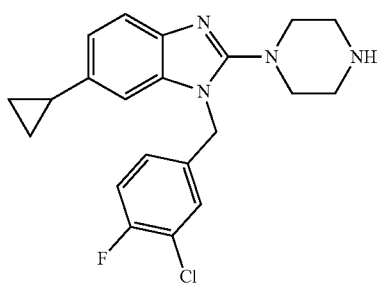 [SMILES: Fc1ccc(Cn2c(N3CCNCC3)nc3ccc(C4CC4)cc32)cc1Cl]

The title compound was obtained according to a procedure analogous to general procedure E: 20% yield. MS (ESI) (M+H$^+$) m/z=385.00. LCMS Ret time (UV 214/254): 1.179 min.

Example 63: 6-bromo-1-(3-chloro-4-fluorobenzyl)-2-(piperazin-1-yl)-1H-benzo[d]imidazole trifluoroacetate

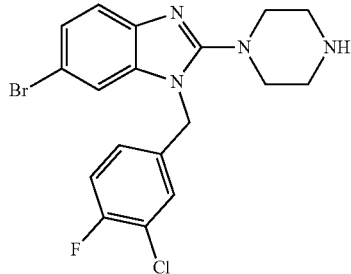

The title compound was obtained according to a procedure analogous to general procedure E: 12% yield. MS (ESI) (M+H$^+$) m/z=424.90. LCMS Ret time (UV 214/254): 1.222 min.

Example 64: N$^1$-(6-bromo-1-(3-chloro-4-fluorobenzyl)-5-methyl-1H-benzo[d]imidazol-2-yl)ethane-1,2-diamine trifluoroacetate

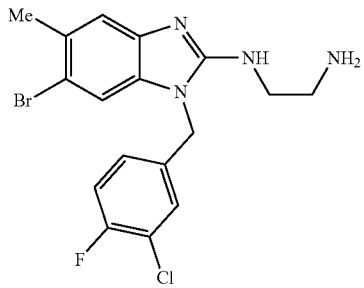 [SMILES: Cc1cc2nc(NCCN)n(Cc3ccc(F)c(Cl)c3)c2cc1Br]

The title compound was obtained according to a procedure analogous to general procedure E: 60% yield. $^1$H NMR (400 MHz, CD$_3$OD) δ 7.58 (s, 1H), 7.45 (ovlp s, 2H), 7.29 (t, J=8.8 Hz, 1H), 7.22 (m, 1H), 5.39 (s, 2H), 3.85 (t, J=6.2 Hz, 2H), 3.35 (t, J=6.2 Hz, 2H), 2.50 (s, 3H). MS (ESI) (M+H$^+$) m/z=411.0. LCMS Ret time (UV 214/254): 1.207 min.

Example 65: N$^1$-(1-(3-chloro-4-fluorobenzyl)-5-methyl-6-vinyl-1H-benzo[d]imidazol-2-yl)ethane-1,2-diamine trifluoroacetate

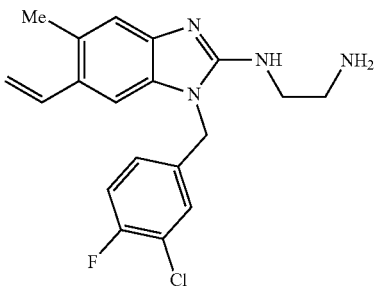 [SMILES: C=Cc1cc2c(cc1C)nc(NCCN)n2Cc1ccc(F)c(Cl)c1]

127

N[1]-(6-bromo-1-(3-chloro-4-fluorobenzyl)-5-methyl-1H-benzo[d]imidazol-2-yl)ethane-1,2-diamine trifluoroacetate (prepared by a procedure analogous to the procedure used to prepare Example 68) (40 mg, 0.0763 mmol), Pd(OAc)$_2$ (1.7 mg, 0.0076 mmol, 0.1 eq), P(Cy$_3$)HBF$_4$ (5.62 mg, 0.015 mmol, 0.2 eq), K$_3$PO$_4$ (49 mg, 0.229 mmol, 3 eq), and vinyl boronic pinnacol ester (15.5 µL, 0.0916 mmol, 1.2 eq) were added to a sealed tube. The tube was purged 3× with argon. A 5:1 mixture of DME:water (0.8 mL) was added to the tube, which was then sealed. The reaction was heated at 85° C. for 24 hours until the starting material was fully converted by LCMS. The reaction was quenched with water and extracted with DCM and filtered through a phase separator. The organic layer was concentrated to the crude mixture, which was purified by reverse-phase HPLC to afford N[1]-(1-(3-chloro-4-fluorobenzyl)-5-methyl-6-vinyl-1H-benzo[d]imidazol-2-yl)ethane-1,2-diamine trifluoroacetate (4 mg, 15% yield). MS (ESI) (M+H$^+$) m/z=359.10. LCMS Ret time (UV 214/254): 1.185 min.

Example 66: 1-(3-chloro-4-fluorobenzyl)-6-ethyl-5-methyl-2-(piperazin-1-yl)-1H-benzo[d]imidazole trifluoroacetate

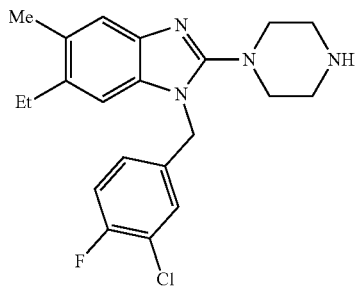 [SMILES: CCc1cc2c(cc1C)nc(N1CCNCC1)n2Cc1ccc(F)c(Cl)c1]

N[1]-(1-(3-chloro-4-fluorobenzyl)-5-methyl-6-vinyl-1H-benzo[d]imidazol-2-yl)ethane-1,2-diamine trifluoroacetate (prepared by a procedure analogous to the procedure used to prepare Example 69) (60 mg, 0.156 mmol) was dissolved in THF (3 mL) in a round bottom flask. 10% palladium on carbon (15 mg) was added to the reaction flask, which was then purged three times with a balloon of hydrogen. The reaction was stirred for several hours until the conversion of the starting material by LCMS. The hydrogen balloon was removed and the solution was filtered through a pad of celite and concentrated to provide a crude solid. The solid was purified by reverse-phase HPLC to afford a white solid (10 mg, 17% yield. $^1$H NMR (400 MHz, CD3OD) δ 7.49 (d, J=4.4 Hz, 1H), 7.42 (s, 1H), 7.30 (t, J=8.7 Hz, 1H), 7.24 (br s, 1H), 7.15 (s, 1H), 5.51 (s, 2H), 3.71 (t, J=5.4 Hz, 4H), 3.47 (t, J=5.4 Hz, 4H), 2.73 (q, J=7.5 Hz, 2H), 2.45 (s, 3H), 1.18 (t, J=7.5 Hz, 3H). MS (ESI) (M+H$^+$) m/z=387.10. LCMS Ret time (UV 214/254): 1.201 min.

128

Example 67: 6-ethyl-1-(3-ethyl-4-fluorobenzyl)-5-methyl-2-(piperazin-1-yl)-1H-benzo[d]imidazole trifluoroacetate

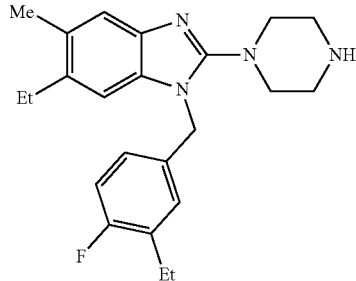

The title compound was prepared in a two step procedure analogous to that used in the preparation of N[1]-(1-(3-chloro-4-fluorobenzyl)-5-methyl-6-vinyl-1H-benzo[d]imidazol-2-yl)ethane-1,2-diamine trifluoroacetate: (prepared by a procedure analogous to the procedure used to prepare Example 69) and 1-(3-chloro-4-fluorobenzyl)-6-ethyl-5-methyl-2-(piperazin-1-yl)-1H-benzo[d]imidazole trifluoroacetate (prepared by a procedure analogous to the procedure used to prepare Example 70) except that excess vinyl boronic pinnacol ester was used in the first step. 10% yield. MS (ESI) (M+H$^+$) m/z=381.10. LCMS Ret time (UV 214/254): 1.244 min.

Example 68: 6-chloro-1-(3-chloro-4-fluorobenzyl)-5-methyl-2-(piperazin-1-yl)-1H-benzo[d]imidazole trifluoroacetate

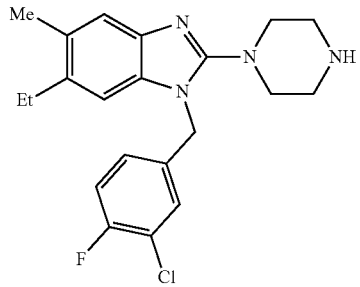

The title compound was obtained according to a procedure analogous to general procedure E: 33% yield. $^1$H NMR (400 MHz, CD$_3$OD) δ 7.56 (s, 1H), 7.49 (dd, J=6.8, 2.2 Hz, 1H), 7.41 (s, 1H), 7.30 (t, J=8.8 Hz, 1H), 7.24 (m, 1H), 5.49 (s, 2H), 3.76 (t, J=5.2 Hz, 4H), 3.47 (t, J=5.2 Hz, 4H), 2.49 (s, 3H). MS (ESI) (M+H$^+$) m/z=393.00. LCMS Ret time (UV 214/254): 1.220 min.

Example 69: N¹-(6-chloro-1-(3-chloro-4-fluorobenzyl)-5-methyl-1H-benzo[d]imidazol-2-yl)ethane-1,2-diamine trifluoroacetate

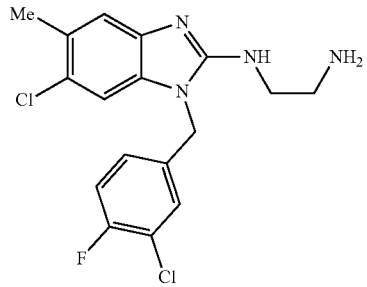 [SMILES: Cc1cc2nc(NCCN)n(Cc3ccc(F)c(Cl)c3)c2cc1Cl]

The title compound was obtained according to a procedure analogous to general procedure E: 26% yield. 1H NMR (400 MHz, CD3OD) δ 7.48 (ovlp dd, J=8.4, 1.8 Hz, 1H), 7.46 (s, 1H), 7.42 (s, 1H), 7.26 (ovlp d, J=8.4 Hz, 1H), 7.23 (ovlp br s, 1H), 5.42 (s, 2H), 3.90 (t, J=6.0 Hz, 2H), 3.36 (t, J=6.0 Hz, 2H), 2.47 (s, 3H). MS (ESI) (M+H⁺) m/z=367.00. LCMS Ret time (UV 214/254): 1.202 min.

Example 70: 5-bromo-1-(3-chloro-4-fluorobenzyl)-6-methyl-2-(piperazin-1-yl)-1H-benzo[d]imidazole trifluoroacetate

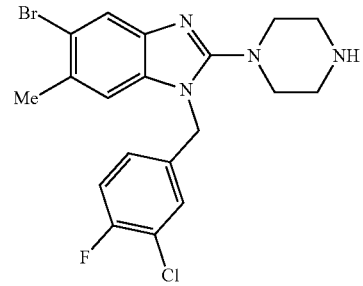 [SMILES: Cc1cc2c(cc1Br)nc(N1CCNCC1)n2Cc1ccc(F)c(Cl)c1]

Step A: 2-chloro-1-(3-chloro-4-fluorobenzyl)-6-methyl-1H-benzo[d]imidazole (34 mg, 0.110 mmol), which was prepared by a procedure analogous to Example 8, Step C, was dissolved in DMF (1 mL) in a reaction vial. NBS (25 mg, 0.144 mmol, 1.3 eq) was added in batches to the reaction, which was stirred at room temperature for 24 hours. Upon conversion of the starting material by LCMS, the reaction was quenched with water and extracted with ethyl acetate. The organic layer was washed with water, a brine solution, dried over magnesium sulfate and concentrated to afford a white solid: 5-bromo-2-chloro-1-(3-chloro-4-fluorobenzyl)-6-methyl-1H-benzo[d]imidazole: ¹H NMR (400 MHz, CDCl₃) δ 7.92 (s, 1H), 7.23 (dd, J=6.7, 2.1, 1H), 7.13 (t, J=8.5 Hz, 1H), 7.08 (s, 1H), 7.01 (m, 1H), 5.31 (s, 2H), 2.49 (s, 3H). MS (ESI) (M+H⁺) m/z=386.80. LCMS Ret time (UV 214/254): 1.790 min. The regioselectivity of the bromination was confirmed by 1D NOE analysis.

Step B: 5-bromo-2-chloro-1-(3-chloro-4-fluorobenzyl)-6-methyl-1H-benzo[d]imidazole (20 mg, 0.52 mmol) was added to a microwave tube and dissolved with DMA (1 mL). Piperazine (50 mg) was added to the tube, which was then sealed. The reaction was heated in a microwave reactor at 165° C. for 30 min. After conversion of the starting material by LCMS, the reaction was diluted in water and extracted with DCM. The solution was passed through a phase separator and the organic layer was concentrated to provide a crude solid. The solid was purified by reverse-phase HPLC to afford the title compound as a white solid (12 mg, 53% yield). MS (ESI) (M+H⁺) m/z=436.90. LCMS Ret time (UV 214/254): 1.237

Example 71: 1-(3-chloro-4-fluorobenzyl)-2-(piperazin-1-yl)-6-(trifluoromethyl)-1H-benzo[d]imidazole trifluoroacetate

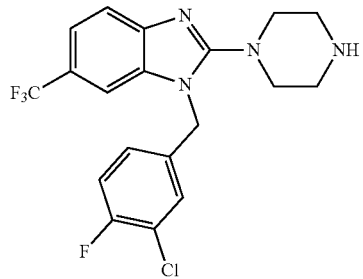 [SMILES: Fc1ccc(Cn2c(N3CCNCC3)nc3ccc(C(F)(F)F)cc32)cc1Cl]

The title compound was obtained according to a procedure analogous to general procedure E: 30% yield. 1H NMR (400 MHz, (CD₃)₂SO)) δ 7.71 (s, 1H), 7.67 (d, J=8.4 Hz, 1H), 7.51 (d, J=5.7 Hz, 1H), 7.48 (d, J=8.4 Hz, 1H), 7.38 (t, J=8.9 Hz, 1H), 7.12 (m, 1H), 5.47 (s, 2H), 3.47 (br s, 4H), 3.28 (br s, 4H). MS (ESI) (M+H⁺) m/z=413.10. LCMS Ret time (UV 214/254): 1.265 min.

Example 72: N¹-(1-(3-chloro-4-fluorobenzyl)-6-(trifluoromethyl)-1H-benzo[d]imidazol-2-yl)ethane-1,2-diamine trifluoroacetate

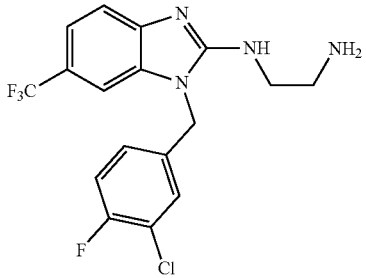 [SMILES: NCCNc1nc2ccc(C(F)(F)F)cc2n1Cc1ccc(F)c(Cl)c1]

The title compound was obtained according to a procedure analogous to general procedure E: 13% yield. MS (ESI) (M+H⁺) m/z=387.00. LCMS Ret time (UV 214/254): 1.181 min.

Example 73: 6-chloro-1-(3-chloro-4-fluorobenzyl)-2-(piperazin-1-yl)-1H-benzo[d]imidazole trifluoroacetate

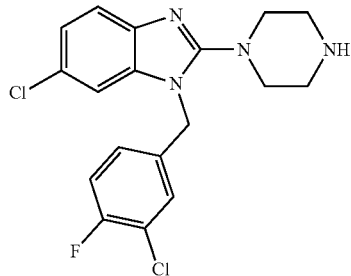

The title compound was obtained according to a procedure analogous to general procedure E: 28% yield. MS (ESI) (M+H$^+$) m/z=379.00. LCMS Ret time (UV 214/254): 1.167 min.

Example 74: N$^1$-(6-chloro-1-(3-chloro-4-fluorobenzyl)-1H-benzo[d]imidazol-2-yl)ethane-1,2-diamine trifluoroacetate

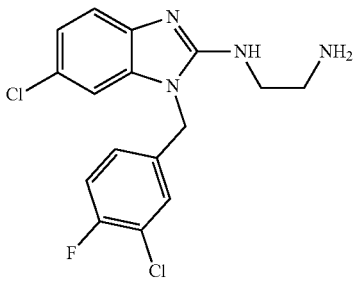 [SMILES: NCCNc1nc2ccc(Cl)cc2n1Cc1ccc(F)c(Cl)c1]

The title compound was obtained according to a procedure analogous to general procedure E: 11% yield. MS (ESI) (M+H$^+$) m/z=353.10. LCMS Ret time (UV 214/254): 1.125 min.

Example 75: N-(azetidin-3-ylmethyl)-6-chloro-1-(3-chloro-4-fluorobenzyl)-1H-benzo[d]imidazol-2-amine trifluoroacetate

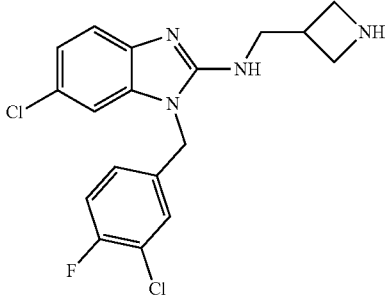 [SMILES: Fc1ccc(Cn2c(NCC3CNC3)nc3ccc(Cl)cc32)cc1Cl]

The title compound was obtained according to a procedure analogous to general procedure E: 21% yield. $^1$H NMR (400 MHz, CD$_3$OD) δ 7.43 (d, J=8.5 Hz, 1H), 7.39 (dd, J=6.6, 1.7, 1H), 7.30 (m, 1H), 7.26 (d, J=8.5 Hz, 1H), 7.16 (m, 1H) 7.07 (m, 1H), 5.36 (s, 2H), 4.19 (t, J=10.1, 2H), 3.97 (dd, J=11.4, 7.2 Hz, 1H), 3.79 (d, J=7.2 Hz, 4H). MS (ESI) (M+H$^+$) m/z=379.00. LCMS Ret time (UV 214/254): 1.118 min.

Example 76: (1-(6-chloro-1-(3-chloro-4-fluorobenzyl)-1H-benzo[d]imidazol-2-yl)azetidin-3-yl)methanamine trifluoroacetate

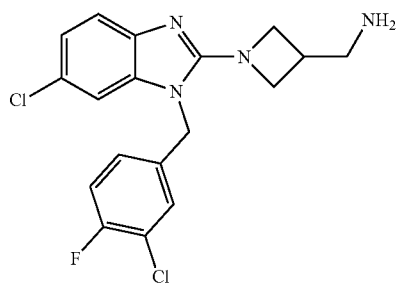 [SMILES: NCC1CN(c2nc3ccc(Cl)cc3n2Cc2ccc(F)c(Cl)c2)C1]

The title compound was obtained according to a procedure analogous to general procedure E: 17% yield. MS (ESI) (M+H$^+$) m/z=379.00. LCMS Ret time (UV 214/254): 1.105 min.

Example 77: 6-chloro-1-(3-chloro-4-fluorobenzyl)-N-(pyrrolidin-3-yl)-1H-benzo[d]imidazol-2-amine trifluoroacetate

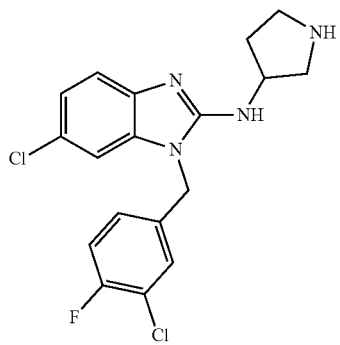 [SMILES: Fc1ccc(Cn2c(NC3CCNC3)nc3ccc(Cl)cc32)cc1Cl]

The title compound was obtained according to a procedure analogous to general procedure E: 22% yield. $^1$H NMR (400 MHz, CD$_3$OD) δ 7.49 (d, J=8.5 Hz, 1H), 7.44 (dd, J=6.6, 1.7, 1H), 7.41 (d, J=1.7 Hz, 1H), 7.36 (dd, J=8.5, 1.9 Hz, 1H), 7.26 (t, J=8.8 Hz, 1H) 7.2 (m, 1H), 5.46 (s, 2H), 4.68 (m, 1H), 3.74 (dd, J=12.8, 6.7 Hz, 1H), 3.56 (m, 2H), 3.50 (m, 1H), 2.54 (m, 1H), 2.32 (m, 1H). MS (ESI) (M+H$^+$) m/z=379.00. LCMS Ret time (UV 214/254): 1.132 min.

Example 82: 1-(3-chloro-4-fluorobenzyl)-6-methyl-1H-benzo[d]imidazol-2-amine

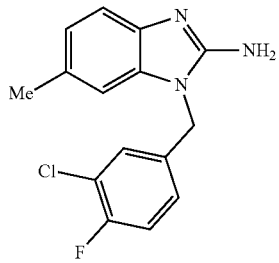 [SMILES: Cc1ccc2nc(N)n(Cc3ccc(F)c(Cl)c3)c2c1]

$N^1$-(3-chloro-4-fluorobenzyl)-5-methylbenzene-1,2-diamine (90 mg, 0.34 mmol), which was prepared by a procedure analogous to the procedure used to prepare Example 60, Step B, was dissolved in a 4:1 mixture of acetonitrile:water (2.5 mL) in a reaction vial at room temperature. Cyanogen bromide (5 M solution in MeCN, 0.140 mL) was added dropwise to the reaction, which was stirred at room temperature for 12 hours. Upon full conversion of the starting material by LCMS, the volatiles were removed in vacuo and the resulting crude solid was purified by reverse-phase HPLC. The title compound was recovered as a white solid (60 mg, 61% yield). $^1$H NMR (400 MHz, CD$_3$OD) δ 7.45 (dd, J=6.8, 2.0 Hz, 1H), 7.33 (d, J=8.1 Hz, 1H), 7.27 (d, J=8.1 Hz, 1H), 7.20 (ovlp m, 3H), 5.38 (s, 2H), 2.43 (s, 3H). MS (ESI) (M+H$^+$) m/z=290.10. LCMS Ret time (UV 214/254): 1.271 min.

Example 79: 1-(3-chloro-4-fluorobenzyl)-2-(piperazin-1-yl)-4-(o-tolyl)-1H-benzo[d]imidazole trifluoroacetate

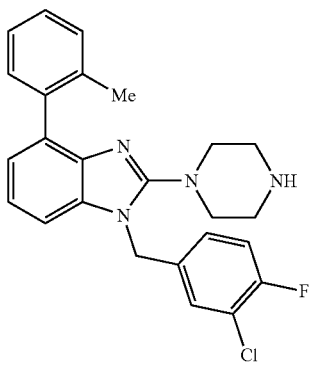 [SMILES: Cc1ccccc1-c1cccc2c1nc(N1CCNCC1)n2Cc1ccc(F)c(Cl)c1]

Step A: To a stirred solution of 3-chloro-4-fluorobenzylamine (250 μL, 2.00 mmol, 1.2 eq) in DMF (6 mL) was added potassium carbonate (460 mg, 3.32 mmol, 2 eq) at room temperature. After 5 min, solid 1-bromo-3-fluoro-2-nitrobenzene (365 mg, 1.66 mmol, 1 eq) was added at room temperature. The reaction was stirred at room temperature overnight (~12 hrs) and monitored by LCMS. Upon conversion to the aniline product, the reaction was quenched with 10% aqueous HCl and diluted with water, and then extracted with ethyl acetate (×2). The organic phase was washed with water and a brine solution, dried over magnesium sulfate, and concentrated to a dark solid. This crude 3-bromo-N-(3-chloro-4-fluorobenzyl)-2-nitroaniline was used without further purification on the subsequent step.

Step B: The crude 3-bromo-N-(3-chloro-4-fluorobenzyl)-2-nitroaniline (~550 mg, 1.5 mmol) from step A was dissolved in MeOH (8 mL) and stirred at 0° C. in an ice bath. Zinc powder (500 mg, 7.75 mmol, 5 eq) and solid ammonium chloride (415 mg, 7.7 mmol, 5 eq) were added to the reaction. The reaction was allowed to slowly warm to room temperature. The reaction was monitored by LCMS. Upon conversion to the reduced product (solution will become clear), the solution was filtered to remove excess zinc powder and then concentrated in vacuo. The crude residue was diluted with water and then extracted with DCM. The organic phase was dried over magnesium sulfate and concentrated to provide crude 3-bromo-$N^1$-(3-chloro-4-fluorobenzyl)benzene-1,2-diamine (470 mg, 95% crude yield). This solid was used without further purification.

Step C: The 3-bromo-N-(3-chloro-4-fluorobenzyl)benzene-1,2-diamine (1.11 g, 3.38 mmol, 1 eq) was dissolved in DCM (25 mL) and then DMAP (40 mg, 0.1 eq) and carbodiimidazole (CDI) (1.10 g, 6.77 mmol, 2 eq) were added at room temperature. The reaction was stirred at room temperature for 12 hours and monitored by LCMS. Upon conversion of the starting material and intermediates to the product by LCMS, the reaction was diluted with water and extracted with DCM. The organic phase was dried over magnesium sulfate and concentrated to a crude yellowish solid. This was purified by column chromatography (0-20% EtOAc in hexanes then 60% EtOAc) to afford the 4-bromo-1-(3-chloro-4-fluorobenzyl)-1,3-dihydro-2H-benzo[d]imidazol-2-one (605 mg, 52% yield).

Step D: The 4-bromo-1-(3-chloro-4-fluorobenzyl)-1,3-dihydro-2H-benzo[d]imidazol-2-one (605 mg) was dissolved in POCl$_3$ (10 mL) and heated at reflux. The reaction was monitored by LCMS. Upon conversion to the chlorobenzimidazole (~2 hrs), the reaction was cooled to room temperature, and then poured incrementally into a large Erlenmeyer flask containing ice water to quench the excess POCl$_3$ (NOTE: This is very exothermic and should be done in an ice bath with a large Erlenmeyer). After the quench, this solution was neutralized with sodium hydroxide pellets to induce precipitation of the product. Upon neutrality, 4-bromo-2-chloro-1-(3-chloro-4-fluorobenzyl)-1H-benzo[d]imidazole crashes out and was collected by filtration and dried under vacuum (500 mg, 77%).

Step E: The 4-bromo-2-chloro-1-(3-chloro-4-fluorobenzyl)-1H-benzo[d]imidazole (30 mg, 0.08 mmol, 1 eq) was dissolved in N,N-Dimethylacetamide (DMA) (0.5 mL) in a microwave tube equipped with a stir bar. Piperazine (42 mg, 6 eq) was added to the tube and then the tube was sealed. The reaction was heated in a microwave reactor at 165° C. for 45 min. Upon conversion by LCMS, the reaction was diluted with water and then extracted with DCM. The resulting crude solution was purified by reverse phase HPLC. 4-Bromo-1-(3-chloro-4-fluorobenzyl)-2-(piperazin-1-yl)-1H-benzo[d]imidazole was recovered as a white solid (12 mg, 35% yield).

Step F: 4-Bromo-1-(3-chloro-4-fluorobenzyl)-2-(piperazin-1-yl)-1H-benzo[d]imidazole (or corresponding TFA salt) (40 mg, 0.0945 mmol, 1 eq), (PCy$_3$)HBF$_4$ (7.0 mg, 0.0189 mmol, 0.2 eq), Pd(OAc)$_2$ (2.15 mg, 0.00945 mmol, 1 eq), K$_3$PO$_4$ (60 mg, 0.284 mmol, 3 eq) and 2-methylphenylboronic acid (14 mg, 0.104 mmol, 1.1 eq) were added to a sealed tube reaction vessel equipped with stir bar. The solid mixture was purged 3× with argon. A 5/1 mixture of dimethoxyethane (DME)/water (1.0 mL) was added to the tube, which was then sealed. The reaction tube was heated at 85°

C. in an oil bath and monitored by LCMS. Upon conversion by LCMS, the reaction was diluted with water and extracted with DCM. The resulting crude solution was concentrated and purified by reverse phase preparative HPLC. The title compound was isolated was a white solid (30 mg, 75% yield). $^1$H NMR (400 MHz, CD$_3$OD): δ 7.50 (dd, J=6.9, 2.1 Hz, 1H), 7.40 (ovlp, 1H), 7.38 (ovlp, 3H), 7.33 (ovlp, 3H), 7.26 (m, 1H), 7.23 (dd, J=7.4, 1.1 Hz, 1H), 5.52 (s, 2H), 3.63 (t, J=5.4 Hz, 4H), 3.43 (t, J=5.4 Hz, 4H), 2.21 (s, 3H). MS (ESI) (M+H$^+$) m/z=435.30. LCMS Ret time (UV 214/254): 1.300 min.

Example 80: 1-(3-chloro-4-fluorobenzyl)-4-phenyl-2-(piperazin-1-yl)-1H-benzo[d]imidazole trifluoroacetate

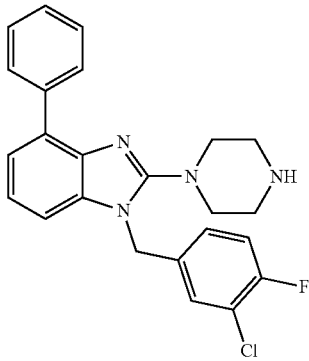 [SMILES: Fc1ccc(Cn2c(N3CCNCC3)nc3c(-c4ccccc4)cccc32)cc1Cl]

The title compound was obtained according to a procedure analogous to general procedure F: $^1$H NMR (400 MHz, CD$_3$OD) δ 7.73 (t, J=2.9 Hz, 2H), 7.57 (m, J=2.9 Hz, 4H), 7.45 (t, J=7.5 Hz, 2H), 7.38 (d, J=7.4 Hz, 1H), 7.3 (q, J=4.7 Hz, 2H), 5.60 (s, 2H), 3.78 (t, J=5.2 Hz, 4H), 3.50 (t, J=5.2 Hz, 4H). MS (ESI) (M+H$^+$) m/z=421.00. LCMS Ret time (UV 214/254): 1.273 min.

Example 81: 1-(3-chloro-4-fluorobenzyl)-4-(2-methoxyphenyl)-2-(piperazin-1-yl)-1H-benzo[d]imidazole trifluoroacetate

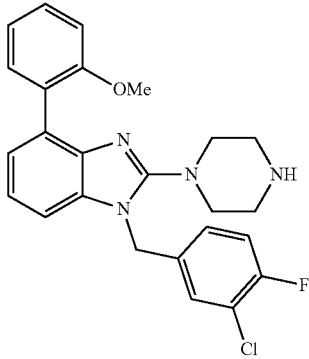 [SMILES: COc1ccccc1-c1cccc2c1nc(N1CCNCC1)n2Cc1ccc(F)c(Cl)c1]

The title compound was obtained according to a procedure analogous to general procedure F: $^1$H NMR (400 MHz, CD$_3$OD) δ 7.57 (d, J=7.3 Hz, 1H), 7.53 (t, J=7.0 Hz, 1H), 7.49 (d, J=7.9 Hz, 1H), 7.42 (t, J=6.9 Hz, 1H), 7.42 (s, 1H), 7.38 (d, J=8.1 Hz, 1H), 7.35 (s, 1H), 7.33 (s, 1H), 7.20 (d, J=8.1 Hz, 1H), 7.14 (t, J=7.5 Hz, 1H), 5.59 (s, 2H), 3.85 (s, 3H), 3.76 (t, J=5.2 Hz, 4H), 3.46 (t, J=5.2 Hz, 4H). MS (ESI) (M+H$^+$) m/z=451.00. LCMS Ret time (UV 214/254): 1.265 min.

Example 82: 1-(3-chloro-4-fluorobenzyl)-4-(2-fluorophenyl)-2-(piperazin-1-yl)-1H-benzo[d]imidazole trifluoroacetate

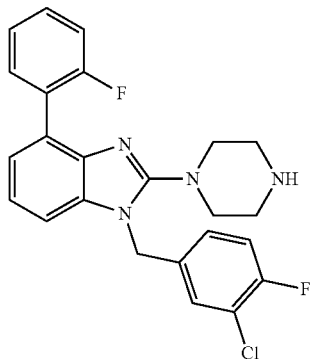 [SMILES: Fc1ccc(Cn2c(N3CCNCC3)nc3c(-c4ccccc4F)cccc32)cc1Cl]

The title compound was obtained according to a procedure analogous to general procedure F: $^1$H NMR (400 MHz, CD$_3$OD) δ 7.63 (dd, J=3.4, 1.7 Hz, 1H), 7.53 (dd, J=7.2, 2.4 Hz, 2H), 7.46 (d, J=7.6 Hz, 1H), 7.44 (s, 1H), 7.38 (td, J=7.84, 1.56 Hz, 1H), 7.30 (m, 3H), 5.55 (s, 2H), 3.71 (t, J=5.2 Hz), 3.45 (t, J=5.2 Hz). MS (ESI) (M+H$^+$) m/z=439.00. LCMS Ret time (UV 214/254): 1.295 min.

Example 83: 2-(1-(3-chloro-4-fluorobenzyl)-2-(piperazin-1-yl)-1H-benzo[d]imidazol-4-yl)aniline trifluoroacetate

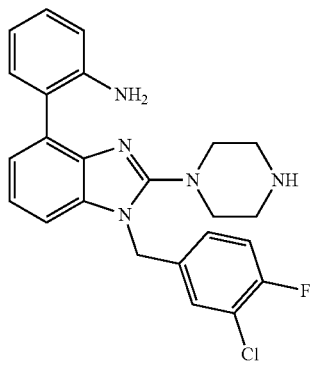 [SMILES: Nc1ccccc1-c1cccc2c1nc(N1CCNCC1)n2Cc1ccc(F)c(Cl)c1]

The title compound was obtained according to a procedure analogous to general procedure F: MS (ESI) (M+H$^+$) m/z=436.00. LCMS Ret time (UV 214/254): 1.159 min.

Example 84: 1-(3-chloro-4-fluorobenzyl)-4-(2-chlorophenyl)-2-(piperazin-1-yl)-1H-benzo[d]imidazole trifluoroacetate

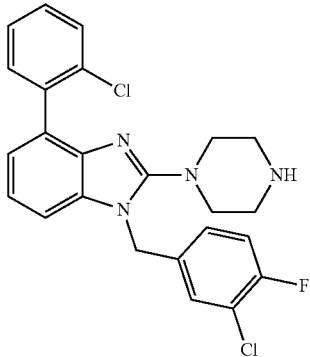 [SMILES: Fc1ccc(Cn2c(N3CCNCC3)nc3c(-c4ccccc4Cl)cccc32)cc1Cl]

The title compound was obtained according to a procedure analogous to general procedure F: MS (ESI) (M+H$^+$) m/z=455.10. LCMS Ret time (UV 214/254): 1.331 min.

Example 85: 1-(3-chloro-4-fluorobenzyl)-2-(piperazin-1-yl)-4-(1,3,5-trimethyl-1H-pyrazol-4-yl)-1H-benzo[d]imidazole trifluoroacetate

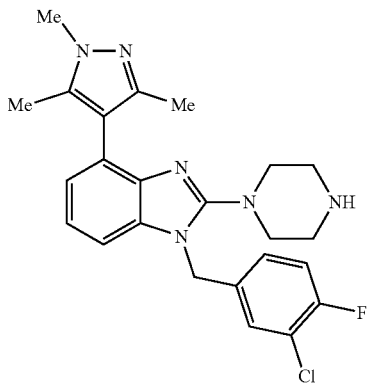 [SMILES: Cc1nn(C)c(C)c1-c1cccc2c1nc(N1CCNCC1)n2Cc1ccc(F)c(Cl)c1]

The title compound was obtained according to a procedure analogous to general procedure F: MS (ESI) (M+H$^+$) m/z=453.10. LCMS Ret time (UV 214/254): 1.132 min.

Example 86: 1-(3-chloro-4-fluorobenzyl)-4-(1-methyl-1H-pyrazol-5-yl)-2-(piperazin-1-yl)-1H-benzo[d]imidazole trifluoroacetate

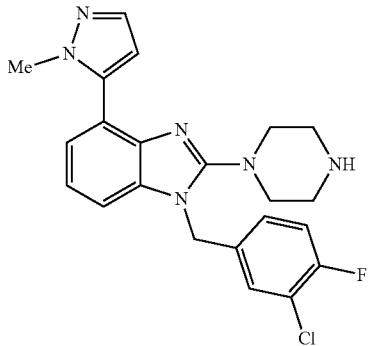 [SMILES: Cn1nccc1-c1cccc2c1nc(N1CCNCC1)n2Cc1ccc(F)c(Cl)c1]

The title compound was obtained according to a procedure analogous to general procedure F: MS (ESI) (M+H$^+$) m/z=425.10. LCMS Ret time (UV 214/254): 1.198 min.

Example 87: 1-(3-chloro-4-fluorobenzyl)-2-(piperazin-1-yl)-4-(4-(trifluoromethyl)phenyl)-1H-benzo[d]imidazole

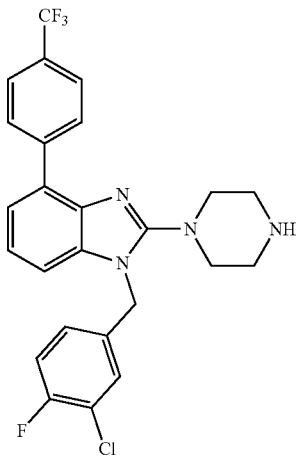 [SMILES: Fc1ccc(Cn2c(N3CCNCC3)nc3c(-c4ccc(C(F)(F)F)cc4)cccc32)cc1Cl]

The title compound was obtained according to a procedure analogous to general procedure F: 1H NMR (400 MHz, CDCl3) δ 8.05 (br s, 2H), 7.81 (br s, 2H), 7.54 (br s, 1H), 7.40 (ovlp bs, 2H), 7.34 (ovlp br s, 2H), 7.27 (ovlp s, 2H), 7.02 (s, 1H), 5.35 (br s, 2H), 4.01 (br s, 2H), 3.88 (br s, 2H), 3.65 (br s, 4H). MS (ESI) (M+H$^+$) m/z=489.43. LCMS Ret time (UV 210/254): 1.61 min.

Example 88: 1-(3-chloro-4-fluorobenzyl)-4-(3,4-dimethoxyphenyl)-2-(piperazin-1-yl)-1H-benzo[d]imidazole

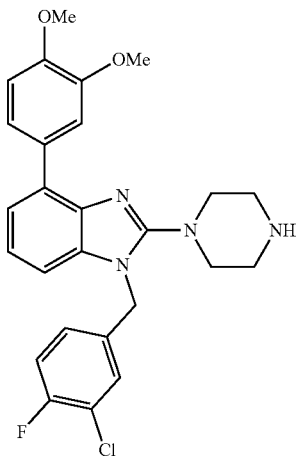 [SMILES: COc1ccc(-c2cccc3c2nc(N2CCNCC2)n3Cc2ccc(F)c(Cl)c2)cc1OC]

The title compound was obtained according to a procedure analogous to general procedure F: $^1$H NMR (400 MHz, CDCl$_3$) δ 7.76 (s, 1H), 7.62 (d, J=8.4 Hz, 1H), 7.43 (d, J=7.2 Hz, 1H), 7.26 (ovlp, 2H), 7.13 (m, 1H), 7.00 (ovlp, 3H), 5.19 (s, 2H), 3.98 (s, 3H), 3.95 (s, 3H), 3.58 (br s, 4H), 3.38 (br s, 4H). MS (ESI) (M+H$^+$) m/z=481.49. LCMS Ret time (UV 210/254): 1.38 min.

Example 89: 1-(3-chloro-4-fluorobenzyl)-2-(piperazin-1-yl)-4-(pyridin-3-yl)-1H-benzo[d]imidazole

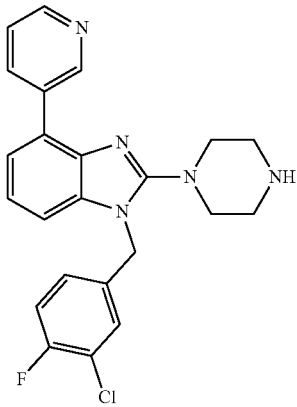 [SMILES: Fc1ccc(Cn2c(N3CCNCC3)nc3c(-c4cccnc4)cccc32)cc1Cl]

The title compound was obtained according to a procedure analogous to general procedure F: ¹H NMR (400 MHz, CDCl₃) δ 8.44 (d, J=8.0 Hz, 1H), 7.55 (m, 1H), 7.42 (d, J=1.2 Hz, 1H), 7.40 (s, 1H), 7.36 (d, J=1.2 Hz, 1H), 7.25 (ovlp, 4H), 7.11 (m, 1H), 5.37 (s, 2H), 3.33 (br s, 4H), 3.06 (br s, 4H).

Example 90: 1-(3,5-difluorobenzyl)-4-(2-fluorophenyl)-2-(piperazin-1-yl)-1H-benzo[d]imidazole

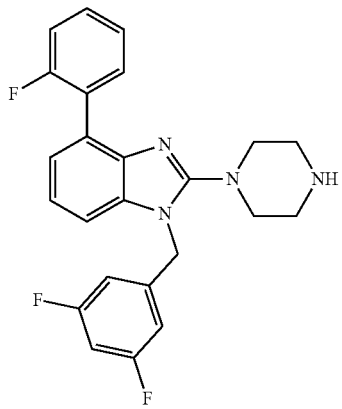 [SMILES: Fc1cc(F)cc(Cn2c(N3CCNCC3)nc3c(-c4ccccc4F)cccc32)c1]

The title compound was obtained according to a procedure analogous to general procedure F: 1H NMR (400 MHz, CDCl₃) δ 7.69 (t, J=1.2 Hz, 1H), 7.41 (m, 1H), 7.24 (ovlp, 5H), 6.91 (t, J=1.2 Hz, 1H), 6.81 (d, J=6.4 Hz, 1H), 5.41 (s, 2H), 3.32 (br s, 4H), 3.11 (br s, 4H). MS (ESI) (M+H⁺) m/z=423.70. LCMS Ret time (UV 210/254): 1.82 min.

Example 91: 4-(3,4-dimethoxyphenyl)-2-(piperazin-1-yl)-1-(4-(trifluoromethyl)benzyl)-1H-benzo[d]imidazole

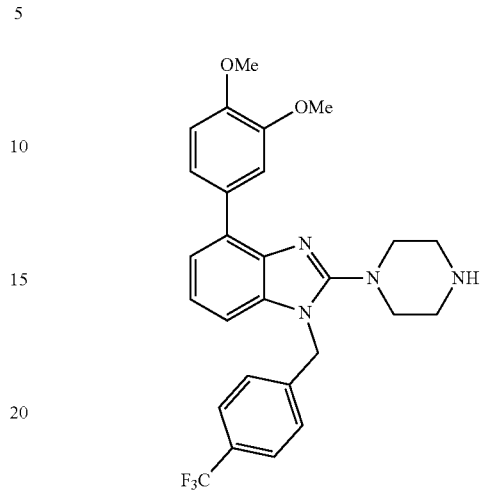

The title compound was obtained according to a procedure analogous to general procedure F: ¹H NMR (400 MHz, CDCl₃) δ 7.83 (s, 1H), 7.63 (d, J=8.4 Hz, 2H), 7.50 (dd, J=8.0, 1.6 Hz, 1H), 7.35 (ovlp s, 1H), 7.34 (ovlp d, J=8.4 Hz, 2H), 7.16 (t, J=7.6 Hz, 1H), 7.02 (ovlp, 2H), 5.40 (s, 2H), 3.94 (s, 3H), 3.90 (s, 3H), 3.23 (br s, 4H), 2.95 (br s, 4H). MS (ESI) (M+H⁺) m/z=497.73. LCMS Ret time (UV 210/254): 1.48 min.

Example 92: 4-(2-(piperazin-1-yl)-1-(4-(trifluoromethyl)benzyl)-1H-benzo[d]imidazol-4-yl)aniline

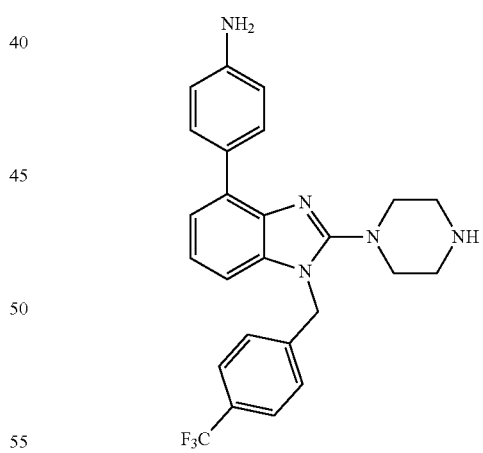

The title compound was obtained according to a procedure analogous to general procedure F: ¹H NMR (400 MHz, CDCl₃) δ 7.66 (d, J=8.4 Hz, 2H), 7.80 (d, J=8.4 Hz, 2H), 7.29 (d, J=1.6 Hz, 1H), 7.21 (ovlp, 4H), 6.94 (d, J=1.6 Hz, 1H), 6.88 (t, J=1.6 Hz, 1H), 5.48 (s, 2H), 3.33 (br s, 4H), 3.12 (br s, 4H). MS (ESI) (M+H⁺) m/z=452.65. LCMS Ret time (UV 210/254): 1.03 min.

Example 93: 1-(3-chloro-4-fluorobenzyl)-4-(1,3-dimethyl-1H-pyrazol-5-yl)-2-(piperazin-1-yl)-1H-benzo[d]imidazole

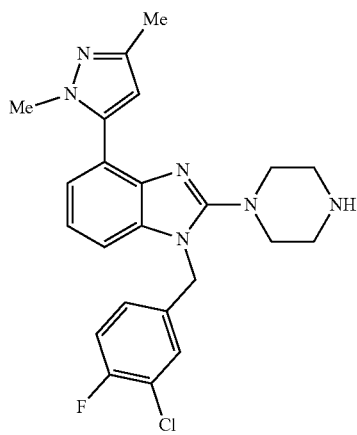 [SMILES: Cc1cc(-c2cccc3c2nc(N2CCNCC2)n3Cc2ccc(F)c(Cl)c2)n(C)n1]

The title compound was obtained according to a procedure analogous to general procedure F: $^1$H NMR (400 MHz, CD$_3$OD) δ 7.31 (d, J=2.4 Hz, 1H), 7.30 (m, 1H), 7.25 (ovlp, 3H), 7.07 (m, 1H), 6.18 (s, 1H), 5.36 (s, 2H), 3.71 (s, 3H), 3.41 (d, J=5.6 Hz, 4H), 3.31 (d, J=5.6 Hz, 4H), 2.24 (s, 3H). MS (ESI) (M+H$^+$) m/z=439.65. LCMS Ret time (UV 210/254): 1.37 min.

Example 94: 1-(3-chloro-4-fluorobenzyl)-4-(2-isopropylphenyl)-2-(piperazin-1-yl)-1H-benzo[d]imidazole

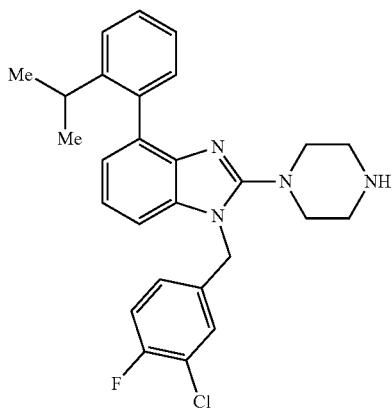 [SMILES: CC(C)c1ccccc1-c1cccc2c1nc(N1CCNCC1)n2Cc1ccc(F)c(Cl)c1]

The title compound was obtained according to a procedure analogous to general procedure F: $^1$H NMR (400 MHz, CD$_3$OD) δ 7.37 (ovlp d, J=7.6 Hz, 1H), 7.36 (ovlp s, 1H), 7.33 (m, 1H), 7.26 (dd, J=6.8, 2.0 Hz, 1H), 7.19 (ovlp, 4H), 7.16 (m, 1H), 6.98 (m, 1H), 5.34 (s, 2H), 3.27 (br s, 4H), 3.21 (br s, 4H), 2.81 (sep, J=6.8 Hz, 1H), 1.07 (br s, 6H). MS (ESI) (M+H$^+$) m/z=463.75 LCMS Ret time (UV 210/254): 1.51 min.

Example 95: 4-(2-isopropylphenyl)-2-(piperazin-1-yl)-1-(4-(trifluoromethyl)benzyl)-1H-benzo[d]imidazole

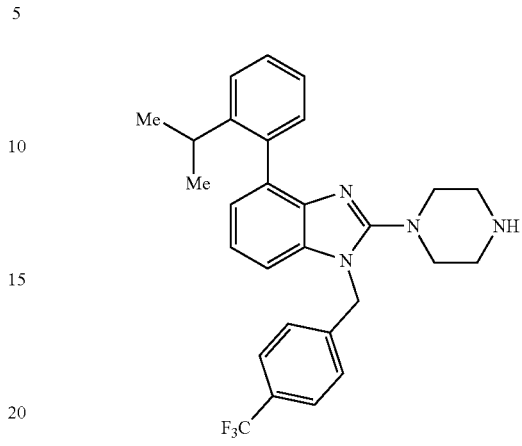

The title compound was obtained according to a procedure analogous to general procedure F: $^1$H NMR (400 MHz, CD$_3$OD) δ 7.61 (d, J=8.4 Hz, 2H), 7.38 (ovlp, 1H), 7.33 (ovlp, 3H), 7.17 (ovlp, 4H), 6.98 (dd, J=6.8, 2.0 Hz, 1H), 5.45 (s, 2H), 3.25 (ovlp br s, 4H), 3.13 (br s, 4H), 2.83 (sept, J=6.8 Hz, 1H), 1.07 (br s, 6H). MS (ESI) (M+H$^+$) m/z=479.96. LCMS Ret time (UV 210/254): 1.52 min.

Example 96: 4-(1,5-dimethyl-1H-pyrazol-3-yl)-2-(piperazin-1-yl)-1-(4-(trifluoromethyl)benzyl)-1H-benzo[d]imidazole

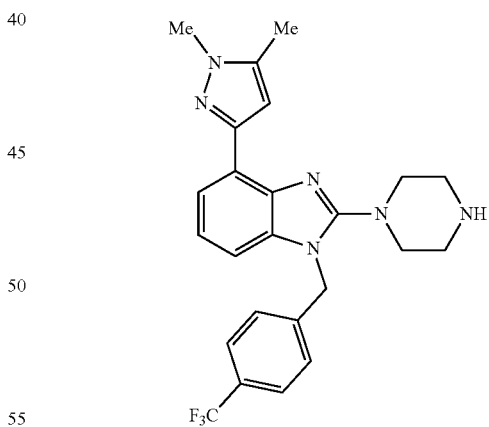

The title compound was obtained according to a procedure analogous to general procedure F: $^1$H NMR (400 MHz, CD$_3$OD) δ 7.60 (d, J=8.4 Hz, 2H), 7.31 (d, J=8.4 Hz, 2H), 7.20 (ovlp, 3H), 6.18 (s, 1H), 5.47 (s, 2H), 3.72 (s, 3H), 3.41 (d, J=5.1 Hz, 4H), 3.25 (d, J=5.1 Hz, 4H), 2.23 (s, 3H). MS (ESI) (M+H$^+$) m/z=455.92. LCMS Ret time (UV 210/254): 0.33 min.

Example 97: 1-(3,5-difluorobenzyl)-4-(2-isopropylphenyl)-2-(piperazin-1-yl)-1H-benzo[d]imidazole

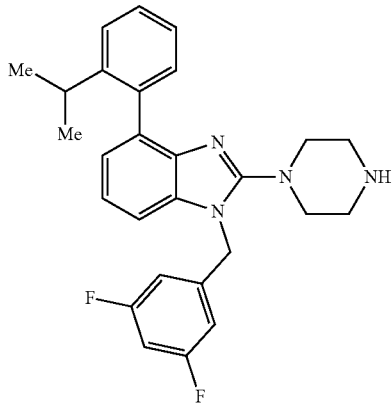 [SMILES: CC(C)c1ccccc1-c1cccc2c1nc(N1CCNCC1)n2Cc1cc(F)cc(F)c1]

The title compound was obtained according to a procedure analogous to general procedure F: $^1$H NMR (400 MHz, CD$_3$OD) δ 7.38 (ovlp d, J=6.8 Hz, 1H), 7.37 (s, 1H), 7.33 (m, 1H), 7.18 (ovlp, 4H), 7.0 (dd, J=6.8, 1.6 Hz, 1H), 6.84 (t, J=8.8 Hz, 1H), 6.71 (d, J=6.4 Hz, 1H), 5.37 (s, 2H), 3.26 (br s, 4H), 3.16 (br s, 4H), 2.83 (sept, J=6.8 Hz, 1H), 1.08 (br s, 6H). MS (ESI) (M+H$^+$) m/z=447.91. LCMS Ret time (UV 210/254): 1.50 min.

Example 98: 2-(1-(3-chloro-4-fluorobenzyl)-2-(piperazin-1-yl)-1H-benzo[d]imidazol-4-yl)ethan-1-amine trifluoroacetate

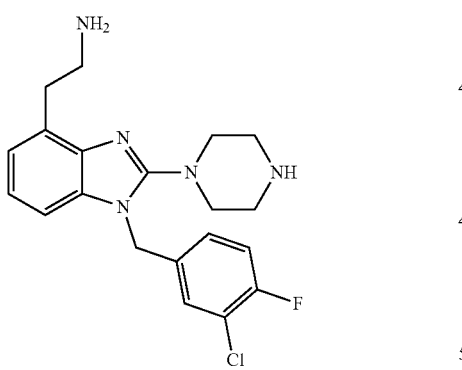

4-Bromo-1-(3-chloro-4-fluorobenzyl)-2-(piperazin-1-yl)-1H-benzo[d]imidazole (50 mg, 0.118 mmol, 1 eq), which was prepared by a procedure analogous to the procedure used to prepare Example 79, Step E, RuPhos (14 mg, 0.0295 mmol, 0.25 eq), Pd(OAc)$_2$ (4.0 mg, 0.012 mmol, 1 eq), K$_3$PO$_4$ (75 mg, 0.354 mmol, 3 eq) and potassium N-Boc-aminoethyltrifluoroborate (33 mg, 0.130 mmol, 1.1 eq) were added to a sealed tube reaction vessel equipped with stir bar. The solid mixture was purged 3× with argon. A 5/1 mixture of dimethoxyethane (DME)/water (1.0 mL) was added to the tube, which was then sealed. The reaction tube was heated at 100° C. in an oil bath and monitored by LCMS. Upon conversion by LCMS, the reaction was diluted with water and extracted with DCM. The resulting crude solution was concentrated to a crude oil. The crude material was dissolved in a 2/1 mixture of DCM/TFA (2 mL) and stirred at room temperature until the free amine was observed by LCMS. Upon conversion to the free amine, the solution was concentrated and purified by reverse phase preparative HPLC. The title compound was isolated was a white solid (21 mg, 45% yield). MS (ESI) (M+H$^+$) m/z=388.10. LCMS Ret time (UV 214/254): 0.954 min.

Example 99: 2-(1-(3,5-difluorobenzyl)-2-(piperazin-1-yl)-1H-benzo[d]imidazol-4-yl)ethan-1-amine trifluoroacetate

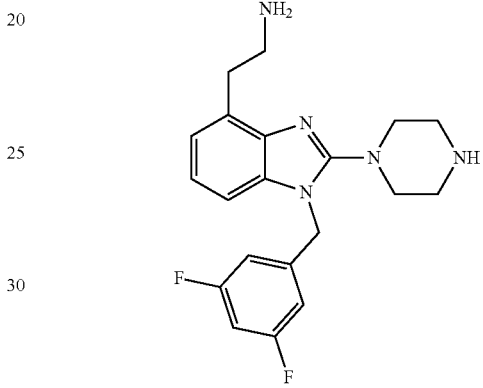

The title compound was obtained according to a procedure analogous to general procedure G: MS (ESI) (M+H$^+$) m/z=372.10. LCMS Ret time (UV 214/254): 0.902 min.

Example 100: 2-(2-(piperazin-1-yl)-1-(4-(trifluoromethyl)benzyl)-1H-benzo[d]imidazol-4-yl)ethan-1-amine trifluoroacetate

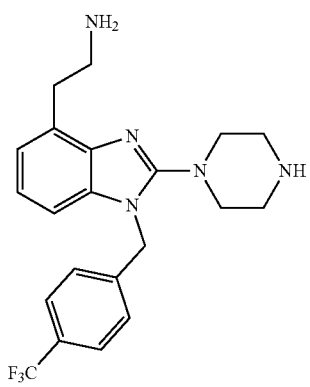 [SMILES: NCCc1cccc2c1nc(N1CCNCC1)n2Cc1ccc(C(F)(F)F)cc1]

The title compound was obtained according to a procedure analogous to general procedure G: MS (ESI) (M+H$^+$) m/z=404.10. LCMS Ret time (UV 214/254): 1.017 min.

Example 101: 2-(1-(3-chloro-4-fluorobenzyl)-5,6-dimethyl-2-(piperazin-1-yl)-1H-benzo[d]imidazol-4-yl)ethan-1-amine trifluoroacetate

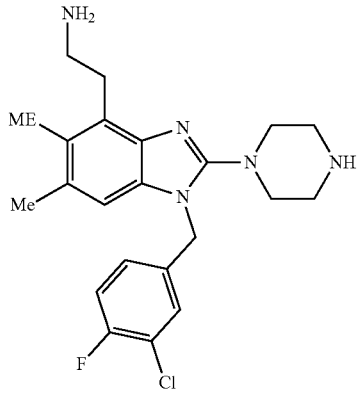

The title compound was obtained according to a procedure analogous to general procedure G, starting from 4-bromo-1-(3-chloro-4-fluorobenzyl)-5,6-dimethyl-2-(piperazin-1-yl)-1H-benzo[d]imidazole, which was prepared by a procedure analogous to the procedure used to prepare Example 118, Step E: $^1$H NMR (400 MHz, CD$_3$OD) δ 7.36 (dd, J=6.8, 2.2 Hz, 1H) 7.25 (t, J=8.8 Hz, 1H), 7.16 (m, 1H), 7.06 (s, 1H), 5.39 (s, 2H), 3.86 (t, J=5.1 Hz, 4H), 3.43 (t, J=5.1 Hz, 4H), 3.40 (t, J=8.2 Hz, 2H), 3.24 (t, J=8.2 Hz, 2H), 2.37 (s, 3H), 2.33 (s, 3H), 2.21 (s, 3H). MS (ESI) (M+H$^+$) m/z=416.10. LCMS Ret time (UV 214/254): 1.049 min.

Example 102: 2-(1-(4-fluoro-3,5-dimethylbenzyl)-5,6-dimethyl-2-(piperazin-1-yl)-1H-benzo[d]imidazol-4-yl)ethan-1-amine trifluoroacetate

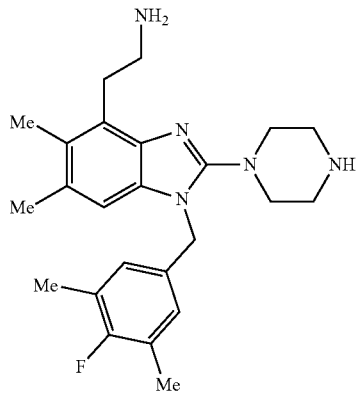 [SMILES: Cc1cc2c(nc(N3CCNCC3)n2Cc2cc(C)c(F)c(C)c2)c(CCN)c1C]

The title compound was obtained according to a procedure analogous to general procedure G, starting from 4-bromo-1-(3-chloro-4-fluorobenzyl)-5,6-dimethyl-2-(piperazin-1-yl)-1H-benzo[d]imidazole, which was prepared by a procedure analogous to the procedure used to prepare Example 118, Step E: MS (ESI) (M+H$^+$) m/z=410.20. LCMS Ret time (UV 214/254): 1.090 min.

Example 103: 1-(4-fluoro-3,5-dimethylbenzyl)-6-methyl-2-(piperazin-1-yl)-4-(1,2,3,6-tetrahydropyridin-4-yl)-1H-benzo[d]imidazole

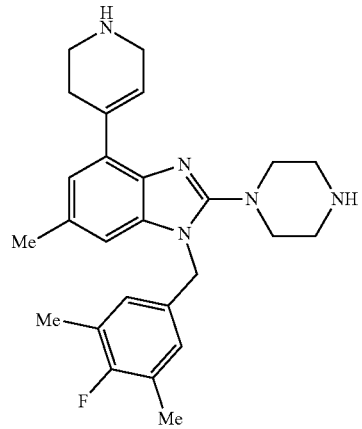 [SMILES: Cc1cc(C2=CCNCC2)c2nc(N3CCNCC3)n(Cc3cc(C)c(F)c(C)c3)c2c1]

The title compound was obtained according to a procedure analogous to general procedure F, starting from 4-bromo-1-(3-chloro-4-fluorobenzyl)-5,6-dimethyl-2-(piperazin-1-yl)-1H-benzo[d]imidazole, which was prepared by a procedure analogous to the procedure used to prepare Example 118, Step E, and (1-(tert-butoxycarbonyl)-1,2,3,6-tetrahydropyridin-4-yl)boronic acid: MS (ESI) (M+H$^+$) m/z=434.30. LCMS Ret time (UV 214/254): 1.091 min.

Example 104: 1-(3-chloro-4-fluorobenzyl)-5,6-dimethyl-4-phenyl-2-(piperazin-1-yl)-1H-benzo[d]imidazole trifluoroacetate

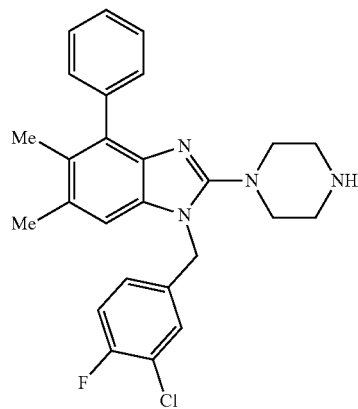 [SMILES: Cc1cc2c(nc(N3CCNCC3)n2Cc2ccc(F)c(Cl)c2)c(-c2ccccc2)c1C]

Step A: Potassium carbonate (535 mg, 3.88 mmol, 2 eq) and 3-chloro-4-fluorobenzyl bromide (286 μL, 2.13 mmol, 1.1 eq) were added sequentially to a stirred solution of 2-chloro-5,6-dimethylbenzimidazole (350 mg, 1.94 mmol) in DMF (6 mL) at room temperature. The reaction was heated to 40° C. Upon conversion of the starting material by LCMS (~3 hr), the reaction was cooled to room temperature and quenched with 10% HCl, extracted with ethyl acetate, and washed thoroughly with water. The combined organic layers were dried over sodium sulfate and concentrated to afford 2-chloro-1-(3-chloro-4-fluorobenzyl)-5,6-dimethyl-1H-benzo[d]imidazole (575 mg, 92% crude yield). The alkylated product was used without any further purification.

Step B: The crude 2-chloro-1-(3-chloro-4-fluorobenzyl)-5,6-dimethyl-1H-benzo[d]imidazole from Step A (356 mg, 1.11 mmol, 1 eq) was dissolved in DMF (10 mL), and NBS (255 mg, 1.45 mmol, 1.3 eq) was added. The mixture was stirred overnight at room temperature. Upon conversion of the starting material by LCMS, the reaction was quenched with water and extracted with ethyl acetate, washed with water and concentrated in vacuo. The crude material was purified by silica gel (0-10% ethyl acetate in hexanes for 10 min then 50% ethyl acetate) to afford 4-bromo-2-chloro-1-(3-chloro-4-fluorobenzyl)-5,6-dimethyl-1H-benzo[d]imidazole as the major product (350 mg, 79% yield). The regiochemistry of the bromination was confirmed by nOe.

Step C: The 4-bromo-2-chloro-1-(3-chloro-4-fluorobenzyl)-5,6-dimethyl-1H-benzo[d]imidazole (300 mg, 0.75 mmol, 1 eq) was dissolved in DMSO (5 mL). Potassium carbonate (204 mg, 1.5 mmol, 2 eq) was added, followed by 1-BOC-piperazine (279 mg, 1.5 mmol, 2 eq). The reaction was heated at 90° C. for 12 hours. Upon full conversion of the starting material by LCMS, the reaction was quenched with water and extracted with ethyl acetate, washed with water and brine, dried over sodium sulfate, and concentrated to a crude solid. The crude solid was purified by silica gel to afford tert-butyl 4-(4-bromo-1-(3-chloro-4-fluorobenzyl)-5,6-dimethyl-1H-benzo[d]imidazol-2-yl)piperazine-1-carboxylate as a white solid (350 mg, 85% yield).

Step D: The tert-butyl 4-(4-bromo-1-(3-chloro-4-fluorobenzyl)-5,6-dimethyl-1H-benzo[d]imidazol-2-yl)piperazine-1-carboxylate (50 mg, 0.0909 mmol, 1 eq), PCy$_3$HBF$_4$ (5.0 mg, 0136 mmol, 0.15 eq), Pd(OAc)$_2$ (2.0 mg, 0.00909 mmol, 0.1 eq), K$_3$PO$_4$ (38 mg, 0.181 mmol, 2 eq) and phenylboronic acid (12.2 mg, 0.10 mmol, 1.1 eq) were added to a sealed tube reaction vessel equipped with stir bar. The solid mixture was purged 3× with Argon. A 5/1 mixture of dimeothoxyethane (DME)/water (1.0 mL) was added to the solid and then the tube was sealed. The reaction tube was heated at 85° C. in an oil bath and monitored by LCMS. Upon conversion of the starting material by LCMS, the reaction was diluted with water and diluted with DCM. The solution was passed through a phase separator and then concentrated. The crude solid was dissolved in a 2/1 mixture of DCM/TFA (1 mL) and stirred for 30 min. After 30 min, the volatiles were removed in vacuo and the deprotected benzimidazole was purified by reverse phase preparative HPLC. The fractions were evaporated to furnish the title compound (15 mg, 37% yield). $^1$H NMR (400 MHz, CDCl$_3$) δ 7.44 (ovlp, 4H), 7.34 (d, J=4.7 Hz, 2H), 7.22 (d, J=8.4 Hz, 1H), 7.14 (s, 1H), 6.97 (s, 1H), 5.35 (s, 2H), 3.72 (br s, 4H), 3.34 (br s, 4H), 2.42 (s, 3H), 2.12 (s, 3H). MS (ESI) (M+H$^+$) m/z=449.10. LCMS Ret time (UV 214/254): 1.326 min.

Example 105: 1-(4-chlorobenzyl)-5,6-dimethyl-4-phenyl-2-(piperazin-1-yl)-1H-benzo[d]imidazole trifluoroacetate

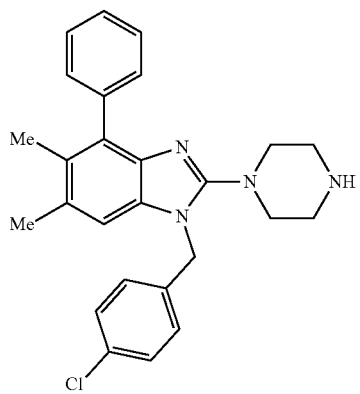 [SMILES: Cc1cc2c(nc(N3CCNCC3)n2Cc2ccc(Cl)cc2)c(-c2ccccc2)c1C]

The title compound was obtained according to a procedure analogous to general procedure H: replacing with 4-chlorobenzyl bromide in Step A: $^1$H NMR (400 MHz, CDCl$_3$) δ 7.44 (m, 5H), 7.23 (d, J=7.8 Hz, 2H), 7.19 (d, J=7.8 Hz, 2H), 6.99 (s, 1H), 5.36 (s, 2H), 3.70 (s, 4H), 3.32 (s, 4H), 2.41 (s, 3H), 2.12 (s, 3H). MS (ESI) (M+H$^+$) m/z=431.10. LCMS Ret time (UV 214/254): 1.314 min.

Example 106: 1-(4-chlorobenzyl)-4-(2-chlorophenyl)-5,6-dimethyl-2-(piperazin-1-yl)-1H-benzo[d]imidazole trifluoroacetate

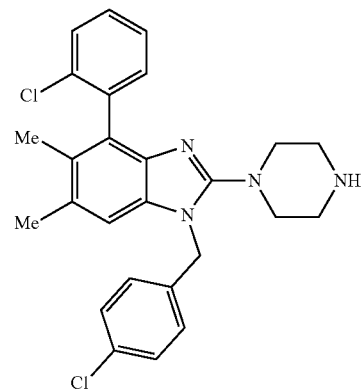 [SMILES: Cc1cc2c(nc(N3CCNCC3)n2Cc2ccc(Cl)cc2)c(-c2ccccc2Cl)c1C]

The title compound was obtained according to a procedure analogous to general procedure H: replacing with 4-chlorobenzyl bromide in Step A: MS (ESI) (M+H$^+$) m/z=465.00. LCMS Ret time (UV 214/254): 1.356 min.

Example 107: 1-(4-chlorobenzyl)-4-(2-fluorophenyl)-5,6-dimethyl-2-(piperazin-1-yl)-1H-benzo[d]imidazole trifluoroacetate

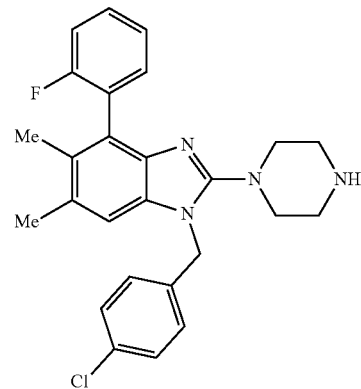 [SMILES: Cc1cc2c(nc(N3CCNCC3)n2Cc2ccc(Cl)cc2)c(-c2ccccc2F)c1C]

The title compound was obtained according to a procedure analogous to general procedure H: replacing with 4-chlorobenzyl bromide in Step A: MS (ESI) (M+H$^+$) m/z=449.10. LCMS Ret time (UV 214/254): 1.325 min.

Example 108: (4-(1-(3-chloro-4-fluorobenzyl)-5,6-dimethyl-2-(piperazin-1-yl)-1H-benzo[d]imidazol-4-yl)phenyl)methanamine trifluoroacetate

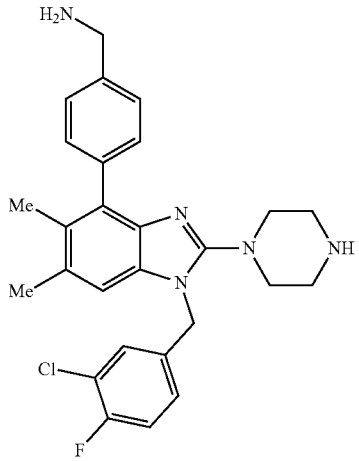 [SMILES: Cc1cc2c(nc(N3CCNCC3)n2Cc2ccc(F)c(Cl)c2)c(-c2ccc(CN)cc2)c1C]

The title compound was obtained according to a procedure analogous to general procedure H, wherein the reaction parameters were modified to the following: PdCl$_2$(dppf), K$_2$CO$_3$, DMF/EtOH (4:1 v/v), 100° C. $^1$H NMR (400 MHz, CD$_3$OD) δ 7.64 (d, J=7.8 Hz, 2H), 7.53 (d, J=6.5 Hz, 1H), 7.43 (d, J=7.8 Hz, 2H), 7.30 (m, 3H), 5.52 (s, 2H), 4.24 (s, 2H), 3.69 (t, J=4.9 Hz, 4H), 3.39 (t, J=4.8 Hz, 4H), 2.41 (s, 3H), 2.11 (s, 3H). MS (ESI) (M+H$^+$) m/z=478.10. LCMS Ret time (UV 214/254): 1.152 min.

Example 109: 1-(3-chloro-4-fluorobenzyl)-4-(2-isopropylphenyl)-5,6-dimethyl-2-(piperazin-1-yl)-1H-benzo[d]imidazole

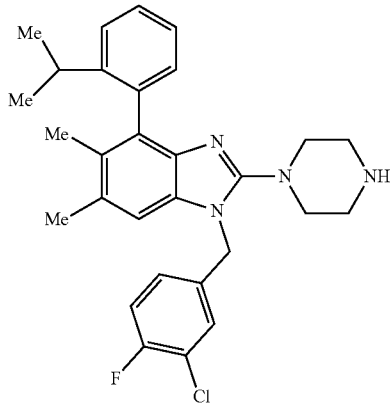 [SMILES: Cc1cc2c(nc(N3CCNCC3)n2Cc2ccc(F)c(Cl)c2)c(-c2ccccc2C(C)C)c1C]

The title compound was obtained according to a procedure analogous to general procedure H: $^1$H NMR (400 MHz, CD$_3$OD) δ 7.39 (d, J=8.0 Hz, 1H), 7.34 (t, J=8.5 Hz, 1H), 7.30 (ovlp, 3H), 7.08 (m, 1H), 7.02 (s, 1H), 7.01 (d, J=8.0 Hz, 1H), 5.29 (s, 2H), 3.21 (ovlp m, 8H), 2.49 (sep, J=6.8 Hz, 1H), 2.31 (s, 3H), 1.91 (s, 3H), 1.03 (d, J=6.8 Hz, 3H), 0.98 (d, J=6.8 Hz, 3H). MS (ESI) (M+H$^+$) m/z=491.11. LCMS Ret time (UV 210/254): 1.49 min.

Example 110: 1-(3-chloro-4-fluorobenzyl)-4-(3,4-dimethoxyphenyl)-5,6-dimethyl-2-(piperazin-1-yl)-1H-benzo[d]imidazole

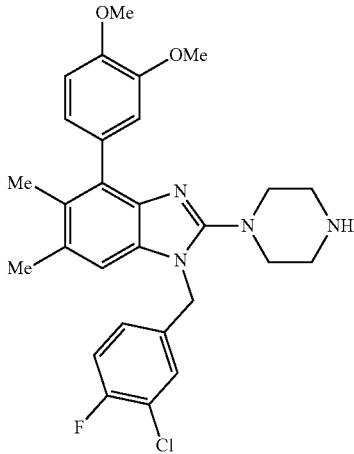 [SMILES: COc1ccc(-c2c(C)c(C)cc3c2nc(N2CCNCC2)n3Cc2ccc(F)c(Cl)c2)cc1OC]

The title compound was obtained according to a procedure analogous to general procedure H: $^1$H NMR (400 MHz, CD$_3$OD) δ 7.28 (dd, J=6.8, 1.6 Hz, 1H), 7.16 (t, J=8.8 Hz, 1H), 7.06 (m, 1H), 7.00 (d, J=8.0 Hz, 1H), 6.98 (s, 1H), 6.88 (s, 1H), 6.82 (dd, J=8.0, 1.6 Hz, 1H), 5.27 (s, 2H), 3.84 (s, 3H), 3.77 (s, 3H), 3.25 (br s, 4H), 3.18 (br s, 4H), 2.29 (s, 3H), 2.06 (s, 3H). MS (ESI) (M+H$^+$) m z=509.91. LCMS Ret time (UV 210/254): 1.42 min.

Example 111: N$^1$-(1-(3-chloro-4-fluorobenzyl)-5,6-dimethyl-4-phenyl-1H-benzo[d]imidazol-2-yl)ethane-1,2-diamine trifluoroacetate

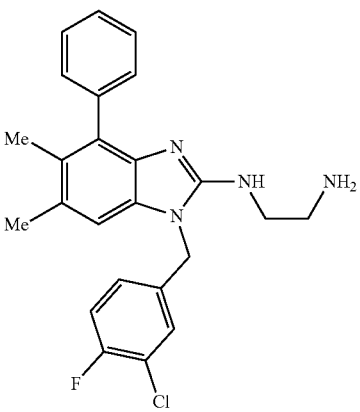 [SMILES: Cc1cc2c(nc(NCCN)n2Cc2ccc(F)c(Cl)c2)c(-c2ccccc2)c1C]

N$^1$-(4-bromo-1-(3-chloro-4-fluorobenzyl)-5,6-dimethyl-1H-benzo[d]imidazol-2-yl)ethane-1,2-diamine (32 mg, 0.075 mmol, 1 eq), which was prepared by a procedure analogous to the procedure used in Example 110, Step C, PCy$_3$HBF$_4$ (5.0 mg, 015 mmol, 0.2 eq), Pd(OAc)$_2$ (2.0 mg, 0.0075 mmol, 0.1 eq), K$_3$PO$_4$ (48 mg, 0.225 mmol, 3 eq) and phenylboronic acid (10 mg, 0.0825 mmol, 1.1 eq) were added to a sealed tube reaction vessel equipped with stir bar. The solid mixture was purged 3× with Argon. A 5/1 mixture of dimeothoxyethane (DME)/water (1.0 mL) was added to the solid and then the tube was sealed. The reaction tube was heated at 85° C. in an oil bath and monitored by LCMS. Upon complete conversion of the starting material by LCMS, the reaction was diluted with water and diluted with DCM. The solution was passed through a phase separator and then concentrated. The crude solid was purified by reverse phase HPLC to afford the title compound as a white solid (10 mg, 32% yield). $^1$H NMR (400 MHz, CDCl$_3$) δ ☐8.62 (br s, 1H), 7.99 (s, 2H), 7.45 (ovlp, 3H), 7.24 (ovlp, 2H), 7.13 (t, J=8.5 Hz, 1H), 7.07 (s, 1H), 6.95 (s, 1H), 5.27, (s, 2H), 3.86 (s, 2H), 3.28 (s, 2H), 2.40 (s, 3H), 2.08 (s, 3H). MS (ESI) (M+H$^+$) m/z=423.10. LCMS Ret time (UV 214/254): 1.312 min.

Example 112: N$^1$-(1-(4-chloro-3-ethylbenzyl)-4-(2-chlorophenyl)-5,6-dimethyl-1H-benzo[d]imidazol-2-yl)ethane-1,2-diamine trifluoroacetate

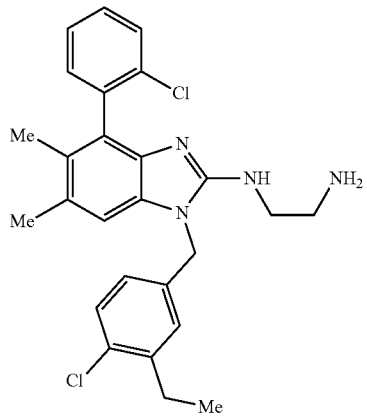 [SMILES: CCc1cc(Cn2c(NCCN)nc3c(-c4ccccc4Cl)c(C)c(C)cc32)ccc1Cl]

The title compound was obtained according to a procedure analogous to the general procedure H used to prepare example 111, replacing with 4-chloro-3-ethylbenzyl bromide: $^1$H NMR (400 MHz, CDCl$_3$) δ 8.20 (bs, 2H), 7.51 (d, J=7.4 Hz, 2H), 7.39 (m, 2H), 7.22 (d, J=5.4 Hz, 1H), 7.13 (s, 1H), 7.00 (s, 1H), 6.86 (d, J=8.0 Hz, 1H), 5.28 (s, 2H), 3.94 (s, 2H), 3.28 (s, 2H), 2.74 (q, J=7.5 Hz, 2H), 2.4 (s, 3H), 2.02 (s, 3H), 1.20 (t, J=7.5 Hz, 3H). MS (ESI) (M+H$^+$) m/z=467.10. LCMS Ret time (UV 214/254): 1.464 min.

Example 113: N$^1$-(1-(3-chloro-4-fluorobenzyl)-4-(2-chlorophenyl)-5,6-dimethyl-1H-benzo[d]imidazol-2-yl)ethane-1,2-diamine trifluoroacetate

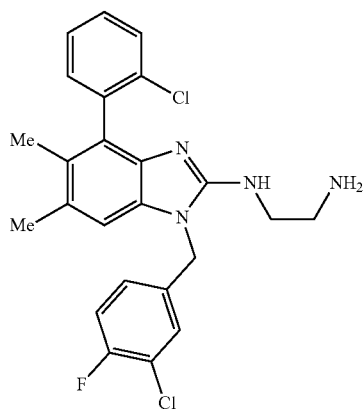 [SMILES: Cc1cc2c(nc(NCCN)n2Cc2ccc(F)c(Cl)c2)c(-c2ccccc2Cl)c1C]

The title compound was obtained according to a procedure analogous to general procedure H used to prepare example 111: MS (ESI) (M+H$^+$) m/z=457.00. LCMS Ret time (UV 214/254): 1.343 min.

Example 114: N$^1$-(1-(3-chloro-4-fluorobenzyl)-5,6-dimethyl-4-(1,3,5-trimethyl-1H-pyrazol-4-yl)-1H-benzo[d]imidazol-2-yl)ethane-1,2-diamine trifluoroacetate

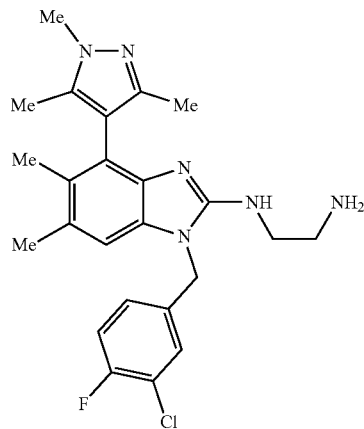 [SMILES: Cc1cc2c(nc(NCCN)n2Cc2ccc(F)c(Cl)c2)c(-c2c(C)nn(C)c2C)c1C]

The title compound was obtained according to a procedure analogous to general procedure H used to prepare example 111: MS (ESI) (M+H$^+$) m/z=455.10. LCMS Ret time (UV 214/254): 1.188 min.

Example 115: N$^1$-(1-(4-chloro-3-ethylbenzyl)-5,6-dimethyl-4-(1,3,5-trimethyl-1H-pyrazol-4-yl)-1H-benzo[d]imidazol-2-yl)ethane-1,2-diamine trifluoroacetate

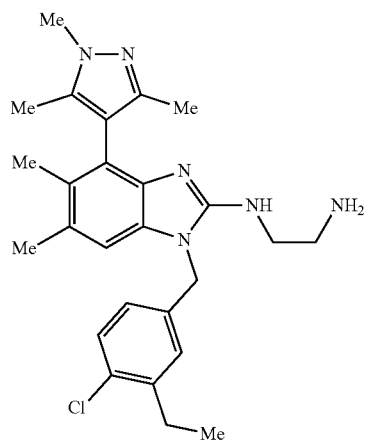 [SMILES: CCc1cc(Cn2c(NCCN)nc3c(-c4c(C)nn(C)c4C)c(C)c(C)cc32)ccc1Cl]

The title compound was obtained according to a procedure analogous to general procedure H used to prepare example 111: MS (ESI) (M+H$^+$) m/z=465.10. LCMS Ret time (UV 214/254): 1.286 min.

Example 116: 3-((2-((2-aminoethyl)amino)-5,6-dimethyl-4-(o-tolyl)-1H-benzo[d]imidazol-1-yl)methyl)benzonitrile trifluoroacetate

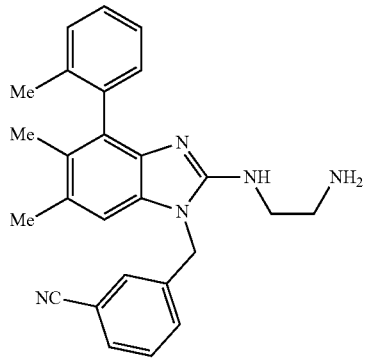 [SMILES: Cc1ccccc1-c1c(C)c(C)cc2c1nc(NCCN)n2Cc1cccc(C#N)c1]

The title compound was obtained according to a procedure analogous to general procedure H used to prepare example 111, replacing with 3-cyanobenzyl bromide: $^1$H NMR (400 MHz, CDCl$_3$) δ 8.70 (br s, 1H), 7.93 (br s, 2H), 7.60 (d, J=7.0 Hz, 1H), 7.47 (ovlp, 3H), 7.36 (d, J=3.2 Hz, 1H), 7.14 (d, J=7.3 Hz, 1H), 6.93 (s, 1H), 5.36 (s, 2H), 3.73 (br s, 2H), 3.25 (br s, 2H), 2.39 (s, 3H), 2.01 (s, 3H), 1.99 (s, 3H). MS (ESI) (M+H$^+$) m/z=410.20. LCMS Ret time (UV 214/254): 1.245 min.

Example 117: 3-((2-((2-aminoethyl)amino)-4-(2-chlorophenyl)-5,6-dimethyl-1H-benzo[d]imidazol-1-yl)methyl)benzonitrile trifluoroacetate

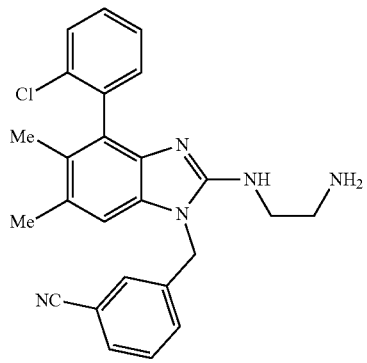 [SMILES: Cc1cc2c(nc(NCCN)n2Cc2cccc(C#N)c2)c(-c2ccccc2Cl)c1C]

The title compound was obtained according to a procedure analogous to general procedure H used to prepare example 111, replacing with 3-cyanobenzyl bromide: MS (ESI) (M+H$^+$) m/z=430.00. LCMS Ret time (UV 214/254): 1.244 min.

Example 118: 1-(3-chloro-4-fluorobenzyl)-4-(2-chlorophenyl)-6-methyl-2-(piperazin-1-yl)-1H-benzo[d]imidazole trifluoroacetate

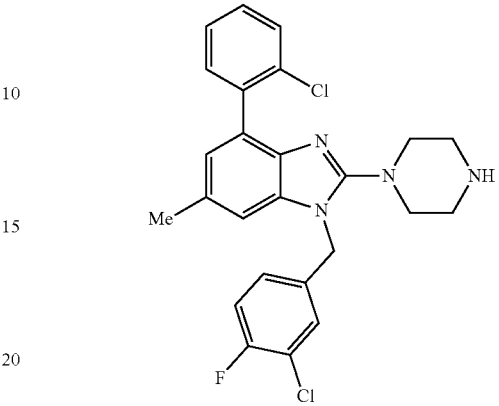

Step A: To a stirred solution of 4-methyl-2-nitroaniline (2.0 g, 13.13 mmol, 1.0 eq) in AcOH (35 mL) was added bromine (725 µL, 14.05 mmol, 1.07 eq) in AcOH (5 mL) via an addition funnel at room temperature. The reaction was stirred at room temperature for 30 min as an orange precipitate forms. The reaction mixture was poured into ice water and then the solid was collected by filtration and washed with ice water. The crude 3-bromo-5-methyl-2-nitroaniline solid was dried prior to use in the next step without any purification.

Step B: The crude 3-bromo-5-methyl-2-nitroaniline (3.0 g, 13 mmol) from Step A was dissolved in MeOH (65 mL) and stirred at 0° C. in an ice bath. Zinc powder (4.0 g, 65 mmol, 5 eq) and solid ammonium chloride (3.50 g, 65 mmol, 5 eq) were added to the reaction. The reaction was allowed to slowly warm to room temperature. The reaction was monitored by LCMS. Upon conversion to the reduced product, the solution was filtered to remove excess zinc powder and then concentrated in vacuo. The crude residue was diluted with water and then extracted with ethyl acetate. The organic phase was dried over magnesium sulfate and concentrated to provide The 3-bromo-3-bromo-5-methyl-benzene-1,2-diamine as a crude solid (~2.4 g, 90% yield). This solid was used without further purification.

Step C: The 3-bromo-5-methylbenzene-1,2-diamine obtained from step B (2.4 g, 11.9 mmol, 1 eq) was dissolved in DCM (50 mL). DMAP (150 mg, 1.19 mmol, 0.1 eq) and CDI (3.85 g, 23.8 mmol, 2 eq) were added and the reaction was allowed to stir overnight at room temperature. A precipitate formed after the addition of CDI. Upon conversion of the starting material by LCMS, the solid precipitate was filtered and dried. The solid was used without any further purification (~2.0 g recovered). The solid (1.5 g) was dissolved in POCl$_3$ (15 mL) and heated at 90° C. The reaction was complete by LCMS after four hours, which was then cooled to 0° C. The reaction was carefully and slowly added to ice water to quench the excess POCl3 and then solid NaOH pellets were added until the solution is neutral. The solid precipitate was filtered off and dried to afford the desired 2-chloro-4-bromo-6-methylbenzimidazole (1.1 g, 67% yield).

Step D: To a stirred solution of the 4-bromo-2-chloro-6-methyl-1H-benzo[d]imidazole (1.08 g, 4.43 mmol) in DMF (15 mL) was added potassium carbonate (917 mg, 6.65 mmol, 1.5 eq) followed by 3-chloro-4-fluorobenzyl bromide (0.595 mL, 4.43 mmol, 1 eq) at room temperature. The reaction was stirred at room temperature. Upon completion by LCMS (~3 hr), the reaction was quenched with 10% HCl, extracted with ethyl acetate, and washed thoroughly with water. The combined organic layers were dried with sodium sulfate and concentrated to afford the crude alkylated product. The crude solid was purified on silica gel (10% ethyl acetate: hexanes to 30% ethyl acetate) to afford 4-bromo-2-chloro-1-(3-chloro-4-fluorobenzyl)-6-methyl-1H-benzo[d]imidazole as a white solid (1.85 g, 72% yield).

Step E: The 4-bromo-2-chloro-1-(3-chloro-4-fluorobenzyl)-6-methyl-1H-benzo[d]imidazole (1.85 g, 4.81 mmol, 1 eq) was dissolved in DMSO (12 mL). Potassium carbonate (1.33 g, 9.6 mmol, 2 eq) was added, followed by 1-BOC-piperazine (1.79 g, 9.6 mmol, 2 eq). The reaction was heated at 90° C. for 12 hours. Upon full conversion by LCMS, the reaction was quenched with water and extracted with ethyl acetate, washed with water and brine, dried over sodium sulfate, and concentrated to a brownish solid. The crude solid was passed through a silica gel to afford tert-butyl 4-(4-bromo-1-(3-chloro-4-fluorobenzyl)-6-methyl-1H-benzo[d]imidazol-2-yl)piperazine-1-carboxylate as a white solid (2.20 g, 85% yield).

Step F: The tert-butyl 4-(4-bromo-1-(3-chloro-4-fluorobenzyl)-6-methyl-1H-benzo[d]imidazol-2-yl)piperazine-1-carboxylate (73 mg, 0.136 mmol, 1 eq), PCy$_3$HBF$_4$ (7.5 mg, 0204 mmol, 0.15 eq), Pd(OAc)$_2$ (3.1 mg, 0.0136 mmol, 0.1 eq), K$_3$PO$_4$ (58 mg, 0.272 mmol, 2 eq) and 2-chlorophenylboronic acid (23.4 mg, 0.150 mmol, 1.1 eq) were added to a sealed tube reaction vessel equipped with stir bar. This solid mixture was purged 3× with Argon. A 5/1 mixture of dimeothoxyethane (DME)/water (1.0 mL) was added to the solid and then the tube was sealed. The reaction tube was heated at 85° C. in an oil bath and monitored by LCMS. Upon conversion of the starting material by LCMS, the reaction was diluted with water and diluted with DCM. The solution was passed through a phase separator and then concentrated. The crude solid was dissolved in a 2/1 mixture of DCM/TFA (1 mL) and stirred for 30 min. After 30 min, the volatiles were removed in vacuo and the deprotected benzimidazole was purified by reverse phase preparative HPLC. The fractions were evaporated to furnish the title compound (25 mg, 39% yield). $^1$H NMR (400 MHz, CDCl$_3$) δ 7.62 (m, 1H), 7.51 (m, 4H), 7.34 (t, J=8.7 Hz, 1H), 7.30 (m, 1H), 7.27 (s, 1H), 7.22 (s, 1H), 5.56 (s, 2H), 3.73 (t, J=3.5 Hz, 4H), 3.43 (t, J=3.5 Hz, 4H), 2.50 (s, 3H). MS (ESI) (M+H$^+$) m/z=469.00. LCMS Ret time (UV 214/254): 1.349 min.

Example 119: 1-(3-chloro-4-fluorobenzyl)-4-(2-fluorophenyl)-6-methyl-2-(piperazin-1-yl)-1H-benzo[d]imidazole trifluoroacetate

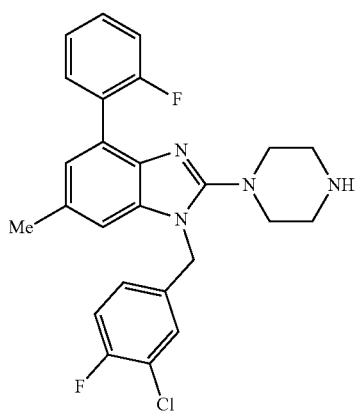 [SMILES: Cc1cc(-c2ccccc2F)c2nc(N3CCNCC3)n(Cc3ccc(F)c(Cl)c3)c2c1]

The title compound was obtained according to a procedure analogous to general procedure I: MS (ESI) (M+H$^+$) m/z=453.10. LCMS Ret time (UV 214/254): 1.303 min.

Example 120: 1-(3-chloro-4-fluorobenzyl)-6-methyl-2-(piperazin-1-yl)-4-(o-tolyl)-1H-benzo[d]imidazole trifluoroacetate

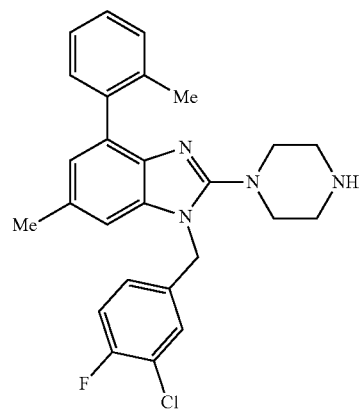 [SMILES: Cc1cc(-c2ccccc2C)c2nc(N3CCNCC3)n(Cc3ccc(F)c(Cl)c3)c2c1]

The title compound was obtained according to a procedure analogous to general procedure I: MS (ESI) (M+H$^+$) m/z=449.10. LCMS Ret time (UV 214/254): 1.350 min.

Example 121: 1-(3-chloro-4-fluorobenzyl)-6-methyl-2-(piperazin-1-yl)-4-(1,3,5-trimethyl-1H-pyrazol-4-yl)-1H-benzo[d]imidazole trifluoroacetate

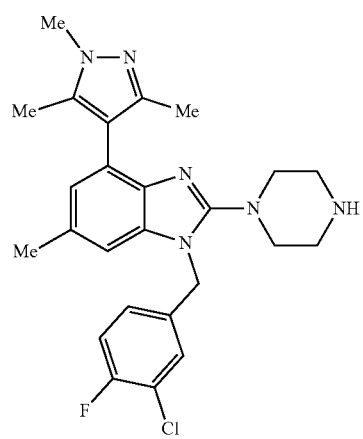 [SMILES: Cc1cc(-c2c(C)nn(C)c2C)c2nc(N3CCNCC3)n(Cc3ccc(F)c(Cl)c3)c2c1]

The title compound was obtained according to a procedure analogous to general procedure I: MS (ESI) (M+H$^+$) m/z=467.10. LCMS Ret time (UV 214/254): 1.162 min.

Example 122: (4-(6-chloro-1-(4-fluoro-3,5-dimethylbenzyl)-2-(piperazin-1-yl)-1H-benzo[d]imidazol-4-yl)phenyl)methanamine trifluoroacetate

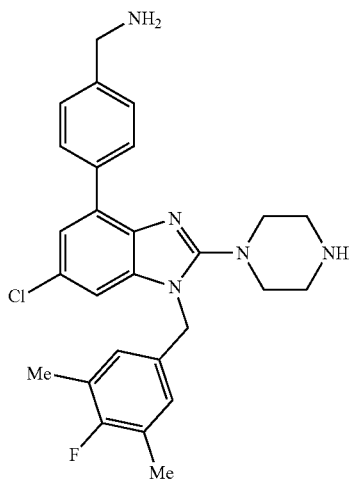 [SMILES: Cc1cc(Cn2c(N3CCNCC3)nc3c(-c4ccc(CN)cc4)cc(Cl)cc32)cc(C)c1F]

The title compound was obtained according to a procedure analogous to general procedure I: MS (ESI) (M+H$^+$) m/z=478.10. LCMS Ret time (UV 214/254): 1.249 min.

Example 123: 6-chloro-1-(4-fluoro-3,5-dimethylbenzyl)-4-(phenylethynyl)-2-(piperazin-1-yl)-1H-benzo[d]imidazole trifluoroacetate

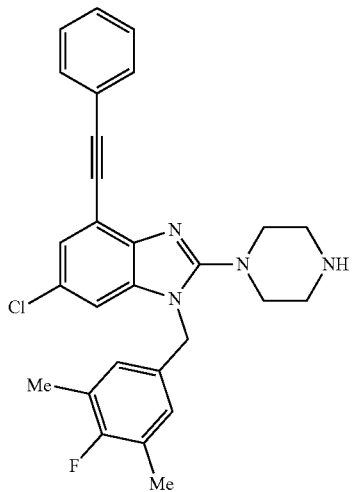 [SMILES: Cc1cc(Cn2c(N3CCNCC3)nc3c(C#Cc4ccccc4)cc(Cl)cc32)cc(C)c1F]

tert-butyl 4-(4-bromo-6-chloro-1-(4-fluoro-3,5-dimethylbenzyl)-1H-benzo[d]imidazol-2-yl)piperazine-1-carboxylate (30 mg, 0.0545 mmol, 1 eq), which was prepared by a procedure analogous to the procedure used to prepare Example 118, Step E, copper iodide (31 mg, 0.00545 mmol, 0.1 eq), Pd(PPh$_3$)Cl$_2$ (4 mg, 0.00545 mmol, 0.1 eq), and phenylacetylene (0.010 mL, 0.0545 mmol, 1 eq) were placed in a microwave tube and then dissolved in DMF (1.0 mL) and triethylamine (0.5 mL). The reaction was heated in a microwave reactor at 110° C. for two hours. Upon full conversion of the starting material by LCMS, the reaction was quenched with water and diluted with ethyl acetate. The organic layer was washed with water and dried over sodium sulfate and concentrated to dryness. The crude residue was dissolved in a 2/1 mixture of DCM/TFA and stirred at room temperature of 30 min. The volatiles were removed and the crude solid was purified by reverse-phase HPLC. The title compound was recovered as a white solid (10 mg, 38% yield). $^1$H NMR (400 MHz, CD$_3$OD) δ 7.67 (m, 2H), 7.43 (m, 3H), 7.40 (d, J=1.8 Hz, 1H), 7.28 (d, J=1.8 Hz, 1H), 6.88 (s, 1H), 6.87 (s, 1H), 5.32 (s, 2H), 3.56 (d, J=5.4 Hz, 4H), 3.43 (d, J=5.4 Hz, 4H), 2.23 (s, 6H). MS (ESI) (M+H$^+$) m/z=473.20. LCMS Ret time (UV 210/254): 1.664 min.

Example 124: 1-(4-fluoro-3,5-dimethylbenzyl)-6-methyl-2-(piperazin-1-yl)-4-(pyrrolidin-1-ylmethyl)-1H-benzo[d]imidazole trifluoroacetate

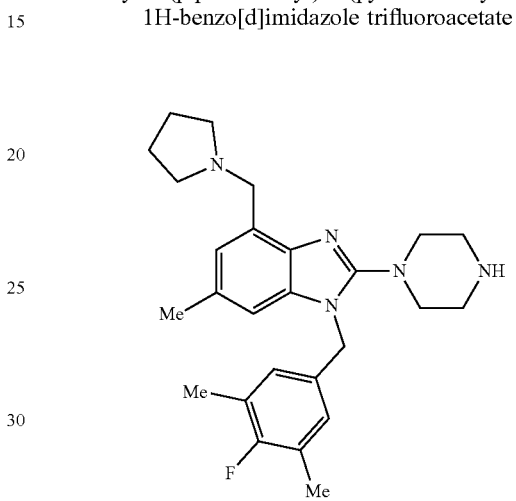

Step A: tert-butyl 4-(4-bromo-1-(4-fluoro-3,5-dimethylbenzyl)-6-methyl-1H-benzo[d]imidazol-2-yl)piperazine-1-carboxylate, prepared by a procedure analogous to that used to prepare Example 118, Step E, (338 mg, 0.636 mmol), Pd(OAc)$_2$ (14 mg, 0.0636 mmol, 0.1 eq), P(Cy$_3$)HBF$_4$ (35 mg, 0.954 mmol, 0.15 eq), K$_3$PO$_4$ (270 mg, 1.27 mmol, 2 eq), and vinyl boronic pinnacol ester (113 μL, 0.668 mmol, 1.05 eq) were added to a microwave tube. The tube was purged 3× with argon. A 5:1 mixture of DME:water (5 mL) was added to the tube, which was then sealed. The reaction was heated in a microwave for 1 hour at 115° C. The reaction was quenched with water and extracted with DCM and filtered through a phase separator. The organic layer was concentrated and the crude mixture was dissolved in a 5:1 mixture of acetone: water (5 mL) in a round bottom flask equipped with a stir bar. 5% wt of OsO$_4$ (20 mg) and sodium periodate (408 mg, 1.9 mmol, 3 eq) was added to the reaction and it was stirred at room temperature. After conversion to the aldehyde by LCMS, the reaction was quenched with 10% sodium thiosulfate, acidified with 10% HCl, and diluted with ethyl acetate. The mixture was stirred for 20 min, then the organic layer was separated and washed with a brine solution. The organic layer was dried over sodium sulfate and concentrated in vacuo to afford the crude aldehyde product. This was purified via silica gel (40% ethyl acetate in hexanes) to afford tert-butyl 4-(1-(4-fluoro-3,5-dimethylbenzyl)-4-formyl-6-methyl-1H-benzo[d]imidazol-2-yl)piperazine-1-carboxylate (250 mg, 79% yield).

Step B: The tert-butyl 4-(1-(4-fluoro-3,5-dimethylbenzyl)-4-formyl-6-methyl-1H-benzo[d]imidazol-2-yl)piperazine-1-carboxylate (21 mg, 0.043 mmol, 1 eq) was dissolved in DCM (1 mL) and cooled to 0° C. Pyrrolidine (10 μL, 0.0645 mmol, 1.5 eq) was added to the reaction and it was stirred for 10 min. Sodium triacetoxyborohydride (15 mg, 0.0645, 1.5 eq) was added to the reaction and then it was warmed to rt and stirred for 2 hours. Upon conversion to the amine by LCMS, the reaction was quenched with 1M NaOH solution and extracted with DCM. TFA (0.5 mL) was added to the DCM solution and this was stirred for 30 min to remove the BOC group. Upon conversion to the free amine by LCMS, the solvent was removed and the crude material was purified by reverse-phase HPLC. The title compound was recovered as a white solid (8.0 mg, 42% yield). $^1$H NMR (400 MHz, CD$_3$OD) δ 7.29 (s, 1H), 7.23 (s, 1H), 6.93 (s, 1H), 6.91 (s, 1H), 5.36 (s, 2H), 4.72 (s, 2H), 3.66 (t, J=5.2 Hz, 4H), 3.58 (br s, 4H), 3.44 (t, J=5.1 Hz, 4H), 2.46 (s, 3H), 2.22 (s, 6H), 2.07 (br s, 4H). MS (ESI) (M+H$^+$) m/z=436.20. LCMS Ret time (UV 214/254): 1.100 min.

Example 125: 1-(4-fluoro-3,5-dimethylbenzyl)-6-methyl-2-(piperazin-1-yl)-4-(piperidin-1-ylmethyl)-1H-benzo[d]imidazole trifluoroacetate

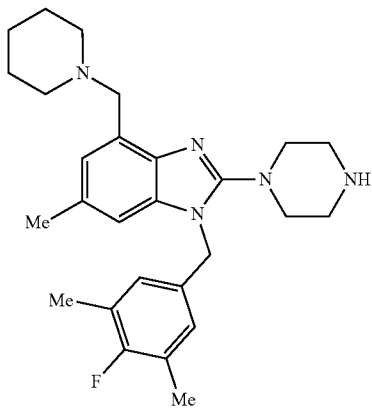 [SMILES: Cc1cc(CN2CCCCC2)c2nc(N3CCNCC3)n(Cc3cc(C)c(F)c(C)c3)c2c1]

The title compound was obtained according to a procedure analogous to general procedure J: MS (ESI) (M+H$^+$) m/z=450.20. LCMS Ret time (UV 214/254): 1.115 min.

Example 126: 1-((1-(4-fluoro-3,5-dimethylbenzyl)-6-methyl-2-(piperazin-1-yl)-1H-benzo[d]imidazol-4-yl)methyl)piperidin-4-ol trifluoroacetate

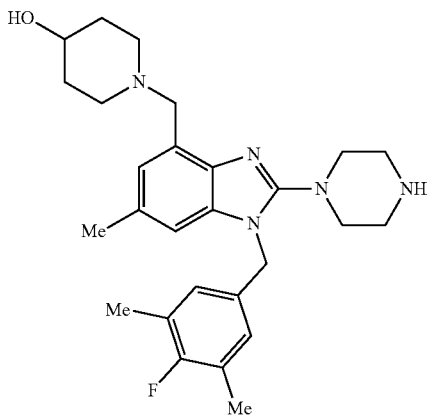 [SMILES: Cc1cc(CN2CCC(O)CC2)c2nc(N3CCNCC3)n(Cc3cc(C)c(F)c(C)c3)c2c1]

The title compound was obtained according to a procedure analogous to general procedure J: MS (ESI) (M+H$^+$) m/z=466.20. LCMS Ret time (UV 214/254): 1.057 min.

Example 127: 4-((1-(4-fluoro-3,5-dimethylbenzyl)-6-methyl-2-(piperazin-1-yl)-1H-benzo[d]imidazol-4-yl)methyl)morpholine trifluoroacetate

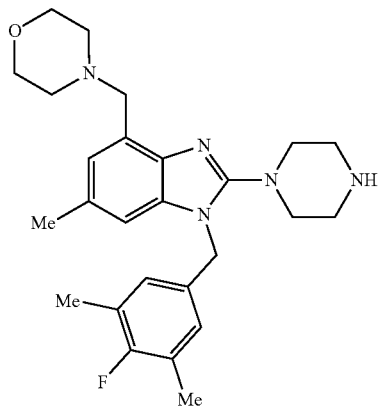 [SMILES: Cc1cc(CN2CCOCC2)c2nc(N3CCNCC3)n(Cc3cc(C)c(F)c(C)c3)c2c1]

The title compound was obtained according to a procedure analogous to general procedure J: MS (ESI) (M+H$^+$) m/z=452.20. LCMS Ret time (UV 214/254): 1.038 min.

Example 128: 1-(1-(4-fluoro-3,5-dimethylbenzyl)-6-methyl-2-(piperazin-1-yl)-1H-benzo[d]imidazol-4-yl)-N,N-dimethylmethanamine trifluoroacetate

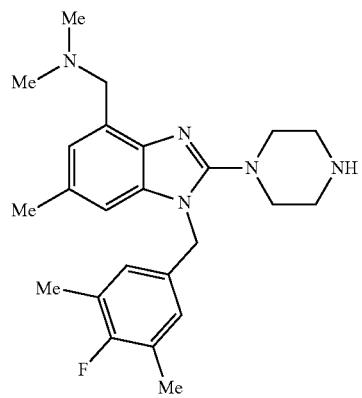 [SMILES: Cc1cc(CN(C)C)c2nc(N3CCNCC3)n(Cc3cc(C)c(F)c(C)c3)c2c1]

The title compound was obtained according to a procedure analogous to general procedure J: MS (ESI) (M+H$^+$) m/z=410.20. LCMS Ret time (UV 214/254): 1.050 min.

Example 129: 1-(6-chloro-1-(4-fluoro-3,5-dimethylbenzyl)-2-(piperazin-1-yl)-1H-benzo[d]imidazol-4-yl)-N-methylmethanamine trifluoroacetate

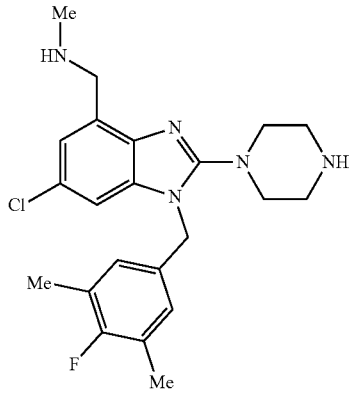 [SMILES: CNCc1cc(Cl)cc2c1nc(N1CCNCC1)n2Cc1cc(C)c(F)c(C)c1]

The title compound was obtained according to a procedure analogous to general procedure J: MS (ESI) (M+H⁺) m/z=416.10. LCMS Ret time (UV 214/254): 1.130 min.

Example 130: 6-chloro-1-(4-fluoro-3,5-dimethylbenzyl)-2-(piperazin-1-yl)-4-(pyrrolidin-1-ylmethyl)-1H-benzo[d]imidazole trifluoroacetate

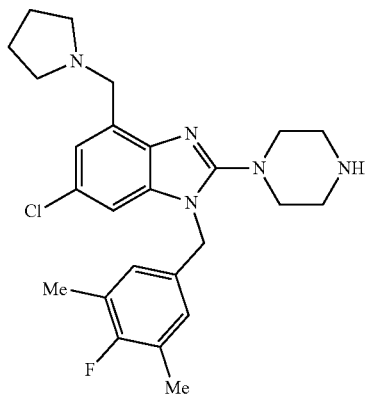 [SMILES: Cc1cc(Cn2c(N3CCNCC3)nc3c(CN4CCCC4)cc(Cl)cc32)cc(C)c1F]

The title compound was obtained according to a procedure analogous to general procedure G. ¹H NMR (400 MHz, CD₃OD) δ 7.38 (s, 1H), 7.35 (s, 1H), 6.87 (s, 1H), 6.85 (s, 1H), 5.29 (s, 2H), 4.69 (s, 2H), 3.56 (bm, 6H), 3.41 (bm, 4H), 3.35 (bm, 2H), 2.19 (2s ovlp, 6H), 2.19 (bm, 2H), 2.04 (bm, 2H). MS (ESI) (M+H⁺) m/z=456.10. LCMS Ret time (UV 214/254): 1.168 min.

Example 131: N-((1-(4-fluoro-3,5-dimethylbenzyl)-5,6-dimethyl-2-(piperazin-1-yl)-1H-benzo[d]imidazol-4-yl)methyl)ethanamine trifluoroacetate

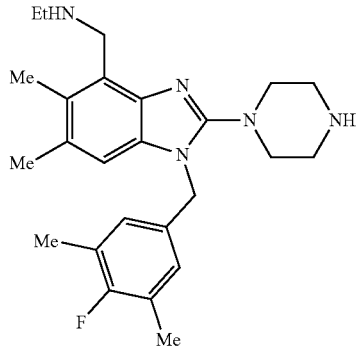

The title compound was obtained according to a procedure analogous to general procedure J, from tert-butyl 4-(1-(4-fluoro-3,5-dimethylbenzyl)-4-formyl-5,6-dimethyl-1H-benzo[d]imidazol-2-yl)piperazine-1-carboxylate, which was obtained by a procedure analogous to that used to prepare Example 124, Step A: ¹H NMR (400 MHz, CD₃OD) δ 7.24 (s, 1H), 6.92 (s, 1H), 6.90 (s, 1H), 5.36 (s, 2H), 4.69 (s, 2H), 3.69 (t, J=5.2 Hz, 4H), 3.45 (t, J=5.2 Hz, 4H), 3.28 (q, J=7.3 Hz, 2H), 2.43 (s, 3H), 2.40 (s, 3H), 2.20 (s, 6H), 1.42 (t, J=7.3 Hz, 3H). MS (ESI) (M+H⁺) m/z=424.20. LCMS Ret time (UV 214/254): 1.096 min.

Example 132: N-((1-(4-fluoro-3,5-dimethylbenzyl)-5,6-dimethyl-2-(piperazin-1-yl)-1H-benzo[d]imidazol-4-yl)methyl)propan-1-amine trifluoroacetate

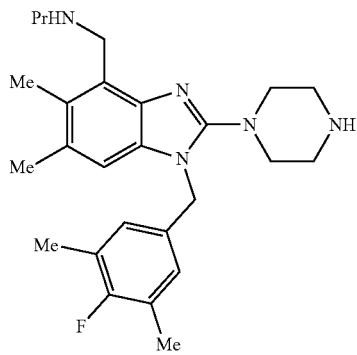

The title compound was obtained according to a procedure analogous to general procedure J, from tert-butyl 4-(1-(4-fluoro-3,5-dimethylbenzyl)-4-formyl-5,6-dimethyl-1H-benzo[d]imidazol-2-yl)piperazine-1-carboxylate, which was obtained by a procedure analogous to that used to prepare Example 124, Step A: ¹H NMR (400 MHz, CD₃OD) δ 7.18 (s, 1H), 6.88 (s, 1H), 6.87 (s, 1H), 5.31 (s, 2H), 4.69 (s, 2H), 3.57 (t, J=5.1 Hz, 4H), 3.43 (t, J=5.1 Hz, 4H), 3.16 (t, J=7.8 Hz, 2H), 2.40 (s, 3H), 2.39 (s, 3H), 2.20 (s, 6H), 1.85 (q, J=7.6 Hz, 3H), 1.08 (t, J=7.4 Hz, 3H). MS (ESI) (M+H⁺) m/z=438.30. LCMS Ret time (UV 214/254): 1.158 min.

Example 133: N-((1-(4-fluoro-3,5-dimethylbenzyl)-6-methyl-2-(piperazin-1-yl)-1H-benzo[d]imidazol-4-yl)methyl)-2-methylpropan-1-amine trifluoroacetate

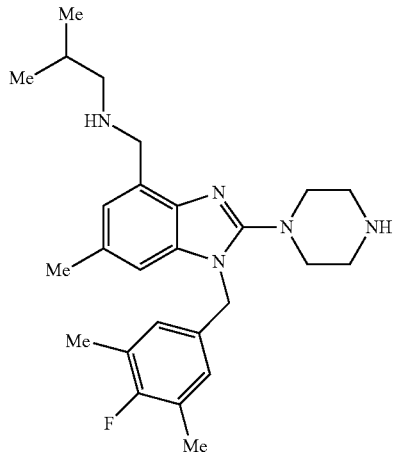 [SMILES: Cc1cc(CNCC(C)C)c2nc(N3CCNCC3)n(Cc3cc(C)c(F)c(C)c3)c2c1]

The title compound was obtained according to a procedure analogous to general procedure J, from tert-butyl 4-(1-(4-fluoro-3,5-dimethylbenzyl)-4-formyl-5,6-dimethyl-1H-benzo[d]imidazol-2-yl)piperazine-1-carboxylate, which was obtained by a procedure analogous to that used to prepare Example 124, Step A: $^1$H NMR (400 MHz, CD$_3$OD) δ 7.19 (s, 1H), 7.18 (s, 1H), 6.89 (s, 1H), 6.87 (s, 1H), 5.33 (s, 2H), 4.57 (s, 2H), 3.57 (t, J=5.1 Hz, 4H), 3.44 (t, J=5.1 Hz, 4H), 2.99 (d, J=7.2 Hz, 2H), 2.45 (s, 3H), 2.20 (s, 6H), 2.11 (sep, J=6.8 Hz, 1H), 1.09 (s, 3H), 1.07 (s, 3H). MS (ESI) (M+H$^+$) m/z=438.30. LCMS Ret time (UV 214/254): 1.147 min.

Example 134: 2-(((6-chloro-1-(3-chloro-4-fluorobenzyl)-2-(piperazin-1-yl)-1H-benzo[d]imidazol-4-yl)methyl)(methyl)amino)ethan-1-ol trifluoroacetate

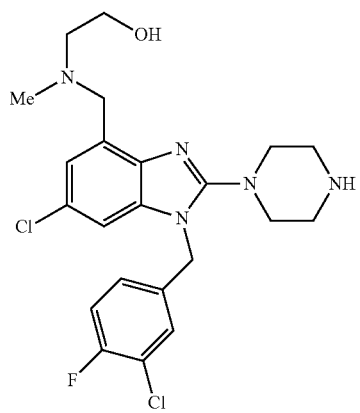 [SMILES: CN(CCO)Cc1cc(Cl)cc2c1nc(N1CCNCC1)n2Cc1ccc(F)c(Cl)c1]

The title compound was obtained according to a procedure analogous to general procedure J, from tert-butyl 4-(6-chloro-1-(3-chloro-4-fluorobenzyl)-4-formyl-1H-benzo[d]imidazol-2-yl)piperazine-1-carboxylate, which was obtained by a procedure analogous to that used to prepare Example 124, Step A: 1H NMR (400 MHz, CD$_3$OD) δ 7.43 (d, J=1.8 Hz, 1H), 7.39 (d, J=1.8 Hz, 1H), 7.36 (dd, J=6.9, 2.2 Hz, 1H), 7.26 (t, J=8.8 Hz, 1H), 7.14 (m, 1H), 5.41 (s, 2H), 3.98 (t, J=5.1 Hz, 1H), 3.61 (t, J=5.1 Hz, 4H), 3.43 (t, J=5.1 Hz, 4H), 2.95 (s, 3H). MS (ESI) m/z=466.20. LCMS Ret time (UV 214/254): 1.091 min.

Example 135: 3-(((6-chloro-1-(3-chloro-4-fluorobenzyl)-2-(piperazin-1-yl)-1H-benzo[d]imidazol-4-yl)methyl)(methyl)amino)propan-1-ol trifluoroacetate

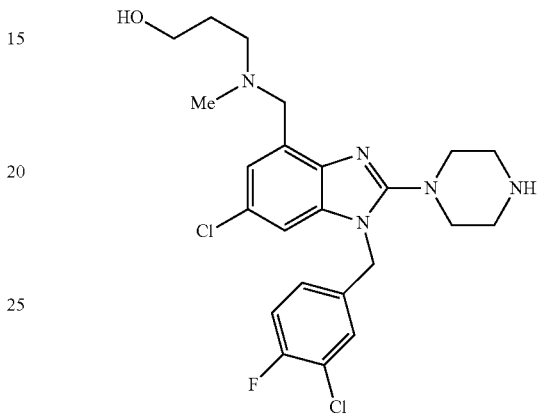

The title compound was obtained according to a procedure analogous to general procedure J, from tert-butyl 4-(6-chloro-1-(3-chloro-4-fluorobenzyl)-4-formyl-1H-benzo[d]imidazol-2-yl)piperazine-1-carboxylate, which was obtained by a procedure analogous to that used to prepare Example 124, Step A: MS (ESI) (M+H$^+$) m/z=480.20. LCMS Ret time (UV 214/254): 1.089 min.

Example 136: N-((6-chloro-1-(3-chloro-4-fluorobenzyl)-2-(piperazin-1-yl)-1H-benzo[d]imidazol-4-yl)methyl)-N-ethylethanamine trifluoroacetate

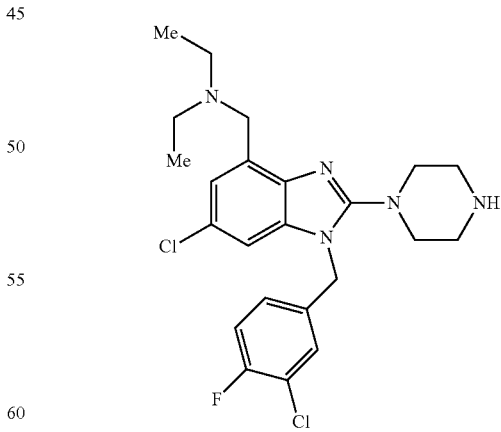

The title compound was obtained according to a procedure analogous to general procedure J, from tert-butyl 4-(6-chloro-1-(3-chloro-4-fluorobenzyl)-4-formyl-1H-benzo[d]imidazol-2-yl)piperazine-1-carboxylate, which was obtained by a procedure analogous to that used to prepare Example 124, Step A: MS (ESI) (M+H⁺) m/z=464.20. LCMS Ret time (UV 214/254): 1.142 min.

Example 137: N¹-((6-chloro-1-(3-chloro-4-fluorobenzyl)-2-(piperazin-1-yl)-1H-benzo[d]imidazol-4-yl)methyl)ethane-1,2-diamine trifluoroacetate

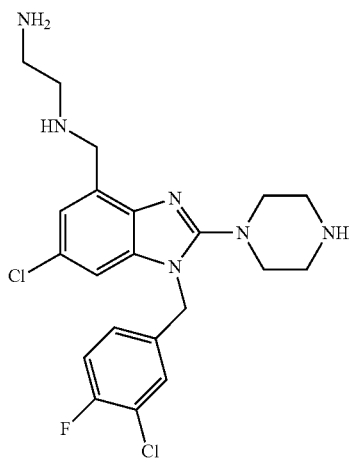 [SMILES: NCCNCc1cc(Cl)cc2c1nc(N1CCNCC1)n2Cc1ccc(F)c(Cl)c1]

The title compound was obtained according to a procedure analogous to general procedure J, from tert-butyl 4-(6-chloro-1-(3-chloro-4-fluorobenzyl)-4-formyl-1H-benzo[d]imidazol-2-yl)piperazine-1-carboxylate, which was obtained by a procedure analogous to that used to prepare Example 124, Step A: MS (ESI) (M+H⁺) m/z=451.00. LCMS Ret time (UV 214/254): 1.023 min.

Example 138: (1-(4-fluoro-3,5-dimethylbenzyl)-5,6-dimethyl-2-(piperazin-1-yl)-1H-benzo[d]imidazol-4-yl)methanol trifluoroacetate

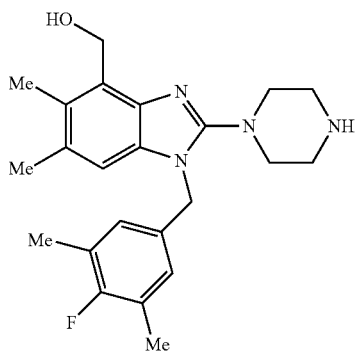 [SMILES: Cc1cc2c(nc(N3CCNCC3)n2Cc2cc(C)c(F)c(C)c2)c(CO)c1C]

The title compound was isolated as a product from Step B of Example 124. ¹H NMR (400 MHz, CD₃OD) δ 7.22 (s, 1H), 7.18 (s, 1H), 6.91 (s, 1H), 6.89 (s, 1H), 5.36 (s, 2H), 4.49 (s, 2H), 3.66 (t, J=5.2 Hz, 4H), 3.44 (t, J=5.1 Hz, 4H), 2.45 (s, 3H), 2.22 (s, 6H).

Example 139: 1-(1-(4-fluoro-3,5-dimethylbenzyl)-6-methyl-2-(piperazin-1-yl)-1H-benzo[d]imidazol-4-yl)-2,3,4,9-tetrahydro-1H-pyrido[3,4-b]indole trifluoroacetate

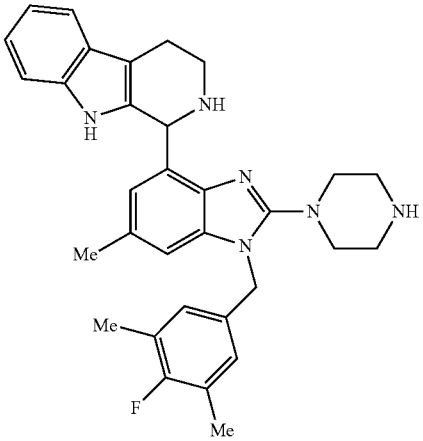

tert-butyl 4-(1-(4-fluoro-3,5-dimethylbenzyl)-4-formyl-6-methyl-1H-benzo[d]imidazol-2-yl)piperazine-1-carboxylate (20 mg, 0.0312 mmol, 1 eq), prepared by a procedure analogous to the procedure used to in Example 124, Step A, was dissolved in a 4/1 mixture of methanol/acetic acid (0.5 mL) in a reaction vial equipped with a stir bar. Tryptophan (5 mg, 0.0313 mmol, 1 eq) was added to the reaction, which was heated at 40° C. for 8 hours. Upon conversion to the adduct by LCMS, the solvent was removed in vacuo. The crude material was dissolved in a 2/1 mixture of DCM/TFA (1 mL) and stirred for 30 min. Upon conversion to the free amine by LCMS, the solvent was removed and the crude material was purified by reverse-phase HPLC. The title compound was recovered as a white solid (7 mg, 43% yield). ¹H NMR (400 MHz, CD₃OD) δ 7.59 (d, J=7.8 Hz, 1H), 7.31 (d, J=8.1 Hz, 1H), 7.22 (s, 1H), 7.18 (t, J=7.0 Hz, 1H), 7.11 (t, J=7.4 Hz, 1H), 6.93 (s, 1H), 6.90 (s, 1H), 6.88 (s, 1H), 6.47 (s, 1H), 5.33 (s, 2H), 3.68 (m, 4H), 3.53 (t, J=5.0 Hz, 4H), 3.40 (t, J=5.0 Hz, 4H), 2.39 (s, 3H), 2.20 (s, 6H). MS (ESI) (M+H⁺) m/z=523.20. LCMS Ret time (UV 214/254): 1.310 min.

Example 140: 1-(6-chloro-1-(4-fluoro-3,5-dimethylbenzyl)-2-(piperazin-1-yl)-1H-benzo[d]imidazol-4-yl)-2,3,4,9-tetrahydro-1H-pyrido[3,4-b]indole trifluoroacetate

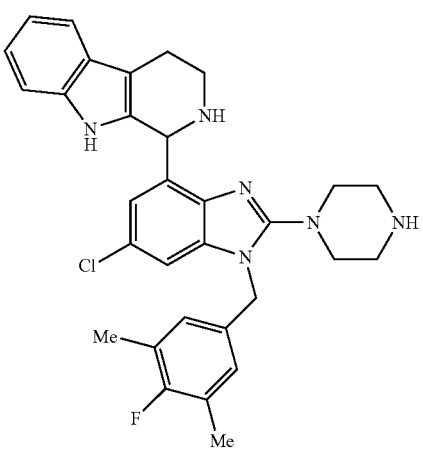 [SMILES: Cc1cc(Cn2c(N3CCNCC3)nc3c(C4NCCc5c4[nH]c4ccccc54)cc(Cl)cc32)cc(C)c1F]

The title compound was obtained according to a procedure analogous to the procedure used to prepare Example 139: MS (ESI) (M+H⁺) m/z=543.10. LCMS Ret time (UV 214/254): 1.342 min.

Example 141: 1-(1-(4-fluoro-3,5-dimethylbenzyl)-6-methyl-2-(piperazin-1-yl)-1H-benzo[d]imidazol-4-yl)-2-methyl-2,3,4,9-tetrahydro-1H-pyrido[3,4-b]indole trifluoroacetate

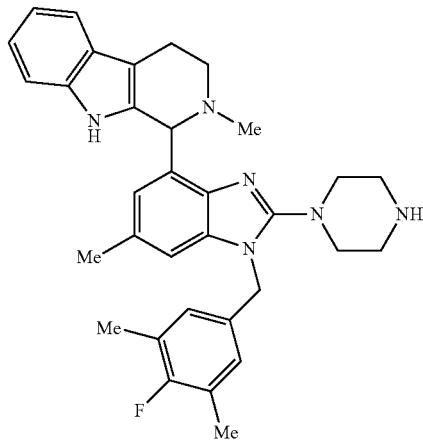 [SMILES: Cc1cc(C2c3[nH]c4ccccc4c3CCN2C)c2nc(N3CCNCC3)n(Cc3cc(C)c(F)c(C)c3)c2c1]

The title compound was obtained according to a procedure analogous to the procedure used to prepare Example 139: $^1$H NMR (400 MHz, CD$_3$OD) δ 7.47 (d, J=7.6 Hz, 1H), 7.16 (d, J=7.9 Hz, 1H), 7.12 (s, 1H), 7.02 (ovlp m, 2H), 6.83 (br s, 1H), 6.78 (d, J=6.3 Hz, 1H), 6.24 (s, 1H), 5.20 (s, 2H), 3.84 (br s, 2H), 3.67 (br s, 2H), 3.41 (m, 4H), 3.28 (m, 4H), 2.94 (s, 3H), 2.29 (s, 3H), 2.09 (s, 6H). MS (ESI) (M+H⁺) m/z=537.30. LCMS Ret time (UV 214/254): 1.283 min.

Example 142: 1-(4-fluoro-3,5-dimethylbenzyl)-6-methyl-4-(o-tolyl)-1H-benzo[d]imidazole

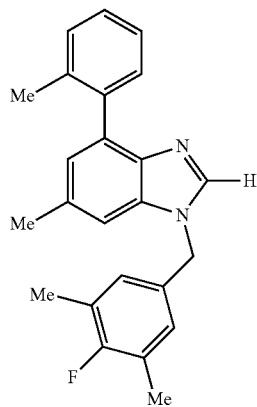 [SMILES: Cc1cc(-c2ccccc2C)c2ncn(Cc3cc(C)c(F)c(C)c3)c2c1]

Step A: 3-bromo-5-methylbenzene-1,2-diamine (2.63 g, 13.1 mmol) was dissolved in a 1/1 mixture of DMF/trimethyl orthoformate at room temperature. Several drops of concentrated HCl were added and the reaction was stirred until conversion to the benzimidazole by LCMS. Upon conversion by LCMS, the reaction was diluted with water and the orange precipitate was filtered off to afford 4-bromo-6-methyl-1H-benzo[d]imidazole as a crude orange solid (2.1 g, 75% yield). The solid was used without any further purification.

Step B: The 4-bromo-6-methyl-1H-benzo[d]imidazole (200 mg, 0.95 mmol, 1 eq) was dissolved in DMF (5 mL) at room temperature. Potassium carbonate (170 mg, 1.05 mmol, 1.3 eq) was added tot eh solution, followed by 3,5-dimethyl-4-fluorobenzyl bromide (226 mg, 1.1 mmol, 1.1 eq). The reaction was monitored by LCMS and quenched with 10% aqueous HCl upon conversion of the starting material. The reaction was extracted with ethyl acetate, washed thoroughly with water, brine, dried over sodium sulfate, and concentrated to afford 4-bromo-1-(4-fluoro-3,5-dimethylbenzyl)-6-methyl-1H-benzo[d]imidazole as a 2/1 mixture of regioisomers. The crude mixture was purified by column chromatography and was carried on to the next step as a mix of regioisomers.

Step C: The 4-bromo-1-(4-fluoro-3,5-dimethylbenzyl)-6-methyl-1H-benzo[d]imidazole (40 mg, 0.115 mmol), PCy$_3$HBF$_4$ (4.0 mg, 0106 mmol, 0.15 eq), Pd(OAc)$_2$ (1.6 mg, 0.0012 mmol, 0.1 eq), K$_3$PO$_4$ (37 mg, 0.177 mmol, 2 eq) and 2-methyl-phenylboronic acid (10.0 mg, 0.0706 mmol, 1.1 eq) were added to a sealed tube reaction vessel equipped with stir bar. This solid mixture was purged 3× with Argon. A 5/1 mixture of dimethoxyethane (DME)/water (1.0 mL) was added to the solid and then the tube was sealed. The reaction tube was heated at 85° C. in an oil bath and monitored by LCMS. Upon conversion of the starting material by LCMS, the reaction was diluted with water and diluted with DCM. The solution was passed through a phase separator and then concentrated. The crude solid was purified by reverse phase HPLC to afford the title compound (25 mg, 61% yield). $^1$H NMR (400 MHz, CDCl$_3$) δ 7.90 (s, 1H), 7.38 (m, 2H), 7.30 (m, 2H), 7.12 (s, 1H), 7.05 (s, 1H), 6.90 (s, 1H), 6.89 (s, 1H), 5.24 (s, 2H), 2.52 (s, 3H), 2.26 (s, 3H), 2.25 (s, 6H). MS (ESI) (M+H⁺) m/z=359.20. LCMS Ret time (UV 214/254): 1.507 min.

Example 143: 1-(3-chloro-4-fluorobenzyl)-6-methyl-4-(o-tolyl)-1H-benzo[d]imidazole

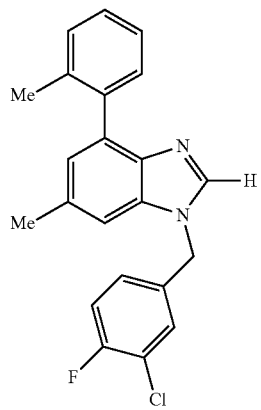 [SMILES: Cc1cc(-c2ccccc2C)c2ncn(Cc3ccc(F)c(Cl)c3)c2c1]

The title compound was obtained according to a procedure analogous to general procedure K: MS (ESI) (M+H⁺) m/z=365.10. LCMS Ret time (UV 214/254): 1.422 min.

Example 144: 1-(3-chloro-4-fluorobenzyl)-6-methyl-4-(piperidin-1-ylmethyl)-1H-benzo[d]imidazole trifluoroacetate

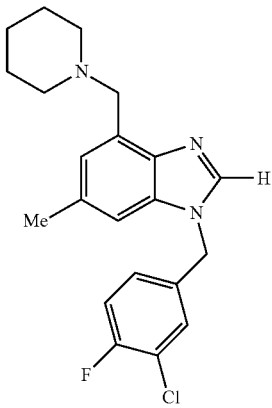 [SMILES: Cc1cc(CN2CCCCC2)c2ncn(Cc3ccc(F)c(Cl)c3)c2c1]

Step A: 4-bromo-1-(3-chloro-4-fluorobenzyl)-6-methyl-1H-benzo[d]imidazole, prepared by a procedure analogous to that used to prepare Example 142, Step B (355 mg, 1.0 mmol), Pd(OAc)$_2$ (23 mg, 0.100 mmol, 0.1 eq), P(Cy$_3$)HBF$_4$ (55 mg, 0.150 mmol, 0.15 eq), K$_3$PO$_4$ (424 mg, 2.00 mmol, 2 eq), and vinyl boronic pinnacol ester (170 µL, 1.00 mmol, 1.05 eq) were added to a microwave tube. The tube was purged 3× with argon. A 5:1 mixture of DME:water (6.5 mL) was added to the tube, which was then sealed. The reaction was heated in a microwave for 1 hour at 115° C. The reaction was quenched with water and extracted with DCM and filtered through a phase separator. The organic layer was concentrated to the crude mixture. The crude mixture was dissolved in a 5:1 mixture of acetone: water (8 mL) in a round bottom flask equipped with a stir bar. 5% wt of OsO$_4$ (50 mg) and sodium periodate (640 mg, 3.0 mmol, 3 eq) were added to the reaction and it was stirred at room temperature. After conversion to the aldehyde by LCMS, the reaction was quenched with 10% sodium thiosulfate, acidified with 10% HCl, and diluted with ethyl acetate. The mixture was stirred for 20 min, then the organic layer was separated and washed with a brine solution. The organic layer was dried over sodium sulfate and concentrated in vacuo to afford the crude aldehyde product, which was purified via silica gel (40% ethyl acetate in hexanes) to afford 1-(3-chloro-4-fluorobenzyl)-6-methyl-1H-benzo[d]imidazole-4-carbaldehyde (200 mg, 66% yield).

Step B: The 1-(3-chloro-4-fluorobenzyl)-6-methyl-1H-benzo[d]imidazole-4-carbaldehyde (45 mg, 0.15 mmol, 1 eq) was dissolved in DCM (1.5 mL) and cooled to 0° C. Piperidine (18.5 µL, 0.225 mmol, 1.5 eq) was added to the reaction and it was stirred for 10 min. Sodium triacetoxyborohydride (47 mg, 0.225, 1.5 eq) was added to the reaction and then it was warmed to room temperature and stirred for two hours. Upon conversion to the amine by LCMS, the reaction was quenched with 1M NaOH solution and extracted with DCM. The organic layer was dried over sodium sulfate and concentrated to afford a crude solid. The solid was purified by reverse phase HPLC to provide the title compound: MS (ESI) (M+H$^+$) m/z=372.10. LCMS Ret time (UV 214/254): 1.110 min.

Example 145: 1-(1-(3-chloro-4-fluorobenzyl)-6-methyl-1H-benzo[d]imidazol-4-yl)-N,N-dimethyl-methanamine trifluoroacetate

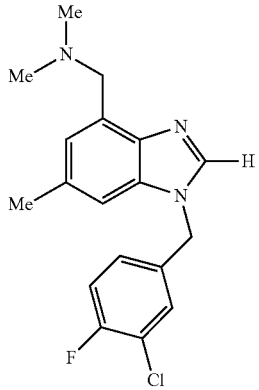 [SMILES: Cc1cc(CN(C)C)c2ncn(Cc3ccc(F)c(Cl)c3)c2c1]

The title compound was obtained according to a procedure analogous to the procedure used to prepare Example 144: MS (ESI) m/z=332.10. LCMS Ret time (UV 214/254): 1.042 min.

Example 146: N$^1$-(1-(3-chloro-4-fluorobenzyl)-5,6-dimethyl-4-(pyrrolidin-1-ylmethyl)-1H-benzo[d]imidazol-2-yl)ethane-1,2-diamine trifluoroacetate

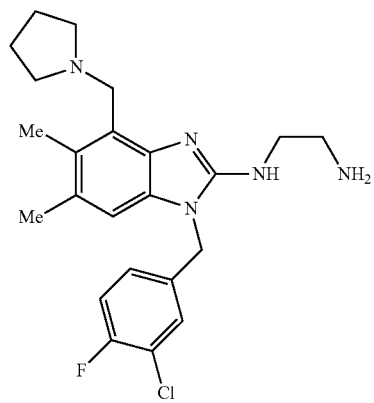 [SMILES: Cc1cc2c(nc(NCCN)n2Cc2ccc(F)c(Cl)c2)c(CN2CCCC2)c1C]

Step A: 4-bromo-2-chloro-1-(3-chloro-4-fluorobenzyl)-5,6-dimethyl-1H-benzo[d]imidazole, prepared by a procedure analogous to the procedure used to prepare Example 118, Step E, (425 mg, 1.06 mmol), Pd(OAc)$_2$ (24 mg, 0.106 mmol, 0.1 eq), P(Cy$_3$)HBF$_4$ (59 mg, 0.159 mmol, 0.15 eq), K$_3$PO$_4$ (450 mg, 2.12 mmol, 2 eq), and vinyl boronic pinnacol ester (180 OL, 1.10 mmol, 1.05 eq) were added to a microwave tube. The tube was purged 3× with argon. A 5:1 mixture of DME:water (8 mL) was added to the tube, which was then sealed. The reaction was heated in a microwave for 1 hour at 115° C. The reaction was quenched with water and extracted with DCM and filtered through a phase separator. The organic layer was concentrated to the crude mixture. The crude mixture was dissolved in a 5:1 mixture of acetone: water (5 mL) in a round bottom flask equipped with a stir bar. 5% wt of OsO4 (200 mg) and sodium periodate (640 mg, 3.0 mmol, 3 eq) were added to the reaction and it was stirred at room temperature. After conversion to the aldehyde by LCMS, the reaction was quenched with 10% sodium thiosulfate, acidified with 10% HCl, and diluted with ethyl acetate. The mixture was stirred for 20 min, then the organic layer was separated and washed with a brine solution. The organic layer was dried over sodium sulfate and concentrated in vacuo to afford the crude aldehyde product. This was purified via silica gel (40% ethyl acetate in hexanes) to afford the 2-chloro-1-(3-chloro-4-fluorobenzyl)-5,6-dimethyl-1H-benzo[d]imidazole-4-carbaldehyde (270 mg, 73% yield).

Step B: The 2-chloro-1-(3-chloro-4-fluorobenzyl)-5,6-dimethyl-1H-benzo[d]imidazole-4-carbaldehyde (50 mg, 0.143 mmol, 1 eq) was dissolved in DCM (1 mL) and cooled to 0° C. Pyrrolidine (17 µL, 0.215 mmol, 1.5 eq) was added to the reaction and it was stirred for 10 min. Sodium cyanoborohydride (14 mg, 0.215, 1.5 eq) was added to the reaction and then it was warmed to rt and stirred for 2 hours. Upon conversion to the amine by LCMS, the reaction was quenched with 1 M NaOH solution and extracted with DCM. The organic layer was concentrated and then redissolved in DMA (1 mL) and placed in a microwave vial with a stir bar. 1,2-ethylene diamine (0.050 mL, 0.7 mmol, 5 eq) was added to the vial, which was then heated at 165° C. in a microwave reactor for one hour. After completion, the reaction was cooled to room temperature and quenched with water. The reaction was extracted with DCM and filtered through a phase separator. The organic layer was concentrated and the crude oil was purified by reverse phase HPLC. After evaporating the fractions, a white solid was obtained (20 mg, 32% yield). MS (ESI) (M+H$^+$) m/z=430.20. LCMS Ret time (UV 214/254): 1.041 min.

Example 147: N$^1$-(1-(3-chloro-4-fluorobenzyl)-4-((ethylamino)methyl)-5,6-dimethyl-1H-benzo[d]imidazol-2-yl)ethane-1,2-diamine trifluoroacetate The title compound was obtained according to a procedure analogous to general procedure L: MS (ESI) (M+H$^+$) m/z=404.10. LCMS Ret time (UV 214/254): 1.014.

Example 148: ((2S,3R)-2-(6-chloro-1-(4-fluoro-3,5-dimethylbenzyl)-2-(piperazin-1-yl)-1H-benzo[d]imidazol-4-yl)-1-propylpyrrolidin-3-yl)(phenyl)methanone trifluoroacetate

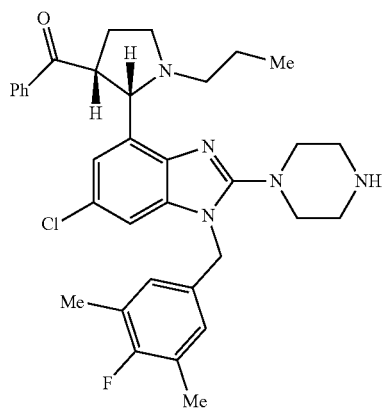

The tert-butyl 4-(6-chloro-1-(4-fluoro-3,5-dimethylbenzyl)-4-formyl-1H-benzo[d]imidazol-2-yl)piperazine-1-carboxylate (105 mg, 0.21 mmol), prepared by a procedure analogous to the procedure used to prepare Example 124, Step A, was dissolved in THF (2 mL) in a reaction vial. N-Propylamine (0.0173 mL, 0.21 mmol) was added to the reaction while stirring at room temperature. The reaction was stirred for 10 min. Magnesium iodide (58.4 mg, 0.21 mmol) was added to the reaction, followed by cyclopropyl phenylketone (0.029 mL, 0.21 mmol). The reaction was then heated at 60° C. and was monitored by LCMS. Upon full conversion of the aldehyde, the reaction was quenched with a 10% solution of sodium thiosulfate and extracted with ethyl acetate. The organic layer was washed with a brine solution, dried over sodium sulfate, and concentrated in vacuo to afford a crude red oil. The crude oil was dissolved in a 2/1 mixture of DCM/TFA (1 mL) and stirred at room temperature for 30 min. The reaction was then concentrated and purified by reverse-phase HPLC to afford a 3:1 mixture of two diastereomeric products. 13 mg (10% yield) of the title compound was isolated, $^1$H NMR (400 MHz, CD$_3$OD) δ 7.50 (d, J=7.3 Hz, 2H), 7.43 (t, J=6.9 Hz, 1H), 7.23 (t, J=7.8 Hz, 2H), 7.10 (s, 1H), 7.04 (s, 1H), 6.78 (s, 1H), 6.76 (s, 1H), 5.47 (d, J=8.6 Hz, 1H), 5.14 (s, 2H), 4.96 (dd, J=13.0, 7.7 Hz, 1H), 4.35 (m, 1H), 3.64 (ovlp, 1H), 3.57 (br s, 4H), 3.46 (br s, 4H), 3.28 (t, J=7.8 Hz, 1H), 2.84 (m, 1H), 2.59 (m, 1H), 1.81 (m, 1H), 0.95 (t, J=7.3 Hz, 3H). MS (ESI) (M+H$^+$) m/z=588.10. LCMS Ret time (UV 214/254): 1.413 min.

Example 149: ((2S,3R)-2-(6-chloro-1-(4-fluoro-3,5-dimethylbenzyl)-2-(piperazin-1-yl)-1H-benzo[d]imidazol-4-yl)-1-propylpyrrolidin-3-yl)(phenyl)methanone trifluoroacetate

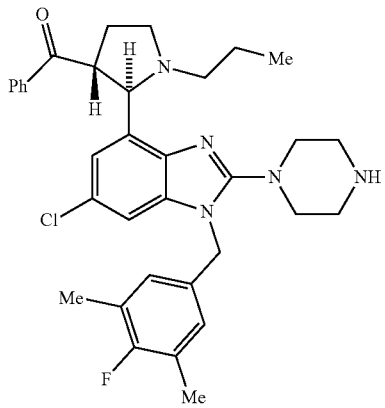

The title compound was obtained according to a procedure analogous to general procedure M: 50 mg, 41% yield: $^1$H NMR (400 MHz, CD$_3$OD) δ 7.93 (d, J=7.6 Hz, 2H), 7.62 (t, J=7.4 Hz, 1H), 7.47 (t, J=7.8 Hz, 2H), 7.41 (s, 1H), 7.33 (s, 1H), 6.89 (s, 1H), 6.87 (s, 1H), 5.49 (d, J=8.0 Hz, 1H), 5.30 (s, 2H), 4.89 (m, 1H), 4.17 (m, 1H), 3.61 (t, J=5.0 Hz, 4H), 3.52 (m, 1H), 3.44 (t, J=5.0 Hz, 4H), 3.30 (s, 1H), 2.98 (m, 1H), 2.46 (m, 1H), 1.76 (m, 1H), 0.95 (t, J=7.0 Hz, 3H). MS (ESI) (M+H$^+$) m/z=588.10. LCMS Ret time (UV 214/254): 1.327 min.

Example 150: ((2S,3R)-2-(6-chloro-1-(3-chloro-4-fluorobenzyl)-2-(piperazin-1-yl)-1H-benzo[d]imidazol-4-yl)-1-isobutylpyrrolidin-3-yl)(phenyl)methanone trifluoroacetate

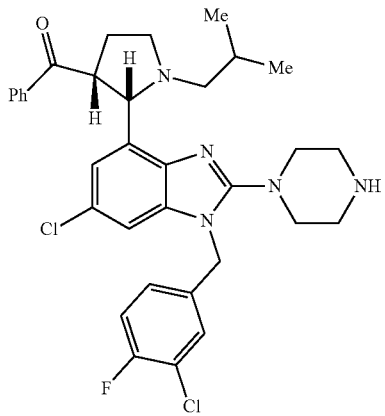

The title compound was obtained according to a procedure analogous to general procedure M: MS (ESI) (M+H$^+$) m/z=608.10. LCMS Ret time (UV 214/254): 1.279 min.

Example 151: ((2R,3R)-2-(6-chloro-1-(3-chloro-4-fluorobenzyl)-2-(piperazin-1-yl)-1H-benzo[d]imidazol-4-yl)-1-isobutylpyrrolidin-3-yl)(phenyl)methanone trifluoroacetate

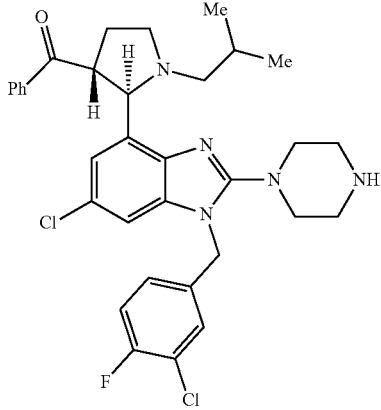

The title compound was obtained according to a procedure analogous to general procedure M: $^1$H NMR (400 MHz, CD$_3$OD) δ 7.91 (d, J=7.6 Hz, 2H), 7.61 (t, J=7.4 Hz, 1H), 7.48 (t, J=7.8 Hz, 2H), 7.41 (d, J=7.9 Hz, 1H), 7.39 (s, 1H), 7.34 (dd, J=6.9, 2.1 Hz, 1H), 7.26 (t, J=8.8 Hz, 1H), 7.14 (m, 1H), 5.50 (d, J=8.4 Hz, 1H), 5.41 (s, 2H), 4.70 (m, 1H), 4.24 (nm, 1H), 3.59 (t, J=5.0 Hz, 4H), 3.45 (t, J=5.0 Hz, 4H), 3.09 (m, 1H), 2.95 (m, 1H), 2.50 (m, 1H), 2.14 (m, 1H), 1.01 (d, J=6.6 Hz, 3H), 0.91 (d, J=6.6 Hz, 3H). MS (ESI) (M+H$^+$) m/z=608.10. LCMS Ret time (UV 214/254): 1.369 min.

Example 152: ((2S,3R)-2-(6-chloro-1-(3-chloro-4-fluorobenzyl)-2-(piperazin-1-yl)-1H-benzo[d]imidazol-4-yl)-1-isopropylpyrrolidin-3-yl)(phenyl)methanone trifluoroacetate

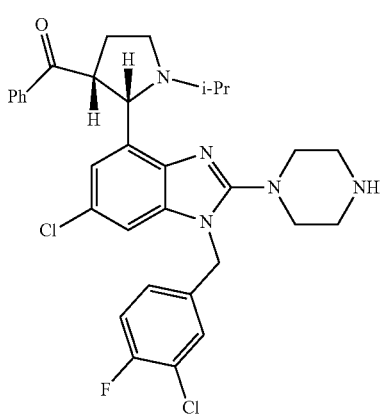

The title compound was obtained according to a procedure analogous to general procedure M: MS (ESI) (M+H$^+$) m/z=594.10. LCMS Ret time (UV 214/254): 1.270 min.

Example 153: ((2R,3R)-2-(6-chloro-1-(3-chloro-4-fluorobenzyl)-2-(piperazin-1-yl)-1H-benzo[d]imidazol-4-yl)-1-isopropylpyrrolidin-3-yl)(phenyl)methanone trifluoroacetate

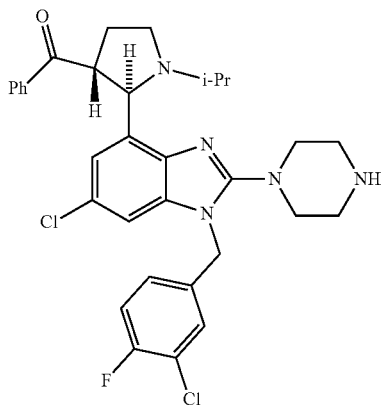

The title compound was obtained according to a procedure analogous to general procedure M: MS (ESI) m/z=594.10. LCMS Ret time (UV 214/254): 1.337 min.

Example 154: ((2S,3R)-2-(6-chloro-1-(3-chloro-4-fluorobenzyl)-2-(piperazin-1-yl)-1H-benzo[d]imidazol-4-yl)-1-propylpyrrolidin-3-yl)(phenyl)methanone trifluoroacetate

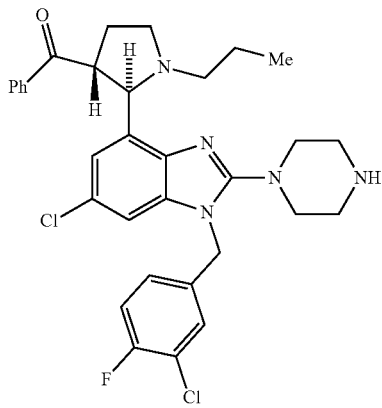

The title compound was obtained according to a procedure analogous to general procedure M: MS (ESI) (M+H$^+$) m/z=594.10. LCMS Ret time (UV 214/254): 1.335 min.

Example 155: (S)-1-(6-chloro-1-(4-fluoro-3,5-dimethylbenzyl)-2-(piperazin-1-yl)-1H-benzo[d]imidazol-4-yl)prop-2-en-1-amine trifluoroacetate

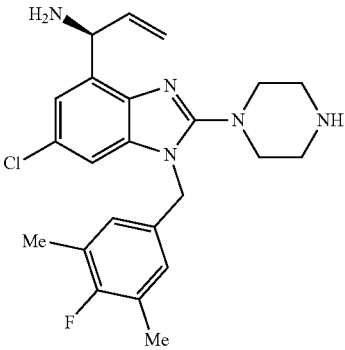 [SMILES: C=C[C@H](N)c1cc(Cl)cc2c1nc(N1CCNCC1)n2Cc1cc(C)c(F)c(C)c1]

Step A: 2,6-dichloro-1-(4-fluoro-3,5-dimethylbenzyl)-1H-benzo[d]imidazole-4-carbaldehyde (195 mg, 0.56 mmol), prepared by a procedure analogous to that used to prepare Example 124, Step A, was dissolved in THF (5.0 mL) in a reaction flask at room temperature. Ti(OEt)$_4$ (0.235 mL, 1.12 mmol, 2 eq) was added to the solution, followed by (R)-($^+$)-t-Butylsulfinamide (74 mg, 0.613 mmol, 1.1 eq). The reaction was stirred at room temperature for 16 hours and monitored by LCMS. Upon conversion to the imine, the reaction was quenched with a brine solution and then filtered through a pad of Celite. The filtered solution was extracted with ethyl acetate and washed with brine. The organic layer was dried over sodium sulfate and concentrated in vacuo to afford a crude yellow solid. The crude material was purified by column chromatography (0-50% ethyl acetate in hexanes) to afford (E)-N-(tert-butyl(oxidanyl)-sulfanyl)-1-(2,6-dichloro-1-(4-fluoro-3,5-dimethylbenzyl)-1H-benzo[d]imidazol-4-yl)methanimine as a white solid (175 mg, 69% yield).

Step B: The (E)-N-(tert-butyl(oxidanyl)-sulfanyl)-1-(2,6-dichloro-1-(4-fluoro-3,5-dimethylbenzyl)-1H-benzo[d]imidazol-4-yl)methanimine (55 mg, 0.121 mmol) from Step A was dissolved in DCM (1.2 mL in a reaction vial equipped with a stir bar and was cooled to −78° C. in a dry ice/acetone bath. Vinyl magnesium bromide (1 M solution in ether: 0.243 mL, 0.243 mmol, 2 eq) was added dropwise to the reaction while maintaining the temperature at −78° C. The reaction was stirred for 4 hours at −78° C., then slowly warmed to room temperature. Once the reaction reached room temperature, it was quenched with 1 M HCl, extracted with DCM, and then concentrated to provide tert-butyl 4-(4-((1S)-1-((tert-butylsulfinyl)amino)allyl)-6-chloro-1-(4-fluoro-3,5-dimethylbenzyl)-1H-benzo[d]imidazol-2-yl)piperazine-1-carboxylate as a crude solid, as a >10:1 diastereomeric mixture. $^1$H NMR (400 MHz, CDCl$_3$) δ 7.20 (s, 1H), 7.15 (s, 1H), 6.84 (s, 1H), 6.82 (s, 1H), 6.09 (m, 1H), 5.35 (m, 2H), 5.23 (m, 3H), 2.23 (s, 6H), 1.29 (s, 9H). MS (ESI) (M+H$^+$) m/z=482.10. LCMS Ret time (UV 214/254): 1.826 min.

Step C: The crude tert-butyl 4-(4-((1S)-1-((tert-butylsulfinyl)amino)allyl)-6-chloro-1-(4-fluoro-3,5-dimethylbenzyl)-1H-benzo[d]imidazol-2-yl)piperazine-1-carboxylate (30 mg, 0.0621 mmol) from above was dissolved in DMSO (1 mL) and transferred to a microwave tube. Solid piperazine (20 mg, 0.186 mmol, 3 eq) was added to the tube, which was then sealed and heated in a microwave reactor at 120° C. for 45 min. The addition of piperazine was confirmed by LCMS. The reaction was quenched with water and then extracted with ethyl acetate (3×), washed with water, dried over sodium sulfate, and concentrated to a crude oil. The crude oil was dissolved in methanol (1 mL) and 4 M HCl in dioxane (0.3 mL) was added to the solution and stirred at room temperature for 1 hour. Upon conversion to the primary amine by LCMS, the volatiles were removed in vacuo and the crude material was purified by reverse-phase HPLC. (S)-1-(6-chloro-1-(4-fluoro-3,5-dimethylbenzyl)-2-(piperazin-1-yl)-1H-benzo[d]imidazol-4-yl)prop-2-en-1-amine was recovered as its TFA salt as a white solid (7 mg, 26% yield). $^1$H NMR (400 MHz, CD$_3$OD) δ 7.32 (d, J=1.8 Hz 1H), 7.26 (d, J=1.8 Hz 1H), 6.87 (s, 1H), 6.86 (s, 1H), 6.31 (m, 1H), 5.54 (d, J=17.2 Hz 1H), 5.52 (d, J=10.4 Hz 1H), 5.43 (d, J=7.2 Hz, 1H), 5.31 (s, 2H), 3.59 (t, J=5.2 Hz, 4H), 3.43 (t, J=5.2 Hz, 4H), 2.21 (s, 6H). MS (ESI) (M+H$^+$) m/z=428.10. LCMS Ret time (UV 214/254): 1.180 min.

Example 156: (S)—N$^1$-(4-(1-aminoallyl)-6-chloro-1-(4-fluoro-3,5-dimethylbenzyl)-1H-benzo[d]imidazol-2-yl)ethane-1,2-diamine trifluoroacetate

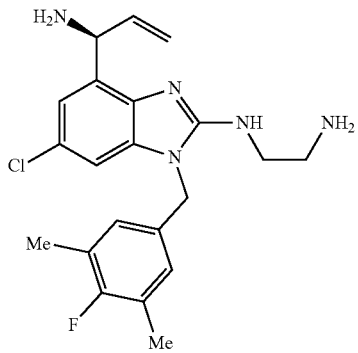 [SMILES: C=C[C@H](N)c1cc(Cl)cc2c1nc(NCCN)n2Cc1cc(C)c(F)c(C)c1]

The title compound was obtained according to a procedure analogous to general procedure N, using 1,2-ethylenediamine in place of BOC-piperazine (5 mg, 20% yield). MS (ESI) (M+H$^+$) m/z=402.10. LCMS Ret time (UV 214/254): 1.137 min.

Example 157: (S)-1-(6-chloro-1-(4-fluoro-3,5-dimethylbenzyl)-2-(piperazin-1-yl)-1H-benzo[d]imidazol-4-yl)propan-1-amine trifluoroacetate

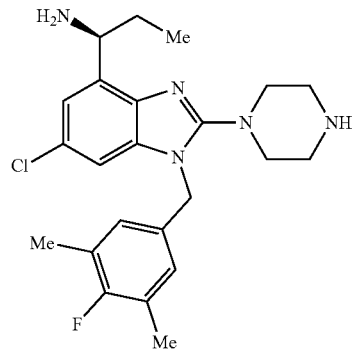 [SMILES: CC[C@H](N)c1cc(Cl)cc2c1nc(N1CCNCC1)n2Cc1cc(C)c(F)c(C)c1]

The title compound was obtained according to a procedure analogous to general procedure M: MS (ESI) (M+H$^+$) m/z=430.20. LCMS Ret time (UV 214/254): 1.194 min.

Example 158: (S)—N$^1$-(4-(1-aminopropyl)-6-chloro-1-(4-fluoro-3,5-dimethylbenzyl)-1H-benzo[d]imidazol-2-yl)ethane-1,2-diamine trifluoroacetate

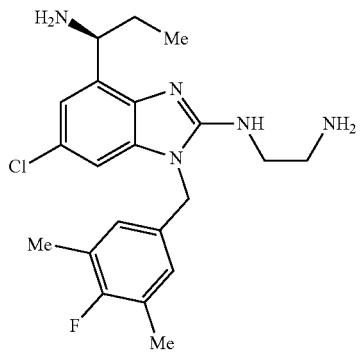 [SMILES: CC[C@H](N)c1cc(Cl)cc2c1nc(NCCN)n2Cc1cc(C)c(F)c(C)c1]

The title compound was obtained according to a procedure analogous to general procedure N, using 1,2-ethylenediamine in place of BOC-piperazine: (5 mg, 20% yield). MS (ESI) (M+H$^+$) m/z=404.10. LCMS Ret time (UV 214/254): 1.124 min.

Example 159: (S)-(6-chloro-1-(4-fluoro-3,5-dimethylbenzyl)-2-(piperazin-1-yl)-1H-benzo[d]imidazol-4-yl)(phenyl)methanamine trifluoroacetate

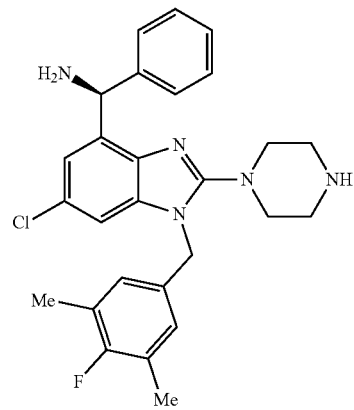 [SMILES: Cc1cc(Cn2c(N3CCNCC3)nc3c([C@@H](N)c4ccccc4)cc(Cl)cc32)cc(C)c1F]

The title compound was obtained according to a procedure analogous to general procedure N: $^1$H NMR (400 MHz, (CD$_3$)$_2$SO)) δ 7.56 (m, 2H), 7.47 (m, 3H), 7.19 (d, J=1.8 Hz 1H), 7.06 (d, J=1.8 Hz 1H), 6.89 (s, 1H), 6.87 (s, 1H), 6.00 (s, 1H), 5.19 (s, 2H), 3.86 (t, J=5.7 Hz, 2H), 3.29 (t, J=5.7 Hz, 2H), 2.21 (s, 6H). MS (ESI) (M+H$^+$) m/z=478.20. LCMS Ret time (UV 214/254): 1.280 min.

Example 160: (S)—N¹-(4-(amino(phenyl)methyl)-6-chloro-1-(4-fluoro-3,5-dimethylbenzyl)-1H-benzo[d]imidazol-2-yl)ethane-1,2-diamine trifluoroacetate

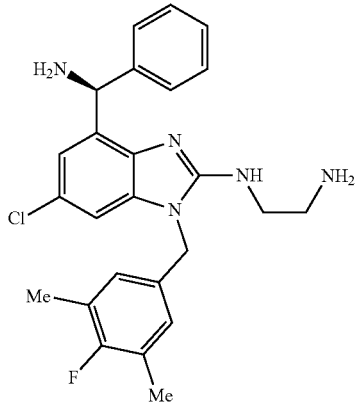 [SMILES: Cc1cc(Cn2c(NCCN)nc3c([C@@H](N)c4ccccc4)cc(Cl)cc32)cc(C)c1F]

The title compound was obtained according to a procedure analogous to general procedure N, using 1,2-ethylenediamine in place of BOC-piperazine: (5 mg, 20% yield). MS (ESI) (M+H⁺) m/z=452.10. LCMS Ret time (UV 214/254): 1.244 min.

Example 161: (S)-1-(1-(4-fluoro-3,5-dimethylbenzyl)-6-methyl-2-(piperazin-1-yl)-1H-benzo[d]imidazol-4-yl)propan-1-amine trifluoroacetate

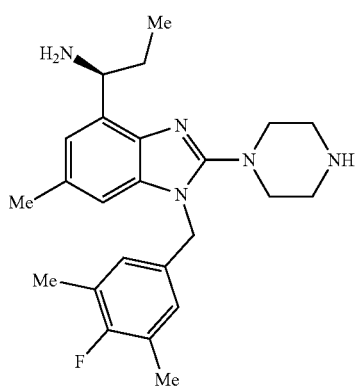 [SMILES: CC[C@H](N)c1cc(C)cc2c1nc(N1CCNCC1)n2Cc1cc(C)c(F)c(C)c1]

The title compound was obtained according to a procedure analogous to general procedure N, starting from 2-chloro-1-(4-fluoro-3,5-dimethylbenzyl)-6-methyl-1H-benzo[d]imidazole-4-carbaldehyde, which was prepared by a procedure analogous to the procedure used to prepare Example 124, Step A: MS (ESI) m/z=410.20. LCMS Ret time (UV 214/254): 1.122 min.

Example 162: (S)-1-(1-(4-fluoro-3,5-dimethylbenzyl)-6-methyl-2-(piperazin-1-yl)-1H-benzo[d]imidazol-4-yl)prop-2-en-1-amine trifluoroacetate

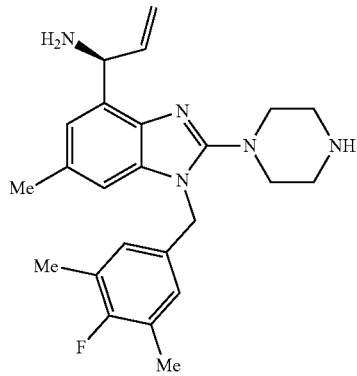 [SMILES: C=C[C@H](N)c1cc(C)cc2c1nc(N1CCNCC1)n2Cc1cc(C)c(F)c(C)c1]

The title compound was obtained according to a procedure analogous to general procedure N, starting from 2-chloro-1-(4-fluoro-3,5-dimethylbenzyl)-6-methyl-1H-benzo[d]imidazole-4-carbaldehyde, which was prepared by a procedure analogous to the procedure used to prepare Example 124, Step A: MS (ESI) (M+H⁺) m/z=408.10. LCMS Ret time (UV 214/254): 1.111 min.

Example 163: (R)-1-(1-(4-fluoro-3,5-dimethylbenzyl)-6-methyl-2-(piperazin-1-yl)-1H-benzo[d]imidazol-4-yl)prop-2-en-1-amine trifluoroacetate

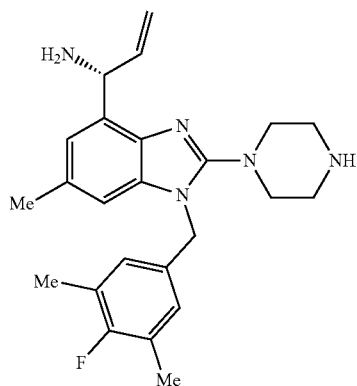 [SMILES: C=C[C@@H](N)c1cc(C)cc2c1nc(N1CCNCC1)n2Cc1cc(C)c(F)c(C)c1]

The title compound was obtained according to a procedure analogous to general procedure N, starting from 2-chloro-1-(4-fluoro-3,5-dimethylbenzyl)-6-methyl-1H-benzo[d]imidazole-4-carbaldehyde, which was prepared by a procedure analogous to the procedure used to prepare Example 124, Step A, and exchanging for (S)-(−)-t-Butylsulfinamide: MS (ESI) (M+H⁺) m/z=408.00. LCMS Ret time (UV 214/254): 1.119 min.

Example 164: (S)-1-(6-chloro-1-(4-fluoro-3,5-dimethylbenzyl)-2-(piperazin-1-yl)-1H-benzo[d]imidazol-4-yl)butan-1-amine trifluoroacetate

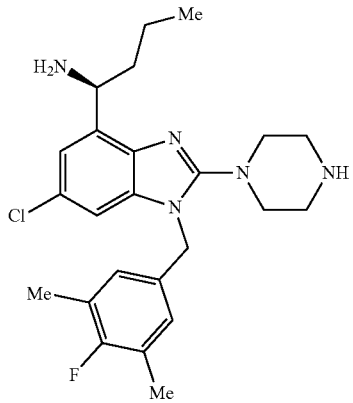 [SMILES: CCC[C@H](N)c1cc(Cl)cc2c1nc(N1CCNCC1)n2Cc1cc(C)c(F)c(C)c1]

The title compound was obtained according to a procedure analogous to general procedure N, starting from 2-chloro-1-(4-fluoro-3,5-dimethylbenzyl)-6-methyl-1H-benzo[d]imidazole-4-carbaldehyde, which was prepared by a procedure analogous to the procedure used to prepare Example 124, Step A: $^1$H NMR (400 MHz, CD$_3$OD) δ 7.30 (d, J=1.8 Hz, 1H), 7.27 (d, J=1.8 Hz, 1H), 6.87 (s, 1H), 6.85 (s, 1H), 5.30 (s, 2H), 4.78 (dd, J=8.9, 6.0, 1H), 3.59 (t, J=5.1 Hz, 4H), 3.44 (t, J=5.1 Hz, 4H), 2.20 (s, 6H), 2.1 (m, 2H) 1.33 (m, 2H), 0.98 (t, J=7.3 Hz, 3H). MS (ESI) (M+H$^+$) m/z=444.10. LCMS Ret time (UV 214/254): 1.226 min.

Example 165: (S)-1-(1-(3-chloro-4-fluorobenzyl)-2-(piperazin-1-yl)-1H-benzo[d]imidazol-4-yl)butan-1-amine trifluoroacetate

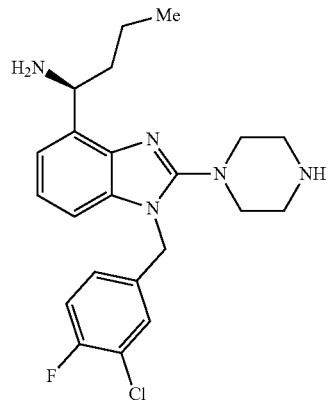 [SMILES: CCC[C@H](N)c1cccc2c1nc(N1CCNCC1)n2Cc1ccc(F)c(Cl)c1]

The title compound was obtained according to a procedure analogous to general procedure N, starting from 2-chloro-1-(3-chloro-4-fluorobenzyl)-1H-benzo[d]imidazole-4-carbaldehyde, which was prepared by a procedure analogous to the procedure used to prepare Example 124, Step A: MS (ESI) (M+H$^+$) m/z=416.10. LCMS Ret time (UV 214/254): 1.097 min.

Example 166 (S)-1-(6-chloro-1-(3-chloro-4-fluorobenzyl)-2-(piperazin-1-yl)-1H-benzo[d]imidazol-4-yl)-2-phenylethan-1-amine trifluoroacetate

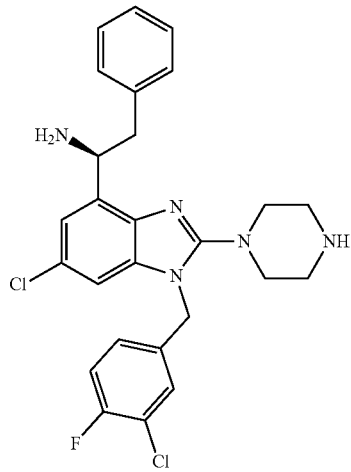 [SMILES: N[C@@H](Cc1ccccc1)c1cc(Cl)cc2c1nc(N1CCNCC1)n2Cc1ccc(F)c(Cl)c1]

The title compound was obtained according to a procedure analogous to general procedure N, starting from 2-chloro-1-(3-chloro-4-fluorobenzyl)-1H-benzo[d]imidazole-4-carbaldehyde, which was prepared by a procedure analogous to the procedure used to prepare Example 124, Step A: MS (ESI) (M+H$^+$) m/z=497.80. LCMS Ret time (UV 214/254): 1.238 min.

Example 167: (S)-(6-chloro-1-(3-chloro-4-fluorobenzyl)-2-(piperazin-1-yl)-1H-benzo[d]imidazol-4-yl)(cyclopropyl)methanamine trifluoroacetate

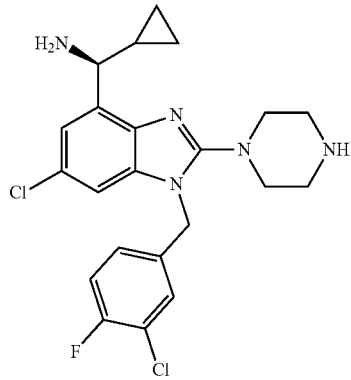 [SMILES: N[C@H](c1cc(Cl)cc2c1nc(N1CCNCC1)n2Cc1ccc(F)c(Cl)c1)C1CC1]

The title compound was obtained according to a procedure analogous to general procedure N, starting from 2-chloro-1-(3-chloro-4-fluorobenzyl)-1H-benzo[d]imidazole-4-carbaldehyde, which was prepared by a procedure analogous to the procedure used to prepare Example 124, Step A: MS (ESI) (M+H$^+$) m/z=430.90. LCMS Ret time (UV 214/254): 1.151 min.

Example 169: 6-chloro-1-(3-chloro-4-fluorobenzyl)-4-(1-(4-methoxyphenyl)-1H-pyrazol-5-yl)-2-(piperazin-1-yl)-1H-benzo[d]imidazole trifluoroacetate

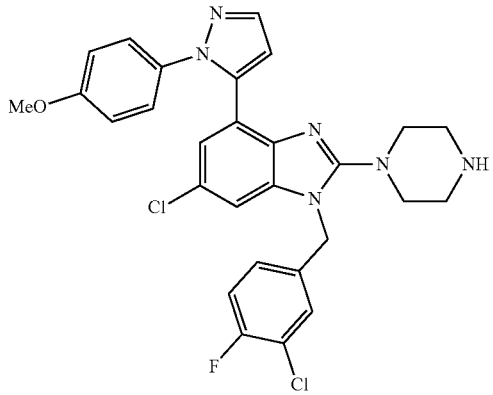 [SMILES: COc1ccc(-n2nccc2-c2cc(Cl)cc3c2nc(N2CCNCC2)n3Cc2ccc(F)c(Cl)c2)cc1]

Step A: The tert-butyl 4-(4-bromo-6-chloro-1-(3-chloro-4-fluorobenzyl)-1H-benzo[d]imidazol-2-yl)piperazine-1-carboxylate (300 mg, 0.54 mmol, 1 eq), prepared by a procedure analogous to the procedure used to prepare Example 124, Step E and Pd(dppf)Cl$_2$ (47 mg, 0.065 mmol, 0.12 eq) were added to a microwave tube equipped with a stir bar. The tube was purged 3× with an atmosphere of argon. DMA (2 mL) was added to the tube, followed by tributyl(1-ethoxyvinyl)stannane (0.200 mL, 0.593 mmol, 1.1 eq). The reaction was heated in a microwave at 130° C. for 45 min. Upon cooling to room temperature, 10% aqueous HCl was added to hydrolyze the ethyl ether. After stirring for 10 min, the mixture was diluted with ethyl acetate. The organic layer was washed with water and brine, dried over sodium sulfate, and concentrated in vacuo to afford a crude oil. The oil was purified on silica gel (40% ethyl acetate) to provide the tert-butyl 4-(4-acetyl-6-chloro-1-(3-chloro-4-fluorobenzyl)-1H-benzo[d]imidazol-2-yl)piperazine-1-carboxylate as a white solid (175 mg, 63% yield).

Step B: The tert-butyl 4-(4-acetyl-6-chloro-1-(3-chloro-4-fluorobenzyl)-1H-benzo[d]imidazol-2-yl)piperazine-1-carboxylate (60 mg, 0.115 mmol) from Step A was dissolved in DMFDMA (dimethylformamide dimethylacetal) (1 mL) and heated while stirring at 100° C. Upon conversion to the enaminone by LCMS, reaction was concentrated in vacuo to afford tert-butyl (E)-4-(6-chloro-1-(3-chloro-4-fluorobenzyl)-4-(3-(dimethylamino)acryloyl)-1H-benzo[d]imidazol-2-yl)piperazine-1-carboxylate as a crude oil, which was used without any further purification.

Step C: 4-Methoxyphenylhydrazine hydrochloride (7 mg, 0.0402 mmol, 1 eq) was added to the crude tert-butyl (E)-4-(6-chloro-1-(3-chloro-4-fluorobenzyl)-4-(3-(dimethylamino)acryloyl)-1H-benzo[d]imidazol-2-yl)piperazine-1-carboxylate from Step B (21 mg, 0.0365 mmol, 1 eq) in ethanol (0.5 mL) in a sealed tube equipped with a stir bar. The reaction mixture was heated at 75° C. for 3 hours. Upon conversion to the alkylated pyrazole by LCMS, the reaction was cooled to rt and the volatiles were removed in vacuo. The crude reaction was dissolved in a 2/1 mixture of DCM/TFA (1 mL) and stirred at rt for 30 min. Upon conversion by LCMS to the free amine, the solvent was removed and the crude oil was purified by reverse phase HPLC. The title compound was recovered as a white solid (7 mg, 34% yield). $^1$H NMR (400 MHz, CD$_3$OD) δ 7.80 (d, J=1.9 Hz, 1H), 7.32 (d, J=1.9 Hz, 1H), 7.22 (ovlp m, 4H), 6.92 (m, 1H), 6.87 (d, J=7.0 Hz, 1H), 6.81 (d, J=1.9 Hz, 1H), 5.32 (s, 2H), 3.78 (s, 3H), 3.33 (ovlp bs, 8H). MS (ESI) (M+H$^+$) m/z=551.00. LCMS Ret time (UV 214/254): 1.459 min.

Example 169: 6-chloro-1-(3-chloro-4-fluorobenzyl)-4-(1-(4-isopropylphenyl)-1H-pyrazol-5-yl)-2-(piperazin-1-yl)-1H-benzo[d]imidazole trifluoroacetate

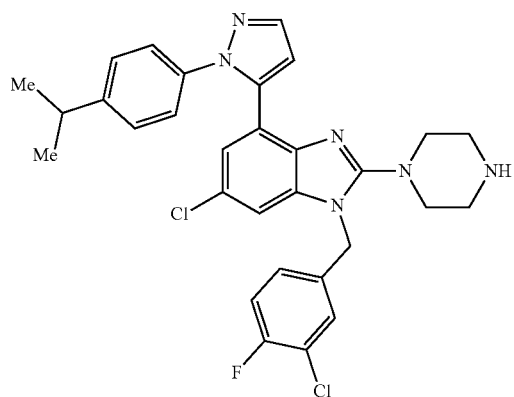 [SMILES: CC(C)c1ccc(-n2nccc2-c2cc(Cl)cc3c2nc(N2CCNCC2)n3Cc2ccc(F)c(Cl)c2)cc1]

The title compound was obtained according to a procedure analogous to general procedure O: $^1$H NMR (400 MHz, CD$_3$OD) δ 7.82 (d, J=1.9 Hz, 1H), 7.35 (d, J=1.9 Hz, 1H), 7.19 (s, 1H), 6.96 (m, 4H), 6.81 (d, J=1.9 Hz, 1H), 5.31 (s, 2H), 3.28 (ovlp m, 8H), 2.90 (sep, J=6.9 Hz, 1H), 1.22 (s, 3H), 1.20 (s, 3H). MS (ESI) (M+H$^+$) m/z=563.10. LCMS Ret time (UV 214/254): 1.594 min.

Example 170: 4-(1-(4-bromophenyl)-1H-pyrazol-5-yl)-6-chloro-1-(3-chloro-4-fluorobenzyl)-2-(piperazin-1-yl)-1H-benzo[d]imidazole trifluoroacetate

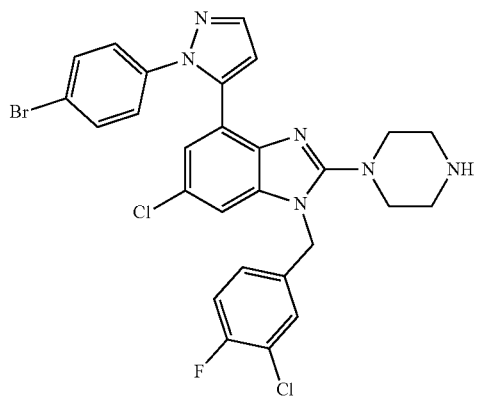 [SMILES: Fc1ccc(Cn2c(N3CCNCC3)nc3c(-c4ccnn4-c4ccc(Br)cc4)cc(Cl)cc32)cc1Cl]

The title compound was obtained according to a procedure analogous to general procedure O: MS (ESI) (M+H$^+$) m/z=600.90. LCMS Ret time (UV 214/254): 1.541 min.

Example 171: 1-(3-chloro-4-fluorobenzyl)-5,6-dimethyl-4-(1-phenyl-1H-pyrazol-5-yl)-2-(piperazin-1-yl)-1H-benzo[d]imidazole trifluoroacetate

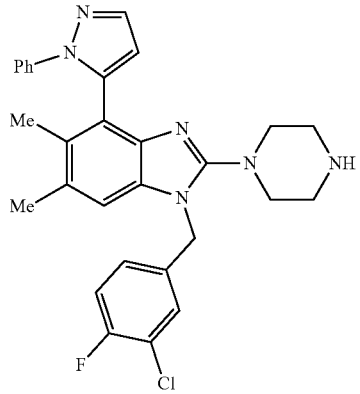 [SMILES: Cc1cc2c(nc(N3CCNCC3)n2Cc2ccc(F)c(Cl)c2)c(-c2ccnn2-c2ccccc2)c1C]

The title compound was obtained according to a procedure analogous to general procedure O starting from tert-butyl 4-(4-bromo-1-(3-chloro-4-fluorobenzyl)-5,6-dimethyl-1H-benzo[d]imidazol-2-yl)piperazine-1-carboxylate, which was prepared by a procedure analogous to the procedure used to prepare Example 124, Step A: $^1$H NMR (400 MHz, CD$_3$OD) δ 7.92 (d, J=1.8 Hz, 1H), 7.35 (d, J=2.9 Hz, 1H), 7.27 (ovlp, 8H), 7.10 (m, 1H), 6.66 (d, J=1.8 Hz, 1H), 5.44 (s, 2H), 3.55 (m, 4H), 3.37 (m, 4H), 2.32 (s, 3H), 2.03 (s, 3H). MS (ESI) (M+H$^+$) m/z=515.10. LCMS Ret time (UV 214/254): 1.314 min.

Example 172: 4-(1-(4-bromophenyl)-1H-pyrazol-5-yl)-1-(3-chloro-4-fluorobenzyl)-5,6-dimethyl-2-(piperazin-1-yl)-1H-benzo[d]imidazole trifluoroacetate

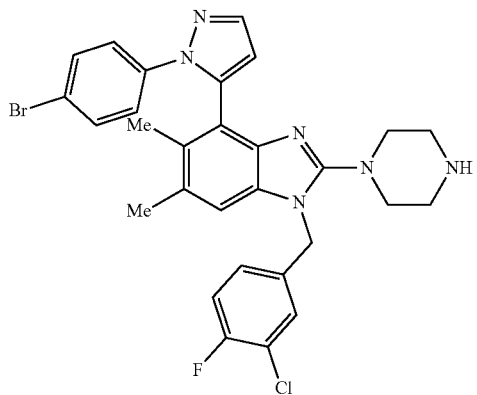 [SMILES: Cc1cc2c(nc(N3CCNCC3)n2Cc2ccc(F)c(Cl)c2)c(-c2ccnn2-c2ccc(Br)cc2)c1C]

The title compound was obtained according to a procedure analogous to general procedure O, starting from tert-butyl 4-(4-bromo-1-(3-chloro-4-fluorobenzyl)-5,6-dimethyl-1H-benzo[d]imidazol-2-yl)piperazine-1-carboxylate, which was prepared by a procedure analogous to the procedure used to prepare Example 124, Step A: MS (ESI) (M+H$^+$) m/z=595.00. LCMS Ret time (UV 214/254): 1.440 min.

Example 173: 1-(3-chloro-4-fluorobenzyl)-4-(1-(4-isopropylphenyl)-1H-pyrazol-5-yl)-5,6-dimethyl-2-(piperazin-1-yl)-1H-benzo[d]imidazole trifluoroacetate

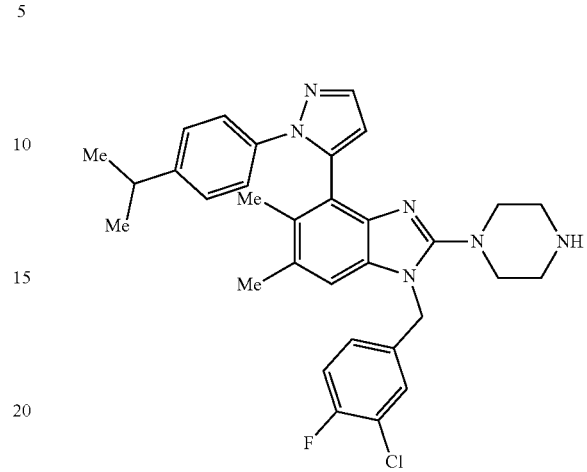

The title compound was obtained according to a procedure analogous to general procedure O, starting from tert-butyl 4-(4-bromo-1-(3-chloro-4-fluorobenzyl)-5,6-dimethyl-1H-benzo[d]imidazol-2-yl)piperazine-1-carboxylate, which was prepared by a procedure analogous to the procedure used to prepare Example 124, Step A: $^1$H NMR (400 MHz, CD$_3$OD) δ 7.89 (d, J=1.9 Hz, 1H), 7.37 (dd, J=6.8, 2.2 Hz, 1H), 7.28 (t, J=8.8, 1H), 7.24 (s, 1H), 7.14 (ovlp m, 4H), 6.63 (d, J=1.9 Hz, 1H), 5.43 (s, 2H), 3.53 (m, 4H), 3.38 (m, 4H), 2.87 (sep, J=3.3 Hz, 1H), 2.32 (s, 3H), 2.02 (s, 3H), 1.20 (d, J=3.3 Hz, 3H), 1.18 (d, J=3.3 Hz, 3H). MS (ESI) (M+H$^+$) m/z=557.10. LCMS Ret time (UV 214/254): 1.472 min.

Example 174: 6-chloro-1-(3-chloro-4-fluorobenzyl)-4-(1-isobutyl-1H-pyrazol-5-yl)-2-(piperazin-1-yl)-1H-benzo[d]imidazole trifluoroacetate

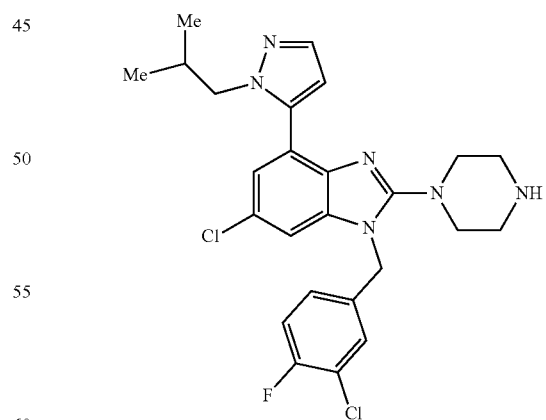

The title compound was obtained according to a procedure analogous to general procedure O: $^1$H NMR (400 MHz, CD$_3$OD) δ 7.64 (d, J=1.9 Hz, 1H), 7.42 (d, J=1.9 Hz, 1H), 7.34 (dd, J=6.9, 2.2 Hz 1H), 7.26 (ovlp, 3H), 7.14 (m, 1H), 6.50 (d, J=1.9 Hz, 1H), 5.43 (s, 2H), 4.09 (d, J=7.5 Hz, 2H), 3.52 (d, J=5.5 Hz, 4H), 3.41 (d, J=5.5 Hz, 4H), 1.95 (m, 1H), 0.70 (s, 3H), 0.68 (s, 3H). MS (ESI) m/z=501.10. LCMS Ret time (UV 214/254): 1.468 min.

Example 175: 2-(5-(6-chloro-1-(3-chloro-4-fluorobenzyl)-2-(piperazin-1-yl)-1H-benzo[d]imidazol-4-yl)-1H-pyrazol-1-yl)-N,N-dimethylethan-1-amine trifluoroacetate

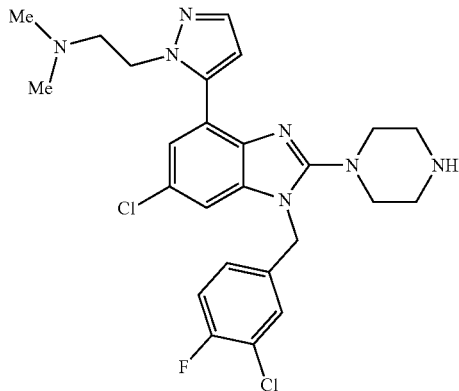 [SMILES: CN(C)CCn1nccc1-c1cc(Cl)cc2c1nc(N1CCNCC1)n2Cc1ccc(F)c(Cl)c1]

The title compound was obtained according to a procedure analogous to general procedure O: ¹H NMR (400 MHz, CD₃OD) δ 7.74 (d, J=1.9 Hz, 1H), 7.44 (d, J=1.9 Hz, 1H), 7.41 (dd, J=6.9, 2.2 Hz 1H), 7.32 (d, J=1.8 Hz, 1H), 7.27 (t, J=7.5 Hz, 1H), 7.16 (m, 1H), 6.56 (d, J=1.9 Hz, 1H), 5.43 (s, 2H), 4.59 (t, J=5.4 Hz, 2H), 3.69 (t, J=5.4 Hz, 2H), 3.53 (t, J=5.0 Hz, 4H), 3.42 (t, J=5.0 Hz, 4H), 2.99 (br s, 6H). MS (ESI) (M+H⁺) m/z=516.10. LCMS Ret time (UV 214/254): 1.164 min.

Example 176: 6-chloro-1-(3-chloro-4-fluorobenzyl)-4-(1-isopropyl-1H-pyrazol-5-yl)-2-(piperazin-1-yl)-1H-benzo[d]imidazole trifluoroacetate

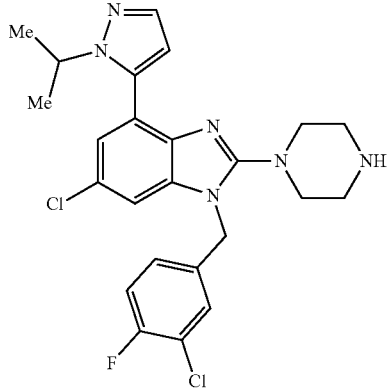 [SMILES: CC(C)n1nccc1-c1cc(Cl)cc2c1nc(N1CCNCC1)n2Cc1ccc(F)c(Cl)c1]

The title compound was obtained according to a procedure analogous to general procedure O: ¹H NMR (400 MHz, CD₃OD) δ 7.65 (d, J=1.8 Hz, 1H), 7.41 (d, J=2.2 Hz, 1H), 7.27 (t, J=8.8 Hz 1H), 7.24 (d, J=1.9 Hz, 1H), 7.15 (m, 1H), 642 (d, J=1.9 Hz, 1H), 5.42 (s, 2H), 4.58 (sep, J=6.5 Hz, 1H), 3.50 (t, J=3.4 Hz, 4H), 3.40 (d, J=3.4 Hz, 4H), 1.48 (s, 3H), 1.47 (s, 3H). MS (ESI) (M+H⁺) m/z=487.00. LCMS Ret time (UV 214/254): 1.423 min.

Example 177: 6-chloro-1-(4-fluoro-3,5-dimethylbenzyl)-4-(1-(naphthalen-1-yl)-1H-pyrazol-5-yl)-2-(piperazin-1-yl)-1H-benzo[d]imidazole trifluoroacetate

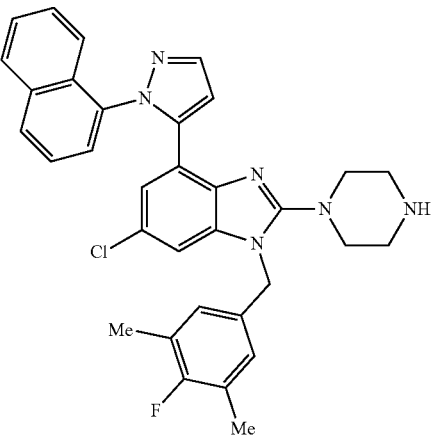 [SMILES: Cc1cc(Cn2c(N3CCNCC3)nc3c(-c4ccnn4-c4cccc5ccccc45)cc(Cl)cc32)cc(C)c1F]

The title compound was obtained according to a procedure analogous to general procedure O, starting from tert-butyl 4-(4-bromo-6-chloro-1-(4-fluoro-3,5-dimethylbenzyl)-1H-benzo[d]imidazol-2-yl)piperazine-1-carboxylate, which was prepared by a procedure analogous to the procedure used to prepare Example 118, Step A: MS (ESI) (M+H⁺) m/z=565.00. LCMS Ret time (UV 214/254): 1.601 min.

Example 178: 4-(1-(4-(tert-butyl)phenyl)-1H-pyrazol-5-yl)-6-chloro-1-(4-fluoro-3,5-dimethylbenzyl)-2-(piperazin-1-yl)-1H-benzo[d]imidazole trifluoroacetate

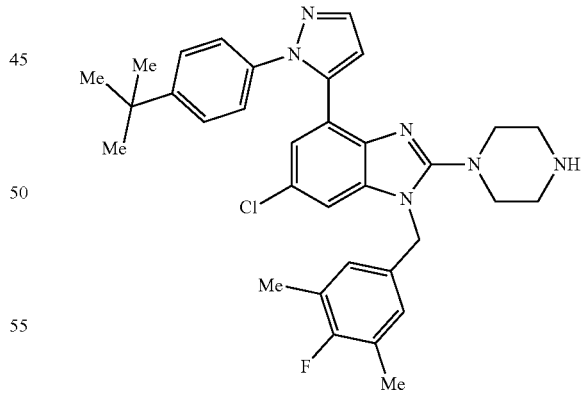

The title compound was obtained according to a procedure analogous to general procedure O, starting from tert-butyl 4-(4-bromo-6-chloro-1-(4-fluoro-3,5-dimethylbenzyl)-1H-benzo[d]imidazol-2-yl)piperazine-1-carboxylate, which was prepared by a procedure analogous to the procedure used to prepare Example 118, Step A: MS (ESI) (M+H⁺) m/z=571.20. LCMS Ret time (UV 214/254): 1.700 min.

Example 179: methyl 5-(1-(3-chloro-4-fluorobenzyl)-6-methyl-2-(piperazin-1-yl)-1H-benzo[d]imidazol-4-yl)-1-isobutyl-1H-pyrazole-4-carboxylate

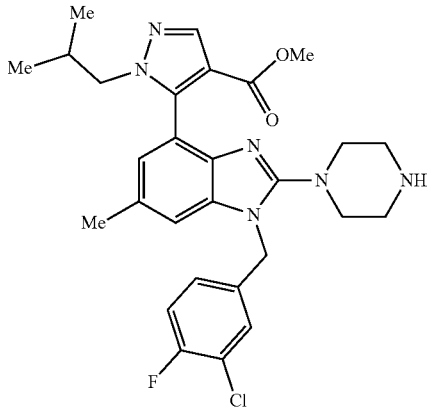 [SMILES: COC(=O)c1cnn(CC(C)C)c1-c1cc(C)cc2c1nc(N1CCNCC1)n2Cc1ccc(F)c(Cl)c1]

To a dry reaction flask was added sodium hydride (60%, 30 mg, 0.6 mmol, 3 eq), toluene (1 mL) and dimethyl carbonate (0.035 mL, 0.4 mmol, 2 eq). The reaction was heated to 100° C., and then tert-butyl 4-(4-acetyl-6-chloro-1-(4-fluoro-3,5-dimethylbenzyl)-1H-benzo[d]imidazol-2-yl)piperazine-1-carboxylate (100 mg, 0.20 mmol), prepared by a procedure analogous to the procedure used to prepare Example 118, Step A, in toluene (1 mL) was added to the flask and heated for three hours. The solution turned a reddish color when complete. The reaction was cooled to room temperature and quenched with 1 M aqueous HCl and extracted with ethyl acetate. The organic layer was washed with water, dried over sodium sulfate and concentrated in vacuo to afford a crude reddish oil, which was used without any further purification. The crude oil was dissolved in DMFDMA (dimethylformamide dimethylacetal) (2 mL) in a sealed tube and heated while stirring at 100° C. Upon conversion to the enaminone by LCMS, reaction was concentrated in vacuo to afford a crude oil, which was used without any further purification. Isobutylhydrazine hydrochloride (37 mg, 0.30 mmol, 3 eq) was added to the crude enaminone in ethanol (0.5 mL) in a small reaction vial equipped with a stir bar. The reaction mixture was stirred at room temperature for one hour, until it was complete by LCMS. The volatiles were removed in vacuo and the crude reaction was dissolved in a 2/1 mixture of DCM/TFA (1 mL) and stirred at room temperature for 30 min. Upon conversion by LCMS to the free amine, the solvent was removed and the crude oil was purified by reverse phase HPLC. The title compound was recovered as a white solid: (18 mg, 17% yield). $^1$H NMR (400 MHz, CD$_3$OD) δ 7.94 (s, 1H), 7.19 (dd, J=7.0, 1.2 Hz, 1H), 7.13 (t, J=8.8 Hz, 1H), 7.07 (s, 1H), 7.03 (m, 1H), 6.91 (s, 1H), 5.25 (s, 2H), 3.71 (m, 2H), 3.53 (s, 3H), 3.11 (br s, 4H), 2.91 (br s, 4H), 2.34 (s, 3H), 1.89 (sep, J=6.7 Hz, 1H), 0.62 (d, J=6.7 Hz, 3H), 0.56 (d, J=6.7 Hz, 3H). MS (ESI) (M+H$^+$) m/z=539.20. LCMS Ret time (UV 214/254): 1.400 min.

Example 180: methyl 5-(1-(3-chloro-4-fluorobenzyl)-6-methyl-2-(piperazin-1-yl)-1H-benzo[d]imidazol-4-yl)-1-(2-(dimethylamino)ethyl)-1H-pyrazole-4-carboxylate

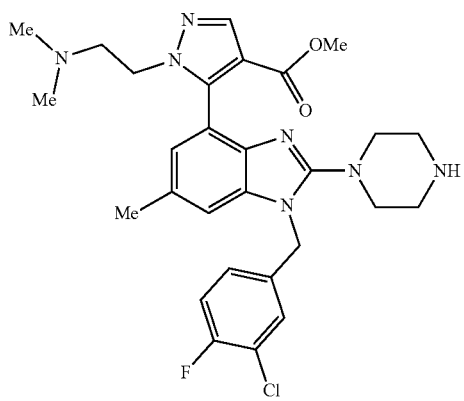 [SMILES: COC(=O)c1cnn(CCN(C)C)c1-c1cc(C)cc2c1nc(N1CCNCC1)n2Cc1ccc(F)c(Cl)c1]

The title compound was obtained according to a procedure analogous to general procedure O, starting from tert-butyl 4-(4-acetyl-6-chloro-1-(4-fluoro-3,5-dimethylbenzyl)-1H-benzo[d]imidazol-2-yl)piperazine-1-carboxylate, which was prepared by a procedure analogous to the procedure used to prepare Example 179: MS (ESI) (M+H$^+$) m/z=554.20. LCMS Ret time (UV 214/254): 1.093 min.

Example 181: 5-(1-(4-fluoro-3,5-dimethylbenzyl)-6-methyl-2-(piperazin-1-yl)-1H-benzo[d]imidazol-4-yl)-1-isobutyl-N-propyl-1H-pyrazole-4-carboxamide trifluoroacetate

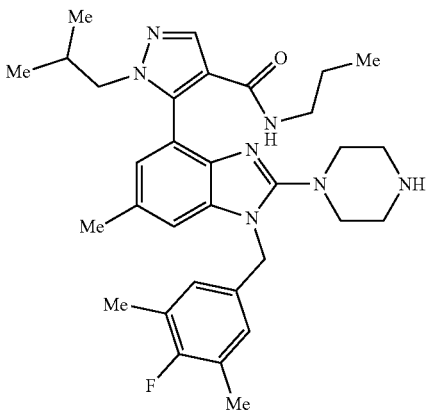 [SMILES: CCCNC(=O)c1cnn(CC(C)C)c1-c1cc(C)cc2c1nc(N1CCNCC1)n2Cc1cc(C)c(F)c(C)c1]

tert-butyl 4-(1-(4-fluoro-3,5-dimethylbenzyl)-4-(1-isobutyl-4-(methoxycarbonyl)-1H-pyrazol-5-yl)-6-methyl-1H-benzo[d]imidazol-2-yl)piperazine-1-carboxylate (50 mg, 0.08 mmol, 1 eq), which was prepared by a procedure analogous to the procedure used to prepare Example 179, was dissolved in THF (1 mL) in a reaction vial and 3 M NaOH (1 mL) was added to the vial. The reaction was stirred at 40° C. for 18 hours. Upon conversion to the acid by LCMS, the reaction was quenched with 1 M aqueous HCl and extracted with ethyl acetate. The organic layer was dried over sodium sulfate and concentrated in vacuo to afford a crude white solid. The solid (30 mg, 0.05 mmol, 1 eq), HOBt (7 mg, 0.05, 1 eq), EDCi (12 mg, 0.064 mmol, 1.3 eq), propylamine (0.06 mL, 0.073 mmol, 1.5 eq) and diisopropylethylamine (0.020 mL, 0.1 mmol, 2 eq) were dissolved in dichloromethane in a reaction flask. The reaction was stirred at room temperature for 18 hours until the starting material had converted by LCMS. The reaction was quenched with water and extracted with dichloromethane. The solution was passed through a phase separator and the organic layer was concentrated to dryness. The resulting oil was dissolved in a 2/1 mixture of DCM/TFA and stirred at room temperature for 30 min. The volatiles were removed and the material was purified by reverse-phase HPLC. The title compound was recovered as a yellowish solid (11 mg, 24% yield). $^1$H NMR (400 MHz, CD$_3$OD) δ 8.03 (s, 1H), 7.29 (s, 1H), 7.12 (s, 1H), 6.94 (s, 1H), 6.92 (s, 1H), 5.37 (s, 2H), 3.84 (d, J=7.0 Hz, 1H), 3.82 (d, J=7.0 Hz, 1H), 3.52 (m, 4H), 3.37 (m, 4H), 3.13 (q, J=7.2 Hz, 2H), 2.68 (s, 3H), 2.48 (s, 6H), 2.23 (ovlp s, 6H), 2.05 (m, 1H), 1.36 (m, 2H), 0.72 (s, 3H). MS (ESI) (M+H$^+$) m/z=560.40. LCMS Ret time (UV 214/254): 1.412 min.

Example 182: 6-chloro-1-(4-fluoro-3,5-dimethylbenzyl)-4-(2-(phenylethynyl)phenyl)-2-(piperazin-1-yl)-1H-benzo[d]imidazole trifluoroacetate

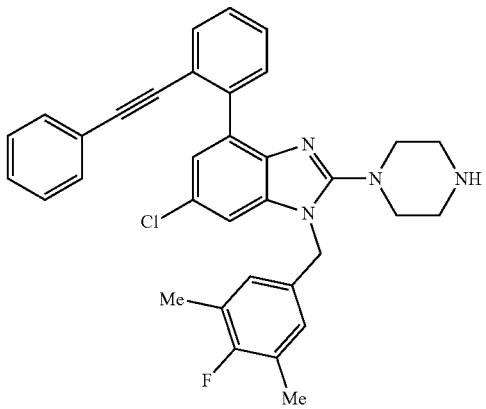 [SMILES: Cc1cc(Cn2c(N3CCNCC3)nc3c(-c4ccccc4C#Cc4ccccc4)cc(Cl)cc32)cc(C)c1F]

Step A: 2-Iodobromobenzene (0.065 mL, 0.50 mmol), copper iodide (7.6 mg, 0.04 mmol, 0.08 eq), PdCl$_2$(PPh3)$_2$ (35 mg, 0.05 mmol, 0.1 eq) were placed in a reaction vial under an atmosphere of argon. A solution of phenylacetylene (0.055 mL, 0.5 mmol, 1 eq) in triethylamine (5 mL) was added to the vial and the reaction was stirred at room temperature for several hours. Upon conversion of the starting material by TLC, the reaction was quenched with an aqueous ammonium chloride solution and extracted with ethyl acetate. The organic layers were combined and washed with brine, dried over sodium sulfate, and concentrated to afford a crude oil. The crude oil was purified by column chromatography (100% hexanes) to provide as 1-bromo-2-(phenylethynyl)benzene a clear oil (115 mg, 90% yield).

Step B: The 1-bromo-2-(phenylethynyl)benzene (100 mg, 0.392 mmol) from Step A was dissolved in THF (3.5 mL) in a round bottom flask and cooled to −78° C. in a dry ice bath. After the flask had cooled, n-BuLi (2.5 M, 0.173 mL, 1.1 eq) was added dropwise to the reaction while maintaining the temperature. The reaction was stirred for 10 min, then triisopropylborate (0.136 mL, 0.588 mmol, 1.5 eq) was added to the solution. The reaction was slowly allowed to warm to room temperature over an hour. When the reaction reached room temperature, a 10% HCl solution was added and the reaction was stirred for 10 min. The reaction was extracted with ethyl acetate, washed with water and brine, dried over sodium sulfate, and concentrated. The crude (2-(phenylethynyl)phenyl)boronic acid (~80 mg) was used in the next step without purification.

Step C: The crude (2-(phenylethynyl)phenyl)boronic acid (40 mg, 0.180 mmol, 1.1 eq), tert-butyl 4-(4-bromo-6-chloro-1-(4-fluoro-3,5-dimethylbenzyl)-1H-benzo[d]imidazol-2-yl)piperazine-1-carboxylate (90 mg, 0.163 mmol), prepared by a procedure analogous to the procedure used to prepare Example 118, Step E, Pd(OAc)$_2$ (4.0 mg, 0.0163 mmol, 0.1 eq), P(Cy$_3$)HBF$_4$ (9.0 mg, 0.0246 mmol, 0.15 eq), and K$_3$PO$_4$ (70 mg, 0.33 mmol, 2 eq) were added to a sealed tube equipped with a stir bar. The tube was purged 3× with an atmosphere of nitrogen. A 5/1 mixture of DME/H$_2$O (1.5 mL) was added to the tube, which was then sealed. The reaction was then heated at 95° C. for 16 hours in an oil bath and then monitored by LCMS. Upon completion by LCMS, the reaction was quenched with water and extracted with DCM. The organic layer was filtered through a phase separator and concentrated to a crude solid. The solid was purified by reverse-phase HPLC to provide a white solid. The solid was dissolved in a 4/1 mixture of DCM/TFA (1 mL) and stirred at room temperature until the conversion to the free amine by LCMS. Upon conversion of the starting material, the reaction was diluted with water and an aqueous solution of sodium bicarbonate was added. The quenched reaction was extracted with DCM, passed through a phase separator, and concentrated to afford the title compound as a white solid (20 mg, 20% yield): $^1$H NMR (400 MHz, CD$_3$OD) δ 7.68 (d, J=7.52 Hz, 2H), 7.43 (ovlp m, 4H), 7.26 (ovlp m, 4H), 7.11 (d, J=7.52 Hz, 2H), 6.92 (s, 1H), 6.90 (s, 1H), 5.27 (s, 2H), 3.30 (t, J=5.2 Hz, 4H), 3.14 (t, J=5.2 Hz, 4H), 2.19 (s, 6H). MS (ESI) (M+H$^+$) m/z=549.10. LCMS Ret time (UV 214/254): 1.735 min.

Example 183: 6-chloro-4-(2-((2-chlorophenyl)ethynyl)phenyl)-1-(4-fluoro-3,5-dimethylbenzyl)-2-(piperazin-1-yl)-1H-benzo[d]imidazole trifluoroacetate

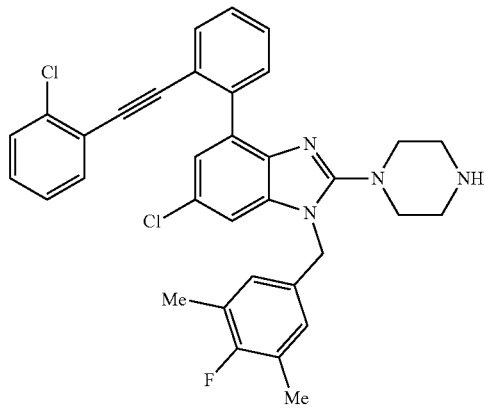 [SMILES: Cc1cc(Cn2c(N3CCNCC3)nc3c(-c4ccccc4C#Cc4ccccc4Cl)cc(Cl)cc32)cc(C)c1F]

The title compound was obtained according to a procedure analogous to general procedure P: 1H NMR (400 MHz, CD$_3$OD) δ 7.64 (d, J=7.2 Hz, 1H), 7.53 (d, J=7.7 Hz, 1H), 7.41 (m, 2H), 7.24 (ovlp m, 3H), 7.17 (ovlp m, 2H), 7.10 (m, 2H), 6.83 (d, J=6.6 Hz, 2H), 5.21 (s, 2H), 3.29 (m, 4H), 3.21 (ovlp m, 4H), 2.12 (s, 6H). MS (ESI) (M+H$^+$) m/z=583.20. LCMS Ret time (UV 214/254): 1.795 min.

Example 184: 6-chloro-4-(2-((2-chlorophenyl)ethynyl)-6-methylphenyl)-1-(4-fluoro-3,5-dimethylbenzyl)-2-(piperazin-1-yl)-1H-benzo[d]imidazole trifluoroacetate

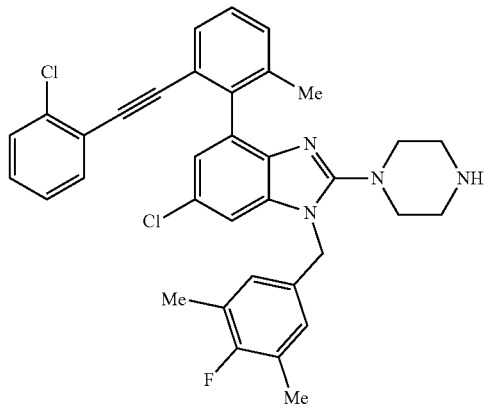 [SMILES: Cc1cc(Cn2c(N3CCNCC3)nc3c(-c4c(C)cccc4C#Cc4ccccc4Cl)cc(Cl)cc32)cc(C)c1F]

The title compound was obtained according to a procedure analogous to general procedure P: $^1$H NMR (400 MHz, CD$_3$OD) δ 7.47 (t, J=4.5 Hz, 2H), 7.32 (d, J=4.6 Hz, 2H), 7.30 (s, 1H), 7.20 (ovlp, 2H), 7.13 (m, 3H), 6.83 (d, J=6.5 Hz, 2H), 5.26 (s, 2H), 3.40 (br s, 4H), 3.22 (br s, 4H), 2.09 (s, 6H), 2.05 (s, 3H). MS (ESI) (M+H$^+$) m/z=597.20. LCMS Ret time (UV 214/254): 1.812 min.

Example 185: 6-chloro-1-(4-fluoro-3,5-dimethylbenzyl)-2-(piperazin-1-yl)-4-(2-(o-tolylethynyl)phenyl)-1H-benzo[d]imidazole trifluoroacetate

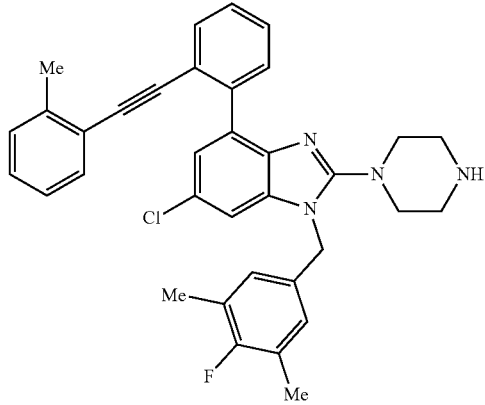 [SMILES: Cc1ccccc1C#Cc1ccccc1-c1cc(Cl)cc2c1nc(N1CCNCC1)n2Cc1cc(C)c(F)c(C)c1]

The title compound was obtained according to a procedure analogous to general procedure P: MS (ESI) (M+H$^+$) m/z=563.20. LCMS Ret time (UV 214/254): 1.803 min.

Example 186: 6-chloro-1-(4-fluoro-3,5-dimethylbenzyl)-4-(2-((2-methoxyphenyl)ethynyl)phenyl)-2-(piperazin-1-yl)-1H-benzo[d]imidazole trifluoroacetate

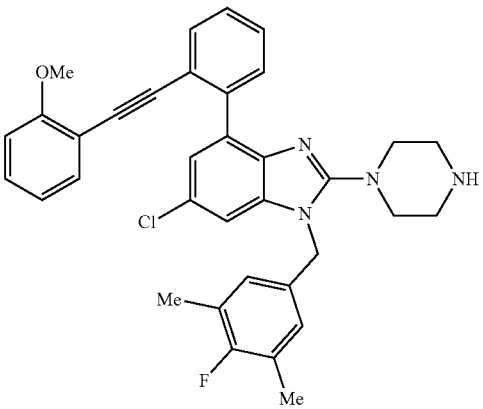 [SMILES: COc1ccccc1C#Cc1ccccc1-c1cc(Cl)cc2c1nc(N1CCNCC1)n2Cc1cc(C)c(F)c(C)c1]

The title compound was obtained according to a procedure analogous to general procedure P: MS (ESI) (M+H$^+$) m/z=579.30. LCMS Ret time (UV 214/254): 1.714 min.

Example 187: 6-chloro-1-(4-fluoro-3,5-dimethylbenzyl)-4-(4-methylpiperazin-1-yl)-2-(piperazin-1-yl)-1H-benzo[d]imidazole trifluoroacetate

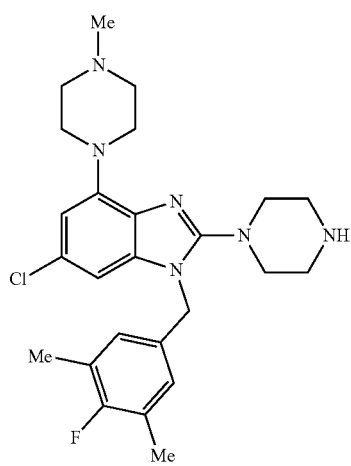 [SMILES: Cc1cc(Cn2c(N3CCNCC3)nc3c(N4CCN(C)CC4)cc(Cl)cc32)cc(C)c1F]

The tert-butyl 4-(4-bromo-6-chloro-1-(4-fluoro-3,5-dimethylbenzyl)-1H-benzo[d]imidazol-2-yl)piperazine-1-carboxylate (40 mg, 0.0727 mmol), prepared by a procedure analogous to the procedure used to prepare Example 118, Step E, Pd(OAc)$_2$ (2.0 mg, 0.00727 mmol, 0.1 eq), RuPhos (5 mg, 0.0.11 mmol, 0.15 eq), K$_3$PO$_4$ (30 mg, 0.145 mmol, 2 eq), and 4-Me-piperazine (25 □L, 0.220 mmol, 3.0 eq) were added to a sealed tube. The tube was purged 3× with argon DME (5 mL) was added to the tube, which was then sealed. The reaction was heated at 90° C. and monitored by LCMS. Upon conversion of the starting material by LCMS, the reaction was cooled to room temperature and was quenched with water. The quenched reaction was extracted with DCM and filtered through a phase separator. The organic layer was concentrated to the crude mixture. The crude mixture was purified using reverse phase HPLC. TFA (~0.5 mL) was added to the fractions to remove the BOC group during evaporation. The resulting solid was dissolved in DCM and washed with sodium bicarbonate and then concentrated to afford the title compound as a white solid (12.0 mg, 35% yield). $^1$H NMR (400 MHz, CD$_3$OD) δ 6.92 (d, J=1.6 Hz 1H), 6.86 (s, 1H), 6.84 (s, 1H), 6.73 (d, J=1.6 Hz 1H), 5.26 (s, 2H), 4.42 (d, J=13.6 Hz, 2H), 3.66 (d, J=13.6 Hz, 2H), 3.49 (t, J=4.6 Hz, 4H), 3.41 (t, J=4.6 Hz, 4H), 3.21 (m, 2H), 3.02 (s, 3H) 2.21 (s, 6H). MS (ESI) (M+H$^+$) m/z=471.30. LCMS Ret time (UV 214/254): 1.77 min.

Example 188: 1-(1-(4-fluoro-3,5-dimethylbenzyl)-6-methyl-2-(piperazin-1-yl)-1H-benzo[d]imidazol-4-yl)piperidin-4-amine trifluoroacetate

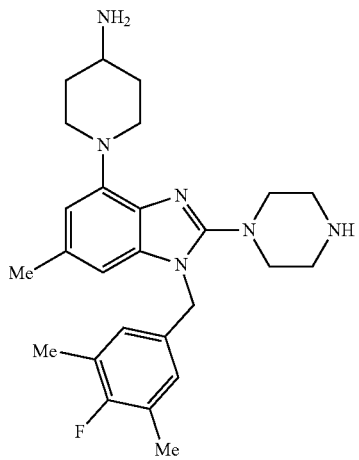 [SMILES: Cc1cc(N2CCC(N)CC2)c2nc(N3CCNCC3)n(Cc3cc(C)c(F)c(C)c3)c2c1]

The title compound was obtained according to a procedure analogous to general procedure Q starting from tert-butyl 4-(4-bromo-1-(4-fluoro-3,5-dimethylbenzyl)-6-methyl-1H-benzo[d]imidazol-2-yl)piperazine-1-carboxylate, which was prepared by a procedure analogous to the procedure used to prepare Example 118, Step A: $^1$H NMR (400 MHz, CD$_3$OD) δ 6.85 (s, 1H), 6.82 (s, 2H), 6.80 (s, 1H), 5.23 (s, 2H), 3.88 (s, 2H), 3.71 (d, J=12.6 Hz, 2H), 3.54 (t, J=5.0 Hz, 4H), 3.49 (s, 1H), 3.31 (t, J=5.0 Hz, 4H), 3.21 (t, J=1.6 Hz, 2H), 3.17 (m, 4H), 2.30 (s, 3H), 2.10 (s, 6H). MS (ESI) (M+H$^+$) m/z=451.00. LCMS Ret time (UV 214/254): 1.072 min.

Example 189: (1-(1-(4-fluoro-3,5-dimethylbenzyl)-6-methyl-2-(piperazin-1-yl)-1H-benzo[d]imidazol-4-yl)pyrrolidin-3-yl)methanamine trifluoroacetate

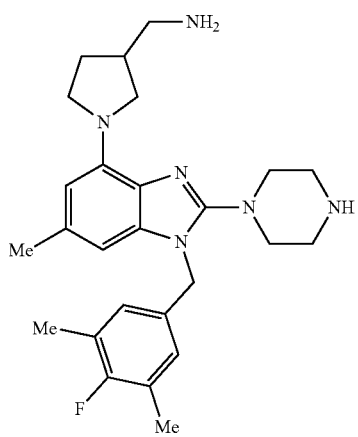 [SMILES: Cc1cc(N2CCC(CN)C2)c2nc(N3CCNCC3)n(Cc3cc(C)c(F)c(C)c3)c2c1]

The title compound was obtained according to a procedure analogous to general procedure Q starting from tert-butyl 4-(4-bromo-1-(4-fluoro-3,5-dimethylbenzyl)-6-methyl-1H-benzo[d]imidazol-2-yl)piperazine-1-carboxylate, which was prepared by a procedure analogous to the procedure used to prepare Example 118, Step A: MS (ESI) (M+H$^+$) m/z=451.00. LCMS Ret time (UV 214/254): 1.100 min.

Example 190: 1-(4-fluoro-3,5-dimethylbenzyl)-6-methyl-2,4-di(piperazin-1-yl)-1H-benzo[d]imidazole trifluoroacetate

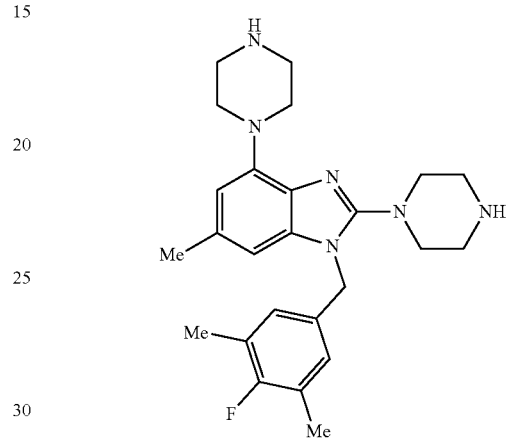

The title compound was obtained according to a procedure analogous to general procedure Q starting from tert-butyl 4-(4-bromo-1-(4-fluoro-3,5-dimethylbenzyl)-6-methyl-1H-benzo[d]imidazol-2-yl)piperazine-1-carboxylate, which was prepared by a procedure analogous to the procedure used to prepare Example 118, Step A: MS (ESI) (M+H$^+$) m/z=437.10. LCMS Ret time (UV 214/254): 1.073 min.

Example 191: N$^1$-(1-(4-fluoro-3,5-dimethylbenzyl)-6-methyl-2-(piperazin-1-yl)-1H-benzo[d]imidazol-4-yl)-N$^1$,N$^2$,N$^2$-trimethylethane-1,2-diamine trifluoroacetate

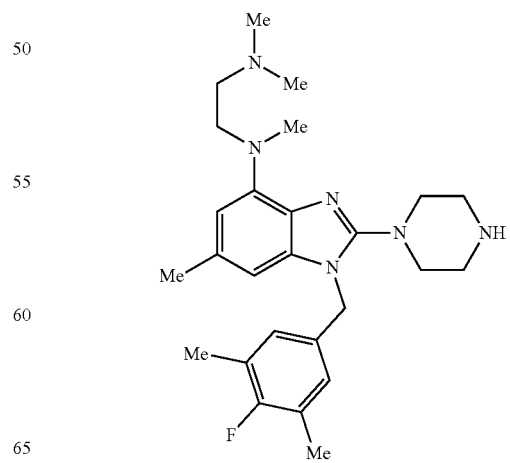

The title compound was obtained according to a procedure analogous to general procedure Q starting from tert-butyl 4-(4-bromo-1-(4-fluoro-3,5-dimethylbenzyl)-6-methyl-1H-benzo[d]imidazol-2-yl)piperazine-1-carboxylate, which was prepared by a procedure analogous to the procedure used to prepare Example 118, Step A: $^1$H NMR (400 MHz, CD$_3$OD) δ 6.89 (s, 1H), 6.88 (s, 1H), 6.74 (s, 1H), 6.69 (s, 1H), 5.28 (s, 2H), 3.81 (t, J=5.7 Hz, 2H), 3.52 (t, J=5.7 Hz, 2H), 3.45 (ovlp, 8H), 3.09 (s, 6H), 2.96 (s, 3H), 2.39 (s, 3H) 2.21 (s, 6H). MS (ESI) (M+H$^+$) m/z=453.00. LCMS Ret time (UV 214/254): 1.174 min.

Example 192: N$^1$-(1-(4-fluoro-3,5-dimethylbenzyl)-6-methyl-2-(piperazin-1-yl)-1H-benzo[d]imidazol-4-yl)-N$^1$,N$^2$-dimethylethane-1,2-diamine trifluoroacetate

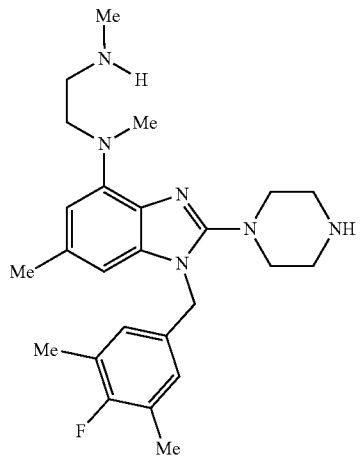 [SMILES: CNCCN(C)c1cc(C)cc2c1nc(N1CCNCC1)n2Cc1cc(C)c(F)c(C)c1]

The title compound was obtained according to a procedure analogous to general procedure Q starting from tert-butyl 4-(4-bromo-1-(4-fluoro-3,5-dimethylbenzyl)-6-methyl-1H-benzo[d]imidazol-2-yl)piperazine-1-carboxylate, which was prepared by a procedure analogous to the procedure used to prepare Example 118, Step A: MS (ESI) (M+H$^+$) m/z=439.00. LCMS Ret time (UV 214/254): 1.185 min.

Example 193: 1-(4-fluoro-3,5-dimethylbenzyl)-6-methyl-N-(2-morpholinoethyl)-2-(piperazin-1-yl)-1H-benzo[d]imidazol-4-amine trifluoroacetate

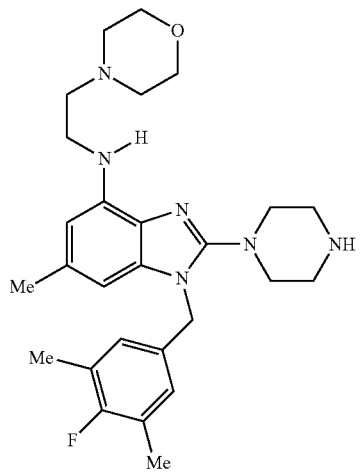 [SMILES: Cc1cc(NCCN2CCOCC2)c2nc(N3CCNCC3)n(Cc3cc(C)c(F)c(C)c3)c2c1]

The title compound was obtained according to a procedure analogous to general procedure Q starting from tert-butyl 4-(4-bromo-1-(4-fluoro-3,5-dimethylbenzyl)-6-methyl-1H-benzo[d]imidazol-2-yl)piperazine-1-carboxylate, which was prepared by a procedure analogous to the procedure used to prepare Example 118, Step A: MS (ESI) (M+H$^+$) m/z=481.00. LCMS Ret time (UV 214/254): 1.089 min.

Example 194: 1-(4-fluoro-3,5-dimethylbenzyl)-4-(4-isopropylpiperazin-1-yl)-6-methyl-2-(piperazin-1-yl)-1H-benzo[d]imidazole trifluoroacetate

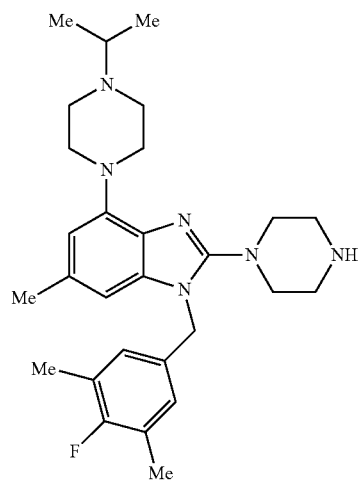 [SMILES: Cc1cc(N2CCN(C(C)C)CC2)c2nc(N3CCNCC3)n(Cc3cc(C)c(F)c(C)c3)c2c1]

The title compound was obtained according to a procedure analogous to general procedure Q starting from tert-butyl 4-(4-bromo-1-(4-fluoro-3,5-dimethylbenzyl)-6-methyl-1H-benzo[d]imidazol-2-yl)piperazine-1-carboxylate, which was prepared by a procedure analogous to the procedure used to prepare Example 118, Step A: MS (ESI) (M+H$^+$) m/z=479.40. LCMS Ret time (UV 214/254): 1.098 min.

Example 195: 1-(4-fluoro-3,5-dimethylbenzyl)-4-(4-(2-methoxyethyl)piperazin-1-yl)-6-methyl-2-(piperazin-1-yl)-1H-benzo[d]imidazole trifluoroacetate

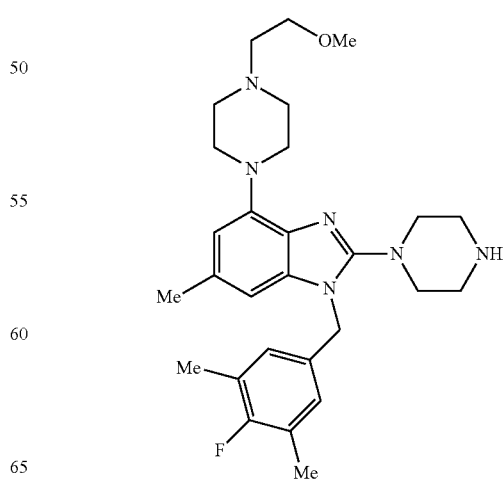

The title compound was obtained according to a procedure analogous to general procedure Q starting from tert-butyl 4-(4-bromo-1-(4-fluoro-3,5-dimethylbenzyl)-6-methyl-1H-benzo[d]imidazol-2-yl)piperazine-1-carboxylate, which was prepared by a procedure analogous to the procedure used to prepare Example 118, Step A: MS (ESI) (M+H$^+$) m z=495.40. LCMS Ret time (UV 214/254): 1.088 mm.

Example 196: N$^1$-(1-(4-fluoro-3,5-dimethylbenzyl)-6-methyl-2-(piperazin-1-yl)-1H-benzo[d]imidazol-4-yl)-N$^4$,N$^4$-dimethylbutane-1,4-diamine trifluoroacetate

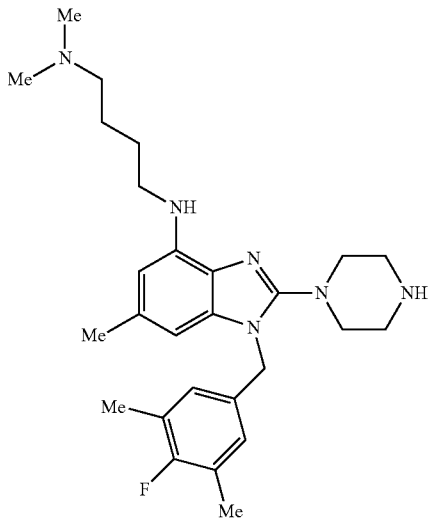 [SMILES: Cc1cc(NCCCCN(C)C)c2nc(N3CCNCC3)n(Cc3cc(C)c(F)c(C)c3)c2c1]

The title compound was obtained according to a procedure analogous to general procedure Q starting from tert-butyl 4-(4-bromo-1-(4-fluoro-3,5-dimethylbenzyl)-6-methyl-1H-benzo[d]imidazol-2-yl)piperazine-1-carboxylate, which was prepared by a procedure analogous to the procedure used to prepare Example 118, Step A: $^1$H NMR (400 MHz, CD$_3$OD) δ 6.96 (s, 1H), 6.94 (s, 1H), 6.59 (s, 1H), 6.57 (s, 1H), 5.36 (s, 2H), 3.71 (t, J=5.2 Hz, 4H), 3.42 (ovlp, 6H), 3.21 (t, J=5.2 Hz, 4H), 2.91 (s, 6H), 2.38 (s, 3H), 2.23 (s, 6H) 1.91 (m, 3H), 1.82 (m, 3H). MS (ESI) (M+H$^+$) m/z=467.10. LCMS Ret time (UV 214/254): 1.100 min.

Example 197: N$^1$-(1-(4-fluoro-3,5-dimethylbenzyl)-6-methyl-2-(piperazin-1-yl)-1H-benzo[d]imidazol-4-yl)-N$^3$,N$^3$-dimethylpropane-1,3-diamine trifluoroacetate

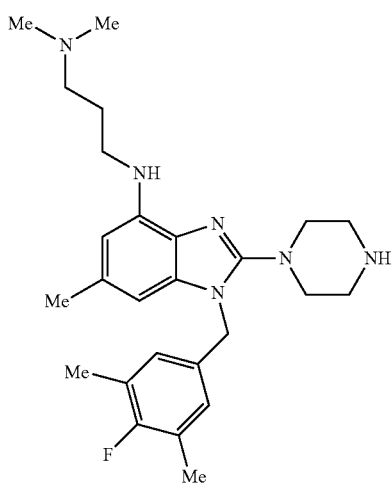 [SMILES: Cc1cc(NCCCN(C)C)c2nc(N3CCNCC3)n(Cc3cc(C)c(F)c(C)c3)c2c1]

The title compound was obtained according to a procedure analogous to general procedure Q starting from tert-butyl 4-(4-bromo-1-(4-fluoro-3,5-dimethylbenzyl)-6-methyl-1H-benzo[d]imidazol-2-yl)piperazine-1-carboxylate, which was prepared by a procedure analogous to the procedure used to prepare Example 118, Step A: MS (ESI) (M+H$^+$) m/z=453.00. LCMS Ret time (UV 214/254): 1.117 min.

Example 198: (S)-1-(4-fluoro-3,5-dimethylbenzyl)-6-methyl-2-(piperazin-1-yl)-N-(pyrrolidin-3-ylmethyl)-1H-benzo[d]imidazol-4-amine trifluoroacetate

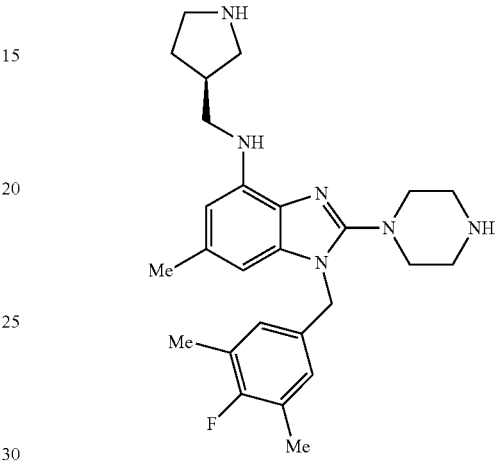

The title compound was obtained according to a procedure analogous to general procedure Q starting from tert-butyl 4-(4-bromo-1-(4-fluoro-3,5-dimethylbenzyl)-6-methyl-1H-benzo[d]imidazol-2-yl)piperazine-1-carboxylate, which was prepared by a procedure analogous to the procedure used to prepare Example 124, Step A: $^1$H NMR (400 MHz, CD$_3$OD) δ 6.96 (s, 1H), 6.94 (s, 1H), 6.62 (s, 1H), 6.57 (s, 1H), 5.37 (s, 2H), 3.98 (m, 1H), 3.76 (t, J=5.2 Hz, 4H), 3.65 (m, 2H), 3.45 (t, J=5.2 Hz, 4H), 3.39 (m, 2H), 2.39 (s, 3H), 2.31 (m, 2H), 2.15 (m, 2H). MS (ESI) (M+H$^+$) m/z=451.00. LCMS Ret time (UV 214/254): 1.083 min.

Example 199: 2-((2-((1-(4-fluoro-3,5-dimethylbenzyl)-6-methyl-2-(piperazin-1-yl)-1H-benzo[d]imidazol-4-yl)oxy)ethyl)amino)ethan-1-ol

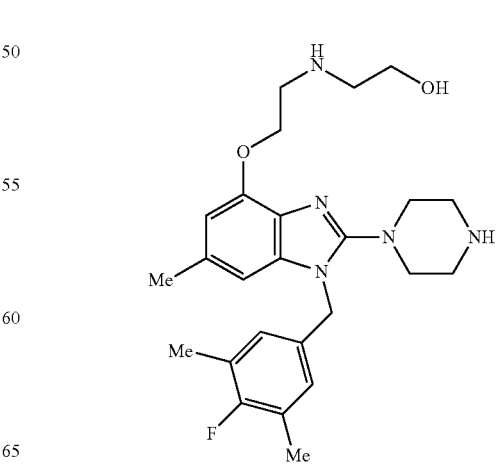

tert-Butyl 4-(4-bromo-1-(4-fluoro-3,5-dimethylbenzyl)-6-methyl-1H-benzo[d]imidazol-2-yl)piperazine-1-carboxylate (100 mg, 0.19 mmol, 1.00 eq), 1-aziridineethanol (164 mg, 1.88 mmol, 10.00 eq), potassium phosphate tribasic (80 mg, 0.38 mmol, 2.00 eq), copper(I) iodide (~2 mg, 0.01 mmol, 0.05 eq), and 8-hydroxyquinoline (~3 mg, 0.02 mmol, 0.10 eq) were weighed into a vial. The vial was sealed, evacuated, and refilled with argon. The evacuation/refill process was repeated two additional times. The vial was then heated to 110° C. and the progress of the reaction was monitored by LCMS. When the starting material had been completely consumed, the reaction mixture was allowed to cool to room temperature. $CH_2Cl_2$ (5 mL) was added and solid materials were removed by filtration. To the filtrate thus obtained was added trifluoroacetic acid (1 mL). The resulting solution was stirred at room temperature and the progress of the reaction was monitored by LCMS. When the intermediate tert-butyl 4-(4-(2-(aziridin-1-yl)ethoxy)-1-(4-fluoro-3,5-dimethylbenzyl)-6-methyl-1H-benzo[d]imidazol-2-yl)piperazine-1-carboxylate had been completely consumed, the reaction mixture was concentrated in vacuo. The residual oil was purified by reverse phase preparative HPLC. The title compound was obtained as its corresponding trifluoroacetate salt as a white solid (41 mg, 38% yield). $^1$H NMR (400 MHz, $CD_3OD$): δ 6.85 (s, 1H), 6.83 (s, 1H), 6.76 (s, 1H), 6.70 (s, 1H), 5.27 (s, 2H), 4.45 (t, J=4.8 Hz, 2H) 3.89 (m, 2H), 3.60 (t, J=5.1 Hz, 2H), 3.46 (m, 4H), 3.41 (m, 4H), 3.28 (m, 2H) 2.40 (s, 3H), 2.19 (s, 3H), 2.18 (s, 3H). MS (ESI) (M+H$^+$) m/z=456.30. LCMS Ret time (UV 214/254): 1.081 min.

Example 200: (S)-1-(4-fluoro-3,5-dimethylbenzyl)-6-methyl-2-(piperazin-1-yl)-4-(pyrrolidin-3-yloxy)-1H-benzo[d]imidazole

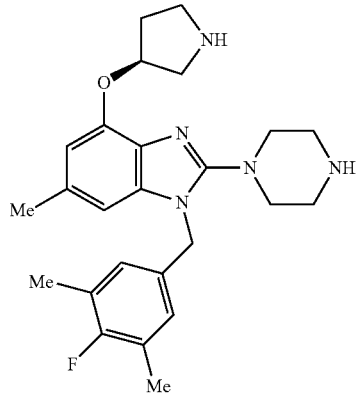 [SMILES: Cc1cc(O[C@H]2CCNC2)c2nc(N3CCNCC3)n(Cc3cc(C)c(F)c(C)c3)c2c1]

The title compound was obtained as its corresponding trifluoroacetate salt in 54% yield using general procedure AF. $^1$H NMR (400 MHz, $CD_3OD$) δ 6.94 (s, 1H), 6.92 (s, 1H), 6.86 (s, 1H), 6.82 (s, 1H), 5.41 (m, 1H), 5.29 (s, 2H), 3.98 (t, J=5.8 Hz, 2H), 3.58 (2m ovlp, 4H), 3.31 (m, 2H), 2.41 (s, 3H), 2.39 (m, 2H), 2.20 (2s ovlp, 6H). MS (ESI) (M+H$^+$) m/z=412.30. LCMS Ret time (UV 214/254): 1.015 min.

Example 201: 1-(4-fluoro-3,5-dimethylbenzyl)-6-methyl-4-(2-(4-methylpiperazin-1-yl)ethoxy)-2-(piperazin-1-yl)-1H-benzo[d]imidazole

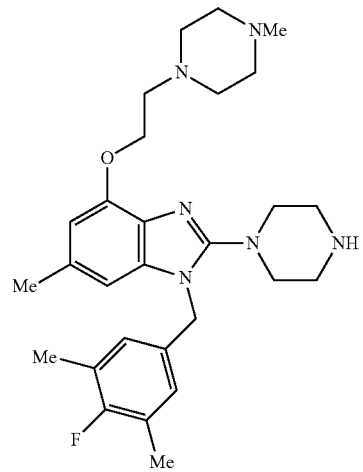 [SMILES: Cc1cc(OCCN2CCN(C)CC2)c2nc(N3CCNCC3)n(Cc3cc(C)c(F)c(C)c3)c2c1]

The title compound was obtained according to a procedure analogous to general procedure R: $^1$H NMR (400 MHz, $CD_3OD$) δ 6.90 (s, 1H), 6.88 (s, 1H), 6.80 (s, 1H), 6.78 (s, 1H), 5.32 (s, 2H), 4.44 (t, J=5.07 Hz, 2H), 3.56 (bm, 4H), 3.41 (m, 4H), 3.35 (bm, 4H), 3.28 (bm, 2H), 3.21 (bm, 4H), 2.88 (s, 3H), 2.41 (s, 3H), 2.20 (2s ovlp, 6H). MS (ESI) (M+H$^+$) m/z=495.40. LCMS Ret time (UV 214/254): 1.053 min.

Example 202: 1-(4-fluoro-3,5-dimethylbenzyl)-6-methyl-2-(piperazin-1-yl)-4-(piperidin-4-ylmethoxy)-1H-benzo[d]imidazole

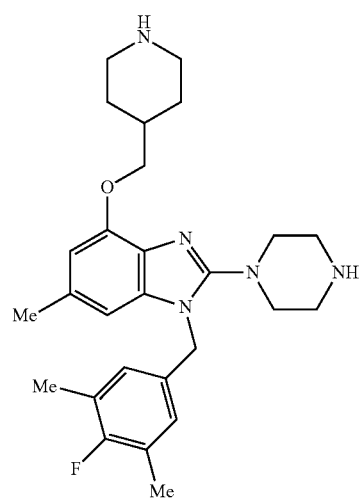 [SMILES: Cc1cc(OCC2CCNCC2)c2nc(N3CCNCC3)n(Cc3cc(C)c(F)c(C)c3)c2c1]

The title compound was obtained according to a procedure analogous to general procedure R: $^1$H NMR (400 MHz, $CD_3OD$) δ 6.91 (s, 1H), 6.89 (s, 1H), 6.80 (s, 1H), 6.76 (s, 1H), 5.33 (s, 2H), 4.11 (d, J=6.2 Hz, 2H), 3.60 (bm, 4H), 3.49 (bm, 1H), 3.46 (bm, 1H), 3.40 (bm, 4H), 3.08 (td, J=12.9, 2.8 Hz, 2H), 2.41 (s, 3H), 2.28 (m, 1H), 2.23 (m, Example 203: 2-((1-(4-fluoro-3,5-dimethylbenzyl)-6-methyl-2-(piperazin-1-yl)-1H-benzo[d]imidazol-4-yl)oxy)-N,N-dimethylethan-1-amine

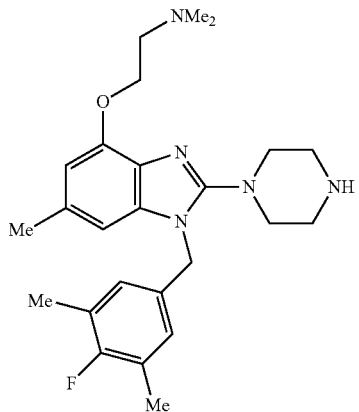 [SMILES: Cc1cc(OCCN(C)C)c2nc(N3CCNCC3)n(Cc3cc(C)c(F)c(C)c3)c2c1]

The title compound was obtained according to a procedure analogous to general procedure R: $^1$H NMR (400 MHz, CD$_3$OD) δ 6.87 (s, 1H), 6.86 (s, 1H), 6.79 (s, 1H), 6.76 (s, 1H), 5.29 (s, 2H), 4.51 (bm, 2H), 3.67 (t, J=5.2 Hz, 2H), 3.50 (br m, 4H), 3.41 (br m, 4H), 3.04 (s, 6H), 2.41 (s, 3H), 2.19 (2s ovlp, 6H). MS (ESI) (M+H$^+$) m/z=440.30. LCMS Ret time (UV 214/254): 1.100 min.

Example 204: 1-(4-fluoro-3,5-dimethylbenzyl)-6-methyl-2-(piperazin-1-yl)-4-((tetrahydrofuran-3-yl)oxy)-1H-benzo[d]imidazole

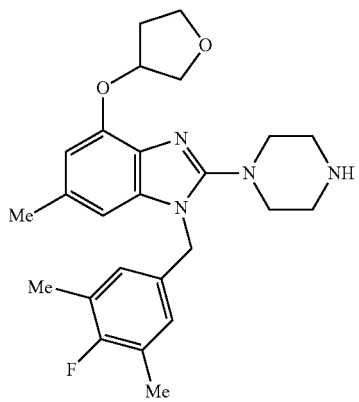 [SMILES: Cc1cc(OC2CCOC2)c2nc(N3CCNCC3)n(Cc3cc(C)c(F)c(C)c3)c2c1]

tert-Butyl 4-(4-bromo-1-(4-fluoro-3,5-dimethylbenzyl)-6-methyl-1H-benzo[d]imidazol-2-yl)piperazine-1-carboxylate (100 mg, 0.19 mmol, 1.00 eq), potassium hydroxide (21 mg, 0.38 mmol, 2.00 eq), tris(dibenzylideneacetone)dipalladium(0) (7 mg, 0.015 mmol Pd, 0.08 eq Pd), and 2-di-tert-butylphosphino-3,4,5,6-tetramethyl-2',4',6'-triisopropyl-1,1'-biphenyl (Me$_4$-t-BuXPhos) (14 mg, 0.030 mmol, 0.16 eq) were weighed into a vial. The vial was sealed, evacuated, and refilled with argon. The evacuation/refill process was repeated two additional times. A solution of 1,4-dioxane/water (1:1 v/v) (0.4 mL)—which had been degassed using three evacuation/refill cycles—was added. The vial was then heated to 90° C. and the progress of the reaction was monitored by LCMS. When the starting material had been completely consumed, the reaction mixture was allowed to cool to room temperature. Potassium hydroxide (21 mg, 0.38 mmol, 2.00 eq), hexadecyltrimethylammonium bromide (7 mg, 0.02 mmol), and 3-bromotetrahydrofuran (57 mg, 0.38 mmol) were added. The vial was then heated to 100° C. and the progress of the reaction was monitored by LCMS. When the intermediate tert-butyl 4-(1-(4-fluoro-3,5-dimethylbenzyl)-4-hydroxy-6-methyl-1H-benzo[d]imidazol-2-yl)piperazine-1-carboxylate had been completely consumed, the reaction mixture was allowed to cool to room temperature. CH$_2$Cl$_2$ (5 mL) and saturated aqueous NH$_4$Cl (5 mL) were added. The resulting biphasic mixture was stirred for ten min before being passed through a phase separator. To the filtrate thus obtained was added trifluoroacetic acid (1 mL). The resulting solution was stirred at room temperature and the progress of the reaction was monitored by LCMS. When the intermediate tert-butyl 4-(1-(4-fluoro-3,5-dimethylbenzyl)-6-methyl-4-((tetrahydrofuran-3-yl)oxy)-1H-benzo[d]imidazol-2-yl)piperazine-1-carboxylate had been completely consumed, the reaction mixture was concentrated in vacuo. The residual oil was purified by reverse phase preparative HPLC. The title compound was obtained as a white solid as its corresponding trifluoroacetate salt (30 mg, 29% yield). $^1$H NMR (400 MHz, CD$_3$OD) δ 6.93 (s, 1H), 6.92 (s, 1H), 6.78 (2s ovlp, 2H), 5.34 (s, 2H), 5.29 (m, 1H), 4.05 (m, 3H), 3.91 (td, J=8.3, 4.6 Hz, 1H), 3.64 (m, 4H), 3.41 (m, 4H), 2.41 (s, 3H), 2.37 (m, 1H), 2.24 (m, 1H), 2.21 (2s ovlp, 6H). MS (ESI) (M+H$^+$) m/z=439.30. LCMS Ret time (UV 214/254): 1.188 min.

Example 205: 1-(4-fluoro-3-methylbenzyl)-4-((1-methylpiperidin-4-yl)oxy)-2-(piperazin-1-yl)-1H-benzo[d]imidazole

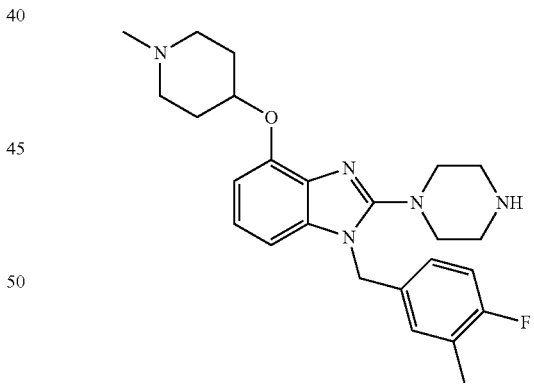

Step A: To a stirred, cooled (0° C.) solution of DMF (75 mL) was added sodium hydride (0.45 g, 18.9 mmol). The ice-bath was removed from the resulting white slurry and benzyl alcohol (1.70 mL, 16.5 mmol) was added dropwise. The mixture was stirred 15 min, then the 1,3-difluoro-2-nitrobenzene (1.66 mL, 15.71 mmol) was added in one portion. The reaction was stirred about 90 min. The reaction was diluted with EtOAc and water. The aqueous layer was separated and extracted with EtOAc (2×). The combined organic layers were washed with water (3×), brine (2×), dried over Na$_2$SO$_4$, concentrated and the residue was chromatographed on silica gel (120 g) eluting with a 0-to-20%

EtOAc/hexane gradient, to give 1-(benzyloxy)-3-fluoro-2-nitrobenzene as a yellow oil, 2.87 g (74%). $^1$H NMR (400 MHz, DMSO-d$_6$): δ 7.58 (m, 1H), 7.32 (m, 5H), 7.28 (d, J=8.7, Hz, 1H), 7.11 (m, 1H), 5.32 (s, 2H).

Step B: The 1-(benzyloxy)-3-fluoro-2-nitrobenzene (1.56 g, 6.3 mmol) was stirred in DMSO (13 mL) under argon. The DIEA (1.37 mL, 7.9 mmol) and 4-fluoro-3-methylbenzylamine (0.91 mL, 6.9 mmol) were added. The reaction was heated to 60° C. and stirred for 3 hrs. LC/MS indicates remaining SM so the reaction was stirred overnight at 65° C. Still SM is present, so an additional 0.2 mL of benzylamine was added and the reaction stirred at 75° C. for 2 hrs, then heated to 90° C. and stirred for 6 hrs, cooled to 60° C. and stirred overnight. The reaction was quenched with water, then, extracted with EtOAc (3×). The combined organic layers were washed with water (2×), brine (2×), dried over Na$_2$SO$_4$ and concentrated under vacuum. The residue was chromatographed on silica gel (120 g) eluting with a 0-to-10% EtOAc/hexane gradient to give 3-(benzyloxy)-N-(4-fluoro-3-methylbenzyl)-2-nitroaniline, 2.18 g (94%). $^1$H NMR (400 MHz, DMSO-d$_6$): δ 7.29 (m, 6H), 7.20 (m, 1H), 7.11 (m, 2H), 7.03 (m, 1H), 6.73 (t, J=6.0, Hz, 1H), 6.45 (d, J=7.9, Hz, 1H), 6.28 (d, J=8.3, Hz, 1H), 5.15 (s, 2H), 4.30 (d, J=6.0, Hz, 2H), 2.18 (s, 3H).

Step C: The 3-(benzyloxy)-N-(4-fluoro-3-methylbenzyl)-2-nitroaniline (2.18 g, 5.9 mmol) was stirred in 1:1 MeOH/THF (120 mL). Rainey nickel (633 mg, 0.23 mmol) was added. The flask was purged with argon/vacuum (3×), then H$_2$/vacuum (3×). Next, H$_2$ was applied at 1 atm (balloon) for about 45 min. LC/MS indicates no remaining SM. The reaction was diluted with MeOH/DCM. The mixture was allowed to settle, the solvent was poured through a plug of celite, washing with MeOH/DCM. The filtrate was concentrated and dried in a vacuum oven at 50° C. to give crude 3-(benzyloxy)-N$^1$-(4-fluoro-3-methylbenzyl)benzene-1,2-diamine as a dark solid, 1.86 g (93%). MS (ESI) (M+H$^+$) m/z=337. LCMS Ret time (UV 215/254): 1.05 min.

Step D: The crude aniline (1.85 g, 5.5 mmol) from Step C was stirred in DMF (22 mL) under argon. Carbodiimidazole (CDI) (2.23 g, 13.8 mmol) was added, followed by DMAP (67 mg, 0.55 mmol). The reaction was heated to 85° C. and stirred 30 min. LC/MS indicates the reaction is done. The reaction was cooled to rt and poured into ice/water (220 mL). The ice was allowed to melt, and the resulting slurry was poured through filter paper, washing the tan solid with ice cold water. The solid was dried in a vacuum oven at 50° C. to give crude 4-(benzyloxy)-1-(4-fluoro-3-methylbenzyl)-1,3-dihydro-2H-benzo[d]imidazol-2-one as a light tan solid, 1.92 g (96%). MS (ESI) (M+H$^+$) m/z=363. LCMS Ret time (UV 215/254): 1.20 min.

Step E: The 4-(benzyloxy)-1-(4-fluoro-3-methylbenzyl)-1,3-dihydro-2H-benzo[d]-imidazol-2-one (1.5 g, 4.14 mmol) was stirred in POCl$_3$ (20 mL) at reflux for 5 hrs. The excess POCl$_3$ was removed under vacuum. The flask containing the residue was placed in an ice-bath and aqueous (sat) NaHCO$_3$ was added slowly with ice and EtOAc, until the aqueous layer was neutral. The aqueous layer was then separated and extracted with EtOAc (3×). The combined organics were washed with brine, dried over Na$_2$SO$_4$, and concentrated under vacuum to give crude 4-(benzyloxy)-2-chloro-1-(4-fluoro-3-methylbenzyl)-1H-benzo[d]imidazole as a dark oil, 1.57 g (99%). MS (ESI) (M+H$^+$) m/z=381. LCMS Ret time (UV 215/254): 1.33 min.

Step F: The 4-(benzyloxy)-2-chloro-1-(4-fluoro-3-methylbenzyl)-1H-benzo[d]-imidazole (1.57 g, 4.12 mmol) and N-Boc-piperazine (3.1 g, 16.5 mmol) were stirred in NMP (4 mL). The DIEA (1.1 mL, 16.2 mmol) was added and the reaction was stirred at 110° C. for about 36 hrs, then cooled to RT and diluted with EtOAc and water. The aqueous layer was separated and extracted with EtOAc (3×). The combined organic layers were washed with water, brine, dried over Na$_2$SO$_4$, concentrated and the residue chromatographed on silica gel (80 g) eluting with a 0-to-35% EtOAc/hexane gradient to give tert-butyl 4-(4-(benzyloxy)-1-(4-fluoro-3-methylbenzyl)-1H-benzo[d]imidazol-2-yl)piperazine-1-carboxylate as a white solid, 1.97 g (90%). MS (ESI) (M+H$^+$) m/z=531. LCMS Ret time (UV 215/254): 1.12 min.

Step G: The tert-butyl 4-(4-(benzyloxy)-1-(4-fluoro-3-methylbenzyl)-1H-benzo[d]-imidazol-2-yl)piperazine-1-carboxylate (1.97 g, 3.71 mmol) and 10% Pd/C (400 mg, 0.37 mmol) were stirred in EtOH (65 mL, plus 35 mL THF to aid solubility). The reaction flask was purged with vacuum/argon (3×), then vacuum/H$_2$ (3×). The mixture was then stirred under H$_2$ at 1 atm (balloon) for 45 min. LC/MS indicates the reaction is done. The mixture was diluted with MeOH/DCM and poured through a pad of Celite, washing with MeOH/DCM. The eluent was concentrated under vacuum to give tert-butyl 4-(1-(4-fluoro-3-methylbenzyl)-4-hydroxy-1H-benzo[d]imidazol-2-yl)piperazine-1-carboxylate as grey crystals, 1.42 g (87%). MS (ESI) (M+H$^+$) m/z=441. LCMS Ret time (UV 215/254): 1.01 min.

Step H: The tert-butyl 4-(1-(4-fluoro-3-methylbenzyl)-4-hydroxy-1H-benzo[d]-imi-dazol-2-yl)piperazine-1-carboxylate (100 mg, 0.23 mmol) was stirred in THF (2.0 mL) with triphenylphosphine (77 mg, 0.30 mmol) and N-methyl-4-piperidinol (34 mg, 0.30 mmol) under argon at 0° C. The DIAD (60 mg, 0.30 mmol) was added dropwise and the reaction was allowed to warm slowly to RT and stirred overnight. The reaction mixture was concentrated and purified by acidic reverse-phase HPLC (ACN/water with 0.1% TFA, 15-to-50% gradient over 8 minute, then free-based to give the Boc-protected intermediate. The intermediate was stirred in 20% TFA/DCM (5 mL) for 30 min, concentrated under vacuum and the residue free-based to give the title compound, 1-(4-fluoro-3-methylbenzyl)-4-((1-methylpiperidin-4-yl)oxy)-2-(piperazin-1-yl)-1H-benzo[d]imidazole as a light tan solid, 40 mg (40%). $^1$H NMR (400 MHz, DMSO-d$_6$): δ 7.04 (m, 2H), 6.88 (m, 2H), 6.73 (d, J=7.8, Hz, 1H), 6.62 (d, J=7.8, Hz, 1H), 5.17 (s, 2H), 4.72 (m, 1H), 3.04 (m, 4H), 2.82 (m, 4H), 2.67 (m, 2H), 2.07 (m, 7H), 1.92 (m, 2H), 1.61 (m, 2H), 1.22 (br s, 1H). MS (ESI) (M+H$^+$) m/z=438. LCMS Ret time (UV 215/254): 0.73 min.

Example 206: 1-(4-fluoro-3-methylbenzyl)-2-(piperazin-1-yl)-4-(pyrrolidin-3-yloxy)-1H-benzo[d]imidazole

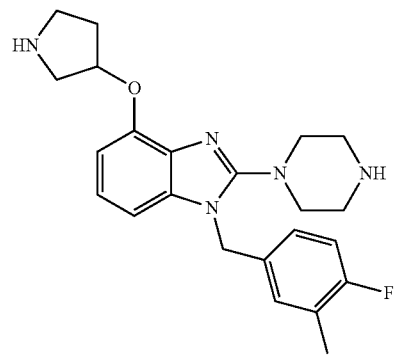 [SMILES: Cc1cc(Cn2c(N3CCNCC3)nc3c(OC4CCNC4)cccc32)ccc1F]

The title compound was obtained according to a procedure analogous to general procedure S: ¹H NMR (400 MHz, DMSO-d$_6$): δ 7.03 (m, 2H), 6.91 (m, 2H), 6.76 (d, J=7.8, Hz, 1H), 6.64 (d, J=8.0, Hz, 1H), 5.19 (s, 2H), 4.24 (t, J=6.1, Hz, 2H), 3.10 (m, 4H), 2.84 (m, 6H), 2.56 (m, 4H), 2.15 (s, 3H), 1.69 (m, 4H). MS (ESI) (M+H$^+$) m/z=410. LCMS Ret time (UV 215/254): 0.75 min.

Example 207: N$^1$-(1-(4-fluoro-3-methylbenzyl)-4-(2-(pyrrolidin-1-yl)ethoxy)-1H-benzo[d]imidazol-2-yl)ethane-1,2-diamine

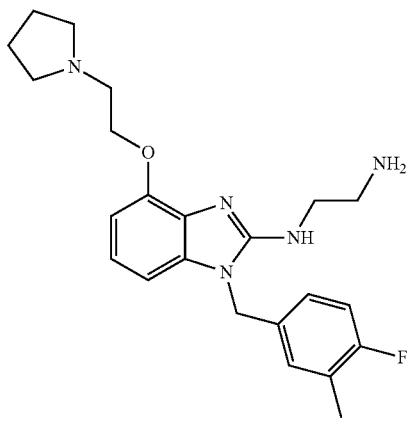 [SMILES: Cc1cc(Cn2c(NCCN)nc3c(OCCN4CCCC4)cccc32)ccc1F]

The title compound was obtained according to a procedure analogous to general procedure S: MS (ESI) (M+H$^+$) m/z=412. LCMS Ret time (UV 215/254): 0.73 min.

Example 208: 1-(4-fluoro-3-methylbenzyl)-2-(piperazin-1-yl)-4-(2-(pyrrolidin-1-yl)ethoxy)-1H-benzo[d]imidazole

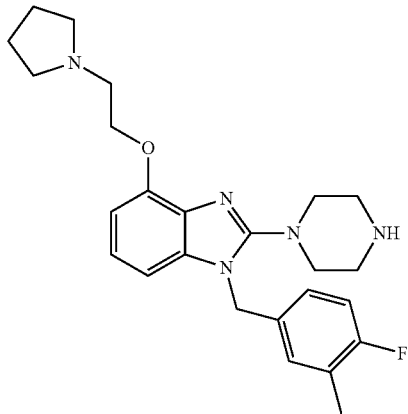 [SMILES: Cc1cc(Cn2c(N3CCNCC3)nc3c(OCCN4CCCC4)cccc32)ccc1F]

The title compound was obtained according to a procedure analogous to general procedure S: ¹H NMR (400 MHz, DMSO-d$_6$): δ 7.03 (m, 2H), 6.91 (m, 2H), 6.76 (d, J=7.8, Hz, 1H), 6.64 (d, J=8.0, Hz, 1H), 5.19 (s, 2H), 4.24 (t, J=6.1, Hz, 2H), 3.10 (m, 4H), 2.84 (m, 6H), 2.56 (m, 4H), 2.15 (s, 3H), 1.69 (m, 4H), 1.22 (br s, 1H). MS (ESI) (M+H$^+$) m/z=438. LCMS Ret time (UV 215/254): 0.78 min.

Example 209: 1-(4-fluoro-3-methylbenzyl)-4-(2-(4-methylpiperazin-1-yl)ethoxy)-2-(piperazin-1-yl)-1H-benzo[d]imidazole

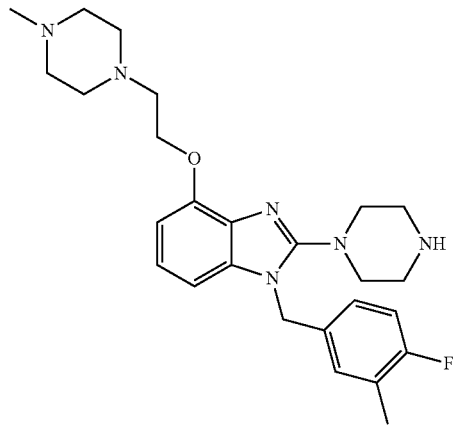 [SMILES: Cc1cc(Cn2c(N3CCNCC3)nc3c(OCCN4CCN(C)CC4)cccc32)ccc1F]

The title compound was obtained according to a procedure analogous to general procedure S: ¹H NMR (400 MHz, DMSO-d$_6$): δ 7.03 (m, 2H), 6.90 (m, 2H), 6.75 (d, J=7.9, Hz, 1H), 6.64 (d, J=7.9, Hz, 1H), 5.18 (s, 2H), 4.24 (t, J=6.0, Hz, 2H), 3.06 (m, 4H), 2.84 (m, 4H), 2.70 (t, J=6.0, Hz, 2H), 2.52 (m, 4H), 2.31 (m, 4H), 2.14 (m, 6H), 1.22 (br s, 1H). MS (ESI) (M+H$^+$) m/z=467. LCMS Ret time (UV 215/254): 0.73 min.

Example 210: 2-((1-(4-fluoro-3-methylbenzyl)-2-(piperazin-1-yl)-1H-benzo[d]imidazol-4-yl)oxy)-N,N-dimethylethan-1-amine

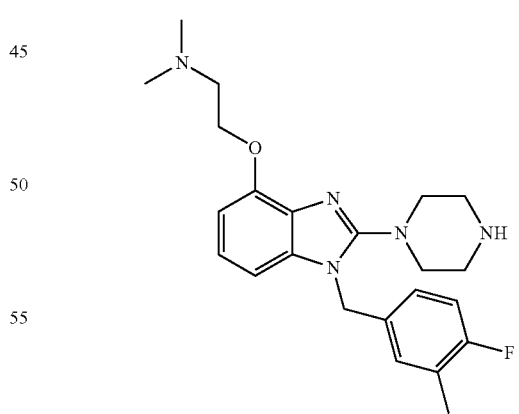

The title compound was obtained according to a procedure analogous to general procedure S: MS (ESI) (M+H$^+$) m/z=412. LCMS Ret time (UV 215/254): 0.76 min.

Example 211: 2-((1-(3-chloro-4-fluorobenzyl)-5,6-dimethyl-1H-benzo[d]imidazol-2-yl)sulfonyl)ethan-1-amine trifluoroacetate

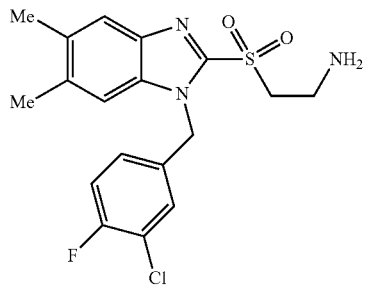 [SMILES: Cc1cc2nc(S(=O)(=O)CCN)n(Cc3ccc(F)c(Cl)c3)c2cc1C]

Step A: 2-chloro-1-(3-chloro-4-fluorobenzyl)-5,6-dimethyl-1H-benzo[d]imidazole (100 mg, 0.31, 1 eq), which was prepared by a procedure analogous to the procedure used to prepare Example 60, Step C was dissolved in methanol (1.0 mL) in a microwave tube. Thiourea (95 mg, 1.24 mmol, 4 eq) was added to the tube, which was then sealed and heated in oil bath at 65° C. for 18 hours. Upon conversion of the starting material by LCMS, the reaction was cooled to room temperature and the methanol was removed in vacuo. The crude residue was suspended in ethyl acetate and water and the organic layer was washed with 1M aqueous HCl. The organic layer was washed with a brine solution, dried over sodium sulfate, and concentrated to afford a white solid (95 mg recovered). The solid was used in the next step without any further purification.

Step B: The crude solid from Step A (50 mg, 0.156 mmol, 1 eq) was dissolved in DMF (1.6 mL) in a reaction vial. Cesium carbonate (61 mg, 0.187, 1.2 eq) was added to the vial, followed by tert-butyl (2-bromoethyl)carbamate (38 mg, 0.171, 1.1 eq). The reaction mixture was stirred at room temperature and monitored by LCMS. Upon conversion of the starting material by LCMS (90 min), the reaction was quenched with water and extracted with ethyl ether. The organic layer was washed with water, dried over sodium sulfate and concentrated in vacuo to provide a white solid. The solid was dissolved in methylene chloride (1.5 mL) and cooled to 0° C. in a reaction vial. To the reaction vial, was added m-CPBA (77% by weight, 65 mg, 0.30 mmol, 2 eq). The reaction was allowed to warm to room temperature. After three hours, the reaction had fully converted to the sulfone by LCMS. The reaction was quenched with sodium bisulfate and diluted with dichloromethane. The organic layer was passed through a phase separator and the organic layer was concentrated to afford a crude solid, which was purified by reverse-phase HPLC to afford the title compound as a white TFA salt (20 mg, 35% yield). $^1$H NMR (400 MHz, CD$_3$OD) δ 7.64 (s, 1H), 7.42 (d, J=7.0 Hz, 1H), 7.39 (s, 1H), 7.22 (ovlp, 2H), 5.82 (s, 2H), 4.08 (t, J=6.4 Hz, 2H), 3.62 (t, J=6.4 Hz, 2H), 2.42 (s, 6H). MS (ESI) (M+H$^+$) m/z=396.10. LCMS Ret time (UV 214/254): 1.317 min.

Example 212: 10-(3-chloro-4-fluorobenzyl)-2,3,4,10-tetrahydrobenzo[4,5]imidazo[1,2-a]pyrimidine

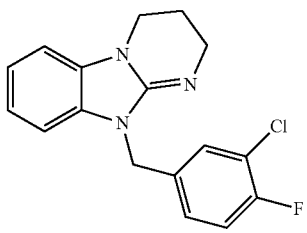 [SMILES: Fc1ccc(CN2C3=NCCCN3c3ccccc32)cc1Cl]

1-(3-chloro-4-fluorobenzyl)-1H-benzo[d]imidazol-2-amine (9.0 mg, 0.031 mmol), prepared by a procedure analogous to the procedure used to prepare Example 1, was dissolved in DMF (1 mL) in a reaction vial. Sodium hydride (2 mg, 0.05 mmol, 1.6 eq) was added to the reaction vial at room temperature, followed by 1,3-dibromopropane (4 DL, 0.037 mmol, 1.2 eq). The reaction was stirred at room temperature and monitored by LCMS. Upon conversion of the starting material by LCMS, the reaction as quenched with 10% aqueous HCl and extracted with methylene chloride. The solution was passed through a phase separator and concentrated to dryness. The crude solid was purified by reverse-phase HPLC to afford the title compound as a white solid (2 mg, 20% yield). $^1$H NMR (400 MHz, CD$_3$OD) δ 7.52 (t, J=8.3 Hz, 2H), 7.39 (ovlp m, 3H), 7.28 (ovlp, 2H), 5.37 (s, 2H), 4.25 (t, J=6.0 Hz, 2H), 3.69 (t, J=6.0 Hz, 2H), 2.34 (quint, J=6.0, 2H). MS (ESI) m/z=316.10. LCMS Ret time (UV 214/254): 1.265 min.

Example 213: 10-(3-chloro-4-fluorobenzyl)-7,8-dimethyl-2,3,4,10-tetrahydrobenzo[4,5]imidazo[1,2-a]pyrimidine

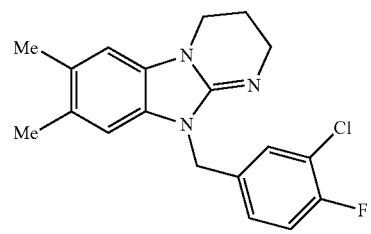 [SMILES: Cc1cc2c(cc1C)N(Cc1ccc(F)c(Cl)c1)C1=NCCCN12]

The title compound was obtained according to a procedure analogous to general procedure S: 25% yield. MS (ESI) (M+H$^+$) m/z=344.10. LCMS Ret time (UV 214/254): 1.411 min.

Example 214: 7-chloro-10-(3-chloro-4-fluorobenzyl)-2,3,4,10-tetrahydrobenzo[4,5]imidazo[1,2-a]pyrimidine

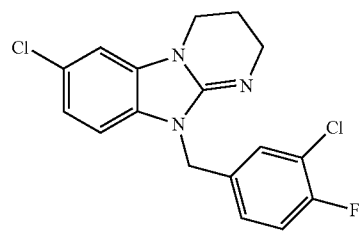 [SMILES: Fc1ccc(CN2C3=NCCCN3c3cc(Cl)ccc32)cc1Cl]

The title compound was obtained according to a procedure analogous to general procedure T: 53% yield. MS (ESI) (M+H$^+$) m/z=350.10. LCMS Ret time (UV 214/254): 1.384 min.

Example 215: 10-(3-bromobenzyl)-7,8-dimethyl-2,3,4,10-tetrahydrobenzo[4,5]imidazo[1,2-a]pyrimidine

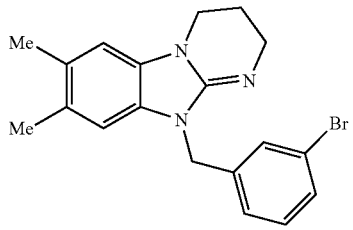 [SMILES: Cc1cc2c(cc1C)N(Cc1cccc(Br)c1)C1=NCCCN12]

The title compound was obtained according to a procedure analogous to general procedure T: 45% yield. MS (ESI) (M+H+) m/z=370.00. LCMS Ret time (UV 214/254): 1.453 min.

Example 216: (1-(1-(4-fluoro-3-methylbenzyl)-4-(2-fluorophenyl)-6-methyl-1H-imidazo[4,5-c]pyridin-2-yl)azetidin-3-yl)methanamine

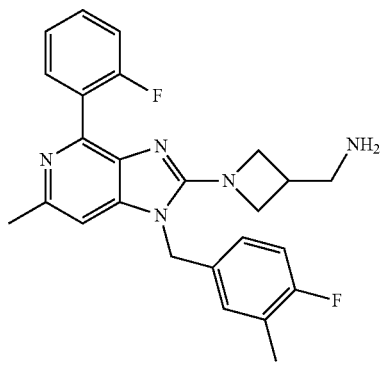 [SMILES: Cc1cc2c(nc(N3CC(CN)C3)n2Cc2ccc(F)c(C)c2)c(-c2ccccc2F)n1]

Step A: A stirred solution of 4-hydroxy-6-methyl-3-nitro-2-pyridone (2.24 g, 13.2 mmol) in POCl$_3$ (13 mL) was refluxed overnight. The excess POCl$_3$ was removed under vacuum and ice was added to the black residue. The resulting slurry was carefully neutralized (pH 7) by addition of conc. NH$_4$OH. The resulting slurry was poured through filter paper, washing the solid with cold water. The solid was dried under vacuum at 50° C. overnight to give crude 2,4-dichloro-6-methyl-3-nitropyridine, 2.12 g (78%) as black crystals.

Step B: The crude 2,4-dichloro-6-methyl-3-nitropyridine (1.59 g, 7.7 mmol) was stirred in DMF (11 mL) at 0° C. Triethylamine (1.3 mL, 9.2 mmol) was added. A solution of 4-fluoro-3-methylbenzyl-amine (1.06 mL, 8.07 mmol), diluted in DMF (1 mL), was added dropwise. The reaction was allowed to warm slowly to RT and was left to stir overnight. LCMS indicates no remaining SM. The reaction was diluted with DCM and water. The aqueous layer was separated and extracted with DCM (2×). The combined organics were washed with brine (2×), dried over MgSO$_4$ and concentrated under vacuum. The residue was chromatographed on silica gel (120 g) eluting with a 0-to-20% EtOAc/hexane gradient to give 2-chloro-N-(4-fluoro-3-methylbenzyl)-6-methyl-3-nitropyridin-4-amine, 1.44 g (60%), of as a yellow solid.

Step C: The 2-chloro-N-(4-fluoro-3-methylbenzyl)-6-methyl-3-nitropyridin-4-amine (1.26 g, 4.1 mmol) was stirred in 1:1 MeOH/THF (80 mL). Rainey nickel (433 mg, 0.41 mmol) was added. The flask was purged with argon/vacuum (3×), then with H$_2$/vacuum (3×). To the vigorously stirred solution was applied H$_2$ at 1 atm (balloon) for about 45 min. LC/MS indicates no remaining SM. The reaction was diluted with MeOH/DCM. The mixture was allowed to settle, the solvent was poured through a plug of celite, washing with MeOH/DCM. The filtrate was concentrated under vacuum to give crude 2-chloro-N$^4$-(4-fluoro-3-methylbenzyl)-6-methylpyridine-3,4-diamine 1.14 g (100%), as a light tan solid. MS (ESI) (M+H+) m/z=280. LCMS Ret time (UV 215/254): 0.76 min.

Step D: The crude 2-chloro-N$^4$-(4-fluoro-3-methylbenzyl)-6-methylpyridine-3,4-diamine (893 mg, 3.2 mmol) was stirred in toluene (16 mL), followed by the addition of triethyl orthoformate (0.59 mL, 3.5 mmol). The reaction was heated to 95° C. and stirred for 1 hr. LC/MS indicates no remaining SM. The reaction was concentrated under vacuum and the residue was chromatographed on silica gel (40 g) eluting with a 0-to-2.5% MeOH/DCM (with 1% conc. NH$_4$OH) gradient to give 4-chloro-1-(4-fluoro-3-methylbenzyl)-6-methyl-1H-imidazo[4,5-c]pyridine 754 mg (82%), as a clear oil. MS (ESI) (M+H+) m/z=290. LCMS Ret time (UV 215/254): 0.93 min.

Step E: To a dried 25 mL RBF with stir bar was added THF (5.0 mL) and diisopropylamine (0.250 mL, 1.8 mmol). Under argon, the stirred mixture was cooled to −78° C. Then, 1.6 M n-BuLi/in hexanes (1.1 mL, 1.75 mmol) was added slowly, and the reaction was stirred 1 hr. A solution of 4-chloro-1-(4-fluoro-3-methylbenzyl)-6-methyl-1H-imidazo[4,5-c]pyridine (250 mg, 0.86 mmol) dissolved in THF (2.5 mL) was added dropwise. The reaction was stirred 1 hr, then hexachloroethane (410 mg, 1.75 mmol), dissolved in THF (1.5 mL), was added dropwise. The reaction was stirred at −78° C. for approx. 3 hrs, then warmed slowly to RT and stirred 30 min. LC/MS indicates no remaining SM. The reaction was quenched with aqueous saturated NH$_4$Cl and diluted with water and EtOAc. The aqueous layer was separated and extracted with EtOAc (2×). The combined organics were washed with brine (2×), dried over Na$_2$SO$_4$, and concentrated under vacuum. The residue was chromatographed on silica gel (12 g) eluting with a 0-to-2% MeOH/DCM (with 1% conc. NH$_4$OH) gradient to give 2,4-dichloro-1-(4-fluoro-3-methylbenzyl)-6-methyl-1H-imidazo[4,5-c]pyridine 250 mg (90%). MS (ESI) (M+H+) m/z=324. LCMS Ret time (UV 215/254): 1.09 min.

Step F: A solution of 2,4-dichloro-1-(4-fluoro-3-methylbenzyl)-6-methyl-1H-imidazo[4,5-c]pyridine (125 mg, 0.39 mmol), 3-Boc-3-aminomethyl)azetidine (172 mg, 0.77 mmol), DIEA (0.200 mL, 1.2 mmol) and NMP (0.400 mL) were added to a microwave reaction vial. The vial was sealed and the reaction was irradiated at 110 degrees for 30 min. LC/MS indicates no remaining SM. The reaction was diluted with EtOAc and water. The aqueous layer was separated and extracted with EtOAc (2×). The combined organics were washed with water (2×), brine (2×), dried over Na$_2$SO$_4$ and concentrated under vacuum. The crude residue was chromatographed on silica gel (12 g) eluting with a 0-to-4% gradient of MeOH/DCM (with 1% conc. NH$_4$OH) to give tert-butyl ((1-(4-chloro-1-(4-fluoro-3-methylbenzyl)-6-methyl-1H-imidazo[4,5-c]pyridin-2-yl)azetidin-3-yl)methyl)carbamate 131 mg (72%), as an oil. MS (ESI) (M+H+) m/z=474. LCMS Ret time (UV 215/254): 0.97 min.

Step G: A solution of tert-butyl ((1-(4-chloro-1-(4-fluoro-3-methylbenzyl)-6-methyl-1H-imidazo[4,5-c]pyridin-2-yl)

azetidin-3-yl)methyl)carbamate (130 mg, 0.27 mmol) dissolved in 10:1 THF/water (2 mL) was added to a microwave reaction vial containing 2-fluorophenyl boronic acid (46 mg, 0.33 mmol), PdCl2(dppf):DCM (22 mg, 0.03 mmol) and Cs2CO3 (180 mg, 0.55 mmol). The vial was sealed, degassed by bubbling with argon, and then heated at 85° C. in an oil bath with stirring for about 36 hrs. LC/MS indicates no remaining SM. The reaction mixture was diluted with EtOAc and poured through a plug of Celite, washing with EtOAc. The eluent was concentrated, diluted with MeOH/DCM and filtered again through a syringe filter, then concentrated. The crude residue was treated with 20% TFA/DCM (5 mL) for about 30 min to remove the Boc group. The reaction was then concentrated and the residue was purified by acidic reverse-phase HPLC (ACN/water with 0.1% TFA, 5-to-35% gradient over 5 min), then free-based to give the title compound (1-(1-(4-fluoro-3-methylbenzyl)-4-(2-fluorophenyl)-6-methyl-1H-imidazo[4,5-c]pyridin-2-yl)azetidin-3-yl)methanamine, 75 mg (63%) as an oil. $^1$H NMR (400 MHz, DMSO-d$_6$): δ 7.62 (m, 1H), 7.41 (m, 1H), 7.24 (m, 2H), 7.08 (m, 3H), 6.93 (m, 1H), 5.19 (s, 2H), 4.07 (t, J=7.9, Hz, 2H), 3.82 (m, 2H), 2.74 (d, J=6.8 Hz, 2H), 2.62 (m, 1H), 2.47 (s, 3H), 2.19 (d, J=1.5, Hz, 3H). MS (ESI) (M+H$^+$) m/z=434. LCMS Ret time (UV 215/254): 0.95 min.

Example 217: 1-(4-fluoro-3-methylbenzyl)-4-(2-fluorophenyl)-6-methyl-2-(piperazin-1-yl)-1H-imidazo[4,5-c]pyridine

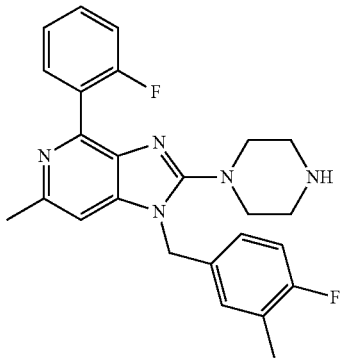 [SMILES: Cc1cc2c(nc(N3CCNCC3)n2Cc2ccc(F)c(C)c2)c(-c2ccccc2F)n1]

Step A: A stirred solution of 4-hydroxy-6-methyl-3-nitro-2-pyridone (2.24 g, 13.2 mmol) in POCl$_3$ (13 mL) was refluxed overnight. The excess POCl$_3$ was removed under vacuum and ice was added to the black residue. The resulting slurry was carefully neutralized (pH 7) by addition of conc. NH$_4$OH. The resulting slurry was poured through filter paper, washing the solid with cold water. The solid was dried under vacuum at 50° C. overnight to give crude 2,4-dichloro-6-methyl-3-nitropyridine, 2.12 g (78%) as black crystals.

Step B: The crude 2,4-dichloro-6-methyl-3-nitropyridine (1.59 g, 7.7 mmol) was stirred in DMF (11 mL) at 0° C. Triethylamine (1.3 mL, 9.2 mmol) was added. A solution of 4-fluoro-3-methylbenzyl-amine (1.06 mL, 8.07 mmol), diluted in DMF (1 mL), was added dropwise. The reaction was allowed to warm slowly to RT and was left to stir overnight. LCMS indicates no remaining SM. The reaction was diluted with DCM and water. The aqueous layer was separated and extracted with DCM (2×). The combined organics were washed with brine (2×), dried over MgSO$_4$ and concentrated under vacuum. The residue was chromatographed on silica gel (120 g) eluting with a 0-to-20% EtOAc/hexane gradient to give 2-chloro-N-(4-fluoro-3-methylbenzyl)-6-methyl-3-nitropyridin-4-amine, 1.44 g (60%) as a yellow solid.

Step C: The 2-chloro-N-(4-fluoro-3-methylbenzyl)-6-methyl-3-nitropyridin-4-amine (1.26 g, 4.1 mmol) was stirred in 1:1 MeOH/THF (80 mL). Rainey nickel (433 mg, 0.41 mmol) was added. The flask was purged with argon/vacuum (3×), then with H$_2$/vacuum (3×). To the vigorously stirred solution was applied H$_2$ at 1 atm (balloon) for about 45 min. LC/MS indicates no remaining SM. The reaction was diluted with MeOH/DCM. The mixture was allowed to settle, the solvent was poured through a plug of celite, washing with MeOH/DCM. The filtrate was concentrated under vacuum to give crude 2-chloro-N$^4$-(4-fluoro-3-methylbenzyl)-6-methylpyridine-3,4-diamine 1.14 g (100%), as a light tan solid. MS (ESI) (M+H$^+$) m/z=280. LCMS Ret time (UV 215/254): 0.76 min.

Step D: The crude 2-chloro-N$^4$-(4-fluoro-3-methylbenzyl)-6-methylpyridine-3,4-diamine (893 mg, 3.2 mmol) was stirred in toluene (16 mL), followed by the addition of triethyl orthoformate (0.59 mL, 3.5 mmol). The reaction was heated to 95° C. and stirred for 1 hr. LC/MS indicates no remaining SM. The reaction was concentrated under vacuum and the residue was chromatographed on silica gel (40 g) eluting with a 0-to-2.5% MeOH/DCM (with 1% conc. NH$_4$OH) gradient to give 4-chloro-1-(4-fluoro-3-methylbenzyl)-6-methyl-1H-imidazo[4,5-c]pyridine 754 mg (82%), as a clear oil. MS (ESI) (M+H$^+$) m/z=290. LCMS Ret time (UV 215/254): 0.93 min.

Step E: To a dried 25 mL RBF with stir bar was added THF (5.0 mL) and diisopropylamine (0.250 mL, 1.8 mmol). Under argon, the stirred mixture was cooled to −78° C. Then, 1.6M n-BuLi/in hexanes (1.1 mL, 1.75 mmol) was added slowly, and the reaction was stirred 1 hr. A solution of 4-chloro-1-(4-fluoro-3-methylbenzyl)-6-methyl-1H-imidazo[4,5-c]pyridine (250 mg, 0.86 mmol) dissolved in THF (2.5 mL) was added dropwise. The reaction was stirred 1 hr, then hexachloroethane (410 mg, 1.75 mmol), dissolved in THF (1.5 mL), was added dropwise. The reaction was stirred at −78° C. for approx. 3 hrs, then warmed slowly to RT and stirred 30 min. LC/MS indicates no remaining SM. The reaction was quenched with aqueous saturated NH$_4$Cl and diluted with water and EtOAc. The aqueous layer was separated and extracted with EtOAc (2×). The combined organics were washed with brine (2×), dried over Na$_2$SO$_4$, and concentrated under vacuum. The residue was chromatographed on silica gel (12 g) eluting with a 0-to-2% MeOH/DCM (with 1% conc. NH$_4$OH) gradient to give 2,4-dichloro-1-(4-fluoro-3-methylbenzyl)-6-methyl-1H-imidazo[4,5-c]pyridine 250 mg (90%). MS (ESI) (M+H$^+$) m/z=324. LCMS Ret time (UV 215/254): 1.09 min.

Step F: A solution of 2,4-dichloro-1-(4-fluoro-3-methylbenzyl)-6-methyl-1H-imidazo[4,5-c]pyridine (125 mg, 0.39 mmol) and piperazine (66 mg, 0.77 mmol) in NMP (0.400 mL) were added to a microwave reaction vial. The vial was sealed and the reaction was irradiated at 150 degrees for 20 min. LC/MS indicates no remaining SM. The reaction was diluted with EtOAc and water. The aqueous layer was separated and extracted with EtOAc (2×). The combined organics were washed with water (2×), brine (2×), dried over Na$_2$SO$_4$ and concentrated under vacuum. The crude residue was chromatographed on silica gel (12 g) eluting with a 0-to-10% gradient of MeOH/DCM (with 1% conc. NH$_4$OH) to give 4-chloro-1-(4-fluoro-3-methylbenzyl)-6-methyl-2-

(piperazin-1-yl)-1H-imidazo[4,5-c]pyridine 82 mg (57%), as an oil. MS (ESI) (M+H⁺) m/z=374. LCMS Ret time (UV 215/254): 0.78 min.

Step G: A solution of 4-chloro-1-(4-fluoro-3-methylbenzyl)-6-methyl-2-(piperazin-1-yl)-1H-imidazo[4,5-c]pyridine (82 mg, 0.22 mmol) was dissolved in 10:1 THF/water (1.5 mL), then added to a microwave reaction vial containing 2-fluorophenyl boronic acid (37 mg, 0.26 mmol), PdCl$_2$(dppf):DCM (20 mg, 0.02 mmol) and Cs$_2$CO3 (145 mg, 0.44 mmol). The vial was sealed, degassed by bubbling with argon, and then heated at 85° C. in an oil bath with stirring for about 36 hrs. LC/MS indicates no remaining SM. The reaction mixture was diluted with EtOAc and poured through a plug of Celite, washing with EtOAc. The eluent was concentrated, diluted with MeOH/DCM and filtered again through a syringe filter, then concentrated. The residue was purified by acidic reverse-phase HPLC (ACN/water with 0.1% TFA, 5-to-35% gradient over 5 min), then freebased to give the title compound, 1-(4-fluoro-3-methylbenzyl)-4-(2-fluorophenyl)-6-methyl-2-(piperazin-1-yl)-1H-imidazo[4,5-c]pyridine, 42 mg (44%), a light yellow solid. $^1$H NMR (400 MHz, DMSO-d$_6$): δ 7.65 (m, 1H), 7.44 (m, 1H), 7.26 (m, 2H), 7.16 (m, 2H), 7.08 (m, 2H), 6.98 (m, 1H), 5.24 (s, 2H), 3.05 (m, 4H), 2.75 (m, 4H), 2.48 (s, 3H), 2.19 (d, J=1.5, Hz, 3H). MS (ESI) (M+H⁺) m/z=434. LCMS Ret time (UV 215/254): 0.96 min.

Example 218: 4-chloro-1-(4-fluoro-3-methylbenzyl)-6-methyl-2-(piperazin-1-yl)-1H-imidazo[4,5-c]pyridine

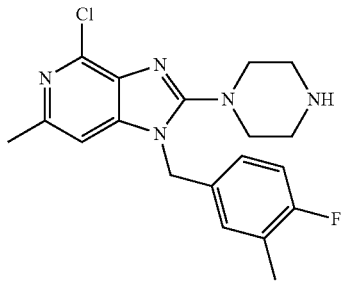 [SMILES: Cc1cc2c(nc(N3CCNCC3)n2Cc2ccc(F)c(C)c2)c(Cl)n1]

The title compound was prepared by a procedure analogous to the procedure used to prepare Example 217, Step F: $^1$H NMR (400 MHz, DMSO-d$_6$): δ 7.06 (m, 3H), 6.93 (m, 1H), 5.23 (s, 2H), 3.12 (m, 4H), 2.76 (m, 4H), 2.40 (s, 3H), 2.17 (d, J=1.6 Hz, 3H). MS (ESI) (M+H⁺) m/z=374. LCMS Ret time (UV 215/254): 0.81 min.

Example 219: 1-(4-fluoro-3-methylbenzyl)-4-(2-isopropylphenyl)-6-methyl-2-(piperazin-1-yl)-1H-imidazo[4,5-c]pyridine

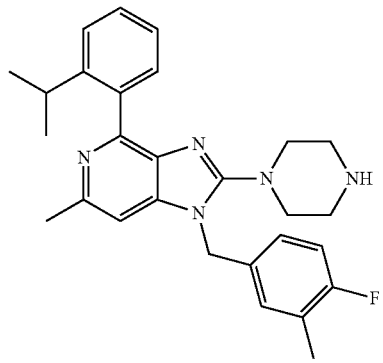 [SMILES: Cc1cc2c(nc(N3CCNCC3)n2Cc2ccc(F)c(C)c2)c(-c2ccccc2C(C)C)n1]

The title compound was prepared by a procedure analogous to General Procedure V: MS (ESI) (M+H⁺) m/z=458. LCMS Ret time (UV 215/254): 0.79 min.

Example 220: 1-(4-fluoro-3-methylbenzyl)-4-phenyl-2-(piperazin-1-yl)-1H-imidazo[4,5-c]pyridine

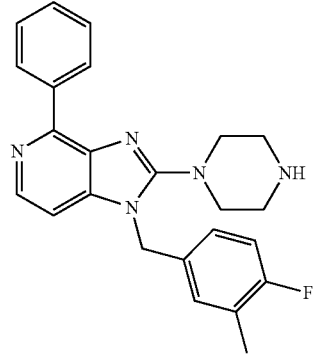 [SMILES: Cc1cc(Cn2c(N3CCNCC3)nc3c(-c4ccccc4)nccc32)ccc1F]

Step A: A stirred solution of 2,4-dihydroxy-3-nitropyridine (1.79 g, 11.5 mmol) in POCl$_3$ (12 mL) was refluxed overnight. The excess POCl$_3$ was removed under vacuum and ice was added to the black residue. The resulting slurry was carefully neutralized (pH 7) by addition of conc. NH$_4$OH. The resulting slurry was poured through filter paper, washing the solid with cold water. The solid was dried under vacuum at 50° C. overnight to give crude 2,4-dichloro-3-nitropyridine 1.27 g (57%).

Step B: The crude 2,4-dichloro-3-nitropyridine (869 mg, 4.5 mmol) was stirred in DMF (6 mL) at 0° C. Triethylamine (0.75 mL, 5.4 mmol) was added. A solution of 4-fluoro-3-methylbenzyl-amine (0.262 mL, 4.7 mmol), diluted in DMF (1.0 mL), was added dropwise. The reaction was allowed to warm slowly to RT and was left to stir for about 90 min. LCMS indicates no remaining SM. The reaction was diluted with EtOAc and water. The aqueous layer was separated and extracted with EtOAc (2×). The combined organics were washed with brine, dried over Na$_2$SO$_4$ and concentrated under vacuum to give 1.4 g of crude product which was chromatographed on silica gel (40 g) eluting with a 0-to-20% EtOAc/hexane gradient to give 2-chloro-N-(4-fluoro-3-methylbenzyl)-3-nitropyridin-4-amine, 764 mg (57%) as a yellow solid. MS (ESI) (M+H⁺) m/z=296. LCMS Ret time (UV 215/254): 1.08 min.

Step C: A stirred solution of 2-chloro-N-(4-fluoro-3-methylbenzyl)-3-nitropyridin-4-amine (0.76 g, 1.1 mmol) in 1:1 MeOH/THF (50 mL) was treated with Rainey nickel (275 mg, 0.26 mmol). The flask was purged with argon/vacuum (3×), then H$_2$/vacuum (3×). The flask was then treated with H$_2$, applied at 1 atm (balloon) for about 60 min. LC/MS indicates no remaining SM. The reaction was diluted with MeOH/DCM. The mixture was allowed to settle, the solvent was poured through a plug of celite, washing with MeOH/DCM. The filtrate was concentrated under vacuum to give 2-chloro-N4-(4-fluoro-3-methylbenzyl)pyridine-3,4-diamine, 670 mg (98%) as a light tan solid. MS (ESI) (M+H⁺) m/z=266. LCMS Ret time (UV 215/254): 0.69 min.

Step D: A stirred solution of 2-chloro-N$^4$-(4-fluoro-3-methylbenzyl)pyridine-3,4-diamine (670 mg, 2.5 mmol), trimethyl orthoformate (10 mL) and acetic Anhydride (0.93 mL, 10 mmol) was heated to 100° C. for 90 min. LC/MS indicates no remaining SM. The reaction was concentrated under vacuum to give 825 mg of crude residue. The residue was chromatographed on silica gel (80 g) eluting with a 0-to-4% MeOH/DCM (with 1% conc. NH$_4$OH) gradient to give 4-chloro-1-(4-fluoro-3-methylbenzyl)-1H-imidazo[4,5-c]pyridine, 315 mg (45%) as a clear oil. MS (ESI) (M+H$^+$) m/z=276. LCMS Ret time (UV 215/254): 0.87 min.

Step E: A solution of 4-chloro-1-(4-fluoro-3-methylbenzyl)-1H-imidazo[4,5-c]pyridine (153 mg, 0.55 mmol), 2-chloro-phenylboronic acid (104 mg, 0.67 mmol), PdCl$_2$(dppf):DCM (45 mg, 0.06 mmol) and Cs$_2$CO$_3$ (362 mg, 1.11 mmol) in 10:1 THF/water (3.7 mL) was added to a microwave reaction vial. The vial was sealed and irradiated at 120° C. for 20 min. LC/MS indicates no remaining SM. The reaction mixture was diluted with EtOAc and poured through a plug of Celite, washing with EtOAc. The eluent was concentrated and the residue was chromatographed on silica gel (40 g) eluting with a 0-to-4% MeOH/DCM (with 1% conc. NH$_4$OH) gradient to give 1-(4-fluoro-3-methyl-benzyl)-4-phenyl-1H-imidazo[4,5-c]pyridine, 123 mg (70%) as a light tan solid. MS (ESI) (M+H$^+$) m/z=318. LCMS Ret time (UV 215/254): 0.81 min.

Step F: To a dried 10 mL RBF with stir bar was added THF (3.0 mL) and diisopropylamine (0.180 mL, 1.0 mmol). Under argon, the stirred mixture was cooled to −78° C. A solution of 1.6M n-BuLi/in hexanes (0.77 mL, 1.24 mmol) was added slowly, the reaction was stirred 1 hr, then 1-(4-fluoro-3-methylbenzyl)-4-phenyl-1H-imidazo[4,5-c]pyridine (196 mg, 0.62 mmol), dissolved in THF (2.0 mL) was added dropwise. The reaction was stirred 1 hr. A solution of hexachloroethane (292 mg, 1.24 mmol), dissolved in THF (1.0 mL), was added dropwise. The reaction was stirred at −78° C. for approx. 2 hrs, then warmed slowly to RT and stirred 30 min. LC/MS indicates no remaining SM. The reaction was quenched with aqueous saturated NH$_4$Cl and diluted with water and EtOAc. The aqueous layer was separated and extracted with EtOAc (2×). The combined organics were washed with brine (2×), dried over Na$_2$SO$_4$, concentrated to give the crude product residue. The residue was chromatographed on silica gel (24 g) eluting with a 0-to-1% MeOH/DCM (with 1% conc. NH$_4$OH) gradient to give 2-chloro-1-(4-fluoro-3-methylbenzyl)-4-phenyl-1H-imidazo[4,5-c]pyridine, 143 mg (66%) as a tan solid. MS (ESI) (M+H$^+$) m/z=352. LCMS Ret time (UV 215/254): 0.89 min.

Step G: A solution of 2-chloro-1-(4-fluoro-3-methylbenzyl)-4-phenyl-1H-imidazo[4,5-c]pyridine (40 mg, 0.11 mmol), piperazine (40 mg, 0.45 mmol) and NMP (0.120 mL) were added to a microwave reaction vial. The vial was sealed and the reaction was irradiated at 120° C. for 20 min. The crude residue was purified by acidic reverse-phase HPLC (5-to-35% ACN/water with 0.1% TFA over 5 min), then free-based, to give the title compound, 1-(4-fluoro-3-methylbenzyl)-4-phenyl-2-(piperazin-1-yl)-1H-imidazo[4,5-c]pyridine, 24 mg (52%) as an oil. $^1$H NMR (400 MHz, DMSO-d$_6$): δ 8.68 (m, 2H), 8.26 (dd, J=9.1 and 5.3 Hz, 1H), 7.46 (m, 2H), 7.37 (m, 1H), 7.24 (d, J=5.3 Hz, 1H), 7.17 (m, 1H), 7.00 (m, 2H), 5.32 (m, 2H), 3.48 (m, 2H), 3.32 (m, 2H), 3.21 (m, 2H), 2.64 (m, 2H), 2.18 (s, 3H). MS (ESI) (M+H$^+$) m/z=402. LCMS Ret time (UV 215/254): 0.97 min.

Example 221: N$^1$-(1-(4-fluoro-3-methylbenzyl)-4-phenyl-1H-imidazo[4,5-c]pyridin-2-yl)ethane-1,2-diamine

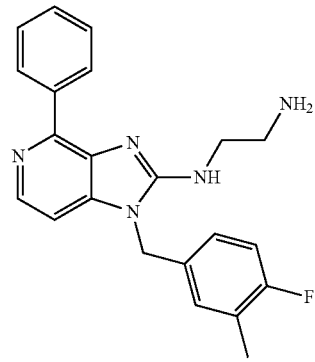 [SMILES: Cc1cc(Cn2c(NCCN)nc3c(-c4ccccc4)nccc32)ccc1F]

The title compound was prepared by a procedure analogous to General Procedure W: $^1$H NMR (400 MHz, DMSO-d$_6$): δ 8.70 (m, 2H), 8.12 (d, J=5.1 Hz, 1H), 7.43 (m, 2H), 7.32 (m, 2H), 7.18 (m, 1H), 7.14 (d, J=5.2 Hz, 1H), 7.01 (m, 3H), 5.30 (s, 2H), 3.54 (t, J=6.1 Hz, 2H), 2.91 (t, J=6.1 Hz, 2H), 2.17 (s, 3H). MS (ESI) (M+H$^+$) m/z=376. LCMS Ret time (UV 215/254): 0.95 min.

Example 222: 1-(4-fluoro-3-methylbenzyl)-4-phenyl-N-(pyrrolidin-3-yl)-1H-imidazo[4,5-c]pyridin-2-amine

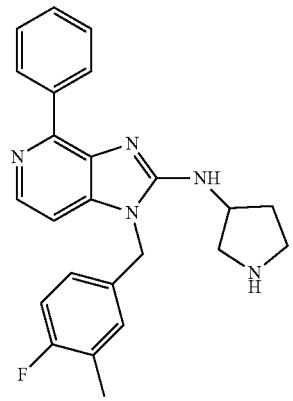 [SMILES: Cc1cc(Cn2c(NC3CCNC3)nc3c(-c4ccccc4)nccc32)ccc1F]

The title compound was prepared by a procedure analogous to General Procedure W: MS (ESI) (M+H$^+$) m/z=402. LCMS Ret time (UV 215/254): 1.00 min.

Example 223: N$^1$-(4-chloro-1-(4-fluoro-3-methylbenzyl)-1H-imidazo[4,5-c]pyridin-2-yl)ethane-1,2-diamine

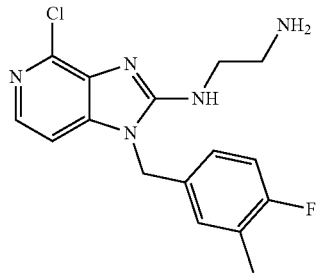 [SMILES: Cc1cc(Cn2c(NCCN)nc3c(Cl)nccc32)ccc1F]

The title compound was prepared by a procedure analogous to General Procedure W: MS (ESI) (M+H$^+$) m/z=334. LCMS Ret time (UV 215/254): 0.94 min.

Example 224: N$^1$-(1-(4-fluoro-3-methylbenzyl)-6-methyl-4-(o-tolyl)-1H-imidazo[4,5-c]pyridin-2-yl)ethane-1,2-diamine

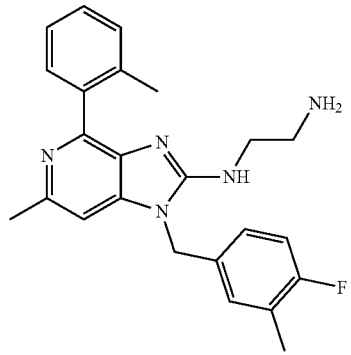 [SMILES: Cc1cc2c(nc(NCCN)n2Cc2ccc(F)c(C)c2)c(-c2ccccc2C)n1]

Step A: A stirred solution of 4-hydroxy-6-methyl-3-nitro-2-pyridone (2.24 g, 13.2 mmol) in POCl$_3$ (13 mL) was refluxed overnight. The excess POCl$_3$ was removed under vacuum and ice was added to the black residue. The resulting slurry was carefully neutralized (pH 7) by addition of conc. NH$_4$OH. The resulting slurry was poured through filter paper, washing the solid with cold water. The solid was dried under vacuum at 50° C. overnight to give crude 2,4-dichloro-6-methyl-3-nitropyridine, 2.12 g (78%) as black crystals.

Step B: The crude 2,4-dichloro-6-methyl-3-nitropyridine (1.59 g, 7.7 mmol) was stirred in DMF (11 mL) at 0° C. Triethylamine (1.3 mL, 9.2 mmol) was added. A solution of 4-fluoro-3-methylbenzyl-amine (1.06 mL, 8.07 mmol), diluted in DMF (1 mL), was added dropwise. The reaction was allowed to warm slowly to RT and was left to stir overnight. LCMS indicates no remaining SM. The reaction was diluted with DCM and water. The aqueous layer was separated and extracted with DCM (2×). The combined organics were washed with brine (2×), dried over MgSO$_4$ and concentrated under vacuum. The residue was chromatographed on silica gel (120 g) eluting with a 0-to-20% EtOAc/hexane gradient to give 2-chloro-N-(4-fluoro-3-methylbenzyl)-6-methyl-3-nitropyridin-4-amine, 1.44 g (60%), as a yellow solid.

Step C: The 2-chloro-N-(4-fluoro-3-methylbenzyl)-6-methyl-3-nitropyridin-4-amine (1.26 g, 4.1 mmol) was stirred in 1:1 MeOH/THF (80 mL). Rainey nickel (433 mg, 0.41 mmol) was added. The flask was purged with argon/vacuum (3×), then with H$_2$/vacuum (3×). To the vigorously stirred solution was applied H$_2$ at 1 atm (balloon) for about 45 min. LC/MS indicates no remaining SM. The reaction was diluted with MeOH/DCM. The mixture was allowed to settle, the solvent was poured through a plug of celite, washing with MeOH/DCM. The filtrate was concentrated under vacuum to give crude 2-chloro-N$^4$-(4-fluoro-3-methylbenzyl)-6-methylpyridine-3,4-diamine, 1.14 g (100%), as a light tan solid. MS (ESI) (M+H$^+$) m/z=280. LCMS Ret time (UV 215/254): 0.76 min.

Step D: The crude 2-chloro-N$^4$-(4-fluoro-3-methylbenzyl)-6-methylpyridine-3,4-diamine (893 mg, 3.2 mmol) was stirred in toluene (16 mL), followed by the addition of triethyl orthoformate (0.59 mL, 3.5 mmol). The reaction was heated to 95° C. and stirred for 1 hr. LC/MS indicates no remaining SM. The reaction was concentrated under vacuum and the residue was chromatographed on silica gel (40 g) eluting with a 0-to-2.5% MeOH/DCM (with 1% conc. NH$_4$OH) gradient to give 4-chloro-1-(4-fluoro-3-methylbenzyl)-6-methyl-1H-imidazo[4,5-c]pyridine, 754 mg (82%), as a clear oil. MS (ESI) (M+H$^+$) m/z=290. LCMS Ret time (UV 215/254): 0.93 min.

Step E: A solution of 4-chloro-1-(4-fluoro-3-methylbenzyl)-6-methyl-1H-imidazo[4,5-c]pyridine (170 mg, 0.59 mmol) in 10:1 THF/water (4 mL) was added to a microwave reaction vial containing o-Tolylboronic acid (96 mg, 0.70 mmol), PdCl$_2$(dppf):DCM (48 mg, 0.06 mmol) and Cs$_2$CO$_3$ (383 mg, 1.2 mmol). The vial was sealed, purged with argon, and irradiated at 100° C. for 45 min. LC/MS indicates no remaining SM. The reaction mixture was diluted with EtOAc and poured through a plug of Celite, washing with EtOAc. The eluent was concentrated and the residue was chromatographed on silica gel (12 g) eluting with a 0-to-2.5% MeOH/DCM (with 1% conc. NH$_4$OH) gradient to give 1-(4-fluoro-3-methylbenzyl)-6-methyl-4-(o-tolyl)-1H-imidazo[4,5-c]pyridine, 200 mg (98%) as a tan oil. MS (ESI) (M+H$^+$) m/z=346. LCMS Ret time (UV 215/254): 0.82 min.

Step F: To a dried 10 mL RBF with stir bar was added THF (3.0 mL) and diisopropylamine (0.170 mL, 1.2 mmol). Under argon, the stirred mixture was cooled to −78° C. A solution of 1.6M n-BuLi/in hexanes (0.72 mL, 1.16 mmol) was added slowly and the reaction was then stirred 1 hr. A solution of 1-(4-fluoro-3-methylbenzyl)-6-methyl-4-(o-tolyl)-1H-imidazo[4,5-c]pyridine (200 mg, 0.58 mmol), dissolved in THF (2.0 mL) was added dropwise. The reaction was stirred 1 hr, then hexachloroethane (275 mg, 1.16 mmol), dissolved in THF (1.0 mL) was added dropwise. The reaction was stirred at −78° C. for approx. 2 hrs, then warmed slowly to RT and stirred 30 min. LC/MS indicates no remaining SM. The reaction was quenched with aqueous saturated NH$_4$Cl and diluted with water and EtOAc. The aqueous layer was separated and extracted with EtOAc (2×). The combined organics were washed with brine (2×), dried over Na$_2$SO$_4$ and concentrated to give the crude product residue. The residue was chromatographed on silica gel (12 g) eluting with a 0-to-1% MeOH/DCM (with 1% conc. NH$_4$OH) gradient to give 2-chloro-1-(4-fluoro-3-methylbenzyl)-6-methyl-4-(o-tolyl)-1H-imidazo[4,5-c]pyridine, 60 mg (27%) as a tan solid. MS (ESI) (M+H$^+$) m/z=380. LCMS Ret time (UV 215/254): 0.94 min.

Step G: A solution of 2-chloro-1-(4-fluoro-3-methylbenzyl)-6-methyl-4-(o-tolyl)-1H-imidazo[4,5-c]pyridine (30 mg, 0.08 mmol), ethylenediamine (47 mg, 0.80 mmol) and NMP (0.160 mL) were stirred in a microwave reaction vial. The vial was sealed and the reaction was irradiated at 150° C. for 15 min. The crude reaction was diluted with DMSO and purified by acidic reverse-phase HPLC (ACN/water with 0.1% TFA, 5-to-35% gradient over 5 min), then free-based to give the title compound N$^1$-(1-(4-fluoro-3-methylbenzyl)-6-methyl-4-(o-tolyl)-1H-imidazo[4,5-c]pyridin-2-yl)ethane-1,2-diamine, 15 mg (47%) as an oil. $^1$H NMR (400 MHz, DMSO-d$_6$): δ 7.40 (d, J=7.0, Hz, 1H), 7.18 (m, 4H), 7.08 (m, 2H), 7.01 (m, 2H) 5.24 (s, 2H), 2.75 (d, J=6.1, Hz, 2H), 2.43 (s, 3H), 2.24 (s, 3H), 2.19 (d, J=1.6, Hz, 3H). MS (ESI) (M+H$^+$) m/z=404. LCMS Ret time (UV 215/254): 0.98 min.

Example 225: 1-(4-fluoro-3-methylbenzyl)-6-methyl-2-(piperazin-1-yl)-4-(o-tolyl)-1H-imidazo[4,5-c]pyridine

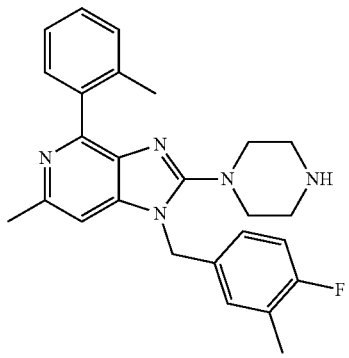 [SMILES: Cc1cc2c(nc(N3CCNCC3)n2Cc2ccc(F)c(C)c2)c(-c2ccccc2C)n1]

The title compound was prepared by a procedure analogous to General Procedure X: ¹H NMR (400 MHz, DMSO-d₆): δ 7.44 (m, 1H), 7.23 (m, 3H), 7.07 (m, 3H), 6.97 (m, 1H), 5.31 (m, 2H), 3.36 (m, 4H), 3.20 (m, 4H), 2.49 (m, 3H), 2.24 (d, J=4.0, Hz, 3H), 2.19 (m, 3H). MS (ESI) (M+H⁺) m/z=430. LCMS Ret time (UV 215/254): 0.74 min.

Example 226: 1-(4-fluoro-3-methylbenzyl)-6-methyl-2-(piperazin-1-yl)-4-(pyridin-4-yl)-1H-imidazo[4,5-c]pyridine

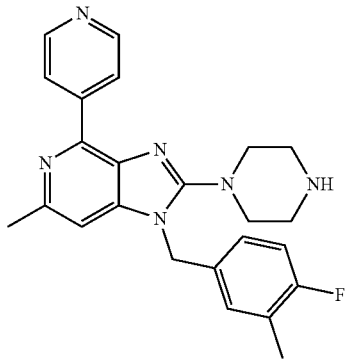 [SMILES: Cc1cc2c(nc(N3CCNCC3)n2Cc2ccc(F)c(C)c2)c(-c2ccncc2)n1]

Step A: A stirred solution of 4-hydroxy-6-methyl-3-nitro-2-pyridone (2.24 g, 13.2 mmol) in POCl₃ (13 mL) was refluxed overnight. The excess POCl₃ was removed under vacuum and ice was added to the black residue. The resulting slurry was carefully neutralized (pH 7) by addition of conc. NH₄OH. The resulting slurry was poured through filter paper, washing the solid with cold water. The solid was dried under vacuum at 50° C. overnight to give crude 2,4-dichloro-6-methyl-3-nitropyridine, 2.12 g (78%) as black crystals.

Step B: The crude 2,4-dichloro-6-methyl-3-nitropyridine (1.59 g, 7.7 mmol) was stirred in DMF (11 mL) at 0° C. Triethylamine (1.3 mL, 9.2 mmol) was added. A solution of 4-fluoro-3-methylbenzyl-amine (1.06 mL, 8.07 mmol), diluted in DMF (1 mL), was added dropwise. The reaction was allowed to warm slowly to RT and was left to stir overnight. LCMS indicates no remaining SM. The reaction was diluted with DCM and water. The aqueous layer was separated and extracted with DCM (2×). The combined organics were washed with brine (2×), dried over MgSO₄ and concentrated under vacuum. The residue was chromatographed on silica gel (120 g) eluting with a 0-to-20% EtOAc/hexane gradient to give 2-chloro-N-(4-fluoro-3-methylbenzyl)-6-methyl-3-nitropyridin-4-amine, 1.44 g (60%), of as a yellow solid.

Step C: The 2-chloro-N-(4-fluoro-3-methylbenzyl)-6-methyl-3-nitropyridin-4-amine (1.26 g, 4.1 mmol) was stirred in 1:1 MeOH/THF (80 mL). Rainey nickel (433 mg, 0.41 mmol) was added. The flask was purged with argon/vacuum (3×), then with H₂/vacuum (3×). To the vigorously stirred solution was applied H₂ at 1 atm (balloon) for about 45 min. LC/MS indicates no remaining SM. The reaction was diluted with MeOH/DCM. The mixture was allowed to settle, the solvent was poured through a plug of celite, washing with MeOH/DCM. The filtrate was concentrated under vacuum to give crude 2-chloro-N⁴-(4-fluoro-3-methylbenzyl)-6-methylpyridine-3,4-diamine, 1.14 g (100%), as a light tan solid. MS (ESI) (M+H⁺) m/z=280. LCMS Ret time (UV 215/254): 0.76 min.

Step D: To a stirred solution of 2-chloro-N⁴-(4-fluoro-3-methylbenzyl)-6-methylpyridine-3,4-diamine (797 mg, 2.85 mmol) in DMF (11 mL) was added 1,1'-carbonyldiimidazole (1.16 g, 7.12 mmol) and DMAP (35 mg, 0.28 mmol). The reaction was heated to 75° C. and stirred under argon overnight. The reaction was cooled to rt and poured into 110 g of crushed ice. The resulting slurry was allowed to warm until the ice was melted, then was poured through filter paper, washing the light yellow solid with cold water. The solid was then dried under vacuum at 50° C. to give 4-chloro-1-(4-fluoro-3-methylbenzyl)-6-methyl-1,3-dihydro-2H-imidazo[4,5-c]pyridin-2-one, 800 mg (92%) as a light yellow solid. MS (ESI) (M+H⁺) m/z=306. LCMS Ret time (UV 215/254): 0.92 min.

Step E: A solution of 4-chloro-1-(4-fluoro-3-methylbenzyl)-6-methyl-1,3-dihydro-2H-imidazo[4,5-c]pyridin-2-one (0.80 g, 2.6 mmol) was stirred in POCl₃ (20 mL) at reflux for 60 hrs. The excess POCl₃ was removed under vacuum. The flask containing the residue was placed in an ice-bath. Aqueous (sat) NaHCO₃ was added, along with EtOAc until the aqueous layer was neutral. The aqueous layer was then separated and extracted with EtOAc (3×). The combined organics were washed with brine, dried over Na₂SO₄, concentrated and chromatographed on silica gel (24 g) eluting with a 0-to-2% MeOH/DCM (with 1% conc. NH₄OH) gradient to give 2,4-dichloro-1-(4-fluoro-3-methylbenzyl)-6-methyl-1H-imidazo[4,5-c]pyridine, 650 mg (77%) as a clear oil. MS (ESI) (M+H⁺) m/z=324. LCMS Ret time (UV 215/254): 1.10 min.

Step F: A solution of 2,4-dichloro-1-(4-fluoro-3-methylbenzyl)-6-methyl-1H-imidazo[4,5-c]pyridine (650 mg, 2.01 mmol), N-Boc-piperazine (560 mg, 3.01 mmol), NMP (2.0 mL) and DIEA (0.53 mL, 3.01 mmol) were stirred at 80° C. overnight. LC/MS indicates no remaining SM. The reaction was cooled to rt, and diluted with EtOAc and water. The aqueous layer was separated and extracted with EtOAc (2×). The combined organics were washed with water (2×), brine (2×), dried over Na₂SO₄, and concentrated to give the crude product residue. The residue was chromatographed on silica gel (24 g) eluting with a 0-to-3% MeOH/DCM (with 1% conc. NH₄OH) gradient to give tert-butyl 4-(4-chloro-1-(4-fluoro-3-methylbenzyl)-6-methyl-1H-imidazo[4,5-c]pyridin-2-yl)piperazine-1-carboxylate, 896 mg (94%) light yellow solid. MS (ESI) (M+H⁺) m/z=474 v. LCMS Ret time (UV 215/254): 1.16 min.

Step G: A solution of tert-butyl 4-(4-chloro-1-(4-fluoro-3-methylbenzyl)-6-methyl-1H-imidazo[4,5-c]pyridin-2-yl)piperazine-1-carboxylate (50 mg, 0.11 mmol), Pd(OAc)$_2$ (2 mg, 0.01 mmol), P(Cy)$_3$HBF$_4$ (6 mg, 0.11 mmol), pyridine-4-boronic acid (21 mg, 0.17 mmol), K$_3$PO$_4$ (45 mg, 0.21 mmol) and 5:1 DME/water (1 mL) was added to a reaction vial. The vial was sealed, then purged with argon and stirred in an oil-bath at 105° C. overnight. The reaction was diluted with EtOAc and poured through Celite, washing with EtOAc. The eluent was concentrated under vacuum and the residue treated with 5 mL of 20% TFA/DCM for 20 min. The solution was concentrated under vacuum and the residue purified by acidic reverse-phase HPLC (ACN/water with 0.1% TFA, 5-to-30% gradient over 5 min), then free-based to give the title compound 1-(4-fluoro-3-methylbenzyl)-6-methyl-2-(piperazin-1-yl)-4-(pyridin-4-yl)-1H-imidazo[4,5-c]pyridine, 21 mg (39%) as a light tan solid. $^1$H NMR (400 MHz, DMSO-d$_6$): δ 8.67 (t, J=6.0 Hz, 2H), 8.62 (m, 2H), 7.21 (d, J=3.4 Hz, 1H), 7.15 (m, 1H), 7.07 (m, 1H), 6.99 (m, 1H) 5.30 (m, 2H), 3.50 (m, 2H), 3.21 (m, 2H), 2.61 (m, 2H), 2.54 (s, 3H), 2.18 (s, 3H). MS (ESI) (M+H$^+$) m/z=417. LCMS Ret time (UV 215/254): 0.71 min.

Example 227: 1-(4-fluoro-3-methylbenzyl)-6-methyl-4-(2-methylpyridin-3-yl)-2-(piperazin-1-yl)-1H-imidazo[4,5-c]pyridine

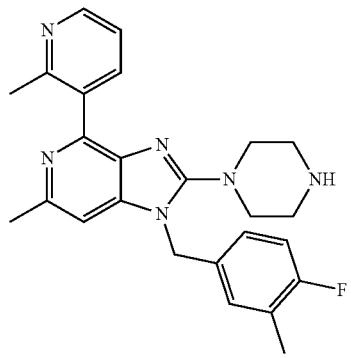 [SMILES: Cc1cc2c(nc(N3CCNCC3)n2Cc2ccc(F)c(C)c2)c(-c2cccnc2C)n1]

The title compound was prepared by a procedure analogous to General Procedure Y: $^1$H NMR (400 MHz, DMSO-d$_6$): δ 8.51 (m, 1H), 7.89 (m, 1H), 7.32 (m, 1H), 7.08 (m, 3H), 6.98 (m, 1H), 5.25 (m, 2H), 3.38 (m, 2H), 3.32 (s, 3H), 3.17 (m, 4H), 2.58 (m, 2H), 2.47 (m, 3H), 2.20 (m, 3H). MS (ESI) (M+H$^+$) m/z=431. LCMS Ret time (UV 215/254): 0.82 min.

Example 228: 1-(4-fluoro-3-methylbenzyl)-4-(2-methoxyphenyl)-6-methyl-2-(piperazin-1-yl)-1H-imidazo[4,5-c]pyridine

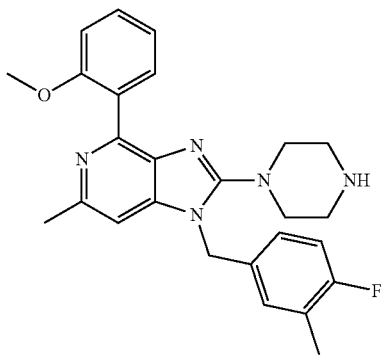 [SMILES: COc1ccccc1-c1nc(C)cc2c1nc(N1CCNCC1)n2Cc1ccc(F)c(C)c1]

The title compound was prepared by a procedure analogous to General Procedure Y: MS (ESI) (M+H$^+$) m/z=446. LCMS Ret time (UV 215/254): 0.99 min.

Example 229: (4-(1-(4-fluoro-3-methylbenzyl)-6-methyl-2-(piperazin-1-yl)-1H-imidazo[4,5-c]pyridin-4-yl)phenyl)methanamine

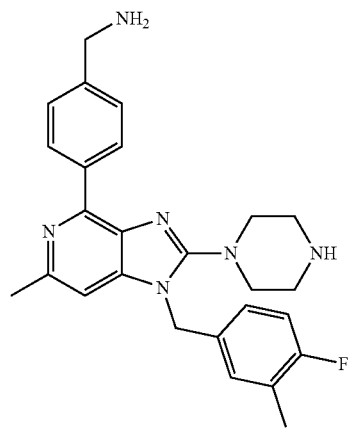 [SMILES: Cc1cc2c(nc(N3CCNCC3)n2Cc2ccc(F)c(C)c2)c(-c2ccc(CN)cc2)n1]

The title compound was prepared by a procedure analogous to General Procedure Y: MS (ESI) (M+H$^+$) m/z=445. LCMS Ret time (UV 215/254): 0.99 min.

Example 230: 4-(3,4-dimethoxyphenyl)-1-(4-fluoro-3-methylbenzyl)-6-methyl-2-(piperazin-1-yl)-1H-imidazo[4,5-c]pyridine

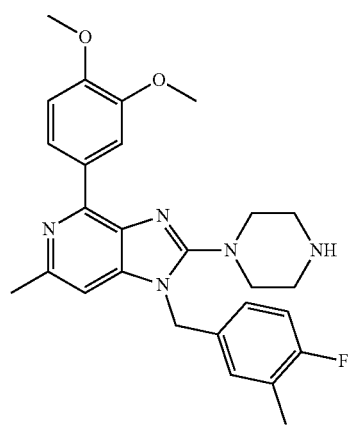 [SMILES: COc1ccc(-c2nc(C)cc3c2nc(N2CCNCC2)n3Cc2ccc(F)c(C)c2)cc1OC]

The title compound was prepared by a procedure analogous to General Procedure Y: MS (ESI) (M+H$^+$) m/z=476. LCMS Ret time (UV 215/254): 1.99 min.

Example 231: N-((1-(4-fluoro-3-methylbenzyl)-6-methyl-2-(piperazin-1-yl)-1H-imidazo[4,5-c]pyridin-4-yl)methyl)-2-methylpropan-1-amine

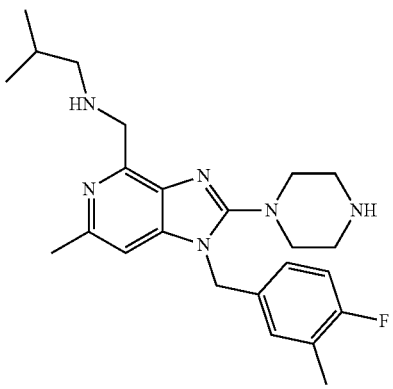 [SMILES: Cc1cc2c(nc(N3CCNCC3)n2Cc2ccc(F)c(C)c2)c(CNCC(C)C)n1]

Step A: A stirred solution of 4-hydroxy-6-methyl-3-nitro-2-pyridone (2.24 g, 13.2 mmol) in POCl$_3$ (13 mL) was refluxed overnight. The excess POCl$_3$ was removed under vacuum and ice was added to the black residue. The resulting slurry was carefully neutralized (pH 7) by addition of conc. NH$_4$OH. The resulting slurry was poured through filter paper, washing the solid with cold water. The solid was dried under vacuum at 50° C. overnight to give crude 2,4-dichloro-6-methyl-3-nitropyridine, 2.12 g (78%) as black crystals.

Step B: The crude 2,4-dichloro-6-methyl-3-nitropyridine (1.59 g, 7.7 mmol) was stirred in DMF (11 mL) at 0° C. Triethylamine (1.3 mL, 9.2 mmol) was added. A solution of 4-fluoro-3-methylbenzyl-amine (1.06 mL, 8.07 mmol), diluted in DMF (1 mL), was added dropwise. The reaction was allowed to warm slowly to RT and was left to stir overnight. LCMS indicates no remaining SM. The reaction was diluted with DCM and water. The aqueous layer was separated and extracted with DCM (2×). The combined organics were washed with brine (2×), dried over MgSO$_4$ and concentrated under vacuum. The residue was chromatographed on silica gel (120 g) eluting with a 0-to-20% EtOAc/hexane gradient to give 2-chloro-N-(4-fluoro-3-methylbenzyl)-6-methyl-3-nitropyridin-4-amine, 1.44 g (60%), of as a yellow solid.

Step C: The 2-chloro-N-(4-fluoro-3-methylbenzyl)-6-methyl-3-nitropyridin-4-amine (1.26 g, 4.1 mmol) was stirred in 1:1 MeOH/THF (80 mL). Rainey nickel (433 mg, 0.41 mmol) was added. The flask was purged with argon/vacuum (3×), then with H$_2$/vacuum (3×). To the vigorously stirred solution was applied H$_2$ at 1 atm (balloon) for about 45 min. LC/MS indicates no remaining SM. The reaction was diluted with MeOH/DCM. The mixture was allowed to settle, the solvent was poured through a plug of celite, washing with MeOH/DCM. The filtrate was concentrated under vacuum to give crude 2-chloro-N$^4$-(4-fluoro-3-methylbenzyl)-6-methylpyridine-3,4-diamine, 1.14 g (100%), as a light tan solid. MS (ESI) (M+H$^+$) m/z=280. LCMS Ret time (UV 215/254): 0.76 min.

Step D: To a stirred solution of 2-chloro-N$^4$-(4-fluoro-3-methylbenzyl)-6-methylpyridine-3,4-diamine (797 mg, 2.85 mmol) in DMF (11 mL) was added 1,1'-carbonyldiimidazole (1.16 g, 7.12 mmol) and DMAP (35 mg, 0.28 mmol). The reaction was heated to 75° C. and stirred under argon overnight. The reaction was cooled to rt and poured into 110 g of crushed ice. The resulting slurry was allowed to warm until the ice was melted, then was poured through filter paper, washing the light yellow solid with cold water. The solid was then dried under vacuum at 50° C. to give 4-chloro-1-(4-fluoro-3-methylbenzyl)-6-methyl-1,3-dihydro-2H-imidazo[4,5-c]pyridin-2-one, 800 mg (92%) as a light yellow solid. MS (ESI) (M+H$^+$) m/z=306. LCMS Ret time (UV 215/254): 0.92 min.

Step E: A solution of 4-chloro-1-(4-fluoro-3-methylbenzyl)-6-methyl-1,3-dihydro-2H-imidazo[4,5-c]pyridin-2-one (0.80 g, 2.6 mmol) was stirred in POCl$_3$ (20 mL) at reflux for 60 hrs. The excess POCl$_3$ was removed under vacuum. The flask containing the residue was placed in an ice-bath. Aqueous (sat) NaHCO$_3$ was added, along with EtOAc until the aqueous layer was neutral. The aqueous layer was then separated and extracted with EtOAc (3×). The combined organics were washed with brine, dried over Na$_2$SO$_4$, concentrated and chromatographed on silica gel (24 g) eluting with a 0-to-2% MeOH/DCM (with 1% conc. NH$_4$OH) gradient to give 2,4-dichloro-1-(4-fluoro-3-methylbenzyl)-6-methyl-1H-imidazo[4,5-c]pyridine, 650 mg (77%) as a clear oil. MS (ESI) (M+H$^+$) m/z=324. LCMS Ret time (UV 215/254): 1.10 min.

Step F: A solution of 2,4-dichloro-1-(4-fluoro-3-methylbenzyl)-6-methyl-1H-imidazo[4,5-c]pyridine (650 mg, 2.01 mmol), N-Boc-piperazine (560 mg, 3.01 mmol), NMP (2.0 mL) and DIEA (0.53 mL, 3.01 mmol) were stirred at 80° C. overnight. LC/MS indicates no remaining SM. The reaction was cooled to RT, and diluted with EtOAc and water. The aqueous layer was separated and extracted with EtOAc (2×). The combined organics were washed with water (2×), brine (2×), dried over Na$_2$SO$_4$, and concentrated to give the crude product residue. The residue was chromatographed on silica gel (24 g) eluting with a 0-to-3% MeOH/DCM (with 1% conc. NH$_4$OH) gradient to give tert-butyl 4-(4-chloro-1-(4-fluoro-3-methylbenzyl)-6-methyl-1H-imidazo[4,5-c]pyridin-2-yl)piperazine-1-carboxylate, 896 mg (94%) light yellow solid. MS (ESI) (M+H$^+$) m/z=474. LCMS Ret time (UV 215/254): 1.16 min.

Step G: A solution of tert-butyl 4-(4-chloro-1-(4-fluoro-3-methylbenzyl)-6-methyl-1H-imidazo[4,5-c]pyridin-2-yl)piperazine-1-carboxylate (346 mg, 0.73 mmol), Pd(OAc)$_2$ (16 mg, 0.07 mmol), P(Cy)$_3$HBF$_4$ (40 mg, 0.11 mmol), K$_3$PO$_4$ (310 mg, 1.46 mmol), 5:1 DME/water (5 mL) and Vinylboronic acid pinacol ester (0.198 mL, 1.2 mmol) was stirred in a reaction vial. The vial was sealed, purged with argon and stirred in an oil-bath at 105° C. overnight. LC/MS indicates the reaction is done. The mixture was diluted with EtOAc and poured through Celite, washing with EtOAc. The eluent was washed with water, brine, dried over Na$_2$SO$_4$, concentrated and chromatographed on silica gel (24 g) eluting with a 0-to-4% MeOH/DCM (with 1% conc. NH$_4$OH) gradient to give tert-butyl 4-(1-(4-fluoro-3-methylbenzyl)-6-methyl-4-vinyl-1H-imidazo[4,5-c]pyridin-2-yl)piperazine-1-carboxylate, 320 mg (94%) as a yellow oil. MS (ESI) (M+H$^+$) m/z=466. LCMS Ret time (UV 215/254): 1.03 min.

Step H: To a stirred solution of tert-butyl 4-(1-(4-fluoro-3-methylbenzyl)-6-methyl-4-vinyl-1H-imidazo[4,5-c]pyridin-2-yl)piperazine-1-carboxylate (320 mg, 0.69 mmol) in 2:1 dioxane/water (7 mL) was added polymer-supported OsO$_4$ (90 mg, 0.018 mmol, 5 wt %). The reaction was stirred for 30 min, then NaIO$_4$ (370 mg, 1.7 mmol) was added. The reaction was stirred at RT for 12 hrs, LC/MS indicates no remaining SM. The resulting slurry was diluted with EtOAc and water, and stirred until homogeneous, then poured through filter paper to remove the polymer. The aqueous layer was separated and extracted with EtOAc (2×). The combined organic layers were washed with brine, dried over Na₂SO₄, concentrated and chromatographed on silica gel (12 g), eluting with a 0-to-3% MeOH/DCM gradient (NO NH₄OH) to give tert-butyl 4-(1-(4-fluoro-3-methylbenzyl)-4-formyl-6-methyl-1H-imidazo[4,5-c]pyridin-2-yl)piperazine-1-carboxylate, 254 mg (79%) as a clear light yellow oil. MS (ESI) (M+H⁺) m/z=486. LCMS Ret time (UV 215/254): 0.95 min.

Step H: A solution of tert-butyl 4-(1-(4-fluoro-3-methylbenzyl)-4-formyl-6-methyl-1H-imidazo[4,5-c]pyridin-2-yl)piperazine-1-carboxylate (60 mg, 0.13 mmol) and isobutylamine (0.015 mL, 0.15 mmol) was stirred in DCE (1 mL) with acetic acid (0.015 mL, 0.26 mmol) for 10 min, then NaBH(AcO)₃ (54 mg, 0.26 mmol) was added. The reaction was stirred at rt for 90 min, LCMS indicates the reaction is complete. The reaction was diluted with water and DCM. The aqueous layer was separated and extracted with DCM (2×). The combined organics were washed with brine, dried over MgSO₄ and concentrated under vacuum. The residue was treated with 5 mL of 20% TFA/DCM for 30 min, then concentrated under vacuum. The residue was purified by acidic reverse-phase HPLC (ACN/water with 0.1% TFA, 5-to-30% gradient over 5 min), then free-based to give the title compound N-((1-(4-fluoro-3-methylbenzyl)-6-methyl-2-(piperazin-1-yl)-1H-imidazo[4,5-c]pyridin-4-yl)methyl)-2-methylpropan-1-amine, 20 mg, (36%) as a light tan solid. ¹H NMR (400 MHz, DMSO-d₆): δ 7.04 (m, 3H), 6.94 (m, 1H), 5.30 (s, 2H), 4.13 (s, 2H), 3.15 (m, 4H), 2.88 (m, 2H), 2.53 (m, 4H), 2.44 (s, 3H), 2.17 (s, 3H), 1.80 (m, 1H), 0.88 (d, J=6.6, Hz, 6H). MS (ESI) (M+H⁺) m/z=425. LCMS Ret time (UV 215/254): 0.70 min.

Example 232: N-((1-(4-fluoro-3-methylbenzyl)-6-methyl-2-(piperazin-1-yl)-1H-imidazo[4,5-c]pyridin-4-yl)methyl)cyclopentanamine

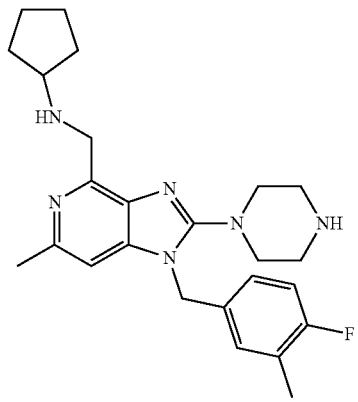 [SMILES: Cc1cc2c(nc(N3CCNCC3)n2Cc2ccc(F)c(C)c2)c(CNC2CCCC2)n1]

The title compound was prepared by a procedure analogous to General Procedure Z: ¹H NMR (400 MHz, DMSO-d₆): δ 7.07 (m, 3H), 6.94 (m, 1H), 5.25 (s, 2H), 4.28 (d, J=6.3, Hz, 2H), 3.41 (m, 1H), 3.23 (m, 4H), 2.93 (m, 2H), 2.57 (m, 2H), 2.48 (s, 3H), 2.17 (s, 3H), 1.90 (m, 2H), 1.49 (m, 6H). MS (ESI) (M+H⁺) m/z=437. LCMS Ret time (UV 215/254): 0.71 min.

Example 233: N-((1-(4-fluoro-3-methylbenzyl)-6-methyl-2-(piperazin-1-yl)-1H-imidazo[4,5-c]pyridin-4-yl)methyl)propan-2-amine

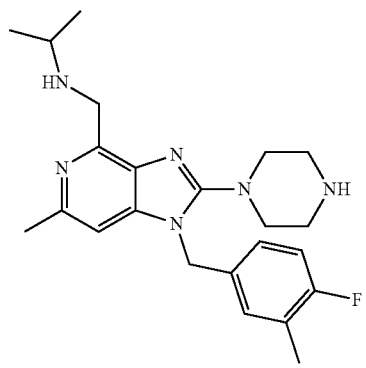 [SMILES: Cc1cc2c(nc(N3CCNCC3)n2Cc2ccc(F)c(C)c2)c(CNC(C)C)n1]

The title compound was prepared by a procedure analogous to General Procedure Z: ¹H NMR (400 MHz, DMSO-d₆): δ 7.20 (s, 1H), 7.07 (m, 2H), 6.92 (m, 1H), 5.27 (s, 2H), 4.42 (s, 2H), 3.40 (m, 1H), 3.20 (m, 4H), 3.13 (m, 1H), 2.58 (m, 4H), 2.50 (s, 3H), 2.17 (s, 3H), 1.29 (d, J=6.5, Hz, 6H). MS (ESI) (M+H⁺) m/z=411. LCMS Ret time (UV 215/254): 0.65 min.

Example 234: N-((1-(4-fluoro-3-methylbenzyl)-6-methyl-2-(piperazin-1-yl)-1H-imidazo[4,5-c]pyridin-4-yl)methyl)-3-methylbutan-1-amine

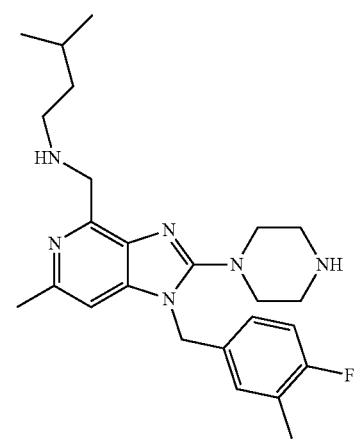 [SMILES: Cc1cc2c(nc(N3CCNCC3)n2Cc2ccc(F)c(C)c2)c(CNCCC(C)C)n1]

The title compound was prepared by a procedure analogous to General Procedure Z: MS (ESI) (M+H⁺) m/z=439. LCMS Ret time (UV 215/254): 0.73 min.

Example 235: 1-(4-fluoro-3-methylbenzyl)-6-methyl-2-(piperazin-1-yl)-4-(piperidin-1-ylmethyl)-1H-imidazo[4,5-c]pyridine

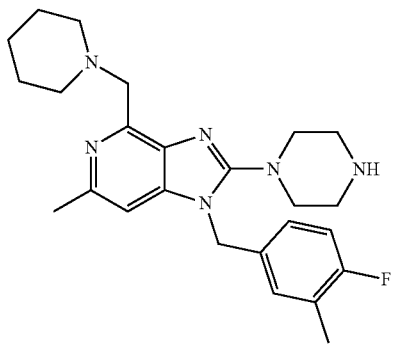 [SMILES: Cc1cc2c(nc(N3CCNCC3)n2Cc2ccc(F)c(C)c2)c(CN2CCCCC2)n1]

The title compound was prepared by a procedure analogous to General Procedure Z: $^1$H NMR (400 MHz, DMSO-$d_6$): δ 7.13 (m, 3H), 7.01 (m, 1H), 5.30 (m, 2H), 4.38 (s, 2H), 3.28 (m, 4H), 3.04 (m, 4H), 2.63 (m, 4H), 2.54 (s, 3H), 2.23 (s, 3H), 1.72 (m, 4H), 1.52 (m, 2H). MS (ESI) (M+H$^+$) m/z=437. LCMS Ret time (UV 215/254): 0.68 min.

Example 236: 1-(4-fluoro-3-methylbenzyl)-6-methyl-2-(piperazin-1-yl)-4-(pyrrolidin-1-ylmethyl)-1H-imidazo[4,5-c]pyridine

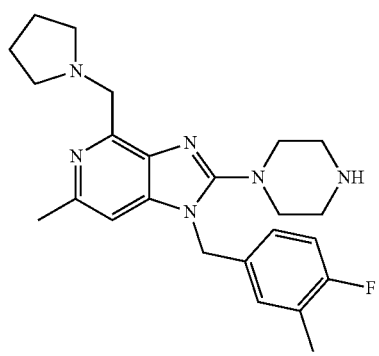 [SMILES: Cc1cc2c(nc(N3CCNCC3)n2Cc2ccc(F)c(C)c2)c(CN2CCCC2)n1]

The title compound was prepared by a procedure analogous to General Procedure Z: MS (ESI) (M+H$^+$) m/z=423. LCMS Ret time (UV 215/254): 0.81 min.

Example 237: 4-((1-(4-fluoro-3-methylbenzyl)-6-methyl-2-(piperazin-1-yl)-1H-imidazo[4,5-c]pyridin-4-yl)methyl)morpholine

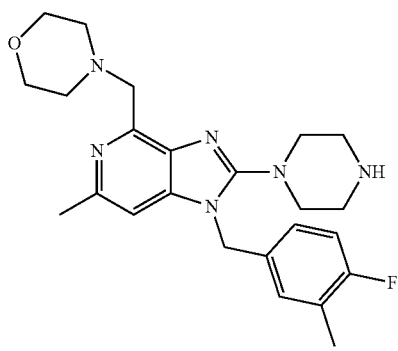 [SMILES: Cc1cc2c(nc(N3CCNCC3)n2Cc2ccc(F)c(C)c2)c(CN2CCOCC2)n1]

The title compound was prepared by a procedure analogous to General Procedure Z: MS (ESI) (M+H$^+$) m/z=439. LCMS Ret time (UV 215/254): 0.65 min.

Example 238: 1-((1-(4-fluoro-3-methylbenzyl)-6-methyl-2-(piperazin-1-yl)-1H-imidazo[4,5-c]pyridin-4-yl)methyl)piperidin-4-ol

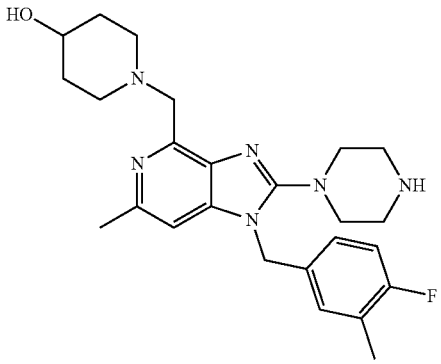 [SMILES: Cc1cc2c(nc(N3CCNCC3)n2Cc2ccc(F)c(C)c2)c(CN2CCC(O)CC2)n1]

The title compound was prepared by a procedure analogous to General Procedure Z: MS (ESI) (M+H$^+$) m/z=453. LCMS Ret time (UV 215/254): 0.62 min.

Example 239: 1-(4-fluoro-3-methylbenzyl)-6-methyl-2-(piperazin-1-yl)-4-vinyl-1H-imidazo[4,5-c]pyridine

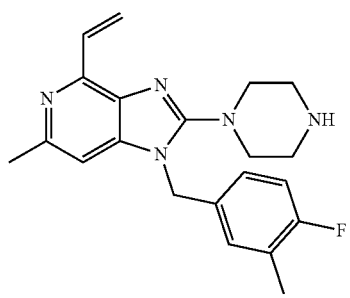

The title compound was prepared by a procedure analogous to General Procedure Y: MS (ESI) (M+H$^+$) m/z=366. LCMS Ret time (UV 215/254): 0.90 min.

Example 240: 1-(1-(4-fluoro-3-methylbenzyl)-6-methyl-1H-imidazo[4,5-b]pyridin-2-yl)piperidin-3-amine

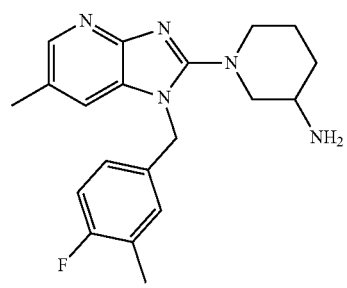

Step A: To a stirred solution of 3-amino-2-chloro-5-methylpyridine (400 mg, 2.81 mmol) and 4-fluoro-3-methylbenzaldehyde (0.38 mL, 3.1 mmol) in EtOAc (4.4 mL) at rt under argon was added TFA (0.43 mL, 5.6 mmol). The solution was stirred 5 min, then NaBH(OAc)$_3$ (713 mg, 3.4 mmol) was added in two portions. The reaction was left to stir overnight. The reaction was diluted with EtOAc, then treated with aqueous 10% NaOH (about 7 mL), until the pH was 8. The aqueous layer was separated and extracted with EtOAc (2×). The combined organic layers were washed with brine, dried over Na$_2$SO$_4$ and concentrated to give 755 mg of crude product as a thick oil. The oil was triturated with MeOH and the resulting solid dried under vacuum to give 2-chloro-N-(4-fluoro-3-methylbenzyl)-5-methylpyridin-3-amine, 527 mg (71%) as a light yellow solid. MS (ESI) (M+H$^+$) m/z=265. LCMS Ret time (UV 215/254): 1.12 min.

Step B: To an oven-dried reaction vial was added 2-chloro-N-(4-fluoro-3-methylbenzyl)-5-methylpyridin-3-amine (400 mg, 1.5 mmol), t-butyl-BrettPhos (37 mg, 0.08 mmol), Pd$_2$(dba)$_3$:CHCl$_3$ (16 mg, 0.02 mmol) and K$_3$PO$_4$ (481 mg, 2.3 mmol). The vial was sealed with a rubber septum and via inserted needle the reaction vial was purged with vacuum/argon (3×). Then formamide (0.09 mL, 2.3 mmol) was added, followed by tert-butanol (7.5 mL), both by needle under argon. The reaction vial was inserted into an oil-bath pre-heated to 110° C. and the reaction was stirred for about 14 hrs. The reaction was cooled to RT, diluted with MeOH (7 mL) and poured through Celite, washing with MeOH. The eluent was concentrated under vacuum. The residue was dissolved in EtOAc and water. The aqueous layer was separated and extracted with EtOAc. The combined organics were washed with brine, dried over Na$_2$SO$_4$, concentrated, and chromatographed on silica gel (40 g), eluting with a 0-to-5% MeOH/DCM (with 1% conc. NH$_4$OH) to give 1-(4-fluoro-3-methylbenzyl)-6-methyl-1H-imidazo[4,5-b]pyridine, 306 mg (79%) as a dark oil. MS (ESI) (M+H$^+$) m/z=256. LCMS Ret time (UV 215/254): 0.75 min.

Step C: To a dried 25 mL RBF with stir-bar was added THF (4.0 mL) and diisopropylamine (0.310 mL, 2.21 mmol). Under argon, the stirred mixture was cooled to −78° C. A solution of 1.6M/in hexanes n-BuLi (1.35 mL, 2.15 mmol) was added slowly, the reaction was stirred 1 hr, then 1-(4-fluoro-3-methylbenzyl)-6-methyl-1H-imidazo[4,5-b]pyridine (297 mg, 01.08 mmol), dissolved in THF (2.5 mL) was added dropwise. The reaction was stirred 1 hr. A solution of hexachloroethane (510 mg, 2.15 mmol) dissolved in THF (1.0 mL), was added slowly. The reaction was stirred at −78° C. for approx. 3 hrs, then warmed slowly to RT and stirred 30 min. LC/MS indicates no remaining SM. The reaction was quenched with aqueous saturated NH$_4$Cl and diluted with water and EtOAc. The aqueous layer was separated and extracted with EtOAc (3×). The combined organics were washed with brine (2×), dried over Na$_2$SO$_4$ and concentrated to give the crude product as a dark oil. The residue was chromatographed on silica gel (40 g) eluting with a 0-to-1.8% gradient of MeOH/DCM (with 1% conc. NH$_4$OH) to give 2-chloro-1-(4-fluoro-3-methylbenzyl)-6-methyl-1H-imidazo[4,5-b]pyridine, 223 mg (71%) as a tan solid. MS (ESI) (M+H$^+$) m/z=290. LCMS Ret time (UV 215/254): 0.87 min.

Step D: A solution of 2-chloro-1-(4-fluoro-3-methylbenzyl)-6-methyl-1H-imidazo[4,5-b]pyridine (70 mg, 0.24 mmol), tert-Butyl N-(3-piperidinyl)-carbamate (97 mg, 0.48 mmol), NMP (0.24 mL) and DIEA (0.084 mL, 0.48 mmol) was added to a microwave reaction vial. The vial was sealed and the reaction was irradiated at 120 degrees for 20 min. LC/MS indicates no remaining SM. The reaction was diluted with EtOAc and water. The aqueous layer was separated and extracted with EtOAc (2×). The combined organics were washed with water (2×), brine (2×), dried over Na$_2$SO$_4$ and concentrated under vacuum. The crude residue was treated with 20% TFA/DCM (5 mL) for about 45 min, then concentrated under vacuum. The residue was chromatographed on silica gel (12 g) eluting with a 0-to-20% gradient of MeOH/DCM (with 1% conc. NH$_4$OH) to give the title compound 1-(1-(4-fluoro-3-methylbenzyl)-6-methyl-1H-imidazo[4,5-b]pyridin-2-yl)piperidin-3-amine, 61 mg (72%) as an oil. $^1$H NMR (400 MHz, DMSO-d$_6$): δ 8.00 (d, J=1.3 Hz, 1H), 7.34 (d, J=1.3 Hz, 1H), 7.05 (m, 2H), 6.95 (m, 1H), 5.21 (s, 2H), 3.48 (m, 1H), 3.33 (m, 1H), 2.83 (m, 2H), 2.67 (m, 1H), 2.28 (s, 3H), 2.17 (d, J=1.3 Hz, 3H), 1.81 (m, 1H), 1.69 (m, 1H), 1.52 (m, 1H), 1.17 (m, 1H). MS (ESI) (M+H$^+$) m/z=354. LCMS Ret time (UV 215/254): 0.71 min.

Example 241: 1-(1-(4-fluoro-3-methylbenzyl)-6-methyl-1H-imidazo[4,5-b]pyridin-2-yl)pyrrolidin-3-amine

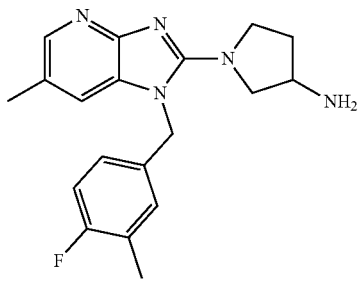

The title compound was prepared by a procedure analogous to General Procedure AA: $^1$H NMR (400 MHz, DMSO-d$_6$): δ 7.88 (d, J=1.2 Hz, 1H), 7.25 (d, J=1.5 Hz, 1H), 7.05 (m, 2H), 7.87 (m, 1H), 5.32 (s, 2H), 3.62 (m, 2H), 3.46 (m, 2H), 3.18 (m, 1H), 2.25 (s, 3H), 2.17 (d, J=1.5 Hz, 3H), 1.90 (m, 1H), 1.58 (m, 1H). MS (ESI) (M+H$^+$) m/z=340. LCMS Ret time (UV 215/254): 0.68 min.

Example 242: 1-(3-chloro-4-fluorobenzyl)-6-methyl-2-(piperazin-1-yl)-1H-imidazo[4,5-b]pyridine

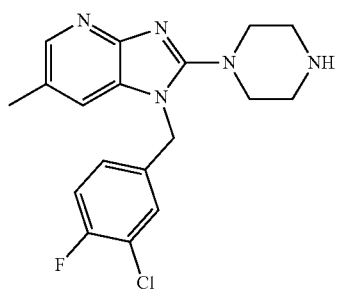

The title compound was prepared by a procedure analogous to General Procedure AA: $^1$H NMR (400 MHz, DMSO-d$_6$): δ 8.03 (d, J=1.4 Hz, 1H), 7.42 (m, 2H), 7.34 (t, J=9.0 Hz, 1H), 7.05 (m, 1H), 5.28 (s, 2H), 3.11 (m, 4H), 2.76 (m, 4H), 2.29 (s, 3H). MS (ESI) (M+H$^+$) m/z=360. LCMS Ret time (UV 215/254): 0.68 min.

Example 243: 1-(3-chloro-4-fluorobenzyl)-6-methyl-1H-imidazo[4,5-b]pyridine

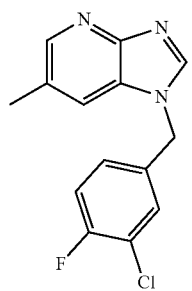

The title compound was prepared by a procedure analogous to General Procedure AA: $^1$H NMR (400 MHz, DMSO-d$_6$): δ 8.57 (s, 1H), 8.25 (d, J=7.4 Hz, 1H), 7.84 (d, J=2.3 Hz), 7.63 (m, 1H), 7.31 (m, 2H), 5.47 (s, 2H), 2.39 (s, 3H). MS (ESI) (M+H$^+$) m/z=276. LCMS Ret time (UV 215/254): 0.76 min.

Example 244: 1-(4-fluoro-3-methylbenzyl)-6-methyl-2-(piperazin-1-yl)-1H-imidazo[4,5-b]pyridine

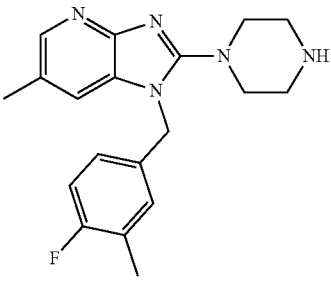

The title compound was prepared by a procedure analogous to General Procedure AA: MS (ESI) (M+H$^+$) m/z=340. LCMS Ret time (UV 215/254): 0.67 min.

Example 245: N$^1$-(1-(4-fluoro-3-methylbenzyl)-6-methyl-1H-imidazo[4,5-b]pyridin-2-yl)ethane-1,2-diamine

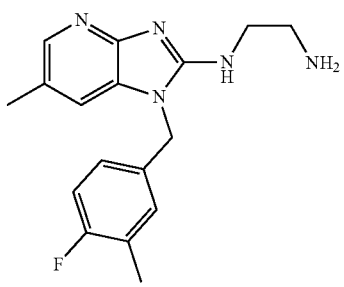

The title compound was prepared by a procedure analogous to General Procedure AA: MS (ESI) (M+H$^+$) m/z=314. LCMS Ret time (UV 215/254): 0.1 min.

Example 246: N$^1$-(1-(3-chloro-4-fluorobenzyl)-6-methyl-1H-imidazo[4,5-b]pyridin-2-yl)ethane-1,2-diamine

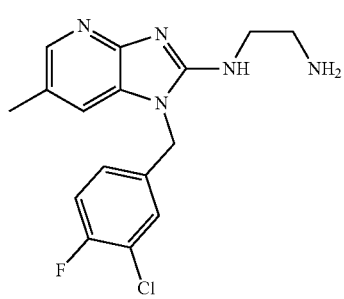

The title compound was prepared by a procedure analogous to General Procedure AA: MS (ESI) (M+H$^+$) m/z=334. LCMS Ret time (UV 215/254): 0.71 min.

Example 247: 1-(3-chloro-4-fluorobenzyl)-6-methyl-N-(pyrrolidin-3-yl)-1H-imidazo[4,5-b]pyridin-2-amine

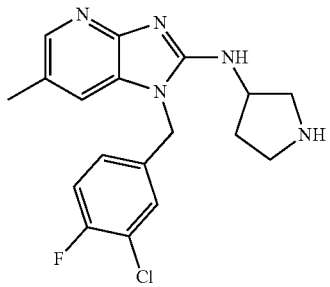

The title compound was prepared by a procedure analogous to General Procedure AA: MS (ESI) (M+H$^+$) m/z=360. LCMS Ret time (UV 215/254): 0.68 min.

Example 248: (1-(1-(4-fluoro-3-methylbenzyl)-6-methyl-1H-imidazo[4,5-b]pyridin-2-yl)azetidin-3-yl)methanamine

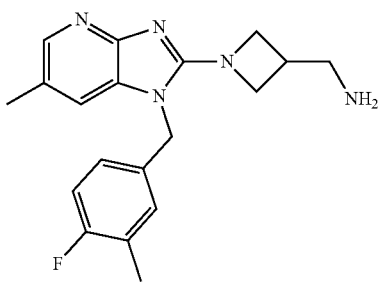

The title compound was prepared by a procedure analogous to General Procedure AA: MS (ESI) (M+H⁺) m/z=340. LCMS Ret time (UV 215/254): 0.72 min.

Example 249: 1-(4-fluorobenzyl)-2-(piperazin-1-yl)-1H-imidazo[4,5-b]pyridine

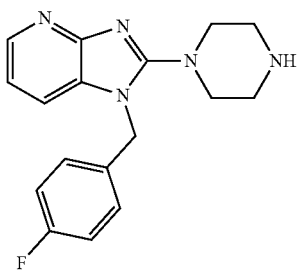

Step A: To a stirred solution of 2-chloro-3-aminopyridine (500 mg, 3.9 mmol), 4-fluorobenzaldehyde (0.45 mL, 4.3 mmol) and EtOAc (6 mL) at rt under argon was added TFA (0.60 mL, 7.8 mmol). The solution was stirred 5 min, then NaBH(OAc)$_3$ (990 mg, 4.7 mmol) was added in two portions. The reaction was stirred overnight. The reaction was treated with aqueous 10% NaOH (5 mL), then the pH was adjusted to 8 by addition of solid NaOH. The aqueous layer was separated and extracted with EtOAc (2×). The combined organic layers were washed with brine, dried over Na$_2$SO$_4$ and concentrated to give 1.0 g of the crude product as a clear, yellow oil. The oil was triturated with MeOH to give 2-chloro-N-(4-fluorobenzyl)pyridin-3-amine, 501 mg (54%) as an off-white solid. MS (ESI) (M+H⁺) m/z=237. LCMS Ret time (UV 215/254): 1.02 min.

Step B: To an oven-dried reaction vial was added 2-chloro-N-(4-fluorobenzyl)pyridin-3-amine (233 mg, 1.0 mmol), t-butyl-BrettPhos (48 mg, 0.10 mmol), Pd$_2$(dba)$_3$: CHCl$_3$ (20 mg, 0.02 mmol) and K$_3$PO$_4$ (314 mg, 1.5 mmol). The vial was sealed with a rubber septum and via inserted needle the reaction vial was purged with vacuum/argon (3×). Then formamide (0.06 mL, 1.48 mmol) was added, followed by tert-butanol (5 mL), both by needle under argon. The reaction vial was inserted into an oil-bath pre-heated to 110° C. and the reaction was stirred for 5 hrs, LC/MS indicates no remaining SM. The reaction was cooled to rt, diluted with MeOH (5 mL) and poured through Celite, washing with MeOH. The eluent was concentrated under vacuum. The residue was dissolved in EtOAc and water. The aqueous layer was separated and extracted with EtOAc. The organics were washed with brine, dried over Na$_2$SO$_4$, concentrated and chromatographed on silica gel (40 g), eluting with a 0-to-5% MeOH/DCM (with 1% conc. NH$_4$OH) to give 1-(4-fluorobenzyl)-1H-imidazo[4,5-b]pyridine, 173 mg (77%) as a dark oil. MS (ESI) (M+H⁺) m/z=228. LCMS Ret time (UV 215/254): 0.26 min.

Step C: To a dried 10 mL RBF with stirbar was added THF (2.8 mL) and diisopropylamine (0.195 mL, 1.40 mmol). Under argon the stirred mixture was cooled to −78° C. A solution of 1.6M/in hexanes n-BuLi (0.85 mL, 1.36 mmol) was added slowly, the reaction was stirred 1 h. A solution of 1-(4-fluorobenzyl)-1H-imidazo[4,5-b]pyridine (154 mg, 0.68 mmol) dissolved in THF (1.65 mL) was added slowly. The reaction was stirred 1 hr. A solution of hexachloroethane (321 mg, 1.36 mmol), dissolved in THF (0.80 mL), was added slowly. The reaction was stirred 3 h at −78° C., warmed to RT and stirred 30 min. LC/MS indicates no remaining SM. The reaction was quenched with aqueous saturated NH$_4$Cl and diluted with water and EtOAc. The aqueous layer was separated and extracted with EtOAc (3×). The combined organics were washed with brine, dried over Na$_2$SO$_4$, concentrated to give 214 mg of crude residue. The residue was chromatographed on silica gel 12 g, eluting with a 0-to-3% MeOH/DCM (with 1% conc. NH$_4$OH) to give 2-chloro-1-(4-fluorobenzyl)-1H-imidazo[4,5-b]pyridine, 84 mg (47%) as a tan solid. MS (ESI) (M+H⁺) m/z=262. LCMS Ret time (UV 215/254): 0.76 min.

Step D: A solution of 2-chloro-1-(4-fluorobenzyl)-1H-imidazo[4,5-b]pyridine (40 mg, 0.15 mmol), piperazine (26 mg, 0.31 mmol) and NMP (0.75 mL) was added to a reaction vial. The vial was sealed and the reaction stirred at 110 degrees for 45 min. LC/MS indicates no remaining SM. The reaction mixture was diluted with DMSO (0.3 mL), filtered and purified by basic reverse-phase HPLC (ACN/water with 0.05% conc. NH$_4$OH) to give the title 1-(4-fluorobenzyl)-2-(piperazin-1-yl)-1H-imidazo[4,5-b]pyridine compound, 35 mg (73%). $^1$H NMR (400 MHz, DMSO-d$_6$): δ 8.16 (dd, J=4.9 and 1.5 Hz, 1H), 7.51 (dd, J=7.8 and 1.5 Hz, 1H), 7.12 (m, 4H), 6.98 (dd, J=7.8 and 4.9 Hz, 1H), 5.29 (s, 2H), 3.16 (m, 4H), 2.78 (m, 4H). MS (ESI) (M+H⁺) m/z=312. LCMS Ret time (UV 215/254): 0.46 min.

Example 250: N$^1$-(1-(4-fluorobenzyl)-1H-imidazo[4,5-b]pyridin-2-yl)ethane-1,2-diamine

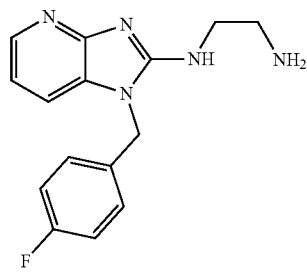

The title compound was prepared by a procedure analogous to General Procedure AB: $^1$H NMR (400 MHz, DMSO-d$_6$): δ 7.94 (dd, J=5.0 and 1.5 Hz, 1H), 7.34 (dd, J=7.6 and 1.4 Hz, 1H), 7.12 (m, 5H), 6.77 (dd, J=7.6 and 5.0 Hz, 1H), 5.26 (s, 2H), 3.38 (t, J=6.3 Hz, 2H), 2.74 (t, J=6.3 Hz, 2H). MS (ESI) (M+H⁺) m/z=286. LCMS Ret time (UV 215/254): 0.54 min.

Example 251: 1-(4-chlorobenzyl)-2-(piperazin-1-yl)-1H-imidazo[4,5-b]pyridine

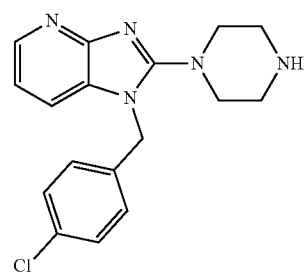

The title compound was prepared by a procedure analogous to General Procedure AB: MS (ESI) (M+H⁺) m/z=328. LCMS Ret time (UV 215/254): 0.59 min.

Example 252: 2-chloro-1-(4-fluorobenzyl)-1H-imidazo[4,5-b]pyridine

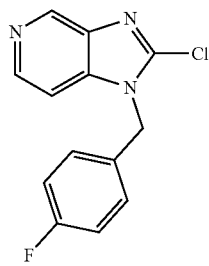

The title compound was prepared by a procedure analogous to General Procedure AB: MS (ESI) (M+H⁺) m/z=262. LCMS Ret time (UV 215/254): 0.76 min.

Example 253: 1-(4-fluorobenzyl)-1H-imidazo[4,5-b]pyridine

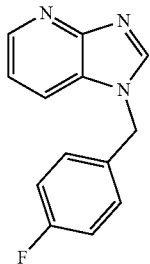 [SMILES: Fc1ccc(Cn2cnc3ncccc32)cc1]

The title compound was prepared by a procedure analogous to General Procedure AB: MS (ESI) (M+H⁺) m/z=228. LCMS Ret time (UV 215/254): 0.26 min.

Example 254: 2-chloro-1-(4-chlorobenzyl)-1H-imidazo[4,5-b]pyridine

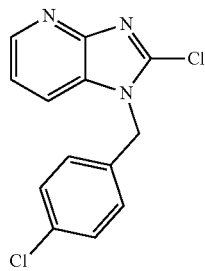 [SMILES: Clc1ccc(Cn2c(Cl)nc3ncccc32)cc1]

The title compound was prepared by a procedure analogous to General Procedure AB: MS (ESI) (M+H⁺) m/z=278. LCMS Ret time (UV 215/254): 0.87 min.

Example 255: 1-(4-chlorobenzyl)-1H-imidazo[4,5-b]pyridine

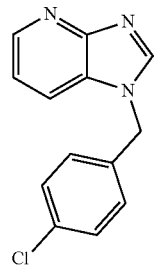 [SMILES: Clc1ccc(Cn2cnc3ncccc32)cc1]

The title compound was prepared by a procedure analogous to General Procedure AB: MS (ESI) (M+H⁺) m/z=244. LCMS Ret time (UV 215/254): 0.71 min.

Example 256: 1-(3-chloro-4-fluorobenzyl)-5-methyl-2-(piperazin-1-yl)-1H-imidazo[4,5-b]pyridine

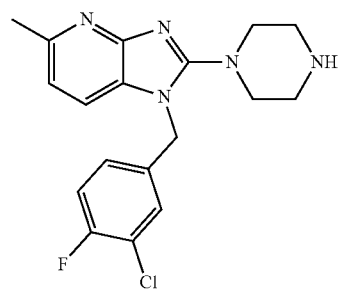 [SMILES: Cc1ccc2c(n1)nc(N1CCNCC1)n2Cc1ccc(F)c(Cl)c1]

Step A: To a stirred solution of 3-amino-2-chloro-6-methylpyridine (1 g, 7 mmol), 4-fluoro-3-chlorobenzaldehyde (0.98 mL, 8.4 mmol) and EtOAc (11 mL) at RT under argon was added TFA (1.1 mL, 14 mmol). The solution was stirred 5 min, then NaBH(OAc)₃ (1.93 g, 9.1 mmol) was added in two portions. LC/MS indicates the reaction is complete after about 60 min. The reaction was diluted with EtOAc and treated with aqueous 10% NaOH (about 14 mL), until the pH was about 8. The aqueous layer was separated and extracted with EtOAc (2×). The combined organic layers were washed with brine, dried over Na₂SO₄ and concentrated to give the crude product as a dark thick oil. The material was triturated with MeOH and the solid dried under vacuum to give 2-chloro-N-(3-chloro-4-fluorobenzyl)pyridin-3-amine, 863 mg (43%) of the product as a light tan solid. The MeOH layer was concentrated and triturated with EtOH, then MeOH to give 375 mg (19%) additional material. MS (ESI) (M+H⁺) m/z=285. LCMS Ret time (UV 215/254): 1.10 min.

Step B: To an oven-dried reaction vial was added 2-chloro-N-(3-chloro-4-fluorobenzyl)pyridin-3-amine (775 mg, 2.72 mmol), Me4-t-butylXPhos (65 mg, 0.14 mmol), Pd₂(dba)₃:CHCl₃ (28 mg, 0.03 mmol) and K₃PO₄ (865 mg, 4.1 mmol). The vial was sealed with a rubber septum and via inserted needle the reaction vial was purged with vacuum/argon (3×). Then formamide (0.165 mL, 4.1 mmol) was added, followed by tert-butanol (13 mL), both by needle under argon. The reaction vial was inserted into an oil-bath pre-heated to 110° C. and the reaction was stirred for approximately 24 hrs. The reaction was cooled to rt, diluted with MeOH (15 mL) and poured through Celite, washing with MeOH. The eluent was concentrated under vacuum. The residue was dissolved in EtOAc and water. The aqueous layer was separated and extracted with EtOAc. The organics were washed with brine, dried over $Na_2SO_4$ and concentrated under vacuum to give 875 mg of crude residue. The residue was material chromatographed on silica gel (80 g), eluting with a 0-to-7% MeOH/DCM (with 1% conc. $NH_4OH$) to give 1-(3-chloro-4-fluorobenzyl)-1H-imidazo[4,5-b]pyridine, 185 mg (25%) as a tan solid. MS (ESI) $(M+H^+)$ m/z=276. LCMS Ret time (UV 215/254): 0.73 min.

Step C: To a dried 10 mL RBF with stir bar was added THF (2.4 mL) and diisopropylamine (0.190 mL, 1.33 mmol). Under argon the stirred mixture was cooled to −78° C. A solution of 1.6M/in hexanes n-BuLi (0.81 mL, 1.29 mmol) was added slowly. The reaction was stirred 1 hr. A solution of 1-(3-chloro-4-fluorobenzyl)-1H-imidazo[4,5-b]pyridine (178 mg, 0.65 mmol) dissolved in THF (2.0 mL) was added slowly. The reaction was stirred 1 hr, then hexachloroethane (306 mg, 1.3 mmol) dissolved in THF (1.0 mL), was added slowly. The reaction was stirred at −78° C. for approx. 3 hrs, then warmed slowly to rt and stirred overnight. The reaction was quenched with aqueous saturated $NH_4Cl$ and diluted with water and EtOAc. The aqueous layer was separated and extracted with EtOAc (3×). The combined organics were washed with brine (2×), dried over $Na_2SO_4$ and concentrated to give the crude product as a dark oil. Chromatography on silica gel (24 g), eluting with a 0-to-20% MeOH/DCM (1% conc. $NH_4OH$) gave 2-chloro-1-(3-chloro-4-fluorobenzyl)-1H-imidazo[4,5-b]pyridine, 150 mg (75%) as a dark oil. MS (ESI) $(M+H^+)$ m/z=310. LCMS Ret time (UV 215/254): 0.85 min.

Step D: A solution of 2-chloro-1-(3-chloro-4-fluorobenzyl)-1H-imidazo[4,5-b]pyridine (75 mg, 0.24 mmol), piperazine (22 mg, 0.48 mmol) and DMSO (0.80 mL) was added to a reaction vial. The vial was sealed and the reaction stirred at 55 degrees overnight. LC/MS indicates no remaining SM. The reaction mixture was diluted with DMSO (0.3 mL), filtered and purified by basic reverse-phase HPLC (15-45% ACN/water with 0.05% conc. $NH_4OH$ gradient over 8 min) to give the title compound 1-(3-chloro-4-fluorobenzyl)-5-methyl-2-(piperazin-1-yl)-1H-imidazo[4,5-b]pyridine, 26 mg (30%) as a tan solid. $^1H$ NMR (400 MHz, DMSO-$d_6$): δ 7.41 (m, 2H), 7.33 (t, J=9.0 Hz, 1H), 7.05 (m, 1H), 6.86 (d, J=8.0 Hz, 1H), 5.27 (s, 2H), 3.13 (m, 4H), 2.77 (m, 4H), 2.44 (s, 3H). MS (ESI) $(M+H^+)$ m/z=360. LCMS Ret time (UV 215/254): 0.66 min.

Example 257: $N^1$-(1-(3-chloro-4-fluorobenzyl)-5-methyl-1H-imidazo[4,5-b]pyridin-2-yl)ethane-1,2-diamine

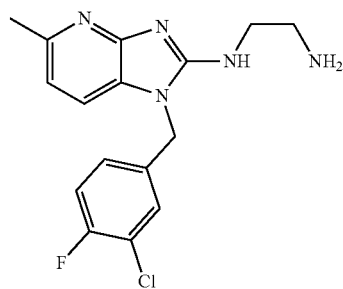 [SMILES: Cc1ccc2c(n1)nc(NCCN)n2Cc1ccc(F)c(Cl)c1]

The title compound was prepared by a procedure analogous to General Procedure AC: $^1H$ NMR (400 MHz, DMSO-$d_6$): δ 7.41 (m, 1H), 7.33 (t, J=8.9 Hz, 1H), 7.28 (d, J=7.8 Hz, 1H), 7.09 (m, 2H), 6.65 (d, J=7.8 Hz, 1H), 5.23 (s, 2H), 3.36 (t, J=6.2 Hz, 2H), 2.72 (t, J=6.3 Hz, 2H), 2.37 (s, 3H). MS (ESI) $(M+H^+)$ m/z=334. LCMS Ret time (UV 215/254): 0.66 min.

Example 258: 3-(4-fluoro-3-methylbenzyl)-2-(piperazin-1-yl)-5-((1,1,1-trifluoropropan-2-yl)oxy)-3H-imidazo[4,5-b]pyridine

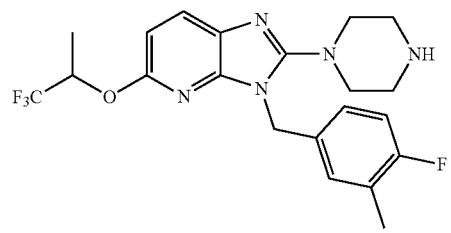 [SMILES: Cc1cc(Cn2c(N3CCNCC3)nc3ccc(OC(C)C(F)(F)F)nc32)ccc1F]

Step A: To a stirred solution of 2-amino-6-chloro-3-nitropyridine (535 mg, 3.1 mmol) in DMF (5 mL) was added 4-fluoro-3-methylbenzyl bromide (657 mg, 3.2 mmol). The mixture was cooled to 0° C. and NaH 78 mg, 3.2 mmol) was added in 3 portions 5 min apart. The reaction was allowed to warm slowly to RT and stirred overnight. The reaction was diluted with EtOAc and water. The aqueous layer was separated and extracted with EtOAc (3×). The combined organics were washed with water (2×), brine (2×), dried over $Na_2SO_4$ and concentrated under vacuum. The residue was chromatographed on silica gel (80 g), eluting with a 1-to-5% EtOAc/hexane gradient to give 6-chloro-N-(4-fluoro-3-methylbenzyl)-3-nitropyridin-2-amine, 808 mg (89%) as a yellow solid. MS (ESI) $(M+H^+)$ m/z=296. LCMS Ret time (UV 215/254): 1.24 min.

Step B: To a stirred solution of 1,1,1-trifluoro-2-propanol (0.092 mL, 1.0 mmol) in DMF (9 mL) at 0° C. under argon was added NaH (50 mg, 2.03 mmol). The reaction was stirred 5 min, then 6-chloro-N-(4-fluoro-3-methylbenzyl)-3-nitropyridin-2-amine (545 mg, 1.84 mmol) was added. The reaction was allowed to warm slowly to rt and was stirred overnight. The reaction was diluted with EtOAc and water. The aqueous layer was separated and extracted with EtOAc (3×). The combined organics were washed with water (2×), brine (2×), dried over $Na_2SO_4$ and concentrated under vacuum. The residue was chromatographed on silica gel (40 g), eluting with a 0-to-5% EtOAc/hexane gradient to give N-(4-fluoro-3-methylbenzyl)-3-nitro-6-((1,1,1-trifluoropropan-2-yl)oxy)pyridin-2-amine, 673 mg (98%) as a yellow solid. MS (ESI) $(M+H^+)$ m/z=374. LCMS Ret time (UV 215/254): 1.35 min.

Step D: A solution of N-(4-fluoro-3-methylbenzyl)-3-nitro-6-((1,1,1-trifluoropropan-2-yl)oxy)pyridin-2-amine (609 mg, 1.63 mmol) and 10% Pd/carbon (87 mg, 0.08 mmol) were stirred in 1/1 MeOH:THF (40 mL) at rt. The flask was purged with argon/vacuum (3×), then $H_2$/vacuum (3×). The mixture was treated with $H_2$ at 1 atm (balloon) for about an hour. LC/MS indicate no remaining SM. The reaction mixture was poured through Celite, washing with MeOH. The filtrate was concentrated under vacuum to give $N^2$-(4-fluoro-3-methylbenzyl)-6-((1,1,1-trifluoropropan-2- yl)oxy)pyridine-2,3-diamine, 550 mg (98%) as a dark oil. MS (ESI) (M+H⁺) m/z=344. LCMS Ret time (UV 215/254): 0.98 min.

Step E: A solution of N²-(4-fluoro-3-methylbenzyl)-6-((1,1,1-trifluoropropan-2-yl)oxy)pyridine-2,3-diamine (550 mg, 1.6 mmol) in formic acid (3 mL) was stirred at 90° C. for 45 min. LC/MS indicates the reaction is done. The reaction was poured into ice. The ice was allowed to melt and aqueous saturated Na₂CO₃ was slowly added until the solution was basic. The solution was then extracted with EtOAc (3×). The combined organics were washed with brine, dried over Na₂SO₄ and concentrated under vacuum. The residue was chromatographed on silica gel (24 g), eluting with a 0-to-2% MeOH/DCM (with 1% conc. NH₄OH) gradient to give 3-(4-fluoro-3-methylbenzyl)-5-((1,1,1-trifluoropropan-2-yl)oxy)-3H-imidazo[4,5-b]pyridine, 480 mg (85%) as a light tan solid. MS (ESI) (M+H⁺) m/z=354. LCMS Ret time (UV 215/254): 1.00 min.

Step F: To a dried 25 mL RBF with stirbar was added THF (7.0 mL) and diisopropylamine (0.410 mL, 2.9 mmol). Under argon, the stirred mixture was cooled to −78° C. A solution of 2.5M/in hexanes n-BuLi (1.13 mL, 2.8 mmol) was added slowly. The reaction was stirred 1 hr. A solution of 3-(4-fluoro-3-methylbenzyl)-5-((1,1,1-trifluoropropan-2-yl)oxy)-3H-imidazo[4,5-b]pyridine (500 mg, 1.42 mmol), dissolved in THF (5 mL), was added dropwise. The reaction was stirred 1 hr. A solution of hexachloroethane (670 mg, 2.8 mmol), dissolved in THF (2.0 mL), was added slowly. The reaction was stirred at −78° C. for approx. 2 hrs, then warmed slowly to rt and stirred overnight. LC/MS indicates no remaining SM. The reaction was quenched with aqueous saturated NH₄Cl and diluted with water and EtOAc. The aqueous layer was separated and extracted with EtOAc (2×). The combined organics were washed with brine (2×), dried over Na₂SO₄, and concentrated under vacuum. The residue was chromatographed on silica gel (40 g) eluting with a 0-to-10% EtOAc/hexane gradient to give 2-chloro-3-(4-fluoro-3-methylbenzyl)-5-((1,1,1-trifluoropropan-2-yl)oxy)-3H-imidazo[4,5-b]pyridine, 459 mg (84%) as a grey solid. MS (ESI) (M+H⁺) m/z=388. LCMS Ret time (UV 215/254): 1.31 min.

Step G: A solution of 2-chloro-3-(4-fluoro-3-methylbenzyl)-5-((1,1,1-trifluoropropan-2-yl)oxy)-3H-imidazo[4,5-b]pyridine (70 mg, 0.18 mmol), piperazine (32 mg, 0.36 mmol) and NMP (0.90 mL) were added to a reaction vial. The vial was sealed and the reaction was heated at 90° C. for 45 min. LC/MS indicates mainly SM, so the temperature was increased to 110° C. for 2 hrs, then additional piperazine (31 mg) was added and the reaction stirred at 125° C. for 2 hrs. The reaction was diluted with EtOAc and water. The aqueous layer was separated and extracted with EtOAc (2×). The combined organics were washed with water (2×), brine (2×), dried over Na₂SO₄ and concentrated under vacuum. The crude residue was purified by acidic reverse-phase HPLC (10-to-50% ACN/water with 0.1% TFA over 5 min), then free-based, to give the title compound 3-(4-fluoro-3-methylbenzyl)-2-(piperazin-1-yl)-5-((1,1,1-trifluoropropan-2-yl)oxy)-3H-imidazo[4,5-b]pyridine, 44 mg (55%) as a tan solid. ¹H NMR (400 MHz, DMSO-d₆): δ 7.78 (d, J=8.4 Hz, 1H), 7.24 (m, 1H), 7.04 (m, 2H), 6.65 (d, J=8.4 Hz, 1H), 5.74 (m, 1H), 5.21 (s, 2H), 3.11 (m, 4H), 2.87 (m, 4H), 2.15 (d, J=1.6 Hz, 3H), 1.38 (d, J=6.5 Hz, 3H). MS (ESI) (M+H⁺) m/z=438. LCMS Ret time (UV 215/254): 0.94 min.

Example 259: (1-(3-(4-fluoro-3-methylbenzyl)-5-((1,1,1-trifluorpropan-2-yl)oxy)-3H-imidazo[4,5-b]pyridin-2-yl)azetidin-3-yl)methanamine

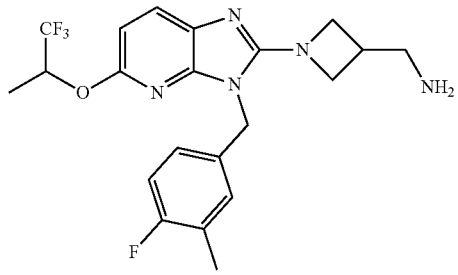 [SMILES: Cc1cc(Cn2c(N3CC(CN)C3)nc3ccc(OC(C)C(F)(F)F)nc32)ccc1F]

The title compound was prepared by a procedure analogous to General Procedure AD: ¹H NMR (400 MHz, DMSO-d₆): δ 7.32 (m, 1H), 7.22 (m, 1H), 7.14 (d, J=8.1 Hz, 1H), 7.02 (m, 1H), 6.34 (d, J=8.1 Hz, 1H), 5.70 (m 1H), 4.88 (s, 2H), 3.91 (m, 1H), 3.48 (m, 2H), 3.11 (m, 2H), 2.63 (m, 2H), 2.16 (d, J=1.5 Hz, 3H), 1.37 (d, J=6.4 Hz, 3H). MS (ESI) (M+H⁺) m/z=438. LCMS Ret time (UV 215/254): 0.91 min.

Example 260: N-(azetidin-3-ylmethyl)-3-(4-fluoro-3-methylbenzyl)-5-((1,1,1-trifluoropropan-2-yl)oxy)-3H-imidazo[4,5-b]pyridin-2-amine

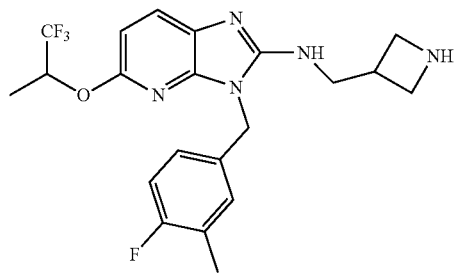 [SMILES: Cc1cc(Cn2c(NCC3CNC3)nc3ccc(OC(C)C(F)(F)F)nc32)ccc1F]

The title compound was prepared by a procedure analogous to General Procedure AD: MS (ESI) (M+H⁺) m/z=438. LCMS Ret time (UV 215/254): 0.88 min.

Example 261: 1-(3-(4-fluoro-3-methylbenzyl)-5-((1,1,1-trifluoroprpan-2-yl)oxy)-3H-imidazo[4,5-b]pyridin-2-yl)piperidin-3-amine

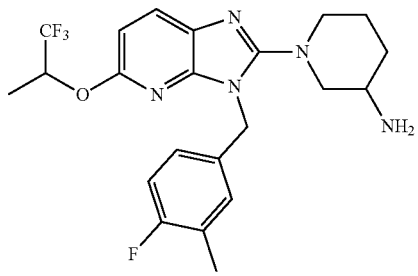 [SMILES: Cc1cc(Cn2c(N3CCCC(N)C3)nc3ccc(OC(C)C(F)(F)F)nc32)ccc1F]

The title compound was prepared by a procedure analogous to General Procedure AD: MS (ESI) (M+H⁺) m/z=452. LCMS Ret time (UV 215/254): 0.94 min.

Example 262: 2-((2-(3-(aminomethyl)azetidin-1-yl)-3-(4-fluoro-3-methylbenzyl)-3H-imidazo[4,5-b]pyridin-5-yl)oxy)-N,N-dimethylethan-1-amine

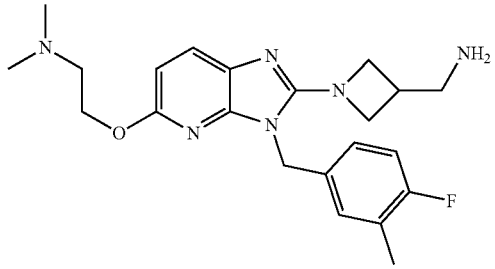 [SMILES: Cc1cc(Cn2c(N3CC(CN)C3)nc3ccc(OCCN(C)C)nc32)ccc1F]

The title compound was prepared by a procedure analogous to General Procedure AD: MS (ESI) (M+H⁺) m/z=413. LCMS Ret time (UV 215/254): 0.57 min.

Example 263: N-(azetidin-3-ylmethyl)-5-(2-(dimethylamino)ethoxy)-3-(4-fluoro-3-methylbenzyl)-3H-imidazo[4,5-b]pyridin-2-amine

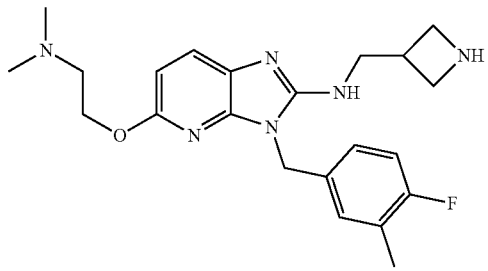 [SMILES: Cc1cc(Cn2c(NCC3CNC3)nc3ccc(OCCN(C)C)nc32)ccc1F]

The title compound was prepared by a procedure analogous to General Procedure AD: MS (ESI) (M+H⁺) m/z=413. LCMS Ret time (UV 215/254): 0.62 min.

Example 264: 4-[1-[(3-chloro-4-fluorophenyl)methyl]-2-piperazin-1-ylbenzimidazol-4-yl]phenol

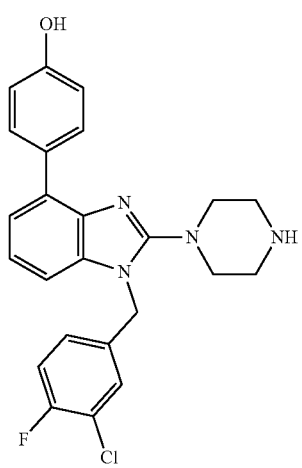 [SMILES: Oc1ccc(-c2cccc3c2nc(N2CCNCC2)n3Cc2ccc(F)c(Cl)c2)cc1]

The title compound was prepared by a procedure analogous to General Procedure F: ¹H NMR (400 MHz, DMSO-d₆) δ 7.80 (d, J=8.8 Hz, 2H), 7.39 (dd, J=7.2, 2.0 Hz, 1H), 7.33-7.31 (m, 1H), 7.26-7.20 (m, 2H), 7.15-7.13 (m, 2H), 6.92 (d, J=8.8 Hz, 2H), 5.41 (s, 2H), 3.56-3.53 (m, 4H), 3.45-3.43 (m, H). MS (ESI) (M+H⁺) m/z=437.40. LCMS Ret time (UV 214/254): 0.892 min.

Example 265: 1-[(3-chloro-4-fluorophenyl)methyl]-5,6-dimethyl-2-piperazin-1-yl-4-pyridin-3-ylbenzimidazole

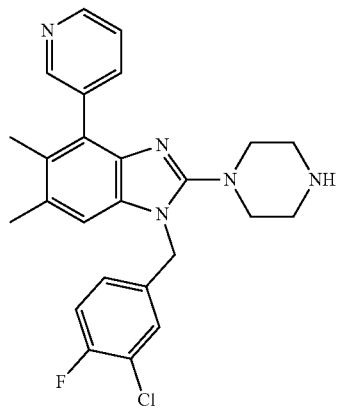 [SMILES: Cc1cc2c(nc(N3CCNCC3)n2Cc2ccc(F)c(Cl)c2)c(-c2cccnc2)c1C]

The title compound was prepared by a procedure analogous to General Procedure H: ¹H NMR (400 MHz, DMSO-d₆) δ 8.51-8.49 (m, 2H), 7.82-7.80 (m, 1H), 7.52 (dd, J=5.2, 2.0 Hz, 1H), 7.29 (dd, J=6.8, 2.0 Hz, 1H), 7.16 (t, J=8.4 Hz, 1H), 7.07-7.03 (m, 2H), 5.29 (s, 2H), 3.26-3.23 (m, 4H), 3.17-3.15 (m, 4H), 2.33 (s, 3H), 2.09 (s, 3H). MS (ESI) (M+H⁺) m/z=450.92. LCMS Ret time (UV 214/254): 0.71 min.

Example 266: 1-[(3-chloro-4-fluorophenyl)methyl]-4-(2-phenylmethoxypyridin-3-yl)-2-piperazin-1-ylbenzimidazole

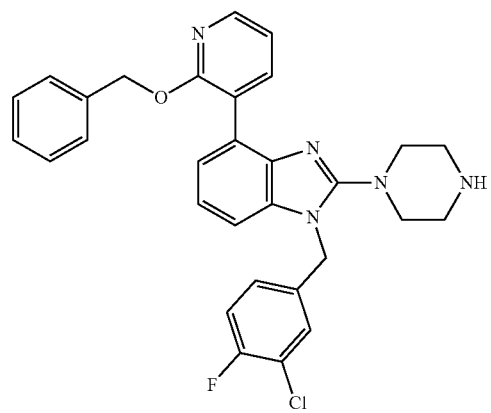 [SMILES: Fc1ccc(Cn2c(N3CCNCC3)nc3c(-c4cccnc4OCc4ccccc4)cccc32)cc1Cl]

The title compound was prepared by a procedure analogous to General Procedure F: MS (ESI) (M+H⁺) m/z=544.10. LCMS Ret time (UV 214/254): 1.51 min.

Example 267: 4-(2-chlorophenyl)-1-[(4-fluoro-3,5-dimethylphenyl)methyl]-6-methyl-2-piperazin-1-ylbenzimidazole

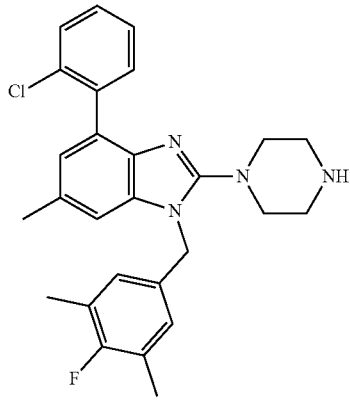 [SMILES: Cc1cc(-c2ccccc2Cl)c2nc(N3CCNCC3)n(Cc3cc(C)c(F)c(C)c3)c2c1]

The title compound was prepared by a procedure analogous to General Procedure I: $^1$H NMR (400 MHz, DMSO-$d_6$) δ 7.57 (dd, J=7.6, 1.6 Hz, 1H), 7.48 (dd, J=7.6, 1.2 Hz, 1H), 7.34-7.27 (m, 2H), 7.09 (s, 1H), 6.87 (s, 1H), 6.81 (s, 1H), 6.79 (s, 1H), 5.07 (s, 2H), 3.37-3.34 (m, 4H), 3.13-3.11 (m, 4H), 2.44 (s, 3H), 2.22 (s, 3H), 2.22 (s 3H). MS (ESI) (M+H$^+$) m/z=463.73. LCMS Ret time (UV 214/254): 1.97 min.

Example 268: 1-(3-chloro-4-fluorobenzyl)-5,6-dimethyl-4-(3-methylthiophen-2-yl)-2-(piperazin-1-yl)-1H-benzo[d]imidazole

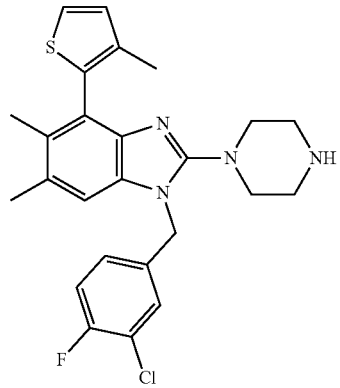 [SMILES: Cc1ccsc1-c1c(C)c(C)cc2c1nc(N1CCNCC1)n2Cc1ccc(F)c(Cl)c1]

The title compound was prepared by a procedure analogous to General Procedure H: $^1$H NMR (400 MHz, DMSO-$d_6$) δ 7.29 (d, J=6.8 Hz, 1H), 7.23 (dd, J=6.8, 2.0 Hz, 1H), 7.11 (t, J=8.4 Hz, 1H), 7.015-6.99 (m, 1H), 6.96 (d, J=4.8 Hz, 1H), 6.85 (s, 1H), 5.11 (s, 2H), 3.39-3.37 (m, 4H), 3.22-3.20 (m, 4H), 2.35 (s, 3H), 2.15 (s, 3H), 2.02 (s, 3H). MS (ESI) (M+H$^+$) m/z=468.96. LCMS Ret time (UV 214/254): 1.60 min.

Example 269: 1-[(3-chloro-4-fluorophenyl)methyl]-5,6-dimethyl-N-piperidin-4-ylbenzimidazol-2-amine

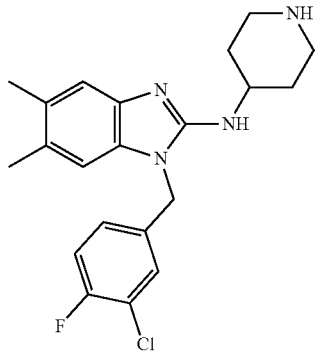 [SMILES: Cc1cc2nc(NC3CCNCC3)n(Cc3ccc(F)c(Cl)c3)c2cc1C]

The title compound was prepared, as its trifluoroacetic acid salt, by a procedure analogous to General Procedure E: MS (ESI) (M+H$^+$) m/z=387.10. LCMS Ret time (UV 214/254): 1.15 min.

Example 270: (S)-1-(1-(3-chlorobenzyl)-6-methyl-1H-benzo[d]imidazol-2-yl)-2-methylpropan-1-amine

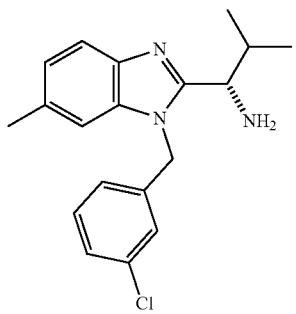 [SMILES: Cc1ccc2nc([C@@H](N)C(C)C)n(Cc3cccc(Cl)c3)c2c1]

To a solution of L-Boc-valine (111 mg, 0.51 mmol) in 3 mL of DCM was added 60 mg (0.21 mmol) of HOBt and 100 mg (0.47 mmol) of EDCI, followed by a mixture of N$^1$-(3-chlorobenzyl)-5-methylbenzene-1,2-diamine (105 mg, 0.43 mmol), prepared by a procedure analogous to that used to prepare Example 60, step B, in 1 mL of DCM, and 150 μL (0.85 mmol) of DIPEA. The reaction mixture was allowed to stir at rt overnight, then quenched by the addition of water and extracted with DCM. The combined organic layers were dried over MgSO$_4$ and the solvents were removed under reduced pressure. The residue was taken up in AcOH and heated at 75° C. overnight. The solvents were removed under reduced pressure and the residue was taken up in a mixture of 2 mL of DCM and 1 mL of TFA and allowed to stir at rt for 3 h. The solvent was removed under reduced pressure and the residue was purified by reverse phase HPLC to give (S)-1-(1-(3-chlorobenzyl)-6-methyl-1H-benzo[d]imidazol-2-yl)-2-methylpropan-1-amine as its trifluoroacetic acid salt: $^1$H NMR (400 MHz, DMSO-$d_6$) δ 8.85 (brs, 3H), 7.62 (d, J=8.0 Hz, 1H), 7.37-7.29 (m, 4H), 7.15-7.13 (m, 2H), 5.70 5.59 (ABq, J$_{AB}$=16.8 Hz, 2H), 2.39 (s, 3H), 2.30-2.28 (m, 1H), 0.98 (d, J=6.0 Hz, 3H), 0.79 (d, J=6.0 Hz, 3H). MS (ESI) (M+H$^+$) m/z=328.20. LCMS Ret time (UV 214/254): 1.34 min.

Example 271: (2S)-2-amino-2-[1-[(3-chlorophenyl)methyl]-6-methylbenzimidazol-2-yl]ethanol

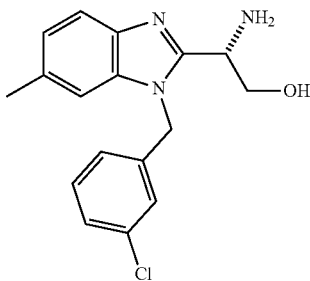 [SMILES: Cc1ccc2nc([C@H](N)CO)n(Cc3cccc(Cl)c3)c2c1]

The title compound was prepared, as its trifluoroacetic acid salt, by a procedure analogous to that used to prepare Example 270: MS (ESI) (M+H$^+$) m/z=316.10. LCMS Ret time (UV 214/254): 1.12 min.

Example 272: 4-[(2S)-2-amino-2-[1-[(4-fluorophenyl)methyl]-6-methylbenzimidazol-2-yl]ethyl]phenol

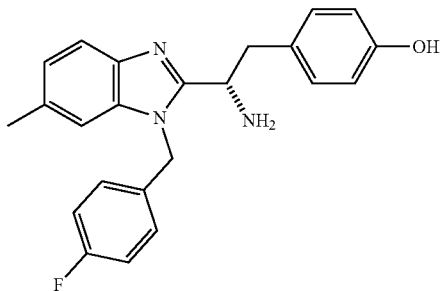 [SMILES: Cc1ccc2nc([C@@H](N)Cc3ccc(O)cc3)n(Cc3ccc(F)cc3)c2c1]

The title compound was prepared, as its hydrochloric acid salt, by a procedure analogous to that used to prepare Example 270: MS (ESI) (M+H$^+$) m/z=376.20. LCMS Ret time (UV 214/254): 1.16 min.

Example 273: (1S)-1-[1-[(4-fluorophenyl)methyl]-6-methylbenzimidazol-2-yl]-2-(1H-imidazol-4-yl)ethanamine VU0604222-1 AJL-2-66B

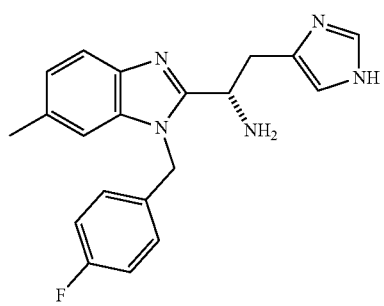 [SMILES: Cc1ccc2nc([C@@H](N)Cc3c[nH]cn3)n(Cc3ccc(F)cc3)c2c1]

The title compound was prepared, as its trifluoroacetic acid salt, by a procedure analogous to that used to prepare Example 270: MS (ESI) (M+H$^+$) m/z=350.10. LCMS Ret time (UV 214/254): 1.02 min.

Example 274: (5S)-5-[1-[(3-chloro-4-fluorophenyl)methyl]-6-methylbenzimidazol-2-yl]pyrrolidin-2-one VU0604400-1 AJL-2-71B

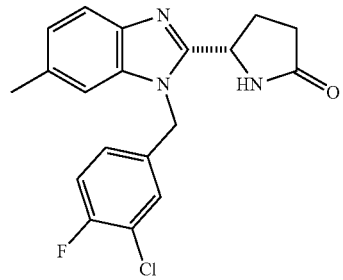

The title compound was prepared by a procedure analogous to that used to prepare Example 270: MS (ESI) (M+H$^+$) m/z=358.00. LCMS Ret time (UV 214/254): 1.19 min.

Example 275: N'-[6-chloro-1-[(3-chloro-4-fluorophenyl)methyl]benzimidazol-2-yl]ethane-1,2-diamine

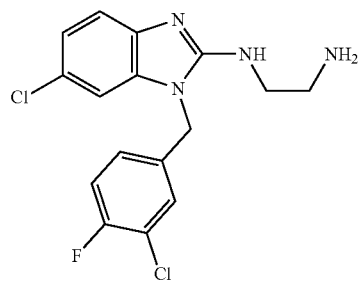 [SMILES: NCCNc1nc2ccc(Cl)cc2n1Cc1ccc(F)c(Cl)c1]

The title compound was prepared, as its trifluoroacetic acid salt, by a procedure analogous to General Procedure E: MS (ESI) (M+H$^+$) m/z=353.10. LCMS Ret time (UV 214/254): 1.12 min.

Example 276: 6-chloro-1-[(3-chloro-4-fluorophenyl)methyl]-2-piperazin-1-ylbenzimidazole VU0657602-1 AJL-3-116C

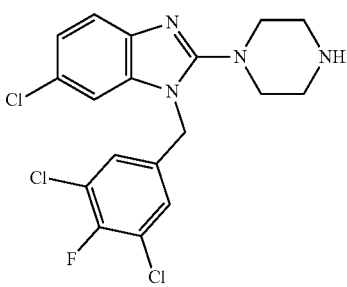 [SMILES: Fc1c(Cl)cc(Cn2c(N3CCNCC3)nc3ccc(Cl)cc32)cc1Cl]

The title compound was prepared, as its trifluoroacetic acid salt, by a procedure analogous to General Procedure E: MS (ESI) (M+H$^+$) m/z=379.10. LCMS Ret time (UV 214/254): 1.16 min.

Example S277: 1-[(3,5-dichloro-4-fluorophenyl)methyl]-5,6-dimethyl-2-piperazin-1-ylbenzimidazole

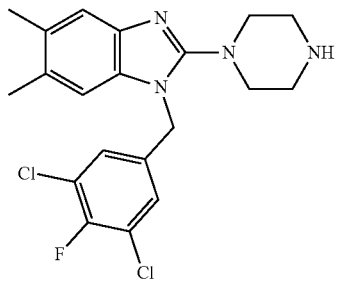 [SMILES: Cc1cc2nc(N3CCNCC3)n(Cc3cc(Cl)c(F)c(Cl)c3)c2cc1C]

The title compound was prepared, as its trifluoroacetic acid salt, by a procedure analogous to General Procedure E: MS (ESI) (M+H$^+$) m/z=407.10. LCMS Ret time (UV 214/254): 1.21 min.

Example 278: [6-chloro-1-[(3-chloro-4-fluorophenyl)methyl]-2-piperazin-1-ylbenzimidazol-4-yl]methanol

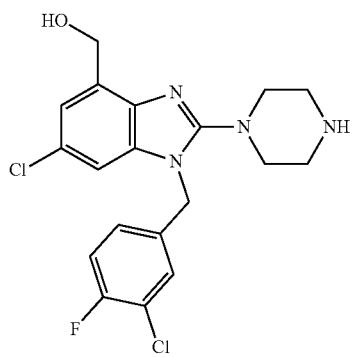 [SMILES: OCc1cc(Cl)cc2c1nc(N1CCNCC1)n2Cc1ccc(F)c(Cl)c1]

The title compound was prepared, as its trifluoroacetic acid salt, by a procedure analogous to General Procedure L: MS (ESI) (M+H$^+$) m/z=409.20. LCMS Ret time (UV 214/254): 1.149 min.

Example 279: 1-[6-chloro-1-[(4-fluoro-3,5-dimethylphenyl)methyl]-2-piperazin-1-ylbenzimidazol-4-yl]pyrrol-3-amine

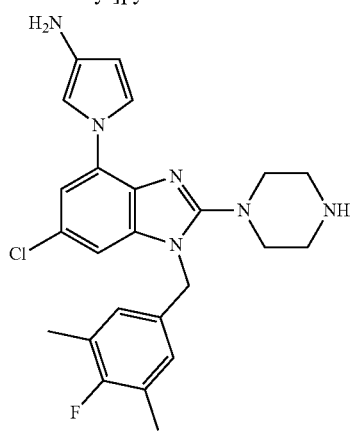

The title compound was prepared by a procedure analogous to General Procedure Q: MS (ESI) (M+H$^+$) m/z=453.10. LCMS Ret time (UV 214/254): 1.48 min.

Example 280: [1-[(4-fluoro-3,5-dimethylphenyl)methyl]-6-methyl-2-piperazin-1-ylbenzimidazol-4-yl]methanol

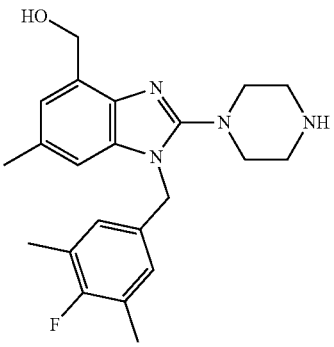 [SMILES: Cc1cc(CO)c2nc(N3CCNCC3)n(Cc3cc(C)c(F)c(C)c3)c2c1]

The title compound was prepared, as its trifluoroacetic acid salt, by a procedure analogous to General Procedure L: MS (ESI) (M+H$^+$) m/z=382.30. LCMS Ret time (UV 214/254): 1.05 min.

Example 281: [1-[(3-chloro-4-fluorophenyl)methyl]-2-piperazin-1-ylbenzimidazol-5-yl]methanamine

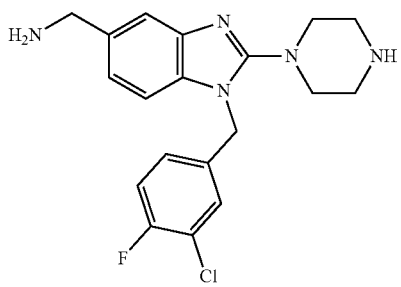 [SMILES: NCc1ccc2c(c1)nc(N1CCNCC1)n2Cc1ccc(F)c(Cl)c1]

Step A: To a solution of methyl 2-(4-(tert-butoxycarbonyl)piperazin-1-yl)-1-(3-chloro-4-fluorobenzyl)-1H-benzo[d]imidazole-5-carboxylate (287 mg, 0.57 mmol), prepared by a procedure analogous to General Procedure E, in 5 mL of THF at 0° C. was added 22 mg (0.57 mmol) of LAH. The reaction was allowed to stir at 0° C. for 30 min, then quenched by the addition of 3 M aqueous NaOH. The mixture was allowed to stir for 30 min, then extracted with EtOAc. The combined organic extracts were dried over MgSO4 and the solvents were removed under reduced pressure to give 260 mg of tert-butyl 4-(1-(3-chloro-4-fluorobenzyl)-5-(hydroxymethyl)-1H-benzo[d]imidazol-2-yl)piperazine-1-carboxylate, which was used in the next reaction with no further purification: MS (ESI) (M+H$^+$) m/z=475.00. LCMS Ret time (UV 214/254): 1.336 min.

Step B: To a solution containing 250 mg (0.53 mmol) of tert-butyl 4-(1-(3-chloro-4-fluorobenzyl)-5-(hydroxymethyl)-1H-benzo[d]imidazol-2-yl)piperazine-1-carboxylate and 5 mL of DCM was added 30 μL (0.32 mmol) of PBr$_3$. The reaction mixture was allowed to stir at rt for 2 h. The reaction mixture was quenched by the addition of water and extracted with DCM. The combined organic extracts were dried over MgSO$_4$ and the solvents were removed under reduced pressure. The residue was taken up in 3 mL of DMF and 65 mg (1 mmol) of sodium azide was added. The reaction mixture was allowed to stir at rt until complete conversion of the bromide was noted by LC/MS. The reaction mixture was partitioned between water and EtOAc and the water later was further extracted with EtOAc. The combined organic layers were dried over MgSO$_4$ and the solvents were removed under reduced pressure. The residue was taken up in 5 mL of a 10:1 mixture of THF:water and 275 mg (1.05 mmol) of triphenylphosphine was added. The reaction mixture was heated at 60° C. overnight, then allowed to cool to rt. The reaction mixture was made acidic with HCl and washed with EtOAc. The aqueous layer was heated until removal of the carbamate was complete. The mixture was concentrated to dryness and the residue was purified by reverse phase HPLC to give [1-[(3-chloro-4-fluorophenyl)methyl]-2-piperazin-1-ylbenzimidazol-5-yl] methanamine as its trifluoroacetic acid salt: $^1$H NMR (400 MHz, DMSO-$d_6$) δ 7.76 (s, 1H), 7.44-7.37 (m, 3H), 7.28 (t, J=8.4 Hz, 1H), 7.26-7.23 (m, 1H), 5.51 (s, 2H), 4.25 (s, 2H), 3.75-3.72 (m, 4H), 3.49-3.47 (m, 4H). MS (ESI) (M+H$^+$) m/z=374.10. LCMS Ret time (UV 214/254): 0.82 min.

Example 282: 2-amino-2-[6-chloro-1-[(4-fluoro-3,5-dimethylphenyl)methyl]-2-piperazin-1-ylbenzimidazol-4-yl]acetic acid

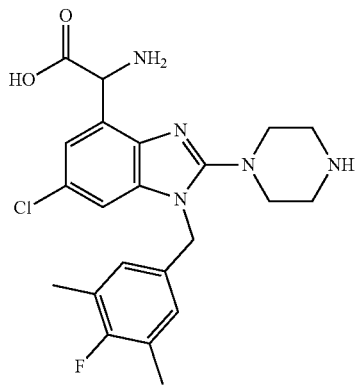 [SMILES: Cc1cc(Cn2c(N3CCNCC3)nc3c(C(N)C(=O)O)cc(Cl)cc32)cc(C)c1F]

A solution containing cyanodiethylaluminum (125 μL of a 1 M solution in toluene, 0.125 mmol), 6.4 μL of iPrOH, and 0.5 mL of THF was cooled to −78° C. and a solution of (E)-N-((6-chloro-1-(4-fluoro-3,5-dimethylbenzyl)-2-(piperazin-1-yl)-1H-benzo[d]imidazol-4-yl)methylene)-2-methylpropane-2-sulfinamide (50 mg, 0.038 mmol), prepared by a procedure analogous to the procedure used to prepare Example 162, Step A, in 0.5 mL of THF was added. The reaction mixture was allowed to warm to rt slowly and quenched by the addition of 10% aqueous HCl. The mixture was extracted with EtOAc and the combined organic layers were washed with brine and dried over MgSO$_4$. The solvents were removed under reduced pressure and the residue was taken up in 1 mL of MeOH and treated with 1 mL of a 4 M solution of HCl in dioxane. The reaction mixture was allowed to stir for 1 h and then evaporated to dryness. The residue was taken up in 6 M aqueous HCl and heated at reflux until conversion to the acid was complete. The reaction mixture was allowed to cool to rt and extracted with EtOAc. The combined organic layers were dried over MgSO$_4$ and the solvents were removed under reduced pressure. The residue was purified by reverse phase HPLC to give 2-amino-2-[6-chloro-1-[(4-fluoro-3,5-dimethylphenyl)methyl]-2-piperazin-1-ylbenzimidazol-4-yl]acetic acid as its trifluoroacetic acid salt: MS (ESI) (M+H$^+$) m/z=374.10. LCMS Ret time (UV 214/254): 0.82 min.

Example 283: 2-amino-2-[6-chloro-1-[(3-chloro-4-fluorophenyl)methyl]-2-piperazin-1-ylbenzimidazol-4-yl]ethanol

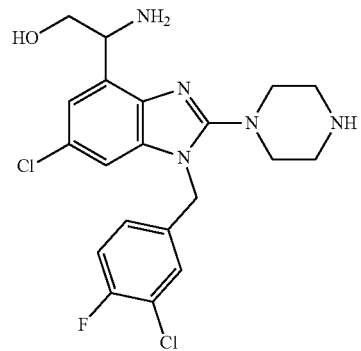 [SMILES: NC(CO)c1cc(Cl)cc2c1nc(N1CCNCC1)n2Cc1ccc(F)c(Cl)c1]

The title compound was prepared, as its trifluoroacetic acid salt, by a procedure analogous to General Procedure N: MS (ESI) (M+H$^+$) m/z=438.00. LCMS Ret time (UV 214/254): 1.08 min.

Example 284: 2-((6-((4-(1-(3-chloro-4-fluorobenzyl)-5,6-dimethyl-2-(piperazin-1-yl)-1H-benzo[d]imidazol-4-yl)benzyl)amino)-6-oxohexyl)carbamoyl)-5-(6-hydroxy-3-oxo-3H-xanthen-9-yl)benzoic acid

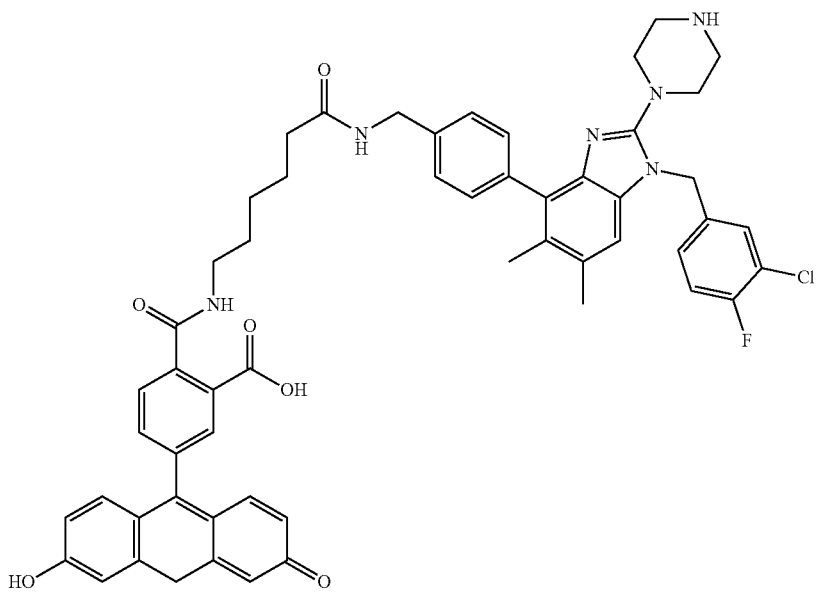 [SMILES: Cc1cc2c(nc(N3CCNCC3)n2Cc2ccc(F)c(Cl)c2)c(-c2ccc(CNC(=O)CCCCCNC(=O)c3ccc(C4=C5C=CC(=O)C=C5Cc5cc(O)ccc54)cc3C(=O)O)cc2)c1C]

To a solution containing 10 mg (0.017 mmol) of tert-butyl 4-(4-(4-(aminomethyl)phenyl)-1-(3-chloro-4-fluorobenzyl)-5,6-dimethyl-1H-benzo[d]imidazol-2-yl)piperazine-1-carboxylate trifluoroacetate, prepared by a procedure analogous to that used to prepare Example 114 and 0.5 mL of a 4:1 mixture of DCM:DMF was added 10 mg (0.017 mmol) of 2-((6-((2,5-dioxopyrrolidin-1-yl)oxy)-6-oxohexyl)carbamoyl)-5-(6-hydroxy-3-oxo-3H-xanthen-9-yl)benzoic acid and ~0.2 mg of DMAP. The reaction mixture was allowed to stir at rt overnight and 0.5 mL of TFA was added slowly. The reaction mixture was allowed to stir until LCMS indicated complete removal of the carbamate, and the solvents were removed under reduced pressure. The residue was purified by reverse phase HPLC to give the title compound as a yellow solid, as its trifluoroacetic acid salt: MS (ESI) (M+H⁺) m/z=949.00. LCMS Ret time (UV 214/254): 1.350 min.

Example 285: 4-((4-(6-chloro-1-(4-fluoro-3,5-dimethylbenzyl)-2-(piperazin-1-yl)-1H-benzo[d]imidazol-4-yl)benzyl)carbamoyl)-2-(2,7-difluoro-6-hydroxy-3-oxo-3H-xanthen-9-yl)benzoic acid

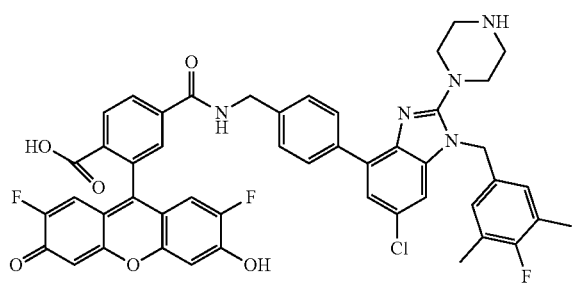 [SMILES: Cc1cc(Cn2c(N3CCNCC3)nc3c(-c4ccc(CNC(=O)c5ccc(C(=O)O)c(-c6c7cc(F)c(=O)cc-7oc7cc(O)c(F)cc67)c5)cc4)cc(Cl)cc32)cc(C)c1F]

The title compound was prepared, as its trifluoroacetic acid salt, tert-butyl 4-(4-(4-(aminomethyl)phenyl)-6-chloro-1-(4-fluoro-3,5-dimethylbenzyl)-1H-benzo[d]imidazol-2-yl)piperazine-1-carboxylate trifluoroacetate, which was prepared by a procedure analogous to General Procedure F, by a procedure analogous to that used to prepare example 284: MS (ESI) (M+H⁺) m/z=872.20. LCMS Ret time (UV 214/254): 1.581 min.

Example 286: 1-(3-chloro-4-fluorobenzyl)-4-(1,3-dimethyl-1H-pyrazol-5-yl)-5,6-dimethyl-2-(piperazin-1-yl)-1H-benzo[d]imidazole

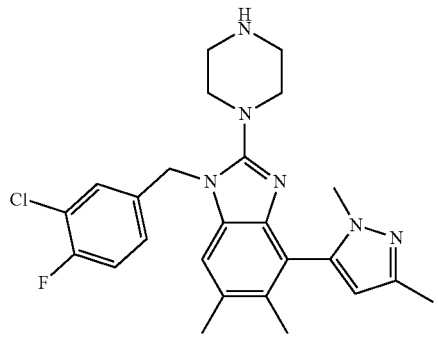 [SMILES: Cc1cc(-c2c(C)c(C)cc3c2nc(N2CCNCC2)n3Cc2ccc(F)c(Cl)c2)n(C)n1]

The title compound was prepared according to a procedure analogous to General Procedure I: ¹H NMR (400 MHz, CD₃OD) δ 7.26 (dd, J=7.2, 2.4 Hz), 7.157 (t, J=8.8 Hz), 7.07-7.05 (m, 2H), 6.03 (s, 1H), 5.25 (s, 1H), 3.46 (s, 3H), 3.14-3.11 (m, 4H), 2.94-2.92 (m, 4H), 2.30 (s, 3H), 2.26 (s, 3H), 2.05 (s, 3H); MS (ESI) (M+H⁺) m/z=467.92. LCMS Ret time (UV 214/254): 1.45 min.

Example 287: 4-((6-(((1-(3-chloro-4-fluorobenzyl)-5,6-dimethyl-2-(piperazin-1-yl)-1H-benzo[d]imidazol-4-yl)methyl)amino)-6-oxohexyl)carbamoyl)-2-(6-hydroxy-3-oxo-3H-xanthen-9-yl)benzoic acid

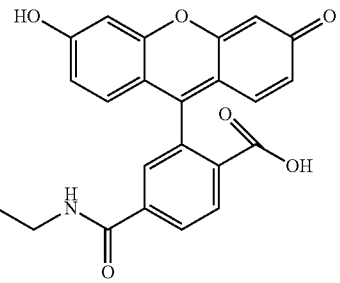

The title compound was prepared, as its trifluoroacetic acid salt, from tert-butyl 4-(4-(aminomethyl)-1-(3-chloro-4-fluorobenzyl)-5,6-dimethyl-1H-benzo[d]imidazol-2-yl)piperazine-1-carboxylate trifluoroacetate, which was prepared by a procedure analogous to General Procedure J, by a procedure analogous to that used to prepare example 284: MS (ESI) (M+H⁺) m/z=873.00. LCMS Ret time (UV 214/254): 1.253 min.

Example 288: (1-(1-(3-chloro-4-fluorobenzyl)-5,6-dimethyl-1H-benzo[d]imidazol-2-yl)azetidin-3-yl)methanamine

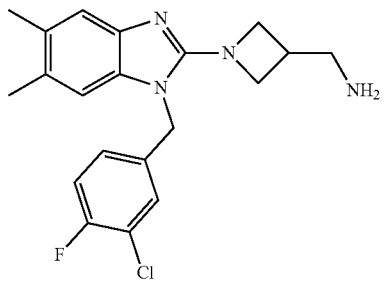 [SMILES: Cc1cc2nc(N3CC(CN)C3)n(Cc3ccc(F)c(Cl)c3)c2cc1C]

Step A: A solution of 2-chloro-5,6-dimethyl-1H-benzo[d]imidazole (135 mg, 0.75 mmol), t-Butyl(azetidin-3-yl)methyl-carbamate:HCl (333 mg, 1.50 mmol) and DIEA (0.33 mL, 1.9 mmol) in DMSO (1.5 mL) were stirred at 100° C. for 12 hrs. The reaction was diluted with EtOAc and water. The aqueous layer was separated and extracted with EtOAc (3×). The combined organics were washed with water, brine, dried over $Na_2SO_4$, concentrated and chromatographed on silica gel (24 g) eluting with a 0-to-5% MeOH/DCM (with 1% conc. $NH_4OH$) gradient to give 128 mg (52%) of tert-butyl ((1-(5,6-dimethyl-1H-benzo[d]imidazol-2-yl)azetidin-3-yl)methyl)carbamate as a light tan solid. MS (ESI) (M+H$^+$) m/z=331. LCMS Ret time (UV 215/254): 0.83 min.

Step B: A solution of tert-butyl ((1-(5,6-dimethyl-1H-benzo[d]imidazol-2-yl)azetidin-3-yl)methyl)carbamate (125 mg, 0.38 mmol), 3-chloro-4-fluorobenzyl bromide (101 mg, 0.45 mmol) and $Cs_2CO_3$ (310 mg, 0.95 mmol) was stirred in 4:1 ACN/DMF (4 mL) at RT under argon overnight. The reaction was diluted with EtOAc and water. The aqueous layer was separated and extracted with EtOAc (2×). The combined organic layers were washed with water (3×), brine, dried over $Na_2SO_4$ and concentrated under vacuum. The residue was chromatographed on silica gel (12 g), eluting with a 0-to-4% MeOH/DCM (with 1% conc. $NH_4OH$) gradient to afford 140 mg (78%) of tert-butyl ((1-(1-(3-chloro-4-fluorobenzyl)-5,6-dimethyl-1H-benzo[d]imidazol-2-yl)azetidin-3-yl)methyl)carbamate as a clear oil. MS (ESI) (M+H$^+$) m/z=473. LCMS Ret time (UV 215/254): 1.03 min.

Step C: A solution of tert-butyl ((1-(1-(3-chloro-4-fluorobenzyl)-5,6-dimethyl-1H-benzo[d]imidazol-2-yl)azetidin-3-yl)methyl)carbamate (145 mg, 0.31 mmol) was stirred in 20% TFA/DCM (6 mL) for 45 min. The reaction mixture was diluted with DCM and quenched with aqueous saturated $Na_2CO_3$. The aqueous layer was separated and extracted with DCM (2×). The combined organic layers were washed with brine, dried over $Na_2SO_4$ and concentrated under vacuum. The residue was purified via basic reverse-phase HPLC (ACN/water with 0.05% conc. $NH_4OH$) to give the title compound: (1-(1-(3-chloro-4-fluorobenzyl)-5,6-dimethyl-1H-benzo[d]imidazol-2-yl)azetidin-3-yl)methanamine. $^1$H NMR (400 MHz, DMSO-d$_6$): δ 7.33-7.37 (m, 2H), 7.09 (s, 1H), 7.01-7.05 (m, 1H), 6.94 (s, 1H), 5.15 (s, 2H), 4.02 (m, 2H), 3.74 (m, 2H), 2.70 (d, J=6.9 Hz, 2H), 2.56-2.63 (m, 1H), 2.22 (s, 3H). 2.19 (s, 3H). MS (ESI) (M+H$^+$) m/z=373. LCMS Ret time (UV 215/254): 0.83 min.

Example 289: 1-(1-(3-chloro-4-fluorobenzyl)-5,6-dimethyl-1H-benzo[d]imidazol-2-yl)pyrrolidin-3-amine

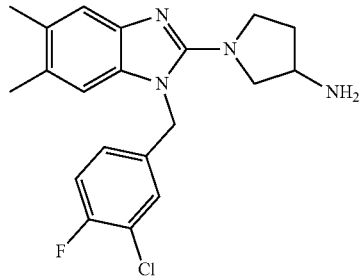 [SMILES: Cc1cc2nc(N3CCC(N)C3)n(Cc3ccc(F)c(Cl)c3)c2cc1C]

A solution of 2-chloro-1-(3-chloro-4-fluorobenzyl)-5,6-dimethyl-1H-benzo[d]imidazole (100 mg, 0.3 mmol), 3-(tert-butoxycarbonyl-amino)-pyrrolidine, which was prepared by a procedure analogous to general procedure B, (115 mg, 0.6 mmol) and DIEA (0.081 mL, 0.46 mmol) in DMSO (0.60 mL) was stirred at 100° C. for 36 hrs. The reaction mixture was diluted with EtOAc and water. The aqueous layer was separated and extracted with EtOAc (2×). The combined organics were washed with water (2×), brine (2×), dried over $Na_2SO_4$ and concentrated under vacuum. The crude residue was stirred in 20% TFA/DCM (5 mL) for about 45 min, then concentrated under vacuum. The crude residue was purified by basic reverse-phase HPLC (25-75% gradient over 5 min of ACN/water with 0.05% conc. $NH_4OH$) to give the title compound, 1-(1-(3-chloro-4-fluorobenzyl)-5,6-dimethyl-1H-benzo[d]imidazol-2-yl)pyrrolidin-3-amine as a white solid. $^1$H NMR (400 MHz, DMSO-d$_6$): δ 7.30-7.37 (m, 2H), 7.06 (s, 1H), 6.98-7.02 (m, 1H), 6.90 (s, 1H), 5.29 (s, 2H), 3.52-3.60 (m, 2H), 3.41-3.46 (m, 2H), 3.07-3.10 (m, 1H), 2.21 (s, 3H). 2.19 (s, 3H), 1.90-1.98 (m, 1H), 1.55-1.62 (m, 1H). MS (ESI) (M+H$^+$) m/z=373. LCMS Ret time (UV 215/254): 0.85 min.

Example 290: 1-(1-(3-chloro-4-fluorobenzyl)-5,6-dimethyl-1H-benzo[d]imidazol-2-yl)piperidin-3-amine

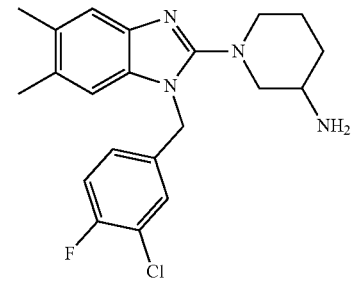 [SMILES: Cc1cc2nc(N3CCCC(N)C3)n(Cc3ccc(F)c(Cl)c3)c2cc1C]

The title compound was obtained according to a procedure analogous to general procedure B: 1H NMR (400 MHz, DMSO-d$_6$): δ 7.32-7.39 (m, 2H), 7.19 (s, 1H), 7.03-7.07 (m, 1H), 6.99 (s, 1H), 5.20 (s, 2H), 3.29-3.32 (m, 1H), 3.17-3.20 (m, 1H), 2.77-2.82 (m, 2H), 2.54-2.59 (m, 1), 2.22 (s, 3H). 2.20 (s, 3H), 1.78-1.82 (m, 1H), 1.66-1.72 (m, 1H), 1.51-1.60 (m, 1H), 1.10-1.19. MS (ESI) (M+H$^+$) m/z=387. LCMS Ret time (UV 215/254): 0.83 min.

Example 291: N-(azetidin-3-ylmethyl)-1-(3-chloro-4-fluorobenzyl)-5,6-dimethyl-1H-benzo[d]imidazol-2-amine

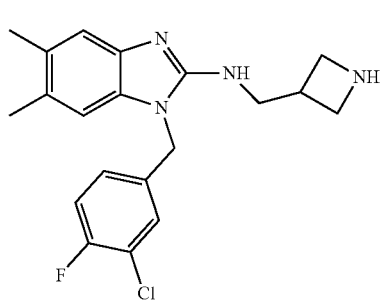 [SMILES: Cc1cc2nc(NCC3CNC3)n(Cc3ccc(F)c(Cl)c3)c2cc1C]

The title compound was obtained according to a procedure analogous to general procedure B: MS (ESI) (M+H$^+$) m/z=373. LCMS Ret time (UV 215/254): 0.88 min.

Example 292: (1s,3s)-N$^1$-(1-(3-chloro-4-fluorobenzyl)-5,6-dimethyl-1H-benzo[d]imidazol-2-yl)cyclobutane-1,3-diamine

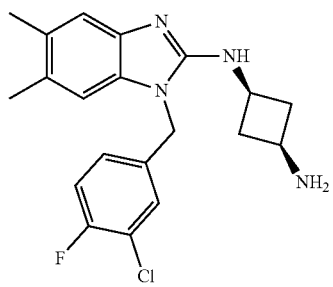 [SMILES: Cc1cc2nc(N[C@H]3C[C@@H](N)C3)n(Cc3ccc(F)c(Cl)c3)c2cc1C]

The title compound was obtained according to a procedure analogous to general procedure B: MS (ESI) (M+H$^+$) m/z=373. LCMS Ret time (UV 215/254): 0.87 min.

Example 293: 1-(3-chloro-4-fluorobenzyl)-5,6-dimethyl-N-(pyrrolidin-3-yl)-1H-benzo[d]imidazol-2-amine

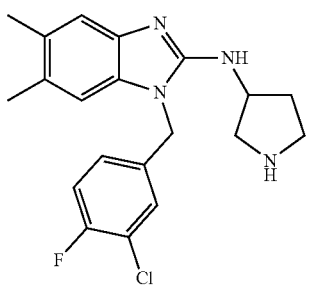

The title compound was obtained according to a procedure analogous to general procedure B: MS (ESI) (M+H$^+$) m/z=373. LCMS Ret time (UV 215/254): 0.81 min.

Example 294: 1-(1-(3-chloro-4-fluorobenzyl)-5,6-dimethyl-1-benzo[d]imidazol-2-yl)piperidin-4-amine

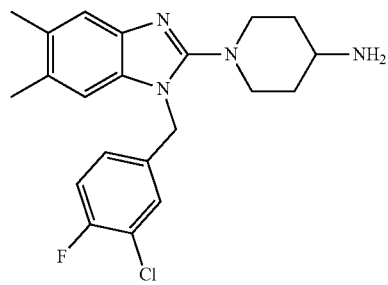 [SMILES: Cc1cc2nc(N3CCC(N)CC3)n(Cc3ccc(F)c(Cl)c3)c2cc1C]

The title compound was obtained according to a procedure analogous to general procedure B: $^1$H NMR (400 MHz, DMSO-d$_6$): δ 7.33-7.39 (m, 2H), 7.19 (s, 1H), 7.04-7.07 (m, 1H), 6.98 (s, 1H), 5.19 (s, 2H), 3.30 (m, 2H), 2.83-2.89 (m, 2H), 2.68-2.73 (m, 1H), 2.23 (s, 3H), 2.21 (s, 3H), 1.71-1.74 (m, 2H), 1.32-1.41 (m, 2H). MS (ESI) (M+H$^+$) m/z=387. LCMS Ret time (UV 215/254): 0.83 min.

Example 295: 2-((2-aminoethyl)amino)-1-(4-fluoro-3-methylbenzyl)-1H-benzo[d]imidazol-4-ol

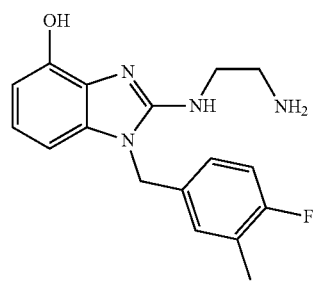 [SMILES: Cc1cc(Cn2c(NCCN)nc3c(O)cccc32)ccc1F]

The title compound was obtained according to a procedure analogous to general procedure S: MS (ESI) (M+H$^+$) m/z=315. LCMS Ret time (UV 215/254): 0.74 min.

Example 296: 6-chloro-1-(4-fluoro-3,5-dimethylbenzyl)-N,N-dimethyl-2-(piperazin-1-yl)-1H-benzo[d]imidazol-4-amine

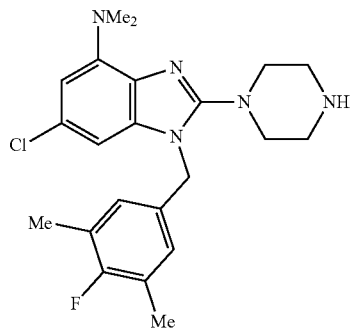 [SMILES: Cc1cc(Cn2c(N3CCNCC3)nc3c(N(C)C)cc(Cl)cc32)cc(C)c1F]

The title compound was obtained as its corresponding trifluoroacetate salt in 42% yield using a procedure analogous to general procedure Q, wherein the reaction parameters were modified to the following: Pd(OAc)$_2$, (±)-BINAP, NaOt-Bu, PhMe, 80° C. $^1$H NMR (400 MHz, CD$_3$OD) δ 6.83 (s, 1H), 6.82 (s, 1H), 6.72 (d, J=1.9 Hz, 1H), 6.53 (d, J=1.8 Hz, 1H), 5.20 (s, 2H), 3.44 (bm, 4H), 3.38 (bm, 4H), 3.15 (s, 6H), 2.19 (2s ovlp, 6H). MS (ESI) (M+H$^+$) m/z=416.00. LCMS Ret time (TIC): 1.143 min.

Example 297: 6-chloro-1-(4-fluoro-3,5-dimethylbenzyl)-2-(piperazin-1-yl)-4-(piperidin-1-yl)-1H-benzo[d]imidazole

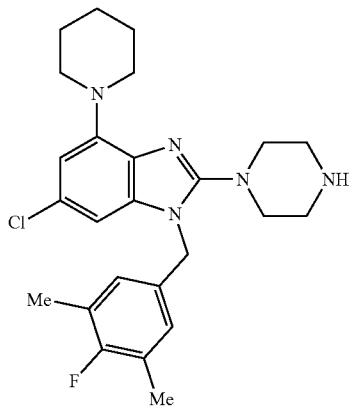 [SMILES: Cc1cc(Cn2c(N3CCNCC3)nc3c(N4CCCCC4)cc(Cl)cc32)cc(C)c1F]

The title compound was obtained as its corresponding trifluoroacetate salt in 45% yield using a a procedure analogous to general procedure Q, wherein the reaction parameters were modified to the following: Pd(OAc)$_2$, (±)-BINAP, NaOt-Bu, PhMe, 80° C. $^1$H NMR (400 MHz, CD$_3$OD) δ 7.21 (d, J=1.7 Hz, 1H), 7.18 (d, J=1.7 Hz, 1H), 6.87 (s, 1H), 6.85 (s, 1H), 5.28 (s, 2H), 3.81 (t, J=5.5 Hz, 4H), 3.56 (dd, J=6.8, 5.0 Hz, 4H), 3.41 (dd, J=5.5, 3.8 Hz, 4H), 2.20 (s, 3H), 2.19 (s, 3H), 1.99 (m, 4H), 1.78 (m, 2H). MS (ESI) (M+H$^+$) m/z=456.00. LCMS Ret time (TIC): 1.124 min.

Example 298: N$^1$-(4-(4-aminopiperidin-1-yl)-6-chloro-1-(4-fluoro-3,5-dimethylbenzyl)-1H-benzo[d]imidazol-2-yl)ethane-1,2-diamine

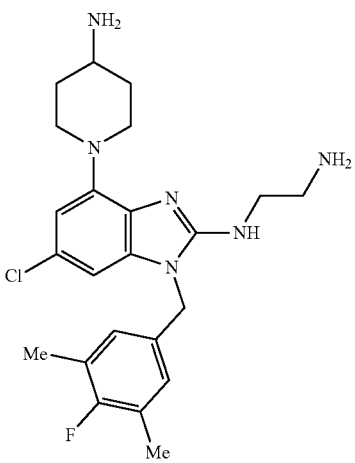 [SMILES: Cc1cc(Cn2c(NCCN)nc3c(N4CCC(N)CC4)cc(Cl)cc32)cc(C)c1F]

The title compound was obtained as its corresponding trifluoroacetate salt in 17% yield using a procedure analogous to general procedure Q, wherein the reaction parameters were modified to the following: Pd$_2$(dba)$_3$, JohnPhos, K$_3$PO$_4$, DME, 80° C. $^1$H NMR (400 MHz, CD$_3$OD) δ 6.91 (d, J=1.6 Hz, 1H), 6.89 (s, 1H), 6.87 (s, 1H), 6.83 (d, J=1.6 Hz, 1H), 5.19 (s, 2H), 3.85 (bt, J=5.8 Hz, 4H), 3.29 (m, 2H), 2.90 (bt, J=12.1 Hz, 2H), 2.20 (2s ovlp, 6H), 2.13 (bd, J=12.0 Hz, 2H), 1.93 (m, 2H). * MS (ESI) (M+H$^+$) m/z=445.00. LCMS Ret time (UV 214/254): 1.327 min.

Example 299: N$^1$-(6-chloro-1-(4-fluoro-3,5-dimethylbenzyl)-4-(piperazin-1-yl)-1H-benzo[d]imidazol-2-yl)ethane-1,2-diamine

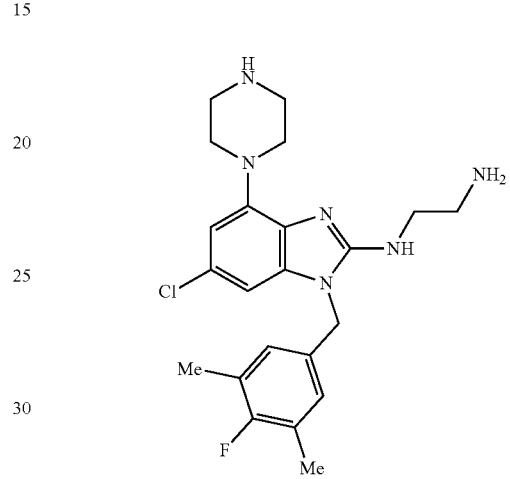

The title compound was obtained as its corresponding trifluoroacetate salt in 47% yield using a procedure analogous to general procedure Q, wherein the reaction parameters were modified to the following: Pd$_2$(dba)$_3$, JohnPhos, K$_3$PO$_4$, DME, 80° C. $^1$H NMR (400 MHz, CD$_3$OD) δ 7.00 (d, J=1.6 Hz, 1H), 6.90 (s, 1H), 6.88 (s, 1H), 6.87 (d, J=1.7 Hz, 1H), 5.21 (s, 2H), 3.88 (t, J=5.9 Hz, 2H), 3.48 (s, 8H), 3.29 (m, 2H), 2.21 (s, 3H), 2.20 (s, 3H). MS (ESI) (M+H$^+$) m/z=431.10. LCMS Ret time (UV 214/254): 1.273 min.

Example 300: N$^1$-(6-chloro-1-(4-fluoro-3,5-dimethylbenzyl)-4-(4-methylpiperazin-1-yl)-1H-benzo[d]imidazol-2-yl)ethane-1,2-diamine

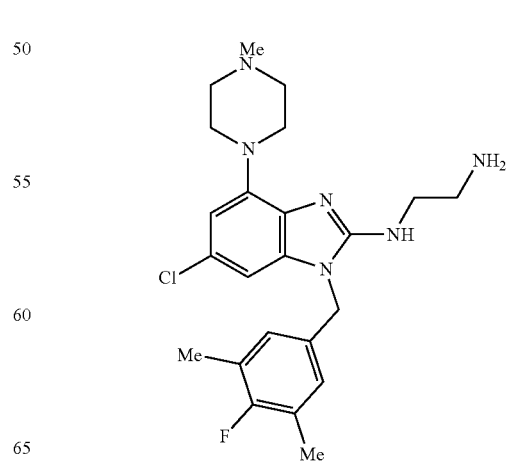

The title compound was obtained as its corresponding trifluoroacetate salt in 40% yield using a procedure analogous to general procedure Q, wherein the reaction parameters were modified to the following: Pd$_2$(dba)$_3$, JohnPhos, K$_3$PO$_4$, DME, 80° C. $^1$H NMR (400 MHz, CD$_3$OD) δ 6.99 (d, J=1.7 Hz, 1H), 6.90 (s, 1H), 6.88 (s, 1H), 6.87 (d, J=1.8 Hz, 1H), 5.21 (s, 2H), 3.93 (bm, 2H), 3.89 (t, J=5.9 Hz, 2H), 3.65 (bd, J=11.9 Hz, 2H), 3.42 (bt, J=11.6 Hz, 2H), 3.29 (m, 2H), 3.15 (bt, J=11.7 Hz, 2H), 3.00 (s, 3H), 2.20 (2s ovlp, 6H). MS (ESI) (M+H$^+$) m/z=445.00. LCMS Ret time (TIC): 1.081 min.

Example 301: N-(azetidin-3-ylmethyl)-6-chloro-1-(4-fluoro-3,5-dimethylbenzyl)-4-(4-methylpiperazin-1-yl)-1H-benzo[d]imidazol-2-amine

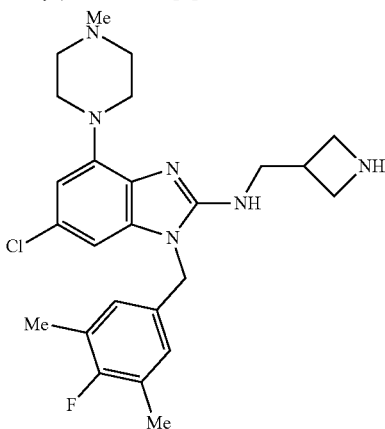

The title compound was obtained as its corresponding trifluoroacetate salt in 36% yield using a procedure analogous to general procedure Q, wherein the reaction parameters were modified to the following: Pd$_2$(dba)$_3$, JohnPhos, K$_3$PO$_4$, DME, 80° C. $^1$H NMR (400 MHz, CD3OD) δ 7.04 (d, J=1.5 Hz, 1H), 6.91 (d, J=1.4 Hz, 1H), 6.87 (s, 1H), 6.85 (s, 1H), 5.22 (s, 2H), 4.14 (dd, J=11.3, 9.3 Hz, 2H), 3.97 (dd, J=11.3, 7.3 Hz, 2H), 3.87 (bd, J=7.1 Hz, 4H), 3.65 (bd, J=11.6 Hz, 2H), 3.42 (bt, J=11.5 Hz, 2H), 3.31 (m, 1H), 3.15 (bt, J=12.2 Hz, 2H), 3.00 (s, 3H), 2.21 (s, 3H), 2.20 (s, 3H). MS (ESI) (M+H$^+$) m/z=471.00. LCMS Ret time (TIC): 1.069 min.

Example 302: N-(azetidin-3-ylmethyl)-6-chloro-1-(4-fluoro-3,5-dimethylbenzyl)-4-(1,2,3,6-tetrahydropyridin-4-yl)-1H-benzo[d]imidazol-2-amine

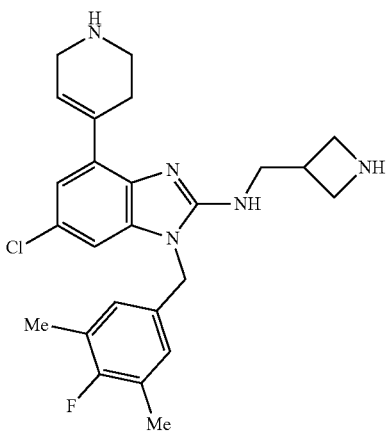 [SMILES: Cc1cc(Cn2c(NCC3CNC3)nc3c(C4=CCNCC4)cc(Cl)cc32)cc(C)c1F]

The title compound was obtained as its corresponding trifluoroacetate salt in 80% yield using general procedure I, wherein the reaction parameters were modified to the following: PdCl$_2$(dppf), K$_2$CO$_3$, DMF/EtOH (4:1 v/v), 90° C. $^1$H NMR (400 MHz, CD$_3$OD) δ 7.31 (d, J=1.8 Hz, 1H), 7.21 (d, J=1.9 Hz, 1H), 6.91 (s, 1H), 6.90 (s, 1H), 6.23 (bm, 1H), 5.29 (s, 2H), 4.15 (dd, J=11.6, 9.3 Hz, 2H), 3.93 (m, 6H), 3.52 (t, J=6.1 Hz, 2H), 2.84 (m, 2H), 2.22 (s, 3H), 2.21 (s, 3H). * MS (ESI) (M+H$^+$) m/z=454.00. LCMS Ret time (UV 214/254): 1.248 min.

Example 303: N$^1$-(6-chloro-1-(4-fluoro-3,5-dimethylbenzyl)-4-(1,2,3,6-tetrahydropyridin-4-yl)-1H-benzo[d]imidazol-2-yl)ethane-1,2-diamine

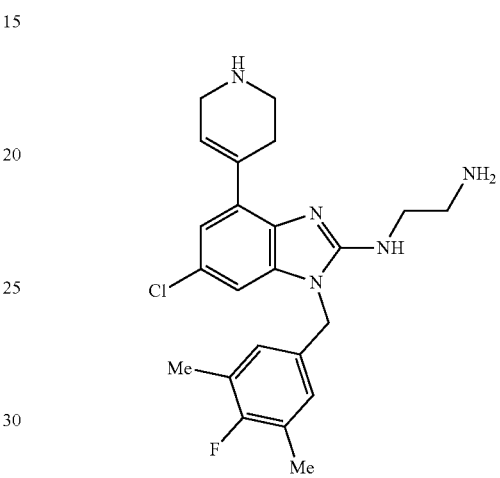

The title compound was obtained as its corresponding trifluoroacetate salt in 75% yield using a general procedure I, wherein the reaction parameters were modified to the following: PdCl$_2$(dppf), K$_2$CO$_3$, DMF/EtOH (4:1 v/v), 90° C. $^1$H NMR (400 MHz, CD$_3$OD) δ 7.27 (d, J=1.8 Hz, 1H), 7.20 (d, J=1.8 Hz, 1H), 6.94 (s, 1H), 6.93 (s, 1H), 6.27 (bm, 1H), 5.29 (s, 2H), 3.96 (t, J=5.7 Hz, 2H), 3.89 (bm, 2H), 3.52 (t, J=6.1 Hz, 2H), 3.33 (m, 2H), 2.85 (bm, 2H), 2.21 (2s ovlp, 6H). MS (ESI) (M+H$^+$) m/z=428.00. LCMS Ret time (TIC): 1.106 min.

Example 304: 6-chloro-1-(4-fluoro-3,5-dimethylbenzyl)-2-(piperazin-1-yl)-4-(1,2,3,6-tetrahydropyridin-4-yl)-1H-benzo[d]imidazole

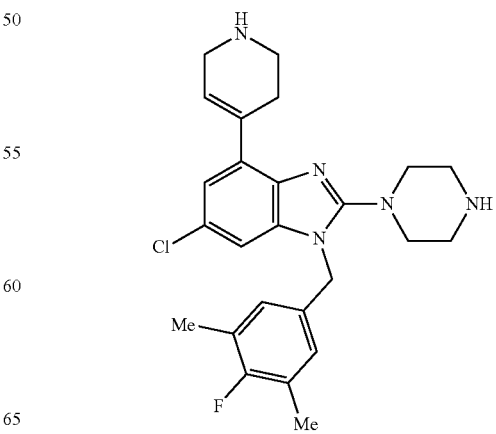

The title compound was obtained as its corresponding trifluoroacetate salt in 36% yield using a general procedure I, wherein the reaction parameters were modified to the following: PdCl$_2$(dppf), K$_2$CO$_3$, DMF/EtOH (4:1 v/v), 90° C. $^1$H NMR (400 MHz, CD$_3$OD) δ 7.20 (s, 2H), 6.84 (s, 1H), 6.93 (s, 1H), 6.81 (bm, 1H), 5.27 (s, 2H), 3.93 (bm, 2H), 3.52 (bm, 6H), 3.40 (bm, 4H), 3.05 (bm, 2H), 2.20 (s, 3H), 2.19 (s, 3H). MS (ESI) (M+H$^+$) m/z=454.00. LCMS Ret time (UV 214/254): 1.328 min.

Example 305: N-(azetidin-3-ylmethyl)-6-chloro-4-(2-chlorophenyl)-1-(4-fluoro-3,5-dimethylbenzyl)-1H-benzo[d]imidazol-2-amine

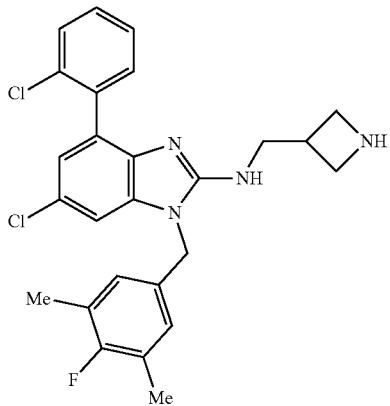 [SMILES: Cc1cc(Cn2c(NCC3CNC3)nc3c(-c4ccccc4Cl)cc(Cl)cc32)cc(C)c1F]

The title compound was obtained as its corresponding trifluoroacetate salt in 88% yield using general procedure I, wherein the reaction parameters were modified to the following: PdCl$_2$(dppf), K$_2$CO$_3$, DMF/EtOH (4:1 v/v), 90° C. $^1$H NMR (400 MHz, CD$_3$OD) δ 7.61 (dt, J=7.6, 0.9 Hz, 1H), 7.51 (m, 4H), 7.23 (d, J=1.9 Hz, 1H), 6.97 (s, 1H), 6.96 (s, 1H), 5.36 (s, 2H), 4.14 (dd, J=11.3, 9.1 Hz, 2H), 3.91 (dd, J=11.3, 7.1 Hz, 2H), 3.80 (d, J=7.2 Hz, 2H), 3.24 (m, 1H), 2.24 (s, 3H), 2.23 (s, 3H). MS (ESI) (M+H$^+$) m/z=483.00. LCMS Ret time (UV 214/254): 1.587 min.

Example 306: N$^1$-(6-chloro-4-(2-chlorophenyl)-1-(4-fluoro-3,5-dimethylbenzyl)-1H-benzo[d]imidazol-2-yl)ethane-1,2-diamine

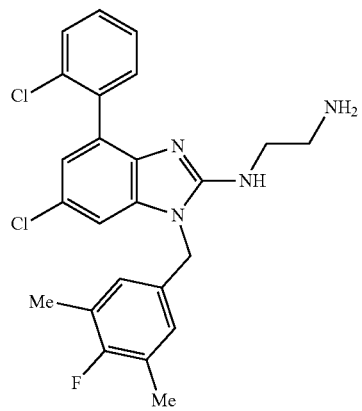 [SMILES: Cc1cc(Cn2c(NCCN)nc3c(-c4ccccc4Cl)cc(Cl)cc32)cc(C)c1F]

The title compound was obtained as its corresponding trifluoroacetate salt in 48% yield using general procedure I, wherein the reaction parameters were modified to the following: PdCl$_2$(dppf), K$_2$CO$_3$, DMF/EtOH (4:1 v/v), 90° C. $^1$H NMR (400 MHz, CD$_3$OD) δ 7.61 (dt, J=7.3, 1.2 Hz, 1H), 7.49 (m, 3H), 7.42 (d, J=1.8 Hz, 1H), 7.21 (d, J=1.9 Hz, 1H), 7.00 (s, 1H), 6.98 (s, 1H), 5.35 (s, 2H), 3.82 (t, J=5.4 Hz, 2H), 3.24 (t, J=5.6 Hz, 2H), 2.24 (s, 3H), 2.23 (s, 3H). MS (ESI) (M+H$^+$) m/z=456.90. LCMS Ret time (UV 214/254): 1.573 min.

Example 307: 6-chloro-4-(2-chlorophenyl)-1-(4-fluoro-3,5-dimethylbenzyl)-2-(piperazin-1-yl)-1H-benzo[d]imidazole

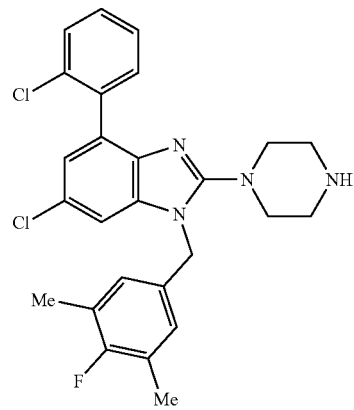 [SMILES: Cc1cc(Cn2c(N3CCNCC3)nc3c(-c4ccccc4Cl)cc(Cl)cc32)cc(C)c1F]

The title compound was obtained as its corresponding trifluoroacetate salt in 35% yield using general procedure I, wherein the reaction parameters were modified to the following: PdCl$_2$(dppf), K$_2$CO$_3$, DMF/EtOH (4:1 v/v), 90° C. $^1$H NMR (400 MHz, CD$_3$OD) δ 7.56 (m, 1H), 7.49 (m, 1H), 7.43 (m, 2H), 7.33 (d, J=1.9 Hz, 1H), 7.19 (d, J=1.9 Hz, 1H), 6.92 (s, 1H), 6.90 (s, 1H), 5.34 (s, 2H), 3.50 (m, 4H), 3.36 (m, 4H), 2.22 (2s ovlp, 6H). MS (ESI) (M+H$^+$) m/z=483.00. LCMS Ret time (UV 214/254): 1.648 min.

Example 308: N$^1$-(6-chloro-1-(4-fluoro-3,5-dimethylbenzyl)-4-(2-isopropoxyphenyl)-1H-benzo[d]imidazol-2-yl)ethane-1,2-diamine

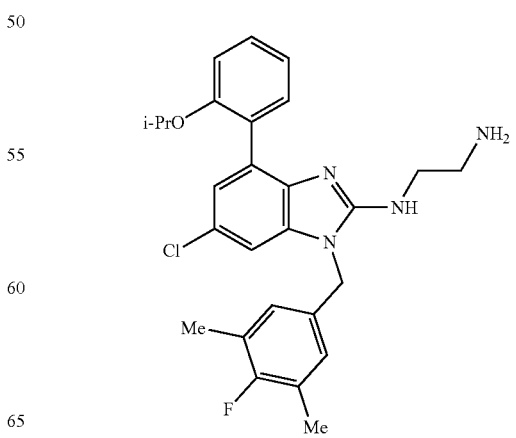

The title compound was obtained as its corresponding trifluoroacetate salt in 72% yield using a general procedure I, wherein the reaction parameters were modified to the following: PdCl$_2$(dppf), K$_2$CO$_3$, DMF/EtOH (4:1 v/v), 90° C. $^1$H NMR (400 MHz, CD$_3$OD) δ 7.48 (ddd, J=8.3, 7.4, 1.8 Hz, 1H), 7.42 (dd, J=7.5, 1.6 Hz, 1H), 7.39 (d, J=1.9 Hz, 1H), 7.26 (d, J=1.9 Hz, 1H), 7.18 (d, J=8.3 Hz, 1H), 7.12 (td, J=7.5, 1.0 Hz, 1H), 6.94 (s, 1H), 6.92 (s, 1H), 5.39 (s, 2H), 4.59 (sep, J=6.1 Hz, 1H), 3.85 (t, J=5.7 Hz, 2H), 3.24 (t, J=5.8 Hz, 2H), 2.23 (s, 3H), 2.22 (s, 3H), 1.15 (d, J=6.0 Hz, 6H). MS (ESI) (M+H$^+$) m/z=481.00. LCMS Ret time (UV 214/254): 1.624 min.

Example 309: N-(azetidin-3-ylmethyl)-6-chloro-1-(4-fluoro-3,5-dimethylbenzyl)-4-(piperazin-1-yl)-1H-benzo[d]imidazol-2-amine

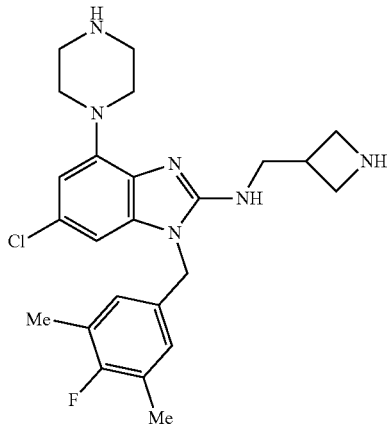 [SMILES: Cc1cc(Cn2c(NCC3CNC3)nc3c(N4CCNCC4)cc(Cl)cc32)cc(C)c1F]

The title compound was obtained as its corresponding trifluoroacetate salt in 29% yield using a general procedure Q, wherein the reaction parameters were modified to the following: Pd$_2$(dba)$_3$, JohnPhos, K$_3$PO$_4$, DME, 80° C. $^1$H NMR (400 MHz, CD$_3$OD) δ 7.09 (d, J=1.6 Hz, 1H), 6.97 (d, J=1.5 Hz, 1H), 6.89 (s, 1H), 6.87 (s, 1H), 5.25 (s, 2H), 4.15 (dd, J=11.3, 9.6 Hz, 2H), 3.97 (dd, J=11.3, 7.2 Hz, 2H), 3.89 (d, J=7.2 Hz, 2H), 3.47 (m, 4H), 3.42 (m, 4H), 3.33 (m, 1H), 2.21 (2s ovlp, 6H). MS (ESI) (M+H$^+$) m/z=457.00. LCMS Ret time (TIC): 1.071 min.

Example 310: 2-(6-chloro-1-(4-fluoro-3,5-dimethylbenzyl)-2-(piperazin-1-yl)-1H-benzo[d]imidazol-4-yl)acetic acid

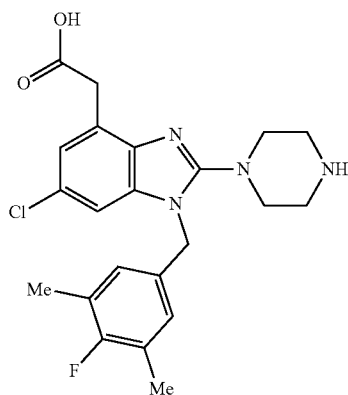 [SMILES: Cc1cc(Cn2c(N3CCNCC3)nc3c(CC(=O)O)cc(Cl)cc32)cc(C)c1F]

Step A: tert-butyl 4-(4-bromo-6-chloro-1-(4-fluoro-3,5-dimethylbenzyl)-1H-benzo[d]imidazol-2-yl)piperazine-1-carboxylate (25 mg, 0.05 mmol, 1.00 eq), which was prepared by a procedure analogous to the procedure used to prepare Example 118, Step E, isoxazole-4-boronic acid (8 mg, 0.07 mmol, 1.50 eq), potassium fluoride (14 mg, 0.14 mmol, 3.00 eq), and [1,1'-Bis(diphenylphosphino)ferrocene]dichloropalladium(II) (3 mg, 0.01 mmol, 0.10 eq) were weighed into a vial. The vial was sealed, evacuated, and refilled with argon. The evacuation/refill process was repeated two additional times. Dimethylformamide (0.25 mL) and water (0.002 mL)—both of which had been degassed using three evacuation/refill cycles—were added. The vial was then heated to 90° C. and the progress of the reaction was monitored by LCMS. After 20 h, more isoxazole-4-boronic acid (8 mg, 0.07 mmol, 1.50 eq) and Bis(diphenylphosphino)-ferrocene]dichloropalladium(II) (3 mg, 0.01 mmol, 0.10 eq) were added. When the starting material had been completely consumed, three more drops of water were added and the temperature was increased to 110° C. When the intermediate tert-butyl 4-(6-chloro-1-(4-fluoro-3,5-dimethylbenzyl)-4-(isoxazol-4-yl)-1H-benzo[d]imidazol-2-yl)piperazine-1-carboxylate had been converted to the corresponding tert-butyl 4-(6-chloro-4-(cyanomethyl)-1-(4-fluoro-3,5-dimethylbenzyl)-1H-benzo[d]imidazol-2-yl)piperazine-1-carboxylate, the reaction mixture was cooled to room temperature. The reaction mixture was then diluted with CH$_2$Cl$_2$ (15 mL) and saturated aqueous NH$_4$Cl (15 mL). The resulting biphasic mixture was stirred for 10 min, passed through a phase separator, and concentrated in vacuo. The residue was purified by silica gel chromatography to provide tert-butyl 4-(6-chloro-4-(cyanomethyl)-1-(4-fluoro-3,5-dimethylbenzyl)-1H-benzo[d]imidazol-2-yl)piperazine-1-carboxylate (14 mg, 60% yield).

Step B: The nitrile obtained in Step A was dissolved in 6 M HCl (0.2 mL). The reaction mixture was heated to 90° C. and the progress of the reaction was monitored by LCMS. When the nitrile hydrolysis was complete, the mixture was concentrated in vacuo. The residual oil was purified by reverse phase preparative HPLC. The title compound was obtained as its corresponding trifluoroacetate salt as a white solid (10 mg, 43% yield). $^1$H NMR (400 MHz, CD$_3$OD) δ 7.18 (s, 2H), 6.89 (s, 1H), 6.87 (s, 1H), 5.28 (s, 2H), 3.99 (s, 2H), 3.54 (bm, 4H), 3.40 (dd, J=6.8, 4.7 Hz, 4H), 2.20 (2s ovlp, 6H). MS (ESI) (M+H$^+$) m/z=431.00. LCMS Ret time (UV 214/254): 1.392 min.

Example 311: 2-(6-chloro-1-(3-chloro-4-fluorobenzyl)-2-(piperazin-1-yl)-1H-benzo[d]imidazol-4-yl)acetic acid

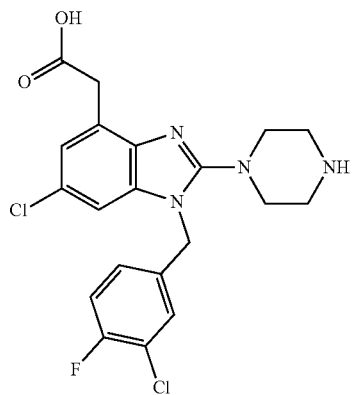 [SMILES: O=C(O)Cc1cc(Cl)cc2c1nc(N1CCNCC1)n2Cc1ccc(F)c(Cl)c1]

The title compound was obtained as its corresponding trifluoroacetate salt in 13% yield using a procedure analogous to the procedure used to prepare Example 310. $^1$H NMR (400 MHz, CD$_3$OD) δ 7.37 (dd, J=6.8, 2.1 Hz, 1H), 7.23 (t, J=8.8 Hz, 1H), 7.20 (d, J=1.9 Hz, 1H), 7.18 (d, J=1.8 Hz, 1H), 7.11 (m, 1H), 5.36 (s, 2H), 3.99 (s, 2H), 3.53 (dd, 7.2, 4.8 Hz, 4H), 3.41 (dd, J=7.0, 4.7 Hz, 4H). MS (ESI) (M+H$^+$) m/z=436.90. LCMS Ret time (TIC): 0.168 min.

Example 312: 4-(6-chloro-1-(4-fluoro-3,5-dimethylbenzyl)-2-(piperazin-1-yl)-1H-benzo[d]imidazol-4-yl)morpholine

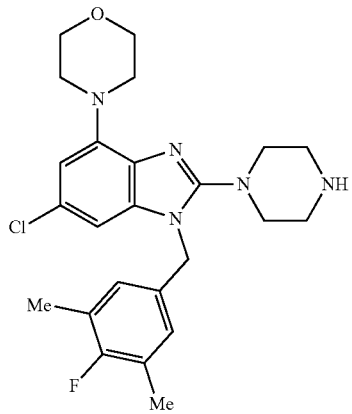 [SMILES: Cc1cc(Cn2c(N3CCNCC3)nc3c(N4CCOCC4)cc(Cl)cc32)cc(C)c1F]

The title compound was obtained as its corresponding trifluoroacetate salt in 37% yield using a general procedure Q, wherein the reaction parameters were modified to the following: Pd(OAc)$_2$, (±)-BINAP, NaOt-Bu, PhMe, 80° C. $^1$H NMR (400 MHz, CD$_3$OD) δ 6.83 (s, 1H), 6.81 (s, 1H), 6.81 (d, J=1.4 Hz, 1H), 6.61 (d, J=1.8 Hz, 1H), 5.21 (s, 2H), 3.90 (dd, J=5.4, 4.7 Hz, 4H), 3.47 (m, 4H), 3.43 (m, 4H), 3.37 (m, 4H), 2.19 (2s ovlp, 6H). MS (ESI) (M+H$^+$) m/z=458.00. LCMS Ret time (TIC): 1.194 min.

Example 313: N$^1$-(4-bromo-1-(4-fluoro-3,5-dimethylbenzyl)-6-methyl-1H-benzo[d]imidazol-2-yl)ethane-1,2-diamine

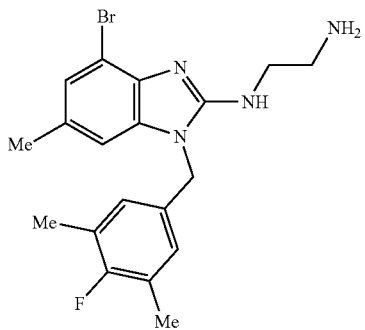 [SMILES: Cc1cc(Br)c2nc(NCCN)n(Cc3cc(C)c(F)c(C)c3)c2c1]

The title compound was obtained as its corresponding trifluoroacetate salt in 95% yield using a general procedure I. $^1$H NMR (400 MHz, CD$_3$OD) δ 7.32 (s, 1H), 7.10 (s, 1H), 6.92 (s, 1H), 6.91 (s, 1H), 5.28 (s, 2H), 3.92 (m, 2H), 3.31 (m, 2H), 2.38 (s, 3H), 2.21 (s, 3H), 2.20 (s, 3H). MS (ESI) (M+H$^+$) m/z=405.10. LCMS Ret time (UV 214/254): 1.250 min.

Example 314: N$^1$-(1-(4-fluoro-3,5-dimethylbenzyl)-6-methyl-4-(piperidin-4-yloxy)-1H-benzo[d]imidazol-2-yl)ethane-1,2-diamine

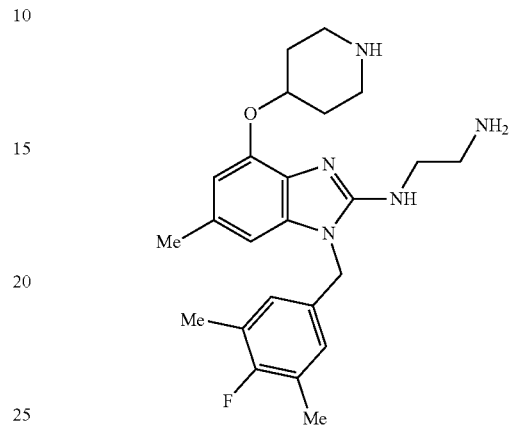

The title compound was obtained as its corresponding trifluoroacetate salt in 53% yield using general procedure AF. $^1$H NMR (400 MHz, CD$_3$OD) δ 6.94 (s, 1H), 6.92 (s, 1H), 6.90 (s, 1H), 6.78 (s, 1H), 5.29 (s, 2H), 4.92 (m, 1H), 3.95 (t, J=5.9 Hz, 2H), 3.54 (ddd, J=12.5, 8.2, 3.7 Hz, 2H), 3.33 (m, 2H), 3.25 (ddd, J=12.5, 7.7, 3.9 Hz, 2H), 2.40 (s, 3H), 2.27 (m, 2H), 2.21 (s, 3H), 2.20 (s, 3H), 2.13 (m, 2H). MS (ESI) (M+H$^+$) m/z=426.30. LCMS Ret time (UV 214/254): 1.142 min.

Example 315: 1-(4-fluoro-3,5-dimethylbenzyl)-6-methyl-2-(piperazin-1-yl)-4-(piperidin-4-yloxy)-1H-benzo[d]imidazole

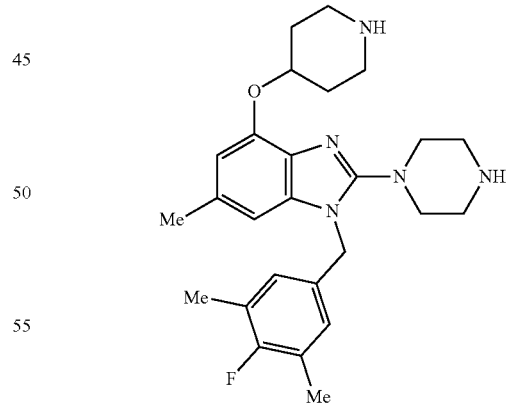

The title compound was obtained as its corresponding trifluoroacetate salt in 55% yield using general procedure AF. 1H NMR (400 MHz, CD$_3$OD) δ 6.95 (2s ovlp, 2H), 6.94 (s, 1H), 6.81 (s, 1H), 5.37 (s, 2H), 4.99 (sep, J=3.2 Hz, 1H), 3.70 (m, 4H), 3.55 (ddd, J=12.6, 8.8, 3.7 Hz, 2H), 3.42 (m, 4H), 3.27 (ddd, J=12.6, 7.1, 3.9 Hz, 2H), 2.42 (s, 3H), 2.26 (m, 2H), 2.21 (2s ovlp, 6H), 2.16 (m, 2H). MS (ESI) (M+H$^+$) m/z=452.30. LCMS Ret time (UV 214/254): 1.055 min.

Example 316: 1-(4-fluoro-3,5-dimethylbenzyl)-6-methyl-2-(piperazin-1-yl)-4-(2-(pyrrolidin-1-yl)ethoxy)-1H-benzo[d]imidazole

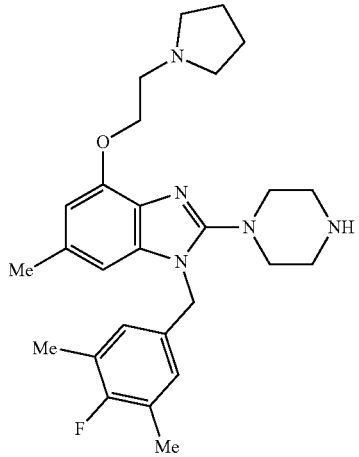 [SMILES: Cc1cc(OCCN2CCCC2)c2nc(N3CCNCC3)n(Cc3cc(C)c(F)c(C)c3)c2c1]

The title compound was obtained as its corresponding trifluoroacetate salt in 20% yield using general procedure AE. 1H NMR (400 MHz, CD$_3$OD) δ 6.85 (2s ovlp, 2H). 6.78 (s, 1H), 6.72 (s, 1H), 5.28 (s, 2H), 4.48 (m, 2H), 3.74 (t, J=5.2 Hz, 2H), 3.74 (bm, 2H), 3.48 (m, 4H), 3.40 (m, 4H), 3.31 (bm, 2H), 2.41 (s, 3H), 2.19 (2s ovlp, 6H), 2.16 (m, 2H). MS (ESI) (M+H$^+$) m/z=466.30. LCMS Ret time (UV 214/254): 1.114 min.

Example 317: 1-(4-fluoro-3,5-dimethylbenzyl)-6-methyl-2-(piperazin-1-yl)-4-(pyrrolidin-3-yloxy)-1H-benzo[d]imidazole

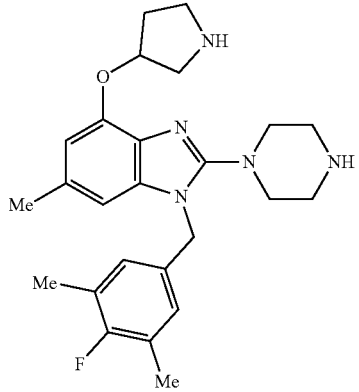 [SMILES: Cc1cc(OC2CCNC2)c2nc(N3CCNCC3)n(Cc3cc(C)c(F)c(C)c3)c2c1]

The title compound was obtained as its corresponding trifluoroacetate salt in 68% yield using general procedure AF. $^1$H NMR (400 MHz, CD$_3$OD) δ 6.91 (s 1H), 6.89 (s, 1H), 6.82 (2s ovlp, 2H), 5.48 (bt, J=3.3 Hz, 1H), 5.32 (s, 2H), 3.68 (d, J=13.0 Hz, 1H), 3.60 (2bm ovlp, 5H), 3.54 (m, 2H), 3.41 (m, 4H), 2.41 (s, 3H), 2.37 (m, 2H), 2.21 (s, 3H), 2.20 (s, 3H). MS (ESI) (M+H$^+$) m/z=438.30. LCMS Ret time (UV 214/254): 1.068 min.

Example 318: (4-(1-(4-fluoro-3,5-dimethylbenzyl)-6-methyl-2-(piperazin-1-yl)-1H-benzo[d]imidazol-4-yl)phenyl)methanamine

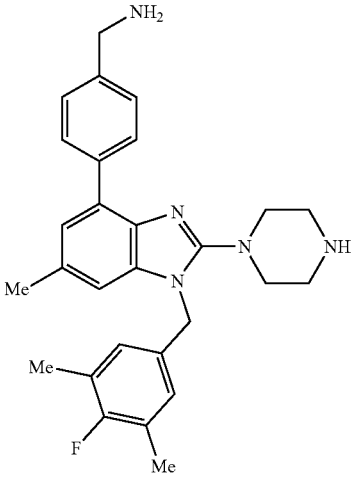 [SMILES: Cc1cc(-c2ccc(CN)cc2)c2nc(N3CCNCC3)n(Cc3cc(C)c(F)c(C)c3)c2c1]

The title compound was obtained as its corresponding trifluoroacetate salt in 26% yield using general procedure I. $^1$H NMR (400 MHz, CD$_3$OD) δ 7.84 (d, J=8.1 Hz, 2H), 7.60 (d, J=8.1 Hz, 2H), 7.28 (s, 1H), 7.18 (s, 1H), 6.98 (s, 1H), 6.97 (s, 1H), 5.41 (s, 2H), 4.21 (s, 2H), 3.68 (t, J=4.8 Hz, 4H), 3.40 (t, J=5.0 Hz, 4H), 2.47 (s, 3H), 2.23 (2s ovlp, 6H). MS (ESI) (M+H$^+$) m/z=458.40. LCMS Ret time (UV 214/254): 1.173 min.

Example 319: 1-(6-chloro-1-(4-fluoro-3,5-dimethylbenzyl)-2-(piperazin-1-yl)-1H-benzo[d]imidazol-4-yl)piperidin-4-amine

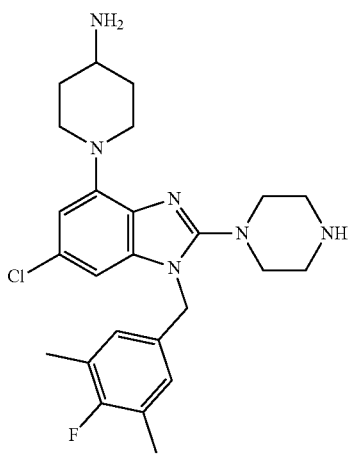 [SMILES: Cc1cc(Cn2c(N3CCNCC3)nc3c(N4CCC(N)CC4)cc(Cl)cc32)cc(C)c1F]

The title compound was obtained using general procedure Q: $^1$H NMR (400 MHz, CD$_3$OD) δ 6.84 (s, 1H), 6.83 (d, J=1.7 Hz, 1H), 6.82 (s, 1H), 6.69 (d, J=1.7 Hz, 1H), 5.23 (s, 2H), 4.26 (bd, J=12.6 Hz, 2H), 3.47 (m, 4H), 3.40 (m, 4H), 3.31 (m, 1H), 2.92 (td, J=12.5, 1.65 Hz, 2H), 2.19 (2s ovlp, 6H), 2.12 (bd, J=12.5 Hz, 2H), 1.90 (ddd, J=15.7, 12.1, 3.7 Hz, 2H). MS (ESI) (M+H$^+$) m/z=456.00. LCMS Ret time (UV 214/254): 1.319 min.

Example 320: N¹-(4-(2-aminoethoxy)-1-(4-fluoro-3,5-dimethylbenzyl)-6-methyl-1H-benzo[d]imidazol-2-yl)ethane-1,2-diamine

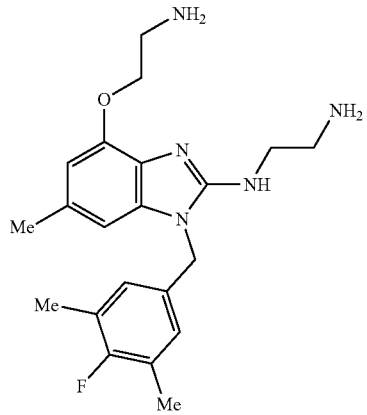 [SMILES: Cc1cc(OCCN)c2nc(NCCN)n(Cc3cc(C)c(F)c(C)c3)c2c1]

The title compound was obtained as its corresponding trifluoroacetate salt in 24% yield using general procedure AF. ¹H NMR (400 MHz, CD₃OD) δ 6.92 (s, 1H), 6.91 (s, 1H), 6.85 (s, 1H), 6.82 (s, 1H), 5.29 (s, 2H), 4.43 (t, J=5.1 Hz, 2H), 3.98 (m, 2H), 3.45 (t, J=5.2 Hz, 2H), 3.31 (m, 2H), 2.41 (s, 3H), 2.21 (s, 3H), 2.20 (s, 3H). MS (ESI) (M+H⁺) m/z=386.30. LCMS Ret time (UV 214/254): 1.003 min.

Example 321: 2-((1-(4-fluoro-3,5-dimethylbenzyl)-6-methyl-2-(piperazin-1-yl)-1H-benzo[d]imidazol-4-yl)oxy)ethan-1-amine

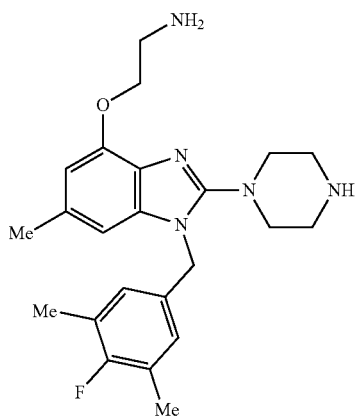 [SMILES: Cc1cc(OCCN)c2nc(N3CCNCC3)n(Cc3cc(C)c(F)c(C)c3)c2c1]

tert-butyl 4-(1-(4-fluoro-3,5-dimethylbenzyl)-4-hydroxy-6-methyl-1H-benzo[d]imidazol-2-yl)piperazine-1-carboxylate (100 mg, 0.21 mmol, 1.00 eq), which was prepared by a procedure analogous to the procedure used to prepare Example 204, tert-butyl N-(2-bromoethyl)carbamate (72 mg, 0.32 mmol, 1.50 eq), potassium tert-butoxide (100 mg, 0.53 mmol, 2.50 eq), and 18-crown-6 (235 mg, 0.53 mmol, 2.50 eq) were suspended in tert-butanol (0.5 mL). The reaction mixture was heated to 80° C. and the progress of the reaction was monitored by LCMS. When the starting material had been completely consumed, the reaction mixture was allowed to cool to room temperature. Water (30 mL) was added and the resulting mixture was extracted with EtOAc (3×20 mL). The organic phases were then combined, washed with brine, dried over Na₂SO₄, and concentrated in vacuo. The residue was dissolved in CH₂Cl₂ (5 mL) and treated with trifluoroacetic acid (1 mL). The resulting solution was stirred at room temperature and the progress of the reaction was monitored by LCMS. When the intermediate tert-butyl 4-(4-(2-((tert-butoxycarbonyl)amino)ethoxy)-1-(4-fluoro-3,5-dimethylbenzyl)-6-methyl-1H-benzo[d]imidazol-2-yl)piperazine-1-carboxylate had been completely consumed, the reaction mixture was concentrated in vacuo. The residual oil was purified by reverse phase preparative HPLC to give the title compound as its corresponding trifluoroacetate salt (74 mg, 66% yield). H NMR (400 MHz, CD₃OD) δ 6.93 (s, 1H), 6.91 (s, 1H), 6.85 (s, 1H), 6.83 (s, 1H), 5.36 (s, 2H), 4.43 (t, J=4.9 Hz, 2H), 3.69 (t, J=4.7 Hz, 4H), 3.47 (t, J=4.9 Hz, 2H), 3.43 (bm, 4H), 2.42 (s, 3H), 2.21 (2s ovlp, 6H). MS (ESI) (M+H⁺) m/z=412.30. LCMS Ret time (UV 214/254): 1.093 min.

Example 322: 1-(4-fluoro-3,5-dimethylbenzyl)-6-methyl-4-(4-methylpiperazin-1-yl)-2-(piperazin-1-yl)-1H-benzo[d]imidazole

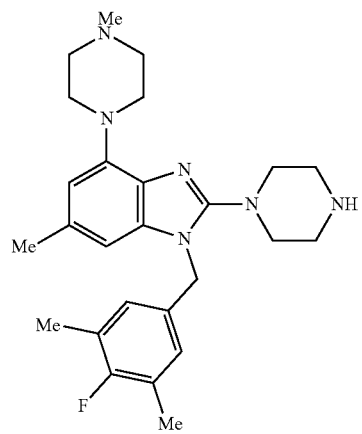 [SMILES: Cc1cc(N2CCN(C)CC2)c2nc(N3CCNCC3)n(Cc3cc(C)c(F)c(C)c3)c2c1]

The title compound was obtained as its corresponding trifluoroacetate salt in 97% yield using a general procedure Q, wherein the reaction parameters were modified to the following: Pd(OAc)₂, (±)-BINAP, NaOt-Bu, PhMe, 80° C. ¹H NMR (400 MHz, CD₃OD) δ 6.84 (s, 1H), 6.83 (s, 1H), 6.75 (s, 1H), 6.06 (s, 1H), 5.24 (s, 2H), 4.27 (d, J=13.0, 2H), 3.65 (d, J=12.3, 2H), 3.45 (m, 4H), 3.38 (m, 4H), 3.13 (t, J=12.6 Hz, 2H), 3.01 (s, 3H), 2.38 (s, 3H), 2.18 (2s ovlp, 6H). MS (ESI) (M+H⁺) m/z=451.20. LCMS Ret time (UV 214/254): 1.099 min.

Example 323: 1-(4-fluoro-3,5-dimethylbenzyl)-6-methyl-2-(piperazin-1-yl)-1H-benzo[d]imidazole

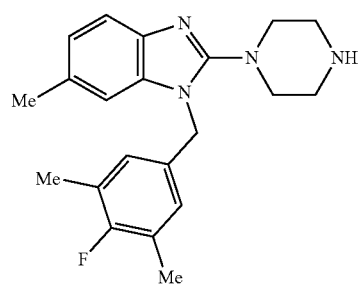 [SMILES: Cc1ccc2nc(N3CCNCC3)n(Cc3cc(C)c(F)c(C)c3)c2c1]

The title compound was isolated as a byproduct from the reactions described in general procedure AE. $^1$H NMR (400 MHz, CD$_3$OD) δ 7.50 (d, J=8.3 Hz, 1H), 7.28 (d, J=8.3 Hz, 1H), 7.19 (s, 1H), 6.95 (2s ovlp, 2H), 5.40 (s, 2H), 3.71 (bm, 4H), 3.43 (bm, 4H), 2.43 (s, 3H), 2.22 (s, 3H), 2.21 (s, 3H). MS (ESI) (M+H$^+$) m/z=353.30. LCMS Ret time (UV 214/254): 1.117 min.

Example 324: 4-bromo-1-(4-fluoro-3,5-dimethyl-benzyl)-6-methyl-2-(piperazin-1-yl)-1H-benzo[d]imidazole

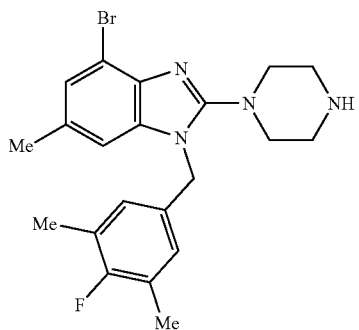 [SMILES: Cc1cc(Br)c2nc(N3CCNCC3)n(Cc3cc(C)c(F)c(C)c3)c2c1]

The title compound was obtained as its corresponding trifluoroacetate salt in 105% yield using general procedure I. $^1$H NMR (400 MHz, CD$_3$OD) δ 7.32 (s, 1H), 7.07 (s, 1H), 6.88 (s, 1H), 6.86 (s, 1H), 5.30 (s, 2H), 3.57 (bm, 4H), 3.40 (bm, 4H), 2.39 (s, 3H), 2.20 (s, 3H), 2.19 (s, 3H). MS (ESI) (M+H$^+$) m/z=433.20. LCMS Ret time (UV 214/254): 1.374 min.

Example 325: 1-(4-fluoro-3,5-dimethylbenzyl)-6-methyl-2-(piperazin-1-yl)-1H-benzo[d]imidazol-4-ol

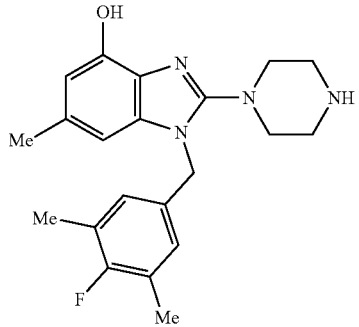

The title compound was obtained as its corresponding trifluoroacetate salt in 69% yield using general procedure AE. $^1$H NMR (400 MHz, CD$_3$OD) δ 6.96 (s, 1H), 6.94 (s, 1H), 6.70 (s, 1H), 6.66 (s, 1H), 5.35 (s, 2H), 3.71 (bm, 4H), 3.42 (bm, 4H), 2.35 (s, 3H), 2.22 (s, 3H), 2.21 (s, 3H). MS (ESI) (M+H$^+$) m/z=369.30. LCMS Ret time (UV 214/254): 1.083 min.

Example 326: 4-(2-((1-(4-fluoro-3,5-dimethylbenzyl)-6-methyl-2-(piperazin-1-yl)-1H-benzo[d]imidazol-4-yl)oxy)ethyl)morpholine

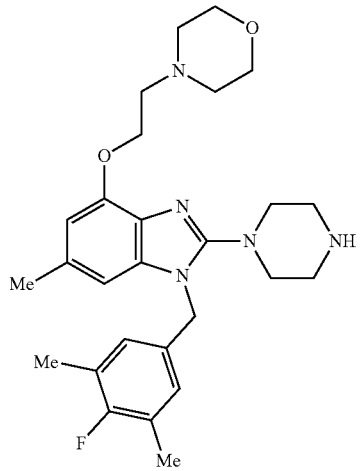 [SMILES: Cc1cc(OCCN2CCOCC2)c2nc(N3CCNCC3)n(Cc3cc(C)c(F)c(C)c3)c2c1]

The title compound was obtained in 18% using general procedure AE. $^1$H NMR (400 MHz, CD$_3$OD) δ 6.84 (s, 1H), 6.83 (s, 1H), 6.75 (s, 1H), 6.68 (s, 1H), 5.25 (s, 2H), 4.51 (t, J=5.3 Hz, 2H), 3.97 (t, J=4.6 Hz, 4H), 3.66 (t, J=5.1 Hz, 2H), 3.41 (m, 12H), 2.39 (s, 3H), 2.18 (2s ovlp, 6H). MS (ESI) (M+H$^+$) m/z=482.40. LCMS Ret time (UV 214/254): 1.228 min.

Example 327: 1-(4-fluoro-3,5-dimethylbenzyl)-6-methyl-2-(piperazin-1-yl)-4-(pyrrolidin-3-yloxy)-1H-benzo[d]imidazole

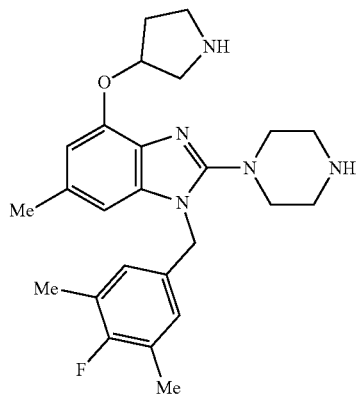 [SMILES: Cc1cc(OC2CCNC2)c2nc(N3CCNCC3)n(Cc3cc(C)c(F)c(C)c3)c2c1]

The title compound was obtained by passing the corresponding trifluoroacetate salt, which was prepared by a procedure analogous to the procedure used to prepare Example 317 through a strong cation exchange (SCX) column. $^1$H NMR (400 MHz, CD$_3$OD) δ 6.83 (s, 1H), 6.82 (s, 1H), 6.60 (s, 1H), 6.57 (s, 1H), 5.16 (s, 2H), 5.16 (m, 1H), 3.23 (m, 3H), 3.14 (m, 4H), 3.00 (dd, J=12.7, 4.4 Hz, 1H), 2.93 (m, 4H), 2.36 (s, 3H), 2.18 (s, 3H), 2.17 (s, 3H), 2.13 (m, 2H). MS (ESI) (M+H$^+$) m/z=438.10. LCMS Ret time (UV 214/254): 1.304 min.

Example 328: 2-((2-aminoethyl)amino)-1-(4-fluoro-3,5-dimethylbenzyl)-6-methyl-1H-benzo[d]imidazol-4-ol

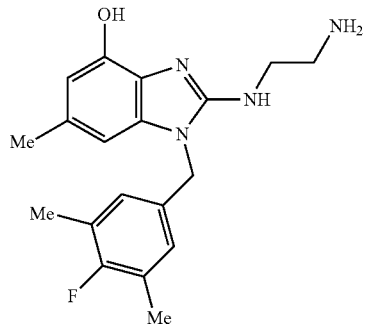 [SMILES: Cc1cc(O)c2nc(NCCN)n(Cc3cc(C)c(F)c(C)c3)c2c1]

The title compound was obtained as its corresponding trifluoroacetate salt in 50% yield using general procedure AE. $^1$H NMR (400 MHz, CD$_3$OD) δ 6.93 (s, 1H), 6.91 (s, 1H), 6.62 (2s ovlp, 2H), 5.26 (s, 2H), 3.87 (t, J=6.0 Hz, 2H), 3.31 (m, 2H), 2.32 (s, 3H), 2.20 (2s ovlp, 6H). MS (ESI) (M+H$^+$) m/z=343.30. LCMS Ret time (UV 214/254): 1.091 min.

Example 329: N$^1$-(1-(4-fluoro-3,5-dimethylbenzyl)-6-methyl-4-((tetrahydrofuran-3-yl)oxy)-1H-benzo[d]imidazol-2-yl)ethane-1,2-diamine

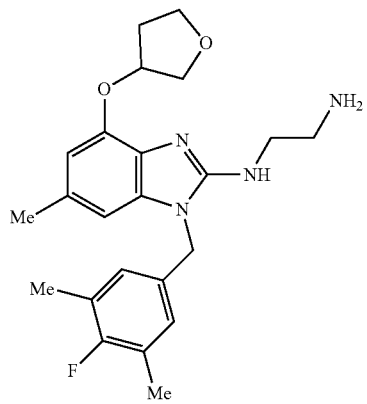 [SMILES: Cc1cc(OC2CCOC2)c2nc(NCCN)n(Cc3cc(C)c(F)c(C)c3)c2c1]

The title compound was obtained as its corresponding trifluoroacetate salt in 31% yield using general procedure AF. $^1$H NMR (400 MHz, CD$_3$OD) δ 6.93 (s, 1H), 6.91 (s, 1H), 6.79 (s, 1H), 6.76 (s, 1H), 5.29 (s, 2H), 5.24 (bt, J=4.3 Hz, 1H), 4.05 (m, 3H), 3.89 (m, 3H), 3.29 (s, 2H), 2.40 (s, 3H), 2.36 (m, 1H), 2.23 (m, 1H), 2.20 (2s ovlp, 6H). MS (ESI) (M+H$^+$) m/z=413.30. LCMS Ret time (UV 214/254): 1.179 min.

Example 330: N$^1$-(1-(4-fluoro-3,5-dimethylbenzyl)-6-methyl-4-(piperidin-4-ylmethoxy)-1H-benzo[d]imidazol-2-yl)ethane-1,2-diamine

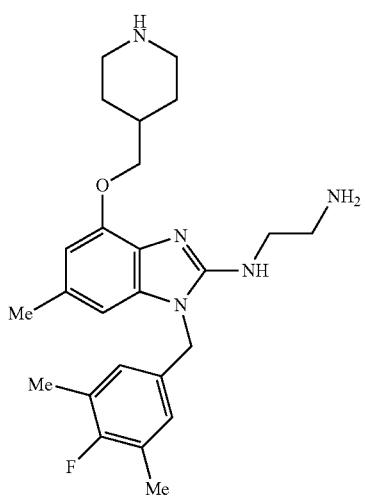 [SMILES: Cc1cc(OCC2CCNCC2)c2nc(NCCN)n(Cc3cc(C)c(F)c(C)c3)c2c1]

The title compound was obtained as its corresponding trifluoroacetate salt in 52% yield using general procedure AF. $^1$H NMR (400 MHz, CD$_3$OD) δ 6.92 9s, 1H), 6.91 (s, 1H), 6.82 (s, 1H), 6.76 (s, 1H), 5.29 (s, 2H), 4.09 (d, J=6.5 Hz, 2H), 3.94 (t, J=5.9 Hz, 2H), 3.49 (bs, 1H), 3.45 (bs, 1H), 3.31 (m, 2H), 3.06 (td, J=13.1, 2.6 Hz, 2H), 2.39 (s, 3H), 2.20 (2s ovlp, 6H), 2.20 (m, 3H), 1.62 (td, J=13.6, 4.1 Hz, 2H). MS (ESI) (M+H$^+$) m/z=440.30. LCMS Ret time (TIC): 1.220 min.

Example 331: N$^1$-(1-(4-fluoro-3,5-dimethylbenzyl)-6-methyl-4-(2-(4-methylpiperazin-1-yl)ethoxy)-1H-benzo[d]imidazol-2-yl)ethane-1,2-diamine

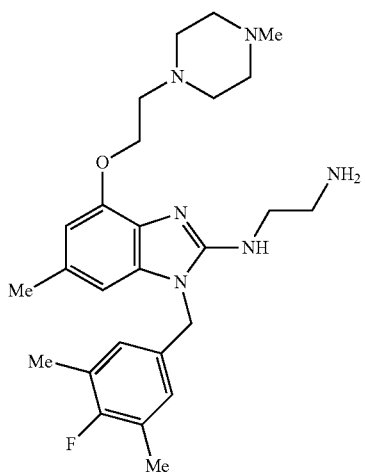 [SMILES: Cc1cc(OCCN2CCN(C)CC2)c2nc(NCCN)n(Cc3cc(C)c(F)c(C)c3)c2c1]

The title compound was obtained as its corresponding trifluoroacetate salt in 1% yield using general procedure AF. MS (ESI) (M+H$^+$) m/z=469.30. LCMS Ret time (TIC): 1.201 min.

Example 332: 4-(1-(4-fluoro-3,5-dimethylbenzyl)-5,6-dimethyl-1H-benzo[d]imidazol-2-yl)piperazin-2-one

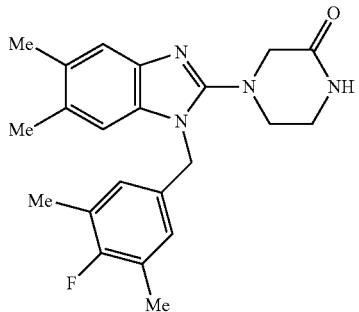 [SMILES: Cc1cc2nc(N3CCNC(=O)C3)n(Cc3cc(C)c(F)c(C)c3)c2cc1C]

The title compound was obtained as its corresponding trifluoroacetate salt in 4% yield using a general procedure B, wherein the reaction parameters were modified to the following: i-Pr$_2$NEt, NMP, 200° C. μW. 1H NMR (400 MHz, CD$_3$OD) δ 7.35 (s, 1H), 7.17 (s, 1H), 6.98 (s, 1H), 6.96 (s, 1H), 5.40 (s, 2H), 4.20 (s, 2H), 3.76 (t, J=5.1 Hz, 2H), 3.49 (t, J=5.3 Hz, 2H), 2.40 (s, 3H), 2.34 (s, 3H), 2.22 (2s ovlp, 6H). MS (ESI) (M+H$^+$) m/z=381.10. LCMS Ret time (UV 214/254): 1.312 min.

Example 333: (R)-1-(4-fluoro-3,5-dimethylbenzyl)-5,6-dimethyl-2-(2-methylpiperazin-1-yl)-1H-benzo[d]imidazole

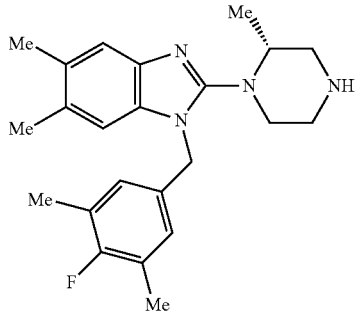 [SMILES: Cc1cc2nc(N3CCNC[C@H]3C)n(Cc3cc(C)c(F)c(C)c3)c2cc1C]

The title compound was obtained as its corresponding trifluoroacetate salt in 4% yield using a general procedure B, wherein the reaction parameters were modified to the following: PdCl$_2$(dppf), dppf, NaOt-Bu, PhMe, 100° C. $^1$H NMR (400 MHz, CD$_3$OD) δ 7.42 (s, 1H), 7.22 (s, 1H), 6.89 (s, 1H), 6.88 (s, 1H), 5.37 (s, 2H), 3.78 (m, 1H), 3.48 (m, 1H), 3.37 (m, 3H), 3.10 (m, 2H), 2.39 (s, 3H), 2.36 (s, 3H), 2.19 (2s ovlp, 6H), 1.09 (d, J=6.6 Hz, 3H). MS (ESI) (M+H$^+$) m/z=381.20. LCMS Ret time (UV 214/254): 1.247 min.

Example 334: (S)-1-(4-fluoro-3,5-dimethylbenzyl)-5,6-dimethyl-2-(2-methylpiperazin-1-yl)-1H-benzo[d]imidazole

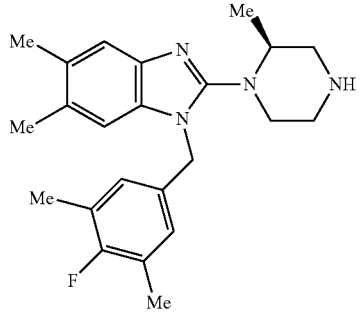 [SMILES: Cc1cc2nc(N3CCNC[C@@H]3C)n(Cc3cc(C)c(F)c(C)c3)c2cc1C]

The title compound was obtained as its corresponding trifluoroacetate salt in 6% yield using a general procedure B, wherein the reaction parameters were modified to the following: PdCl$_2$(dppf), dppf, NaOt-Bu, PhMe, 100° C. $^1$H NMR (400 MHz, CD$_3$OD) δ 7.42 (s, 1H), 7.28 (s, 1H), 6.93 (s, 1H), 6.91 (s, 1H), 5.42 (s, 2H), 3.90 (m, 1H), 3.52 (m, 3H), 3.38 (t, J=5.3 Hz, 2H), 3.16 (dd, J=13.1, 7.2 Hz, 1H), 2.41 (s, 3H), 2.37 (s, 3H), 2.20 (2s ovlp, 6H), 1.17 (d, J=6.6 Hz, 3H). MS (ESI) (M+H$^+$) m/z=381.20. LCMS Ret time (UV 214/254): 1.241 min.

Example 336: (R)-1-(4-fluoro-3,5-dimethylbenzyl)-5,6-dimethyl-2-(3-methylpiperazin-1-yl)-1H-benzo[d]imidazole

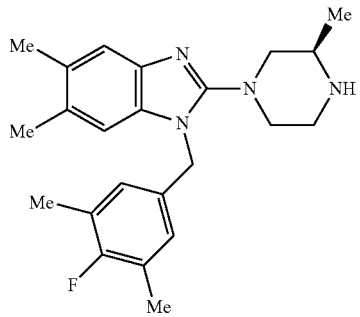 [SMILES: Cc1cc2nc(N3CCN[C@H](C)C3)n(Cc3cc(C)c(F)c(C)c3)c2cc1C]

The title compound was obtained as its corresponding trifluoroacetate salt in 86% yield using a general procedure B, wherein the reaction parameters were modified to the following: i-Pr$_2$NEt, NMP, 120° C. μW. $^1$H NMR (400 MHz, CD$_3$OD) δ 7.41 (s, 1H), 7.22 (s, 1H), 6.98 (s, 1H), 6.96 (s, 1H), 5.41 (s, 2H), 3.86 (bd, J=13.0 Hz, 2H), 3.58 (m, 3H), 3.38 (m, 2H), 2.40 (s, 3H), 2.35 (s, 3H), 2.22 (2s ovlp, 6H), 1.32 (d, J=6.6 Hz, 3H). MS (ESI) (M+H$^+$) m/z=381.20. LCMS Ret time (UV 214/254): 1.215 min.

Example 336: 2-((3S,5R)-3,5-dimethylpiperazin-1-yl)-1-(4-fluoro-3,5-dimethylbenzyl)-5,6-dimethyl-1H-benzo[d]imidazole

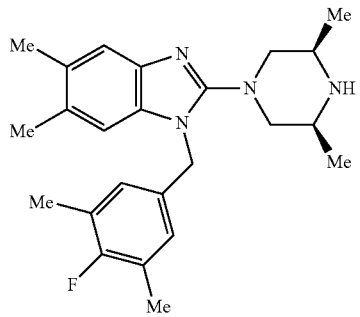 [SMILES: Cc1cc2nc(N3C[C@@H](C)N[C@@H](C)C3)n(Cc3cc(C)c(F)c(C)c3)c2cc1C]

The title compound was obtained as its corresponding trifluoroacetate salt in 91% yield using a general procedure B, wherein the reaction parameters were modified to the following: i-Pr$_2$NEt, NMP, 200° C. μW. 1H NMR (400 MHz, CD$_3$OD) δ 7.41 (s, 1H), 7.25 (s, 1H), 6.99 (s, 1H), 6.98 (s, 1H), 5.42 (s, 2H), 3.87 (dd, J=13.9, 1.6 Hz, 2H), 3.60 (m, 2H), 3.35 (m, 2H), 2.40 (s, 3H), 2.36 (s, 3H), 2.23 (s, 3H), 2.22 (s, 3H), 1.31 (d, J=6.6 Hz, 6H). MS (ESI) (M+H$^+$) m/z=395.20. LCMS Ret time (UV 214/254): 1.205 min.

Example 337: N-(4-(1-(3-chloro-4-fluorobenzyl)-5,6-dimethyl-2-(piperazin-1-yl)-1H-benzo[d]imidazol-4-yl)benzyl)-5-((3aS,4S,6aR)-2-oxohexahydro-1H-thieno[3,4-d]imidazol-4-yl)pentanamide

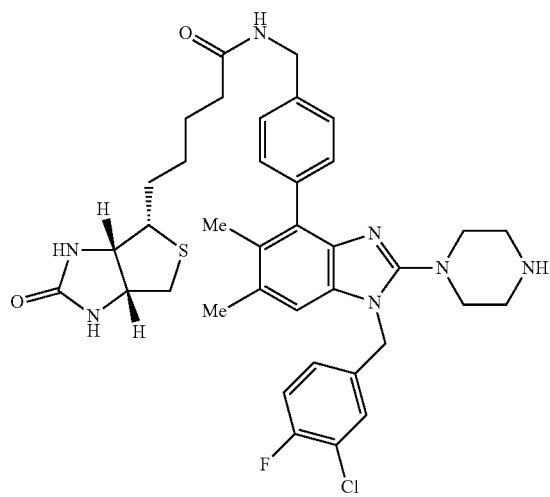 [SMILES: Cc1cc2c(nc(N3CCNCC3)n2Cc2ccc(F)c(Cl)c2)c(-c2ccc(CNC(=O)CCCC[C@@H]3SC[C@@H]4NC(=O)N[C@@H]43)cc2)c1C]

The title compound was obtained as its corresponding trifluoroacetate salt in 8% yield using a procedure analogous to that used to prepare Example 284. $^1$H NMR (400 MHz, CD$_3$OD) δ 7.51 (m, 1H), 7.48 (d, J=7.5 Hz, 2H), 7.32 (d, J=7.9 Hz, 2H), 7.27 (m, 3H), 5.50 (s, 2H), 4.50 (m, 1H), 4.49 (s, 2H), 4.31 (dd, J=7.8, 4.5 Hz, 1H), 3.64 (bm, 4H), 3.38 (bm, 4H), 3.23 (quin, J=4.3 Hz, 1H), 2.92 (dd, J=12.8, 4.9 Hz, 1H), 2.70 (d, J=12.8 Hz, 1H), 2.40 (s, 3H), 2.32 (t, J=7.1 Hz, 2H), 2.11 (s, 3H), 1.65 (m, 6H). MS (ESI) (M+H$^+$) m/z=704.00. LCMS Ret time (UV 214/254): 1.276 min.

Example 338 N-(4-(1-(4-fluoro-3,5-dimethylbenzyl)-6-methyl-2-(piperazin-1-yl)-1H-benzo[d]imidazol-4-yl)benzyl)-5-((3aS,4S,6aR)-2-oxohexahydro-1H-thieno[3,4-d]imidazol-4-yl)pentanamide

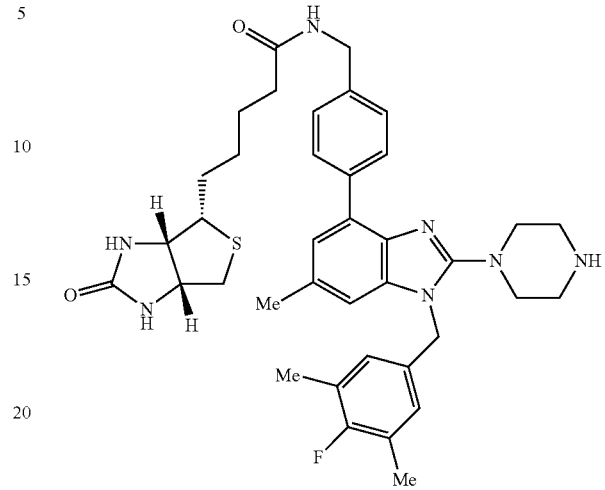

The title compound was obtained as its corresponding trifluoroacetate salt in 66% yield using a procedure analogous to that used to prepare Example 284. $^1$H NMR (400 MHz, CD$_3$OD) δ 7.68 (d, J=8.2 Hz, 2H), 7.46 (d, J=8.0 Hz, 2H), 7.26 (s, 1H), 7.16 (s, 1H), 7.00 (s, 1H), 6.99 (s, 1H), 5.41 (s, 2H), 4.48 (m, 1H), 4.45 (s, 2H), 4.28 (dd, J=7.8, 4.5 Hz, 1H), 3.71 (bm, 4H), 3.40 (bm, 4H), 3.20 (quin, J=4.3 Hz, 1H), 2.90 (dd, J=12.9, 5.0 Hz, 1H), 2.69 (d, J=12.8 Hz, 1H), 2.46 (s, 3H), 2.30 (t, J=7.2 Hz, 2H), 2.23 (2s ovlp, 6H), 1.61 (m, 6H). MS (ESI) (M+H$^+$) m/z=684.30. LCMS Ret time (UV 214/254): 1.309 min.

Example 339: 2-((2-(2,6-dioxopiperidin-3-yl)-1,3-dioxoisoindolin-4-yl)oxy)-N-(4-(1-(4-fluoro-3,5-dimethylbenzyl)-6-methyl-2-(piperazin-1-yl)-1H-benzo[d]imidazol-4-yl)benzyl)acetamide

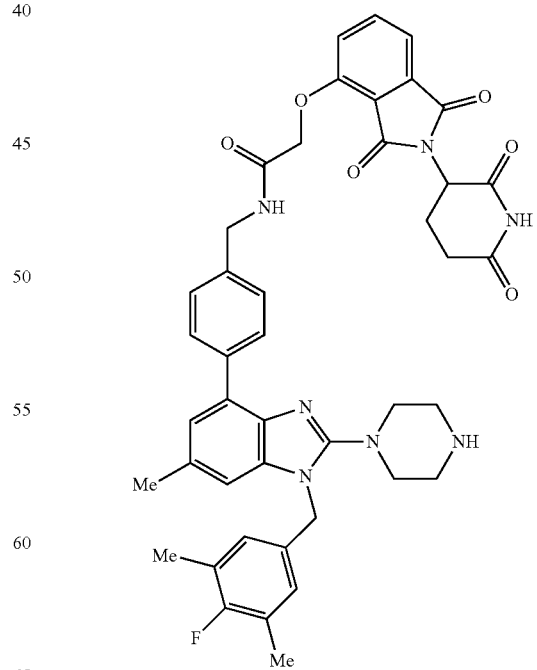

The title compound was obtained as its corresponding trifluoroacetate salt in 26% yield using a procedure analogous to that used to prepare Example 284. $^1$H NMR (400 MHz, CD$_3$OD) δ 8.61 (t, J=5.9 Hz, 1H), 7.80 (m, 3H), 7.55 (dd, J=7.2, 3.2 Hz, 1H), 7.47 (dd, J=8.0, 2.2 Hz, 2H), 7.24 (s, 1H), 7.08 (bd, J=9.7 Hz, 1H), 6.93 (bm, 2H), 5.36 (s, 2H), 5.08 (dd, J=12.5, 5.4 Hz, 1H), 4.59 (m, 2H), 3.58 (bm, 4H), 3.39 (bm, 4H), 2.80 (m, 1H), 2.65 (m, 2H), 2.46 (s, 3H), 2.21 (2s ovlp, 6H), 2.08 (m, 1H). MS (ESI) (M+H$^+$) m/z=771.90. LCMS Ret time (UV 214/254): 1.491 min.

Biological Examples

Compounds of the present invention were assessed for their ability to affect the function of Ras in biochemical and cell proliferation assays.

A. SOS-Mediated Nucleotide Exchange on Ras

Compounds of the present invention were tested for their ability to modify the rate at which Ras exchanges a labeled nucleotide guanosine diphosphate (GDP) analog for guanosine triphosphate (GTP). Briefly, test compounds, then GTP and the Ras GEF SOS (Son of Sevenless) are added to a buffered solution containing Ras protein loaded with BODIPY-GDP. Changes in fluoresence indicating exchange of the labeled GDP for GTP are monitored over time. Raw fluorescence data was fit to a single exponential decay function and derived rates were plotted as mean values. EC$_{50}$ values were calculated by plotting mean derived rates as a function of compound concentration and fit using a four-parameter dose-response curve. This assay is performed in a method analogous to the assay disclosed in: Burns, M. C.; Sun, Q.; Daniels, R. N.; Camper, D. V.; Kennedy, J. P.; Phan, J.; Olejniczak, E. O.; Lee, T.; Waterson, A. G.; Rossanese, O. W.; Fesik, S. W. "Approach for targeting Ras with small molecules that activate SOS-mediated nucleotide exchange" Proc. Natl. Acad. Sci. 2014; 11(9): 3401-3406. PMCID: PMC3948241.

Many of the exemplified compounds Examples 1-339 were run in the recited assay and the results are reported in the following Table 1. In the following table:

"+" indicates a nucleotide exchange EC$_{50}$ measurement greater than 30 μM but less than 100 μM or a level of nucleotide exchange at 100 μM at least 30% of that observed for Compound 4 reported in Burns, et al, Proc. Natl. Acad. Sci. 2014; 11(9): 3401-3406.

"++" indicates at least one nucleotide exchange EC$_{50}$ measurement less than 30 μM but no measurement less than 5 μM; and "+++" indicates at least one nucleotide exchange EC$_{50}$ measurement less than 5 μM but no measurement less than 1 μM; and "++++" indicates at least one nucleotide exchange EC$_{50}$ measurement less than 1 μM.

TABLE 1

Nucleotide exchange activity for example compounds

| Example | Activity | Example | Activity | Example | Activity | Example | Activity | Example | Activity |
|---|---|---|---|---|---|---|---|---|---|
| 1 | + | 64 | +++ | 127 | +++ | 193 | +++ | 261 | + |
| 2 | + | 65 | +++ | 128 | ++++ | 195 | +++ | 262 | + |
| 3 | + | 66 | ++ | 129 | ++++ | 196 | +++ | 263 | + |
| 4 | ++ | 67 | ++ | 130 | ++++ | 197 | +++ | 264 | ++ |
| 5 | + | 68 | +++ | 131 | +++ | 198 | +++ | 265 | +++ |
| 6 | + | 69 | ++++ | 132 | ++++ | 201 | ++++ | 266 | ++ |
| 7 | ++ | 70 | +++ | 133 | +++ | 203 | ++++ | 267 | ++++ |
| 8 | + | 71 | +++ | 134 | ++++ | 204 | ++++ | 269 | + |
| 9 | + | 72 | +++ | 135 | ++++ | 205 | ++++ | 270 | + |
| 10 | + | 73 | ++++ | 136 | ++++ | 206 | ++++ | 271 | + |
| 11 | +++ | 74 | ++++ | 137 | +++ | 207 | ++++ | 272 | + |
| 12 | ++ | 75 | +++ | 138 | +++ | 208 | ++++ | 274 | +++ |
| 13 | + | 76 | ++++ | 139 | +++ | 209 | ++++ | 275 | ++++ |
| 14 | ++ | 77 | ++++ | 140 | +++ | 210 | ++++ | 276 | ++++ |
| 15 | ++ | 78 | ++ | 142 | + | 213 | +++ | 277 | +++ |
| 16 | +++ | 79 | +++ | 143 | ++ | 214 | + | 278 | ++++ |
| 17 | +++ | 81 | +++ | 144 | + | 215 | ++ | 279 | +++ |
| 18 | ++ | 82 | +++ | 145 | + | 216 | ++++ | 280 | ++++ |
| 19 | ++ | 83 | +++ | 146 | +++ | 217 | +++ | 281 | ++ |
| 20 | ++ | 84 | +++ | 147 | ++++ | 218 | ++ | 282 | +++ |
| 21 | ++ | 85 | +++ | 148 | +++ | 219 | ++ | 283 | ++ |
| 22 | ++ | 86 | +++ | 149 | ++ | 220 | ++ | 288 | ++++ |
| 23 | + | 87 | ++ | 150 | ++ | 221 | + | 289 | +++ |
| 24 | +++ | 88 | +++ | 151 | ++ | 222 | ++ | 290 | +++ |
| 25 | ++ | 89 | +++ | 152 | +++ | 223 | ++ | 291 | ++++ |
| 26 | ++ | 90 | +++ | 153 | ++ | 224 | ++ | 292 | +++ |
| 27 | + | 91 | ++ | 154 | +++ | 225 | ++ | 293 | +++ |
| 28 | +++ | 92 | +++ | 155 | ++++ | 226 | ++ | 294 | ++ |
| 29 | + | 93 | +++ | 156 | ++++ | 227 | +++ | 295 | ++ |
| 30 | ++ | 94 | +++ | 157 | ++++ | 228 | ++ | 296 | +++ |
| 31 | ++ | 95 | +++ | 158 | +++ | 229 | +++ | 297 | +++ |
| 32 | ++ | 96 | +++ | 159 | ++++ | 230 | ++ | 298 | ++++ |
| 33 | +++ | 97 | +++ | 160 | +++ | 231 | ++ | 299 | ++++ |
| 34 | ++ | 98 | +++ | 161 | ++++ | 232 | ++ | 300 | ++++ |
| 35 | +++ | 99 | ++ | 162 | +++ | 233 | ++ | 301 | +++ |
| 36 | ++ | 100 | +++ | 163 | +++ | 234 | ++ | 302 | ++++ |
| 37 | ++ | 101 | +++ | 164 | +++ | 235 | + | 303 | ++++ |
| 38 | ++ | 102 | +++ | 165 | +++ | 236 | + | 304 | ++++ |
| 39 | +++ | 103 | +++ | 167 | ++++ | 237 | + | 305 | ++++ |
| 40 | ++ | 104 | +++ | 168 | +++ | 238 | + | 306 | +++ |
| 41 | +++ | 105 | +++ | 169 | +++ | 239 | + | 307 | +++ |
| 42 | +++ | 106 | +++ | 170 | +++ | 240 | +++ | 308 | +++ |
| 43 | ++ | 107 | +++ | 171 | +++ | 241 | +++ | 309 | +++ |

TABLE 1-continued

Nucleotide exchange activity for example compounds

| Example | Activity | Example | Activity | Example | Activity | Example | Activity | Example | Activity |
|---|---|---|---|---|---|---|---|---|---|
| 44 | ++ | 108 | ++++ | 172 | +++ | 242 | +++ | 310 | ++++ |
| 45 | ++ | 109 | +++ | 173 | ++ | 243 | + | 311 | ++++ |
| 46 | ++ | 110 | +++ | 174 | +++ | 244 | ++ | 312 | ++++ |
| 48 | +++ | 111 | +++ | 175 | ++++ | 245 | +++ | 313 | +++ |
| 49 | +++ | 112 | ++ | 176 | +++ | 246 | +++ | 315 | ++++ |
| 50 | +++ | 113 | +++ | 177 | + | 247 | +++ | 316 | ++++ |
| 51 | ++ | 114 | +++ | 178 | ++ | 248 | ++++ | 317 | ++++ |
| 52 | ++ | 115 | ++ | 180 | ++++ | 249 | ++ | 318 | ++++ |
| 53 | + | 116 | +++ | 182 | +++ | 250 | ++ | 319 | ++++ |
| 54 | + | 117 | +++ | 183 | +++ | 251 | + | 320 | ++++ |
| 55 | ++ | 118 | +++ | 184 | +++ | 252 | + | 322 | ++++ |
| 56 | ++ | 119 | +++ | 185 | ++ | 253 | + | 323 | ++++ |
| 57 | ++ | 120 | +++ | 186 | ++ | 254 | + | 327 | ++++ |
| 58 | ++ | 121 | ++++ | 187 | ++++ | 255 | + | 330 | ++++ |
| 59 | ++ | 122 | +++ | 188 | +++ | 256 | ++ | 331 | ++++ |
| 60 | +++ | 123 | +++ | 189 | +++ | 257 | ++ | 332 | ++ |
| 61 | +++ | 124 | ++++ | 190 | ++++ | 258 | ++ | | |
| 62 | ++ | 125 | +++ | 191 | +++ | 259 | ++ | | |
| 63 | ++++ | 126 | +++ | 192 | +++ | 260 | ++ | | |

B. Binding to SOS

Compounds of the present invention were tested for their ability to bind to the Ras guanine exchange factor (GEF) Son of Sevenless (SOS). Binding to SOS was measured using a Fluorescence polarization anisotropy (FPA) assay that assesses the ability of a test compound to displace a fluorescent FITC-conjugated compound (Example 285). Briefly, the labeled probe compound is incubated with SOS in buffer. Changes in anisotropy indicative of displacement of the labeled probe for a test compound are assessed over a dose range of test compound. Data was analyzed by plotting fluorescence anisotropy values as a function of compound concentration. $IC_{50}$ values were determined using a four-parameter dose-response (variable slope) and binding affinities were calculated from this $IC_{50}$ value. This assay is performed in a method analogous to the assay disclosed in:

Burns, M. C.; Sun, Q.; Daniels, R. N.; Camper, D. V.; Kennedy, J. P.; Phan, J.; Olejniczak, E. O.; Lee, T.; Waterson, A. G.; Rossanese, O. W.; Fesik, S. W. "Approach for targeting Ras with small molecules that activate SOS-mediated nucleotide exchange" *Proc. Natl. Acad. Sci.* 2014; 11(9): 3401-3406. PMCID: PMC3948241.

Many of the exemplified compounds Examples 1-339 were run in the recited assay and the results are reported in the following Table 2. In the following table:

"+" indicates no binding affinity measurement less than 5 µM

"++" indicates at least one binding affinity measurement less than 5 µM but no measurement less than 1.0 µM; and "+++" indicates at least one binding affinity measurement less than 1.0 µM but no measurement less than 0.5 µM; and "++++" indicates at least one binding affinity measurement less than 0.5 µM.

TABLE 2

Binding affinities for example compounds

| Example | Activity | Example | Activity | Example | Activity | Example | Activity | Example | Activity |
|---|---|---|---|---|---|---|---|---|---|
| 7 | + | 76 | ++++ | 145 | + | 198 | +++ | 277 | + |
| 10 | + | 77 | +++ | 147 | ++ | 199 | +++ | 278 | ++ |
| 16 | ++ | 78 | + | 148 | +++ | 200 | + | 279 | ++++ |
| 17 | ++ | 81 | +++ | 149 | ++ | 201 | +++ | 280 | ++ |
| 18 | + | 83 | ++ | 150 | + | 202 | +++ | 282 | +++ |
| 19 | + | 89 | ++ | 151 | + | 203 | +++ | 283 | + |
| 20 | + | 90 | ++ | 153 | + | 204 | ++ | 288 | ++ |
| 21 | + | 93 | ++ | 154 | ++ | 205 | ++ | 290 | ++ |
| 22 | + | 94 | ++ | 156 | ++++ | 206 | + | 291 | ++ |
| 24 | + | 98 | + | 159 | ++++ | 207 | ++ | 292 | ++ |
| 26 | + | 101 | ++ | 160 | ++++ | 208 | + | 293 | ++ |
| 31 | + | 102 | + | 161 | +++ | 209 | + | 294 | + |
| 33 | + | 103 | ++++ | 162 | ++ | 210 | + | 296 | ++++ |
| 34 | + | 104 | ++ | 163 | +++ | 211 | + | 297 | ++++ |
| 35 | ++ | 105 | + | 164 | ++++ | 213 | + | 298 | ++++ |
| 36 | + | 106 | ++ | 165 | ++ | 214 | + | 299 | ++++ |
| 37 | + | 107 | ++ | 166 | +++ | 216 | +++ | 300 | ++++ |
| 38 | + | 108 | +++ | 167 | +++ | 217 | + | 301 | ++++ |
| 39 | + | 109 | +++ | 168 | +++ | 218 | + | 302 | +++ |
| 40 | + | 110 | ++ | 169 | + | 219 | + | 303 | ++++ |
| 41 | + | 111 | ++ | 170 | ++++ | 224 | + | 304 | ++++ |
| 42 | ++ | 112 | ++ | 171 | ++ | 225 | + | 305 | ++++ |
| 43 | + | 113 | ++++ | 172 | ++ | 226 | + | 306 | ++++ |
| 44 | + | 114 | ++ | 173 | + | 227 | + | 307 | ++++ |
| 45 | + | 115 | + | 174 | ++++ | 228 | + | 308 | ++++ |
| 46 | + | 116 | ++ | 175 | +++ | 229 | + | 309 | ++++ |

TABLE 2-continued

Binding affinities for example compounds

| Example | Activity | Example | Activity | Example | Activity | Example | Activity | Example | Activity |
|---|---|---|---|---|---|---|---|---|---|
| 48 | ++ | 118 | ++++ | 176 | ++++ | 230 | + | 310 | +++ |
| 49 | + | 119 | ++++ | 177 | ++ | 231 | + | 311 | ++ |
| 50 | + | 120 | ++++ | 178 | + | 232 | + | 312 | ++++ |
| 51 | + | 121 | ++++ | 179 | +++ | 233 | + | 313 | ++ |
| 52 | + | 122 | +++ | 180 | ++ | 234 | + | 315 | ++ |
| 56 | + | 123 | ++ | 181 | +++ | 235 | + | 316 | ++ |
| 58 | + | 124 | ++ | 182 | + | 240 | + | 317 | +++ |
| 61 | ++ | 125 | ++ | 183 | +++ | 241 | + | 318 | ++++ |
| 62 | + | 126 | ++ | 184 | +++ | 245 | + | 319 | ++++ |
| 63 | +++ | 127 | ++ | 185 | + | 246 | ++ | 320 | +++ |
| 64 | +++ | 128 | +++ | 187 | ++++ | 247 | ++ | 322 | ++++ |
| 65 | ++ | 129 | ++++ | 188 | +++ | 248 | +++ | 323 | ++ |
| 66 | + | 130 | ++++ | 189 | +++ | 251 | + | 327 | +++ |
| 67 | + | 132 | ++ | 190 | +++ | 259 | + | 330 | +++ |
| 68 | ++ | 134 | +++ | 191 | +++ | 260 | + | 331 | +++ |
| 69 | +++ | 135 | ++ | 192 | +++ | 265 | ++ | 332 | + |
| 70 | ++ | 136 | ++ | 193 | +++ | 266 | + | 336 | ++ |
| 72 | ++ | 137 | ++ | 194 | +++ | 267 | ++++ | | |
| 73 | +++ | 139 | ++ | 195 | +++ | 274 | + | | |
| 74 | +++ | 142 | + | 196 | +++ | 275 | +++ | | |
| 75 | ++ | 143 | + | 197 | +++ | 276 | ++++ | | |

C. Modulation of Ras Cellular Signaling

Several examples of the present invention were assessed for their ability to affect cellular signaling downstream of Ras in cancer cell lines. Experiments were conducted according to Western blotting procedures known to those skilled in the art, in a manner analogous to the assay disclosed in: Burns, M. C.; Sun, Q.; Daniels, R. N.; Camper, D. V.; Kennedy, J. P.; Phan, J.; Olejniczak, E. O.; Lee, T.; Waterson, A. G.; Rossanese, O. W.; Fesik, S. W. "Approach for targeting Ras with small molecules that activate SOS-mediated nucleotide exchange" Proc. Natl. Acad. Sci. 2014; 11(9): 3401-3406. PMCID: PMC3948241.

Briefly, cells (NCI-H727, SKMEL28, and HeLa, obtained from the ATCC) were cultured in an appropriate media, such as DMEM or RPMI supplemented with 10% (vol/vol) FBS, in a humidified incubator at 37° C. and 5% CO$_2$. 24 hours after plating, cells were treated with DMSO vehicle control or the stated concentration of compound [in µM] for 30 minutes. Cells were stimulated with 50 ng/mL EGF for 5 minutes. Lysates were prepared using 1× protein loading buffer (LiCor) supplemented with protease and phosphatase inhibitors (Thermo Scientific) and 10 mM DTT. Samples were boiled at 95° C. for 10 minutes. Lysates were analyzed by SDS/PAGE and western blotting using Immobilon-FL PVDF membranes (Millipore) and scanned on an Odyssey imager (LiCor). Antibodies for ERK, phospho-ERK, AKT and phospho-AKT (S473), were obtained from Cell Signaling. Fluorescently labeled secondary antibodies were obtained from LiCor.

D. Inhibition of Cancer Cell Proliferation

Compounds of the present invention were measured for their ability to kill H727 lung cancer cell lines, which contain a G12V K-Ras mutation. Cell proliferation experiments were conducted in 96-well plates. Cells were plated at 1000 cells/well, incubated overnight, followed by treatment with a dose range of compound for 3 days at 37° C. Cell proliferation was assessed using a CellTiter-Glo assay (Promega) according to the manufacturer's protocol. Data were normalized to DMSO control. IC$_{50}$ values were determined using a four-parameter dose-response (variable slope) equation. These assays are performed in a manner analogous to the assay disclosed in: Burns, M. C.; Sun, Q.; Daniels, R. N.; Camper, D. V.; Kennedy, J. P.; Phan, J.; Olejniczak, E. O.; Lee, T.; Waterson, A. G.; Rossanese, O. W.; Fesik, S. W. "Approach for targeting Ras with small molecules that activate SOS-mediated nucleotide exchange" Proc. Natl. Acad. Sci. 2014; 11(9): 3401-3406. PMCID: PMC3948241.

Many of the exemplified compounds Examples 1-339 were run in the recited assay and the results are reported in the following Table 3. In the following table:

"+" indicates no H727 cancer cell line proliferation IC$_{50}$ less than 20 µM

"++" indicates at least one H727 cancer cell line proliferation IC$_{50}$ less than 20 µM but no measurement less than 5 µM; and "+++" indicates at least H727 cancer cell line proliferation IC$_{50}$ less than 5 µM but no measurement less than 1 µM; and "++++" indicates at least H727 cancer cell line proliferation IC$_{50}$ less than 1 µM.

TABLE 3

Cell proliferation activity for example compounds

| Example | Activity | Example | Activity | Example | Activity | Example | Activity |
|---|---|---|---|---|---|---|---|
| 46 | +++ | 92 | +++ | 124 | +++ | 161 | +++ |
| 48 | +++ | 93 | +++ | 125 | +++ | 162 | +++ |
| 49 | +++ | 94 | +++ | 126 | +++ | 164 | ++++ |
| 50 | +++ | 95 | ++++ | 127 | +++ | 170 | ++ |
| 51 | +++ | 96 | +++ | 128 | +++ | 223 | + |
| 52 | + | 97 | ++++ | 129 | +++ | 240 | ++ |
| 75 | +++ | 104 | +++ | 130 | +++ | 241 | + |
| 76 | +++ | 106 | +++ | 131 | ++++ | 248 | ++ |
| 77 | +++ | 107 | ++ | 132 | +++ | 258 | +++ |
| 79 | ++ | 108 | +++ | 133 | +++ | 259 | ++++ |
| 81 | ++ | 109 | +++ | 138 | ++ | 260 | ++++ |
| 82 | ++ | 110 | +++ | 139 | +++ | 261 | ++++ |
| 84 | +++ | 111 | +++ | 140 | +++ | 262 | ++ |
| 85 | ++ | 113 | +++ | 155 | ++++ | 263 | ++ |
| 86 | ++ | 114 | ++ | 156 | +++ | 267 | +++ |
| 87 | ++ | 118 | +++ | 157 | +++ | 286 | +++ |
| 89 | ++ | 119 | + | 158 | ++ | 317 | ++ |
| 91 | +++ | 120 | +++ | 159 | ++++ | | |

We claim:
1. A compound of the following formula:

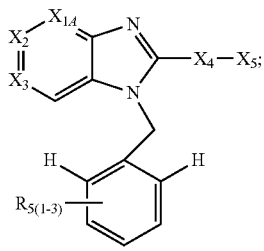

$X_{1A}$ is C—R;
$X_2$ is C—$R_6$;
$X_3$ is C—$R_6$;
$X_4$ and $X_5$ together form

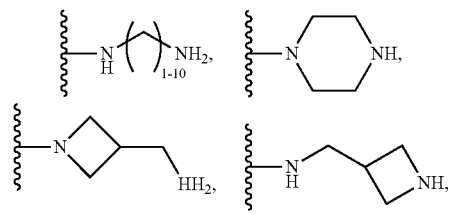

or substituted or unsubstituted cyclic amine (provided that the term cyclic amine excludes piperazine and azetidine);

R is unsubstituted or substituted with one or more independent $R_5$, and is independently chosen from alkyl, cycloalkyl, phenyl, hydroxyl, heterocycloalkyl, cyclic amine, halogen, $CF_3$, Cl, $CONR_3R_4$, aryl, heteroaryl, O—$R_4$, O-alkyl-$R_4$, O-aryl, O-heteroaryl, N—$R_4$, N-aryl, N-heteroaryl, $NHR_4$, $NR_2R_3$, heteroalkyl, benzyl, heteroaryl benzyl ($CH_2$-heteroaryl), alkenyl, alkynyl, alkyl-cycloalkyl, $CH_2$-cycloalkyl, $CH_2$—$CF_3$, hydroxyalkyl, alkyl-alkoxy, alkyl-cycloheteroalkyl, alkyl-heteroaryl, alkyl-carboxylic acid, CO—$CF_3$, alkyl-CO—O-alkyl, alkyl-CO—$NR_3R_4$, CO-alkyl-sulfonyl-alkyl, CO-cycloheteroalkyl, CO—NH-cycloalkyl, CN, alkoxy-cycloalkyl, alkoxy-cycloheteroalkyl, O-alkoxy, O-dioxothian, alkoxy, O-heteroalkyl, alkoxy-heteroalkyl, methylsulfonyl, O-cycloheteroalkyl, O-alkoxy-cycloheteroalkyl, O-alkoxy-aryl, O-heteroaryl, $NR_3COR_2$, amino-cycloalkyl, amino-cycloheteroalkyl, $NR_3$-alkoxy, $NR_3$-dioxothian, $NR_3$-heteroalkyl, amino-heteroalkyl, $NR_3$-cycloheteroalkyl, $NR_3$-cycloheteroalkyl, $NR_3$-aryl, $NR_3$-heteroaryl, $NR_3$—CO—$CF_3$, alkyl-CO—$NR_3R_4$, $NR_3$—CO-alkyl-sulfonyl-alkyl, $NR_3$—CO— cycloheteroalkyl, CO—$NR_3$-cycloalkyl, alkyl-carboxylic acid, alkoxy-heteroaryl, alkyl-phenyl, cycloheteroalkyl, amino, amino-heteroaryl, amino-phenyl, CO-alkyl, $CONR_3$-alkyl, $CH_3$, $NH_2$, alkyl-amino, pyridine, pyrazole, furan, thiophene, pyrimidine, thiazole, isothiazole, oxazole, isoxazole, piperazine, pyrrole, pyrazine, dioxane, morpholine, thiomorpholine, triazole, imidazole, alkoxy;

$R_4$ is unsubstituted or substituted with one or more independent $R_5$, and is independently chosen from H, alkyl, cycloalkyl, phenyl, hydroxyl, heterocycloalkyl, cyclic amine, halogen, $CF_3$, Cl, $CONR_3R_4$, aryl, heteroaryl, O—$R_3$, O-alkyl-$R_3$, O-aryl, O-heteroaryl, N—$R_3$, N-aryl, N-heteroaryl, $NR_2R_3$, heteroalkyl, benzyl, heteroaryl benzyl ($CH_2$-heteroaryl), alkenyl, alkynyl, alkyl-cycloalkyl, $CH_2$-cycloalkyl, $CH_2$—$CF_3$, hydroxyalkyl, alkyl-alkoxy, alkyl-cycloheteroalkyl, alkyl-heteroaryl, alkyl-carboxylic acid, CO—$CF_3$, alkyl-CO—O-alkyl, alkyl-CO—$NR_3R_4$, CO-alkyl-sulfonyl-alkyl, CO-cycloheteroalkyl, CO—NH-cycloalkyl, CN, alkoxy-cycloalkyl, alkoxy-cycloheteroalkyl, O-alkoxy, O-dioxothian, alkoxy, O-heteroalkyl, alkoxy-heteroalkyl, methylsulfonyl, O-cycloheteroalkyl, O-alkoxy-cycloheteroalkyl, O-alkoxy-aryl, O-heteroaryl, $NR_3COR_2$, amino-cycloalkyl, amino-cycloheteroalkyl, $NR_3$-alkoxy, $NR_3$-dioxothian, $NR_3$-heteroalkyl, amino-heteroalkyl, $NR_3$-cycloheteroalkyl, $NR_3$-cycloheteroalkyl, $NR_3$-aryl, $NR_3$-heteroaryl, $NR_3$—CO—$CF_3$, alkyl-CO—$NR_3R_4$, $NR_3$—CO-alkyl-sulfonyl-alkyl, $NR_3$—CO— cycloheteroalkyl, CO—$NR_3$-cycloalkyl, alkyl-carboxylic acid, alkoxy-heteroaryl, alkyl-phenyl, cycloheteroalkyl, amino, amino-heteroaryl, amino-phenyl, CO-alkyl, $CONR_3$-alkyl, $CH_3$, $NH_2$, alkyl-amino, pyridine, pyrazole, furan, thiophene, pyrimidine, thiazole, isothiazole, oxazole, isoxazole, piperazine, pyrrole, pyrazine, dioxane, morpholine, thiomorpholine, triazole, imidazole, alkoxy;

$R_2$ is substituted by one or more $R_5$, or unsubstituted and is selected from H, alkyl, alkene, alkyne, alkyl-heteroaryl, alkyl-heterocycloalkyl, alkyl-amino, or together with $R_3$ forms a 3-6 membered ring;

$R_3$ is substituted by one or more $R_5$ or unsubstituted and is selected from H, alkyl, alkenyl, alkynyl, alkyl-heteroaryl, alkyl-heterocycloalkyl, alkyl-amino, or together with $R_2$ forms a ring;

$R_4$ is substituted by one or more $R_5$, or unsubstituted and is selected from benzyl, methylcycloalkyl, cycloalkyl, alkyl-cycloalkyl;

$R_5$ (i) appears once and is a halogen;
(ii) appears twice and is
two halogens,
alkyl and halogen,
$CF_3$ and halogen;
(iii) appears three times and is:
a halogen, alkyl, and alkenyl,
a halogen, a alkyl, and alkynyl,
two alkyls and a halogen; or
three halogens;

$R_6$ is independently selected from H, halogen, $CH_3$, or $CF_3$, provided that in connection with $X_2R_6$ is H or methyl, and in connection with $X_3$, $R_6$ is methyl, $CF_3$, or halogen;

or a pharmaceutically acceptable salt thereof or a pharmaceutically acceptable derivative thereof.

2. A compound of claim 1, wherein $R_6$ is halogen, alkyl, alkenyl, alkynyl, or cycloalkyl.

3. A compound of claim 1, wherein $X_{1A}$ is C—R; and wherein R is of the following formula:

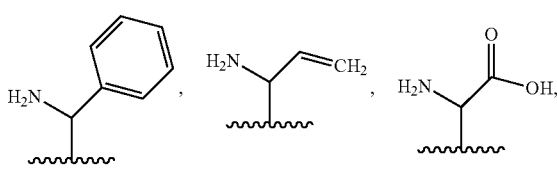

-continued

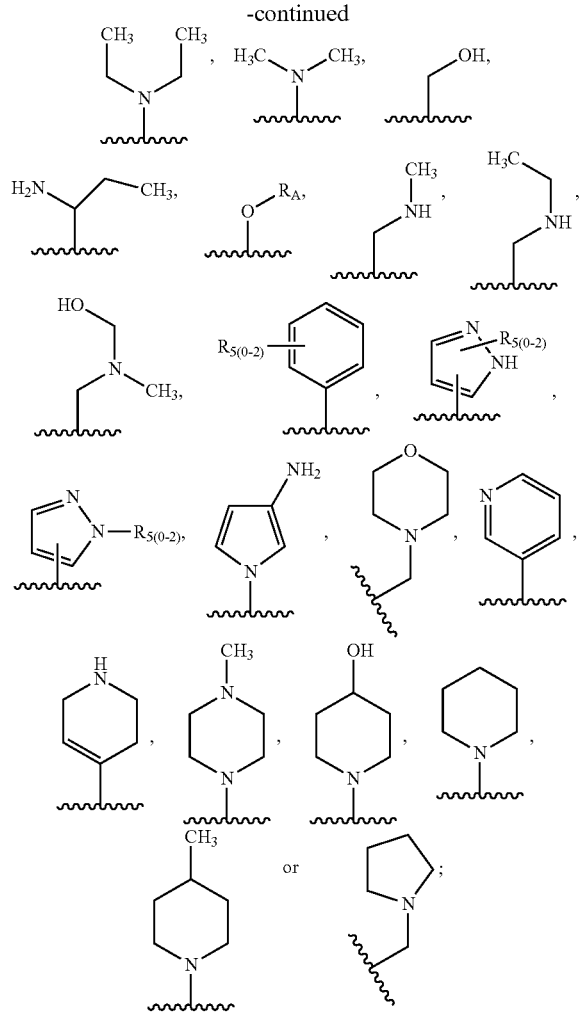

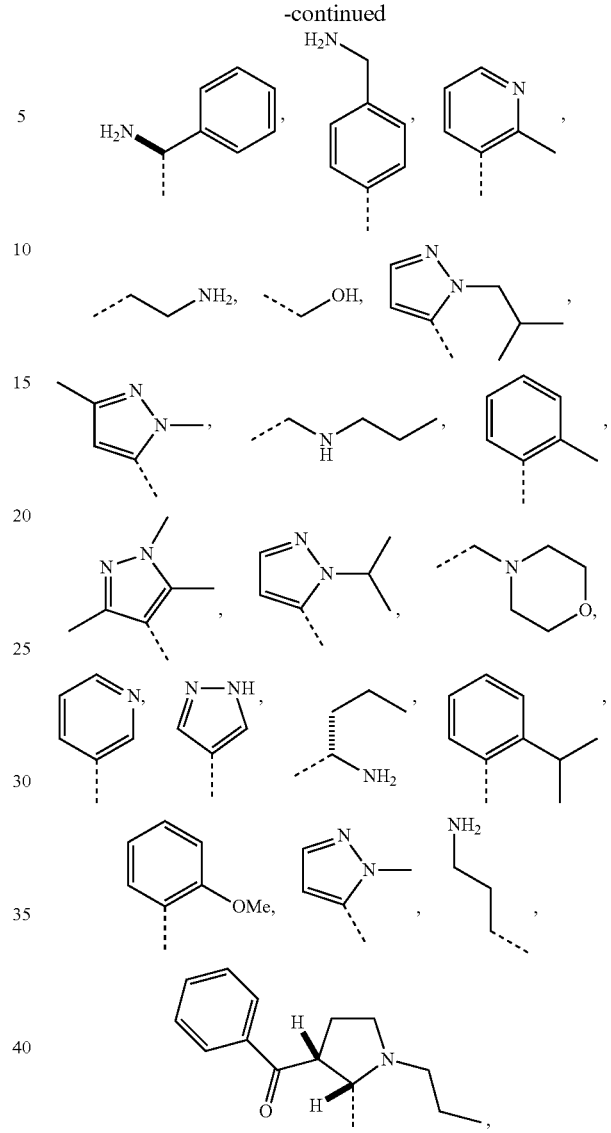

or a pharmaceutically acceptable salt thereof or a pharmaceutically acceptable derivative thereof.

4. A compound of claim 1, wherein $R_6$ is H, halogen, or $C_{1-6}$ alkyl.

5. A compound of claim 1, wherein $R_2$ is selected from H, alkyl, alkyl-heterocycloalkyl, alkyl-azetidine, alkyl-amino.

6. A compound of claim 1, wherein $R_3$ is selected from H, alkyl, alkyl-heterocycloalkyl, alkyl-azetidine, alkyl-amino.

7. A compound of claim 1, wherein $R_5$ is independently selected from H, halogen, alkyl, $CH_3$, alkene, heteroaryl, amino-alkyl, alkoxy.

8. A compound of claim 1, wherein $R_1$ and $X_5$ further cyclize form a 6-membered ring containing one or two nitrogen ring members.

9. A compound of claim 1, wherein $X_{14}$ is C—R, and R is chosen from:

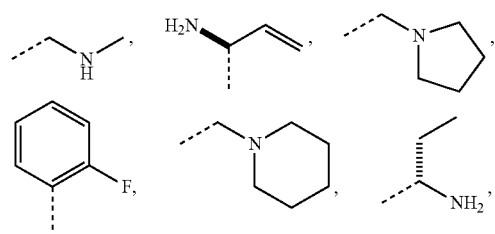

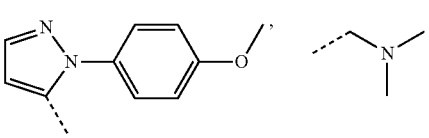

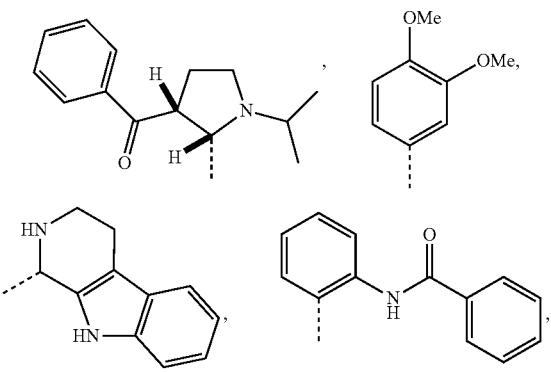

-continued
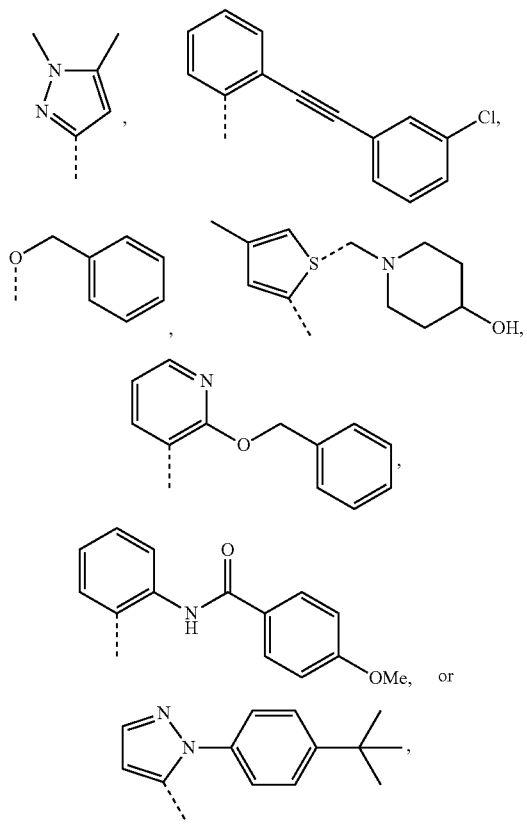
and stereoisomers thereof.
10. The compound of claim 1, wherein when R₅ is alkyl, the alkyl is methyl.
11. A compound of claim 1 the following formula:
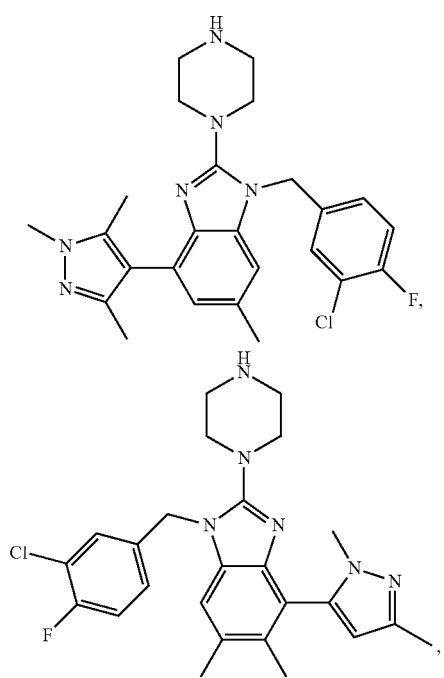
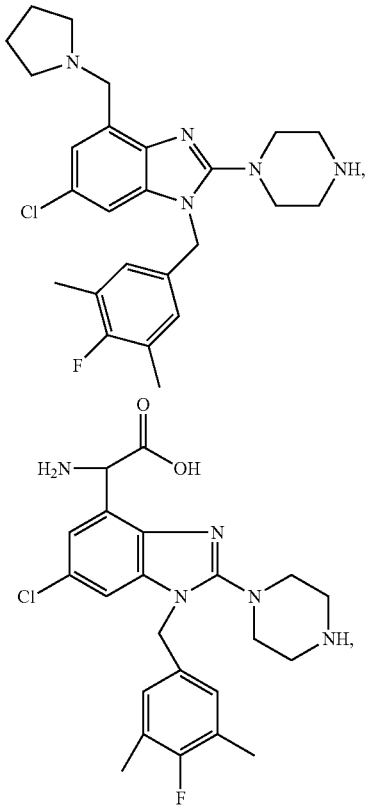
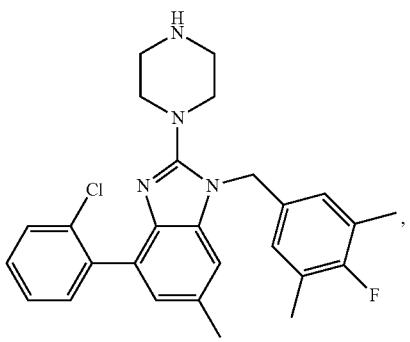
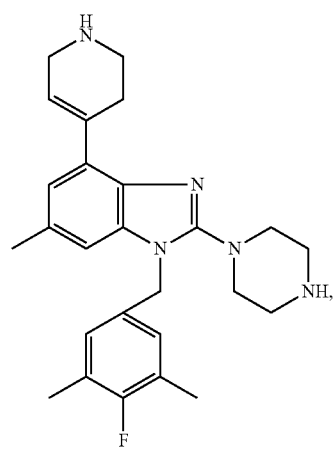

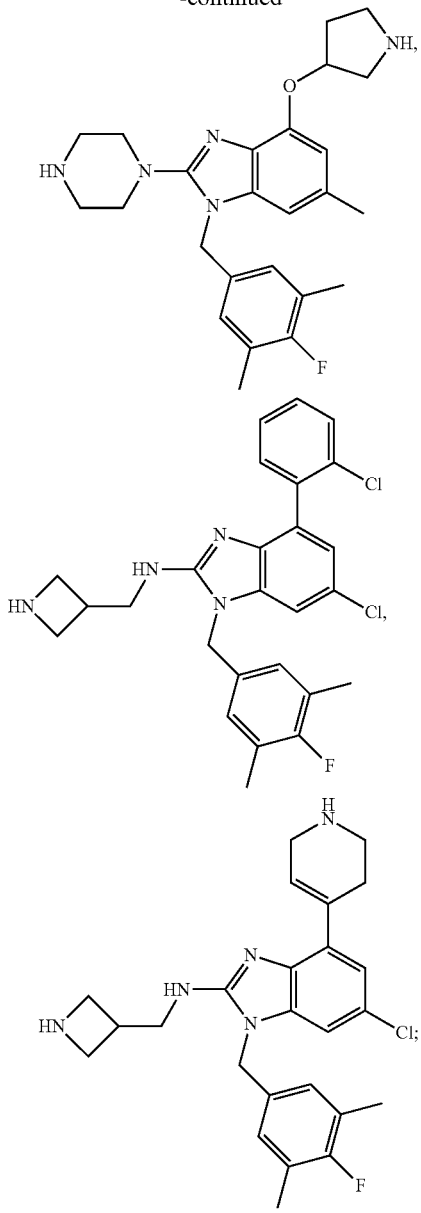
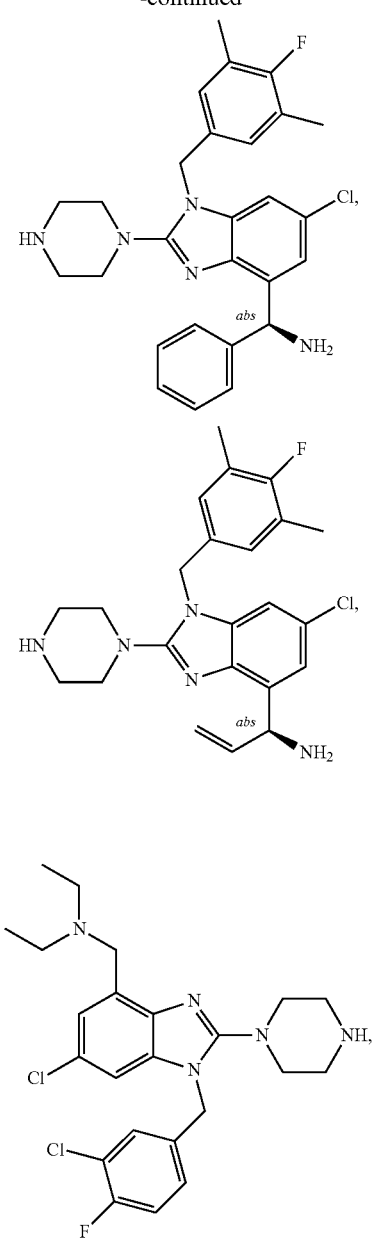
pharmaceutically acceptable salt thereof.
12. A compound of claim 1 the following formula:
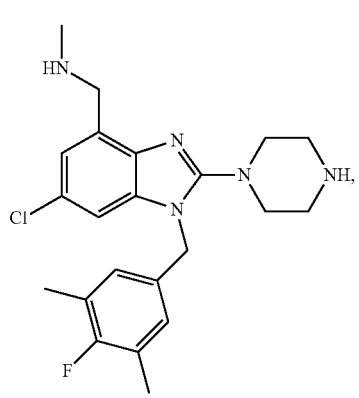
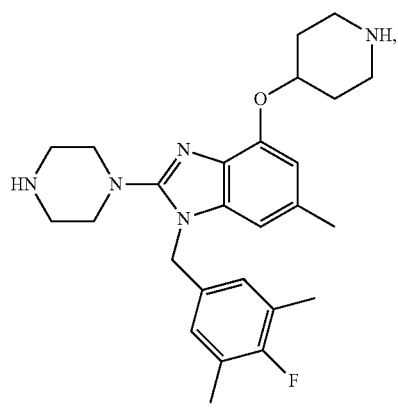

-continued
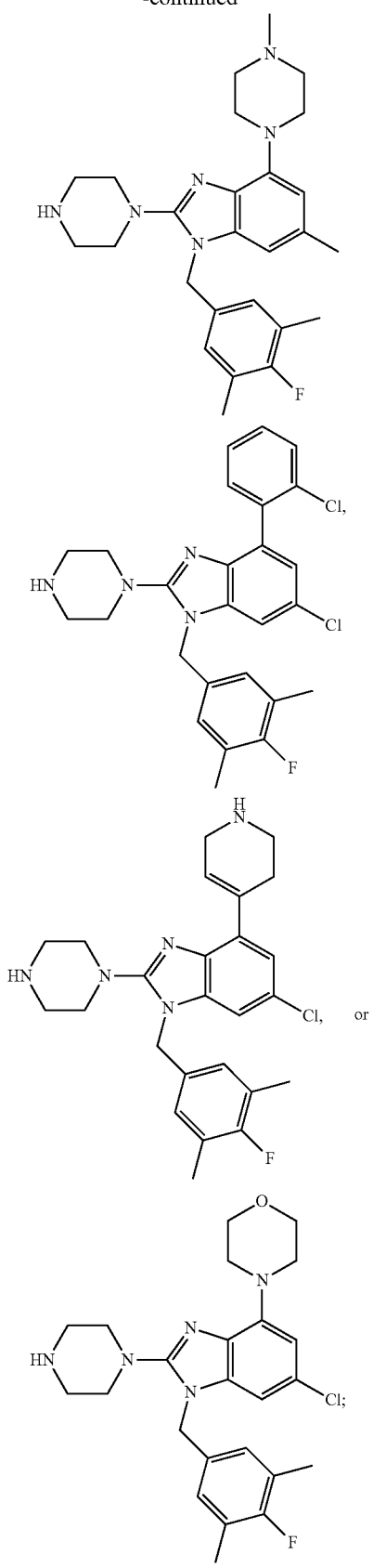
pharmaceutically acceptable salt thereof.
13. A compound of claim 1 of the following formula:
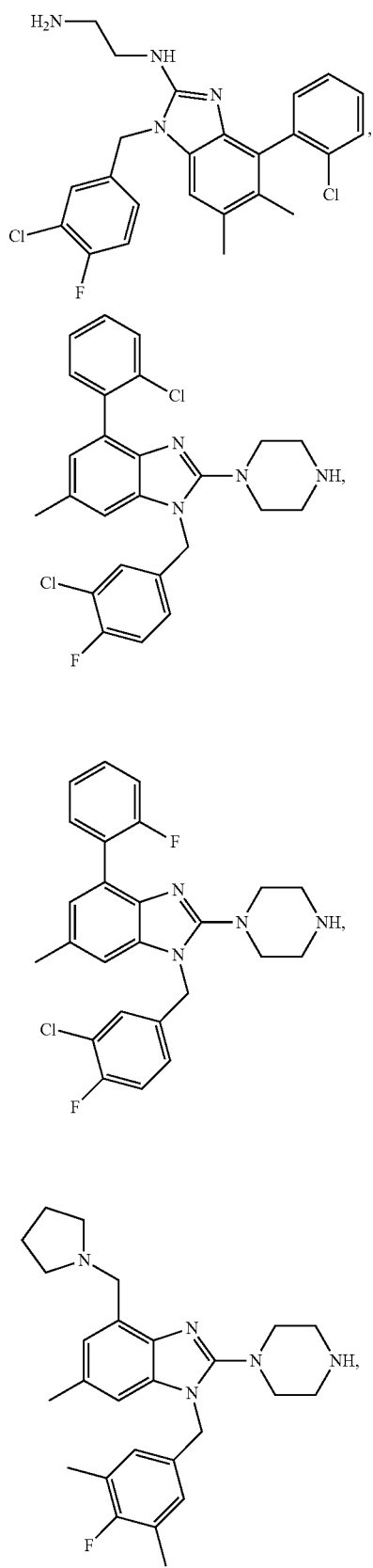

297
-continued
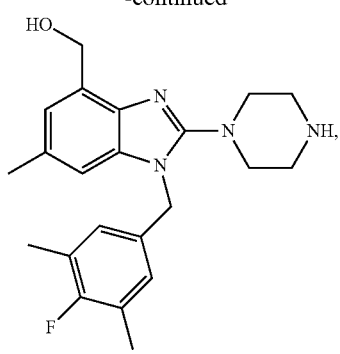
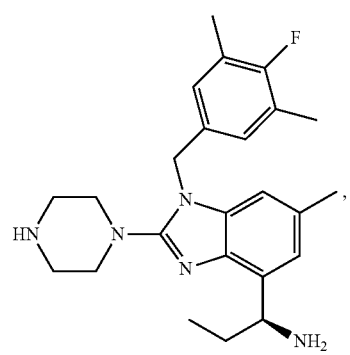
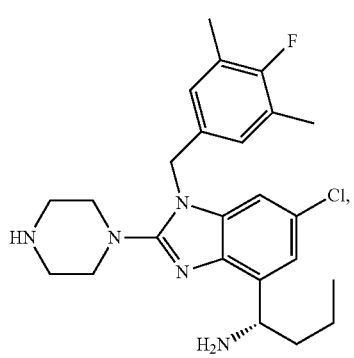
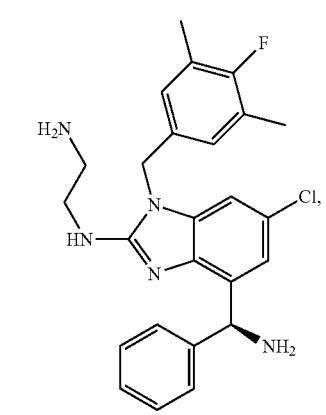
298
-continued
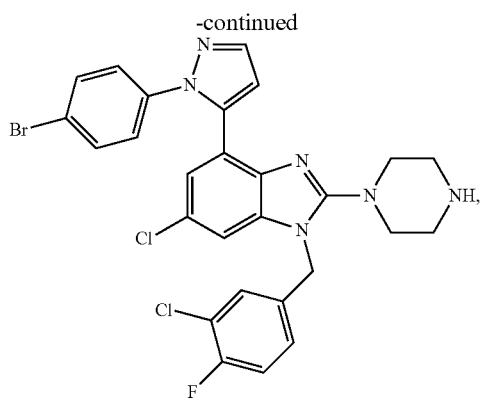
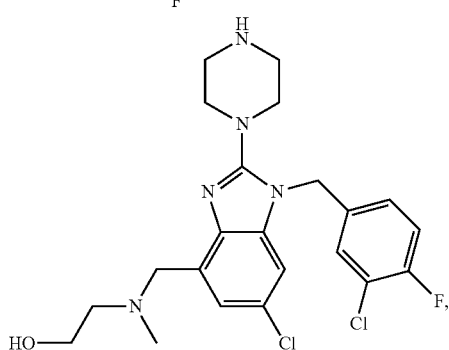
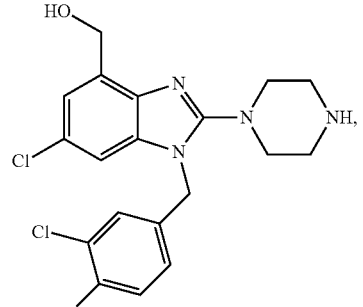
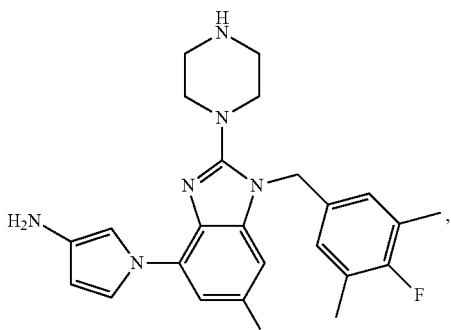
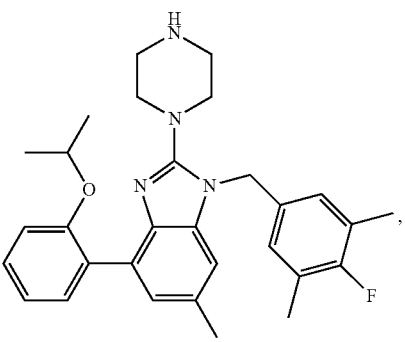

299
-continued
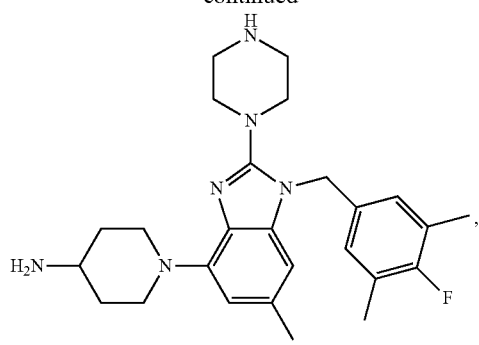
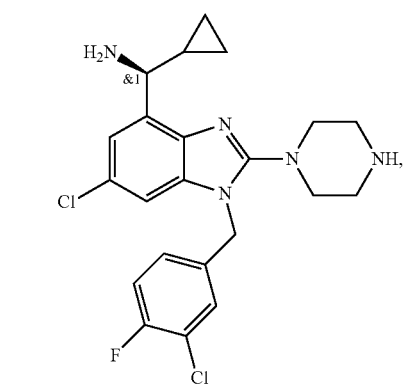
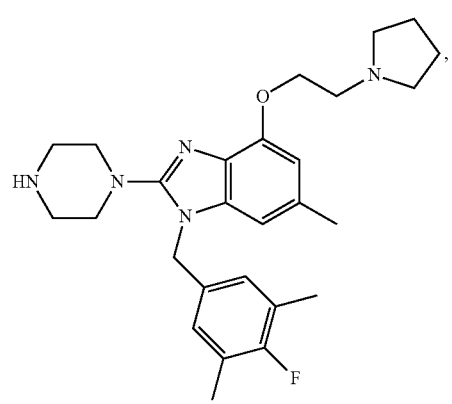
300
-continued
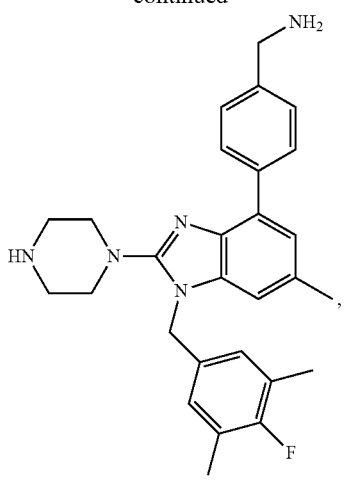
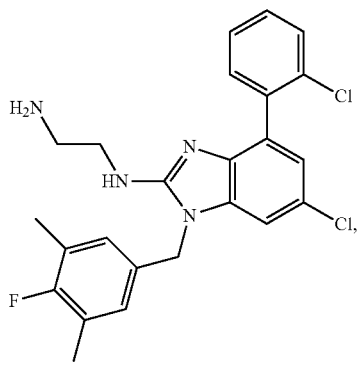
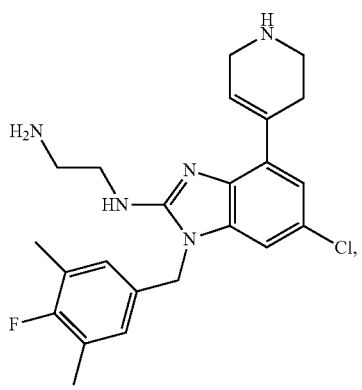
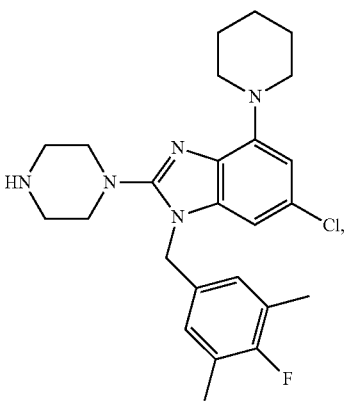

301
-continued
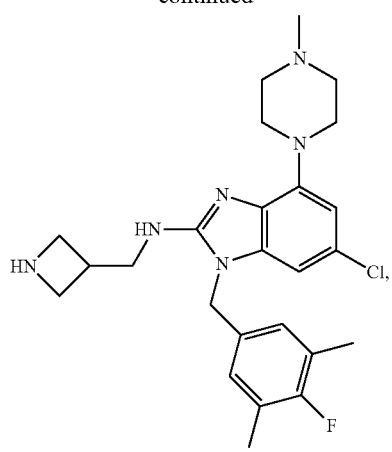
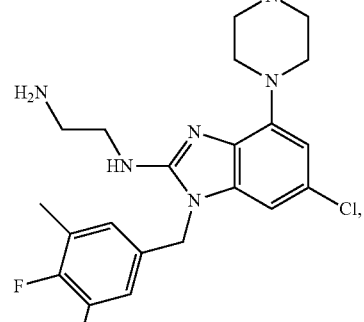
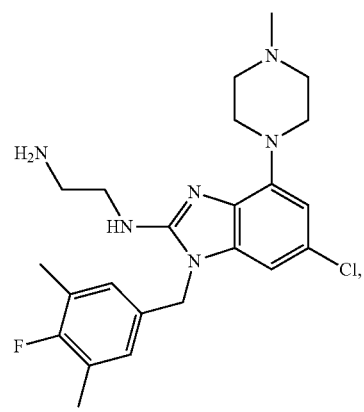
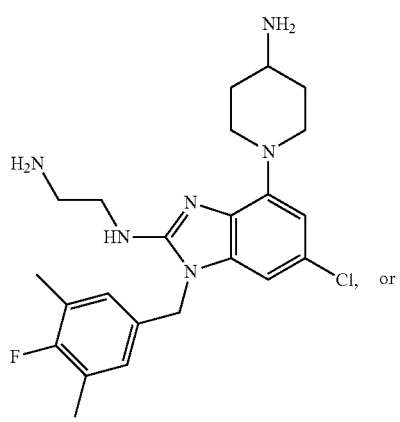
302
-continued
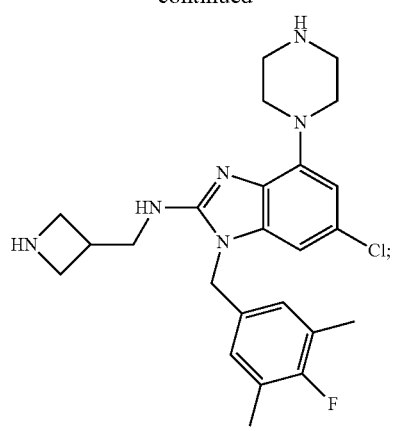
or a pharmaceutically acceptable salt thereof.
14. A compound of claim 1 the following formula:
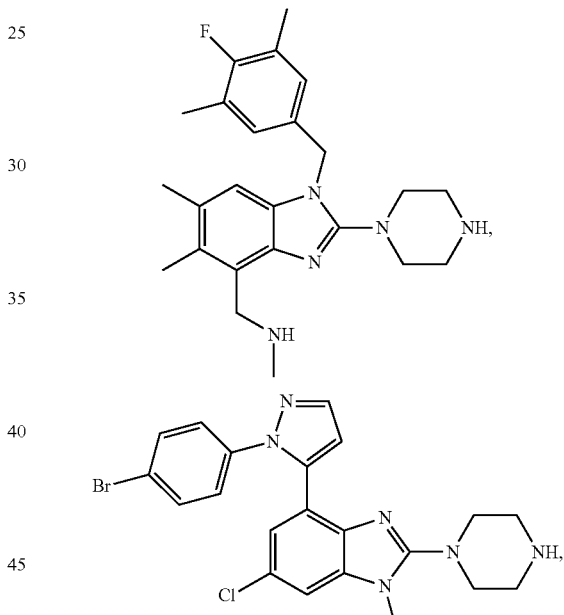
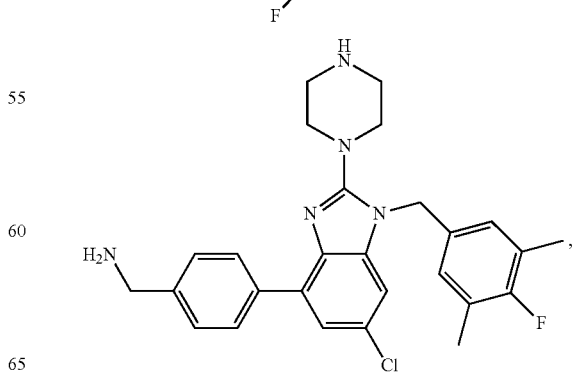

303
-continued
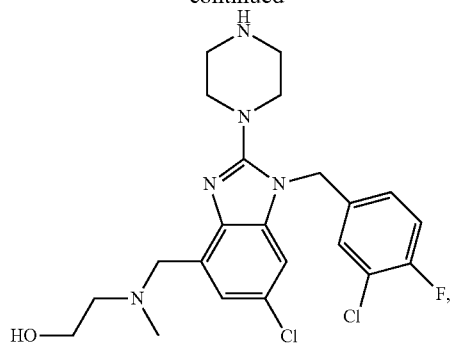
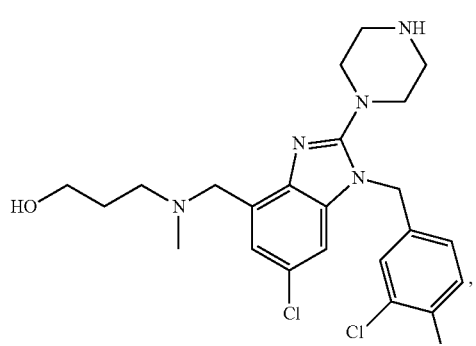
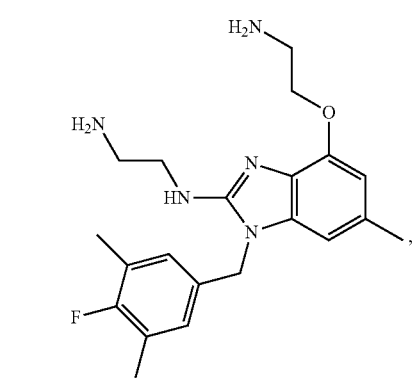
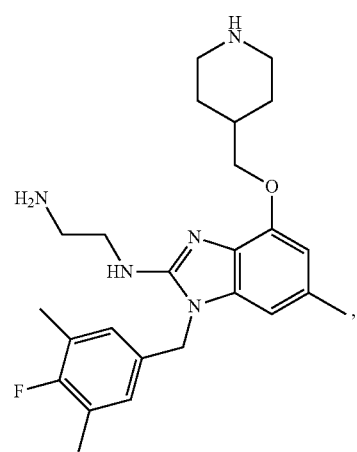
304
-continued
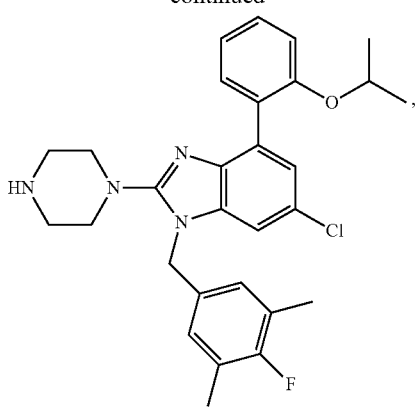
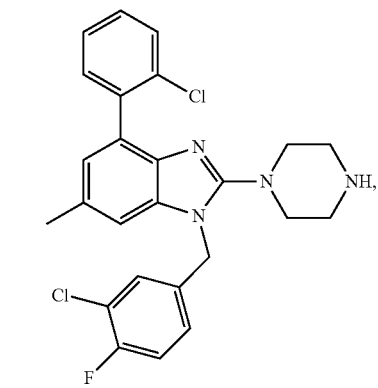
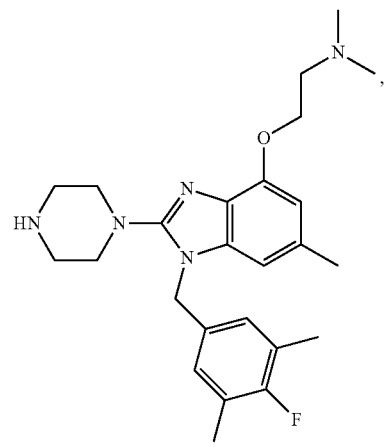
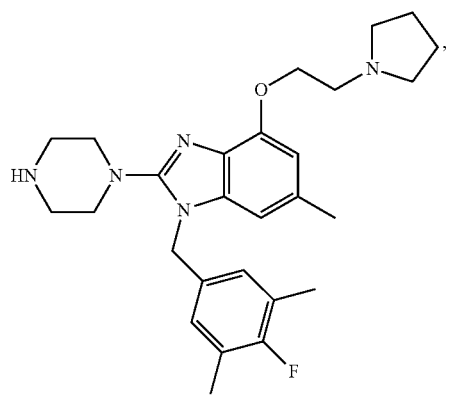

305
-continued
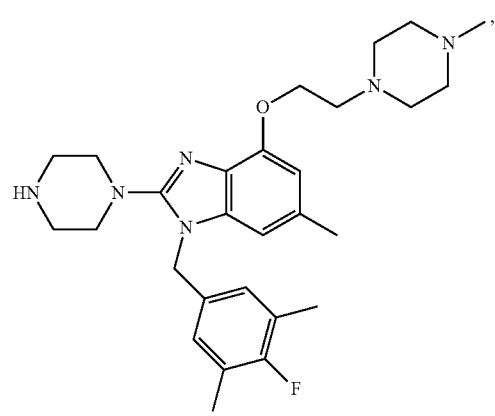
306
-continued
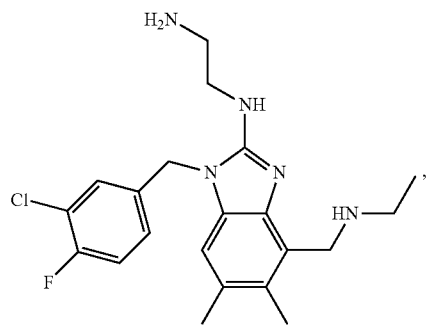
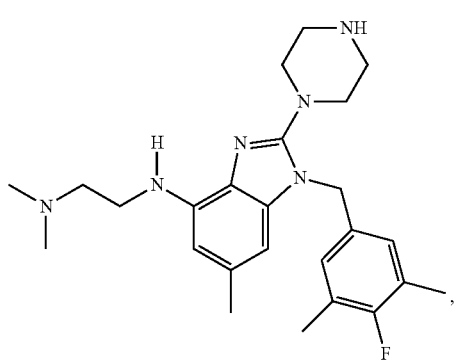
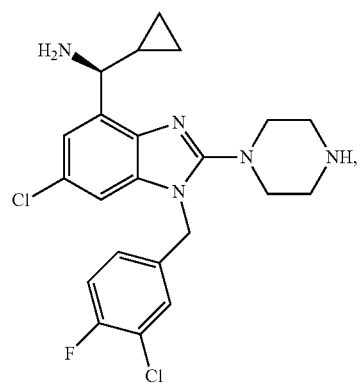
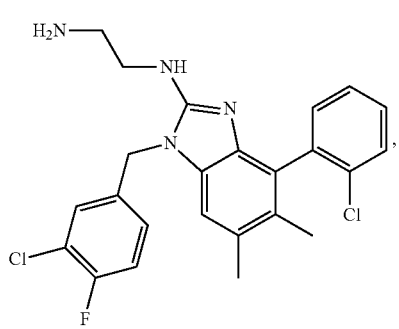

307
-continued
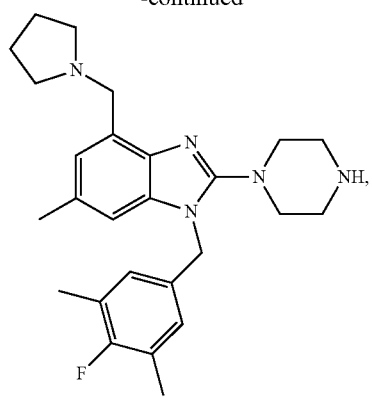
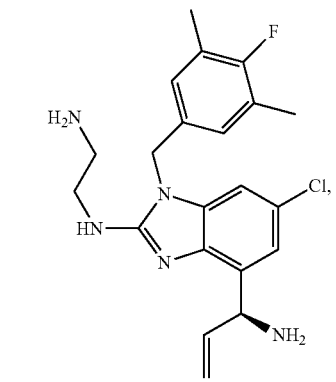
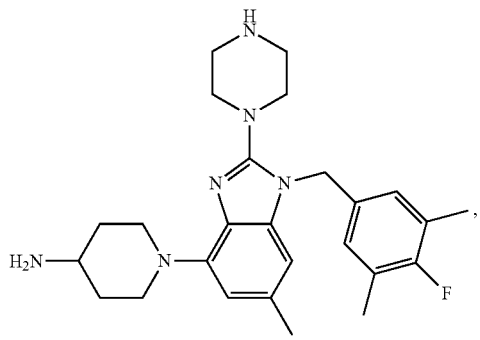
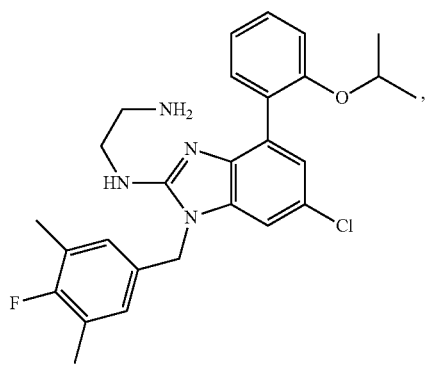
308
-continued
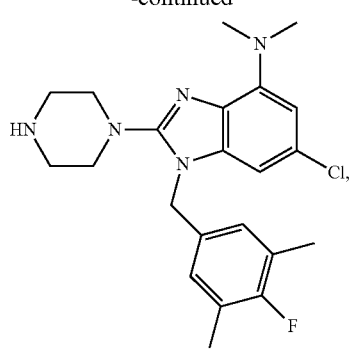
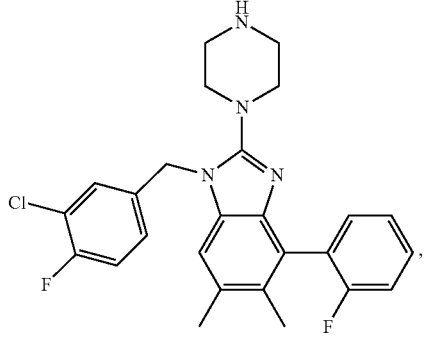
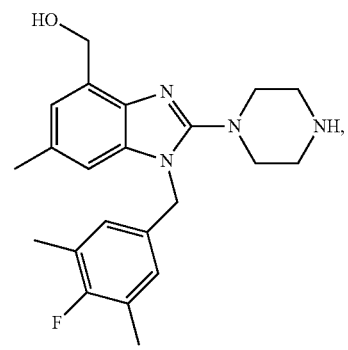
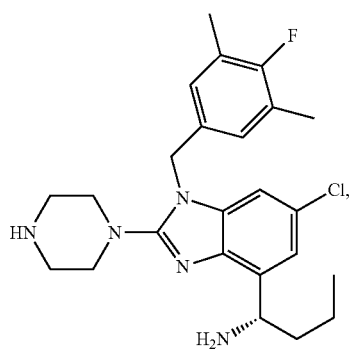
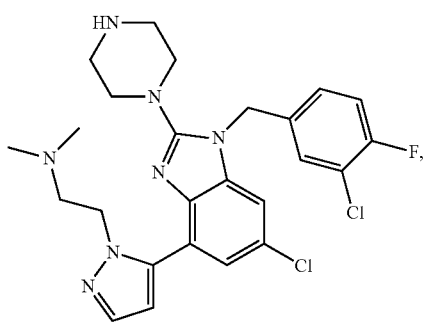

309
-continued
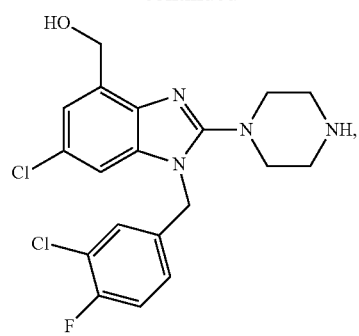
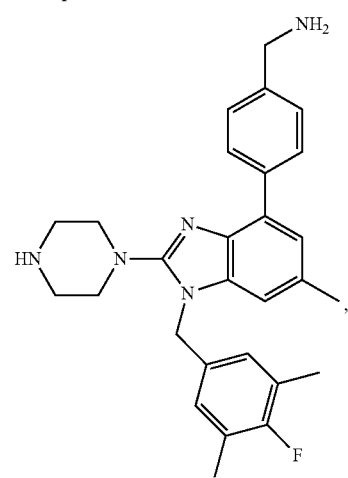
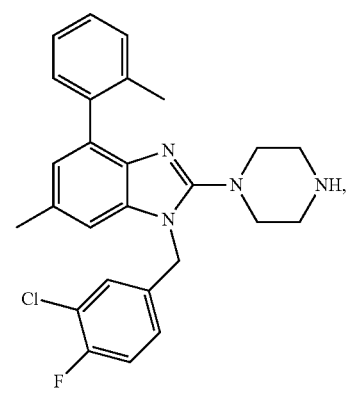
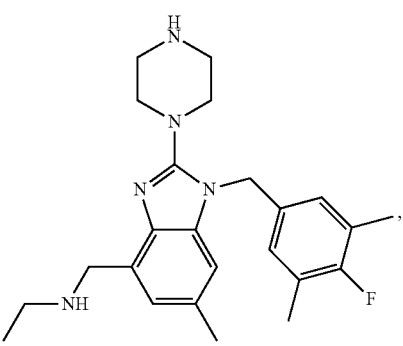
310
-continued
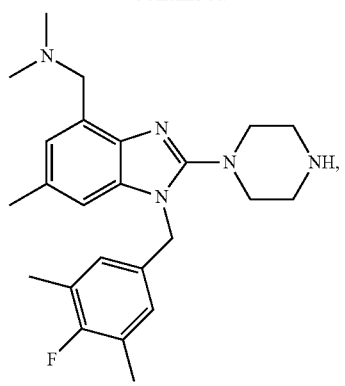
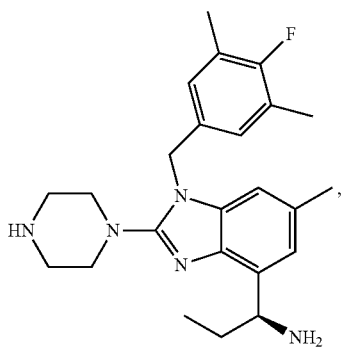
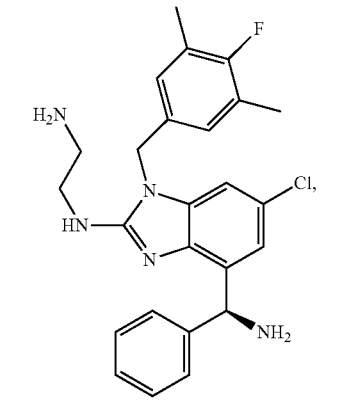
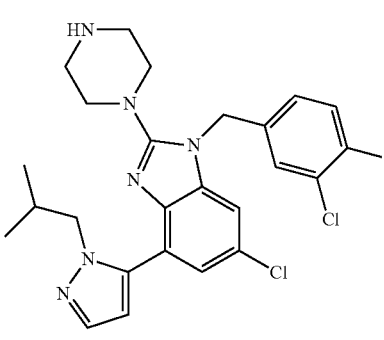

-continued
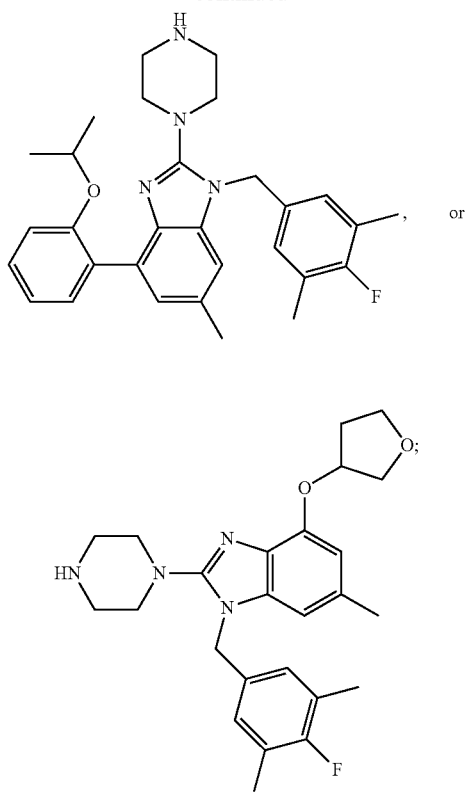
or a pharmaceutically acceptable salt thereof.
15. A compound of the following formula:
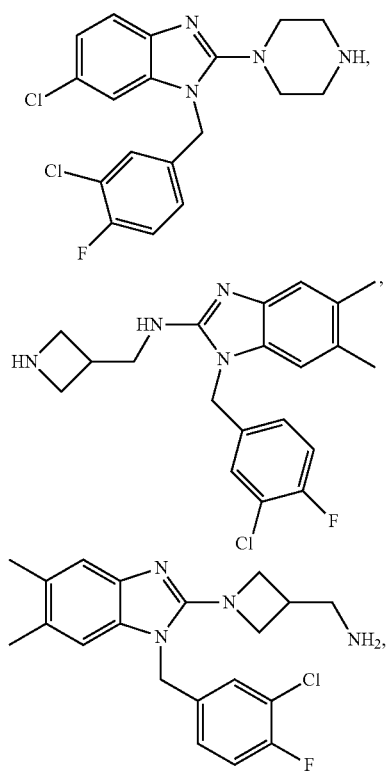
-continued
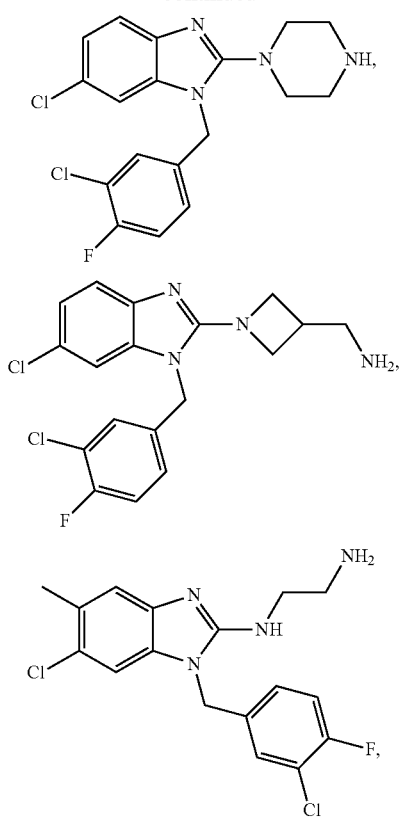
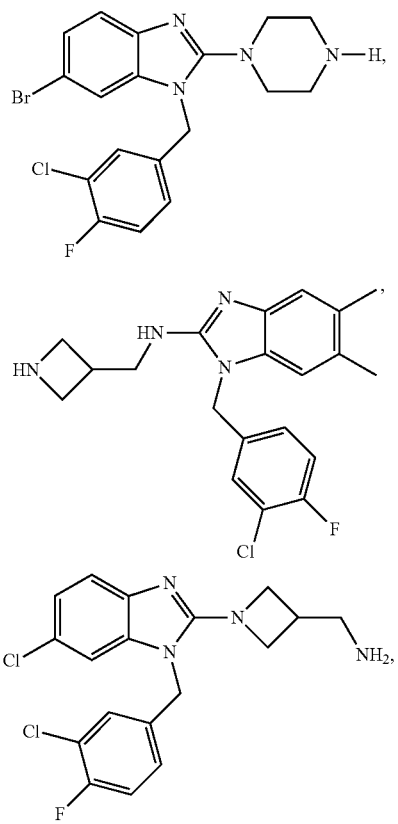

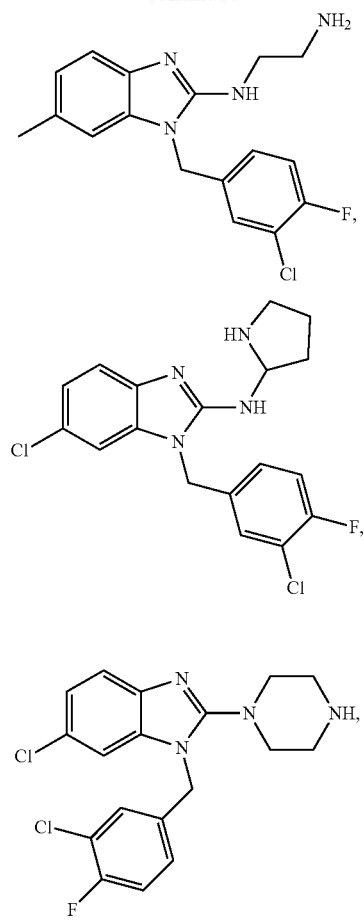
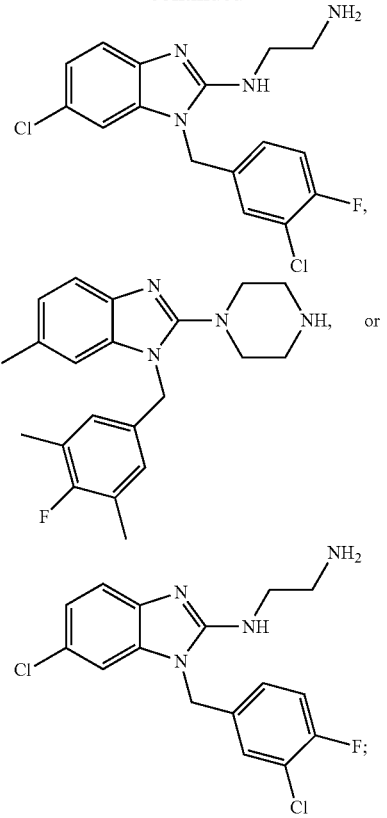
or a pharmaceutically acceptable salt thereof.
16. A pharmaceutical composition, comprising a compound of claim 1 and a pharmaceutically acceptable carrier.
* * * * *